United States Patent
Williams et al.

(10) Patent No.: US 12,384,845 B2
(45) Date of Patent: Aug. 12, 2025

(54) ACTIVATABLE MASKED ANTI-CTLA4 BINDING PROTEINS

(71) Applicants: Xilio Development, Inc., Waltham, MA (US); City of Hope, Duarte, CA (US)

(72) Inventors: John C. Williams, Duarte, CA (US); Margaret Karow, Waltham, MA (US)

(73) Assignees: Xilio Development, Inc., Waltham, MA (US); City of Hope, Duarte, CA (US)

( * ) Notice: Subject to any disclaimer, the term of this patent is extended or adjusted under 35 U.S.C. 154(b) by 1079 days.

(21) Appl. No.: 17/417,239

(22) PCT Filed: Dec. 26, 2019

(86) PCT No.: PCT/US2019/068538
§ 371 (c)(1),
(2) Date: Jun. 22, 2021

(87) PCT Pub. No.: WO2020/139920
PCT Pub. Date: Jul. 2, 2020

(65) Prior Publication Data
US 2022/0073613 A1 Mar. 10, 2022

Related U.S. Application Data

(60) Provisional application No. 62/785,111, filed on Dec. 26, 2018.

(51) Int. Cl.
| | | |
|---|---|---|
| C07K 16/28 | (2006.01) | |
| A61K 39/00 | (2006.01) | |
| A61K 47/68 | (2017.01) | |
| A61P 35/00 | (2006.01) | |

(52) U.S. Cl.
CPC ...... *C07K 16/2818* (2013.01); *A61K 47/6849* (2017.08); *A61P 35/00* (2018.01); *A61K 2039/505* (2013.01); *C07K 2317/24* (2013.01); *C07K 2317/31* (2013.01); *C07K 2317/40* (2013.01); *C07K 2317/52* (2013.01); *C07K 2317/55* (2013.01); *C07K 2317/565* (2013.01); *C07K 2317/72* (2013.01); *C07K 2317/732* (2013.01); *C07K 2317/76* (2013.01); *C07K 2317/92* (2013.01); *C07K 2319/50* (2013.01)

(58) Field of Classification Search
CPC ............ C07K 16/2818; C07K 2317/24; C07K 2317/31; C07K 2317/40; C07K 2317/52; C07K 2317/522; C07K 2317/524; C07K 2317/526; C07K 2317/55; C07K 2317/565; C07K 2317/72; C07K 2317/732; C07K 2317/76; C07K 2317/92; C07K 2319/50; A61K 47/6849; A61K 2039/505; A61P 35/00
See application file for complete search history.

(56) References Cited

U.S. PATENT DOCUMENTS

| | | | |
|---|---|---|---|
| 5,859,205 A | 1/1999 | Adair et al. | |
| 6,051,227 A | 4/2000 | Allison et al. | |
| 7,452,535 B2 | 11/2008 | Davis et al. | |
| 7,465,446 B2 | 12/2008 | Lowy et al. | |
| 7,744,875 B2 | 6/2010 | Lowy et al. | |
| 8,475,790 B2 | 7/2013 | Jure-Kunkel et al. | |
| 8,518,404 B2 | 8/2013 | Daugherty et al. | |
| 8,993,524 B2 | 3/2015 | Bedi et al. | |
| 9,562,073 B2 | 2/2017 | Moore et al. | |
| 9,944,689 B2 | 4/2018 | Wang et al. | |
| 10,167,337 B2 | 1/2019 | Allison et al. | |
| 10,174,113 B2 | 1/2019 | Yang et al. | |
| 10,196,445 B1 | 2/2019 | Engelhardt et al. | |
| 10,463,686 B2 | 11/2019 | Agrawal et al. | |
| 10,842,743 B2 | 11/2020 | Roth et al. | |
| 10,842,763 B2 | 11/2020 | Slusher et al. | |
| 10,869,926 B2 | 12/2020 | Zhou et al. | |
| 11,078,281 B2 | 8/2021 | Wang et al. | |
| 11,643,463 B2 | 5/2023 | Wang et al. | |
| 2009/0215991 A1 | 8/2009 | Lazar et al. | |
| 2010/0189651 A1* | 7/2010 | Stagliano ................ | A61P 29/00 424/9.1 |
| 2014/0212422 A1 | 7/2014 | Korman et al. | |
| 2014/0255313 A1* | 9/2014 | Vasiljeva ........... | C07K 16/2896 424/9.6 |
| 2015/0104409 A1 | 4/2015 | Hanson et al. | |
| 2016/0145355 A1 | 5/2016 | Saha et al. | |
| 2016/0347848 A1 | 12/2016 | Hammond et al. | |
| 2016/0368989 A1 | 12/2016 | Dijk et al. | |
| 2018/0086828 A1* | 3/2018 | Van Berkel ............. | A61P 35/02 |
| 2019/0055321 A1 | 2/2019 | Krystek et al. | |

(Continued)

FOREIGN PATENT DOCUMENTS

| | | | |
|---|---|---|---|
| AU | 2015295936 A1 | 3/2017 | |
| CN | 101287492 A | 10/2008 | |

(Continued)

OTHER PUBLICATIONS

Gershoni (Biodrugs (2007) 21(3): 145-156) (Year: 2007).*

(Continued)

*Primary Examiner* — Julie Wu
*Assistant Examiner* — Elizabeth A Shupe
(74) *Attorney, Agent, or Firm* — Proskauer Rose LLP

(57) ABSTRACT

The invention provides activatable masked anti-CTLA4 binding proteins (e.g., antibodies, bispecific antibodies, and chimeric receptors) and their use in treating and preventing cancer, as well as compositions and kits comprising the activatable masked anti-CTLA4 binding proteins.

14 Claims, 84 Drawing Sheets
Specification includes a Sequence Listing.

(56) References Cited

U.S. PATENT DOCUMENTS

| | | | |
|---|---|---|---|
| 2019/0076452 | A1 | 3/2019 | Rios-Doria et al. |
| 2019/0169245 | A1* | 6/2019 | Williams ......... C07K 14/70521 |
| 2019/0241660 | A1 | 8/2019 | Giroir et al. |
| 2019/0241662 | A1 | 8/2019 | Luo et al. |
| 2019/0241886 | A1 | 8/2019 | Du et al. |
| 2019/0292599 | A1 | 9/2019 | Liu et al. |
| 2019/0300606 | A1 | 10/2019 | Woods et al. |
| 2019/0300967 | A1 | 10/2019 | Bachireddy et al. |
| 2019/0352398 | A1 | 11/2019 | Allison et al. |
| 2019/0359714 | A1 | 11/2019 | Tipton et al. |
| 2019/0382490 | A1 | 12/2019 | Loffredo et al. |
| 2020/0055937 | A1 | 2/2020 | Calzone et al. |
| 2020/0115451 | A1 | 4/2020 | Homet Moreno et al. |
| 2020/0148771 | A1 | 5/2020 | Baeuerle et al. |
| 2020/0206346 | A1 | 7/2020 | Li et al. |
| 2020/0255524 | A1 | 8/2020 | Bonivi et al. |
| 2020/0277377 | A1 | 9/2020 | Wang et al. |
| 2020/0405890 | A1 | 12/2020 | Vasiljeva et al. |
| 2021/0023151 | A1 | 1/2021 | Deng et al. |
| 2021/0032344 | A1 | 2/2021 | Bhagavatheeswaran et al. |
| 2021/0040177 | A1 | 2/2021 | Roberts |
| 2021/0047410 | A1 | 2/2021 | Liu et al. |
| 2022/0306743 | A1 | 9/2022 | O'Neil et al. |

FOREIGN PATENT DOCUMENTS

| | | |
|---|---|---|
| CN | 104292334 A | 1/2015 |
| CN | 108948194 A | 12/2018 |
| CN | 108948194 B | 2/2023 |
| EP | 2418278 A2 | 2/2012 |
| EP | 2734232 B1 | 11/2017 |
| WO | 0037504 A2 | 6/2000 |
| WO | 0114424 A2 | 3/2001 |
| WO | 2006101692 A1 | 9/2006 |
| WO | WO 2010/081173 A2 | 7/2010 |
| WO | 2012120125 A1 | 9/2012 |
| WO | 2016015675 A1 | 2/2016 |
| WO | 2016130986 A1 | 8/2016 |
| WO | 2016185016 A1 | 11/2016 |
| WO | 2016196237 A1 | 12/2016 |
| WO | 2017157964 A1 | 9/2017 |
| WO | 2017220990 A1 | 12/2017 |
| WO | 2018085555 A1 | 5/2018 |
| WO | WO 2018/106862 A1 | 6/2018 |
| WO | 2018148555 A1 | 8/2018 |
| WO | 2018156802 A1 | 8/2018 |
| WO | WO2018/209701 A1 | 11/2018 |
| WO | WO 2018/218076 A1 | 11/2018 |
| WO | 2018222711 A2 | 12/2018 |
| WO | 2019018841 A2 | 1/2019 |
| WO | 2019075468 A1 | 4/2019 |
| WO | 2019094352 A1 | 5/2019 |
| WO | WO 2019/148444 A1 | 8/2019 |
| WO | WO 2019/148445 A1 | 8/2019 |
| WO | 2019183036 A1 | 9/2019 |
| WO | 2019243471 A1 | 12/2019 |
| WO | 2020007368 A1 | 1/2020 |
| WO | 2020024932 A1 | 2/2020 |
| WO | 2020057610 A1 | 3/2020 |
| WO | 2020061526 A1 | 3/2020 |
| WO | 2020092155 A1 | 5/2020 |
| WO | 2020139920 A2 | 7/2020 |
| WO | 2020214748 A1 | 10/2020 |
| WO | 2020252349 A1 | 12/2020 |
| WO | 2020252358 A1 | 12/2020 |
| WO | 2021062323 A1 | 4/2021 |
| WO | 2021064188 A1 | 4/2021 |

OTHER PUBLICATIONS

Lee et al., 2011, Nature Reviews Cancer 11: 211-218, see p. 211; Cancer Prevention Overview (PDQ®)—Patient Version, National Cancer Institute (Year: 2011).*

Sela-Culang (Frontiers in Immunology (2013) 4: 302) (Year: 2013).*
Almagro, Frontiers in Immunology (2018) 8: 1751 (Year: 2018).*
PDQ® Screening and Prevention Editorial Board. PDQ Cancer Prevention Overview. Bethesda, MD: National Cancer Institute. Updated Oct. 23, 2023. Available at: https://www.cancer.gov/about-cancer/causes-prevention/patient-prevention-overview-pdq. Accessed Mar. 22, 2024. [PMID: 26389424] (Year: 2023).*
U.S. Appl. No. 18/622,421. Combination of Masked CTLA4 and PD1/PDL1 Antibodies for Treating Cancer, filed 2024. (Year: 2024).*
Brown et al. "Tolerance of single, but not multiple, amino acid replacements in antibody VH CDR 2: a means of minimizing B cell wastage from somatic hypermutation" J. Immuno. May 1996, 3285-91. (Year: 1996).
Donaldson et al. "Design and Development of Masked Therapeutic Antibodies to Limit Off-Target Effects: Application to anti-EGFR Antibodies", Cancer Biology and Therapy, vol. 8, No. 22, Nov. 15, 2009.
Edwards et al., "The remarkable flexibility of the human antibody repertoire; isolation of over one thousand different antibodies to a single protein", BLyS. J Mol Biol. Nov. 14, 2003;334(1): 103-18. (Year: 2003).
Goel et al., "Plasticity within the antigen-combining site may manifest as molecular mimicry in the humoral immune response", J Immunol. Dec. 15, 2004; 173(12):7358-67. (Year: 2004).
International Search Report and Written Opinion for PCT/US2019/068538, dated Jun. 23, 2020.
Kanyavuz et al., "Breaking the law: unconventional strategies for antibody diversification", Nat Rev Immunol. Jun. 2019; 19(6):355-368. (Year: 2019).
Kirkwood et al., "Phase II trial of tremelimumab (CP-675,206) in patients with advanced refractory or relapsed melanoma," Clin Cancer Res 16(3):1042-1048 (2010). (Year: 2010).
Korman et al. "Tumor Immunotherapy: Preclinical and Clinical Activity of anti-CTLA4 Antibodies", Current Opinion in Investigational Drugs, 6:582-591, 2005.
Lloyd et al., "Modelling the human immune response: performance of a 1011 human antibody repertoire against a broad panel of therapeutically relevant antigens", Protein Eng Des Sel. Mar. 2009;22(3):159-68. (Year: 2009).
Polu et al. "Probody Therapeutics for Targeting Antibodies to Diseased Tissue", Expert Opinion on Biological Therapy, vol. 14, No. 8, pp. 1049-1053, Aug. 1, 2014.
Prieto et al., "CTLA-4 blockade with ipilimumab: long-term follow-up of 177 patients with metastatic melanoma", Clin Cancer Res 18 (7):2039-2047 (2012). (Year: 2012).
Quezada et al. "Blockade of CTLA-4 on both effector and regulatory T cell compartments contributes to the antitumor activity of anti-CTLA-4 antibodies", Journal of Experimental Medicine, 206(8):1717-1725, 2009.
Selby et al. "Anti-CTLA-4 Antibodies of IgG2a Isotype Enhance Antitumor Activity through Reduction of Intratumoral Regulatory T Cells", Cancer Immunology Research, 1(1):32-42, 2013.
Vajdos et al. "Comprehensive functional maps of the antigen-binding site of an anti-ErbB2 antibody obtained with shotgun scanning mutagenesis", J. Mol. Biol. Jul 5, 2002, 320(2):415-28. (Year: 2002).
Vandenborre et al. "Interaction of CTLA-4 (CD152) with CD80 or CD86 inhibits human T-cell activation. Immunology", Nov. 1999;98(3):413-21. (Year: 1999).
Weber et al. "Phase I/II Study of Ipilimumab for Patients with Metastatic Melanoma", Journal of Clinical Oncology, 26: 5950-5956, 2008.
Wolchok et al. "Nivolumab plus Ipilimumab in Advanced Melanoma", The New England Journal of Medicine, 369:122-133, 2013.
Dondelinger et al: "Understanding the Significance and Implications of Antibody Numbering and Antigen-Binding Surface/Residue Definition", Frontiers in Immunology, vol. 9, Oct. 16, 2018 (Oct. 16, 2018), pp. 1-15, XP055572450, DOI: 10.3389/fimmu.2018.02278.
International Search Report for PCT/US2019/068538 dated Jun. 23, 2020 (9 pages).
International Search Report for PCT/US2022/018376 dated Jun. 20, 2022 (5 pages).
International Search Report for PCT/US2022/018378 dated Jun. 20, 2022 (5 pages).

(56) References Cited

OTHER PUBLICATIONS

Almagro, Juan C., et al., "Humanization of antibodies", Frontiers in Bioscience, vol. 13, 2008, pp. 1619-1633, (15 pages).

Altshuler, E., et al., "Preparation of Recombinant Antibodies and Methods for Increasing Their Affinity", Advances in Biological Chemistry, vol. 50, 2010, pp. 203-258, English Translation (4 pages).

Casset, Florence, et al., "A peptide mimetic of an anti-CD4 monoclonal antibody by rational design", Biochemical and Biophysical Research Communications, vol. 307, No. 1, Jul. 18, 2003, pp. 198-205, DOI: 10.1016/s0006-291x(03)01131-8, (8 pages).

Chen, Ching, et al., "Enhancement and destruction of antibody function by somatic mutation: unequal occurrence is controlled by V gene combinatorial associations", The EMBO Journal, vol. 14, No. 12, 1995, pp. 2784-2794, DOI: 10.1002/j.1460-2075.1995.tb07278.x, (11 pages).

Coico, R., et al., "Immunology", Textbook, Moscow, Publishing Center Academy, 2008, pp. 61-62, English Translation (6 pages).

Gutierrez, Martin, et al., "Anti-CTLA-4 probody BMS-986249 alone or in combination with nivolumab in patients with advanced cancers: Initial phase I results", Journal of Clinical Oncology, vol. 38, No. 15 Suppl., pp. 3058-3058, DOI: 10.1200/JCO.2020.38.15_suppl.3058, (4 pages).

Jenkins, Kurt, et al., "Tumor-activated Anti-CTLA-4 Monoclonal Antibody, XTX101, Demonstrates Monotherapy and Anti-PD-1 Combination Benefit in Preclinical Models", Xilio Therapeutics, Poster Presentation, May 12, 2021, retrieved on Jun. 9, 2022 from URL: https://xiliotx.com/wp-content/uploads/2021/09/2021-NYAS_XTX101-Poster.pdf, (1 page).

Jenkins, Kurt, et al., "Tumor-activated Fc-engineered Anti-CTLA-4 Monoclonal Antibody, XTX101, Demonstrates Tumor-selective PD and Efficacy in Preclinical Models", Xilio Therapeutics, Poster Presentation, Nov. 13, 2020, retrieved on Jun. 9, 2022 from URL: https://xiliotx.com/wp-content/uploads/2021/09/2020-SITC_XTX101-Poster.pdf, (1 page).

Kussie, Paul H., et al., "A single engineered amino acid substitution changes antibody fine specificity", The Journal of Immunology, vol. 152, No. 1, Jan. 1994, pp. 146-152, DOI: 10.4049/jimmunol.152.1.146 (8 pages).

Lazar, Greg A., et al., "Engineered antibody Fc variants with enhanced effector function", Proceedings of the National Academy of Science, vol. 103, No. 11, 2006, pp. 4005-4010, DOI: 10.1073/pnas.0508123103, (6 pages).

MacCallum, Robert M., et al., "Antibody-antigen Interactions: Contact Analysis and Binding Site Topography", Journal of Molecular Biology, vol. 262, No. 5, Oct. 11, 1996, pp. 732-745, DOI: 10.1006/jmbi.1996.0548, (14 pages).

Matsui, Toshihiro, et al., "Autoantibodies to T Cell Costimulatory Molecules in Systemic Autoimmune Diseases", The Journal of Immunology, vol. 162, No. 7, Apr. 1, 1999, pp. 4328-4335, DOI: 10.4049/jimmunol.162.7.4328, (9 pages).

Oroudjev, Emin, et al., "Maytansinoid-Antibody Conjugates Induce Mitotic Arrest by Suppressing Microtubule Dynamic Instability", Molecular Cancer Therapeutics, vol. 9, No. 10, 2010, pp. 2700-2713, DOI: 10.1158/1535-7163.MCT-10-0645, (14 pages).

Padlan, Eduardo A., et al., "Anatomy of the antibody molecule", Molecular Immunology, vol. 31, No. 3, Feb. 1994, pp. 169-217, DOI: 10.1016/0161-5890(94)90001-9, (49 pages).

Padlan, Eduardo A., et al., "Structure of an antibody-antigen complex: crystal structure of the HyHEL-10 Fab-lysozyme complex", PNAS USA, vol. 86, No. 15, 1989, pp. 5938-5942, DOI: 10.1073/pnas.86.15.5938, (5 pages).

Paul, William E., "Fundamental Immunology", Third Edition, 1993, pp. 292-295, (6 pages).

Portolano, S., et al., "Lack of promiscuity in autoantigen-specific H and L chain combinations as revealed by human H and L chain "roulette"", The Journal of Immunology, vol. 150, No. 3, Feb. 1, 1993, pp. 880-887, DOI: 10.4049/jimmunol.150.3.880, (9 pages).

Postow, Michael A., et al., "Immune Checkpoint Blockade in Cancer Therapy", Journal of Clinical Oncology, vol. 33, No. 17, 2015, pp. 1974-1982, DOI: 10.1200/JCO.2014.59.4358, (10 pages).

Queen, Cary, et al., "A humanized antibody that binds to the interleukin 2 receptor", PNAS USA, vol. 86, No. 24, Dec. 1989, pp. 10029-10033, DOI: 10.1073/pnas.86.24.1002, (5 pages).

Reichmann, Lutz, et al., "Reshaping human antibodies for therapy", Nature, vol. 332, 1988, pp. 323-327, DOI: 10.1038/332323a0 (5 pages).

Rudikoff, Stuart, et al., "Single amino acid substitution altering antigen-binding specificity", Proceedings of the National Academy of Sciences USA, Immunology, vol. 79, Mar. 1982, pp. 1979-1983 (5 pages).

Snyder, Alexandra, et al., "Genetic Basis for Clinical Response to CTLA-4 Blockade in Melanoma", The New England Journal of Medicine, vol. 371, No. 23, 2014, pp. 2189-2199, DOI: 10.1056/NEJMoa1406498, (11 pages).

International Search Report for PCT/CN2017/085134 dated Feb. 23, 2018 (10 pages).

Bakacs, Tibor et al., "Anti-CTLA-4 therapy may have mechanisms similar to those occurring in inherited human CTLA4 haploinsufficiency", Immunobiology, vol. 220, No. 5, May 2015, pp. 624-625, DOI: 10.1016/j.imbio.2014.11.019 (2 pages).

Briney, Bryan et al., "Commonality despite exceptional diversity in the baseline human antibody repertoire", Nature, vol. 566, Feb. 21, 2019; https://doi.org/10.1038/s41586-019-0879-y (19 pages).

Carbonnel, Franck et al., "Inflammatory bowel disease and cancer response due to anti-CTLA-4: is it in the flora?", Seminars in Immunopathology, vol. 39, No. 3, 2017, pp. 327-331, DOI: 10.1007/s00281-016-0613-x (5 pages).

Janeway, Jr., Charles A. et al., Immunology, 3rd Edition, Garland Publishing Inc., pp. 3:1-3:11 (1997) (14 pages).

Simmons, Andrew D. et al., "Local secretion of anti-CTLA-4 enhances the therapeutic efficacy of a cancer immunotherapy with reduced evidence of systemic autoimmunity", Cancer Immunology, Immunotherapy, vol. 57, 2008, pp. 1263-1270, DOI: 10.1007/s00262-008-0451-3 (8 pages).

Sun, Jingjing et al., "Concurrent decrease in IL-10 with development of immune-related adverse events in a patient treated with anti-CTLA-4 therapy", Cancer Immunity, vol. 8, May 27, 2008, p. 9 (7 pages).

Tang, Derek Ng et al., "Increased Frequency of ICOS+ CD4 T Cells as a Pharmacodynamic Biomarker for Anti-CTLA-4 Therapy", Cancer Immunology Research, vol. 1, No. 4, 2013, pp. 229-234, DOI: 10.1158/2326-6066.CIR-13-0020 (8 pages).

Zhu, Tongbo et al., "Cytokines Promote Adequate Activation of T Cells", Medical Immunology, Chengdu Sichuan University Press, p. 142, Feb. 28, 2017 (4 pages).

\* cited by examiner

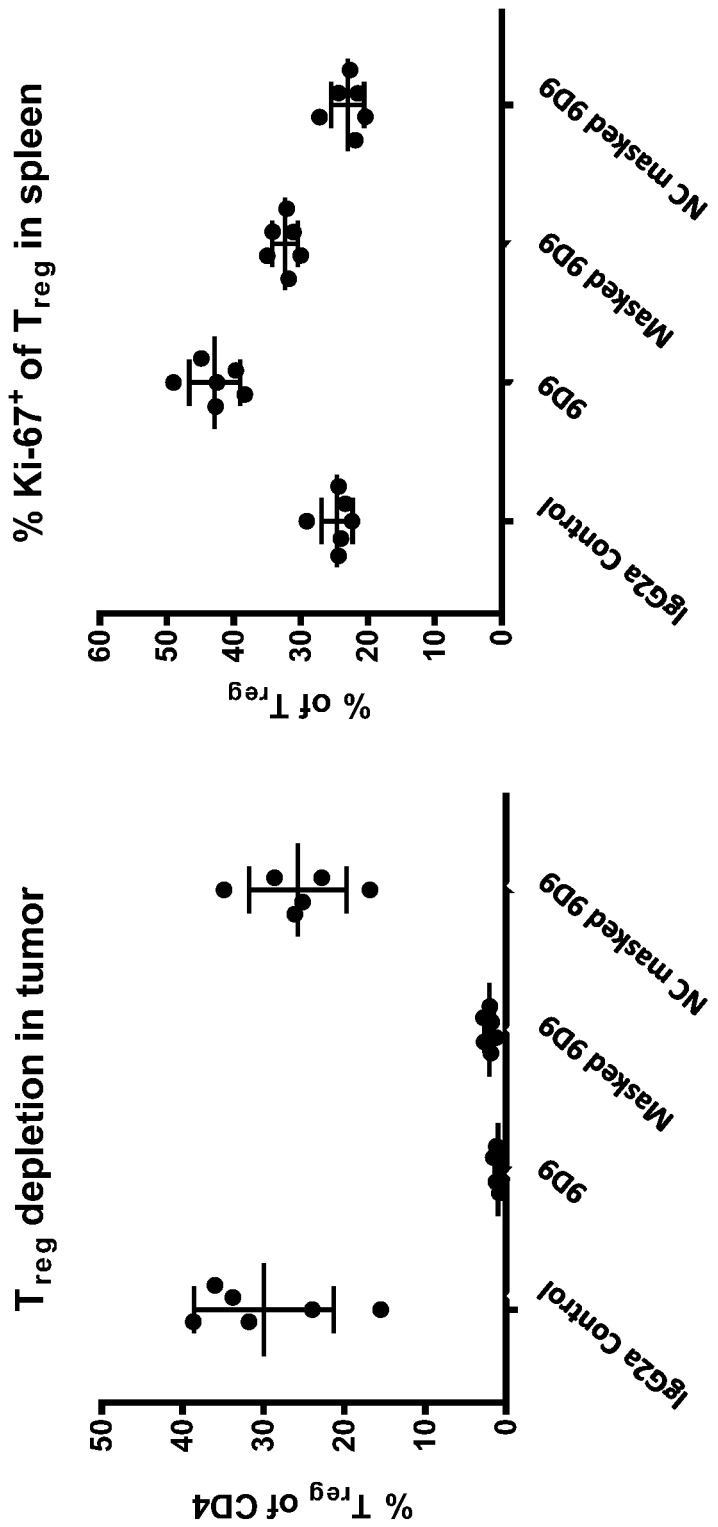

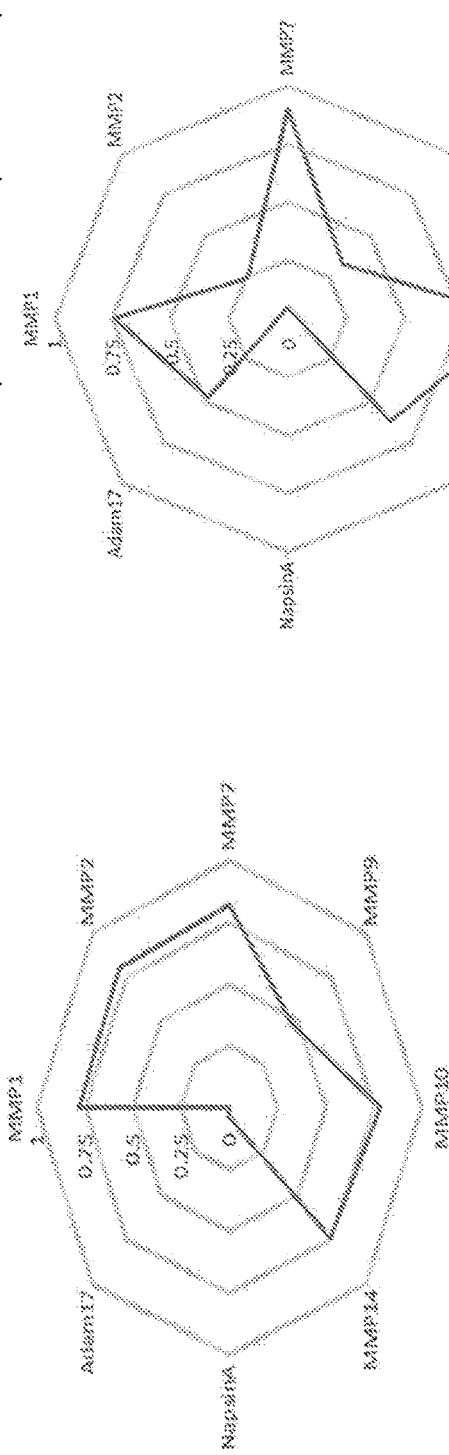
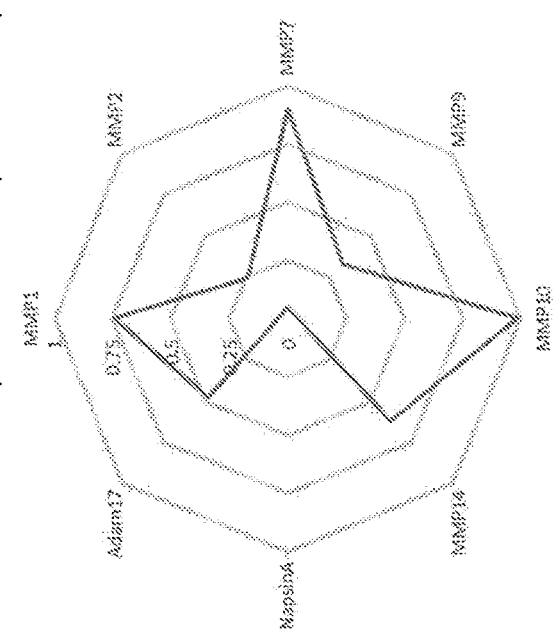
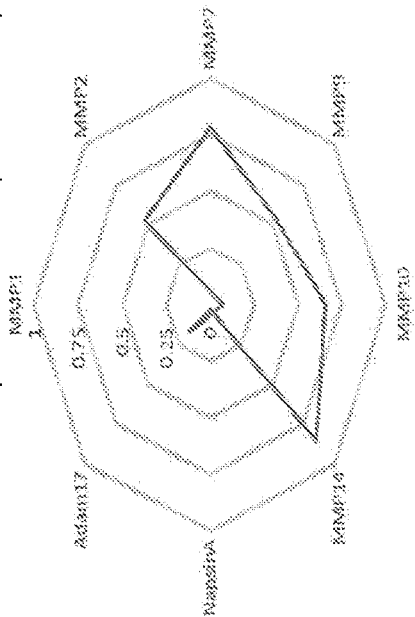
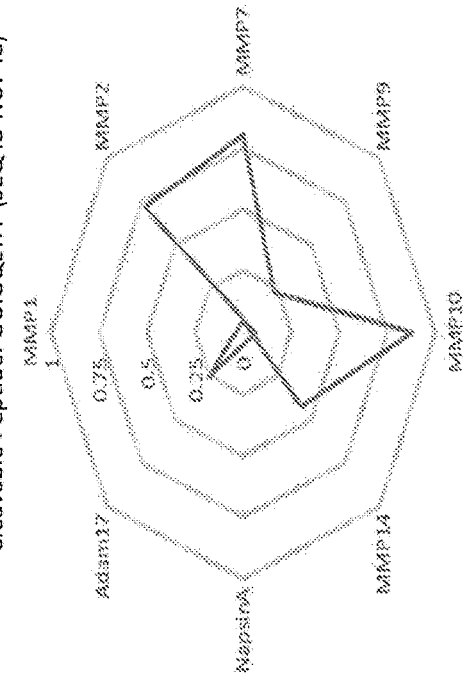
FIG. 11A  Antibody 2-14  Cleavable Peptide: VPLSLY (SEQ ID NO: 86)
FIG. 11B  Antibody 2-18  Cleavable Peptide: MPYDLYHP (SEQ ID NO: 47)
FIG. 11C  Antibody 2-16  Cleavable Peptide: DSGFMLT (SEQ ID NO: 50)
FIG. 11D  Antibody 2-17  Cleavable Peptide: GGIGQLTA (SEQ ID NO: 48)

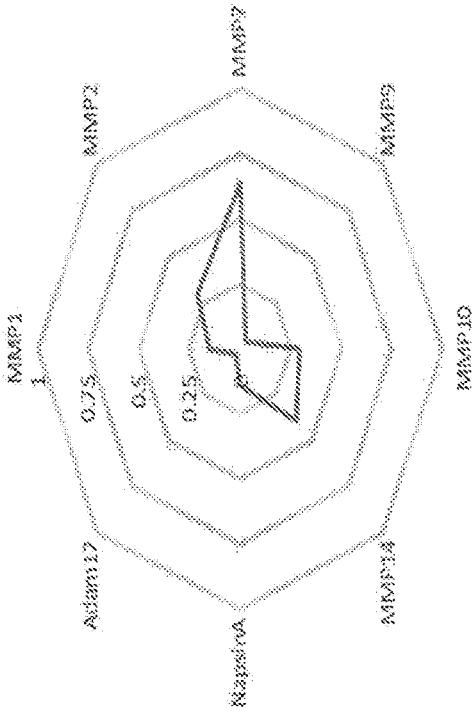
FIG. 11E  Antibody 2-20
Cleavable Peptide: RAAAVKSP (SEQ ID NO: 72)
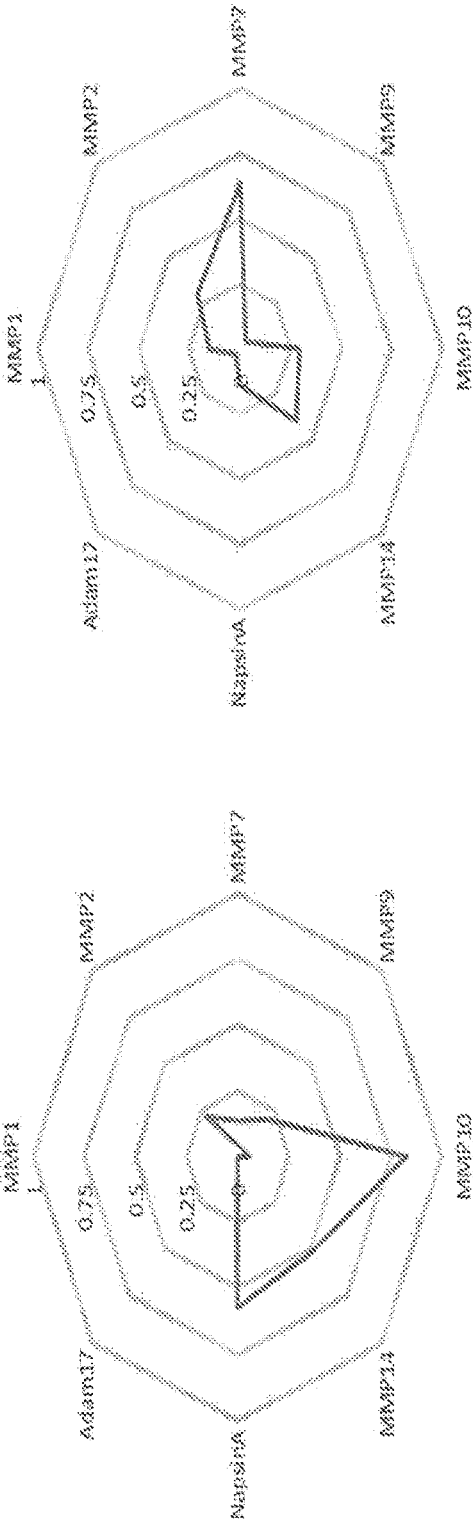
FIG. 11F  Antibody 2-19
Cleavable Peptide: HEQLTV (SEQ ID NO: 57)
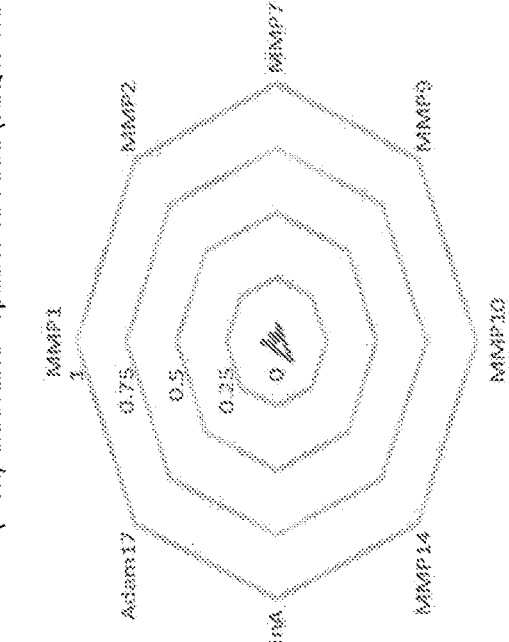
FIG. 11G  Antibody 2-21
Cleavable Peptide: TSVLMAAP (SEQ ID NO: 51)
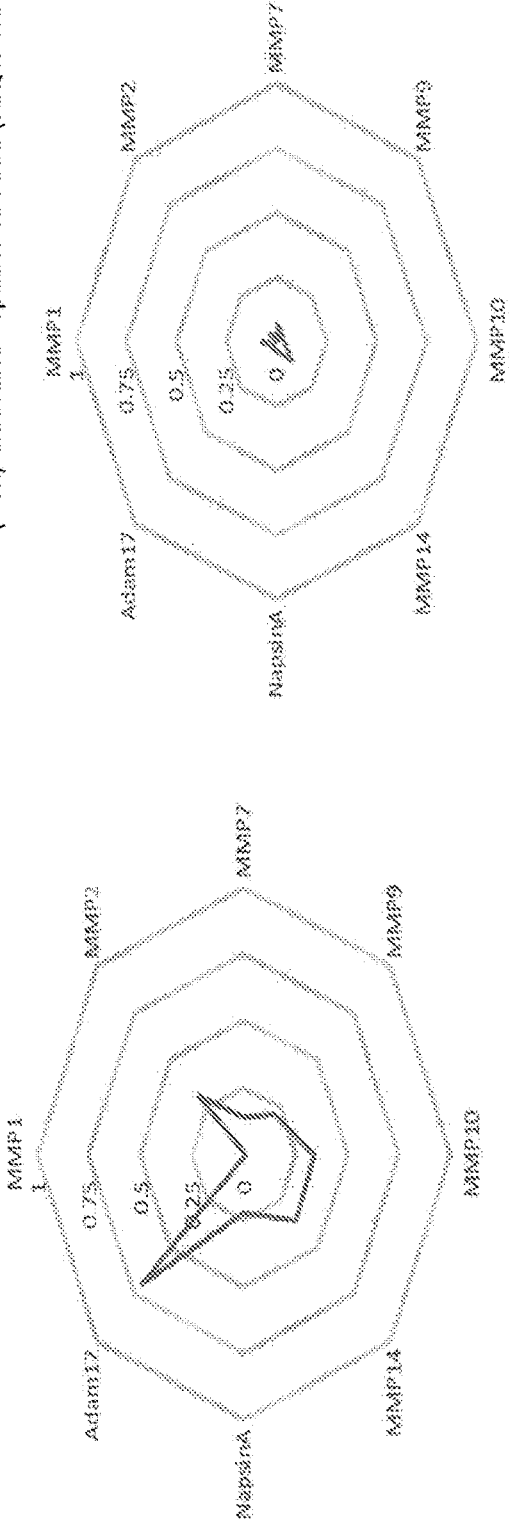
FIG. 11H  Antibody 2-15
(Non)-Cleavable Peptide: GSGGSG (SEQ ID NO: 414)

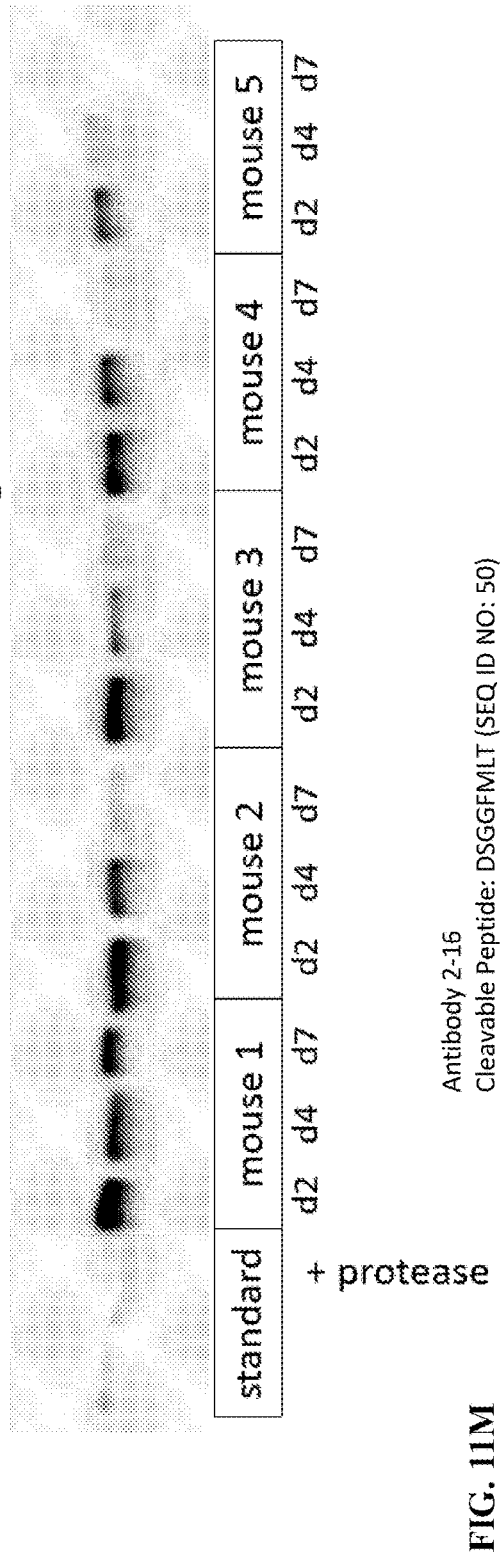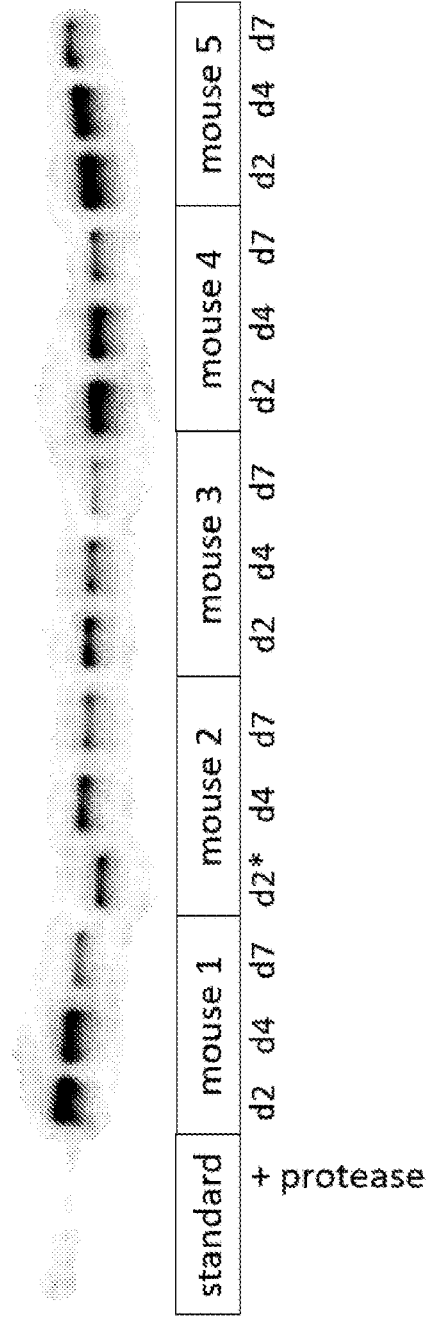
FIG. 11L
FIG. 11M

FIG. 19E  Splenic
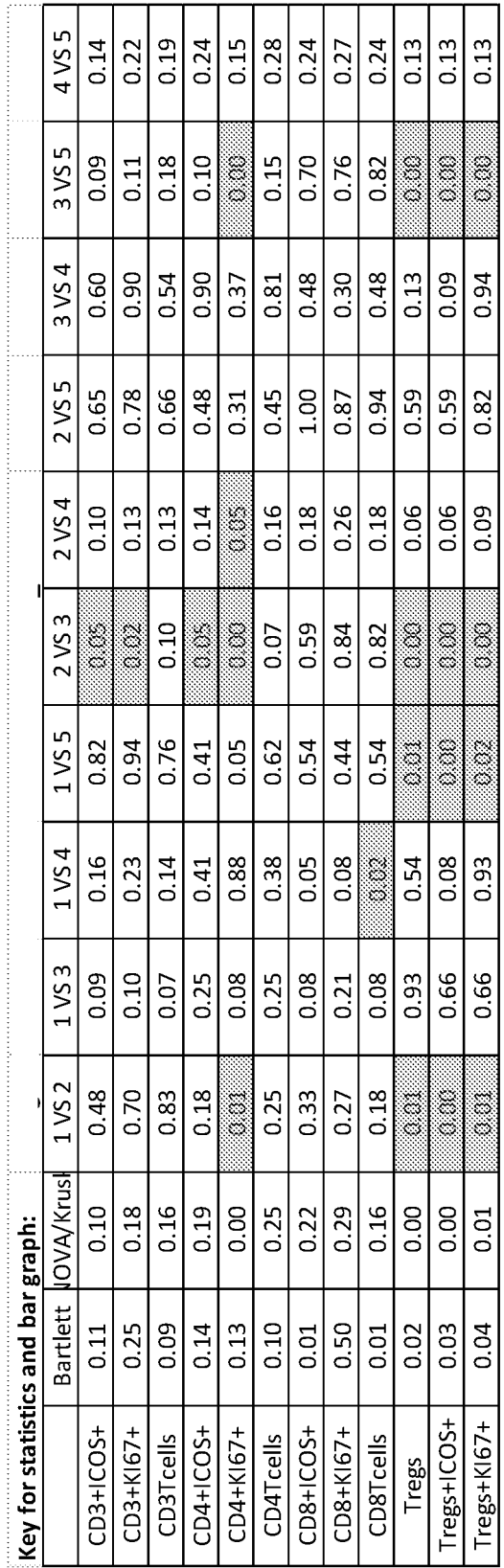
FIG. 19F  Intratumoral
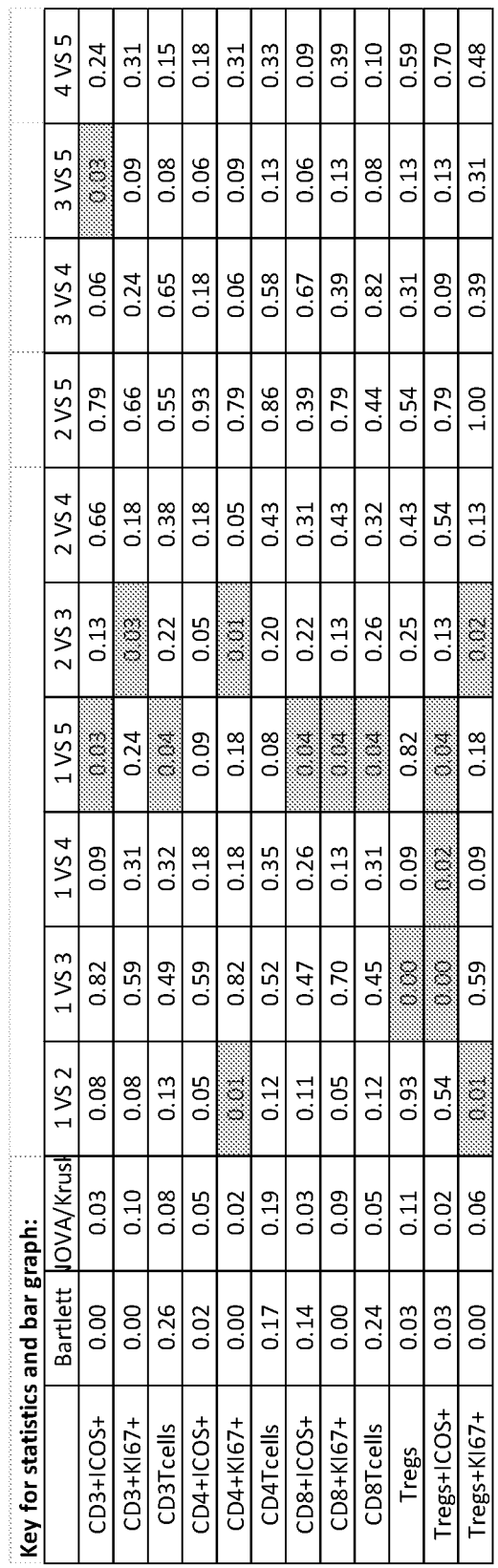

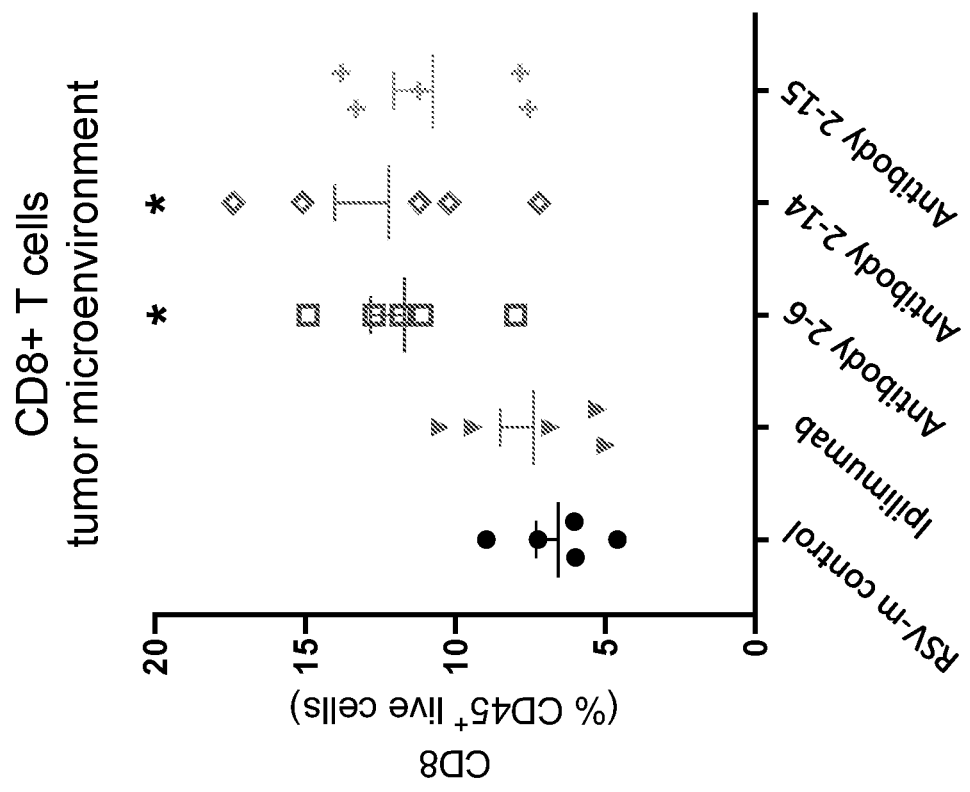
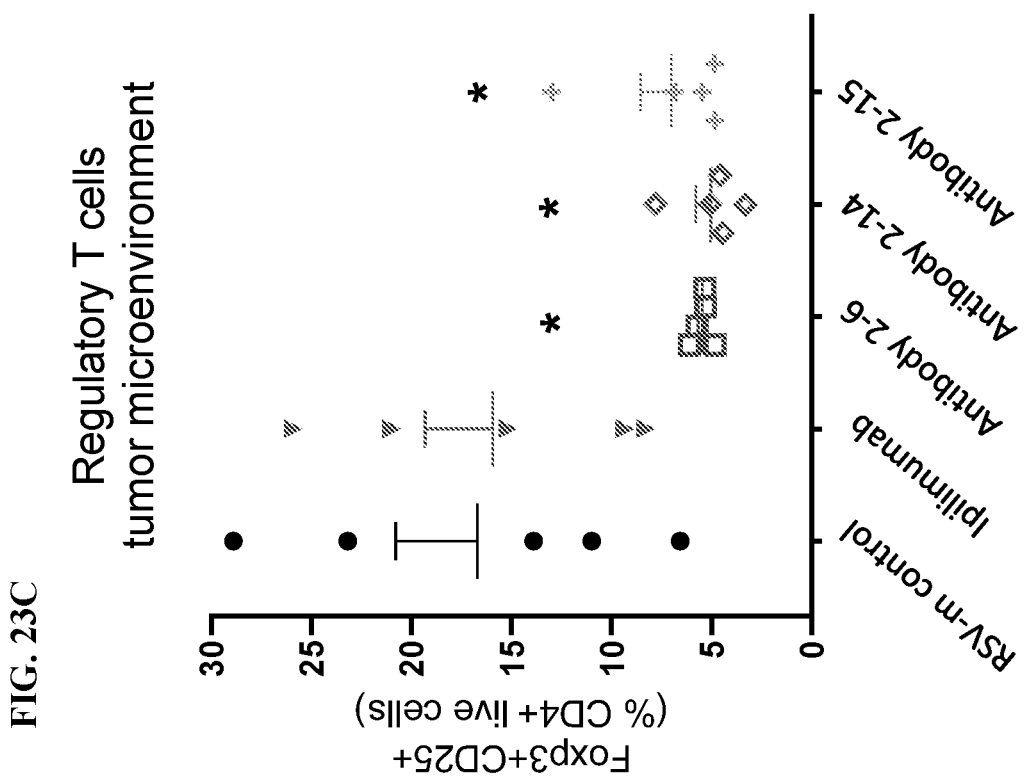
FIG. 23C

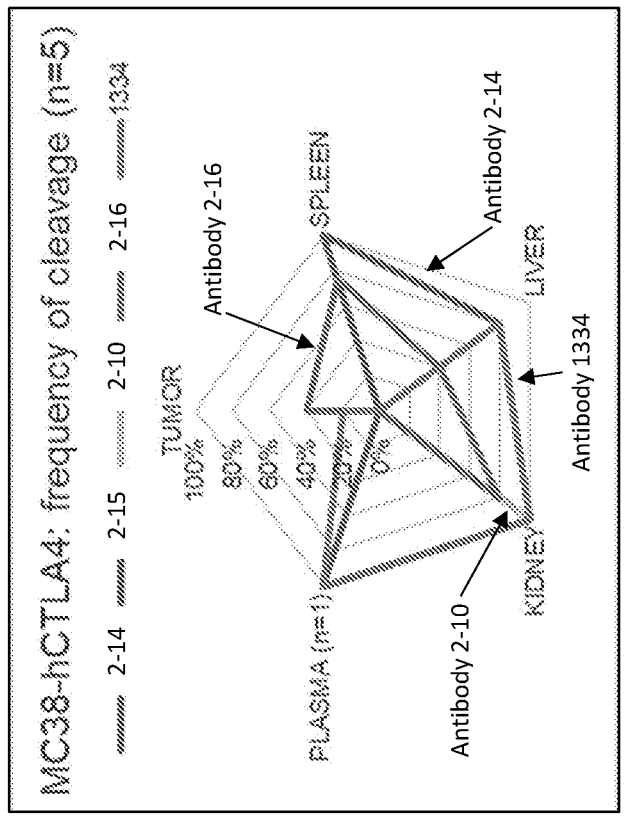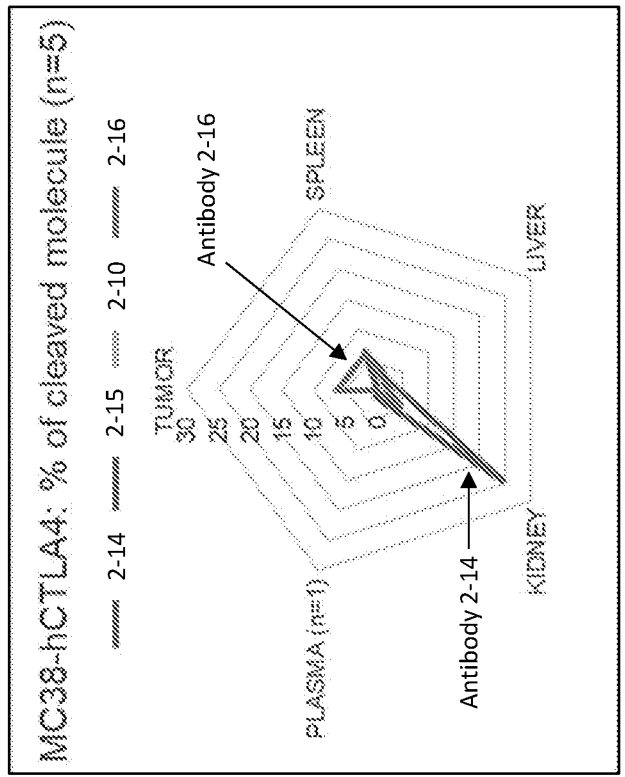
FIG. 25C

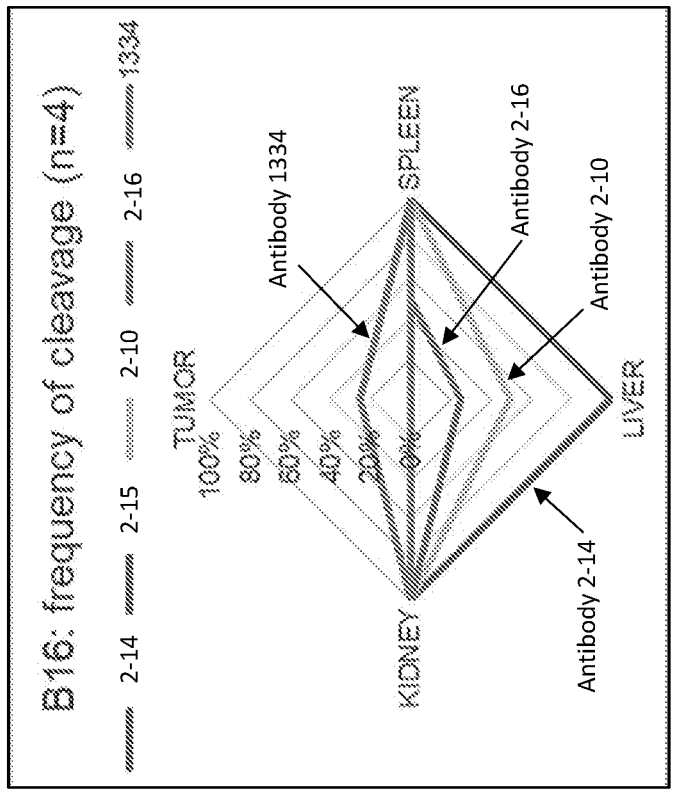
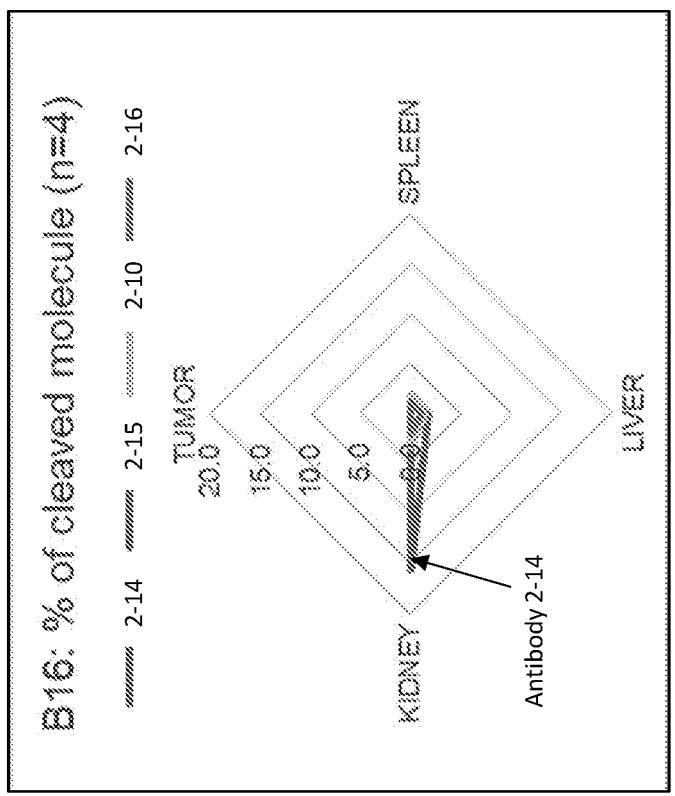
FIG. 25F

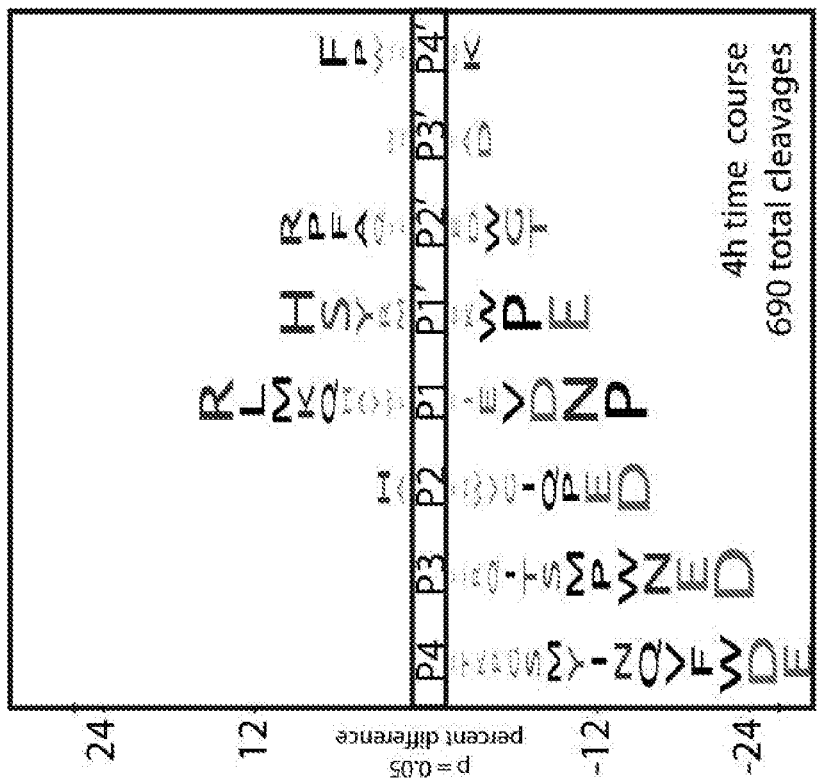
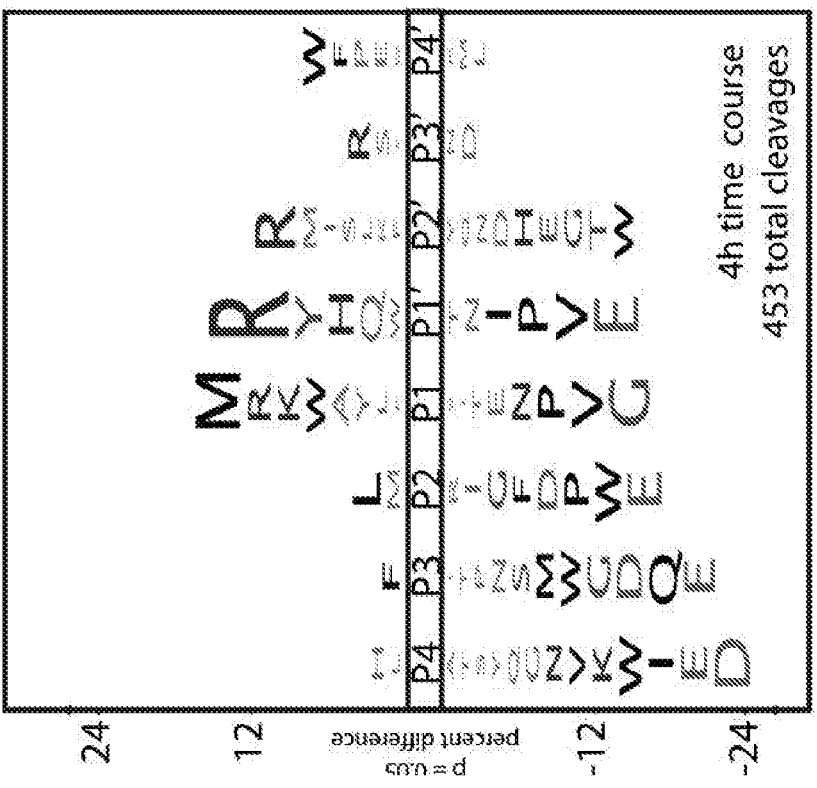
FIG. 30

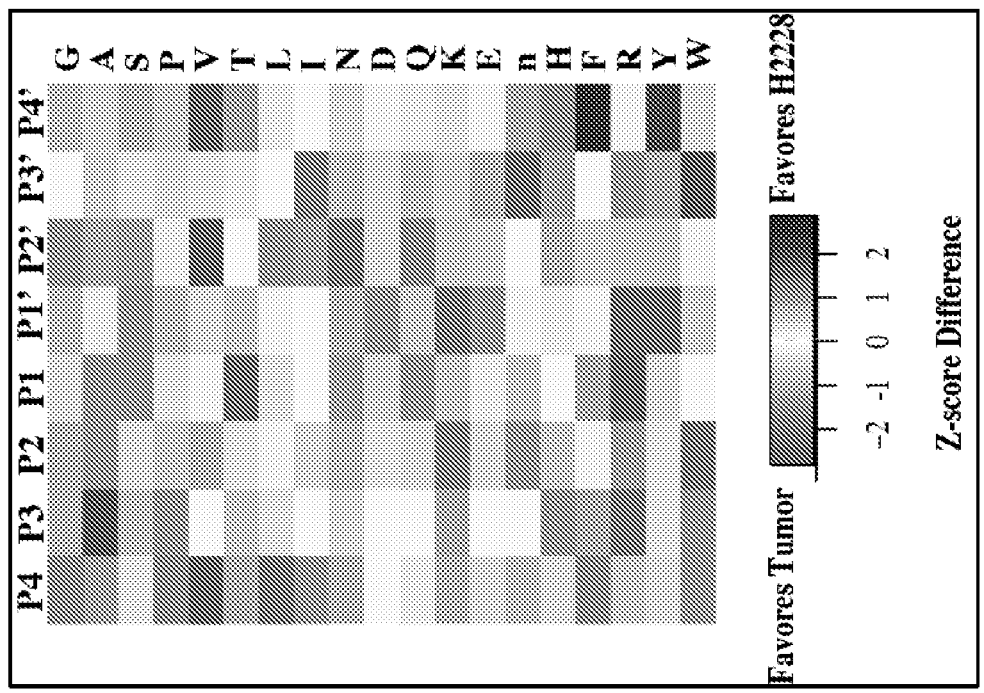
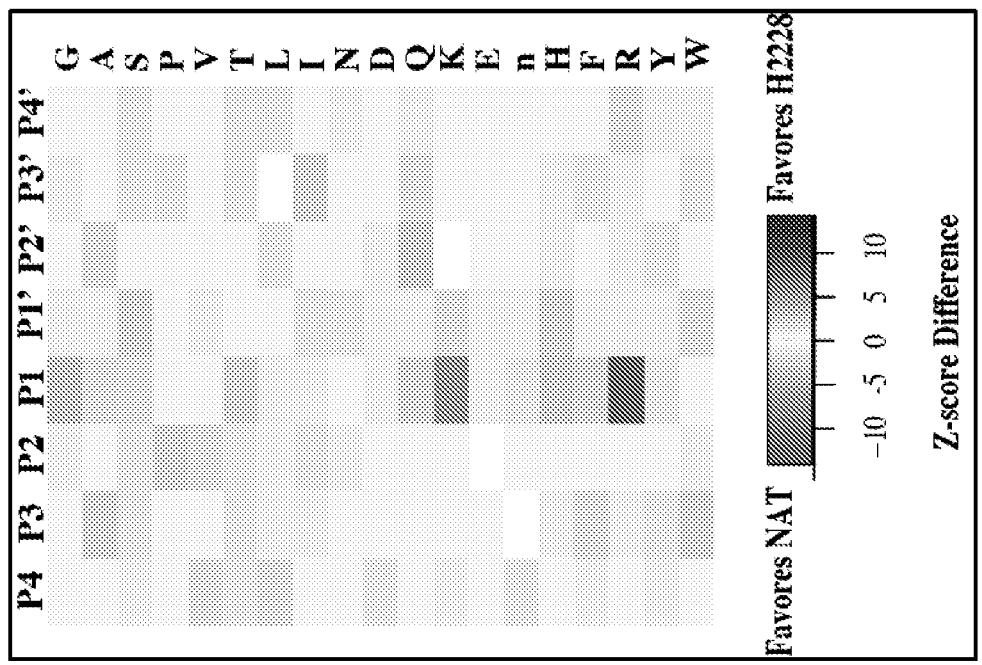
FIG. 31D

FIG. 32B
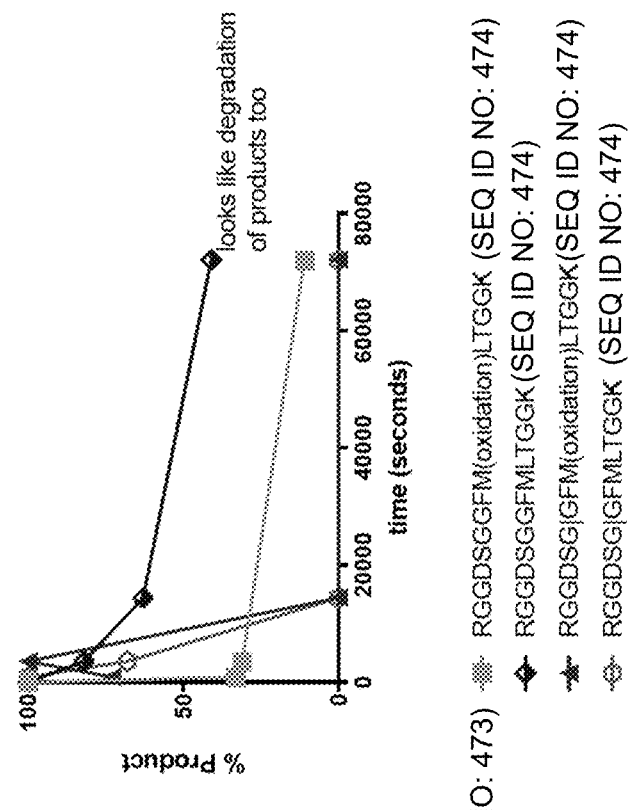
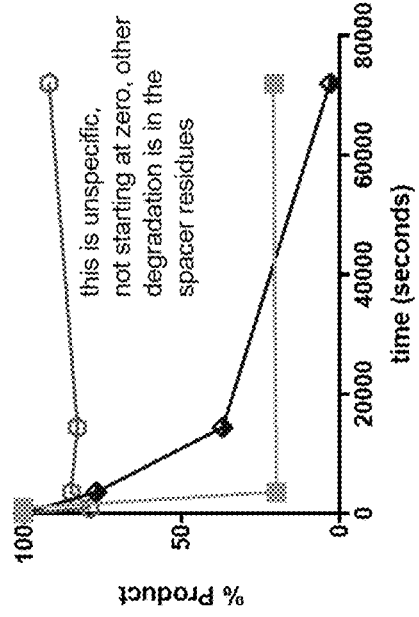

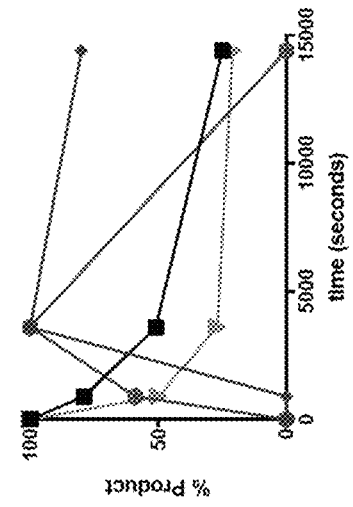
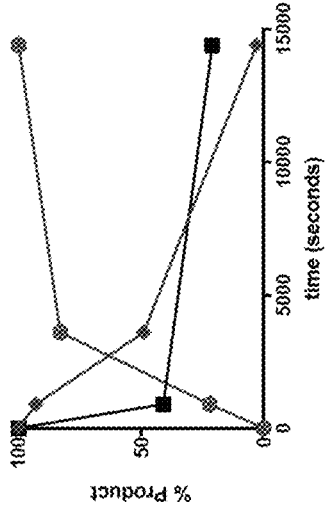
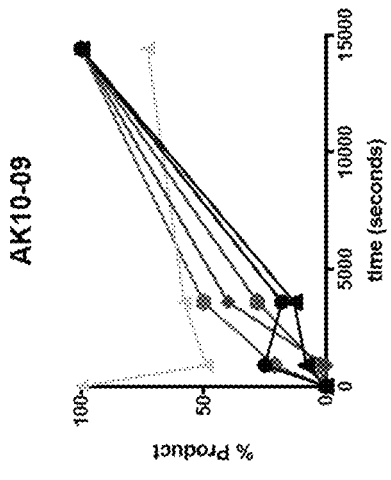
FIG. 36B

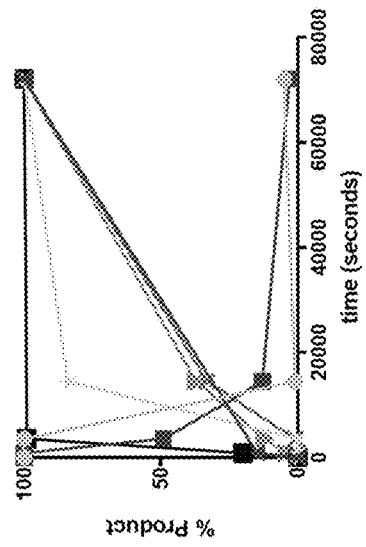
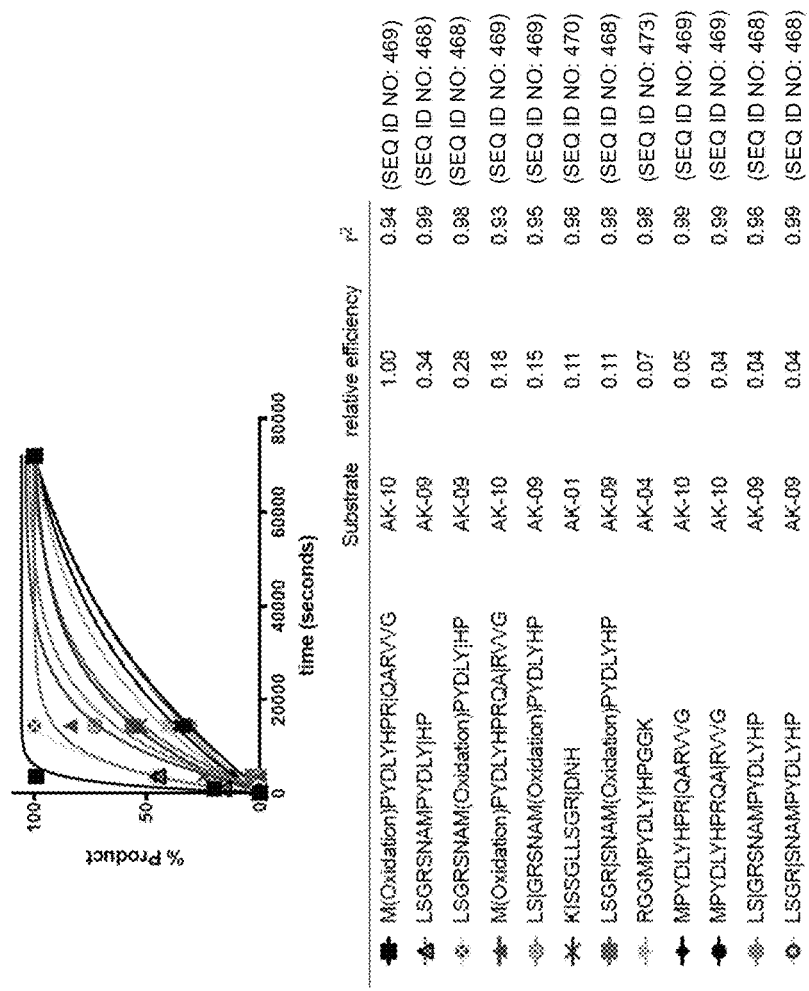
FIG. 37D
FIG. 37E

# ACTIVATABLE MASKED ANTI-CTLA4 BINDING PROTEINS

CROSS-REFERENCE TO RELATED APPLICATIONS

This application is a 35 U.S.C. § 371 National Stage Application of International Application No. PCT/US2019/068538, filed on Dec. 26, 2019, which claims priority from U.S. provision application 62/785,111, filed Dec. 26, 2018, the content of which is incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 737762001641.txt, date created: Dec. 27, 2019, size: 532,480 bytes.

FIELD OF THE INVENTION

This invention relates to activatable masked anti-cytotoxic T-lymphocyte-associated protein 4 (CTLA4) binding proteins (e.g., anti-CTLA4 antibodies) and methods related to use of the same.

BACKGROUND OF THE INVENTION

Cancer is the second leading cause of death in the United States, accounting for more deaths than the next five leading causes (chronic respiratory disease, stroke, accidents, Alzheimer's disease and diabetes). While great strides have been made especially with targeted therapies, there remains a great deal of work to do in this space. Immunotherapy and a branch of this field, immuno-oncology, is creating viable and exciting therapeutic options for treating malignancies. Specifically, it is now recognized that one hallmark of cancer is immune evasion and significant efforts have identified targets and developed therapies to these targets to reactivate the immune system to recognize and treat cancer. In fact, the anti-cytotoxic T-lymphocyte-associated protein 4 (CTLA4) antibody, ipilimumab, has led to long-term survival of patients suffering from stage III/IV malignant melanoma. Ipilimumab is an immune checkpoint antagonist that interrupts the inhibition of T cells by blocking CTLA4, and may lead to the depletion of T Regulatory cells (Treg). [Korman, A., et al., 2005. Tumor immunotherapy: preclinical and clinical activity of anti-CTLA4 antibodies. Current Opinion in Investigational Drugs 6:582-591; Quezada et al., J. Exp. Med., 206 (8): 1717-1725, 2009; Selby et al. Cancer Immunol Res., 1 (1): 32-42, 2013.] Unfortunately, ipilimumab causes generalized (not tumor-specific) activation of T-cell dependent immune responses that leads to immune-related adverse effects which can be life-threatening and are often dose and treatment duration-limiting (Weber, J. S., et al., 2008. Phase I/II study of ipilimumab for patients with metastatic melanoma. Journal of Clinical Oncology 26:5950-5956). These include enterocolitis, dermatitis, hypophysitis, uveitis, hepatitis, nephritis and death. Enterocolitis is the most common major toxicity (affecting approximately 20% of patients). The severe safety risks related to immune-mediated adverse reactions prompted the FDA to approve ipilimumab with a Risk Evaluation and Mitigation Strategy (REMS). Recently, coadministration of ipilimumab and a second immune checkpoint modulator targeting PD1 (e.g., nivolumab) has been shown to significantly increase efficacy of immunotherapy of melanoma when compared to ipilimumab alone. This gain, however, was associated with increased frequencies of grade 3/4 adverse effects, which affected more than 50% of patients receiving combination treatment (Wolchok, J. D., et al. 2013. Nivolumab plus Ipilimumab in Advanced Melanoma. N Engl J Med).

These findings illustrate the need for developing anti-CTLA4 protein therapeutics that effectively target tumors without the side effects associated with systemic immune activation. Provided herein are anti-CTLA binding proteins, compositions thereof and methods of use thereof for addressing this need.

All references cited herein, including patent applications, patent publications, and scientific literature, are herein incorporated by reference in their entirety, as if each individual reference were specifically and individually indicated to be incorporated by reference.

SUMMARY OF THE INVENTION

Provided herein are activatable masked anti-cytotoxic T-lymphocyte-associated protein 4 (CTLA4) binding proteins, compositions comprising thereof, and methods of using the same.

Provided herein is a masked antibody containing an antibody or antigen-binding fragment thereof that binds to CTLA4, wherein the antibody or antigen-binding fragment thereof containing a first chain and a second chain, and a masking peptide comprising an amino acid sequence selected from SEQ ID NOs: 1-46, wherein the masking peptide is linked via a linker comprising a cleavable peptide to an amino-terminus or carboxy-terminus of the first chain or the second chain of the antibody or antigen-binding fragment thereof. In some embodiments, the first chain is a light chain; and the second chain is a heavy chain.

In some embodiments, the antibody or antigen-binding fragment thereof containing two first chains and two second chains. In some embodiments, the first chain is or comprises a light chain variable domain; and the second chain is or comprises a heavy chain variable domain. In some of any such embodiments, the antigen-binding fragment is a dAb, Fab, Fab'-SH, Fv, scFv, or (Fab')$_2$ fragment. In some of any such embodiments, the amino-terminus or carboxy-terminus of the masking peptide is linked to the linker comprising a cleavable peptide. In some of any such embodiments the linker comprising a cleavable peptide containing a spacer linker and a cleavable peptide. In some of any such embodiments, the cleavable peptide containing an amino acid sequence selected from SEQ ID NOs: 47-88, 464-469, and 479-508. In some of any such embodiments, the spacer linker is directly linked to the N-terminus and/or the C-terminus of the cleavable peptide. In some of any such embodiments, the spacer linker containing an amino acid sequence is selected from SEQ ID NOs: 89-112 and 415-420. In some of any such embodiments, at least one amino acid but no more than 20 amino acids is directly linked to the N-terminus of the masking peptide. In some of any such embodiments, at least one amino acid is alanine (A) or glycine-alanine (GA).

In some of any such embodiments, the masked antibody containing in an N- to C-terminal or in a C- to N-terminal direction: a) a masking peptide: b) a cleavable peptide; and c) an antibody or antigen-binding fragment thereof that binds CTLA4. In some of any such embodiments, the masked antibody containing a spacer linker between the masking peptide and the cleavable peptide; and the masked antibody containing a spacer linker between the cleavable peptide and the antibody or antigen-binding fragment thereof that binds to CTLA4.

In some of any such embodiments, the antibody is a murine antibody. In some of any such embodiments, the antibody is a humanized antibody, a chimeric antibody, or a human antibody. In some of any such embodiments, the antibody has an IgG1, IgG2, IgG3 or IgG4 isotype. In some of any such embodiments, the IgG1 contain the amino acid substitutions, S298A, E333A, and K334A; S239D and I332E; S239D, A330L, and I332E; P247I and A339D or A339Q; D280H, K290S with or without S298D or S298V; F243L, R292P, and Y300L; F243L, R292P, Y300L, and P396L; F243L, R292P, Y300L, V305I, and P396L; G236A, S239D, and I332E; K326A and E333A; K326W and E333S; or K290E or K290N, S298G, T299A, and/or K326E; wherein the amino acid residues are numbered according to the EU index as in Kabat.

In some of any such embodiments, the antibody or antigen-binding fragment thereof containing a light chain variable region and a heavy chain variable region, wherein the light chain variable region containing (i) CDR-L1 comprising the amino acid sequence of SEQ ID NO:402 or 408, (ii) CDR-L2 comprising the amino acid sequence of SEQ ID NO: 403 or 409, and (iii) CDR-L3 comprising the amino acid sequence of SEQ ID NO:404 or 410; and/or wherein the heavy chain variable region containing (i) CDR-H1 comprising the amino acid sequence of SEQ ID NO:405 or 411, (ii) CDR-H2 comprising the amino acid sequence of SEQ ID NO:406 or 412, and (iii) CDR-H3 comprising the amino acid sequence of SEQ ID NO:407 or 413. In some of any such embodiments, the antibody or antigen-binding fragment containing a light chain variable region comprising the amino acid sequence of SEQ ID NO:232; and/or a heavy chain variable region comprising the amino acid sequence of SEQ ID NO:233.

In some of any such embodiments, the antibody or antigen-binding fragment comprises a light chain variable region and a heavy chain variable region, wherein the light chain variable region comprises (i) a CDR-L1 comprising the amino acid sequence of SEQ ID NO: 402, (ii) a CDR-L2 comprising the amino acid sequence of SEQ ID NO:403, and (iii) a CDR-L3 comprising the amino acid sequence of SEQ ID NO:404; and/or wherein the heavy chain variable region comprises (i) a CDR-H1 comprising the amino acid sequence of SEQ ID NO:405, (ii) a CDR-H2 comprising the amino acid sequence of SEQ ID NO:406, and (iii) a CDR-H3 comprising the amino acid sequence of SEQ ID NO:407. In some embodiments, the antibody or antigen-binding fragment comprises a light chain variable region and a heavy chain variable region, wherein the light chain variable region comprises (i) a CDR-L1 comprising the amino acid sequence of SEQ ID NO:402, (ii) a CDR-L2 comprising the amino acid sequence of SEQ ID NO:403, and (iii) a CDR-L3 comprising the amino acid sequence of SEQ ID NO:404; and the heavy chain variable region comprises (i) a CDR-H1 comprising the amino acid sequence of SEQ ID NO:405, (ii) a CDR-H2 comprising the amino acid sequence of SEQ ID NO:406, and (iii) a CDR-H3 comprising the amino acid sequence of SEQ ID NO:407.

In some of any such embodiments, the antibody or antigen-binding fragment comprises a light chain variable region and a heavy chain variable region, wherein the light chain variable region comprises (i) a CDR-L1 comprising the amino acid sequence of SEQ ID NO: 432, (ii) a CDR-L2 comprising the amino acid sequence of SEQ ID NO:433, and (iii) a CDR-L3 comprising the amino acid sequence of SEQ ID NO:444; and/or wherein the heavy chain variable region comprises (i) a CDR-H1 comprising the amino acid sequence of SEQ ID NO:435, (ii) a CDR-H2 comprising the amino acid sequence of SEQ ID NO:436, and (iii) a CDR-H3 comprising the amino acid sequence of SEQ ID NO:437. In some of any such embodiments, the antibody or antigen-binding fragment comprises a light chain variable region and a heavy chain variable region, wherein the light chain variable region comprises (i) a CDR-L1 comprising the amino acid sequence of SEQ ID NO:432, (ii) a CDR-L2 comprising the amino acid sequence of SEQ ID NO:433, and (iii) a CDR-L3 comprising the amino acid sequence of SEQ ID NO:434; and the heavy chain variable region comprises (i) a CDR-H1 comprising the amino acid sequence of SEQ ID NO:435, (ii) a CDR-H2 comprising the amino acid sequence of SEQ ID NO:436, and (iii) a CDR-H3 comprising the amino acid sequence of SEQ ID NO:437.

In some of any such embodiments, the antibody or antigen-binding fragment comprises a light chain variable region and a heavy chain variable region, wherein the light chain variable region comprises (i) a CDR-L1 comprising the amino acid sequence of SEQ ID NO: 408, (ii) a CDR-L2 comprising the amino acid sequence of SEQ ID NO:409, and (iii) a CDR-L3 comprising the amino acid sequence of SEQ ID NO:410; and/or wherein the heavy chain variable region comprises (i) a CDR-H1 comprising the amino acid sequence of SEQ ID NO:411, (ii) a CDR-H2 comprising the amino acid sequence of SEQ ID NO:412, and (iii) a CDR-H3 comprising the amino acid sequence of SEQ ID NO:413. In some of any such embodiments, the antibody or antigen-binding fragment comprises a light chain variable region and a heavy chain variable region, wherein the light chain variable region comprises (i) a CDR-L1 comprising the amino acid sequence of SEQ ID NO:408, (ii) a CDR-L2 comprising the amino acid sequence of SEQ ID NO:409, and (iii) a CDR-L3 comprising the amino acid sequence of SEQ ID NO:410; and the heavy chain variable region comprises (i) a CDR-H1 comprising the amino acid sequence of SEQ ID NO:411, (ii) a CDR-H2 comprising the amino acid sequence of SEQ ID NO:412, and (iii) a CDR-H3 comprising the amino acid sequence of SEQ ID NO:413.

In some of any such embodiments, the antibody or antigen-binding fragment comprises a light chain variable region and a heavy chain variable region, wherein the light chain variable region comprises (i) a CDR-L1 comprising the amino acid sequence of SEQ ID NO: 438, (ii) a CDR-L2 comprising the amino acid sequence of SEQ ID NO:439, and (iii) a CDR-L3 comprising the amino acid sequence of SEQ ID NO:440; and/or wherein the heavy chain variable region comprises (i) a CDR-H1 comprising the amino acid sequence of SEQ ID NO:441, (ii) a CDR-H2 comprising the amino acid sequence of SEQ ID NO:442, and (iii) a CDR-H3 comprising the amino acid sequence of SEQ ID NO:443. In some of any such embodiments, the antibody or antigen-binding fragment comprises a light chain variable region and a heavy chain variable region, wherein the light chain variable region comprises (i) a CDR-L1 comprising the amino acid sequence of SEQ ID NO:438, (ii) a CDR-L2 comprising the amino acid sequence of SEQ ID NO:439, and (iii) a CDR-L3 comprising the amino acid sequence of SEQ ID NO:440; and the heavy chain variable region comprises (i) a CDR-H1 comprising the amino acid sequence of SEQ ID NO:441, (ii) a CDR-H2 comprising the amino acid sequence of SEQ ID NO:442, and (iii) a CDR-H3 comprising the amino acid sequence of SEQ ID NO:443.

In some of any such embodiments, the antibody containing a light chain comprising the amino acid sequence selected from SEQ ID NOs: 237-318; and/or a heavy chain comprising the amino acid sequence selected from SEQ ID NOs: 319 or 320. In some of any such embodiments, the antibody or antigen-binding fragment containing a light chain variable region comprising the amino acid sequence selected from SEQ ID NOs: 321 or 322; and/or a heavy chain variable region comprising the amino acid sequence selected from SEQ ID NOs: 323 or 324. In some of any such embodiments, the antibody or antigen-binding fragment thereof comprises a light chain variable region comprising the amino acid sequence of SEQ ID NO: 321, and a heavy chain variable region comprising the amino acid sequence of SEQ ID NO: 323. In some of any such embodiments, the antibody or antigen-binding fragment thereof comprises a light chain variable region comprising the amino acid sequence of SEQ ID NO: 322, and a heavy chain variable region comprising the amino acid sequence of SEQ ID NO: 324.

In some of any such embodiments, the antibody containing a light chain comprising the amino acid sequence selected from SEQ ID NOs: 327-341; and/or a heavy chain comprising the amino acid sequence selected from SEQ ID NOs: 366-380, 421, and 478. In some of any such embodiments, the antibody containing a light chain comprising the amino acid sequence selected from SEQ ID NOs: 327, 334, or 342-365; and/or a heavy chain comprising the amino acid sequence selected from SEQ ID NOs: 366 or 380-397. In some of any such embodiments, the antibody or antigen binding fragment thereof comprises a light chain comprising the amino acid sequence of SEQ ID NO: 327, and a heavy chain comprising the amino acid sequence of SEQ ID NO: 366. In some of any such embodiments, the antibody or antigen binding fragment thereof comprises a light chain comprising the amino acid sequence of SEQ ID NO: 327, and a heavy chain comprising the amino acid sequence of SEQ ID NO: 478. In some of any such embodiments, the antibody or antigen binding fragment thereof comprises a light chain comprising the amino acid sequence of SEQ ID NO: 334, and a heavy chain comprising the amino acid sequence of SEQ ID NO: 380. In some of any such embodiments, the antibody or antigen binding fragment thereof comprises a light chain comprising the amino acid sequence of SEQ ID NO: 334, and a heavy chain comprising the amino acid sequence of SEQ ID NO: 421.

In some of any such embodiments, the cleavable peptide is a substrate for a protease that is co-localized in a region with a cell or a tissue expressing CTLA4. In some of any such embodiments, the cleavable peptide is cleaved by one or more enzyme selected from the group consisting of: ABHD12, ADAM12, ABHD12B, ABHD13, ABHD17A, ADAM19, ADAM20, ADAM21, ADAM28, ADAM30, ADAM33, ADAM8, ABHD17A, ADAMDEC1, ADAMTS1, ADAMTS10, ADAMTS12, ADAMTS13, ADAMTS14, ADAMTS15, ADAMTS16, ADAMTS17, ADAMTS18, ADAMTS19, ADAMTS2, ADAMTS20, ADAMTS3, ADAMTS4, ABHD17B, ADAMTS5, ADAMTS6, ADAMTS7, ADAMTS8, ADAMTS9, ADAMTSL1, ADAMTSL2, ADAMTSL3, ABHD17C, ADAMTSL5, ASTL, BMP1, CELA1, CELA2A, CELA2B, CELA3A, CELA3B, ADAM10, ADAM15, ADAM17, ADAM9, ADAMTS4, CTSE, CTSF, ADAMTSL4, CMA1, CTRB1, CTRC, CTSO, CTR1, CTSA, CTSW, CTSB, CTSC, CTSD, ESP1, CTSG, CTSH, GZMA, GZMB, GZMH, CTSK, GZMM, CTSL, CTSS, CTSV, CTSZ, HTRA4, KLK10, KLK11, KLK13, KLK14, KLK2, KLK4, DPP4, KLK6, KLK7, KLKB1, ECE1, ECE2, ECEL1, MASP2, MEP1A, MEP1B, ELANE, FAP, GZMA, MMP11, GZMK, HGFAC, HPN, HTRA1, MMP11, MMP16, MMP17, MMP19, HTRA2, MMP20, MMP21, HTRA3, HTRA4, KEL, MMP23B, MMP24, MMP25, MMP26, MMP27, MMP28, KLK5, MMP3, MMP7, MMP8, MMP9, LGMN, LNPEP, MASP1, PAPPA, PAPPA2, PCSK1, NAPSA, PCSK5, PCSK6, MME, MMP1, MMP10, PLAT, PLAU, PLG, PRSS1, PRSS12, PRSS2, PRSS21, PRSS3, PRSS33, PRSS4, PRSS55, PRSS57, MMP12, PRSS8, PRSS9, PRTN3, MMP13, MMP14, ST14, TMPRSS10, TMPRSS11A, TMPRSS11D, TMPRSS11E, TMPRSS11F, TMPRSS12, TMPRSS13, MMP15, TMPRSS15, MMP2, TMPRSS2, TMPRSS3, TMPRSS4, TMPRSS5, TMPRSS6, TMPRSS7, TMPRSS9, NRDC, OVCH1, PAMR1, PCSK3, PHEX, TINAG, TPSAB1, TPSD1, and TPSG1.

In some of any such embodiments, the cleavable peptide is cleaved by one or more enzyme selected from the group consisting of: ADAM17, HTRA1, PRSS1, FAP, GZMK, NAPSA, MMP1, MMP2, MMP9, MMP10, MMP7, MMP12, MMP28, ADAMTS9, HGFAC, and HTRA3. In some of any such embodiments, the antibody or antigen-binding fragment thereof is conjugated to an agent. In some of any such embodiments, the agent is an inhibitor of tubulin polymerization, a DNA damaging agent, or a DNA synthesis inhibitor. In some of any such embodiments, the agent is a maytansinoid, an auristatin, a pyrrolobenzodiazepine (PBD) dimer, a calicheamicin, a duocarmycin, a indo-linobenzodiazepine dimer or exatecan derivative Dxd.

In some of any such embodiments, the masked antibody provided herein exhibits an optimal occlusion ratio of about 20 to about 10,000. In a further embodiment, the optimal occlusion ratio is about 20 to about 1,000. In a further embodiment, the optimal occlusion ratio is about 80 to about 100.

In some of any such embodiments, the masked antibody comprises the amino acid sequence of SEQ ID NO: 421, and comprises an amino acid sequence that is selected from the group consisting of SEQ ID NOs: 358 and 422-431.

Also provide herein is a masked bispecific antibody containing a light chain and a heavy chain of a first pair that specifically binds to CTLA4, light chain and a heavy chain of a second pair that specifically binds to an antigen, and a masking peptide comprising an amino acid sequence selected from SEQ ID NOs: 1-46, wherein the masking peptide is linked via a linker comprising a cleavable peptide to an amino-terminus or carboxy-terminus of the light chain or the heavy chain of the first pair. In some embodiments, the amino-terminus or carboxy-terminus of the masking peptide is linked to the linker comprising a cleavable peptide. In some of any such embodiments, the linker comprising a cleavable peptide containing a spacer linker and a cleavable peptide.

In some of any such embodiments, the cleavable peptide containing an amino acid sequence selected from SEQ ID NOs: 47-88, 464-469, and 479-508. In some of any such embodiments, a spacer linker is directly linked to the N-terminus or the C-terminus of the cleavable peptide. In some of any such embodiments, the spacer linker containing an amino acid sequence is selected from SEQ ID NOs: 89-112 and 415-420. In some of any such embodiments, at least one amino acid but no more than 20 amino acids is directly linked to the N-terminus of the masking peptide. In some of any such embodiments, the at least one amino acid is alanine (A) or glycine-alanine (GA).

In some of any such embodiments, the light chain or heavy chain of the first pair containing in an N- to C-terminal or in a C- to N-terminal direction: a) a masking peptide: b) a cleavable peptide; and c) a light chain or heavy chain. In some of any such embodiments, the first pair containing a spacer linker between the masking peptide and the cleavable peptide; and the first pair containing a spacer linker between the cleavable peptide and the light chain or heavy chain.

In some of any such embodiments, the bispecific antibody is a murine antibody. In some of any such embodiments, the bispecific antibody is a humanized antibody, a chimeric antibody, or a human antibody. In some of any such embodiments, the bispecific antibody has an IgG1, IgG2, IgG3 or IgG4 isotype. In some of any such embodiments, the IgG1 contain the amino acid substitutions, such as S298A, E333A, and K334A: S239D and I332E; S239D, A330L, and I332E; P247I and A339D or A339Q; D280H, K290S with or without S298D or S298V: F243L, R292P, and Y300L; F243L, R292P, Y300L, and P396L; F243L, R292P, Y300L, V305I, and P396L; G236A, S239D, and I332E; K326A and E333A; K326W and E333S; or K290E or K290N, S298G, T299A, and/or K326E, wherein the amino acid residues are numbered according to the EU index as in Kabat.

In some of any such embodiments, the first pair containing a light chain variable region and a heavy chain variable region, wherein the light chain variable region containing (i) CDR-L1 comprising the amino acid sequence of SEQ ID NO:402 or 408, (ii) CDR-L2 comprising the amino acid sequence of SEQ ID NO:403 or 409, and (iii) CDR-L3 comprising the amino acid sequence of SEQ ID NO:404 or 410; and/or wherein the heavy chain variable region containing (i) CDR-H1 comprising the amino acid sequence of SEQ ID NO:405 or 411, (ii) CDR-H2 comprising the amino acid sequence of SEQ ID NO:406 or 412, and (iii) CDR-H3 comprising the amino acid sequence of SEQ ID NO:407 or 413.

In some of any such embodiments, the first pair comprises a light chain variable region and a heavy chain variable region, wherein the light chain variable region comprises (i) a CDR-L1 comprising the amino acid sequence of SEQ ID NO:402, (ii) a CDR-L2 comprising the amino acid sequence of SEQ ID NO:403, and (iii) a CDR-L3 comprising the amino acid sequence of SEQ ID NO:404; and/or wherein the heavy chain variable region comprises (i) a CDR-H1 comprising the amino acid sequence of SEQ ID NO:405, (ii) a CDR-H2 comprising the amino acid sequence of SEQ ID NO:406, and (iii) a CDR-H3 comprising the amino acid sequence of SEQ ID NO:407. In some embodiments, the first pair comprises a light chain variable region and a heavy chain variable region, wherein the light chain variable region comprises (i) a CDR-L1 comprising the amino acid sequence of SEQ ID NO: 402, (ii) a CDR-L2 comprising the amino acid sequence of SEQ ID NO:403, and (iii) a CDR-L3 comprising the amino acid sequence of SEQ ID NO:404; and the heavy chain variable region comprises (i) a CDR-H1 comprising the amino acid sequence of SEQ ID NO: 405, (ii) a CDR-H2 comprising the amino acid sequence of SEQ ID NO:406, and (iii) a CDR-H3 comprising the amino acid sequence of SEQ ID NO:407.

In some of any such embodiments, the first pair comprises a light chain variable region and a heavy chain variable region, wherein the light chain variable region comprises (i) a CDR-L1 comprising the amino acid sequence of SEQ ID NO:432, (ii) a CDR-L2 comprising the amino acid sequence of SEQ ID NO:433, and (iii) a CDR-L3 comprising the amino acid sequence of SEQ ID NO:444; and/or wherein the heavy chain variable region comprises (i) a CDR-H1 comprising the amino acid sequence of SEQ ID NO:435, (ii) a CDR-H2 comprising the amino acid sequence of SEQ ID NO:436, and (iii) a CDR-H3 comprising the amino acid sequence of SEQ ID NO:437. In some of any such embodiments, the first pair comprises a light chain variable region and a heavy chain variable region, wherein the light chain variable region comprises (i) a CDR-L1 comprising the amino acid sequence of SEQ ID NO:432, (ii) a CDR-L2 comprising the amino acid sequence of SEQ ID NO: 433, and (iii) a CDR-L3 comprising the amino acid sequence of SEQ ID NO:434; and the heavy chain variable region comprises (i) a CDR-H1 comprising the amino acid sequence of SEQ ID NO:435, (ii) a CDR-H2 comprising the amino acid sequence of SEQ ID NO:436, and (iii) a CDR-H3 comprising the amino acid sequence of SEQ ID NO:437.

In some of any such embodiments, the first pair comprises a light chain variable region and a heavy chain variable region, wherein the light chain variable region comprises (i) a CDR-L1 comprising the amino acid sequence of SEQ ID NO:408, (ii) a CDR-L2 comprising the amino acid sequence of SEQ ID NO:409, and (iii) a CDR-L3 comprising the amino acid sequence of SEQ ID NO:410; and/or wherein the heavy chain variable region comprises (i) a CDR-H1 comprising the amino acid sequence of SEQ ID NO:411, (ii) a CDR-H2 comprising the amino acid sequence of SEQ ID NO:412, and (iii) a CDR-H3 comprising the amino acid sequence of SEQ ID NO:413. In some of any such embodiments, the first pair comprises a light chain variable region and a heavy chain variable region, wherein the light chain variable region comprises (i) a CDR-L1 comprising the amino acid sequence of SEQ ID NO:408, (ii) a CDR-L2 comprising the amino acid sequence of SEQ ID NO: 409, and (iii) a CDR-L3 comprising the amino acid sequence of SEQ ID NO:410; and the heavy chain variable region comprises (i) a CDR-H1 comprising the amino acid sequence of SEQ ID NO:411, (ii) a CDR-H2 comprising the amino acid sequence of SEQ ID NO:412, and (iii) a CDR-H3 comprising the amino acid sequence of SEQ ID NO:413.

In some of any such embodiments, the first pair comprises a light chain variable region and a heavy chain variable region, wherein the light chain variable region comprises (i) a CDR-L1 comprising the amino acid sequence of SEQ ID NO:438, (ii) a CDR-L2 comprising the amino acid sequence of SEQ ID NO:439, and (iii) a CDR-L3 comprising the amino acid sequence of SEQ ID NO:440; and/or wherein the heavy chain variable region comprises (i) a CDR-H1 comprising the amino acid sequence of SEQ ID NO:441, (ii) a CDR-H2 comprising the amino acid sequence of SEQ ID NO:442, and (iii) a CDR-H3 comprising the amino acid sequence of SEQ ID NO:443. In some of any such embodiments, the first pair comprises a light chain variable region and a heavy chain variable region, wherein the light chain variable region comprises (i) a CDR-L1 comprising the amino acid sequence of SEQ ID NO:438, (ii) a CDR-L2 comprising the amino acid sequence of SEQ ID NO: 439, and (iii) a CDR-L3 comprising the amino acid sequence of SEQ ID NO:440; and the heavy chain variable region comprises (i) a CDR-H1 comprising the amino acid sequence of SEQ ID NO:441, (ii) a CDR-H2 comprising the amino acid sequence of SEQ ID NO:442, and (iii) a CDR-H3 comprising the amino acid sequence of SEQ ID NO:443.

In some of any such embodiments, the first pair containing a light chain variable region comprising the amino acid sequence of SEQ ID NO:232; and/or a heavy chain variable region comprising the amino acid sequence of SEQ ID NO:233. In some of any such embodiments, the first pair containing a light chain comprising the amino acid sequence selected from SEQ ID NOs: 237-318; and/or a heavy chain comprising the amino acid sequence selected from SEQ ID NOs: 319 or 320. In some of any such embodiments, the first pair containing a light chain variable region comprising the amino acid sequence selected from SEQ ID NOs: 321 or 322; and/or a heavy chain variable region comprising the amino acid sequence selected from SEQ ID NOs: 323 or 324. In some of any such embodiments, the first pair comprises a light chain variable region comprising the amino acid sequence of SEQ ID NO: 321, and a heavy chain variable region comprising the amino acid sequence of SEQ ID NO: 323. In some of any such embodiments, the first pair comprises a light chain variable region comprising the amino acid sequence of SEQ ID NO: 322, and a heavy chain variable region comprising the amino acid sequence of SEQ ID NO: 324.

In some of any such embodiments, the first pair containing a light chain comprising the amino acid sequence selected from SEQ ID NOs: 327-341; and/or a heavy chain comprising the amino acid sequence selected from SEQ ID NOs: 366-380, 421, and 478. In some of any such embodiments, the first pair containing a light chain comprising the amino acid sequence selected from SEQ ID NOs: 327, 334, or 342-365; and/or a heavy chain comprising the amino acid sequence selected from SEQ ID NOs: 366 or 380-397. In some of any such embodiments, the first pair comprises a light chain comprising the amino acid sequence of SEQ ID NO: 327, and a heavy chain comprising the amino acid sequence of SEQ ID NO: 366. In some of any such embodiments, first pair comprises a light chain comprising the amino acid sequence of SEQ ID NO: 327, and a heavy chain comprising the amino acid sequence of SEQ ID NO: 478. In some of any such embodiments, the first pair comprises a light chain comprising the amino acid sequence of SEQ ID NO: 334, and a heavy chain comprising the amino acid sequence of SEQ ID NO: 380. In some of any such embodiments, the first pair comprises a light chain comprising the amino acid sequence of SEQ ID NO: 334, and a heavy chain comprising the amino acid sequence of SEQ ID NO: 421.

In some of any such embodiments, the cleavable peptide is a substrate for a protease that is co-localized in a region with a cell or a tissue expressing CTLA4. In some of any such embodiments, the cleavable peptide is cleaved by one or more enzyme selected from the group consisting of: ABHD12, ADAM12, ABHD12B, ABHD13, ABHD17A, ADAM19, ADAM20, ADAM21, ADAM28, ADAM30, ADAM33, ADAM8, ABHD17A, ADAMDEC1, ADAMTS1, ADAMTS10, ADAMTS12, ADAMTS13, ADAMTS14, ADAMTS15, ADAMTS16, ADAMTS17, ADAMTS18, ADAMTS19, ADAMTS2, ADAMTS20, ADAMTS3, ADAMTS4, ABHD17B, ADAMTS5, ADAMTS6, ADAMTS7, ADAMTS8, ADAMTS9, ADAMTSL1, ADAMTSL2, ADAMTSL3, ABHD17C, ADAMTSL5, ASTL, BMP1, CELA1, CELA2A, CELA2B, CELA3A, CELA3B, ADAM10, ADAM15, ADAM17, ADAM9, ADAMTS4, CTSE, CTSF, ADAMTSL4, CMA1, CTRB1, CTRC, CTSO, CTR1, CTSA, CTSW, CTSB, CTSC, CTSD, ESP1, CTSG, CTSH, GZMA, GZMB, GZMH, CTSK, GZMM, CTSL, CTSS, CTSV, CTSZ, HTRA4, KLK10, KLK11, KLK13, KLK14, KLK2, KLK4, DPP4, KLK6, KLK7, KLKB1, ECE1, ECE2, ECEL1, MASP2, MEP1A, MEP1B, ELANE, FAP, GZMA, MMP11, GZMK, HGFAC, HPN, HTRA1, MMP11, MMP16, MMP17, MMP19, HTRA2, MMP20, MMP21, HTRA3, HTRA4, KEL, MMP23B, MMP24, MMP25, MMP26, MMP27, MMP28, KLK5, MMP3, MMP7, MMP8, MMP9, LGMN, LNPEP, MASP1, PAPPA, PAPPA2, PCSK1, NAPSA, PCSK5, PCSK6, MME, MMP1, MMP10, PLAT, PLAU, PLG, PRSS1, PRSS12, PRSS2, PRSS21, PRSS3, PRSS33, PRSS4, PRSS55, PRSS57, MMP12, PRSS8, PRSS9, PRTN3, MMP13, MMP14, ST14, TMPRSS10, TMPRSS11A, TMPRSS11D, TMPRSS11E, TMPRSS11F, TMPRSS12, TMPRSS13, MMP15, TMPRSS15, MMP2, TMPRSS2, TMPRSS3, TMPRSS4, TMPRSS5, TMPRSS6, TMPRSS7, TMPRSS9, NRDC, OVCH1, PAMR1, PCSK3, PHEX, TINAG, TPSAB1, TPSD1, and TPSG1. In some of any such embodiments, the cleavable peptide is cleaved by one or more enzyme selected from the group consisting of: ADAM17, HTRA1, PRSS1, FAP, GZMK, NAPSA, MMP1, MMP2, MMP9, MMP10, MMP7, MMP12, MMP28, ADAMTS9, HGFAC, and HTRA3. In some of any such embodiments, the bispecific antibody is conjugated to an agent. In some of any such embodiments, the agent is an inhibitor of tubulin polymerization, a DNA damaging agent, or a DNA synthesis inhibitor. In some of any such embodiments, the agent is a maytansinoid, an auristatin, a pyrrolobenzodiazepine (PBD) dimer, a calicheamicin, a duocarmycin, a indo-linobenzodiazepine dimer or exatecan derivative Dxd.

In some of any such embodiments, the first pair and the second pair of the masked bispecific antibody provided herein each exhibit an optimal occlusion ratio which may be the same or different from each other. In some embodiments, the optimal occlusion ratio is about 20 to about 10,000. In a further embodiment, the optimal occlusion ratio is about 20 to about 1,000. In a further embodiment, the optimal occlusion ratio is about 80 to about 100.

Also provided herein is a masked chimeric receptor, contain, a ligand-binding domain comprising a first chain and a second chain that binds to CTLA4: a masking peptide comprising an amino acid sequence selected from SEQ ID NOs: 1-46, a transmembrane domain; and an intracellular signaling domain comprising a signaling domain, wherein the masking peptide is linked via a linker comprising a cleavable peptide to an amino-terminus or carboxy-terminus of the first chain or the second chain of the ligand-binding domain.

In some embodiments, the first chain is a light chain variable domain; and the second chain is a heavy chain variable domain. In some embodiments, the amino-terminus or carboxy-terminus of the masking peptide is linked to the linker comprising a cleavable peptide. In some of any such embodiments, the linker comprising a cleavable peptide containing a spacer linker and a cleavable peptide. In some of any such embodiments, the cleavable peptide containing an amino acid sequence selected from SEQ ID NOs: 47-88, 464-469, and 479-508. In some of any such embodiments, a spacer linker is directly linked to the N-terminus or the C-terminus of the cleavable peptide. In some of any such embodiments, the spacer linker containing an amino acid sequence is selected from SEQ ID NOs: 89-112 and 415-420. In some of any such embodiments, at least one amino acid but no more than 20 amino acids is directly linked to the N-terminus of the masking peptide. In some of any such embodiments, the at least one amino acid is alanine (A) or glycine-alanine (GA). In some of any such embodiments, the first chain or the second chain of the ligand binding domain containing in an N- to C-terminal or in a C- to N-terminal direction: a) a masking peptide: b) a cleavable peptide; and c) the first chain or the second chain. In some of any such embodiments, the ligand-binding domain containing a spacer linker between the masking peptide and the cleavable peptide; and the ligand-binding domain containing a spacer linker between the cleavable peptide and the first chain or second chain.

In some of any such embodiments, the ligand-binding domain containing a first chain and a second chain, wherein the first chain containing (i) CDR-L1 comprising the amino acid sequence of SEQ ID NO:402 or 408, (ii) CDR-L2 comprising the amino acid sequence of SEQ ID NO:403 or 409, and (iii) CDR-L3 comprising the amino acid sequence of SEQ ID NO:404 or 410; and/or wherein the second chain containing (i) CDR-H1 comprising the amino acid sequence of SEQ ID NO:405 or 411, (ii) CDR-H2 comprising the amino acid sequence of SEQ ID NO:406 or 412, and (iii) CDR-H3 comprising the amino acid sequence of SEQ ID NO:407 or 413.

In some of any such embodiments, the first chain comprises (i) a CDR-L1 comprising the amino acid sequence of SEQ ID NO:402, (ii) a CDR-L2 comprising the amino acid sequence of SEQ ID NO:403, and (iii) a CDR-L3 comprising the amino acid sequence of SEQ ID NO:404; and/or the second chain comprises (i) a CDR-H1 comprising the amino acid sequence of SEQ ID NO:405, (ii) a CDR-H2 comprising the amino acid sequence of SEQ ID NO:406, and (iii) a CDR-H3 comprising the amino acid sequence of SEQ ID NO:407. In some embodiments, the first chain comprises (i) a CDR-L1 comprising the amino acid sequence of SEQ ID NO:402, (ii) a CDR-L2 comprising the amino acid sequence of SEQ ID NO:403, and (iii) a CDR-L3 comprising the amino acid sequence of SEQ ID NO:404; and the second chain comprises (i) a CDR-H1 comprising the amino acid sequence of SEQ ID NO:405, (ii) a CDR-H2 comprising the amino acid sequence of SEQ ID NO: 406, and (iii) a CDR-H3 comprising the amino acid sequence of SEQ ID NO:407.

In some of any such embodiments, the first chain comprises (i) a CDR-L1 comprising the amino acid sequence of SEQ ID NO:432, (ii) a CDR-L2 comprising the amino acid sequence of SEQ ID NO:433, and (iii) a CDR-L3 comprising the amino acid sequence of SEQ ID NO:444; and/or the second chain comprises (i) a CDR-H1 comprising the amino acid sequence of SEQ ID NO:435, (ii) a CDR-H2 comprising the amino acid sequence of SEQ ID NO:436, and (iii) a CDR-H3 comprising the amino acid sequence of SEQ ID NO:437. In some of any such embodiments, the first chain comprises (i) a CDR-L1 comprising the amino acid sequence of SEQ ID NO:432, (ii) a CDR-L2 comprising the amino acid sequence of SEQ ID NO:433, and (iii) a CDR-L3 comprising the amino acid sequence of SEQ ID NO:434; and the second chain comprises (i) a CDR-H1 comprising the amino acid sequence of SEQ ID NO:435, (ii) a CDR-H2 comprising the amino acid sequence of SEQ ID NO:436, and (iii) a CDR-H3 comprising the amino acid sequence of SEQ ID NO: 437.

In some of any such embodiments, the first chain comprises (i) a CDR-L1 comprising the amino acid sequence of SEQ ID NO:408, (ii) a CDR-L2 comprising the amino acid sequence of SEQ ID NO:409, and (iii) a CDR-L3 comprising the amino acid sequence of SEQ ID NO:410; and/or the second chain comprises (i) a CDR-H1 comprising the amino acid sequence of SEQ ID NO:411, (ii) a CDR-H2 comprising the amino acid sequence of SEQ ID NO:412, and (iii) a CDR-H3 comprising the amino acid sequence of SEQ ID NO:413. In some of any such embodiments, the first chain comprises (i) a CDR-L1 comprising the amino acid sequence of SEQ ID NO:408, (ii) a CDR-L2 comprising the amino acid sequence of SEQ ID NO:409, and (iii) a CDR-L3 comprising the amino acid sequence of SEQ ID NO:410; and the second chain comprises (i) a CDR-H1 comprising the amino acid sequence of SEQ ID NO:411, (ii) a CDR-H2 comprising the amino acid sequence of SEQ ID NO:412, and (iii) a CDR-H3 comprising the amino acid sequence of SEQ ID NO: 413.

In some of any such embodiments, the first chain comprises (i) a CDR-L1 comprising the amino acid sequence of SEQ ID NO:438, (ii) a CDR-L2 comprising the amino acid sequence of SEQ ID NO:439, and (iii) a CDR-L3 comprising the amino acid sequence of SEQ ID NO:440; and/or the second chain comprises (i) a CDR-H1 comprising the amino acid sequence of SEQ ID NO:441, (ii) a CDR-H2 comprising the amino acid sequence of SEQ ID NO:442, and (iii) a CDR-H3 comprising the amino acid sequence of SEQ ID NO:443. In some of any such embodiments, the first chain comprises (i) a CDR-L1 comprising the amino acid sequence of SEQ ID NO:438, (ii) a CDR-L2 comprising the amino acid sequence of SEQ ID NO:439, and (iii) a CDR-L3 comprising the amino acid sequence of SEQ ID NO:440; and the second chain comprises (i) a CDR-H1 comprising the amino acid sequence of SEQ ID NO:441, (ii) a CDR-H2 comprising the amino acid sequence of SEQ ID NO:442, and (iii) a CDR-H3 comprising the amino acid sequence of SEQ ID NO: 443.

In some of any such embodiments, the first chain containing the amino acid sequence of SEQ ID NO:232; and/or the second chain containing the amino acid sequence of SEQ ID NO:233. In some of any such embodiments, the first chain containing the amino acid sequence selected from SEQ ID NOs: 321 or 322; and/or the second chain containing the amino acid sequence selected from SEQ ID NOs: 323 or 324. In some of any such embodiments, the first chain comprises the amino acid sequence of SEQ ID NO: 321, and the second chain comprises the amino acid sequence of SEQ ID NO: 323. In some of any such embodiments, the first chain comprises the amino acid sequence of SEQ ID NO: 322, and the second chain comprises the amino acid sequence of SEQ ID NO: 324. In some of any such embodiments, the cleavable peptide is a substrate for a protease that is co-localized in a region with a cell or a tissue expressing CTLA4.

In some of any such embodiments, the cleavable peptide is cleaved by one or more enzyme selected from the group consisting of: ABHD12, ADAM12. ABHD12B, ABHD13, ABHD17A, ADAM19, ADAM20), ADAM21, ADAM28, ADAM30, ADAM33. ADAM8, ABHD17A, ADAMDEC1, ADAMTS1, ADAMTS10, ADAMTS12, ADAMTS13, ADAMTS14, ADAMTS15, ADAMTS16, ADAMTS17, ADAMTS18, ADAMTS19, ADAMTS2, ADAMTS20, ADAMTS3, ADAMTS4, ABHD17B, ADAMTS5, ADAMTS6, ADAMTS7, ADAMTS8, ADAMTS9, ADAMTSL1, ADAMTSL2. ADAMTSL3, ABHD17C, ADAMTSL5, ASTL, BMP1, CELA1, CELA2A, CELA2B, CELA3A, CELA3B, ADAM10, ADAM15, ADAM17, ADAM9, ADAMTS4, CTSE, CTSF, ADAMTSL4, CMA1, CTRB1, CTRC, CTSO, CTR1, CTSA, CTSW, CTSB, CTSC, CTSD, ESP1, CTSG, CTSH, GZMA, GZMB, GZMH, CTSK, GZMM, CTSL, CTSS, CTSV, CTSZ, HTRA4, KLK10, KLK11, KLK13, KLK14, KLK2, KLK4, DPP4, KLK6, KLK7, KLKB1, ECE1, ECE2, ECEL1, MASP2, MEP1A, MEP1B, ELANE, FAP, GZMA, MMP11, GZMK, HGFAC, HPN, HTRA1, MMP11, MMP16, MMP17, MMP19, HTRA2, MMP20, MMP21, HTRA3, HTRA4, KEL, MMP23B, MMP24, MMP25, MMP26, MMP27, MMP28, KLK5, MMP3, MMP7, MMP8, MMP9, LGMN, LNPEP, MASP1, PAPPA, PAPPA2, PCSK1, NAPSA, PCSK5, PCSK6, MME, MMP1, MMP10, PLAT, PLAU, PLG, PRSS1, PRSS12, PRSS2, PRSS21, PRSS3, PRSS33, PRSS4, PRSS55, PRSS57, MMP12, PRSS8, PRSS9, PRTN3, MMP13, MMP14, ST14, TMPRSS10, TMPRSS11A, TMPRSS11D, TMPRSS11E, TMPRSS11F, TMPRSS12, TMPRSS13, MMP15, TMPRSS15, MMP2, TMPRSS2, TMPRSS3, TMPRSS4, TMPRSS5, TMPRSS6, TMPRSS7, TMPRSS9, NRDC, OVCH1, PAMR1, PCSK3, PHEX, TINAG, TPSAB1, TPSD1, and TPSG1. In some of any such embodiments, the cleavable peptide is cleaved by one or more enzyme selected from the group consisting of: ADAM17, HTRA1, PRSS1, FAP, GZMK, NAPSA, MMP1, MMP2, MMP9, MMP10, MMP7, MMP12, MMP28, ADAMTS9, HGFAC, and HTRA3.

In some of any such embodiments, the masked chimeric receptor provided herein exhibits an optimal occlusion ratio of about 20 to about 10,000. In a further embodiment, the optimal occlusion ratio is about 20 to about 1,000. In a further embodiment, the optimal occlusion ratio is about 80 to about 100.

Also provided is a nucleic acid encoding the masked antibodies, the masked bispecific antibodies, or the masked chimeric receptor of any one the aforementioned embodiments. Also provided is a vector comprising the nucleic acid of the aforementioned embodiments. In some embodiments, the vector is an expression vector. Also provided is a host cell comprising the aforementioned nucleic acid embodiments.

Also provided is a method of producing a masked antibody, a masked bispecific antibody or a masked chimeric receptor comprising culturing the aforementioned host cells under a condition that produces the masked antibody, masked bispecific antibody or masked chimeric receptor. In some embodiments, the host cell has a alpha1,6-fucosyltransferase (Fut8) knockout. In some embodiments, wherein the host cell overexpresses β1,4-N-acetylglycosminyltransferase III (GnT-III). In some embodiments, the host cell additionally overexpresses Golgi μ-mannosidase II (ManII). Some of any such embodiments, further include recovering the masked antibody, masked bispecific antibody or masked chimeric receptor produced by the host cell. In some embodiments, masked bispecific antibody or masked chimeric receptor produced by the aforementioned methods.

Also provided is a composition containing a masked antibody, a masked bispecific antibody, or a masked chimeric receptor of any one of aforementioned embodiments. Some embodiments encompass a composition comprising the masked antibody, masked bispecific antibody or masked chimeric receptor of the aforementioned embodiments. In some embodiments, the composition is a pharmaceutical composition.

Also provided is a kit containing the masked antibody, the masked bispecific antibody, the masked chimeric receptor, or the composition of any one of aforementioned embodiments.

Also provided is a method of treating or preventing a neoplastic disease in a subject, the method comprising administering to the subject an effective amount of the masked antibody, the masked bispecific antibody, the masked chimeric receptor, or the composition of any one of aforementioned embodiments. In one embodiment, the neoplastic disease is a cancer. In some embodiments, the cancer is leukemia, lymphoma, head and neck cancer, colorectal cancer, prostate cancer, pancreatic cancer, melanoma, breast cancer, neuroblastoma, lung cancer, ovarian cancer, osteosarcoma, bladder cancer, cervical cancer, liver cancer, kidney cancer, skin cancer or testicular cancer.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 2A) Activatable masked anti-CTLA4 antibody exhibited 90-fold lower binding to murine CTLA4-Fc (Masked 9D9, filled squares) compared to parental anti-CTLA4 antibody (9D9, filled circles). Protease activation of the activatable masked anti-CTLA4 antibody fully restored binding to murine CTLA4-Fc (Protease activated, asterisk) at levels comparable to parental anti-CTLA4 antibody. X-axis indicates amount of antibody tested. FIG. 2B) Activatable masked anti-CTLA4 antibody (Masked 9D9, filled inverted triangles) and non-cleavable masked anti-CTLA4 antibody (NC masked 9D9, empty squares) demonstrated approximately 156- and approximately 218-fold lower binding to murine CTLA4 as compared to parental anti-CTLA4 antibody (9D9, filled circles), respectively. X-axis indicates amount of antibody tested. FIG. 2C) EC50 was determined by ELISA for activatable masked anti-CTLA4 antibody (Masked 9D9), non-cleavable masked anti-CTLA4 antibody (NC masked 9D9), and parental anti-CTLA4 antibody (9D9) in the absence or presence of recombinant MMP2. Each group was performed at least three times and mean EC50+/− SE are reported.

FIGS. 7A and 7B is a series of graphs showing A) depletion of regulatory T lymphocytes (Tregs) in tumor and B) Treg proliferation in spleen in mice (n=6) treated with isotype control antibody (IgG2a control), parental anti-CTLA4 antibody (9D9), activatable masked anti-CTLA4 antibody (Masked 9D9), and non-cleavable masked anti-CTLA4 antibody (NC masked 9D9).

FIG. 9A shows the binding of forms of Antibody 1 (Antibody 1-1 and Antibody 1-2) to human CTLA4-Fc across a range of antibody concentrations, which demonstrated similar binding among the antibodies shown. FIG. 9B shows the binding of forms of Antibody 2 (Antibody 2-1, Antibody 2-2, Antibody 2-3, Antibody 2-4, and Antibody 2-5) to human CTLA4-Fc across a range of antibody concentrations, which demonstrates similar binding among the antibodies shown.

FIG. 10A shows binding by masked antibodies in the absence of activation by protease. FIG. 10B shows binding by masked antibodies following activation by protease. Antibody 2-6 is an unmasked parental antibody of Antibody 2-7, Antibody 2-8, Antibody 2-9, Antibody 2-10, Antibody 2-11, Antibody 2-12, and Antibody 2-13. FIGS. 10A and 10B show that following activation by protease, the masked antibodies demonstrate similar binding characteristics to the unmasked parental antibody, Antibody 2-6.

FIGS. 11A-11H show radar plots for masked forms of Antibody 2 that contain various cleavable peptide sequences. Antibody 2-15 includes a cleavable peptide sequence that is not cleavable. The activation of each antibody shown in FIGS. 11A-11H by each protease shown on the radar plot is depicted using a radar plot, where activation is depicted ranging from 0 (no activation) to 1.0 (full activation). FIGS. 11I-11M depict results from am SDSP-PAGE Western blot analysis of protease cleavage with select antibodies in the plasma of healthy mice (FIGS. 11I and 11J), and in the plasma of MC38 tumor-bearing mice (FIGS. 11K-11M).

FIG. 12A includes as controls an isotype control, which is not activatable, and a masked antibody (Antibody 2-15) that is not activatable because its cleavable peptide sequence is non-cleavable. FIG. 12B includes as controls an isotype control and a masked antibody (Antibody 2-10) that is not activatable because its cleavable peptide sequence is non-cleavable. Activation of Antibody 2-14 fully restored its binding to human CTLA4-Fc at a level similar to the unmasked parental antibody, Antibody 2-6 (FIG. 12A).

FIGS. 14A and 14B depict the impact of the antibodies on IL-2 levels (FIG. 14A) and the fold change in IL-2 levels (FIG. 14B) in a non-activated state (i.e., without exposure to protease). The unmasked parental antibody, Antibody 2-6, demonstrated the ability to significantly increase IL-2 levels, with only one of the masked antibodies (Antibody 2-12) showing a significant increase in IL-2 levels, although at a much lower level than Antibody 2-6 (FIGS. 14A and 14B). FIGS. 14C and 14D depict the impact of the antibodies on IL-2 levels (FIG. 14C) and the fold change in IL-2 levels (FIG. 14D) in an activated state (i.e., following exposure to protease). FIGS. 14C and 14D show that exposure to proteases rescues the ability of Antibody 2-7, Antibody 2-8, and Antibody 2-9 to promote IL-2 production at levels similar to the unmasked parental antibody, Antibody 2-6.

FIG. 15B shows a lack of activation of Antibody 2-19. The increase in the percentage of activation from Day 2 to Day 7 is shown in FIG. 15D for Antibody 2-14 and Antibody 2-20.

FIG. 16B shows a lack of activation of Antibody 2-19. The increase in the percentage of activation from Day 2 to Day 7 is shown in FIG. 16D for Antibody 2-14 and Antibody 2-20. The activation percentage of Antibody 2-14 was significantly greater in the MC38 tumor-bearing mice as compared to the health non-tumor-bearing mice, as determined by 2-way ANOVA (adjusted P value=0.0113) (FIG. 16D).

FIG. 17 depicts the extent of reporter activation by an unmasked parental antibody (Antibody 2-6) and by masked versions of Antibody 2-6 (Antibody 2-14 and Antibody 2-15). Antibody 2-15 includes a cleavable peptide sequence that is non-cleavable, for use as a negative control. Also tested was an isotype control. Antibodies having prior exposure to protease are depicted as "activated." The masked antibodies, Antibody 2-14 and Antibody 2-15, demonstrated reduced reporter activation as compared to the unmasked parental antibody (Antibody 2-6) when tested without having prior exposure to protease (FIG. 17). The reduced reporter activation of Antibody 2-15, which is non-activatable by protease, was not rescued by prior exposure to protease (FIG. 17). The reporter activation of Antibody 2-14, which is activatable by protease, was rescued to levels resembling those induced by the unmasked parental antibody, Antibody 2-6 (FIG. 17).

FIG. 18A depicts the ability of an unmasked form of Antibody 2 (Antibody 2-2) and a masked form of Antibody 2 (Antibody 2-14) to block the binding of CTLA4 to its ligands. Antibody 2-14 was tested in a masked state (i.e., without prior exposure to protease) and in an "activated" state due to prior exposure to protease. For comparison, the assay was also run using an isotype control, and was also run without an antibody (i.e., as a no antibody control). FIG. 18A shows that Antibody 2-14, when in a masked (non-activated) form due to the absence of protease, did not demonstrate an ability to effectively block CTLA4 binding to its ligands. An analysis of the fold change above the no antibody control revealed no significant difference between the ability of Antibody 2-14, when in a masked (non-activated) form, and the ability of the isotype control to block the binding of CTLA4 to its ligands (FIG. 18B). FIG. 18A shows, however, that when Antibody 2-14 is in an "activated" form due to prior exposure to protease, it demonstrated an ability to effectively block the binding of CTLA4 to its ligands across a range of concentrations. The ability of "activated" Antibody 2-14 to block CTLA4 binding to its ligands was similar to that of unmasked Antibody 2-2 (FIGS. 18A and 18B). An analysis of the fold change above the no antibody control revealed no significant difference ("ns") between the ability of "activated" Antibody 2-14 and unmasked Antibody 2-2 to block CTLA4 binding to its ligands (FIG. 18B).

FIGS. 19E and 19F provide statistics comparing the antibodies tested (Group 1: IgG, Group 2: Antibody 2-1; Group 3: Antibody 2-10; Group 4: Ipilimumab; Group 5: Ipilimumab-aFuc).

FIG. 22 depicts a graph showing the level of each administered antibody in µg/mL over a period of 14 days.

FIG. 23C depicts graphs showing regulatory T cells in the tumor microenvironment (left) and CD8+ T cells in the tumor microenvironment (right) following administration of RSV-m control, ipilimumab, Antibody 2-6, Antibody 2-14, or Antibody 2-15, in mice.

FIGS. 25A-25F depict radar plots showing frequency of cleavage in conditioned media using the identified murine models (C57/B16-wt, MC38-wt, MC38-hCTLA4, MB49-wt, MCA205-wt, B16-wt). Media was conditioned with tissues as indicated, such as spleen, liver, kidney, plasma, or tumor.

As shown in FIG. 26A, cleavage of Antibody 2-14 was calculated using capillary electrophoresis (CE) and mass spectrometry (MS), as indicated. FIG. 26B depicts a graph showing the proportion of intact and cleavage products of Antibody 2-14 at 1 hour, 24 hours, and 72 hours.

FIG. 30 depicts substrate cleavages for MC38 and H2228 cell lines as an iceLogo graphic.

FIG. 31D depicts differences in Z-scores at the P4-P4' positions as a heat map to highlight residues that are favored in H2228-specific cleavages, compared to either NAT or tumor samples. Norleucine (n) is a proxy for Met in the library.

FIGS. 32A and 32B depict product formation curves for selected substrates with MC38 conditioned media: AK10-01 (FIG. 32A, left), AK10-02 (FIG. 32A, right): AK10-04 (FIG. 32B, left), and AK10-05 (FIG. 32B, right).

FIGS. 36A-36C depict the product formation curves for selected substrates with tumor conditioned media: AK10-01 (FIG. 36A, top left), AK10-02 (FIG. 36A, top middle), AK10-03 (FIG. 36A, bottom), AK10-04 (FIG. 36B, top left), and AK10-05 (FIG. 36B, top right), AK10-09 (FIG. 36B, bottom), AK10-09 oxidized peptides (FIG. 36C, left), and AK10-10 (FIG. 36C, right).

FIGS. 37A-37D depict the product formation curves for selected substrates with NAT conditioned media: AK10-01 (FIG. 37A, top), AK10-02 (FIG. 37A, bottom), AK10-04 (FIG. 37B, top), and AK10-05 (FIG. 37B, bottom), AK10-09 (FIG. 37C, top), AK10-09 oxidized peptides (FIG. 37C, bottom), and AK10-10 (FIG. 37D). FIG. 37E depicts the top cleavages produced by NAT conditioned media with the AK10 library of peptides with relative efficiencies.

DETAILED DESCRIPTION

Figure 1B:
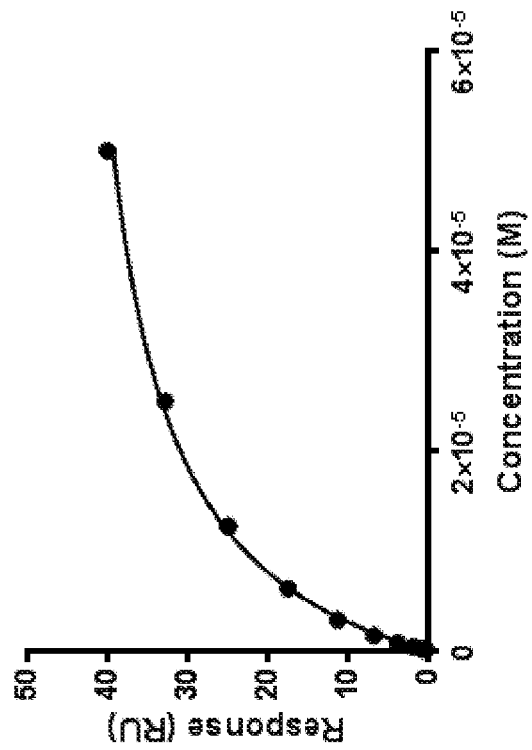
FIGS. 1A and 1B is a series of graphs showing in vitro analyses of anti-CTLA4 antibody occlusion by a masking peptide. Surface plasmon resonance (SPR) was performed to examine A) kinetics and B) affinity between 9D9 antibody (ligand) and masking peptide CNLIVEGHC (SEQ ID NO: 1) (analyte). Analytes were run in increasing concentrations of 2-fold serial dilutions from 0.1 to 50 μM at 37° C. Reference-subtracted response was plotted. SPR was performed three times and representative traces from one experiment are shown.

Therapeutics such as checkpoint inhibitors demonstrates unprecedented responses in cancer but their use is limited by immune-related adverse events (irAEs) and other toxicities (e.g., hypophysitis). Provided herein are protein therapeutics that bind CTLA4 specifically after activation by a protease at a target site, for example in a tumor microenvironment, to achieve increased durable response rates and significantly improved safety profiles. The protein therapeutics provided herein are engineered to precisely target pharmacological activity to the tumor microenvironment by exploiting one of the hallmarks of cancer, high local concentrations of active protease. This feature of the tumor microenvironment is used to transform a systemically inert molecule into a locally active drug. Activation of the drug at the tumor microenvironment significantly reduces systemic toxicities that can be associated with drugs that are administered to a subject in active form.

I. Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "an antibody" optionally includes a combination of two or more such antibodies, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "antibody" includes polyclonal antibodies, monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')$_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see e.g., Basic and Clinical Immunology, 8th Edition, Daniel P. Sties, Abba I. Terr and Tristram G. Parsolw (eds), Appleton & Lange, Norwalk, CT, 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. mAbs Vol 1 Issue 4 1-7) any of which are suitable for use in the invention. Common allotypic variants in human populations are those designated by the letters a,f,n,z.

An "isolated" antibody is one that has been identified, separated and/or recovered from a component of its production environment (e.g., naturally or recombinantly). In some embodiments, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In some embodiments, the polypeptide is purified: (1) to greater than 95% by weight of antibody as determined by, for example, the Lowry method, and in some embodiments, to greater than 99% by weight: (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or silver stain. Isolated antibody includes the antibody in situ within recombinant cells since at least one component of the antibody's natural environment will not be present. Ordinarily, however, an isolated polypeptide or antibody is prepared by at least one purification step.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. In some embodiments, monoclonal antibodies have a C-terminal cleavage at the heavy chain and/or light chain. For example, 1, 2, 3, 4, or 5 amino acid residues are cleaved at the C-terminus of heavy chain and/or light chain. In some embodiments, the C-terminal cleavage removes a C-terminal lysine from the heavy chain. In some embodiments, monoclonal antibodies have an N-terminal cleavage at the heavy chain and/or light chain. For example, 1, 2, 3, 4, or 5 amino acid residues are cleaved at the N-terminus of heavy chain and/or light chain. In some embodiments truncated forms of monoclonal antibodies can be made by recombinant techniques. In some embodiments, monoclonal antibodies are highly specific, being directed against a single antigenic site. In some embodiments, monoclonal antibodies are highly specific, being directed against multiple antigenic sites (such as a bispecific antibody or a multispecific antibody). The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method, recombinant DNA methods, phage-display technologies, and technologies for producing human or human-like antibodies in animals that have parts or all of the human immunoglobulin loci or genes encoding human immunoglobulin sequences.

The term "naked antibody" refers to an antibody that is not conjugated to a cytotoxic moiety or radiolabel.

The term "parental antibody" refers to an antibody prior to modification, such as the masking of an antibody with a masking peptide.

The term "masked antibody" refers to an antibody that has been modified to comprise a masking peptide and in some embodiments other components that allow for activation or removal of the masking peptide in a preferred environment.

An "antibody-drug conjugate" or "ADC" refers to an antibody conjugated to one or more heterologous molecule(s), including but not limited to a cytotoxic agent.

The terms "full-length antibody," "intact antibody" or "whole antibody" are used interchangeably to refer to an antibody in its substantially intact form, as opposed to an antibody fragment. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, the antigen binding and/or the variable region of the intact antibody. Examples of antigen-binding antibody fragments include domain antibodies (dAbs), Fab, Fab', F(ab')$_2$ and Fv fragments; diabodies: linear antibodies (see U.S. Pat. No. 5,641,870, Example 2: Zapata et al., Protein Eng. 8 (10): 1057-1062 [1995]): single-chain antibody molecules, and multispecific antibodies formed from antibody fragments. Single heavy chain antibodies or single light chain antibodies can be engineered, or in the case of the heavy chain, can be isolated from camelids, shark, libraries or mice engineered to produce single heavy chain molecules.

Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences and glycan in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. In some embodiments, the sFv polypeptide further comprises a polypeptide linker between the VH and VL domains which enables the sFv to form the desired structure for antigen binding. For a review of the sFv, see Pluckthun in The Pharmacology of Monoclonal Antibodies, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the Fv region of an antibody which retains or has modified FcR binding capability. Examples of antibody fragments include linear antibody, single-chain antibody molecules and multispecific antibodies formed from antibody fragments.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used as a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as murine, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. In some embodiments, the number of these amino acid substitutions in the FR are no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, for example, Vaswani and Hamilton, Ann. Allergy, Asthma & Immunol. 1:105-115 (1998): Harris, Biochem. Soc. Transactions 23:1035-1038 (1995): Hurle and Gross, Curr. Op. Biotech. 5:428-433 (1994); and U.S. Pat. Nos. 6,982,321 and 7,087,409. In some embodiments, humanized antibodies are directed against a single antigenic site. In some embodiments, humanized antibodies are directed against multiple antigenic sites. An alternative humanization method is described in U.S. Pat. No. 7,981,843 and U.S. Patent Application Publication No. 2006/0134098.

The "variable region" or "variable domain" of an antibody refers to the amino-terminal domains of the heavy or light chain of the antibody. Accordingly, the terms "variable region" and "variable domain" as used herein may be used interchangeably. The variable domains of the heavy chain and light chain may be referred to as "VH" and "VL", respectively. These domains are generally the most variable parts of the antibody (relative to other antibodies of the same class) and contain the antigen binding sites. The variable domains of the heavy chain and the light chain can be determined using any available method or numbering scheme and may include the variable domains as described, e.g., in WO 2018/207701, the contents of which are hereby incorporated by reference. In some embodiments, the variable domain of the heavy chain and/or the light chain may lack one or more amino acid residues on the carboxyl terminus of the variable domain (i.e., at the carboxyl terminus of the fourth framework domain) that may otherwise be included in descriptions of the variable domain based on certain numbering schemes. In some embodiments, the variable domain of the heavy chain and/or the light chain may include one or more amino acid residues on the carboxyl terminus of the variable domain (i.e., at the carboxyl terminus of the fourth framework domain) that may otherwise not be included in descriptions of the variable domain based on certain numbering schemes.

The term "hypervariable region," "HVR," or "HV," when used herein refers to the regions of an antibody-variable domain that are hypervariable in sequence and/or form structurally defined loops. Generally, antibodies comprise six HVRs: three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. Immunity 13:37-45 (2000): Johnson and Wu in Methods in Molecular Biology 248:1-25 (Lo, ed., Human Press, Totowa, NJ, 2003)). Indeed, naturally occurring camelid antibodies consisting of a heavy chain only are functional and stable in the absence of light chain. See, e.g., Hamers-Casterman et al., Nature 363:446-448 (1993) and Sheriff et al., Nature Struct. Biol. 3:733-736 (1996).

A number of HVR delineations are in use and are encompassed herein. The HVRs that are Kabat complementarity-determining regions (CDRs) are based on sequence variability and are the most commonly used (Kabat et al., Sequences of Proteins of Immunological Interest, 5th Ed. Public Health Service, National Institute of Health, Bethesda, MD (1991)). Chothia HVRs refer instead to the location of the structural loops (Chothia and Lesk J. Mol. Biol. 196:901-917 (1987)). The "contact" HVRs are based on an analysis of the available complex crystal structures. The residues from each of these HVRs are noted below.

| Loop | Kabat | Chothia | Contact |
| --- | --- | --- | --- |
| L1 | L24-L34 | L26-L34 | L30-L36 |
| L2 | L50-L56 | L50-L56 | L46-L55 |
| L3 | L89-L97 | L91-L96 | L89-L96 |
| H1 | H31-H35B | H26-H32 | H30-H35B (Kabat Numbering) |
| H1 | H31-H35 | H26-H32 | H30-H35 (Chothia Numbering) |
| H2 | H50-H65 | H53-H56 | H47-H58 |
| H3 | H95-H102 | H95-H102 | H93-H101 |

Unless otherwise indicated, the variable-domain residues (HVR residues and framework region residues) are numbered according to Kabat et al., supra.

"Framework" or "FR" residues are those variable-domain residues other than the HVR residues as herein defined.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

An "acceptor human framework" for the purposes herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less. 9 or less. 8 or less. 7 or less. 6 or less. 5 or less. 4 or less. 3 or less, or 2 or less.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST. BLAST-2. ALIGN or Megalign (DNASTAR) software. Those skilled in the art can determine appropriate parameters for aligning sequences, including any algorithms needed to achieve maximal alignment over the full length of the sequences being compared. For example, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

An antibody that "binds to." "specifically binds to" or is "specific for" a particular a polypeptide or an epitope on a particular polypeptide is one that binds to that particular polypeptide or epitope on a particular polypeptide without substantially binding to any other polypeptide or polypeptide epitope. In some embodiments, binding of an activatable masked anti-CTLA4 binding protein described herein (e.g., activatable masked anti-CTLA4 antibody or antigen-binding fragment thereof) to an unrelated, non-CTLA4 polypeptide is less than about 10% of the antibody binding to CTLA4 as measured by methods known in the art (e.g., enzyme-linked immunosorbent assay (ELISA)). In some embodiments, the binding protein (e.g., antibody) that binds to a CTLA4 (e.g., a murine CTLA4 and/or a human CTLA4) has an equilibrium dissociation constant ($K_D$) of ≤1 μM, ≤100 nM, ≤10 nM, ≤2 nM, ≤1 nM, ≤0.7 nM, ≤0.6 nM, ≤0.5 nM, ≤0.1 nM, ≤0.01 nM, or ≤0.001 nM (e.g. $10^{-8}$ M or less, e.g. from $10^{-8}$ M to $10^{-13}$ M. e.g., from $10^{-9}$ M to $10^{-13}$ M).

The term "CTLA4" or "CTLA4 protein" as provided herein includes any of the recombinant or naturally-occurring forms of the cytotoxic T-lymphocyte-associated protein 4 (CTLA4) or variants or homologs thereof that maintain CTLA4 protein activity (e.g. within at least 50%, 80%, 90%, 95%, 96%, 97%, 98%, 99% or 100% activity compared to CTLA4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA4 polypeptide. In some embodiments, CTLA4 is the protein as identified by the NCBI sequence reference GI: 83700231, homolog or functional fragment thereof. In some embodiments, CTLA4 is a human CTLA4. In some embodiments, CTLA4 is a murine CTLA4.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity: Fc receptor binding: antibody-dependent cell-mediated cytotoxicity (ADCC): phagocytosis: down regulation of cell surface receptors (e.g., B cell receptors); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, Annu. Rev. Immunol. 9:457-92 (1991). In some embodiments, an activatable masked anti-CTLA4 binding protein described herein (e.g., activatable masked anti-CTLA4 antibody or antigen-binding fragment thereof) is engineered or expressed in cells that lack the ability to fucosylate the Fc glycan to have enhanced ADCC. To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., PNAS USA 95:652-656 (1998). Other Fc variants that alter ADCC activity and other antibody properties include those disclosed by Ghetie et al., Nat Biotech. 15:637-40, 1997: Duncan et al, Nature 332:563-564, 1988: Lund et al., J. Immunol 147:2657-2662, 1991: Lund et al, Mol Immunol 29:53-59, 1992: Alegre et al, Transplantation 57:1537-1543, 1994; Hutchins et al., Proc Natl. Acad Sci USA 92:11980-11984, 1995: Jefferis et al, Immunol Lett. 44:111-117, 1995: Lund et al., FASEB J9: 115-119, 1995: Jefferis et al, Immunol Lett 54:101-104, 1996; Lund et al, J Immunol 157:4963-4969, 1996: Armour et al., Eur J Immunol 29:2613-2624, 1999: Idusogie et al, J Immunol 164:4178-4184, 200; Reddy et al, J Immunol 164:1925-1933, 2000; Xu et al., Cell Immunol 200:16-26, 2000; Idusogie et al, J Immunol 166:2571-2575, 2001: Shields et al., J Biol Chem 276:6591-6604, 2001: Jefferis et al, Immunol Lett 82:57-65. 2002; Presta et al., Biochem Soc Trans 30:487-490, 2002: Lazar et al., Proc. Natl. Acad. Sci. USA 103:4005-4010, 2006; U.S. Pat. Nos. 5,624,821; 5,885, 573; 5,677,425; 6,165,745; 6,277,375; 5,869,046; 6,121, 022; 5,624,821; 5,648,260; 6,194,551; 6,737,056; 6,821, 505; 6,277,375; 7,335,742; and 7,317,091.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. Suitable native-sequence Fc regions for use in the antibodies of the invention include human IgG1, IgG2, IgG3 and IgG4.

"Binding affinity" as used herein refers to the strength of the non-covalent interactions between a single binding site of a molecule (e.g., an antibody) and its binding partner (e.g., an antigen). In some embodiments, the affinity of a binding protein (e.g., antibody) for a CTLA4 can generally be represented by an equilibrium dissociation constant ($K_D$). Affinity can be measured by common methods known in the art, including those described herein.

"Binding avidity" as used herein refers to the binding strength of multiple binding sites of a molecule (e.g., an antibody) and its binding partner (e.g., an antigen).

An "isolated" nucleic acid molecule encoding the antibodies herein is a nucleic acid molecule that is identified and separated from at least one contaminant nucleic acid molecule with which it is ordinarily associated in the environment in which it was produced. In some embodiments, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids: antioxidants including ascorbic acid: low molecular weight (less than about 10 residues) polypeptide: proteins, such as serum albumin, gelatin, or immunoglobulins: hydrophilic polymers such as polyvinylpyrrolidone: amino acids such as glycine, glutamine, asparagine, arginine or lysine: monosaccharides, disaccharides, and other carbohydrates including glucose, mannose, or dextrins: chelating agents such as EDTA: sugar alcohols such as mannitol or sorbitol: salt-forming counterions such as sodium; and/or nonionic surfactants such as TWEEN™, polyethylene glycol (PEG), and PLURONICS™.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disorder (e.g., a neoplastic disease) are mitigated or eliminated. For example, an individual is successfully "treated" if treatment results in increasing the quality of life of those suffering from a disease, decreasing the dose of other medications required for treating the disease, reducing the frequency of recurrence of the disease, lessening severity of the disease, delaying the development or progression of the disease, and/or prolonging survival of individuals.

As used herein, "in conjunction with" or "in combination with" refers to administration of one treatment modality in addition to another treatment modality. As such, "in conjunction with" or "in combination with" refers to administration of one treatment modality before, during or after administration of the other treatment modality to the individual.

As used herein, the term "prevention" includes providing prophylaxis with respect to occurrence or recurrence of a disease in an individual. An individual may be predisposed to, susceptible to a disorder, or at risk of developing a disorder, but has not yet been diagnosed with the disorder. In some embodiments, activatable masked anti-CTLA4 binding proteins (e.g., activatable masked anti-CTLA4 antibodies) described herein are used to delay development of a disorder.

As used herein, an individual "at risk" of developing a disorder may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of the disease, as known in the art. An individual having one or more of these risk factors has a higher probability of developing the disorder than an individual without one or more of these risk factors.

An "effective amount" refers to at least an amount effective, at dosages and for periods of time necessary, to achieve the desired or indicated effect, including a therapeutic or prophylactic result. An effective amount can be provided in one or more administrations. A "therapeutically effective amount" is at least the minimum concentration required to affect a measurable improvement of a particular disorder. A therapeutically effective amount herein may vary according to factors such as the disease state, age, sex, and weight of the patient, and the ability of the antibody to elicit a desired response in the individual. A therapeutically effective amount may also be one in which any toxic or detrimental effects of the antibody are outweighed by the therapeutically beneficial effects. A "prophylactically effective amount" refers to an amount effective, at the dosages and for periods of time necessary, to achieve the desired prophylactic result. Typically, but not necessarily, since a prophylactic dose is used in subjects prior to or at the earlier stage of disease, the prophylactically effective amount can be less than the therapeutically effective amount.

"Chronic" administration refers to administration of the medicament(s) in a continuous as opposed to acute mode, so as to main the initial therapeutic effect (activity) for an extended period of time. "Intermittent" administration is treatment that is not consecutively done without interruption, but rather is cyclic in nature.

As used herein, an "individual" or a "subject" is a mammal. A "mammal" for purposes of treatment includes humans, domestic and farm animals, and zoo, sports, or pet animals, such as dogs, horses, rabbits, cattle, pigs, hamsters, gerbils, mice, ferrets, rats, cats, etc. In some embodiments, the individual or subject is human.

II. Activatable Masked Anti-CTLA4 Binding Proteins

In one aspect, there is provided an activatable masked cytotoxic T-lymphocyte-associated protein 4 (CTLA4) binding protein comprising (i) a CTLA4 binding domain: (ii) a CTLA4 binding domain masking peptide (also referred to herein as a "masking peptide"); and (iii) a linker comprising a cleavable peptide connecting the masking peptide to the CTLA4 binding domain. In some embodiments, the activatable masked CTLA4 binding protein is a masked anti-CTLA4 antibody or antigen-binding fragment thereof. In some embodiments, the activatable masked CTLA4 binding protein is a masked bispecific antibody that binds to CTLA4. In some embodiments, the activatable masked CTLA4 binding protein is a masked chimeric receptor that binds to CTLA4.

The activatable masked CTLA4 binding proteins provided herein can bind to CTLA4 from various species, for example, some bind to a human CTLA4 and/or murine CTLA4, or cynomolgus CTLA4. In some embodiments, an activatable masked anti-CTLA4 binding protein described herein has one or more of the following characteristics: (1) binds a CTLA4 (e.g. a human CTLA4): (2) binds a CTLA4 with a higher affinity after protease cleavage of a peptide linker linking a masking peptide to the binding protein (e.g., activation); and (3) binds a CTLA4 in vivo at a tumor site.

In one aspect, provided herein are activatable masked CTLA4 binding proteins useful, inter alia, for the treatment of a neoplastic disease in which CTLA4 plays a role. An activatable masked CTLA4 binding protein as provided herein includes a binding domain capable of interacting with (e.g., binding to) a CTLA4 protein expressed on the surface of a cell (e.g., a cancer cell or T cell). The binding domain, in some embodiments, is connected to a masking peptide through a linker comprising a cleavable peptide such that the masking peptide prevents the CTLA4 binding domain from binding to a CTLA4 protein. Upon cleavage of the cleavable peptide, the masking peptide is released thereby allowing the binding domain to interact with a CTLA4 protein.

Also provided herein, in some embodiments, is a masked CTLA4 binding protein (e.g., a masked anti-CTLA4 antibody or antigen-binding fragment thereof) comprising (a) a CTLA4 binding protein (e.g., an anti-CTLA4 antibody or antigen-binding fragment thereof comprising a first chain and a second chain); and (b) a masking peptide. In some embodiments, the CTLA4 binding protein is an anti-CTLA4 antibody or antigen-binding fragment thereof comprising a first chain and a second chain, and the masking peptide is linked via a linker comprising a cleavable peptide to an amino-terminus or carboxy-terminus of the first chain or the second chain of the antibody or antigen-binding fragment thereof. In some embodiments, the first chain is or comprises a heavy chain, and the second chain is or comprises a light chain; or the first chain is or comprises a light chain, and the second chain is or comprises a heavy chain. In some embodiments, the first chain is or comprises a heavy chain variable region, and the second chain is or comprises a light chain variable region; or the first chain is or comprises a light chain variable region, and the second chain is or comprises a heavy chain variable region. In some embodiments, the linker comprising a cleavable peptide comprises, in an amino-terminus to carboxy-terminus direction: a spacer linker, a cleavable peptide, and a spacer linker. In some embodiments, the C-terminus of the masking peptide is linked to the N-terminus of the linker comprising a cleavable peptide, and the C-terminus of the linker comprising a cleavable peptide is linked to the N-terminus of the first chain, e.g., the light chain or the light chain variable region.

CTLA4 Binding Protein

The term "CTLA4 binding protein" as provided herein refers to a polypeptide comprising a CTLA4 binding domain that is capable of binding to, or otherwise exhibiting an affinity for, a CTLA4 protein. In some embodiments, the CTLA4 binding protein is an anti-CTLA4 antibody or antigen-binding fragment thereof, a bispecific antibody, an antigen binding fragment, a single chain antibody, etc. In some embodiments, the CTLA4 binding protein is an antibody or antigen-binding fragment thereof that binds to CTLA4. In some embodiments, an antibody or antigen-binding fragment thereof that binds to CTLA4 is an anti-CTLA4 antibody or antigen-binding fragment thereof. Accordingly, in some embodiments, the CTLA4 binding protein is an anti-CTLA4 antibody or antigen-binding fragment thereof. In some embodiments, the CTLA4 binding protein is a component of a chimeric antigen receptor that binds CTLA4.

The term "CTLA4 binding domain" refers to a recombinantly expressed polypeptide domain capable of binding to, or otherwise exhibiting an affinity for, a CTLA4 protein found in or on a cell. Methods for determining the extent of binding of a CTLA4 binding domain to CTLA4 are well known in the art.

In some embodiments, the antibody is a humanized antibody, a chimeric antibody, or a human antibody. In some embodiments, an anti-CTLA4 antibody or antigen-binding fragment thereof described herein is a monoclonal antibody. In some embodiments, an anti-CTLA4 antibody or antigen-binding fragment thereof described herein is an antibody fragment (including antigen-binding fragment), e.g., a dAb, Fab, Fab'-SH, Fv, scFv, or (Fab')$_2$ fragment. In some embodiments, the antibody or antigen-binding fragment thereof is a dimer. In some embodiments, the antibody or antigen-binding fragment thereof is a homodimer. In some embodiments, the antibody or antigen-binding fragment thereof is a heterodimer. In some embodiments, the antibody or antigen-binding fragment thereof is a heterodimer comprising a first chain and a second chain, such as a heterodimer comprising a heavy chain and a light chain. In some embodiments, the antibody or antigen-binding fragment comprises a first chain and a second chain. In some embodiments, the first chain is or comprises a heavy chain, and the second chain is or comprises a light chain; or the first chain is or comprises a light chain, and the second chain is or comprises a heavy chain. In some embodiments, the first chain is or comprises a heavy chain variable region, and the second chain is or comprises a light chain variable region; or the first chain is or comprises a light chain variable region, and the second chain is or comprises a heavy chain variable region. In some embodiments, the antibody or antigen-binding fragment thereof comprises a first chain and a second chain (e.g., a light chain and a heavy chain). In some embodiments, the antibody or antigen-binding fragment thereof comprises two first chains and two second chains (e.g., two light chains and two heavy chains). In some embodiments, the antibody or antigen-binding fragment thereof comprises a light chain variable region and a heavy chain variable region, wherein the light chain variable region comprises (i) a CDR-L1 comprising the amino acid sequence of SEQ ID NO:402 or 408, (ii) a CDR-L2 comprising the amino acid sequence of SEQ ID NO:403 or 409, and (iii) a CDR-L3 comprising the amino acid sequence of SEQ ID NO:404 or 410; and/or wherein the heavy chain variable region comprises (i) a CDR-H1 comprising the amino acid sequence of SEQ ID NO:405 or 411, (ii) a CDR-H2 comprising the amino acid sequence of SEQ ID NO:406 or 412, and (iii) a CDR-H3 comprising the amino acid sequence of SEQ ID NO:407 or 413.

In some embodiments, the antibody or antigen-binding fragment comprises a light chain variable region and a heavy chain variable region, wherein the light chain variable region comprises (i) a CDR-L1 comprising the amino acid sequence of SEQ ID NO:402, (ii) a CDR-L2 comprising the amino acid sequence of SEQ ID NO:403, and (iii) a CDR-L3 comprising the amino acid sequence of SEQ ID NO:404; and/or wherein the heavy chain variable region comprises (i) a CDR-H1 comprising the amino acid sequence of SEQ ID NO: 405, (ii) a CDR-H2 comprising the amino acid sequence of SEQ ID NO:406, and (iii) a CDR-H3 comprising the amino acid sequence of SEQ ID NO:407. In some embodiments, the antibody or antigen-binding fragment comprises a light chain variable region and a heavy chain variable region, wherein the light chain variable region comprises (i) a CDR-L1 comprising the amino acid sequence of SEQ ID NO:402, (ii) a CDR-L2 comprising the amino acid sequence of SEQ ID NO:403, and (iii) a CDR-L3 comprising the amino acid sequence of SEQ ID NO:404; and the heavy chain variable region comprises (i) a CDR-H1 comprising the amino acid sequence of SEQ ID NO:405, (ii) a CDR-H2 comprising the amino acid sequence of SEQ ID NO:406, and (iii) a CDR-H3 comprising the amino acid sequence of SEQ ID NO:407.

In some embodiments, the antibody or antigen-binding fragment comprises a light chain variable region and a heavy chain variable region, wherein the light chain variable region comprises (i) a CDR-L1 comprising the amino acid sequence of SEQ ID NO:432, (ii) a CDR-L2 comprising the amino acid sequence of SEQ ID NO:433, and (iii) a CDR-L3 comprising the amino acid sequence of SEQ ID NO:434; and/or wherein the heavy chain variable region comprises (i) a CDR-H1 comprising the amino acid sequence of SEQ ID NO: 435, (ii) a CDR-H2 comprising the amino acid sequence of SEQ ID NO:436, and (iii) a CDR-H3 comprising the amino acid sequence of SEQ ID NO:437. In some embodiments, the antibody or antigen-binding fragment comprises a light chain variable region and a heavy chain variable region, wherein the light chain variable region comprises (i) a CDR-L1 comprising the amino acid sequence of SEQ ID NO:432, (ii) a CDR-L2 comprising the amino acid sequence of SEQ ID NO:433, and (iii) a CDR-L3 comprising the amino acid sequence of SEQ ID NO:434; and the heavy chain variable region comprises (i) a CDR-H1 comprising the amino acid sequence of SEQ ID NO:435, (ii) a CDR-H2 comprising the amino acid sequence of SEQ ID NO:436, and (iii) a CDR-H3 comprising the amino acid sequence of SEQ ID NO:437.

In some embodiments, the antibody or antigen-binding fragment comprises a light chain variable region and a heavy chain variable region, wherein the light chain variable region comprises (i) a CDR-L1 comprising the amino acid sequence of SEQ ID NO:408, (ii) a CDR-L2 comprising the amino acid sequence of SEQ ID NO:409, and (iii) a CDR-L3 comprising the amino acid sequence of SEQ ID NO:410; and/or wherein the heavy chain variable region comprises (i) a CDR-H1 comprising the amino acid sequence of SEQ ID NO: 411, (ii) a CDR-H2 comprising the amino acid sequence of SEQ ID NO:412, and (iii) a CDR-H3 comprising the amino acid sequence of SEQ ID NO:413. In some embodiments, the antibody or antigen-binding fragment comprises a light chain variable region and a heavy chain variable region, wherein the light chain variable region comprises (i) a CDR-L1 comprising the amino acid sequence of SEQ ID NO:408, (ii) a CDR-L2 comprising the amino acid sequence of SEQ ID NO:409, and (iii) a CDR-L3 comprising the amino acid sequence of SEQ ID NO:410; and the heavy chain variable region comprises (i) a CDR-H1 comprising the amino acid sequence of SEQ ID NO:411, (ii) a CDR-H2 comprising the amino acid sequence of SEQ ID NO:412, and (iii) a CDR-H3 comprising the amino acid sequence of SEQ ID NO:413.

In some embodiments, the antibody or antigen-binding fragment comprises a light chain variable region and a heavy chain variable region, wherein the light chain variable region comprises (i) a CDR-L1 comprising the amino acid sequence of SEQ ID NO:438, (ii) a CDR-L2 comprising the amino acid sequence of SEQ ID NO:439, and (iii) a CDR-L3 comprising the amino acid sequence of SEQ ID NO:440; and/or wherein the heavy chain variable region comprises (i) a CDR-H1 comprising the amino acid sequence of SEQ ID NO: 441, (ii) a CDR-H2 comprising the amino acid sequence of SEQ ID NO:442, and (iii) a CDR-H3 comprising the amino acid sequence of SEQ ID NO:443. In some embodiments, the antibody or antigen-binding fragment comprises a light chain variable region and a heavy chain variable region, wherein the light chain variable region comprises (i) a CDR-L1 comprising the amino acid sequence of SEQ ID NO:438, (ii) a CDR-L2 comprising the amino acid sequence of SEQ ID NO:439, and (iii) a CDR-L3 comprising the amino acid sequence of SEQ ID NO:440; and the heavy chain variable region comprises (i) a CDR-H1 comprising the amino acid sequence of SEQ ID NO:441, (ii) a CDR-H2 comprising the amino acid sequence of SEQ ID NO:442, and (iii) a CDR-H3 comprising the amino acid sequence of SEQ ID NO:443.

In some embodiments, the antibody or antigen-binding fragment comprises a light chain variable region comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO:232; and/or comprises a heavy chain variable region comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 233. In some embodiments, the antibody or antigen-binding fragment comprises a light chain variable region comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO:232; and comprises a heavy chain variable region comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 233. In some embodiments, the antibody or antigen-binding fragment comprises a light chain variable region comprising the amino acid sequence of SEQ ID NO:232; and/or a heavy chain variable region comprising the amino acid sequence of SEQ ID NO:233. In some embodiments, the antibody or antigen-binding fragment comprises a light chain variable region comprising the amino acid sequence of SEQ ID NO:232; and a heavy chain variable region comprising the amino acid sequence of SEQ ID NO:233.

In some embodiments, the antibody or antigen-binding fragment thereof comprises a CDR-L1, a CDR-L2, and a CDR-L3 comprised within a VL domain comprising the amino acid sequence of SEQ ID NO: 321, and comprises a CDR-H1, a CDR-H2, and a CDR-H3 comprised within a VH domain comprising the amino acid sequence of SEQ ID NO: 323. In some embodiments, the antibody or antigen-binding fragment thereof comprises a CDR-L1, a CDR-L2, and a CDR-L3 comprised within a VL domain comprising the amino acid sequence of SEQ ID NO: 322, and comprises a CDR-H1, a CDR-H2, and a CDR-H3 comprised within a VH domain comprising the amino acid sequence of SEQ ID NO: 324.

In some embodiments, the antibody or antigen-binding fragment comprises a light chain variable region comprising the amino acid sequence selected from SEQ ID NOs: 321 or 322; and/or a heavy chain variable region comprising the amino acid sequence selected from SEQ ID NOs: 323 or 324. In some embodiments, the antibody or antigen-binding fragment comprises a light chain variable region comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 321; and/or comprises a heavy chain variable region comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 323. In some embodiments, the antibody or antigen-binding fragment comprises a light chain variable region comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 321; and comprises a heavy chain variable region comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 323. In some embodiments, the antibody or antigen-binding fragment comprises a light chain variable region comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 322; and/or comprises a heavy chain variable region comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 324. In some embodiments, the antibody or antigen-binding fragment comprises a light chain variable region comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 322; and comprises a heavy chain variable region comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 324. In some embodiments, the antibody or antigen-binding fragment comprises a light chain variable region comprising the amino acid sequence of SEQ ID NO: 322; and/or comprises a heavy chain variable region comprising the amino acid sequence of SEQ ID NO: 324. In some embodiments, the antibody or antigen-binding fragment comprises a light chain variable region comprising the amino acid sequence of SEQ ID NO: 322; and comprises a heavy chain variable region comprising the amino acid sequence of SEQ ID NO: 324.

In some embodiments, the antibody or antigen-binding fragment thereof comprises a light chain comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 334; and/or comprises a heavy chain comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the antibody or antigen-binding fragment thereof comprises a light chain comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 334; and comprises a heavy chain comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the antibody or antigen-binding fragment thereof comprises a light chain comprising the amino acid sequence of SEQ ID NO: 334; and/or comprises a heavy chain comprising the amino acid sequence of SEQ ID NO: 421. In some embodiments, the antibody or antigen-binding fragment thereof comprises a light chain comprising the amino acid sequence of SEQ ID NO: 334; and comprises a heavy chain comprising the amino acid sequence of SEQ ID NO: 421.

In some embodiments, the antibody or antigen-binding fragment thereof comprises a light chain comprising the amino acid sequence selected from SEQ ID NOs: 237-318; and/or a heavy chain comprising the amino acid sequence selected from SEQ ID NOs: 319 or 320. In some embodiments, the antibody or antigen-binding fragment thereof comprises a light chain comprising the amino acid sequence selected from SEQ ID NOs: 327-341; and/or a heavy chain comprising the amino acid sequence selected from SEQ ID NOs: 366-380, 421, and 478. In some embodiments, the antibody or antigen-binding fragment thereof comprises a light chain comprising the amino acid sequence selected from SEQ ID NOs: 327, 334, or 342-365; and/or a heavy chain comprising the amino acid sequence selected from SEQ ID NOs: 366 or 380-397. In some embodiments, the antibody or antigen-binding fragment thereof has an IgG1, IgG2, IgG3 or IgG4 isotype. In some embodiments, the antibody or antigen-binding fragment thereof has an IgG1 isotype comprising amino acid substitutions that enhance effector function as described herein.

In some embodiments, the CTLA4 binding domain comprises a light chain and a heavy chain of an antigen-binding arm of a bispecific antibody. In some embodiments of the bispecific antibody, the light chain comprises (i) CDR-L1 comprising the amino acid sequence of SEQ ID NO:402 or 408, (ii) CDR-L2 comprising the amino acid sequence of SEQ ID NO:403 or 409, and (iii) CDR-L3 comprising the amino acid sequence of SEQ ID NO: 404 or 410; and/or wherein the heavy chain comprises (i) CDR-H1 comprising the amino acid sequence of SEQ ID NO:405 or 411, (ii) CDR-H2 comprising the amino acid sequence of SEQ ID NO:406 or 412, and (iii) CDR-H3 comprising the amino acid sequence of SEQ ID NO: 407 or 413. In some embodiments of the bispecific antibody, the light chain comprises (i) a CDR-L1 comprising the amino acid sequence of SEQ ID NO:402, (ii) a CDR-L2 comprising the amino acid sequence of SEQ ID NO:403, and (iii) a CDR-L3 comprising the amino acid sequence of SEQ ID NO:404; and the heavy chain comprises (i) a CDR-H1 comprising the amino acid sequence of SEQ ID NO:405, (ii) a CDR-H2 comprising the amino acid sequence of SEQ ID NO:406, and (iii) a CDR-H3 comprising the amino acid sequence of SEQ ID NO:407. In some embodiments of the bispecific antibody, the light chain comprises (i) a CDR-L1 comprising the amino acid sequence of SEQ ID NO:432, (ii) a CDR-L2 comprising the amino acid sequence of SEQ ID NO:433, and (iii) a CDR-L3 comprising the amino acid sequence of SEQ ID NO:434; and the heavy chain comprises (i) a CDR-H1 comprising the amino acid sequence of SEQ ID NO:435, (ii) a CDR-H2 comprising the amino acid sequence of SEQ ID NO:436, and (iii) a CDR-H3 comprising the amino acid sequence of SEQ ID NO:437. In some embodiments of the bispecific antibody, the light chain comprises (i) a CDR-L1 comprising the amino acid sequence of SEQ ID NO:408, (ii) a CDR-L2 comprising the amino acid sequence of SEQ ID NO:409, and (iii) a CDR-L3 comprising the amino acid sequence of SEQ ID NO:410; and the heavy chain comprises (i) a CDR-H1 comprising the amino acid sequence of SEQ ID NO:411, (ii) a CDR-H2 comprising the amino acid sequence of SEQ ID NO:412, and (iii) a CDR-H3 comprising the amino acid sequence of SEQ ID NO:413. In some embodiments of the bispecific antibody, the light chain comprises (i) a CDR-L1 comprising the amino acid sequence of SEQ ID NO:438, (ii) a CDR-L2 comprising the amino acid sequence of SEQ ID NO:439, and (iii) a CDR-L3 comprising the amino acid sequence of SEQ ID NO:440; and the heavy chain comprises (i) a CDR-H1 comprising the amino acid sequence of SEQ ID NO:441, (ii) a CDR-H2 comprising the amino acid sequence of SEQ ID NO:442, and (iii) a CDR-H3 comprising the amino acid sequence of SEQ ID NO:443.

In some embodiments of the bispecific antibody, the light chain comprises a CDR-L1, a CDR-L2, and a CDR-L3 comprised within a VL domain comprising the amino acid sequence of SEQ ID NO: 321, and the heavy chain comprises a CDR-H1, a CDR-H2, and a CDR-H3 comprised within a VH domain comprising the amino acid sequence of SEQ ID NO: 323. In some embodiments of the bispecific antibody, the light chain comprises a CDR-L1, a CDR-L2, and a CDR-L3 comprised within a VL domain comprising the amino acid sequence of SEQ ID NO: 322, and the heavy chain comprises a CDR-H1, a CDR-H2, and a CDR-H3 comprised within a VH domain comprising the amino acid sequence of SEQ ID NO: 324.

In some embodiments of the bispecific antibody, the light chain comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 232; and/or the heavy chain comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 233. In some embodiments of the bispecific antibody, the light chain comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 321; and/or the heavy chain comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 323. In some embodiments of the bispecific antibody, the light chain comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 322; and/or the heavy chain comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 324.

In some embodiments of the bispecific antibody, the light chain comprises the amino acid sequence of SEQ ID NO:232; and/or the heavy chain comprises the amino acid sequence of SEQ ID NO:233. In some embodiments of the bispecific antibody, the light chain comprises the amino acid sequence selected from SEQ ID NOs: 321 or 322; and/or the heavy chain comprises the amino acid sequence selected from SEQ ID NOs: 323 or 324. In some embodiments of the bispecific antibody, the light chain comprises the amino acid sequence selected from SEQ ID NOs: 237-318; and/or the heavy chain comprises the amino acid sequence selected from SEQ ID NOs: 319 or 320.

In some embodiments of the bispecific antibody, the light chain comprises an amino acid sequence having or having about 70%, 75%, 80%, 85%, 90%, 91%, 92%, 93%, 94%, 95%, 96%, 97%, 98%, 99% or 100% homology to an amino acid sequence selected from the group consisting of SEQ ID NOs: 327-341; and/or the heavy chain comprises an amino acid sequence having or having about 70%, 75%, 80%, 85%, 90%, 91%, 92%, 93%, 94%, 95%, 96%, 97%, 98%, 99% or 100% homology to an amino acid sequence selected from the group consisting of SEQ ID NOs: 366-380, 421, and 478. In some embodiments of the bispecific antibody, the light chain comprises the amino acid sequence selected from SEQ ID NOs: 327-341; and/or the heavy chain comprises the amino acid sequence selected from SEQ ID NOs: 366-380, 421, and 478. In some embodiments of the bispecific antibody, the light chain comprises the amino acid sequence selected from SEQ ID NOs: 327, 334, or 342-365; and/or the heavy chain comprises the amino acid sequence selected from SEQ ID NOs: 366,380-397, 421, and 478. In some embodiments of the bispecific antibody, the light chain comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 334; and/or the heavy chain comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments of the bispecific antibody, the light chain comprises the amino acid sequence of SEQ ID NO: 334, and the heavy chain comprises the amino acid sequence of SEQ ID NO: 421. In some embodiments of the bispecific antibody, the CTLA4 is a human CTLA4. In some embodiments of the bispecific antibody, the CTLA4 is a murine CTLA4. In some embodiments, the bispecific antibody is a murine antibody. In some embodiments, the bispecific antibody is a humanized antibody, a chimeric antibody, or a human antibody. In some embodiments, the bispecific antibody has an IgG1, IgG2, IgG3 or IgG4 isotype. In some embodiments, the bispecific antibody has an IgG1 isotype comprising amino acid substitutions that enhance effector function as described herein.

In some embodiments, the CTLA4 binding domain comprises a first chain and a second chain that binds to CTLA4, such as part of a ligand-binding domain for use in a chimeric receptor. In some embodiments of the chimeric receptor, the first chain is a light chain variable domain. In some embodiments, the second chain is a heavy chain variable domain. In some embodiments of the chimeric receptor, the first chain comprises (i) CDR-L1 comprising the amino acid sequence of SEQ ID NO:402 or 408, (ii) CDR-L2 comprising the amino acid sequence of SEQ ID NO:403 or 409, and (iii) CDR-L3 comprising the amino acid sequence of SEQ ID NO:404 or 410; and/or wherein the second chain comprises (i) CDR-H1 comprising the amino acid sequence of SEQ ID NO:405 or 411, (ii) CDR-H2 comprising the amino acid sequence of SEQ ID NO:406 or 412, and (iii) CDR-H3 comprising the amino acid sequence of SEQ ID NO:407 or 413. In some embodiments of the chimeric receptor, the first chain comprises (i) a CDR-L1 comprising the amino acid sequence of SEQ ID NO:402, (ii) a CDR-L2 comprising the amino acid sequence of SEQ ID NO: 403, and (iii) a CDR-L3 comprising the amino acid sequence of SEQ ID NO:404; and the second chain comprises (i) a CDR-H1 comprising the amino acid sequence of SEQ ID NO: 405, (ii) a CDR-H2 comprising the amino acid sequence of SEQ ID NO:406, and (iii) a CDR-H3 comprising the amino acid sequence of SEQ ID NO:407. In some embodiments of the chimeric receptor, the first chain comprises (i) a CDR-L1 comprising the amino acid sequence of SEQ ID NO:432, (ii) a CDR-L2 comprising the amino acid sequence of SEQ ID NO: 433, and (iii) a CDR-L3 comprising the amino acid sequence of SEQ ID NO:434; and the second chain comprises (i) a CDR-H1 comprising the amino acid sequence of SEQ ID NO: 435, (ii) a CDR-H2 comprising the amino acid sequence of SEQ ID NO:436, and (iii) a CDR-H3 comprising the amino acid sequence of SEQ ID NO:437. In some embodiments of the chimeric receptor, the first chain comprises (i) a CDR-L1 comprising the amino acid sequence of SEQ ID NO:408, (ii) a CDR-L2 comprising the amino acid sequence of SEQ ID NO: 409, and (iii) a CDR-L3 comprising the amino acid sequence of SEQ ID NO:410; and the second chain comprises (i) a CDR-H1 comprising the amino acid sequence of SEQ ID NO: 411, (ii) a CDR-H2 comprising the amino acid sequence of SEQ ID NO:412, and (iii) a CDR-H3 comprising the amino acid sequence of SEQ ID NO:413. In some embodiments of the chimeric receptor, the first chain comprises (i) a CDR-L1 comprising the amino acid sequence of SEQ ID NO:438, (ii) a CDR-L2 comprising the amino acid sequence of SEQ ID NO: 439, and (iii) a CDR-L3 comprising the amino acid sequence of SEQ ID NO:440; and the second chain comprises (i) a CDR-H1 comprising the amino acid sequence of SEQ ID NO: 441, (ii) a CDR-H2 comprising the amino acid sequence of SEQ ID NO:442, and (iii) a CDR-H3 comprising the amino acid sequence of SEQ ID NO:443.

In some embodiments of the chimeric receptor, the first chain comprises a CDR-L1, a CDR-L2, and a CDR-L3 comprised within a VL domain comprising the amino acid sequence of SEQ ID NO: 321, and the second chain comprises a CDR-H1, a CDR-H2, and a CDR-H3 comprised within a VH domain comprising the amino acid sequence of SEQ ID NO: 323. In some embodiments of the chimeric receptor, the first chain comprises a CDR-L1, a CDR-L2, and a CDR-L3 comprised within a VL domain comprising the amino acid sequence of SEQ ID NO: 322, and the second chain comprises a CDR-H1, a CDR-H2, and a CDR-H3 comprised within a VH domain comprising the amino acid sequence of SEQ ID NO: 324.

In some embodiments of the chimeric receptor, the first chain comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 232; and/or the second chain comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 233. In some embodiments of the chimeric receptor, the first chain comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 321; and/or the second chain comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 323. In some embodiments of the chimeric receptor, the first chain comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 322; and/or the second chain comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 324. In some embodiments of the chimeric receptor, the first chain comprises the amino acid sequence of SEQ ID NO: 232; and/or the second chain comprises the amino acid sequence of SEQ ID NO:233. In some embodiments of the chimeric receptor, the first chain comprises the amino acid sequence selected from SEQ ID NOs: 321 or 322; and/or the second chain comprises the amino acid sequence selected from SEQ ID NOs: 323 or 324. In some embodiments of the chimeric receptor, the first chain comprises the amino acid sequence of SEQ ID NO: 322, and the second chain comprises the amino acid sequence of SEQ ID NO: 324.

Masking Peptides

A CTLA4 binding domain masking peptide (also referred to as a "masking peptide") as provided herein refers to a peptide capable of binding to, or otherwise exhibiting an affinity for, a CTLA4 binding domain. When bound to the CTLA4 binding domain, the masking peptide blocks, occludes, inhibits (e.g. decreases) or otherwise prevents (e.g., masks) the activity or binding of the CTLA4 binding domain to its cognate receptor or protein (i.e., CTLA4). Methods for determining the extent of binding of a CTLA4 binding domain to a CTLA4 protein are well known in the art.

In embodiments, the masking peptide has a length of at least 4 amino acids. In some embodiments, the masking peptide is a linear peptide. In some embodiments, the linear peptide is a 4-mer to 24-mer. In embodiments, the masking peptide is a cyclic peptide. In embodiments, the cyclic peptide is a 3-mer to 12-mer, as defined by the number of amino acids between the 2 cysteines. In embodiments, the cyclic peptide is a 3-mer to 20-mer. Where the masking peptide is a cyclized peptide, a cyclized peptide is formed by a di-sulfide bond connecting two cysteine amino acid residues. In some embodiments, the cysteine amino acid residues are terminal cysteines (i.e., are located at or near the N-terminus and/or the C-terminus of the masking peptide). In embodiments, the di-sulfide bond connects an N-terminal cysteine with a C-terminal cysteine.

In some embodiments, the masking peptide is linked to the N-terminus of the light chain or the heavy chain of the anti-CTLA4 antibody or antigen-binding fragment thereof. In some embodiments, the masking peptide is linked to the N-terminus of the light chain variable region or the heavy chain variable region of the anti-CTLA4 antibody or antigen-binding fragment thereof. In some embodiments, the masking peptide is linked to the C-terminus of the light chain or the heavy chain of the anti-CTLA4 antibody or antigen-binding fragment thereof. In some embodiments, the masking peptide is linked to the C-terminus of the light chain variable region or the heavy chain variable region of the anti-CTLA4 antibody or antigen-binding fragment thereof.

In some embodiments, the masking peptide is linked to the N-terminus of the light chain or the heavy chain of the anti-CTLA4 antibody or antigen-binding fragment thereof via a linker comprising a cleavable peptide. In some embodiments, the masking peptide is linked to the N-terminus of the light chain of the anti-CTLA4 antibody or antigen-binding fragment thereof via a linker comprising a cleavable peptide. In some embodiments, the masking peptide is linked to the N-terminus of the light chain variable region or the heavy chain variable region of the anti-CTLA4 antibody or antigen-binding fragment thereof via a linker comprising a cleavable peptide. In some embodiments, the masking peptide is linked to the N-terminus of the light chain variable region of the anti-CTLA4 antibody or antigen-binding fragment thereof via a linker comprising a cleavable peptide. In some embodiments, the masking peptide is linked to the C-terminus of the light chain or the heavy chain of the anti-CTLA4 antibody or antigen-binding fragment thereof via a linker comprising a cleavable peptide. In some embodiments, the masking peptide is linked to the C-terminus of the light chain variable region or the heavy chain variable region of the anti-CTLA4 antibody or antigen-binding fragment thereof via a linker comprising a cleavable peptide.

In some embodiments, the masking peptide comprises an amino acid sequence having or having about 70%, 75%, 80%, 85%, 90%, 91%, 92%, 93%, 94%, 95%, 96%, 97%, 98%, 99% or 100% homology to the amino acid sequence selected from SEQ ID NOs: 1-46. Thus, in embodiments, the masking peptide comprises an amino acid sequence having or having about 70%, 75%, 80%, 85%, 90%, 91%, 92%, 93%, 94%, 95%, 96%, 97%, 98%, 99% or 100% homology to the amino acid sequence of CNLIVEGHC (SEQ ID NO:1), MQTRCKEYPRWCEHWL (SEQ ID NO:2), CKHAPYALC (SEQ ID NO:3), CPFPAKILC (SEQ ID NO:4), CPGKGLPSC (SEQ ID NO:5), NWLGEWLPPGKV (SEQ ID NO:6), QFIECPNFPRQCPGKN (SEQ ID NO:7), VRQQCSLNPGRCPYLV (SEQ ID NO:8), VWQECHTAPQLCPGKI (SEQ ID NO:9), DSYTCRGPTWMCAGNM (SEQ ID NO:10), FNHDCSGHWMRCLDQQ (SEQ ID NO:11), NKSPCRPKMVACYGIL (SEQ ID NO:12), PTPQCWNQYYECWIPS (SEQ ID NO:13), SQKCPWTKETCMHYM (SEQ ID NO:14), WHLSMYPKPPAE (SEQ ID NO:15), WHTDGFYTRLPA (SEQ ID NO:16), CIHAPYAKC (SEQ ID NO:17), CPAKIGQEC (SEQ ID NO:18), CPFPALELC (SEQ ID NO:19), CTKPAKALC (SEQ ID NO:20), DTATCYTTTGWCEGMV (SEQ ID NO:21), NSDNCGPAKSTCMYND (SEQ ID NO:22), PPGKCTQPHRCPPLN (SEQ ID NO:23), DDPVCWDSNPTCQTIA (SEQ ID NO:24), ISDQCSVLFLSCNTRV (SEQ ID NO:25), ACHFPHPEGC (SEQ ID NO:26), CLPPFPTKC (SEQ ID NO:27), CPDHVFPKC (SEQ ID NO: 28), CWLPKPDMC (SEQ ID NO:29), CWSWPSKAC (SEQ ID NO:30), CYPFGKYEC (SEQ ID NO:31), ALTPAKWLPADD (SEQ ID NO:32), DDKECDWMHFACTGPQ (SEQ ID NO: 33), DEMKCAWSLEMCVRTS (SEQ ID NO:34), DPILCPNTRMSCDNQT (SEQ ID NO: 35), GNALYDSPGTML (SEQ ID NO:36), KNYECREVMPPCEPNT (SEQ ID NO: 37), NSYTSPYWLPDS (SEQ ID NO:38), SLTPPYWIPREW (SEQ ID NO:39), SPLTPHDRPSFL (SEQ ID NO:40), TADVFSSSRYTR (SEQ ID NO:41), TDLQCPPSSPICQIEH (SEQ ID NO:42), TKCHCDGNCVMCYQMQ (SEQ ID NO:43), TLAYETPLLWLP (SEQ ID NO:44), TNWHCNNDGSSCNVRA (SEQ ID NO:45), or CNLIVQGHC (SEQ ID NO:46).

In some embodiments, the masking peptide comprises an amino acid sequence having about 90% homology to the amino acid sequence selected from SEQ ID NOs: 1-46. For example, the masking peptide comprises an amino acid sequence having about 90% homology to the amino acid sequence of SEQ ID NO: 1.

In some embodiments, the masking peptide comprises an amino acid sequence having about 80% homology to the amino acid sequence selected from SEQ ID NOs: 1-46. For example, the masking peptide comprises an amino acid sequence having about 80% homology to the amino acid sequence of SEQ ID NO:1.

In some embodiments, the masking peptide comprises an amino acid sequence having about 70% homology to the amino acid sequence selected from SEQ ID NOs: 1-46. For example, the masking peptide comprises an amino acid sequence having about 70% homology to the amino acid sequence of SEQ ID NO: 1.

In some embodiments, the masking peptide amino acid sequence is an amino acid sequence selected from SEQ ID NOs: 1-46. For example, the masking peptide amino acid sequence is the amino acid sequence of SEQ ID NO: 1.

In some embodiments, the masking peptide comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 5. In some embodiments, the masking peptide comprises the amino acid sequence of SEQ ID NO: 5.

In some embodiments, the masking peptide comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 19. In some embodiments, the masking peptide comprises the amino acid sequence of SEQ ID NO: 19.

In some embodiments, at least one amino acid but no more than 20 amino acids is directly linked to the N-terminus of the masking peptide. In some embodiments, at least one amino acid but no more than 30 amino acids is directly linked to the N-terminus of the masking peptide. In some embodiments, at least one amino acid but no more than 40 amino acids is directly linked to the N-terminus of the masking peptide. In some embodiments, at least one amino acid but no more than 50 amino acids is directly linked to the N-terminus of the masking peptide. In some embodiments, the at least one amino acid directly linked to the N-terminus of the masking peptide is alanine (A) or glycine-alanine (GA). In some embodiments, the at least one amino acid directly linked to the N-terminus of the masking peptide is a detectable tag. In some embodiments, the at least one amino acid directly linked to the N-terminus of the masking peptide is YPYDVPDYA (SEQ ID NO:398), DYKDDDDK (SEQ ID NO:399), EQKLISEEDL (SEQ ID NO:400), or GLNDIFEAQKIEWHE (SE ID NO: 401). In some embodiments, at least one amino acid but no more than 50 amino acids is directly linked to the N-terminus of a masking peptide comprising an amino acid sequence having or having about 70%, 75%, 80%, 85%, 90%, 91%, 92%, 93%, 94%, 95%, 96%, 97%, 98%, 99% or 100% homology to an amino acid sequence selected from the group consisting of SEQ ID NOs: 1-46. In some embodiments, at least one amino acid but no more than 50 amino acids is directly linked to the N-terminus of a masking peptide selected from the group consisting of SEQ ID NOs: 1-46. In some embodiments, at least one amino acid but no more than 50 amino acids is directly linked to the N-terminus of a masking peptide selected from the group consisting of SEQ ID NOs: 1-46, wherein the at least one amino acid is alanine (A) or glycine-alanine (GA). In some embodiments, at least one amino acid but no more than 50 amino acids is directly linked to the N-terminus of a masking peptide selected from the group consisting of SEQ ID NOs: 1-46, wherein the at least one amino acid is alanine (A).

Linkers

In some embodiments, the activatable masked anti-CTLA4 binding protein comprises a linker, e.g., a spacer linker. In some embodiments, the activatable masked anti-CTLA4 binding protein comprises more than one linker, e.g., a first spacer linker and a second spacer linker. In some embodiments, the activatable masked anti-CTLA4 binding protein comprises a linker comprising a cleavable peptide. A "linker comprising a cleavable peptide" as used herein refers to an enzymatically cleavable linker covalently bonded to a CTLA4 binding domain and covalently bonded to a masking peptide. In some embodiments the linker comprising a cleavable peptide is recombinantly expressed. In some embodiments, the linker comprising a cleavable peptide is a linker formed by reacting a functional (reactive) group attached to the linker with a masking peptide using, for example, conjugate chemistry. In some embodiments, the linker comprising a cleavable peptide is a linker formed by reacting a functional (reactive) group attached to the linker with a CTLA4 binding domain using, for example, conjugate chemistry. In some embodiments, the linker comprising a cleavable peptide connects the masking peptide to the N-terminus of the CTLA4 binding domain (e.g., N-terminus of a light chain). In some embodiments, the linker comprising a cleavable peptide connects the masking peptide to the C-terminus of the CTLA4 binding domain (e.g., C-terminus of a light chain).

In some embodiments, the linker comprising a cleavable peptide is fused with a masking peptide, such as when a nucleic acid encodes the linker and masking peptide and is expressed from a cell as an amino acid sequence encoding the linker and masking peptide. In some embodiments, the linker comprising a cleavable peptide is fused with a CTLA4 binding domain such as when a nucleic acid encodes the linker and CTLA4 binding domain and is expressed from a cell as an amino acid sequence encoding the linker and CTLA4 binding domain. In some embodiments, the linker comprising a cleavable peptide connects the masking peptide to the N-terminus of the CTLA4 binding domain (e.g., N-terminus of a light chain). In some embodiments, the linker comprising a cleavable peptide connects the masking peptide to the C-terminus of the CTLA4 binding domain (e.g., C-terminus of a light chain).

In some embodiments, the linker comprising a cleavable peptide is a flexible linker including one or more glycine residues, serine residues, alanine residues, histidine residues, and/or proline residues. In some embodiments, the linker comprising a cleavable peptide contains a spacer linker directly linked to the N-terminus and/or the C-terminus of the cleavable peptide. In some embodiments, the spacer linker comprises one or more glycine residues, serine residues, alanine residues, histidine residues, and/or proline residues. In some embodiments, the linker comprising a cleavable peptide comprises a spacer linker and a cleavable peptide. In some embodiments, the linker comprising a cleavable peptide comprises a first spacer linker, a cleavable peptide, and a second spacer linker. Accordingly, in some embodiments, the masked CTLA4 binding protein (e.g., masked anti-CTLA4 antibody or antigen-binding fragment thereof) comprises a linker comprising a cleavable peptide comprising a spacer linker (e.g., a first spacer linker, or spacer linker 1) linked to the N-terminus of the cleavable peptide, and a spacer linker (e.g., a second spacer linker, or spacer linker 2) linked to the C-terminus of the cleavable peptide, wherein each spacer linker comprises an amino acid sequence selected from the group consisting of SEQ ID NOs: 89-112 and 415-420. In some embodiments, the C-terminus of the linker comprising a cleavable peptide is linked to the light chain or the light chain variable domain of the anti-CTLA4 antibody or antigen-binding fragment thereof, and the N-terminus of the linker comprising a cleavable peptide is linked to the masking peptide. In some embodiments, the C-terminus of the linker comprising a cleavable peptide is linked to the heavy chain or the heavy chain variable domain of the anti-CTLA4 antibody or antigen-binding fragment thereof, and the N-terminus of the linker comprising a cleavable peptide is linked to the masking peptide. In some embodiments, the N-terminus of the linker comprising a cleavable peptide is linked to the light chain or the light chain variable domain of the anti-CTLA4 antibody or antigen-binding fragment thereof, and the C-terminus of the linker comprising a cleavable peptide is linked to the masking peptide. In some embodiments, the N-terminus of the linker comprising a cleavable peptide is linked to the heavy chain or the heavy chain variable domain of the anti-CTLA4 antibody or antigen-binding fragment thereof, and the C-terminus of the linker comprising a cleavable peptide is linked to the masking peptide.

In some embodiments, the spacer linker comprises an amino acid sequence is selected from SEQ ID NOs: 89-112 and 415-420. In some embodiments, the spacer linker is directly linked to the N-terminus the cleavable peptide and comprises an amino acid sequence selected from SEQ ID NOs: 89-100. In some embodiments, the spacer linker is directly linked to the C-terminus the cleavable peptide and comprises an amino acid sequence is selected from SEQ ID NOs: 101-112 and 415-420. In some embodiments, a masking peptide described herein is directly linked to the N-terminus of the spacer linker. Thus, in some embodiments, the linker comprising a cleavable peptide comprises in the N-terminus to C-terminus direction: 1) a spacer linker (e.g., a spacer linker comprising an amino acid sequence selected from the amino acid sequences of SEQ ID NOs: 89-112 and 415-420), 2) a cleavable peptide such as one described herein (e.g., a cleavable peptide comprising an amino acid sequence selected from the amino acid sequences of SEQ ID NOs: 47-88, 464-469, and 479-508), and 3) a spacer linker (e.g., a spacer linker comprising an amino acid sequence selected from the amino acid sequences of SEQ ID NOs: 89-112 and 415-420).

In some embodiments, the linker comprising a cleavable peptide comprises in the N-terminus to C-terminus direction: 1) a spacer linker comprising an amino acid sequence selected from the group consisting of SEQ ID NOs: 89-112 and 415-420; 2) a cleavable peptide comprising an amino acid sequence selected from the group consisting of SEQ ID NOs: 47-88, 464-469, and 479-508; and 3) a spacer linker comprising an amino acid sequence selected from the group consisting of SEQ ID NOs: 89-112 and 415-420.

In some embodiments, the linker comprising a cleavable peptide comprises in the N-terminus to C-terminus direction: 1) a spacer linker comprising the amino acid sequence of SEQ ID NO: 420; 2) a cleavable peptide comprising the amino acid sequence of SEQ ID NO: 50; and 3) a spacer linker comprising the amino acid sequence of SEQ ID NO: 102.

In some embodiments, the linker comprising a cleavable peptide comprises in the N-terminus to C-terminus direction: 1) a spacer linker comprising the amino acid sequence of SEQ ID NO: 96; 2) a cleavable peptide comprising the amino acid sequence of SEQ ID NO: 86; and 3) a spacer linker comprising the amino acid sequence of SEQ ID NO: 102.

In some embodiments, the linker comprising a cleavable peptide comprises in the N-terminus to C-terminus direction: 1) a spacer linker comprising the amino acid sequence of SEQ ID NO: 415; 2) a cleavable peptide comprising the amino acid sequence of SEQ ID NO: 86; and 3) a spacer linker comprising the amino acid sequence of SEQ ID NO: 102.

In some embodiments, the linker comprising a cleavable peptide comprises in the N-terminus to C-terminus direction: 1) a spacer linker comprising the amino acid sequence of SEQ ID NO: 416; 2) a cleavable peptide comprising the amino acid sequence of SEQ ID NO: 47; and 3) a spacer linker comprising the amino acid sequence of SEQ ID NO: 102.

In some embodiments, the linker comprising a cleavable peptide comprises in the N-terminus to C-terminus direction: 1) a spacer linker comprising the amino acid sequence of SEQ ID NO: 417; 2) a cleavable peptide comprising the amino acid sequence of SEQ ID NO: 57; and 3) a spacer linker comprising the amino acid sequence of SEQ ID NO: 102.

In some embodiments, the linker comprising a cleavable peptide comprises in the N-terminus to C-terminus direction: 1) a spacer linker comprising the amino acid sequence of SEQ ID NO: 418; 2) a cleavable peptide comprising the amino acid sequence of SEQ ID NO: 48; and 3) a spacer linker comprising the amino acid sequence of SEQ ID NO: 102.

In some embodiments, the linker comprising a cleavable peptide comprises in the N-terminus to C-terminus direction: 1) a spacer linker comprising the amino acid sequence of SEQ ID NO: 417; 2) a cleavable peptide comprising the amino acid sequence of SEQ ID NO: 72; and 3) a spacer linker comprising the amino acid sequence of SEQ ID NO: 102.

In some embodiments, the linker comprising a cleavable peptide comprises in the N-terminus to C-terminus direction: 1) a spacer linker comprising the amino acid sequence of SEQ ID NO: 418; 2) a cleavable peptide comprising the amino acid sequence of SEQ ID NO: 51; and 3) a spacer linker comprising the amino acid sequence of SEQ ID NO: 102.

In some embodiments, the linker comprising a cleavable peptide comprises in the N-terminus to C-terminus direction: 1) a spacer linker comprising the amino acid sequence of SEQ ID NO: 419; 2) a cleavable peptide comprising the amino acid sequence of SEQ ID NO: 54; and 3) a spacer linker comprising the amino acid sequence of SEQ ID NO: 102.

In some embodiments, the linker comprising a cleavable peptide comprises an amino acid sequence having or having about 70%, 75%, 80%, 85%, 90%, 91%, 92%, 93%, 94%, 95%, 96%, 97%, 98%, 99%, or 100% homology to an amino acid sequence selected from the group consisting of SEQ ID NOs: 454-462. In some embodiments, the linker comprising a cleavable peptide comprises an amino acid sequence selected from the group consisting of SEQ ID NOs: 454-462. In some embodiments, the linker comprising a cleavable peptide comprises the amino acid sequence of SEQ ID NO: 454. In some embodiments, the linker comprising a cleavable peptide comprises the amino acid sequence of SEQ ID NO: 455.

Linkers can be conjugated to the masking peptide and/or the CTLA4 binding protein by a variety of methods well known in the art. The terms "conjugate" and "conjugate chemistry" refer to reactions with known reactive groups which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, Advanced Organic Chemistry, 3rd Ed., John Wiley & Sons, New York, 1985: Hermanson, Bioconjugate Techniques, Academic Press, San Diego, 1996; and Feeney et al., Modification of Proteins: Advances in Chemistry Series, Vol. 198, American Chemical Society, Washington, D.C., 1982.

Useful reactive functional groups used for conjugate chemistries herein include, for example: (a) carboxyl groups and various derivatives thereof including, but not limited to, N-hydroxysuccinimide esters, N-hydroxy benztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc. (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold; (h) amine or sulfhydryl groups, which can be, for example, acylated, alkylated or oxidized; (i) alkenes, which can undergo, for example, cycloadditions, acylation, Michael addition, etc; (j) epoxides, which can react with, for example, amines and hydroxyl compounds; (k) phosphoramidites and other standard functional groups useful in nucleic acid synthesis; (i) metal silicon oxide bonding; and (1) metal bonding to reactive phosphorus groups (e.g. phosphines) to form, for example, phosphate diester bonds.

The reactive functional groups can be chosen such that they do not participate in, or interfere with, the chemical stability of the compositions described herein. Alternatively, a reactive functional group can be protected from participating in the crosslinking reaction by the presence of a protecting group.

In some embodiments, linkers can be engineered to be fused to the masking peptide and/or the CTLA4 binding protein by a variety of methods well known in the art. For example, a nucleic acid can engineered to encode a linker with a masking peptide and/or a CTLA4 binding protein to produce a fusion protein when recombinantly expressed from a host cell.

Cleavable Peptides

The masked CTLA4 binding protein (e.g., masked anti-CTLA4 antibody or antigen-binding fragment thereof) provided herein, in some embodiments, comprises a cleavable peptide. In some embodiments, the cleavable peptide is contained within a linker comprising a cleavable peptide. The linker comprising a cleavable peptide provided herein may include a protease cleavage site within the cleavable peptide. A "cleavage site" as used herein, refers to a recognizable site for cleavage of a portion of a linker (e.g., linker comprising a cleavable peptide as described above) found in a CTLA4 binding protein described herein. Thus, a cleavage site may be found in the sequence of a cleavable peptide as described herein, including embodiments thereof. In some embodiments, the cleavage site is an amino acid sequence that is recognized and cleaved by a cleaving agent. Exemplary cleaving agents include proteins, enzymes, DNAzymes, RNAzymes, metals, acids, and bases. The cleavable peptide can be any peptide that includes a protease cleavage site. Exemplary cleavable peptides are shown in Table 1.

TABLE 1

| Representative cleavable peptides Exemplary cleavable peptides |
|---|
| MPYDLYHP (SEQ ID NO: 47) |
| GGIGQLTA (SEQ ID NO: 48) |
| DLGRFQTF (SEQ ID NO: 49) |
| DSGGFMLT (SEQ ID NO: 50) |
| TSVLMAAP (SEQ ID NO: 51) |
| TSEFVFAPDQ (SEQ ID NO: 52) |
| KLVLPVLP (SEQ ID NO: 53) |
| KPILFFRL (SEQ ID NO: 54) |
| ANQLKG (SEQ ID NO: 55) |
| QSQLKE (SEQ ID NO: 56) |
| HEQLTV (SEQ ID NO: 57) |
| PANLVAPDP (SEQ ID NO: 58) |
| PAPGVYPGP (SEQ ID NO: 59) |
| APAGLIVPYN (SEQ ID NO: 60) |
| PQALVA (SEQ ID NO: 61) |
| VGNLNF (SEQ ID NO: 62) |
| VANLLYE (SEQ ID NO: 63) |
| VYNLMD (SEQ ID NO: 64) |
| TFNIKQ (SEQ ID NO: 65) |
| DLWKLLP (SEQ ID NO: 66) |
| PGSTKRA (SEQ ID NO: 67) |
| QQYRALKS (SEQ ID NO: 68) |
| YVPRAVL (SEQ ID NO: 69) |
| GVNKWPT (SEQ ID NO: 70) |
| LAQAVRSS (SEQ ID NO: 71) |
| RAAAVKSP (SEQ ID NO: 72) |
| DLLAVVAAS (SEQ ID NO: 73) |
| VQTVTWPD (SEQ ID NO: 74) |
| AIPMSIPP (SEQ ID NO: 75) |
| GYEVHHQK (SEQ ID NO: 76) |
| VHHQKLVF (SEQ ID NO: 77) |
| IRRVSYSF (SEQ ID NO: 78) |
| MPYDLYHPILFFRL (SEQ ID NO: 79) |
| GGIGQLTSVLMAAP (SEQ ID NO: 80) |

TABLE 1-continued

Representative cleavable peptides
Exemplary cleavable peptides

DSGGFMLTLVLPVLP (SEQ ID NO: 81)

TSEFVFAPDLGRFQTF (SEQ ID NO: 82)

TSTSGRSANPR (SEQ ID NO: 83)

TSTSGRSANPG (SEQ ID NO: 84)

TSTSGRSANPH (SEQ ID NO: 85)

VPLSLY (SEQ ID NO: 86)

TSASGASASAA (SEQ ID NO: 87)

PSSPGGGSSP (SEQ ID NO: 88)

ISSGLLSGRSDNH (SEQ ID NO: 464)

AVGLLAPPGGLSGRSDNH (SEQ ID NO: 465)

VPLSLYSG (SEQ ID NO: 466)

RQARVVG (SEQ ID NO: 467)

LSGRSNAMPYDLYHP (SEQ ID NO: 468)

MPYDLYHPRQARVVG (SEQ ID NO: 469)

IPESLRAG (SEQ ID NO: 479)

IPVSLRSG (SEQ ID NO: 480)

IYDQKT (SEQ ID NO: 481)

AHNYKT (SEQ ID NO: 482)

MMDQAN (SEQ ID NO: 483)

MLGEFVSE (SEQ ID NO: 484)

GLVALRGA (SEQ ID NO: 485)

KEHKYKAE (SEQ ID NO: 486)

LAQAVRSS (SEQ ID NO: 487)

LGGSGRSNAQVRLE (SEQ ID NO: 488)

LGGSGRKASLSLE (SEQ ID NO: 489)

SGRIGFLRTA (SEQ ID NO: 490)

SGAIGFLRTA (SEQ ID NO: 491)

RPARSGRSAGGSVA (SEQ ID NO: 492)

VTGRGDSPASS (SEQ ID NO: 493)

PRFKIIGG (SEQ ID NO: 494)

LSGRIGFLRTA (SEQ ID NO: 495)

LSGRSNAGGIGQLTA (SEQ ID NO: 496)

LSGRSNAVPLSLY (SEQ ID NO: 497)

LSGRSNADSGGFMLT (SEQ ID NO: 498)

LSGRSNAHEQLTA (SEQ ID NO: 499)

LSGRSNARAAAVKSP (SEQ ID NO: 500)

LSGRSNATSVLMAAP (SEQ ID NO: 501)

VPLSLYLSGRSNA (SEQ ID NO: 502)

DSGGFMLTLSGRSNA (SEQ ID NO: 503)

TABLE 1-continued

Representative cleavable peptides
Exemplary cleavable peptides

GGIGQLTALSGRSNA (SEQ ID NO: 504)

MPYDLYHPLSGRSNA (SEQ ID NO: 505)

HEQLTVLSGRSNA (SEQ ID NO: 506)

RAAAVKSPLSGRSNA (SEQ ID NO: 507)

TSVLMAAPLSGRSNA (SEQ ID NO: 508)

Accordingly, in some embodiments, the cleavable peptide comprises an amino acid sequence selected from the group consisting of SEQ ID NOs: 47-88, 464-469, and 479-508. In some embodiments, the cleavable peptide comprises the amino acid sequence of SEQ ID NO: 50. In some embodiments, the cleavable peptide comprises the amino acid sequence of SEQ ID NO: 86. In some embodiments, the cleavable peptide comprises the amino acid sequence of SEQ ID NO: 47. In some embodiments, the cleavable peptide comprises the amino acid sequence of SEQ ID NO: 57. In some embodiments, the cleavable peptide comprises the amino acid sequence of SEQ ID NO: 48. In some embodiments, the cleavable peptide comprises the amino acid sequence of SEQ ID NO: 72. In some embodiments, the cleavable peptide comprises the amino acid sequence of SEQ ID NO: 51. In some embodiments, the cleavable peptide comprises the amino acid sequence of SEQ ID NO: 54.

In some embodiments, the protease cleavage site is a tumor-associated protease cleavage site. A "tumor-associated protease cleavage site" as provided herein is an amino acid sequence recognized by a protease, whose expression is specific for a tumor cell or tumor cell environment thereof. In some embodiments, the protease cleavage site is a cleavage site recognized by one or more enzyme selected from the group consisting of: ABHD12, ADAM12, ABHD12B, ABHD13, ABHD17A, ADAM19, ADAM20, ADAM21, ADAM28, ADAM30, ADAM33, ADAM8, ABHD17A, ADAMDEC1, ADAMTS1, ADAMTS10, ADAMTS12, ADAMTS13, ADAMTS14, ADAMTS15, ADAMTS16, ADAMTS17, ADAMTS18, ADAMTS19, ADAMTS2, ADAMTS20, ADAMTS3, ADAMTS4, ABHD17B, ADAMTS5, ADAMTS6, ADAMTS7, ADAMTS8, ADAMTS9, ADAMTSL1, ADAMTSL2, ADAMTSL3, ABHD17C, ADAMTSL5, ASTL, BMP1, CELA1, CELA2A, CELA2B, CELA3A, CELA3B, ADAM10, ADAM15, ADAM17, ADAM9), ADAMTS4, CTSE, CTSF, ADAMTSL4, CMA1, CTRB1, CTRC, CTSO, CTR1, CTSA, CTSW, CTSB, CTSC, CTSD, ESP1, CTSG, CTSH, GZMA, GZMB, GZMH, CTSK, GZMM, CTSL, CTSS, CTSV, CTSZ, HTRA4, KLK10, KLK11, KLK13, KLK14, KLK2, KLK4, DPP4, KLK6, KLK7, KLKB1, ECE1, ECE2, ECEL1, MASP2, MEP1A, MEP1B, ELANE, FAP, GZMA, MMP11, GZMK, HGFAC, HPN, HTRA1, MMP11, MMP16, MMP17, MMP19, HTRA2, MMP20, MMP21, HTRA3, HTRA4, KEL, MMP23B, MMP24, MMP25, MMP26, MMP27, MMP28, KLK5, MMP3, MMP7, MMP8, MMP9, LGMN, LNPEP, MASP1, PAPPA, PAPPA2, PCSK1, NAPSA, PCSK5, PCSK6, MME, MMP1, MMP10, PLAT, PLAU, PLG, PRSS1, PRSS12, PRSS2, PRSS21, PRSS3, PRSS33, PRSS4, PRSS55, PRSS57, MMP12, PRSS8, PRSS9, PRTN3, MMP13, MMP14, ST14, TMPRSS10, TMPRSS11A, TMPRSS11D, TMPRSS11E, TMPRSS11F, TMPRSS12, TMPRSS13, MMP15, TMPRSS15, MMP2, TMPRSS2, TMPRSS3, TMPRSS4, TMPRSS5, TMPRSS6, TMPRSS7, TMPRSS9, NRDC, OVCH1, PAMR1, PCSK3, PHEX, TINAG, TPSAB1, TPSD1, and TPSG1. In some embodiments, the protease cleavage site is a cleavage site recognized by one or more enzyme selected from the group consisting of: ADAM17, HTRA1, PRSS1, FAP, GZMK, NAPSA, MMP1, MMP2, MMP9, MMP10, MMP7, MMP12, MMP28, ADAMTS9, HGFAC, and HTRA3.

In embodiments, the protease cleavage site is a matrix metalloprotease (MMP) cleavage site, a disintegrin and metalloprotease domain-containing (ADAM) metalloprotease cleavage site, a prostate specific antigen (PSA) protease cleavage site, a urokinase-type plasminogen activator (uPA) protease cleavage site, a membrane type serine protease 1 (MT-SP1) protease cleavage site, a matriptase protease cleavage site (ST14) or a legumain protease cleavage site. In embodiments, the matrix metalloprotease (MMP) cleavage site is a MMP9 cleavage site, a MMP13 cleavage site or a MMP2 cleavage site. In embodiments, the disintegrin and metalloprotease domain-containing (ADAM) metalloprotease cleavage site is a ADAM9 metalloprotease cleavage site, a ADAM10 metalloprotease cleavage site or a ADAM17 metalloprotease cleavage site. Protease cleavage sites may be designated by a specific amino acid sequence.

In some embodiments, the cleavable peptide is cleaved by one or more enzyme selected from the group consisting of: ABHD12, ADAM12, ABHD12B, ABHD13, ABHD17A, ADAM19, ADAM20, ADAM21, ADAM28, ADAM30, ADAM33, ADAM8, ABHD17A, ADAMDEC1, ADAMTS1, ADAMTS10, ADAMTS12, ADAMTS13, ADAMTS14, ADAMTS15, ADAMTS16, ADAMTS17, ADAMTS18, ADAMTS19, ADAMTS2, ADAMTS20, ADAMTS3, ADAMTS4, ABHD17B, ADAMTS5, ADAMTS6, ADAMTS7, ADAMTS8, ADAMTS9, ADAMTSL1, ADAMTSL2, ADAMTSL3, ABHD17C, ADAMTSL5, ASTL, BMP1, CELA1, CELA2A, CELA2B, CELA3A, CELA3B, ADAM10, ADAM15, ADAM17, ADAM9, ADAMTS4, CTSE, CTSF, ADAMTSL4, CMA1, CTRB1, CTRC, CTSO, CTR1, CTSA, CTSW, CTSB, CTSC, CTSD, ESP1, CTSG, CTSH, GZMA, GZMB, GZMH, CTSK, GZMM, CTSL, CTSS, CTSV, CTSZ, HTRA4, KLK10, KLK11, KLK13, KLK14, KLK2, KLK4, DPP4, KLK6, KLK7, KLKB1, ECE1, ECE2, ECEL1, MASP2, MEP1A, MEP1B, ELANE, FAP, GZMA, MMP11, GZMK, HGFAC, HPN, HTRA1, MMP11, MMP16, MMP17, MMP19, HTRA2, MMP20, MMP21, HTRA3, HTRA4, KEL, MMP23B, MMP24, MMP25, MMP26, MMP27, MMP28, KLK5, MMP3, MMP7, MMP8, MMP9, LGMN, LNPEP, MASP1, PAPPA, PAPPA2, PCSK1, NAPSA, PCSK5, PCSK6, MME, MMP1, MMP10, PLAT, PLAU, PLG, PRSS1, PRSS12, PRSS2, PRSS21, PRSS3, PRSS33, PRSS4, PRSS55, PRSS57, MMP12, PRSS8, PRSS9, PRTN3, MMP13, MMP14, ST14, TMPRSS10, TMPRSS11A, TMPRSS11D, TMPRSS11E, TMPRSS11F, TMPRSS12, TMPRSS13, MMP15, TMPRSS15, MMP2, TMPRSS2, TMPRSS3, TMPRSS4, TMPRSS5, TMPRSS6, TMPRSS7, TMPRSS9, NRDC, OVCH1, PAMR1, PCSK3, PHEX, TINAG, TPSAB1, TPSD1, and TPSG1. In some embodiments, the cleavable peptide is cleaved by one or more enzyme selected from the group consisting of: ADAM17, HTRA1, PRSS1, FAP, GZMK, NAPSA, MMP1, MMP2, MMP9, MMP10, MMP7, MMP12, MMP28, ADAMTS9, HGFAC, and HTRA3.

In embodiments, the cleavable peptide is a 5-mer (i.e. peptide 5 amino acids in length), 6-mer (i.e. peptide 6 amino acids in length), 7-mer (i.e. peptide 7 amino acids in length), 8-mer (i.e. peptide 8 amino acids in length), 9-mer (i.e. peptide 9) amino acids in length), 10-mer (i.e. peptide 10 amino acids in length), 11-mer (i.e. peptide 11 amino acids in length), 12-mer (i.e. peptide 12 amino acids in length), or 13-mer (i.e. peptide 13 amino acids in length).

Thus, in some embodiments, a masking peptide and linker comprising a cleavable peptide comprises in the N-terminus to C-terminus direction: 1) a masking peptide (e.g., a masking peptide comprising an amino acid sequence selected from the amino acid sequence of SEQ ID NOs: 1-46), 2) a spacer linker (e.g., a spacer linker comprising an amino acid sequence selected from the amino acid sequences of SEQ ID NOs: 89-112 and 415-420), 3) a cleavable peptide such as one described herein (e.g., a cleavable peptide comprising an amino acid sequence selected from the amino acid sequences of SEQ ID NOs: 47-88, 464-469, and 479-508), and 4) a spacer linker (e.g., a spacer linker comprising an amino acid sequence selected from the amino acid sequences of SEQ ID NOs: 89-112 and 415-420). In some embodiments, at least one amino acid but no more than 20 amino acids is directly linked to the N-terminus of the masking peptide. In some embodiments, at least one amino acid but no more than 30 amino acids is directly linked to the N-terminus of the masking peptide. In some embodiments, at least one amino acid but no more than 40 amino acids is directly linked to the N-terminus of the masking peptide. In some embodiments, at least one amino acid but no more than 50 amino acids is directly linked to the N-terminus of the masking peptide. In some embodiments, the at least one amino acid directly linked to the N-terminus of the masking peptide is alanine (A) or glycine-alanine (GA). In some embodiments, the at least one amino acid directly linked to the N-terminus of the masking peptide is a detectable tag. In some embodiments, the at least one amino acid directly linked to the N-terminus of the masking peptide is YPYDVPDYA (SEQ ID NO:398), DYKDDDDK (SEQ ID NO:399), EQKLISEEDL (SEQ ID NO:400), or GLN-DIFEAQKIEWHE (SE ID NO: 401).

In some embodiments, the activatable masked anti-CTLA4 binding protein described herein comprises a peptide comprising a masking peptide, a spacer linker and a cleavable peptide, wherein the peptide comprises an amino acid sequence selected from SEQ ID NOs: 113-231. In some embodiments, the activatable masked anti-CTLA4 binding protein described herein comprises a peptide comprising a masking peptide, a spacer linker and a cleavable peptide, wherein the peptide comprises an amino acid sequence selected from SEQ ID NOs: 113-193. In some embodiments, the activatable masked anti-CTLA4 binding protein described herein comprises a peptide comprising a masking peptide, a spacer linker and a cleavable peptide, wherein the peptide comprises an amino acid sequence selected from SEQ ID NOs: 194-206. In some embodiments, the activatable masked anti-CTLA4 binding protein described herein comprises a peptide comprising a masking peptide, a spacer linker and a cleavable peptide, wherein the peptide comprises an amino acid sequence selected from SEQ ID NOs: 207-231.

In some embodiments, the activatable masked anti-CTLA4 binding protein described herein comprises a peptide comprising a masking peptide, a first spacer linker, a cleavable peptide, and a second spacer linker, wherein the peptide comprises an amino acid sequence having or having about 70%, 75%, 80%, 85%, 90%, 91%, 92%, 93%, 94%, 95%, 96%, 97%, 98%, 99% or 100% homology to an amino acid sequence selected from the group consisting of SEQ ID NOs: 113-231, 444, 446-448, and 450-453. In some embodiments, the activatable masked anti-CTLA4 binding protein described herein comprises a peptide comprising a masking peptide, a first spacer linker, a cleavable peptide, and a second spacer linker, wherein the peptide comprises an amino acid sequence selected from the group consisting of SEQ ID NOs: 113-231, 444, 446-448, and 450-453. In some embodiments, the activatable masked anti-CTLA4 binding protein described herein comprises a peptide comprising a masking peptide, a first spacer linker, a cleavable peptide, and a second spacer linker, wherein the peptide comprises an amino acid sequence having or having about 70%, 75%, 80%, 85%, 90%, 91%, 92%, 93%, 94%, 95%, 96%, 97%, 98%, 99% or 100% homology to an amino acid sequence selected from the group consisting of SEQ ID NOs: 444, 446-448, and 450-453. In some embodiments, the activatable masked anti-CTLA4 binding protein described herein comprises a peptide comprising a masking peptide, a first spacer linker, a cleavable peptide, and a second spacer linker, wherein the peptide comprises an amino acid sequence selected from the group consisting of SEQ ID NOs: 444, 446-448, and 450-453.

Exemplary Masked CTLA4 Binding Proteins

The following describes certain exemplary embodiments of masked CTLA4 binding proteins containing certain features as described above. These embodiments are merely exemplary and are not to be construed as being limiting.

Provided herein, in some embodiments, is a masked antibody comprising a) an antibody or antigen-binding fragment thereof that binds to CTLA4 (e.g., human CTLA4), wherein the antibody or antigen-binding fragment thereof comprises a first chain and a second chain, and b) a masking peptide comprising an amino acid sequence selected from SEQ ID NOs: 1-46, wherein the masking peptide is linked via a linker comprising a cleavable peptide to an amino-terminus or carboxy-terminus of the first chain or the second chain of the antibody or antigen-binding fragment thereof. In some embodiments, the antibody or antigen-binding fragment thereof that binds to CTLA4 is any anti-CTLA4 antibody or antigen-binding fragment thereof described herein. In some embodiments, the antibody or antigen-binding fragment thereof comprises two first chains and two second chains. In some embodiments, the first chain is a light chain and the second chain is a heavy chain. In some embodiments, the first chain is a light chain variable domain and the second chain is a heavy chain variable domain. In some embodiments, the cleavable peptide comprises an amino acid sequence selected from SEQ ID NOs: 47-88, 464-469, and 479-508. In some embodiments, a spacer linker is directly linked to the N-terminus and/or the C-terminus of the cleavable peptide. In some embodiments, the spacer linker comprises an amino acid sequence selected from SEQ ID NOs: 89-112 and 415-420. In some embodiments, at least one amino acid but no more than 20, 30, 40, or 50 amino acids is directly linked to the N-terminus of the masking peptide. In some embodiments, the at least one amino acid is alanine (A) or glycine-alanine (GA). In some embodiments, the at least one amino acid directly linked to the N-terminus of the masking peptide is a detectable tag. In some embodiments, the at least one amino acid directly linked to the N-terminus of the masking peptide is YPYDVPDYA (SEQ ID NO: 398), DYKDDDDK (SEQ ID NO:399), EQKLISEEDL (SEQ ID NO:400), or GLN-DIFEAQKIEWHE (SE ID NO: 401).

Also provided herein, in some embodiments, is a masked antibody comprising a) an antibody or antigen-binding fragment thereof that binds to CTLA4 (e.g., human CTLA4), wherein the antibody or antigen-binding fragment thereof comprises a first chain and a second chain, and b) a masking peptide comprising an amino acid sequence selected from SEQ ID NOs: 1-46, wherein the masking peptide is linked via a linker comprising a cleavable peptide to an amino-terminus of the first chain and of the second chain of the antibody or antigen-binding fragment thereof. In some embodiments, the antibody or antigen-binding fragment thereof that binds to CTLA4 is any anti-CTLA4 antibody or antigen-binding fragment thereof described herein. In some embodiments, the antibody or antigen-binding fragment thereof comprises two first chains and two second chains. In some embodiments, the first chain is a light chain and the second chain is a heavy chain. In some embodiments, the first chain is a light chain variable domain and the second chain is a heavy chain variable domain. In some embodiments, the cleavable peptide comprises an amino acid sequence selected from SEQ ID NOs: 47-88, 464-469, and 479-508. In some embodiments, a spacer linker is directly linked to the N-terminus and/or the C-terminus of the cleavable peptide. In some embodiments, the spacer linker comprises an amino acid sequence selected from SEQ ID NOs: 89-112 and 415-420. In some embodiments, at least one amino acid but no more than 20, 30, 40, or 50 amino acids is directly linked to the N-terminus of the masking peptide. In some embodiments, the at least one amino acid is alanine (A) or glycine-alanine (GA). In some embodiments, the at least one amino acid directly linked to the N-terminus of the masking peptide is a detectable tag. In some embodiments, the at least one amino acid directly linked to the N-terminus of the masking peptide is YPYDVPDYA (SEQ ID NO: 398), DYKDDDDK (SEQ ID NO:399), EQKLISEEDL (SEQ ID NO:400), or GLN-DIFEAQKIEWHE (SE ID NO: 401).

Further provided herein, in some embodiments, is a masked antibody comprising a) an antibody or antigen-binding fragment thereof that binds to CTLA4 (e.g., human CTLA4), wherein the antibody or antigen-binding fragment thereof comprises a first chain and a second chain, and b) a masking peptide comprising an amino acid sequence selected from SEQ ID NOs: 1-46, wherein the masking peptide is linked via a linker comprising a cleavable peptide to a carboxy-terminus of the first chain and the second chain of the antibody or antigen-binding fragment thereof. In some embodiments, the antibody or antigen-binding fragment thereof that binds to CTLA4 is any anti-CTLA4 antibody or antigen-binding fragment thereof described herein. In some embodiments, the antibody or antigen-binding fragment thereof comprises two first chains and two second chains. In some embodiments, the first chain is a light chain and the second chain is a heavy chain. In some embodiments, the first chain is a light chain variable domain and the second chain is a heavy chain variable domain. In some embodiments, the cleavable peptide comprises an amino acid sequence selected from SEQ ID NOs: 47-88, 464-469, and 479-508. In some embodiments, a spacer linker is directly linked to the N-terminus and/or the C-terminus of the cleavable peptide. In some embodiments, the spacer linker comprises an amino acid sequence selected from SEQ ID NOs: 89-112 and 415-420. In some embodiments, at least one amino acid but no more than 20, 30, 40, or 50 amino acids is directly linked to the N-terminus of the masking peptide. In some embodiments, the at least one amino acid is alanine (A) or glycine-alanine (GA). In some embodiments, the at least one amino acid directly linked to the N-terminus of the masking peptide is a detectable tag. In some embodiments, the at least one amino acid directly linked to the N-terminus of the masking peptide is YPYDVPDYA (SEQ ID NO: 398), DYKDDDDK (SEQ ID NO:399), EQKLISEEDL (SEQ ID NO:400), or GLNDIFEAQKIEWHE (SE ID NO: 401).

Further provided herein, in some embodiments, is masking antibody comprising an a) an antibody or antigen-binding fragment thereof that binds to CTLA4 (e.g., human CTLA4), and b) a masking peptide comprising an amino acid sequence selected from SEQ ID NOs: 1-46, wherein a masking peptide is linked via a linker comprising a cleavable peptide to the C-terminus or N-terminus of a first chain of the antibody and a masking peptide is linked via a linker comprising a cleavable peptide to the C-terminus or N-terminus of a second chain of the antibody. In some embodiments, the antibody or antigen-binding fragment thereof that binds to CTLA4 is any anti-CTLA4 antibody or antigen-binding fragment thereof described herein. In some embodiments, the a) the first chain of the antibody is a light chain and the second chain of the antibody is a light chain: b) the first chain of the antibody is a heavy chain and the second chain of the antibody is a heavy chain; or c) the first chain of the antibody is a light chain and the second chain of the antibody is a heavy chain. Thus, in some embodiments, the isolated antibody comprises a masking peptide on the C-terminus and/or N-terminus of each of two light chains and the C-terminus and/or N-terminus of each of two heavy chains. In some embodiments, the cleavable peptide comprises an amino acid sequence selected from SEQ ID NOs: 47-88, 464-469, and 479-508. In some embodiments, a spacer linker is directly linked to the N-terminus and/or the C-terminus of the cleavable peptide. In some embodiments, the spacer linker comprises an amino acid sequence selected from SEQ ID NOs: 89-112 and 415-420. In some embodiments, at least one amino acid but no more than 20, 30, 40, or 50 amino acids is directly linked to the N-terminus of the masking peptide. In some embodiments, the at least one amino acid is alanine (A) or glycine-alanine (GA). In some embodiments, the at least one amino acid directly linked to the N-terminus of the masking peptide is a detectable tag. In some embodiments, the at least one amino acid directly linked to the N-terminus of the masking peptide is YPYDVPDYA (SEQ ID NO:398), DYKDDDDK (SEQ ID NO:399), EQKLISEEDL (SEQ ID NO:400), or GLNDIFEAQKIEWHE (SE ID NO: 401).

Also provided herein, in some embodiments, is a masked anti-CTLA4 antibody or antigen-binding fragment thereof comprising: a) an anti-CTLA4 antibody or antigen-binding fragment thereof comprising a light chain variable region comprising a CDR-L1 comprising the amino acid sequence of SEQ ID NO:438, a CDR-L2 comprising the amino acid sequence of SEQ ID NO:439, and a CDR-L3 comprising the amino acid sequence of SEQ ID NO:440; and a heavy chain variable region comprising a CDR-H1 comprising the amino acid sequence of SEQ ID NO:441, a CDR-H2 comprising the amino acid sequence of SEQ ID NO:442, and a CDR-H3 comprising the amino acid sequence of SEQ ID NO:443: b) a masking peptide comprising an amino acid sequence selected from the group consisting of SEQ ID NOs: 1-46; and c) a cleavable peptide comprising an amino acid sequence selected from the group consisting of SEQ ID NOs: 47-88, 464-469, and 479-508. In some embodiments, the cleavable peptide comprises the amino acid sequence of SEQ ID NO: 50. In some embodiments, the cleavable peptide comprises the amino acid sequence of SEQ ID NO: 86. In some embodiments, at least one amino acid but no more than 20, 30, 40, or 50 amino acids is directly linked to the N-terminus of the masking peptide. In some embodiments, the at least one amino acid is alanine (A) or glycine-alanine (GA). In some embodiments, the at least one amino acid directly linked to the N-terminus of the masking peptide is a detectable tag. In some embodiments, the at least one amino acid directly linked to the N-terminus of the masking peptide is YPYDVPDYA (SEQ ID NO:398), DYKDDDDK (SEQ ID NO:399), EQKLISEEDL (SEQ ID NO:400), or GLNDIFEAQKIEWHE (SE ID NO: 401). In some embodiments, the masking peptide is linked to the cleavable peptide, and the cleavable peptide is linked to the light chain variable region or the heavy chain variable region. In some embodiments, the masked anti-CTLA4 antibody or antigen-binding fragment thereof further comprises a spacer linker comprising an amino acid sequence selected from the group consisting of SEQ ID NOs: 89-112 and 415-420 that links the masking peptide to the cleavable peptide, and further comprises a spacer linker comprising an amino acid sequence selected from the group consisting of SEQ ID NOs: 89-112 and 415-420 that links the cleavable peptide to the light chain variable region or the heavy chain variable region. In some embodiments, the spacer linker that links the masking peptide to the cleavable peptide comprises the amino acid sequence of SEQ ID NO: 420, and the spacer linker that links the cleavable peptide to the light chain variable region or the heavy chain variable region comprises the amino acid sequence of SEQ ID NO: 102. In some embodiments, the spacer linker that links the masking peptide to the cleavable peptide comprises the amino acid sequence of SEQ ID NO: 96, and the spacer linker that links the cleavable peptide to the light chain variable region or the heavy chain variable region comprises the amino acid sequence of SEQ ID NO: 102. In some embodiments, the light chain variable region comprises the amino acid sequence of SEQ ID NO: 322, and the heavy chain variable region comprises the amino acid sequence of SEQ ID NO: 324. In some embodiments, the masked anti-CTLA4 antibody or antigen-binding fragment thereof comprises a heavy chain comprising the amino acid sequence of SEQ ID NO: 421 and a light chain comprising the amino acid sequence of SEQ ID NO: 334, and a peptide comprising an amino acid sequence selected from the group consisting of SEQ ID NOs: 113-231 and 444-453. In some embodiments, the masked anti-CTLA4 antibody or antigen-binding fragment thereof comprises the amino acid sequence of SEQ ID NO: 421, and comprises an amino acid sequence that is selected from the group consisting of SEQ ID NOs: 358 and 422-431.

In one aspect, provided herein is an activatable masked anti-CTLA4 antibody or antigen-binding fragment thereof comprising a light chain variable region comprising the amino acid sequence of SEQ ID NO:232 and/or a heavy chain variable region comprising the amino acid sequence of SEQ ID NO:233. In a further aspect, provided herein is an activatable masked anti-CTLA4 antibody or antigen-binding fragment thereof comprising a light chain comprising the amino acid sequence selected from SEQ ID NOs: 237-318 and/or a heavy chain comprising the amino acid sequence selected from SEQ ID NOs: 319 or 320.

In one aspect, provided herein is an activatable masked anti-CTLA4 antibody or antigen-binding fragment thereof comprising a light chain variable region comprising the amino acid sequence selected from SEQ ID NOs: 321 or 322 and/or a heavy chain variable region comprising the amino acid sequence selected from SEQ ID NOs: 323 or 324. In some embodiments, provided herein is a masked anti-CTLA4 antibody or antigen-binding fragment thereof comprising a light chain variable region comprising the amino acid sequence of SEQ ID NO: 322, and a heavy chain variable region comprising the amino acid sequence of SEQ ID NO: 324. In a further aspect, provided herein is an activatable masked anti-CTLA4 antibody or antigen-binding fragment thereof comprising a light chain comprising the amino acid sequence selected from SEQ ID NOs: 327-341 and/or comprising a heavy chain comprising the amino acid sequence selected from SEQ ID NOs: 366-380, 421, and 478. In yet another further aspect, provided herein is an activatable masked anti-CTLA4 antibody or antigen-binding fragment thereof comprising a light chain comprising the amino acid sequence selected from SEQ ID NOs: 327, 334, or 342-365 and/or comprising a heavy chain comprising the amino acid sequence selected from SEQ ID NOs: 366 or 380-397. In some embodiments, provided herein is a masked anti-CTLA4 antibody or antigen-binding fragment thereof comprising a light chain comprising the amino acid sequence of SEQ ID NO: 334, and a heavy chain comprising the amino acid sequence of SEQ ID NO: 421. In some embodiments, provided herein is a masked anti-CTLA4 antibody or antigen-binding fragment thereof comprising a light chain comprising the amino acid sequence of SEQ ID NO: 327, and a heavy chain comprising the amino acid sequence of SEQ ID NO: 478.

In some embodiments, provided herein is an activatable masked anti-CTLA4 antibody or antigen-binding fragment thereof comprising a heavy chain variable region comprising an amino acid sequence having at least 90%, 91%, 92%, 93%, 94%, 95%, 96%, 97%, 98%, or 99% sequence identity to an amino acid sequence of SEQ ID NO:233. In some embodiments, provided herein is an activatable masked anti-CTLA4 antibody or antigen-binding fragment thereof comprising a heavy chain variable domain comprising an amino acid sequence having at least 90%, 91%, 92%, 93%, 94%, 95%, 96%, 97%, 98%, or 99% sequence identity to an amino acid sequence selected from SEQ ID NOs: 323 or 324. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to CTLA4 (e.g., human CTLA4). In some embodiments, the substitutions, insertions, or deletions (e.g., 1, 2, 3, 4, or 5 amino acids) occur in regions outside the HVRs (i.e., in the FRs). In some embodiments, an activatable masked anti-CTLA4 antibody or antigen-binding fragment thereof comprises a heavy chain variable domain comprising an amino acid sequence of SEQ ID NO:233. In some embodiments, an activatable masked anti-CTLA4 antibody or antigen-binding fragment thereof comprises a heavy chain variable domain comprising an amino acid sequence selected from SEQ ID NOs: 323 or 324.

In some embodiments, provided herein is an activatable masked anti-CTLA4 antibody or antigen-binding fragment thereof comprising a light chain variable domain comprising an amino acid sequence having at least 90%, 91%, 92%, 93%, 94%, 95%, 96%, 97%, 98%, or 99% sequence identity to an amino acid sequence of SEQ ID NO:232. In some embodiments, provided herein is an activatable masked anti-CTLA4 antibody or antigen-binding fragment thereof comprising a light chain variable domain comprising an amino acid sequence having at least 90%, 91%, 92%, 93%, 94%, 95%, 96%, 97%, 98%, or 99% sequence identity to an amino acid sequence selected from SEQ ID NOs: 321 or 322. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to CTLA4 (e.g., human CTLA4). In some embodiments, the substitutions, insertions, or deletions (e.g., 1, 2, 3, 4, or 5 amino acids) occur in regions outside the HVRs (i.e., in the FRs). In some embodiments, an activatable masked anti-CTLA4 antibody or antigen-binding fragment thereof comprises a light chain variable domain comprising an amino acid sequence of SEQ ID NO:232. In some embodiments, an activatable masked anti-CTLA4 antibody or antigen-binding fragment thereof comprises a light chain variable domain comprising an amino acid sequence selected from SEQ ID NOs: 321 or 322.

In some embodiments, provided herein is an activatable masked anti-CTLA4 antibody or antigen-binding fragment thereof comprising a) an amino acid sequence comprising a masking peptide, a linker comprising a cleavable peptide, and a light chain; and b) an amino acid sequence comprising a heavy chain. In some embodiments, the amino acid sequence comprising the masking peptide, the linker comprising a cleavable peptide, and the light chain is selected from the group consisting of SEQ ID NOs: 358, 422, 424-426, and 428-431. In some embodiments, the amino acid sequence comprising the heavy chain comprises the amino acid sequence of SEQ ID NO: 421. In some embodiments, the amino acid sequence comprising the masking peptide, the linker comprising a cleavable peptide, and the light chain is selected from the group consisting of SEQ ID NOs: 358, 422, 424-426, and 428-431; and the amino acid sequence comprising the heavy chain comprises the amino acid sequence of SEQ ID NO: 421.

In some embodiments, provided herein is an activatable masked anti-CTLA4 antibody or antigen-binding fragment thereof comprising an amino acid sequence having or having about 70%, 75%, 80%, 85%, 90%, 91%, 92%, 93%, 94%, 95%, 96%, 97%, 98%, 99% or 100% homology to an amino acid sequence selected from the group consisting of SEQ ID NOs: 358 and 422-431; and/or comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the activatable masked anti-CTLA4 antibody or antigen-binding fragment thereof comprises an amino acid sequence having or having about 70%, 75%, 80%, 85%, 90%, 91%, 92%, 93%, 94%, 95%, 96%, 97%, 98%, 99% or 100% homology to an amino acid sequence selected from the group consisting of SEQ ID NOs: 358 and 422-431; and comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the activatable masked anti-CTLA4 antibody or antigen-binding fragment thereof comprises an amino acid sequence selected from the group consisting of SEQ ID NOs: 358 and 422-431; and/or comprises the amino acid sequence of SEQ ID NO: 421. In some embodiments, the activatable masked anti-CTLA4 antibody or antigen-binding fragment thereof comprises an amino acid sequence selected from the group consisting of SEQ ID NOs: 358 and 422-431; and comprises the amino acid sequence of SEQ ID NO: 421.

In some embodiments, provided herein is an activatable masked anti-CTLA4 antibody or antigen-binding fragment thereof comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 422; and comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the activatable masked anti-CTLA4 antibody or antigen-binding fragment thereof comprises the amino acid sequence of SEQ ID NO: 422, and the amino acid sequence of SEQ ID NO: 421.

In some embodiments, provided herein is an activatable masked anti-CTLA4 antibody or antigen-binding fragment thereof comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 358; and comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the activatable masked anti-CTLA4 antibody or antigen-binding fragment thereof comprises the amino acid sequence of SEQ ID NO: 358, and the amino acid sequence of SEQ ID NO: 421.

In some embodiments, provided herein is a masked anti-CTLA4 antibody or antigen-binding fragment thereof comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 423; and comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the activatable masked anti-CTLA4 antibody or antigen-binding fragment thereof comprises the amino acid sequence of SEQ ID NO: 423, and the amino acid sequence of SEQ ID NO: 421.

In some embodiments, provided herein is an activatable masked anti-CTLA4 antibody or antigen-binding fragment thereof comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 424; and comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the activatable masked anti-CTLA4 antibody or antigen-binding fragment thereof comprises the amino acid sequence of SEQ ID NO: 424, and the amino acid sequence of SEQ ID NO: 421.

In some embodiments, provided herein is an activatable masked anti-CTLA4 antibody or antigen-binding fragment thereof comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 425; and comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the activatable masked anti-CTLA4 antibody or antigen-binding fragment thereof comprises the amino acid sequence of SEQ ID NO: 425, and the amino acid sequence of SEQ ID NO: 421.

In some embodiments, provided herein is an activatable masked anti-CTLA4 antibody or antigen-binding fragment thereof comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 426; and comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the activatable masked anti-CTLA4 antibody or antigen-binding fragment thereof comprises the amino acid sequence of SEQ ID NO: 426, and the amino acid sequence of SEQ ID NO: 421.

In some embodiments, provided herein is a masked anti-CTLA4 antibody or antigen-binding fragment thereof comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 427; and comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the activatable masked anti-CTLA4 antibody or antigen-binding fragment thereof comprises the amino acid sequence of SEQ ID NO: 427, and the amino acid sequence of SEQ ID NO: 421.

In some embodiments, provided herein is an activatable masked anti-CTLA4 antibody or antigen-binding fragment thereof comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 428; and comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the activatable masked anti-CTLA4 antibody or antigen-binding fragment thereof comprises the amino acid sequence of SEQ ID NO: 428, and the amino acid sequence of SEQ ID NO: 421.

In some embodiments, provided herein is an activatable masked anti-CTLA4 antibody or antigen-binding fragment thereof comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 429; and an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the activatable masked anti-CTLA4 antibody or antigen-binding fragment thereof comprises the amino acid sequence of SEQ ID NO: 429, and the amino acid sequence of SEQ ID NO: 421.

In some embodiments, provided herein is an activatable masked anti-CTLA4 antibody or antigen-binding fragment thereof comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 430; and comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the activatable masked anti-CTLA4 antibody or antigen-binding fragment thereof comprises the amino acid sequence of SEQ ID NO: 430, and the amino acid sequence of SEQ ID NO: 421.

In some embodiments, provided herein is an activatable masked anti-CTLA4 antibody or antigen-binding fragment thereof comprising an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 431; and comprises an amino acid sequence having or having about 70%, 75%, 80%, 85%, 90%, 91%, 92%, 93%, 94%, 95%, 96%, 97%, 98%, 99% or 100% homology to the amino acid sequence of SEQ ID NO: 421. In some embodiments, the activatable masked anti-CTLA4 antibody or antigen-binding fragment thereof comprises the amino acid sequence of SEQ ID NO: 431, and the amino acid sequence of SEQ ID NO: 421.

There are five classes of immunoglobulins: IgA, IgD, IgE, IgG and IgM, having heavy chains designated α, δ, ε, γ and μ, respectively. The γ and α classes are further divided into subclasses e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. mAbs Vol 1 Issue 4 1-7) any of which are suitable for use in some of the embodiments herein. Common allotypic variants in human populations are those designated by the letters a,f,n,z or combinations thereof. In some of the embodiments herein, the antibody has an IgG1, IgG2, IgG3, or IgG4 isotype. In some embodiments, an activatable masked anti-CTLA4 antibody or antigen-binding fragment thereof provided herein has an IgG1 isotype (e.g., a human IgG1 isotype). In some embodiments, the antibody provided herein comprises a heavy chain constant domain comprising the amino acid sequence of SEQ ID NO: 235 or 236. In some embodiments, the antibody provided herein comprises a heavy chain constant domain comprising the amino acid sequence of SEQ ID NO: 326. In some embodiments, the antibody provided herein comprises a heavy chain constant domain comprising the amino acid sequence of SEQ ID NO: 463.

In some embodiments, the activatable masked anti-CTLA4 antibody or antigen-binding fragment thereof binds CTLA4 upon cleavage with a protease such as a protease described herein. In some embodiments, the cleavable peptide is a substrate for a protease that is co-localized in a region with a cell or a tissue expressing CTLA4.

In one aspect of the invention, polynucleotides encoding activatable masked anti-CTLA4 antibodies or antigen-binding fragments thereof are provided. In certain embodiments, vectors comprising polynucleotides encoding activatable masked anti-CTLA4 antibodies or antigen-binding fragments thereof are provided. In certain embodiments, host cells comprising such vectors are provided. In another aspect of the invention, compositions comprising activatable masked anti-CTLA4 antibodies described herein or polynucleotides encoding activatable masked anti-CTLA4 antibodies described herein are provided. In certain embodiments, a composition of the invention is a pharmaceutical formulation for the treatment of a neoplastic disease in which CTLA4 plays a role, such as those enumerated herein.

In some embodiments, the CTLA4 binding protein provided herein is a bispecific antibody capable of binding to CTLA4. Bispecific antibodies are monoclonal antibodies that have binding specificities for at least two different antigens. In some embodiments, one of the binding specificities is for CTLA4 and the other is for any other antigen. In certain embodiments, bispecific antibodies may bind to two different epitopes of CTLA4.

In some aspects, provided herein is a masked bispecific antibody comprising a) a light chain and a heavy chain of a first pair that specifically binds to CTLA4: b) a light chain and a heavy chain of a second pair that specifically binds to an antigen; and c) a masking peptide comprising an amino acid sequence selected from SEQ ID NOs: 1-46, wherein the masking peptide is linked via a linker comprising a cleavable peptide to the amino-terminus of the light chain and/or the heavy chain of the first pair. In some aspects, provided herein is a masked bispecific antibody comprising a) a light chain and a heavy chain of a first pair that specifically binds to CTLA4: b) a light chain and a heavy chain of a second pair that specifically binds to an antigen; and c) a masking peptide comprising an amino acid sequence selected from SEQ ID NOs: 1-46, wherein the masking peptide is linked via a linker comprising a cleavable peptide to the carboxy-terminus of the light chain and/or the heavy chain of the first pair. In some embodiments, the antigen is an antigen different from CTLA4. In some embodiments, the light chain of the first pair or the second pair is any light chain described herein. In some embodiments, the heavy chain of the first pair or the second pair is any light chain described herein. In some embodiments, the light chain of the first pair comprises a CDR-L1 comprising the amino acid sequence of SEQ ID NO:438, a CDR-L2 comprising the amino acid sequence of SEQ ID NO:439, and a CDR-L3 comprising the amino acid sequence of SEQ ID NO:440; and the heavy chain of the first pair comprises a CDR-H1 comprising the amino acid sequence of SEQ ID NO:441, a CDR-H2 comprising the amino acid sequence of SEQ ID NO:442, and a CDR-H3 comprising the amino acid sequence of SEQ ID NO:443. In some embodiments, the light chain of the second pair comprises a CDR-L1 comprising the amino acid sequence of SEQ ID NO:438, a CDR-L2 comprising the amino acid sequence of SEQ ID NO:439, and a CDR-L3 comprising the amino acid sequence of SEQ ID NO:440; and the heavy chain of the second pair comprises a CDR-H1 comprising the amino acid sequence of SEQ ID NO:441, a CDR-H2 comprising the amino acid sequence of SEQ ID NO:442, and a CDR-H3 comprising the amino acid sequence of SEQ ID NO:443. In some embodiments, the antigen is to a different epitope of CTLA4. In some embodiments, the cleavable peptide comprises an amino acid sequence selected from SEQ ID NOs: 47-88, 464-469, and 479-508. In some embodiments, a spacer linker is directly linked to the N-terminus and/or the C-terminus of the cleavable peptide. In some embodiments, the spacer linker comprises an amino acid sequence selected from SEQ ID NOs: 89-112 and 415-420. In some embodiments, at least one amino acid but no more than 20, 30, 40, or 50 amino acids is directly linked to the N-terminus of the masking peptide. In some embodiments, the at least one amino acid is alanine (A) or glycine-alanine (GA). In some embodiments, the at least one amino acid directly linked to the N-terminus of the masking peptide is a detectable tag. In some embodiments, the at least one amino acid directly linked to the N-terminus of the masking peptide is YPYDVPDYA (SEQ ID NO: 398), DYKDDDDK (SEQ ID NO:399), EQKLISEEDL (SEQ ID NO:400), or GLNDIFEAQKIEWHE (SE ID NO: 401).

Bispecific antibodies contemplated herein for use in the masked bispecific antibodies include murine bispecific antibodies, humanized bispecific antibodies, chimeric bispecific antibodies, and human bispecific antibodies. In some of the embodiments herein, the bispecific antibody has an IgG1, IgG2, IgG3, or IgG4 isotype. In some embodiments, a bispecific antibody provided herein has an IgG1 isotype (e.g., a human IgG1 isotype). In some embodiments, the antibody has an IgG1 isotype comprising amino acid substitutions or is expressed by cells that have no ability to a reduced ability to fucosylate the Fc glycan. that enhance effector function as described herein. In some embodiments, the masked bispecific antibody provided herein comprises a heavy chain constant domain comprising the amino acid sequence of SEQ ID NO: 235 or 236. In some embodiments, the masked bispecific antibody provided herein comprises a heavy chain constant domain comprising the amino acid sequence of SEQ ID NO:326. In some embodiments, the masked bispecific antibody provided herein comprises a heavy chain constant domain comprising the amino acid sequence of SEQ ID NO:463.

In one aspect, provided herein is an activatable masked anti-CTLA4 bispecific antibody comprising a light chain variable region comprising the amino acid sequence of SEQ ID NO:232 and/or a heavy chain variable region comprising the amino acid sequence of SEQ ID NO:233. In a further aspect, provided herein is an activatable masked anti-CTLA4 bispecific antibody comprising a light chain comprising the amino acid sequence selected from SEQ ID NOs: 237-318 and/or a heavy chain comprising the amino acid sequence selected from SEQ ID NOs: 319 or 320.

In one aspect, provided herein is an activatable masked anti-CTLA4 bispecific antibody comprising a light chain variable region comprising the amino acid sequence selected from SEQ ID NOs: 321 or 322 and/or a heavy chain variable region comprising the amino acid sequence selected from SEQ ID NOs: 323 or 324. In a further aspect, provided herein is an activatable masked anti-CTLA4 bispecific antibody comprising a light chain comprising the amino acid sequence selected from SEQ ID NOs: 327-341 and/or comprising a heavy chain comprising the amino acid sequence selected from SEQ ID NOs: 366-380, 421, and 478. In yet another further aspect, provided herein is an activatable masked anti-CTLA4 bispecific antibody comprising a light chain comprising the amino acid sequence selected from SEQ ID NOs: 327, 334, or 342-365 and/or comprising a heavy chain comprising the amino acid sequence selected from SEQ ID NOs: 366 or 380-397.

In some embodiments, provided herein is an activatable masked anti-CTLA4 bispecific antibody comprising a heavy chain variable region comprising an amino acid sequence having at least 90%, 91%, 92%, 93%, 94%, 95%, 96%, 97%, 98%, or 99% sequence identity to an amino acid sequence of SEQ ID NO:233. In some embodiments, provided herein is an activatable masked anti-CTLA4 bispecific antibody comprising a heavy chain variable domain comprising an amino acid sequence having at least 90%, 91%, 92%, 93%, 94%, 95%, 96%, 97%, 98%, or 99% sequence identity to an amino acid sequence selected from SEQ ID NOs: 323 or 324. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to CTLA4 (e.g., human CTLA4). In some embodiments, the substitutions, insertions, or deletions (e.g., 1, 2, 3, 4, or 5 amino acids) occur in regions outside the HVRs (i.e., in the FRs). In some embodiments, an activatable masked anti-CTLA4 bispecific antibody comprises a heavy chain variable domain comprising an amino acid sequence of SEQ ID NO:233. In some embodiments, an activatable masked anti-CTLA4 bispecific antibody comprises a heavy chain variable domain comprising an amino acid sequence selected from SEQ ID NOs: 323 or 324.

In some embodiments, provided herein is an activatable masked anti-CTLA4 bispecific antibody comprising a light chain variable domain comprising an amino acid sequence having at least 90%, 91%, 92%, 93%, 94%, 95%, 96%, 97%, 98%, or 99% sequence identity to an amino acid sequence of SEQ ID NO:232. In some embodiments, provided herein is an activatable masked anti-CTLA4 bispecific antibody comprising a light chain variable domain comprising an amino acid sequence having at least 90%, 91%, 92%, 93%, 94%, 95%, 96%, 97%, 98%, or 99% sequence identity to an amino acid sequence selected from SEQ ID NOs: 321 or 322. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to CTLA4 (e.g., human CTLA4). In some embodiments, the substitutions, insertions, or deletions (e.g., 1, 2, 3, 4, or 5 amino acids) occur in regions outside the HVRs (i.e., in the FRs). In some embodiments, an activatable masked anti-CTLA4 bispecific antibody comprises a light chain variable domain comprising an amino acid sequence of SEQ ID NO:232. In some embodiments, an activatable masked anti-CTLA4 bispecific antibody comprises a light chain variable domain comprising an amino acid sequence selected from SEQ ID NOs: 321 or 322.

In some embodiments, the CTLA4 binding protein provided herein is a chimeric receptor (e.g., chimeric antigen receptor (CAR)) capable of binding to CTLA4. CARs are molecules that combine antibody-based specificity for a desired antigen (e.g., CTLA4) with a T cell receptor-activating intracellular domain to generate a chimeric protein that exhibits a specific anti-tumor cellular activity. In one embodiment, provided herein is a chimeric receptor engineered to comprise an extracellular domain having a CTLA4 binding domain described herein fused to an intracellular signaling domain of the T cell antigen receptor complex zeta chain (e.g., CD3 zeta). The CTLA4 binding domain is engineered so that it is linked to a masking peptide, such as one described herein, via a linker comprising a cleavable peptide. The activatable masked chimeric receptor provide herein, when expressed in a T cell is able to redirect antigen recognition based on the antigen binding specificity upon cleavage by a protease recognizing the cleavable peptide. In some embodiments, the CTLA4 binding domain is preferably fused with an intracellular domain from one or more of a costimulatory molecule and a zeta chain. In some embodiments, the CTLA4 binding domain is fused with one or more intracellular domains selected from the group of a CD137 (4-1BB) signaling domain, a CD28 signaling domain, a CD3zeta signal domain, and any combination thereof.

In some aspects, provided herein is a masked chimeric receptor comprising a) a ligand-binding domain comprising a first chain and a second chain that binds to CTLA4; b) a masking peptide comprising an amino acid sequence selected from SEQ ID NOs: 1-46,c) a transmembrane domain; and d) an intracellular signaling domain comprising a signaling domain, wherein the masking peptide is linked via a linker comprising a cleavable peptide to the amino-terminus of the first chain and/or the second chain of the ligand-binding domain. In some embodiments the first chain is a light chain variable domain and the second chain is a heavy chain variable domain. In some of the embodiments of the activatable masked chimeric receptors described herein, the first chain comprises the amino acid sequence of SEQ ID NO:232; and/or the second chain comprises the amino acid sequence of SEQ ID NO: 233. In some embodiments, the first chain comprises the amino acid sequence selected from SEQ ID NOs: 321 or 322; and/or the second chain comprises the amino acid sequence selected from SEQ ID NOs: 323 or 324.

In some aspects, provided herein is a masked chimeric receptor comprising a) a ligand-binding domain comprising a first chain and a second chain that binds to CTLA4; b) a masking peptide comprising an amino acid sequence selected from SEQ ID NOs: 1-46,c) a transmembrane domain; and d) an intracellular signaling domain comprising a signaling domain, wherein the masking peptide is linked via a linker comprising a cleavable peptide to the carboxy-terminus of the first chain and/or the second chain of the ligand-binding domain. In some embodiments the first chain is a light chain variable domain and the second chain is a heavy chain variable domain. In some of the embodiments of the activatable masked chimeric receptors described herein, the first chain comprises the amino acid sequence of SEQ ID NO:232; and/or the second chain comprises the amino acid sequence of SEQ ID NO: 233. In some embodiments, the first chain comprises the amino acid sequence selected from SEQ ID NOs: 321 or 322; and/or the second chain comprises the amino acid sequence selected from SEQ ID NOs: 323 or 324.

In some of the embodiments of the activatable masked chimeric receptors described herein, the cleavable peptide comprises an amino acid sequence selected from SEQ ID NOs: 47-88, 464-469, and 479-508. In some embodiments, a spacer linker is directly linked to the N-terminus and/or the C-terminus of the cleavable peptide. In some embodiments, the spacer linker comprises an amino acid sequence selected from SEQ ID NOs: 89-112 and 415-420. In some embodiments, at least one amino acid but no more than 20, 30, 40, or 50 amino acids is directly linked to the N-terminus of the masking peptide. In some embodiments, the at least one amino acid is alanine (A) or glycine-alanine (GA). In some embodiments, the at least one amino acid directly linked to the N-terminus of the masking peptide is a detectable tag. In some embodiments, the at least one amino acid directly linked to the N-terminus of the masking peptide is YPYDVPDYA (SEQ ID NO: 398), DYKDDDDK (SEQ ID NO:399), EQKLISEEDL (SEQ ID NO:400), or GLN-DIFEAQKIEWHE (SEQ ID NO:401).

1. Binding Affinity

The strength, or affinity of immunological binding interactions, such as between an antibody and an antigen for which the antibody is specific, can be expressed in terms of the equilibrium dissociation constant ($K_D$) of the interaction, wherein a smaller $K_D$ represents a greater affinity. Immunological binding properties of proteins can be quantified using methods well known in the art. For example, one method comprises measuring the rates of antigen-binding protein (e.g., antibody)/antigen complex formation and dissociation, wherein those rates depend on the concentrations of the complex partners, the affinity of the interaction, and geometric parameters that equally influence the rate in both directions. Both the "on rate constant" (Kon) and the "off rate constant" (Koff) can be determined by calculation of the concentrations and the actual rates of association and dissociation. The ratio of Koff/Kon enables the cancelation of all parameters not related to affinity, and is equal to the equilibrium dissociation constant $K_D$. See Davies et al., Annual Rev Biochem. 59:439-473, (1990).

In some aspects, an activatable masked anti-CTLA4 binding protein (e.g., activatable masked anti-CTLA4 antibody or antigen-binding fragment thereof) described herein binds to CTLA4 with about the same or higher affinity upon cleavage with a protease as compared to the parental anti-CTLA4 binding protein that does not comprise a cleavable peptide. In certain embodiments, an anti-CTLA4 binding protein provided herein has an equilibrium dissociation constant ($K_D$) of ≤1 µM, ≤150 nM, ≤100 nM, ≤50 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In some embodiments, an anti-CTLA4 binding protein (e.g., anti-CTLA4 antibody or antigen-binding fragment thereof) provided herein binds to a target protein (e.g., CTLA4 protein) with an equilibrium dissociation constant ($K_D$) of about 50 pM to about 5 nM. Assays for assessing binding affinity are well known in the art, for example such as in in the assay described in Example 3A and Example 3B herein.

In some aspects, activatable masked anti-CTLA4 binding proteins (e.g., activatable masked anti-CTLA4 antibody or antigen-binding fragment thereof) that exhibit a desired occlusion ratio are provided. The term "occlusion ratio" as used herein refers a ratio of (a) a maximum detected level of a parameter under a first set of conditions to (b) a minimum detected value of that parameter under a second set of conditions. For example, in the context of an activatable masked anti-CTLA4 antibody or antigen-binding fragment thereof, the occlusion ratio refers to the ratio of (a) a maximum detected level of target protein (e.g., CTLA4 protein) binding to the activatable masked anti-CTLA4 antibody or antigen-binding fragment thereof in the presence of at least one protease capable of cleaving the cleavable peptide of the activatable masked anti-CTLA4 antibody or antigen-binding fragment thereof to (b) a minimum detected level of target protein (e.g., CTLA4 protein) binding to the activatable masked anti-CTLA4 antibody or antigen-binding fragment thereof in the absence of the protease. The occlusion ratio of an activatable masked anti-CTLA4 antibody or antigen-binding fragment thereof can be calculated as the ratio of the dissociation constant of an activatable masked anti-CTLA4 antibody or antigen-binding fragment thereof before cleavage with a protease to the dissociation constant of the activatable masked anti-CTLA4 antibody or antigen-binding fragment thereof after cleavage with a protease. In some embodiments, a greater occlusion ratio for the activatable masked anti-CTLA4 antibody or antigen-binding fragment thereof indicates that target protein (e.g., CTLA4 protein) bound by the activatable masked anti-CTLA4 antibody or antigen-binding fragment thereof occurs to a greater extent (e.g., predominantly occurs) in the presence of a protease capable of cleaving the cleavable peptide of the activatable masked anti-CTLA4 antibody or antigen-binding fragment thereof than in the absence of a protease. In some embodiments, activatable masked anti-CTLA4 binding proteins with an optimal occlusion ratio are provided herein. In some embodiments, an optimal occlusion ratio of an activatable masked anti-CTLA4 antibody or antigen-binding fragment thereof indicates the activatable masked anti-CTLA4 antibody or antigen-binding fragment thereof has desirable properties useful for the methods or compositions contemplated herein. In some embodiments, an activatable masked anti-CTLA4 binding protein provided herein exhibits an optimal occlusion ratio of about 20 to about 10,000, e.g., about 80 to about 100. In a further embodiment, the occlusion ratio is about 20 to about 7,500, about 20 to about 5,000, about 20 to about 2,500, about 20 to about 2,000, about 20 to about 1,000, about 20 to about 900, about 20 to about 800, about 20 to about 700, about 20 to about 600, about 20 to about 500, about 20 to about 400, about 20 to about 300, about 20 to about 200, about 20 to about 100, about 20 to about 50, about 30 to about 100, about 40 to about 100, about 50 to about 100, about 60 to about 100, about 70 to about 100, about 80 to about 100, or about 100 to about 1,000. In some embodiments, an activatable masked anti-CTLA4 binding protein provided herein exhibits an optimal occlusion ratio of about 80 to about 100. In some embodiments, an activatable masked anti-CTLA4 binding protein provided herein exhibits an optimal occlusion ratio of about 20 to about 1,000. Binding of an activatable masked anti-CTLA4 binding protein to a target protein (e.g., CTLA4 protein) before cleavage and/or after cleavage with a protease can be determined using techniques well known in the art such as by ELISA In some aspects, a masking peptide described herein binds to an anti-CTLA4 binding protein (e.g., an anti-CTLA4 antibody or antigen-binding fragment thereof) with lower affinity than the affinity between the anti-CTLA4 binding protein and a target protein (e.g., CTLA4 protein). In certain embodiments, a masking peptide provided herein binds to an anti-CTLA4 binding protein (e.g., an anti-CTLA4 antibody or antigen-binding fragment thereof) with an equilibrium dissociation constant ($K_D$) of ≤1 mM, ≤1 µM, ≤150 nM, ≤100 nM, ≤50 nM, ≤10 nM, ≤1 nM, ≤0.1 nM, ≤0.01 nM, or ≤0.001 nM (e.g., $10^{-5}$ M or less, e.g. from $10^{-5}$ M to $10^{-13}$ M, e.g., from $10^{-5}$ M to $10^{-7}$ M). In some embodiments, a masking peptide provided herein binds to an anti-CTLA4 binding protein (e.g., an anti-CTLA4 antibody or antigen-binding fragment thereof) with an equilibrium dissociation constant ($K_D$) of about 50 nM to about 50 µM. An exemplary assay for assessing binding affinity between the masking peptide and anti-CTLA4 binding protein (e.g., anti-CTLA4 antibody or antigen-binding fragment thereof) can be found in Example 2 herein.

2. Biological Activity Assays

In some aspects, an activatable masked anti-CTLA4 binding protein described herein reduces tumor volume in an in vivo murine tumor model. Assays for assessing reduction of tumor volume are well known in the art, for example such as in in the assay described in Example 4A and Example 4B herein.

III. Masked Anti-CTLA4 Binding Protein Preparation

The masked anti-CTLA4 binding proteins described herein are prepared using techniques available in the art, exemplary methods of which are described in more detail in the following sections.

1. Masked Anti-CTLA4 Binding Protein: Antibody Fragments

The present invention encompasses antibody fragments as masked anti-CTLA4 binding proteins. Masked antibody fragments may be generated by traditional means, such as enzymatic digestion, or by recombinant techniques. In certain circumstances there are advantages of using masked antibody fragments, rather than whole antibodies. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli* and other cell types, thus allowing the facile production of large amounts of these masked fragments. Alternatively, masked Fab'-SH fragments can be directly recovered from culture media and chemically coupled to form F(ab')$_2$ fragments (Carter et al., Bio/Technology 10:163-167 (1992)). According to another approach, masked F(ab')$_2$ fragments can be isolated directly from recombinant host cell culture. Masked Fab and F(ab')$_2$ fragment with increased in vivo half-life comprising FcRN/salvage receptor binding epitope residues are described in U.S. Pat. No. 5,869,046. Other techniques for the production of masked antibody fragments will be apparent to the skilled practitioner. In certain embodiments, a masked antibody is a single chain Fv fragment (scFv). See WO 93/16185; U.S. Pat. Nos. 5,571,894; and 5,587,458. Fv and scFv are the only species with intact combining sites that are devoid of constant regions: thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. Also, bi-scFv comprising two scFvs linked via a polypeptide linker can be used as a bispecific antibody. Alternatively, multi-scFv comprising three or more scFvs may be used as a multispecific antibody.

The present invention includes a linear antibody (e.g., as described in U.S. Pat. No. 5,641,870) or a single chain immunoglobulin comprising heavy and light chain sequences of the antibody linked via an appropriate linker. Such linear antibodies or immunoglobulins may be monospecific or bispecific. Such a single chain immunoglobulin can be dimerized to thereby maintain a structure and activities similar to those of the antibody, which is originally a tetramer. Also, the antibody of the present invention may be an antibody that has a single heavy chain variable region and has no light chain sequence. Such an antibody is called a single domain antibody (sdAb). These antibodies are also encompassed in the meaning of the functional fragment of the antibody according to the present invention.

2. Masked Anti-CTLA4 Binding Protein: Humanized Antibodies

The invention encompasses masked humanized antibodies. Humanized antibodies are masked according to the guidance provided herein. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter (Jones et al. (1986) Nature 321:522-525; Riechmann et al. (1988) Nature 332:323-327: Verhoeven et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

3. Masked Anti-CTLA4 Binding Protein: Human Antibodies

Human anti-CTLA4 antibodies of the invention can be constructed by combining Fv clone variable domain sequence(s) selected from human-derived phage display libraries with known human constant domain sequences(s). Alternatively, human monoclonal anti-CTLA4 antibodies of the invention can be made by the hybridoma method. Human myeloma and murine-human heteromyeloma cell lines for the production of human monoclonal antibodies have been described, for example, by Kozbor J. Immunol., 133:3001 (1984); Brodeur et al., Monoclonal Antibody Production Techniques and Applications, pp. 51-63 (Marcel Dekker, Inc., New York, 1987); and Boerner et al., J. Immunol., 147:86 (1991). Human antibodies are masked according to the guidance provided herein.

4. Masked Anti-CTLA4 Binding Protein: Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for CTLA4 and the other is for any other antigen. In certain embodiments, bispecific antibodies may bind to two different epitopes of CTLA4. Bispecific antibodies may also be used to localize cytotoxic agents to cells which express CTLA4. Bispecific antibodies can be prepared as full length antibodies or antibody fragments (e.g. F(ab')$_2$ bispecific antibodies). Bispecific antibodies are masked according to the guidance provided herein.

Methods for making bispecific antibodies are known in the art. See Milstein and Cuello, Nature, 305:537 (1983), WO 93/08829 published May 13, 1993, Traunecker et al., EMBO J., 10:3655 (1991): Kontermann and Brinkmann, Drug Discovery Today, 20 (7): 838-847. For further details of generating bispecific antibodies see, for example, Suresh et al., Methods in Enzymology, 121:210 (1986). Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking method. Suitable cross-linking agents are well known in the art, and are disclosed in U.S. Pat. No. 4,676,980, along with a number of cross-linking techniques.

5. Masked Anti-CTLA4 Binding Protein: Single-Domain Antibodies

In some embodiments, a single-domain antibody is masked in accordance with the guidance provided herein. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.: see, e.g., U.S. Pat. No. 6,248,516 B1). In one embodiment, a single-domain antibody consists of all or a portion of the heavy chain variable domain of an antibody.

6. Masked Anti-CTLA4 Binding Protein: Antibody Variants

In some embodiments, amino acid sequence modification(s) of the masked antibodies described herein are contemplated. For example, it may be desirable to improve the binding affinity and/or other biological properties of the masked antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as Arg, Asp, His, Lys, and Glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

In some embodiments, FcRn mutations that improve pharmacokinetics include, but are not limited to, M428L, T250Q/M428L, M252Y/S254T/T256E, P257I/N434H, D376V/N434H, P257I/Q3111, N434A, N434W, M428L/N434S, V259I/V308F, M252Y/S254T/T256E, V259I/V308F/M428L, T307Q/N434A, T307Q/N434S, T307Q/E380A/N434A, V308P/N434A, N434H, V308P. In some embodiments, such mutations enhance antibody binding to FcRn at low pH but do not change the antibody affinity at neutral pH.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

In certain embodiments, a glycosylation variant comprises an Fc region, wherein a carbohydrate structure attached to the Fc region lacks fucose or has reduced fucose. Such variants have improved ADCC function. Optionally, the Fc region further comprises one or more amino acid substitutions therein which further improve ADCC, for example, substitutions at positions 298, 333, and/or 334 of the Fc region (EU numbering of residues). Examples of publications related to "afucosylated," "defucosylated" or "fucose-deficient" antibodies include: US 2003/0157108: WO 2000/61739: WO 2001/29246; US 2003/0115614: US 2002/0164328: US 2004/0093621: US 2004/0132140; US 2004/0110704; US 2004/0110282; US 2004/0109865: WO 2003/085119: WO 2003/084570; WO 2005/035586: WO 2005/035778: WO2005/053742: Okazaki et al. J. Mol. Biol. 336:1239-1249 (2004): Yamane-Ohnuki et al. Biotech. Bioeng. 87:614 (2004). Examples of cell lines producing defucosylated antibodies include Lec13 CHO cells deficient in protein fucosylation (Ripka et al. Arch. Biochem. Biophys. 249:533-545 (1986): US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. Biotech. Bioeng. 87:614 (2004)), and cells overexpressing β1,4-N-acetylglycosminyltransferase III (GnT-III) and Golgi μ-mannosidase II (ManII).

In any of the embodiments herein, the masked anti-CTLA4 binding proteins can be engineered to improve antibody-dependent cell-mediated cytotoxicity (ADCC) activity. In some embodiments, the masked anti-CTLA4 binding protein may be produced in a cell line having a alpha1,6-fucosyltransferase (Fut8) knockout. In some further embodiments, the masked anti-CTLA4 binding protein may be produced in a cell line overexpressing β1,4-N-acetylglycosminyltransferase III (GnT-III). In further embodiments, the cell line additionally overexpresses Golgi μ-mannosidase II (ManII). In some of the embodiments herein, the masked anti-CTLA4 binding protein may comprise at least one amino acid substitution in the Fc region that improves ADCC activity.

In one embodiment, the masked antibody is altered to improve its serum half-life. To increase the serum half-life of the antibody, one may incorporate a FcRN/salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule (US 2003/0190311, U.S. Pat. Nos. 6,821,505; 6,165,745; 5,624,821; 5,648,260; 6,165,745; 5,834,597).

Another type of variant is an amino acid substitution variant. These variants have at least one amino acid residue in the antibody molecule replaced by a different residue. Sites of interest for substitutional mutagenesis include the hypervariable regions, but FR alterations are also contemplated. Conservative substitutions are shown in Table 2 under the heading of "preferred substitutions." If such substitutions result in a desirable change in biological activity, then more substantial changes, denominated "exemplary substitutions" in Table 2, or as further described below in reference to amino acid classes, may be introduced and the products screened.

TABLE 2

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or c) the bulk of the side chain. Amino acids may be grouped according to similarities in the properties of their side chains (in A. L. Lehninger, in Biochemistry, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser(S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:
(1) hydrophobic: Norleucine, Met, Ala. Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g., a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibodies thus generated are displayed from filamentous phage particles as fusions to at least part of a phage coat protein (e.g., the gene III product of M13)

packaged within each particle. The phage-displayed variants are then screened for their biological activity (e.g., binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the masked antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In some embodiments, an activatable masked anti-CTLA4 binding protein (e.g., activatable masked anti-CTLA4 antibody or antigen-binding fragment thereof, or activatable masked anti-CTLA4 bispecific antibody) provided herein has an IgG1 isotype with enhanced effector function. In some embodiments, the activatable masked anti-CTLA4 antibody or antigen-binding fragment thereof is afucosylated. In some embodiments, the activatable masked anti-CTLA4 bispecific antibody is afucosylated. In some embodiments, the activatable masked anti-CTLA4 antibody or antigen-binding fragment thereof has increased levels of mannose moieties. In some embodiments, the activatable masked anti-CTLA4 antibody or antigen-binding fragment thereof has increased levels of bisecting glycan moieties. In some embodiments, the activatable masked anti-CTLA4 bispecific antibody has increased levels of mannose moieties. In some embodiments, the IgG1 comprises amino acid mutations.

In some embodiments, an activatable masked anti-CTLA4 antibody or antigen-binding fragment thereof, or activatable masked anti-CTLA4 bispecific antibody provided herein has an IgG1 isotype (e.g., a human IgG1 isotype). In one embodiment, the IgG1 comprises the amino acid substitutions S298A, E333A, and K334A wherein the amino acid residues are numbered according to the EU index as in Kabat. In one embodiment, the IgG1 comprises the amino acid substitutions S239D and I332E wherein the amino acid residues are numbered according to the EU index as in Kabat. In one embodiment, the IgG1 comprises the amino acid substitutions S239D, A330L, and I332E wherein the amino acid residues are numbered according to the EU index as in Kabat. In one embodiment, the IgG1 comprises the amino acid substitutions P247I and A339D or A339Q wherein the amino acid residues are numbered according to the EU index as in Kabat. In one embodiment, the IgG1 comprises the amino acid substitutions D280H, K290S with or without S298D or S298V wherein the amino acid residues are numbered according to the EU index as in Kabat. In one embodiment, the IgG1 comprises the amino acid substitutions F243L, R292P, and Y300L wherein the amino acid residues are numbered according to the EU index as in Kabat. In one embodiment, the IgG1 comprises the amino acid substitutions F243L, R292P, Y300L, and P396L wherein the amino acid residues are numbered according to the EU index as in Kabat. In one embodiment, the IgG1 comprises the amino acid substitutions F243L, R292P, Y300L, V305I, and P396L wherein the amino acid residues are numbered according to the EU index as in Kabat. In one embodiment, the IgG1 comprises the amino acid substitutions G236A, S239D, and I332E wherein the amino acid residues are numbered according to the EU index as in Kabat. In one embodiment, the IgG1 comprises the amino acid substitutions K326A and E333A wherein the amino acid residues are numbered according to the EU index as in Kabat. In one embodiment, the IgG1 comprises the amino acid substitutions K326W and E333S wherein the amino acid residues are numbered according to the EU index as in Kabat. In one embodiment, the IgG1 comprises the amino acid substitutions K290E or K290N, S298G, T299A, and/or K326E wherein the amino acid residues are numbered according to the EU index as in Kabat.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter Nature 322:738-40 (1988); U.S. Pat. Nos. 5,648,260; 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. J. Biol. Chem. 9 (2): 6591-6604 (2001). Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al. J. Immunol. 164:4178-4184 (2000).

7. Masked Antibody—Drug Conjugates

The invention also provides masked antibody-drug conjugates (ADCs) comprising an activatable masked anti-CTLA4 binding protein provided herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, the one or more drugs conjugated to the antibody-drug conjugate, includes but is not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)): an anthracycline such as daunomycin or doxorubicin (see Kratz et al., Current Med. Chem. 13:477-523 (2006): Jeffrey et al., Bioorganic & Med. Chem. Letters 16:358-362 (2006): Torgov et al., Bioconj. Chem. 16:717-721 (2005): Nagy et al., Proc. Natl. Acad. Sci. USA 97:829-834 (2000): Dubowchik et al., Bioorg. & Med. Chem. Letters 12:1529-1532 (2002): King et al., J. Med. Chem. 45:4336-4343 (2002); and U.S. Pat. No. 6,630,579); methotrexate; vindesine: a taxane such as docetaxel, paclitaxel, larotaxel, tesetaxel, and ortataxel: a trichothecene; and CC1065.

In another embodiment the one or more drugs conjugated to the antibody-drug conjugate, includes but is not limited to an inhibitor of tubulin polymerization (e.g., maytansinoids and auristatins), DNA damaging agents (e.g., pyrrolobenzodiazepine (PBD) dimers, calicheamicins, duocarmycins and indo-linobenzodiazepine dimers), and DNA synthesis inhibitors (e.g., exatecan derivative Dxd).

In another embodiment, an antibody-drug conjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an antibody-drug conjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an activatable masked anti-CTLA4 binding protein (e.g., activatable masked anti-CTLA4 antibody or antigen-binding fragment thereof) and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992): U.S. Pat. No. 5,208,020) may be used.

The ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate) which are commercially available (e.g., from Pierce Biotechnology, Inc., Rockford, IL., U.S.A).

8. Vectors, Host Cells, and Recombinant Methods

For recombinant production of an activatable masked anti-CTLA4 binding proteins of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

9. Generating Binding Proteins Using Prokaryotic Host Cells a) Vector Construction Polynucleotide sequences encoding polypeptide components of the activatable masked anti-CTLA4 binding proteins of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes-encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (Trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20:269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, lpp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed with or without the sequences for the masking peptide, linker sequence, etc., folded and assembled to form functional immunoglobulins within the cytoplasm. Certain host strains (e.g., the *E. coli* trxB-strains) provide cytoplasm conditions that are favorable for disulfide bond formation, thereby permitting proper folding and assembly of expressed protein subunits. Proba and Pluckthun Gene, 159:203 (1995).

Activatable masked anti-CTLA4 binding proteins of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

Prokaryotic host cells suitable for expressing activatable masked anti-CTLA4 binding protein of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuΔ (ΔtonΔ) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli*λ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia,* or *Salmonella* species can be suitably used as the host when well-known plasmids such as pBR322, pBR325, pACYC177, or pKN410 are used to supply the replicon. Typically, the host cell should secrete minimal amounts of proteolytic enzymes, and additional protease inhibitors may desirably be incorporated in the cell culture.

b) Binding Protein Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the activatable masked anti-CTLA4 binding proteins of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. In certain embodiments, for *E. coli* growth, growth temperatures range from about 20° C. to about 39° C.; from about 25° C. to about 37° C.; or about 30° C. The pH of the medium may be any pH ranging from about 5 to about 9, depending mainly on the host organism. In certain embodiments, for *E. coli*, the pH is from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In certain embodiments, the phosphate-limiting medium is the C.R.A.P. medium (see, e.g., Simmons et al., J. Immunol. Methods (2002), 263:133-147). A variety of other inducers may be used, according to the vector construct employed, as is known in the art.

In one embodiment, the expressed activatable masked anti-CTLA4 binding proteins of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, activatable masked anti-CTLA4 binding protein production is conducted in large quantity by a fermentation process. Various large-scale fed-batch fermentation procedures are available for production of recombinant proteins. Large-scale fermentations have at least 1000 liters of capacity, and in certain embodiments, about 1,000 to 100,000 liters of capacity. These fermenters use agitator impellers to distribute oxygen and nutrients, especially glucose. Small scale fermentation refers generally to fermentation in a fermenter that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis, trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J. Biol. Chem. 274:19601-19605: Georgiou et al., U.S. Pat. No. 6,083,715: Georgiou et al., U.S. Pat. No. 6,027,888; Bothmann and Pluckthun (2000) J. Biol. Chem. 275:17100-17105: Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra: Georgiou et al., U.S. Pat. No. 5,264,365: Georgiou et al., U.S. Pat. No. 5,508,192: Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

c) Binding Protein Purification

In one embodiment, the masked antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from *Staphylococcus aureus* which binds with a high affinity to the Fc region of antibodies. Lindmark et al (1983) J. Immunol. Meth. 62:1-13. The solid phase to which Protein A is immobilized can be a column comprising a glass or silica surface, or a controlled pore glass column or a silicic acid column. In some applications, the column is coated with a reagent, such as glycerol, to possibly prevent non-specific adherence of contaminants.

As the first step of purification, a preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

10. Generating Binding Proteins Using Eukaryotic Host Cells

A vector for use in a eukaryotic host cell generally includes one or more of the following non-limiting components: a signal sequence, an origin of replication, one or more marker genes, an enhancer element, a promoter, and a transcription termination sequence.

a) Signal Sequence Component

A vector for use in a eukaryotic host cell may also contain a signal sequence or other polypeptide having a specific cleavage site at the N-terminus of the mature protein or polypeptide of interest. The heterologous signal sequence selected may be one that is recognized and processed (i.e., cleaved by a signal peptidase) by the host cell. In mammalian cell expression, mammalian signal sequences as well as viral secretory leaders, for example, the herpes simplex gD signal, are available. The DNA for such a precursor region is ligated in reading frame to DNA encoding the antibody.

b) Origin of Replication

Generally, an origin of replication component is not needed for mammalian expression vectors. For example, the SV40 origin may typically be used only because it contains the early promoter.

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the activatable masked anti-CTLA4 binding protein encoding nucleic acid, such as DHFR, thymidine kinase, metallothionein-I and -II, primate metallothionein genes, adenosine deaminase, ornithine decarboxylase, etc.

For example, in some embodiments, cells transformed with the DHFR selection gene are first identified by culturing all of the transformants in a culture medium that contains methotrexate (Mtx), a competitive antagonist of DHFR. In some embodiments, an appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an activatable masked anti-CTLA4 binding protein, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199. Host cells may include NS0, including cell lines deficient in glutamine synthetase (GS). Methods for the use of GS as a selectable marker for mammalian cells are described in U.S. Pat. Nos. 5,122,464 and 5,891,693.

d) Promoter Component

Expression and cloning vectors usually contain a promoter that is recognized by the host organism and is operably linked to nucleic acid encoding a activatable masked anti-CTLA4 binding protein of interest. Promoter sequences are known for eukaryotes. For example, virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. In certain embodiments, any or all of these sequences may be suitably inserted into eukaryotic expression vectors.

Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982), describing expression of human β-interferon cDNA in murine cells under the control of a thymidine kinase promoter from herpes simplex virus. Alternatively, the Rous Sarcoma Virus long terminal repeat can be used as the promoter.

e) Enhancer Element Component

Transcription of DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the human cytomegalovirus early promoter enhancer, the murine cytomegalovirus early promoter enhancer, the polyoma enhancer on the late side of the replication origin, and adenovirus enhancers. See also Yaniv, Nature 297:17-18 (1982) describing enhancer elements for activation of eukaryotic promoters. The enhancer may be spliced into the vector at a position 5' or 3' to the antibody polypeptide-encoding sequence, but is generally located at a site 5' from the promoter.

f) Transcription Termination Component

Expression vectors used in eukaryotic host cells may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651): human embryonic kidney line (293 or 293 cells subcloned for growth in suspension culture, Graham et al., J. Gen Virol. 36:59 (1977)): baby hamster kidney cells (BHK, ATCC CCL 10): Chinese hamster ovary cells/-DHFR (CHO, Urlaub et al., Proc. Natl. Acad. Sci. USA 77:4216 (1980)): murine sertoli cells (TM4, Mather, Biol. Reprod. 23:243-251 (1980)): monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442): human lung cells (W138, ATCC CCL 75); human liver cells (Hep G2, HB 8065); murine mammary tumor (MMT 060562, ATCC CCL51): TRI cells (Mather et al., Annals N.Y. Acad. Sci. 383:44-68 (1982)): MRC 5 cells: FS4 cells; and a human hepatoma line (Hep G2).

Host cells are transformed with the above-described-expression or cloning vectors for activatable masked anti-CTLA4 binding protein production and cultured in conventional nutrient media modified as appropriate for inducing promoters, selecting transformants, or amplifying the genes encoding the desired sequences.

h) Culturing the Host Cells

The host cells used to produce activatable masked anti-CTLA4 binding proteins of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657, 866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other supplements may also be included at appropriate concentrations that would be known to those skilled in the art. The culture conditions, such as temperature, pH, and the like, are those previously used with the host cell selected for expression, and will be apparent to the ordinarily skilled artisan.

i) Purification of Binding Protein

When using recombinant techniques, the activatable masked anti-CTLA4 binding proteins can be produced intracellularly, or directly secreted into the medium. If the antibody is produced intracellularly, as a first step, the particulate debris, either host cells or lysed fragments, may be removed, for example, by centrifugation or ultrafiltration. Where the activatable masked anti-CTLA4 binding protein is secreted into the medium, supernatants from such expression systems may be first concentrated using a commercially available protein concentration filter, for example, an Amicon or Millipore Pellicon ultrafiltration unit. A protease inhibitor such as PMSF may be included in any of the foregoing steps to inhibit proteolysis, and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a convenient technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Methods 62:1-13 (1983)). Protein G is recommended for all murine isotypes and for human γ3 (Guss et al., EMBO J. 5:15671575 (1986)). The matrix to which the affinity ligand is attached may be agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the masked binding protein of interest and contaminants may be subjected to further purification, for example, by low pH hydrophobic interaction chromatography using an elution buffer at a pH between about 2.5-4.5, performed at low salt concentrations (e.g., from about 0-0.25M salt).

In general, various methodologies for preparing antibodies for use in research, testing, and clinical use are well-established in the art, consistent with the above-described methodologies and/or as deemed appropriate by one skilled in the art for a particular antibody of interest.

IV. Compositions

In some aspects, also provided herein are compositions (e.g., pharmaceutical composition) comprising any of the activatable masked anti-CTLA4 binding proteins described herein.

Therapeutic formulations are prepared for storage by mixing the active ingredient having the desired degree of purity with optional pharmaceutically acceptable carriers, excipients or stabilizers (Remington: The Science and Practice of Pharmacy, 20th Ed., Lippincott Williams & Wiklins, Pub., Gennaro Ed., Philadelphia, Pa. 2000). Acceptable carriers, excipients, or stabilizers are nontoxic to recipients at the dosages and concentrations employed, and include buffers, antioxidants including ascorbic acid, methionine, Vitamin E, sodium metabisulfite: preservatives, isotonicifiers, stabilizers, metal complexes (e.g. Zn-protein complexes): chelating agents such as EDTA and/or non-ionic surfactants.

Buffers can be used to control the pH in a range which optimizes the therapeutic effectiveness, especially if stability is pH dependent. Buffers can be present at concentrations ranging from about 20 mM to about 250 mM. Suitable buffering agents for use with the present invention include both organic and inorganic acids and salts thereof. For example, citrate, phosphate, succinate, tartrate, fumarate, gluconate, oxalate, lactate, acetate. Additionally, buffers may be comprised of histidine and trimethylamine salts such as Tris.

Preservatives can be added to prevent microbial growth, and are typically present in a range from about 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" can be present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between about 0.1% to about 25% by weight or between about 1 to about 5% by weight, taking into account the relative amounts of the other ingredients. In some embodiments, tonicity agents include polyhydric sugar alcohols, trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above): amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, $\alpha$-monothioglycerol and sodium thio sulfate: low molecular weight proteins such as human serum albumin, bovine serum albumin, gelatin or other immunoglobulins: hydrophilic polymers such as polyvinylpyrrolidone: monosaccharides (e.g., xylose, mannose, fructose, glucose: disaccharides (e.g., lactose, maltose, sucrose); trisaccharides such as raffinose; and polysaccharides such as dextrin or dextran.

Non-ionic surfactants or detergents (also known as "wetting agents") can be present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml or about 0.07 mg/ml to about 0.2 mg/ml. In some embodiments, non-ionic surfactants are present in a range of about 0.001% to about 0.1% w/v or about 0.01% to about 0.1% w/v or about 0.01% to about 0.025% w/v.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl cellouse and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the formulations to be used for in vivo administration, they must be sterile. The formulation may be rendered sterile by filtration through sterile filtration membranes. The therapeutic compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

An activatable masked anti-CTLA4 binding protein described herein (e.g., activatable masked anti-CTLA4 antibody or antigen-binding fragment thereof) can be used alone or in combination with other therapeutic agents such is in the methods described herein. The term "in combination with" encompasses two or more therapeutic agents (e.g., an activatable masked anti-CTLA4 binding protein and a therapeutic agent) that are included in the same or separate formulations. In some embodiments, "in combination with" refers to "simultaneous" administration, in which case administration of the activatable masked anti-CTLA4 binding protein of the invention occurs simultaneously to the administration of the one or more additional therapeutic agents (e.g., at the same time or within one hour between administration(s) of the activatable masked anti-CTLA4 binding protein and administration of the one or more additional therapeutic agents). In some embodiments, "in combination with" refers to sequential administration, in which case administration of the activatable masked anti-CTLA4 binding protein of the invention occurs prior to and/or following, administration of the one or more additional therapeutic agents (e.g., greater than one hour between administration(s) of the activatable masked anti-CTLA4 binding protein and administration of the one or more additional therapeutic agents). Agents contemplated herein include, but are not limited to, a cytotoxic agent, a cytokine, an agent targeting an immune checkpoint molecule, an agent targeting an immune stimulatory molecule, or a growth inhibitory agent.

The formulation herein may also contain more than one active compound as necessary for the particular indication being treated, preferably those with complementary activities that do not adversely affect each other. Alternatively, or in addition, the composition may comprise a cytotoxic agent, cytokine, agent targeting an immune checkpoint molecule or stimulatory molecule, or growth inhibitory agent. Such molecules are suitably present in combination in amounts that are effective for the purpose intended.

V. Methods of Treatment

Provided herein are methods for treating or preventing a disease in a subject comprising administering to the subject an effective amount of an activatable masked anti-CTLA4 binding protein described herein (e.g., activatable masked anti-CTLA4 antibody or antigen-binding fragment thereof) or compositions thereof. In some embodiments, the subject (e.g., a human patient) has been diagnosed with a neoplastic disorder (e.g., cancer) or is at risk of developing such a disorder.

For the prevention or treatment of disease, the appropriate dosage of an active agent, will depend on the type of disease to be treated, as defined above, the severity and course of the disease, whether the agent is administered for preventive or therapeutic purposes, previous therapy, the subject's clinical history and response to the agent, and the discretion of the attending physician. The agent is suitably administered to the subject at one time or over a series of treatments. In some embodiments of the methods described herein, an interval between administrations of an activatable masked anti-CTLA4 binding protein (e.g., activatable masked anti-CTLA4 antibody or antigen-binding fragment thereof) described is about one month or longer. In some embodiments, the interval between administrations is about two months, about three months, about four months, about five months, about six months or longer. As used herein, an interval between administrations refers to the time period between one administration of the antibody and the next administration of the antibody. As used herein, an interval of about one month includes four weeks. In some embodiments, the interval between administrations is about two weeks, about three weeks, about four weeks, about eight weeks, about twelve weeks, about sixteen weeks, about twenty weeks, about twenty four weeks, or longer. In some embodiments, the treatment includes multiple administrations of the antibody, wherein the interval between administrations may vary. For example, the interval between the first administration and the second administration is about one month, and the intervals between the subsequent administrations are about three months. In some embodiments, the interval between the first administration and the second administration is about one month, the interval between the second administration and the third administration is about two months, and the intervals between the subsequent administrations are about three months. In some embodiments, an activatable masked anti-CTLA4 binding protein (e.g., activatable masked anti-CTLA4 antibody or antigen-binding fragment thereof) described herein is administered at a flat dose. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg. 4.0 mg/kg or 10 mg/kg (or any combination thereof) may be administered to the patient. In some embodiments, an activatable masked anti-CTLA4 binding protein (e.g., activatable masked anti-CTLA4 antibody or antigen-binding fragment thereof) described herein is administered to a subject at a dosage from about 25 mg to about 500 mg per dose. In some embodiments, an activatable masked anti-CTLA4 binding protein (e.g., activatable masked anti-CTLA4 antibody or antigen-binding fragment thereof) described herein is administered to a subject at a dosage from about 0.1 mg/kg to about 10 mg/kg or about 1.0 mg/kg to about 10 mg/kg. In some embodiments, an activatable masked anti-CTLA4 binding protein (e.g., activatable masked anti-CTLA4 antibody or antigen-binding fragment thereof) described herein is administered to a subject at a dosage of about any of 0.1 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, or 10.0 mg/kg. In some embodiments, an activatable masked anti-CTLA4 binding protein (e.g., activatable masked anti-CTLA4 antibody or antigen-binding fragment thereof) described herein is administered to a subject at a dosage of between or between about 0.1 mg/kg and 10 mg/kg, between or between about 10 mg/kg and 20 mg/kg, between or between about 20 mg/kg and 30 mg/kg, between or between about 30 mg/kg and 40 mg/kg, between or between about 40 mg/kg and 50 mg/kg, between or between about 50 mg/kg and 60 mg/kg, between or between about 60 mg/kg and 70 mg/kg, or between or between about 70 mg/kg and 80 mg/kg. Any of the dosing frequency described above may be used.

A method of treatment contemplated herein is the treatment of a disorder or disease with an activatable masked anti-CTLA4 binding protein (e.g., activatable masked anti-CTLA4 antibody or antigen-binding fragment thereof) described herein. Disorders or diseases that are treatable with the formulations of this present invention include leukemia, lymphoma, head and neck cancer, colorectal cancer, prostate cancer, pancreatic cancer, melanoma, breast cancer, neuroblastoma, lung cancer, ovarian cancer, osteosarcoma, bladder cancer, cervical cancer, liver cancer, kidney cancer, skin cancer (e.g., Merkel cell carcinoma) or testicular cancer.

In some embodiments, provided herein is a method of treatment or prevention of a cancer by administration of an activatable masked anti-CTLA4 binding protein (e.g., activatable masked anti-CTLA4 antibody or antigen-binding fragment thereof) described herein. As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with an activatable masked anti-CTLA4 binding protein (e.g., activatable masked anti-CTLA4 antibody or antigen-binding fragment thereof), pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, Herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

In some embodiments, provided herein is a method of treatment or prevention of a leukemia by administration of an activatable masked anti-CTLA4 binding protein (e.g., activatable masked anti-CTLA4 antibody or antigen-binding fragment thereof) described herein. The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic: (2) the type of cell involved: myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute non-lymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

In some embodiments, provided herein is a method of treatment or prevention of a sarcoma by administration of an activatable masked anti-CTLA4 binding protein (e.g., activatable masked anti-CTLA4 antibody or antigen-binding fragment thereof) described herein. The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

In some embodiments, provided herein is a method of treatment or prevention of a melanoma by administration of an activatable masked anti-CTLA4 binding protein (e.g., activatable masked anti-CTLA4 antibody or antigen-binding fragment thereof) described herein. The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

In some embodiments, provided herein is a method of treatment or prevention of a carcinoma by administration of an activatable masked anti-CTLA4 binding protein (e.g., activatable masked anti-CTLA4 antibody or antigen-binding fragment thereof) described herein. The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

In some embodiments, provided herein is a method of treatment or prevention of metastatic cancer by administration of an activatable masked anti-CTLA4 binding protein (e.g., activatable masked anti-CTLA4 antibody or antigen-binding fragment thereof) described herein. As used herein, the terms "metastasis," "metastatic," and "metastatic cancer" can be used interchangeably and refer to the spread of a neoplastic disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast In some embodiments, diseases or disorders that may benefit by the masked CTLA4 binding proteins described herein include a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) caused by (in whole or in part), or a symptom of the disease is caused by (in whole or in part) CTLA4 or CTLA4 activity or function.

VI. Articles of Manufacture or Kits

In another aspect, an article of manufacture or kit is provided which comprises an activatable masked anti-CTLA4 binding protein (e.g., activatable masked anti-CTLA4 antibody or antigen-binding fragment thereof) described herein. The article of manufacture or kit may further comprise instructions for use of the binding proteins in the methods of the invention. Thus, in certain embodiments, the article of manufacture or kit comprises instructions for the use of an activatable masked anti-CTLA4 binding protein (e.g., activatable masked anti-CTLA4 antibody or antigen-binding fragment thereof) in methods for treating or preventing a disorder (e.g., a cancer) in an individual comprising administering to the individual an effective amount of an activatable masked anti-CTLA4 binding protein (e.g., activatable masked anti-CTLA4 antibody or antigen-binding fragment thereof). In certain embodiments, the individual is a human. In some embodiments, the individual has a disease selected from the group consisting of include leukemia, lymphoma, head and neck cancer, colorectal cancer, prostate cancer, pancreatic cancer, melanoma, breast cancer, neuroblastoma, lung cancer, ovarian cancer, osteosarcoma, bladder cancer, cervical cancer, liver cancer, kidney cancer, skin cancer or testicular cancer.

The article of manufacture or kit may further comprise a container. Suitable containers include, for example, bottles, vials (e.g., dual chamber vials), syringes (such as single or dual chamber syringes) and test tubes. The container may be formed from a variety of materials such as glass or plastic. The container holds the formulation. In some embodiments, the formulation is a lyophilized formulation.

The article of manufacture or kit may further comprise a label or a package insert, which is on or associated with the container, may indicate directions for reconstitution and/or use of the formulation. The label or package insert may further indicate that the formulation is useful or intended for subcutaneous, intravenous, or other modes of administration for treating or preventing a disorder (e.g., a cancer) in an individual. The container holding the formulation may be a single-use vial or a multi-use vial, which allows for repeat administrations of the reconstituted formulation. The article of manufacture or kit may further comprise a second container comprising a suitable diluent. The article of manufacture or kit may further include other materials desirable from a commercial, therapeutic, and user standpoint, including other buffers, diluents, filters, needles, syringes, and package inserts with instructions for use.

In a specific embodiment, the present invention provides kits for a single dose-administration unit. Such kits comprise a container of an aqueous formulation of therapeutic antibody, including both single or multi-chambered pre-filled syringes. Exemplary pre-filled syringes are available from Vetter GmbH, Ravensburg, Germany.

The article of manufacture or kit herein optionally further comprises a container comprising a second medicament, wherein the activatable masked anti-CTLA4 binding protein (e.g., activatable masked anti-CTLA4 antibody or antigen-binding fragment thereof) is a first medicament, and which article or kit further comprises instructions on the label or package insert for treating the subject with the second medicament, in an effective amount.

In another embodiment, provided herein is an article of manufacture or kit comprising the formulations described herein for administration in an auto-injector device. An auto-injector can be described as an injection device that upon activation, will deliver its contents without additional necessary action from the patient or administrator. They are particularly suited for self-medication of therapeutic formulations when the delivery rate must be constant and the time of delivery is greater than a few moments.

Exemplary Embodiments

Among the provided exemplary embodiments are:
1. A masked antibody comprising:
 a) an antibody or antigen-binding fragment thereof that binds to CTLA4, wherein the antibody or antigen-binding fragment thereof comprises a first chain and a second chain, and
 b) a masking peptide comprising an amino acid sequence selected from SEQ ID NOs: 1-46,
 wherein the masking peptide is linked via a linker comprising a cleavable peptide to an amino-terminus or carboxy-terminus of the first chain or the second chain of the antibody or antigen-binding fragment thereof.
2. The masked antibody of embodiment 1, wherein
 a) the first chain is a light chain; and
 b) the second chain is a heavy chain.
3 The masked antibody of embodiment 1 or 2, wherein the antibody or antigen-binding fragment thereof comprises two first chains and two second chains.
4. The masked antibody of embodiment 1, wherein
 a) the first chain is a light chain variable domain; and
 b) the second chain is a heavy chain variable domain.
5. The masked antibody of any one of embodiments 1-4, wherein the antigen-binding fragment is a dAb, Fab, Fab'-SH, Fv, scFv, or (Fab')$_2$ fragment.
6. The masked antibody of any one of embodiments 1-5, wherein the amino-terminus or carboxy-terminus of the masking peptide is linked to the linker comprising a cleavable peptide.
7 The masked antibody of any one of embodiments 1-6, wherein the linker comprising a cleavable peptide comprises:
 a) a first spacer linker and a cleavable peptide; or
 b) a first spacer linker, a cleavable peptide, and a second spacer linker.
8. The masked antibody of any one of embodiments 1-7, wherein the cleavable peptide comprises an amino acid sequence selected from SEQ ID NOs: 47-88, 464-469, and 479-508.
9 The masked antibody of any one of embodiments 1-8, wherein:
 a) the first spacer linker is directly linked to the N-terminus and/or the C-terminus of the cleavable peptide; or
 b) the first spacer linker is directly linked to the N-terminus of the cleavable peptide, and the second spacer linkers is directly linked to the C-terminus of the cleavable peptide.
10. The masked antibody of any one of embodiments 7-9, wherein the first spacer linker comprises an amino acid sequence selected from the group consisting of SEQ ID NOs: 89-112 and 415-420; and/or the second spacer linker comprises an amino acid sequence selected from the group consisting of SEQ ID NOs: 89-112 and 415-420.
11. The masked antibody of any one of embodiments 1-10, wherein the linker comprising a cleavable peptide comprises an amino acid sequence selected from the group consisting of SEQ ID NOs: 454-462.
12. The masked antibody of any one of embodiments 1-10, wherein at least one amino acid but no more than 20 amino acids is directly linked to the N-terminus of the masking peptide.
13. The masked antibody of embodiment 12, wherein the at least one amino acid is alanine (A) or glycine-alanine (GA).
14. The masked antibody of any one of embodiments 1-13, wherein the masked antibody comprises in an N- to C-terminal or in a C- to N-terminal direction: a) the masking peptide: b) the cleavable peptide; and c) the first chain or the second chain of the antibody or antigen-binding fragment thereof that binds CTLA4.
15. The masked antibody of embodiment 14, wherein
 a) the masked antibody comprises a spacer linker between the masking peptide and the cleavable peptide; and
 b) the masked antibody comprises a spacer linker between the cleavable peptide and the antibody or antigen-binding fragment thereof that binds to CTLA4.
16. The masked antibody of any one of embodiments 1-15, wherein the masked antibody comprises an amino acid sequence selected from the group consisting of SEQ ID NOs: 113-231 and 444-453.
17. The masked antibody of any one of embodiments 1-16, wherein the antibody or antigen-binding fragment thereof is a murine antibody.
18. The masked antibody of any one of embodiments 1-16, wherein the antibody or antigen-binding fragment thereof is a humanized antibody, a chimeric antibody, or a human antibody.
19. The masked antibody of any one of embodiments 1-18, wherein the antibody or antigen-binding fragment thereof has an IgG1, IgG2, IgG3 or IgG4 isotype.
20. The masked antibody of embodiment 19, wherein the IgG1 comprises the amino acid substitutions
 a) S298A, E333A, and K334A;
 b) S239D and I332E;
 c) S239D, A330L, and I332E;
 d) P247I and A339D or A339Q;
 e) D280H, K290S with or without S298D or S298V;
 f) F243L, R292P, and Y300L;
 g) F243L, R292P, Y300L, and P396L;
 h) F243L, R292P, Y300L, V305I, and P396L;
 i) G236A, S239D, and I332E;
 j) K326A and E333A;
 k) K326W and E333S; or
 l) K290E or K290N, S298G, T299A, and/or K326E;
 wherein the amino acid residues are numbered according to the EU index as in Kabat.
21. The masked antibody of any one of embodiments 1-20, wherein the antibody or antigen-binding fragment thereof comprises a light chain variable region and a heavy chain variable region, wherein:
 a) the light chain variable region comprises (i) a CDR-L1 comprising the amino acid sequence of SEQ ID NO:402, (ii) a CDR-L2 comprising the amino acid sequence of SEQ ID NO: 403, and (iii) a CDR-L3 comprising the amino acid sequence of SEQ ID NO:404; and/or the heavy chain variable region comprises (i) a CDR-H1 comprising the amino acid sequence of SEQ ID NO:405, (ii) a CDR-H2 comprising the amino acid sequence of SEQ ID NO:406, and (iii) a CDR-H3 comprising the amino acid sequence of SEQ ID NO:407; or b) the light chain variable region comprises (i) a CDR-L1 comprising the amino acid sequence of SEQ ID NO: 408, (ii) a CDR-L2 comprising the amino acid sequence of SEQ ID NO: 409, and (iii) a CDR-L3 comprising the amino acid sequence of SEQ ID NO: 410; and/or the heavy chain variable region comprises (i) a CDR-H1 comprising the amino acid sequence of SEQ ID NO: 411, (ii) a CDR-H2 comprising the amino acid sequence of SEQ ID NO: 412, and (iii) a CDR-H3 comprising the amino acid sequence of SEQ ID NO: 413; or c) the light chain variable region comprises (i) a CDR-L1 comprising the amino acid sequence of SEQ ID NO:432, (ii) a CDR-L2 comprising the amino acid sequence of SEQ ID NO: 433, and (iii) a CDR-L3 comprising the amino acid sequence of SEQ ID NO:434; and/or wherein the heavy chain variable region comprises (i) a CDR-H1 comprising the amino acid sequence of SEQ ID NO:435, (ii) a CDR-H2 comprising the amino acid sequence of SEQ ID NO: 436, and (iii) a CDR-H3 comprising the amino acid sequence of SEQ ID NO:437; or d) the light chain variable region comprises (i) a CDR-L1 comprising the amino acid sequence of SEQ ID NO:438, (ii) a CDR-L2 comprising the amino acid sequence of SEQ ID NO: 439, and (iii) a CDR-L3 comprising the amino acid sequence of SEQ ID NO:440; and/or wherein the heavy chain variable region comprises (i) a CDR-H1 comprising the amino acid sequence of SEQ ID NO:441, (ii) a CDR-H2 comprising the amino acid sequence of SEQ ID NO: 442, and (iii) a CDR-H3 comprising the amino acid sequence of SEQ ID NO:443.

22. The masked antibody of any one of embodiments 1-21, wherein the antibody or antigen-binding fragment thereof comprises a light chain variable region comprising the amino acid sequence of SEQ ID NO:232; and/or a heavy chain variable region comprising the amino acid sequence of SEQ ID NO:233.

23. The masked antibody of embodiment 22, wherein the antibody or antigen-binding fragment thereof comprises a light chain comprising the amino acid sequence selected from SEQ ID NOs: 237-318; and/or a heavy chain comprising the amino acid sequence selected from SEQ ID NOs: 319 or 320.

24. The masked antibody of any one of embodiments 1-21, wherein the antibody or antigen-binding fragment thereof comprises:
a) a light chain variable region comprising the amino acid sequence of SEQ ID NO: 321; and/or a heavy chain variable region comprising the amino acid sequence of SEQ ID NO: 323; or
b) a light chain variable region comprising the amino acid sequence of SEQ ID NO: 322; and/or a heavy chain variable region comprising the amino acid sequence of SEQ ID NO: 324.

25. The masked antibody of embodiment 24, wherein the antibody comprises a light chain comprising the amino acid sequence selected from SEQ ID NOs: 327-341; and/or a heavy chain comprising the amino acid sequence selected from SEQ ID NOs: 366-380, 421, and 478.

26. The masked antibody of embodiment 24 or embodiment 25, wherein the antibody or antigen-binding fragment thereof comprises a light chain comprising the amino acid sequence of SEQ ID NO: 334, and a heavy chain comprising the amino acid sequence of SEQ ID NO: 421; or the antibody or antigen-binding fragment thereof comprises a light chain comprising the amino acid sequence of SEQ ID NO: 327, and a heavy chain comprising the amino acid sequence of SEQ ID NO: 478.

27. The masked antibody of any one of embodiments 1-26, wherein the cleavable peptide is a substrate for a protease that is co-localized in a region with a cell or a tissue expressing CTLA4.

28. The masked antibody of any one of embodiments 1-27, wherein the cleavable peptide is cleaved by one or more enzyme selected from the group consisting of: ABHD12, ADAM12, ABHD12B, ABHD13, ABHD17A, ADAM19, ADAM20, ADAM21, ADAM28, ADAM30, ADAM33, ADAM8, ABHD17A, ADAMDEC1, ADAMTS1, ADAMTS10, ADAMTS12, ADAMTS13, ADAMTS14, ADAMTS15, ADAMTS16, ADAMTS17, ADAMTS18, ADAMTS19, ADAMTS2, ADAMTS20, ADAMTS3, ADAMTS4, ABHD17B, ADAMTS5, ADAMTS6, ADAMTS7, ADAMTS8, ADAMTS9, ADAMTSL1, ADAMTSL2, ADAMTSL3, ABHD17C, ADAMTSL5, ASTL, BMP1, CELA1, CELA2A, CELA2B, CELA3A, CELA3B, ADAM10, ADAM15, ADAM17, ADAM9, ADAMTS4, CTSE, CTSF, ADAMTSL4, CMA1, CTRB1, CTRC, CTSO, CTR1, CTSA, CTSW, CTSB, CTSC, CTSD, ESP1, CTSG, CTSH, GZMA, GZMB, GZMH, CTSK, GZMM, CTSL, CTSS, CTSV, CTSZ, HTRA4, KLK10, KLK11, KLK13, KLK14, KLK2, KLK4, DPP4, KLK6, KLK7, KLKB1, ECE1, ECE2, ECEL1, MASP2, MEP1A, MEP1B, ELANE, FAP, GZMA, MMP11, GZMK, HGFAC, HPN, HTRA1, MMP11, MMP16, MMP17, MMP19, HTRA2, MMP20, MMP21, HTRA3, HTRA4, KEL, MMP23B, MMP24, MMP25, MMP26, MMP27, MMP28, KLK5, MMP3, MMP7, MMP8, MMP9, LGMN, LNPEP, MASP1, PAPPA, PAPPA2, PCSK1, NAPSA, PCSK5, PCSK6, MME, MMP1, MMP10, PLAT, PLAU, PLG, PRSS1, PRSS12, PRSS2, PRSS21, PRSS3, PRSS33, PRSS4, PRSS55, PRSS57, MMP12, PRSS8, PRSS9, PRTN3, MMP13, MMP14, ST14, TMPRSS10, TMPRSS11A, TMPRSS11D, TMPRSS11E, TMPRSS11F, TMPRSS12, TMPRSS13, MMP15, TMPRSS15, MMP2, TMPRSS2, TMPRSS3, TMPRSS4, TMPRSS5, TMPRSS6, TMPRSS7, TMPRSS9, NRDC, OVCH1, PAMR1, PCSK3, PHEX, TINAG, TPSAB1, TPSD1, and TPSG1.

29. The masked antibody of embodiment 28, wherein the cleavable peptide is cleaved by one or more enzyme selected from the group consisting of: ADAM17, HTRA1, PRSS1, FAP, GZMK, NAPSA, MMP1, MMP2, MMP9, MMP10, MMP7, MMP12, MMP28, ADAMTS9, HGFAC, and HTRA3.

30. The masked antibody of any one of embodiments 1-29, wherein the masked antibody comprises the amino acid sequence of SEQ ID NO: 421, and comprises an amino acid sequence that is selected from the group consisting of SEQ ID NOs: 358 and 422-431.

31. The masked antibody of any one of embodiments 1-30, wherein the antibody or antigen-binding fragment thereof is conjugated to an agent.

32. The masked antibody of embodiment 31, wherein the agent is an inhibitor of tubulin polymerization, a DNA damaging agent, or a DNA synthesis inhibitor.

33. The masked antibody of embodiment 32, wherein the agent is a maytansinoid, an auristatin, a pyrrolobenzodiazepine (PBD) dimer, a calicheamicin, a duocarmycin, a indo-linobenzodiazepine dimer or exatecan derivative Dxd.

34. A masked bispecific antibody comprising
a) a light chain and a heavy chain of a first pair that specifically binds to CTLA4;

b) a light chain and a heavy chain of a second pair that specifically binds to an antigen; and
c) a masking peptide comprising an amino acid sequence selected from SEQ ID NOs: 1-46,
wherein the masking peptide is linked via a linker comprising a cleavable peptide to an amino-terminus or carboxy-terminus of the light chain or the heavy chain of the first pair.

35. The masked bispecific antibody of embodiment 34, wherein the amino-terminus or carboxy-terminus of the masking peptide is linked to the linker comprising a cleavable peptide.

36. The masked bispecific antibody of embodiment 34 or 35, wherein the linker comprising a cleavable peptide comprises:
a) a first spacer linker and a cleavable peptide; or
b) a first spacer linker, a cleavable peptide, and a second spacer linker.

37. The masked bispecific antibody of any one of embodiments 34-36, wherein the cleavable peptide comprises an amino acid sequence selected from SEQ ID NOs: 47-88, 464-469, and 479-508.

38. The masked bispecific antibody of embodiment 36 or embodiment 37, wherein:
a) the first spacer linker is directly linked to the N-terminus or the C-terminus of the cleavable peptide; or
b) the first spacer linker is directly linked to the N-terminus of the cleavable peptide, and the second spacer linkers is directly linked to the C-terminus of the cleavable peptide.

39. The masked bispecific antibody of any one of embodiments 36-38, wherein the first spacer linker comprises an amino acid sequence selected from the group consisting of SEQ ID NOs: 89-112 and 415-420; and/or the second spacer linker comprises an amino acid sequence selected from the group consisting of SEQ ID NOs: 89-112 and 415-420.

40. The masked bispecific antibody of any one of embodiments 34-39, wherein the linker comprising a cleavable peptide comprises an amino acid sequence selected from the group consisting of SEQ ID NOs: 454-462.

41. The masked bispecific antibody of any one of embodiments 34-40, wherein at least one amino acid but no more than 20 amino acids is directly linked to the N-terminus of the masking peptide.

42. The masked bispecific antibody of embodiment 41, wherein the at least one amino acid is alanine (A) or glycine-alanine (GA).

43. The masked bispecific antibody of any one of embodiments 34-42, wherein the light chain or heavy chain of the first pair comprises in an N- to C-terminal or in a C- to N-terminal direction: a) the masking peptide: b) the cleavable peptide; and c) the light chain or the heavy chain.

44. The masked bispecific antibody of embodiment 43, wherein
a) the first pair comprises a spacer linker between the masking peptide and the cleavable peptide; and
b) the first pair comprises a spacer linker between the cleavable peptide and the light chain or the heavy chain.

45. The masked bispecific antibody of any one of embodiments 34-44, wherein the masked bispecific antibody comprises an amino acid sequence selected from the group consisting of SEQ ID NOs: 113-231 and 444-453.

46. The masked bispecific antibody of any one of embodiments 34-45, wherein the bispecific antibody is a murine antibody.

47. The masked bispecific antibody of any one of embodiments 34-45, wherein the bispecific antibody is a humanized antibody, a chimeric antibody, or a human antibody.

48. The masked bispecific antibody of any one of embodiments 34-47, wherein the bispecific antibody has an IgG1, IgG2, IgG3 or IgG4 isotype.

49. The masked bispecific antibody of embodiment 48, wherein the IgG1 comprises the amino acid substitutions
a) S298A, E333A, and K334A;
b) S239D and I332E;
c) S239D, A330L, and I332E;
d) P247I and A339D or A339Q;
e) D280H, K290S with or without S298D or S298V;
f) F243L, R292P, and Y300L;
g) F243L, R292P, Y300L, and P396L;
h) F243L, R292P, Y300L, V305I, and P396L;
i) G236A, S239D, and I332E;
j) K326A and E333A;
k) K326W and E333S; or
l) K290E or K290N, S298G, T299A, and/or K326E,
wherein the amino acid residues are numbered according to the EU index as in Kabat.

50. The masked bispecific antibody of any one of embodiments 34-49, wherein the first pair comprises a light chain variable region and a heavy chain variable region, wherein:
a) the light chain variable region comprises (i) a CDR-L1 comprising the amino acid sequence of SEQ ID NO:402, (ii) a CDR-L2 comprising the amino acid sequence of SEQ ID NO: 403, and (iii) a CDR-L3 comprising the amino acid sequence of SEQ ID NO:404; and/or wherein the heavy chain variable region comprises (i) a CDR-H1 comprising the amino acid sequence of SEQ ID NO:405, (ii) a CDR-H2 comprising the amino acid sequence of SEQ ID NO: 406, and (iii) a CDR-H3 comprising the amino acid sequence of SEQ ID NO:407; or
b) the light chain variable region comprises (i) a CDR-L1 comprising the amino acid sequence of SEQ ID NO: 408, (ii) a CDR-L2 comprising the amino acid sequence of SEQ ID NO: 409, and (iii) a CDR-L3 comprising the amino acid sequence of SEQ ID NO: 410; and/or wherein the heavy chain variable region comprises (i) a CDR-H1 comprising the amino acid sequence of SEQ ID NO: 411, (ii) a CDR-H2 comprising the amino acid sequence of SEQ ID NO: 412, and (iii) a CDR-H3 comprising the amino acid sequence of SEQ ID NO: 413; or
c) the light chain variable region comprises (i) a CDR-L1 comprising the amino acid sequence of SEQ ID NO:432, (ii) a CDR-L2 comprising the amino acid sequence of SEQ ID NO: 433, and (iii) a CDR-L3 comprising the amino acid sequence of SEQ ID NO:434; and/or wherein the heavy chain variable region comprises (i) a CDR-H1 comprising the amino acid sequence of SEQ ID NO:435, (ii) a CDR-H2 comprising the amino acid sequence of SEQ ID NO: 436, and (iii) a CDR-H3 comprising the amino acid sequence of SEQ ID NO:437; or
d) the light chain variable region comprises (i) a CDR-L1 comprising the amino acid sequence of SEQ ID NO:438, (ii) a CDR-L2 comprising the amino acid sequence of SEQ ID NO: 439, and (iii) a CDR-L3 comprising the amino acid sequence of SEQ ID NO:440; and/or wherein the heavy chain variable region comprises (i) a CDR-H1 comprising the amino acid sequence of SEQ ID NO:441, (ii) a CDR-H2 comprising the amino acid sequence of SEQ ID NO:

442, and (iii) a CDR-H3 comprising the amino acid sequence of SEQ ID NO:443.

51. The masked bispecific antibody of any one of embodiments 34-50, wherein the first pair comprises a light chain variable region comprising the amino acid sequence of SEQ ID NO:232; and/or a heavy chain variable region comprising the amino acid sequence of SEQ ID NO:233.

52. The masked bispecific antibody of embodiment 51, wherein the first pair comprises a light chain comprising the amino acid sequence selected from SEQ ID NOs: 237-318; and/or a heavy chain comprising the amino acid sequence selected from SEQ ID NOs: 319 or 320.

53. The masked bispecific antibody of any one of embodiments 34-50, wherein the first pair comprises:
   a) a light chain variable region comprising the amino acid sequence of SEQ ID NO: 321; and/or a heavy chain variable region comprising the amino acid sequence of SEQ ID NO: 323; or
   b) a light chain variable region comprising the amino acid sequence of SEQ ID NO: 322; and/or a heavy chain variable region comprising the amino acid sequence of SEQ ID NO: 324.

54. The masked bispecific antibody of embodiment 53, wherein the first pair comprises a light chain comprising the amino acid sequence selected from SEQ ID NOs: 327-341; and/or a heavy chain comprising the amino acid sequence selected from SEQ ID NOs: 366-380, 421, and 478.

55. The masked bispecific antibody of embodiment 53 or embodiment 54, wherein the first pair comprises a light chain comprising the amino acid sequence of SEQ ID NO: 334, and a heavy chain comprising the amino acid sequence of SEQ ID NO: 421; or the first pair comprises a light chain comprising the amino acid sequence of SEQ ID NO: 327, and a heavy chain comprising the amino acid sequence of SEQ ID NO: 478.

56. The masked bispecific antibody of any one of embodiments 34-55, wherein the cleavable peptide is a substrate for a protease that is co-localized in a region with a cell or a tissue expressing CTLA4.

57. The masked bispecific antibody of any one of embodiments 34-56, wherein the cleavable peptide is cleaved by one or more enzyme selected from the group consisting of: ABHD12, ADAM12. ABHD12B, ABHD13, ABHD17A, ADAM19, ADAM20), ADAM21, ADAM28, ADAM30, ADAM33, ADAM8, ABHD17A, ADAMDEC1, ADAMTS1, ADAMTS10, ADAMTS12, ADAMTS13, ADAMTS14, ADAMTS15, ADAMTS16, ADAMTS17, ADAMTS18, ADAMTS19, ADAMTS2, ADAMTS20), ADAMTS3, ADAMTS4, ABHD17B, ADAMTS5, ADAMTS6, ADAMTS7, ADAMTS8, ADAMTS9, ADAMTSL1, ADAMTSL2, ADAMTSL3, ABHD17C, ADAMTSL5, ASTL, BMP1, CELA1, CELA2A, CELA2B, CELA3A, CELA3B, ADAM10, ADAM15, ADAM17, ADAM9, ADAMTS4, CTSE, CTSF, ADAMTSL4, CMA1, CTRB1, CTRC, CTSO, CTR1, CTSA, CTSW, CTSB, CTSC, CTSD, ESP1, CTSG, CTSH, GZMA, GZMB, GZMH, CTSK, GZMM, CTSL, CTSS, CTSV, CTSZ, HTRA4, KLK10, KLK11, KLK13, KLK14, KLK2, KLK4, DPP4, KLK6, KLK7, KLKB1. ECE1, ECE2, ECEL1, MASP2, MEP1A, MEP1B, ELANE, FAP, GZMA, MMP11, GZMK, HGFAC, HPN, HTRA1, MMP11, MMP16, MMP17, MMP19, HTRA2, MMP20, MMP21, HTRA3, HTRA4, KEL, MMP23B, MMP24, MMP25, MMP26, MMP27, MMP28, KLK5, MMP3, MMP7, MMP8, MMP9, LGMN, LNPEP, MASP1, PAPPA, PAPPA2, PCSK1, NAPSA, PCSK5, PCSK6, MME, MMP1, MMP10, PLAT, PLAU, PLG, PRSS1, PRSS12, PRSS2, PRSS21, PRSS3, PRSS33, PRSS4, PRSS55, PRSS57, MMP12, PRSS8, PRSS9, PRTN3, MMP13, MMP14, ST14, TMPRSS10, TMPRSS11A, TMPRSS11D, TMPRSS11E, TMPRSS11F, TMPRSS12, TMPRSS13, MMP15, TMPRSS15, MMP2, TMPRSS2, TMPRSS3, TMPRSS4, TMPRSS5, TMPRSS6, TMPRSS7, TMPRSS9, NRDC, OVCH1, PAMR1, PCSK3, PHEX, TINAG, TPSAB1, TPSD1, and TPSG1.

58. The masked bispecific antibody of embodiment 57, wherein the cleavable peptide is cleaved by one or more enzyme selected from the group consisting of: ADAM17, HTRA1, PRSS1, FAP, GZMK, NAPSA, MMP1, MMP2, MMP9, MMP10, MMP7, MMP12, MMP28, ADAMTS9, HGFAC, and HTRA3.

59. The masked bispecific antibody of any one of embodiments 34-58, wherein the masked bispecific antibody comprises the amino acid sequence of SEQ ID NO: 421, and comprises an amino acid sequence that is selected from the group consisting of SEQ ID NOs: 358 and 422-431.

60. The masked bispecific antibody of any one of embodiments 34-59, wherein the masked bispecific antibody is conjugated to an agent.

61. The masked bispecific antibody of embodiment 60, wherein the agent is an inhibitor of tubulin polymerization, a DNA damaging agent, or a DNA synthesis inhibitor.

62. The masked bispecific antibody of embodiment 60, wherein the agent is a maytansinoid, an auristatin, a pyrrolobenzodiazepine (PBD) dimer, a calicheamicin, a duocarmycin, a indo-linobenzodiazepine dimer or exatecan derivative Dxd.

63. A masked chimeric receptor, comprising:
   a) a ligand-binding domain comprising a first chain and a second chain that binds to CTLA4;
   b) a masking peptide comprising an amino acid sequence selected from SEQ ID NOs: 1-46,
   c) a transmembrane domain; and
   d) an intracellular signaling domain comprising a signaling domain, wherein the masking peptide is linked via a linker comprising a cleavable peptide to an amino-terminus or carboxy-terminus of the first chain or the second chain of the ligand-binding domain.

64. The masked chimeric receptor of embodiment 63, wherein
   a) the first chain is a light chain variable domain; and
   b) the second chain is a heavy chain variable domain.

65. The masked chimeric receptor of embodiment 63 or 64, wherein the amino-terminus or carboxy-terminus of the masking peptide is linked to the linker comprising a cleavable peptide.

66. The masked chimeric receptor of any one of embodiments 63-65, wherein the linker comprising a cleavable peptide comprises:
   a) a first spacer linker and a cleavable peptide; or
   b) a first spacer linker, a cleavable peptide, and a second spacer linker.

67. The masked chimeric receptor of any one of embodiments 63-66, wherein the cleavable peptide comprises an amino acid sequence selected from SEQ ID NOs: 47-88, 464-469, and 479-508.

68. The masked chimeric receptor of embodiment 66 or embodiment 67, wherein:
   a) the first spacer linker is directly linked to the N-terminus or the C-terminus of the cleavable peptide; or
   b) the first spacer linker is directly linked to the N-terminus of the cleavable peptide, and the second spacer linkers is directly linked to the C-terminus of the cleavable peptide.

69. The masked chimeric receptor of embodiment 68, wherein the first spacer linker comprises an amino acid sequence selected from the group consisting of SEQ ID NOs: 89-112 and 415-420; and/or the second spacer linker comprises an amino acid sequence selected from the group consisting of SEQ ID NOs: 89-112 and 415-420.

70. The masked chimeric receptor of any one of embodiments 63-69, wherein the linker comprising a cleavable peptide comprises an amino acid sequence selected from the group consisting of SEQ ID NOs: 454-462.

71. The masked chimeric receptor of any one of embodiments 63-70, wherein at least one amino acid but no more than 20 amino acids is directly linked to the N-terminus of the masking peptide.

72. The masked chimeric receptor of embodiment 71, wherein the at least one amino acid is alanine (A) or glycine-alanine (GA).

73. The masked chimeric receptor of any one of embodiments 63-72, wherein the first chain or the second chain of the ligand binding domain comprises in an N- to C-terminal or in a C- to N-terminal direction: a) the masking peptide: b) the cleavable peptide; and c) the first chain or the second chain.

74. The masked chimeric receptor of embodiment 73, wherein
a) the ligand-binding domain comprises a spacer linker between the masking peptide and the cleavable peptide; and
b) the ligand-binding domain comprises a spacer linker between the cleavable peptide and the first chain or second chain.

75. The masked chimeric receptor of any one of embodiments 63-74, wherein the masked chimeric receptor comprises an amino acid sequence selected from the group consisting of SEQ ID NOs: 113-231 and 444-453.

76. The masked chimeric receptor of any one of embodiments 63-75, wherein:
a) the first chain comprises (i) a CDR-L1 comprising the amino acid sequence of SEQ ID NO: 402, (ii) a CDR-L2 comprising the amino acid sequence of SEQ ID NO:403, and (iii) a CDR-L3 comprising the amino acid sequence of SEQ ID NO:404; and/or wherein the second chain comprises (i) a CDR-H1 comprising the amino acid sequence of SEQ ID NO: 405, (ii) a CDR-H2 comprising the amino acid sequence of SEQ ID NO:406, and (iii) a CDR-H3 comprising the amino acid sequence of SEQ ID NO:407; or
b) the first chain comprises (i) a CDR-L1 comprising the amino acid sequence of SEQ ID NO: 408, (ii) a CDR-L2 comprising the amino acid sequence of SEQ ID NO: 409, and (iii) a CDR-L3 comprising the amino acid sequence of SEQ ID NO: 410; and/or wherein the second chain comprises (i) a CDR-H1 comprising the amino acid sequence of SEQ ID NO: 411, (ii) a CDR-H2 comprising the amino acid sequence of SEQ ID NO: 412, and (iii) a CDR-H3 comprising the amino acid sequence of SEQ ID NO: 413; or
c) the first chain comprises (i) a CDR-L1 comprising the amino acid sequence of SEQ ID NO: 432, (ii) a CDR-L2 comprising the amino acid sequence of SEQ ID NO:433, and (iii) a CDR-L3 comprising the amino acid sequence of SEQ ID NO:434; and/or wherein the heavy chain variable region comprises (i) a CDR-H1 comprising the amino acid sequence of SEQ ID NO:435, (ii) a CDR-H2 comprising the amino acid sequence of SEQ ID NO:436, and (iii) a CDR-H3 comprising the amino acid sequence of SEQ ID NO:437; or
d) the first chain comprises (i) a CDR-L1 comprising the amino acid sequence of SEQ ID NO: 438, (ii) a CDR-L2 comprising the amino acid sequence of SEQ ID NO:439, and (iii) a CDR-L3 comprising the amino acid sequence of SEQ ID NO:440; and/or wherein the heavy chain variable region comprises (i) a CDR-H1 comprising the amino acid sequence of SEQ ID NO:441, (ii) a CDR-H2 comprising the amino acid sequence of SEQ ID NO:442, and (iii) a CDR-H3 comprising the amino acid sequence of SEQ ID NO:443.

77. The masked chimeric receptor of any one of embodiments 63-76, wherein the first chain comprises the amino acid sequence of SEQ ID NO:232; and/or the second chain comprises the amino acid sequence of SEQ ID NO:233.

78. The masked chimeric receptor of any one of embodiments 63-76, wherein:
a) the first chain comprises the amino acid sequence of SEQ ID NO:321; and/or the second chain comprises the amino acid sequence of SEQ ID NO:323; or
b) the first chain comprises the amino acid sequence of SEQ ID NO: 322; and/or the second chain comprises the amino acid sequence of SEQ ID NO: 324.

79. The masked chimeric receptor of any one of embodiments 63-78, wherein the cleavable peptide is a substrate for a protease that is co-localized in a region with a cell or a tissue expressing CTLA4.

80. The masked chimeric receptor of any one of embodiments 63-79, wherein the cleavable peptide is cleaved by one or more enzyme selected from the group consisting of: ABHD12, ADAM12, ABHD12B, ABHD13, ABHD17A, ADAM19, ADAM20, ADAM21, ADAM28, ADAM30, ADAM33, ADAM8, ABHD17A, ADAMDEC1, ADAMTS1, ADAMTS10, ADAMTS12, ADAMTS13, ADAMTS14, ADAMTS15, ADAMTS16, ADAMTS17, ADAMTS18, ADAMTS19, ADAMTS2, ADAMTS20), ADAMTS3, ADAMTS4, ABHD17B, ADAMTS5, ADAMTS6, ADAMTS7, ADAMTS8, ADAMTS9, ADAMTSL1, ADAMTSL2, ADAMTSL3, ABHD17C, ADAMTSL5, ASTL, BMP1, CELA1, CELA2A, CELA2B, CELA3A, CELA3B, ADAM10, ADAM15, ADAM17, ADAM9, ADAMTS4, CTSE, CTSF, ADAMTSL4, CMA1, CTRB1, CTRC, CTSO, CTR1, CTSA, CTSW, CTSB, CTSC, CTSD, ESP1, CTSG, CTSH, GZMA, GZMB, GZMH, CTSK, GZMM, CTSL, CTSS, CTSV, CTSZ, HTRA4, KLK10, KLK11, KLK13, KLK14, KLK2, KLK4, DPP4, KLK6, KLK7, KLKB1, ECE1, ECE2, ECEL1, MASP2, MEP1A, MEP1B, ELANE, FAP, GZMA, MMP11, GZMK, HGFAC, HPN, HTRA1, MMP11, MMP16, MMP17, MMP19, HTRA2, MMP20), MMP21, HTRA3, HTRA4, KEL, MMP23B, MMP24, MMP25, MMP26, MMP27, MMP28, KLK5, MMP3, MMP7, MMP8, MMP9, LGMN, LNPEP, MASP1, PAPPA, PAPPA2, PCSK1, NAPSA, PCSK5, PCSK6, MME, MMP1, MMP10, PLAT, PLAU, PLG, PRSS1, PRSS12, PRSS2, PRSS21, PRSS3, PRSS33, PRSS4, PRSS55, PRSS57, MMP12, PRSS8, PRSS9, PRTN3, MMP13, MMP14, ST14, TMPRSS10, TMPRSS11A, TMPRSS11D, TMPRSS11E, TMPRSS11F, TMPRSS12, TMPRSS13, MMP15, TMPRSS15, MMP2, TMPRSS2, TMPRSS3, TMPRSS4, TMPRSS5, TMPRSS6, TMPRSS7, TMPRSS9, NRDC, OVCH1, PAMR1, PCSK3, PHEX, TINAG, TPSAB1, TPSD1, and TPSG1.

81. The masked chimeric receptor of embodiment 80, wherein the cleavable peptide is cleaved by one or more enzyme selected from the group consisting of: ADAM17, HTRA1, PRSS1, FAP, GZMK, NAPSA, MMP1, MMP2, MMP9, MMP10, MMP7, MMP12, MMP28, ADAMTS9, HGFAC, and HTRA3.

82. A nucleic acid encoding the masked antibody of any one of embodiments 1-33, 100-112, and 139-148, the masked bispecific antibody of any one of embodiments 34-62 and 113-121, or the masked chimeric receptor of any one of embodiments 63-82 and 122-128.

83. A vector comprising the nucleic acid of embodiment 82.

84. The vector of embodiment 83, which is an expression vector.

85. A host cell comprising the nucleic acid of embodiment 82.

86. A method of producing a masked antibody, a masked bispecific antibody or a masked chimeric receptor comprising culturing the host cell of embodiment 85 under a condition that produces the masked antibody, masked bispecific antibody, or the masked chimeric receptor.

87. The method of embodiment 86, wherein the host cell has a alpha1,6-fucosyltransferase (Fut8) knockout.

88. The method of embodiment 86 or 87, wherein the host cell overexpresses β1,4-N-acetylglycosminyltransferase III (GnT-III).

89. The method of embodiment 88, wherein the host cell additionally overexpresses Golgi μ-mannosidase II (ManII).

90. The method of any one of embodiments 86-89, further comprising recovering the masked antibody, the masked bispecific antibody, or the masked chimeric receptor produced by the host cell.

91. A masked antibody, masked bispecific antibody, or masked chimeric receptor produced by the method of any one of embodiments 86-90.

92. A composition comprising the masked antibody of any one of embodiments 1-33, 100-112, and 139-148, the masked bispecific antibody of any one of embodiments 34-62 and 113-121, or the masked chimeric receptor of any one of embodiments 63-82 and 122-128.

93. A composition comprising the masked antibody, the masked bispecific antibody, or the masked chimeric receptor of embodiment 91.

94. A pharmaceutical composition comprising the masked antibody of any one of embodiments 1-33, 100-112, and 139-148, the masked bispecific antibody of any one of embodiments 34-62 and 113-121, or the masked chimeric receptor of any one of embodiments 63-82 and 122-128, and a pharmaceutically acceptable carrier.

95. A pharmaceutical composition comprising the masked antibody, the masked bispecific antibody, or the masked chimeric receptor of embodiments 91, and a pharmaceutically acceptable carrier.

96. A kit comprising the masked antibody of any one of embodiments 1-33, 100-112, and 139-148, the masked bispecific antibody of any one of embodiments 34-62 and 113-121, the masked chimeric receptor of any one of embodiments 63-82 and 122-128, or the composition of any one of embodiments 92-95.

97. A method of treating or preventing a neoplastic disease in a subject, the method comprising administering to the subject an effective amount of the masked antibody of any one of embodiments 1-33, 100-112, and 139-148, the masked bispecific antibody of any one of embodiments 34-62 and 113-121, the masked chimeric receptor of any one of embodiments 63-82 and 122-128, or the composition of any one of embodiments 92-95.

98. The method of embodiment 97, wherein the neoplastic disease is a cancer.

99. The method of embodiment 98, wherein the cancer is leukemia, lymphoma, head and neck cancer, colorectal cancer, prostate cancer, pancreatic cancer, melanoma, breast cancer, neuroblastoma, lung cancer, ovarian cancer, osteosarcoma, bladder cancer, cervical cancer, liver cancer, kidney cancer, skin cancer or testicular cancer.

100. A masked antibody, comprising:
   a) an anti-CTLA4 antibody or antigen-binding fragment thereof comprising a light chain variable (VL) domain and a heavy chain variable (VH) domain; and
   b) a masking peptide comprising an amino acid sequence selected from the group consisting of SEQ ID NOs: 1-46;
   wherein the masking peptide is linked via a linker comprising a cleavable peptide to an amino-terminus or carboxy-terminus of the VL domain or the VH domain.

101. The masked antibody of embodiment 100, wherein the linker comprising a cleavable peptide comprises a cleavable peptide comprising an amino acid sequence selected from the group consisting of SEQ ID NOs: 47-88, 464-469, and 479-508.

102. The masked antibody of embodiment 100 or 101, wherein the cleavable peptide comprises an amino-terminus and a carboxy-terminus, and the linker comprising a cleavable peptide comprises a first spacer linker and a second spacer linker, wherein the first spacer linker is linked to the amino-terminus of the cleavable peptide and comprises an amino acid sequence selected from the group consisting of SEQ ID NOs: 89-112 and 415-420, and the second spacer linker is linked to the carboxy-terminus of the cleavable peptide and comprises an amino acid sequence selected from the group consisting of SEQ ID NOs: 89-112 and 415-420.

103. The masked antibody of any one of embodiments 100-102, wherein the linker comprising a cleavable peptide comprises an amino acid sequence selected from the group consisting of SEQ ID NOs: 454-462.

104. The masked antibody of any one of embodiments 100-103, wherein the masked antibody comprises an amino acid sequence selected from the group consisting of SEQ ID NOs: 113-231 and 444-453.

105. The masked antibody of any one of embodiments 100-104, wherein the anti-CTLA4 antibody or antigen-binding fragment thereof is a humanized antibody, a chimeric antibody, or a human antibody.

106. The masked antibody of any one of embodiments 100-105, wherein:
   a) the VL domain comprises (i) a CDR-L1 comprising the amino acid sequence of SEQ ID NO: 402, (ii) a CDR-L2 comprising the amino acid sequence of SEQ ID NO: 403, and (iii) a CDR-L3 comprising the amino acid sequence of SEQ ID NO: 404; and/or the VH domain comprises (i) a CDR-H1 comprising the amino acid sequence of SEQ ID NO: 405, (ii) a CDR-H2 comprising the amino acid sequence of SEQ ID NO: 406, and (iii) a CDR-H3 comprising the amino acid sequence of SEQ ID NO: 407; or
   b) the VL domain comprises (i) a CDR-L1 comprising the amino acid sequence of SEQ ID NO: 408, (ii) a CDR-L2 comprising the amino acid sequence of SEQ ID NO: 409, and (iii) a CDR-L3 comprising the amino acid sequence of SEQ ID NO: 410; and/or the VH domain comprises (i) a CDR-H1 comprising the amino acid sequence of SEQ ID NO: 411, (ii) a CDR-H2 comprising the amino acid sequence of SEQ ID NO:

412, and (iii) a CDR-H3 comprising the amino acid sequence of SEQ ID NO: 413; or c) the VL domain comprises (i) a CDR-L1 comprising the amino acid sequence of SEQ ID NO: 432, (ii) a CDR-L2 comprising the amino acid sequence of SEQ ID NO: 433, and (iii) a CDR-L3 comprising the amino acid sequence of SEQ ID NO: 434; and/or the VH domain comprises (i) a CDR-H1 comprising the amino acid sequence of SEQ ID NO: 435, (ii) a CDR-H2 comprising the amino acid sequence of SEQ ID NO: 436, and (iii) a CDR-H3 comprising the amino acid sequence of SEQ ID NO: 437; or d) the VL domain comprises (i) a CDR-L1 comprising the amino acid sequence of SEQ ID NO: 438, (ii) a CDR-L2 comprising the amino acid sequence of SEQ ID NO: 439, and (iii) a CDR-L3 comprising the amino acid sequence of SEQ ID NO: 440; and/or the VH domain comprises (i) a CDR-H1 comprising the amino acid sequence of SEQ ID NO: 441, (ii) a CDR-H2 comprising the amino acid sequence of SEQ ID NO: 442, and (iii) a CDR-H3 comprising the amino acid sequence of SEQ ID NO: 443.

107. The masked antibody of any one of embodiments 100-106, wherein:

a) the VL domain comprises the amino acid sequence of SEQ ID NO: 321, and the VH domain comprises the amino acid sequence of SEQ ID NO: 323; or b) the VL domain comprises the amino acid sequence of SEQ ID NO: 322, and the VH domain comprises the amino acid sequence of SEQ ID NO: 324.

108. The masked antibody of any one of embodiments 100-107, wherein the VL domain is contained within a light chain comprising an amino acid sequence selected from the group consisting of SEQ ID NOs: 327-341, and the VH domain is contained within a heavy chain comprising an amino acid sequence selected from the group consisting of SEQ ID NOs: 366-380, 421, and 478.

109. The masked antibody of any one of embodiments 100-108, wherein the masked antibody comprises the amino acid sequence of SEQ ID NO: 421, and comprises an amino acid sequence that is selected from the group consisting of SEQ ID NOs: 358 and 422-431.

110. The masked antibody of any one of embodiments 100-109, wherein the anti-CTLA4 antibody or antigen-binding fragment thereof is conjugated to an agent.

111. The masked antibody of embodiment 110, wherein the agent is an inhibitor of tubulin polymerization, a DNA damaging agent, or a DNA synthesis inhibitor.

112. The masked antibody of embodiment 110, wherein the agent is a maytansinoid, an auristatin, a pyrrolobenzodiazepine (PBD) dimer, a calicheamicin, a duocarmycin, a indo-linobenzodiazepine dimer, or exatecan derivative Dxd.

113. A masked bispecific antibody, comprising:

a) a light chain and a heavy chain of a first pair that specifically binds to CTLA4:

b) a light chain and a heavy chain of a second pair that specifically binds to an antigen; and c) a masking peptide comprising an amino acid sequence selected from the group consisting of SEQ ID NOs: 1-46, wherein the masking peptide is linked via a linker comprising a cleavable peptide to an amino-terminus or carboxy-terminus of the light chain or the heavy chain of the first pair.

114. The masked bispecific antibody of embodiment 113, wherein the linker comprising a cleavable peptide comprises a cleavable peptide comprising an amino acid sequence selected from the group consisting of SEQ ID NOs: 47-88, 464-469, and 479-508.

115. The masked bispecific antibody of embodiment 113 or 114, wherein the cleavable peptide comprises an amino-terminus and a carboxy-terminus, and the linker comprising a cleavable peptide comprises a first spacer linker and a second spacer linker, wherein the first spacer linker is linked to the amino-terminus of the cleavable peptide and comprises an amino acid sequence selected from the group consisting of SEQ ID NOs: 89-112 and 415-420, and the second spacer linker is linked to the carboxy-terminus of the cleavable peptide and comprises an amino acid sequence selected from the group consisting of SEQ ID NOs: 89-112 and 415-420.

116. The masked bispecific antibody of any one of embodiments 113-115, wherein the linker comprising a cleavable peptide comprises an amino acid sequence selected from the group consisting of SEQ ID NOs: 454-462.

117. The masked bispecific antibody of any one of embodiments 113-116, wherein the masked bispecific antibody comprises an amino acid sequence selected from the group consisting of SEQ ID NOs: 113-231 and 444-453.

118. The masked bispecific antibody of any one of embodiments 113-117, wherein the light chain of the first pair comprises a VL domain, and the heavy chain of the first pair comprises a VH domain, wherein:

a) the VL domain comprises (i) a CDR-L1 comprising the amino acid sequence of SEQ ID NO: 402, (ii) a CDR-L2 comprising the amino acid sequence of SEQ ID NO: 403, and (iii) a CDR-L3 comprising the amino acid sequence of SEQ ID NO: 404; and/or the VH domain comprises (i) a CDR-H1 comprising the amino acid sequence of SEQ ID NO: 405, (ii) a CDR-H2 comprising the amino acid sequence of SEQ ID NO: 406, and (iii) a CDR-H3 comprising the amino acid sequence of SEQ ID NO: 407; or b) the VL domain comprises (i) a CDR-L1 comprising the amino acid sequence of SEQ ID NO: 408, (ii) a CDR-L2 comprising the amino acid sequence of SEQ ID NO: 409, and (iii) a CDR-L3 comprising the amino acid sequence of SEQ ID NO: 410; and/or the VH domain comprises (i) a CDR-H1 comprising the amino acid sequence of SEQ ID NO: 411, (ii) a CDR-H2 comprising the amino acid sequence of SEQ ID NO: 412, and (iii) a CDR-H3 comprising the amino acid sequence of SEQ ID NO: 413; or c) the VL domain comprises (i) a CDR-L1 comprising the amino acid sequence of SEQ ID NO: 432, (ii) a CDR-L2 comprising the amino acid sequence of SEQ ID NO: 433, and (iii) a CDR-L3 comprising the amino acid sequence of SEQ ID NO: 434; and/or the VH domain comprises (i) a CDR-H1 comprising the amino acid sequence of SEQ ID NO: 435, (ii) a CDR-H2 comprising the amino acid sequence of SEQ ID NO: 436, and (iii) a CDR-H3 comprising the amino acid sequence of SEQ ID NO: 437; or d) the VL domain comprises (i) a CDR-L1 comprising the amino acid sequence of SEQ ID NO: 438, (ii) a CDR-L2 comprising the amino acid sequence of SEQ ID NO: 439, and (iii) a CDR-L3 comprising the amino acid sequence of SEQ ID NO: 440; and/or the VH domain comprises (i) a CDR-H1 comprising the amino acid sequence of SEQ ID NO: 441, (ii) a CDR-H2 comprising the amino acid sequence of SEQ ID NO: 442, and (iii) a CDR-H3 comprising the amino acid sequence of SEQ ID NO: 443.

119. The masked bispecific antibody of any one of embodiments 113-118, wherein:
  a) the VL domain comprises the amino acid sequence of SEQ ID NO: 321, and the VH domain comprises the amino acid sequence of SEQ ID NO: 323; or
  b) the VL domain comprises the amino acid sequence of SEQ ID NO: 322, and the VH domain comprises the amino acid sequence of SEQ ID NO: 324.

120. The masked bispecific antibody of any one of embodiments 113-119, wherein the light chain of the first pair comprises an amino acid sequence selected from the group consisting of SEQ ID NOs: 327-341, and the heavy chain of the first pair comprises an amino acid sequence selected from the group consisting of SEQ ID NOs: 366-380, 421, and 478.

121. The masked bispecific antibody of any one of embodiments 113-120, wherein the masked bispecific antibody comprises the amino acid sequence of SEQ ID NO: 421, and comprises an amino acid sequence that is selected from the group consisting of SEQ ID NOS: 358 and 422-431.

122. A masked chimeric receptor, comprising:
  a) a ligand-binding domain comprising a VL domain and a VH domain that bind to CTLA4;
  b) a masking peptide comprising an amino acid sequence selected from the group consisting of SEQ ID NOs: 1-46;
  c) a transmembrane domain; and
  d) an intracellular signaling domain comprising a signaling domain, wherein the masking peptide is linked via a linker comprising a cleavable peptide to an amino-terminus or carboxy-terminus of the VL domain or the VH domain.

123. The masked chimeric receptor of embodiment 122, wherein the linker comprising a cleavable peptide comprises a cleavable peptide comprising an amino acid sequence selected from the group consisting of SEQ ID NOs: 47-88, 464-469, and 479-508.

124. The masked chimeric receptor of embodiment 122 or 123, wherein the cleavable peptide comprises an amino-terminus and a carboxy-terminus, and the linker comprising a cleavable peptide comprises a first spacer linker and a second spacer linker, wherein the first spacer linker is linked to the amino-terminus of the cleavable peptide and comprises an amino acid sequence selected from the group consisting of SEQ ID NOs: 89-112 and 415-420, and the second spacer linker is linked to the carboxy-terminus of the cleavable peptide and comprises an amino acid sequence selected from the group consisting of SEQ ID NOs: 89-112 and 415-420.

125. The masked chimeric receptor of any one of embodiments 122-124, wherein the linker comprising a cleavable peptide comprises an amino acid sequence selected from the group consisting of SEQ ID NOs: 454-462.

126. The masked chimeric receptor of any one of embodiments 122-125, wherein the masked chimeric receptor comprises an amino acid sequence selected from the group consisting of SEQ ID NOs: 113-231 and 444-453.

127. The masked chimeric receptor of any one of embodiments 122-126, wherein:
  a) the VL domain comprises (i) a CDR-L1 comprising the amino acid sequence of SEQ ID NO: 402, (ii) a CDR-L2 comprising the amino acid sequence of SEQ ID NO: 403, and (iii) a CDR-L3 comprising the amino acid sequence of SEQ ID NO: 404; and/or the VH domain comprises (i) a CDR-H1 comprising the amino acid sequence of SEQ ID NO: 405, (ii) a CDR-H2 comprising the amino acid sequence of SEQ ID NO: 406, and (iii) a CDR-H3 comprising the amino acid sequence of SEQ ID NO: 407; or
  b) the VL domain comprises (i) a CDR-L1 comprising the amino acid sequence of SEQ ID NO: 408, (ii) a CDR-L2 comprising the amino acid sequence of SEQ ID NO: 409, and (iii) a CDR-L3 comprising the amino acid sequence of SEQ ID NO: 410; and/or the VH domain comprises (i) a CDR-H1 comprising the amino acid sequence of SEQ ID NO: 411, (ii) a CDR-H2 comprising the amino acid sequence of SEQ ID NO: 412, and (iii) a CDR-H3 comprising the amino acid sequence of SEQ ID NO: 413; or
  c) the VL domain comprises (i) a CDR-L1 comprising the amino acid sequence of SEQ ID NO: 432, (ii) a CDR-L2 comprising the amino acid sequence of SEQ ID NO: 433, and (iii) a CDR-L3 comprising the amino acid sequence of SEQ ID NO: 434; and/or the VH domain comprises (i) a CDR-H1 comprising the amino acid sequence of SEQ ID NO: 435, (ii) a CDR-H2 comprising the amino acid sequence of SEQ ID NO: 436, and (iii) a CDR-H3 comprising the amino acid sequence of SEQ ID NO: 437; or
  d) the VL domain comprises (i) a CDR-L1 comprising the amino acid sequence of SEQ ID NO: 438, (ii) a CDR-L2 comprising the amino acid sequence of SEQ ID NO: 439, and (iii) a CDR-L3 comprising the amino acid sequence of SEQ ID NO: 440; and/or the VH domain comprises (i) a CDR-H1 comprising the amino acid sequence of SEQ ID NO: 441, (ii) a CDR-H2 comprising the amino acid sequence of SEQ ID NO: 442, and (iii) a CDR-H3 comprising the amino acid sequence of SEQ ID NO: 443.

128. The masked chimeric receptor of any one of embodiments 122-127, wherein:
  a) the VL domain comprises the amino acid sequence of SEQ ID NO: 321, and the VH domain comprises the amino acid sequence of SEQ ID NO: 323; or
  b) the VL domain comprises the amino acid sequence of SEQ ID NO: 322, and the VH domain comprises the amino acid sequence of SEQ ID NO: 324.

129. A nucleic acid encoding the masked antibody of any one of embodiments 100-112, the masked bispecific antibody of any one of embodiments 113-121, or the masked chimeric receptor of any one of embodiments 122-128.

130. A vector comprising the nucleic acid of embodiment 129.

131. A host cell comprising the nucleic acid of embodiment 129.

132. A method of producing a masked antibody, a masked bispecific antibody, or a masked chimeric receptor, comprising culturing the host cell of embodiment 131 under conditions that produce the masked antibody.

133. A masked antibody, a masked bispecific antibody, or a masked chimeric receptor produced by the method of embodiment 132.

134. A composition comprising the masked antibody of any one of embodiments 100-112, the masked bispecific antibody of any one of embodiments 113-121, or the masked chimeric receptor of any one of embodiments 122-128.

135. A pharmaceutical composition comprising the masked antibody of any one of embodiments 100-112, the masked bispecific antibody of any one of embodiments 113-121, or the masked chimeric receptor of any one of embodiments 122-128, and a pharmaceutically acceptable carrier.

136. A kit comprising the masked antibody of any one of embodiments 100-112, the masked bispecific antibody of any one of embodiments 113-121, or the masked chimeric receptor of any one of embodiments 122-128.

137. A method of treating or preventing a neoplastic disease in a subject, the method comprising administering to a subject an effective amount of the masked antibody of any one of embodiments 100-112, the masked bispecific antibody of any one of embodiments 113-121, or the masked chimeric receptor of any one of embodiments 122-128.

138. A method of treating or preventing a neoplastic disease in a subject, the method comprising administering to a subject an effective amount of the pharmaceutical composition of embodiment 135.

139. A masked antibody, comprising:
  a) an anti-CTLA4 antibody or antigen-binding fragment thereof comprising a light chain variable (VL) domain and a heavy chain variable (VH) domain; and
  b) a masking peptide comprising the amino acid sequence of SEQ ID NO: 5;
  wherein the masking peptide is linked via a linker comprising a cleavable peptide to an amino-terminus of the VL domain;
  wherein the linker comprising a cleavable peptide comprises a cleavable peptide comprising the amino acid sequence of SEQ ID NO: 86;
  wherein (a) the VL domain comprises a CDR-L1 comprising the amino acid sequence of SEQ ID NO: 408, a CDR-L2 comprising the amino acid sequence of SEQ ID NO: 409, and a CDR-L3 comprising the amino acid sequence of SEQ ID NO: 410; and the VH domain comprises a CDR-H1 comprising the amino acid sequence of SEQ ID NO: 411, a CDR-H2 comprising the amino acid sequence of SEQ ID NO: 412, and a CDR-H3 comprising the amino acid sequence of SEQ ID NO: 413; or (b) the VL domain comprises a CDR-L1 comprising the amino acid sequence of SEQ ID NO: 438, a CDR-L2 comprising the amino acid sequence of SEQ ID NO: 439, and a CDR-L3 comprising the amino acid sequence of SEQ ID NO: 440; and the VH domain comprises a CDR-H1 comprising the amino acid sequence of SEQ ID NO: 441, a CDR-H2 comprising the amino acid sequence of SEQ ID NO: 442, and a CDR-H3 comprising the amino acid sequence of SEQ ID NO: 443.

140. The masked antibody of embodiment 139, wherein the linker comprising a cleavable peptide comprises the amino acid sequence of SEQ ID NO: 454.

141. The masked antibody of embodiment 139 or 140, wherein the VL domain comprises the amino acid sequence of SEQ ID NO: 322, and the VH domain comprises the amino acid sequence of SEQ ID NO: 324.

142. The masked antibody of any one of embodiments 139-141, wherein the VL domain is contained in a light chain comprising the amino acid sequence of SEQ ID NO: 334, and the VH domain is contained in a heavy chain comprising the amino acid sequence of SEQ ID NO: 421.

143. The masked antibody of any one of embodiments 139-142, wherein the masked antibody comprises the amino acid sequence of SEQ ID NO: 358, and the amino acid sequence of SEQ ID NO: 421.

144. A masked antibody, comprising:
  a) an anti-CTLA4 antibody or antigen-binding fragment thereof comprising a light chain variable (VL) domain and a heavy chain variable (VH) domain; and
  b) a masking peptide comprising the amino acid sequence of SEQ ID NO: 19;
  wherein the masking peptide is linked via a linker comprising a cleavable peptide to an amino-terminus of the VL domain;
  wherein the linker comprising a cleavable peptide comprises a cleavable peptide comprising the amino acid sequence of SEQ ID NO: 50;
  wherein (a) the VL domain comprises a CDR-L1 comprising the amino acid sequence of SEQ ID NO: 408, a CDR-L2 comprising the amino acid sequence of SEQ ID NO: 409, and a CDR-L3 comprising the amino acid sequence of SEQ ID NO: 410; and the VH domain comprises a CDR-H1 comprising the amino acid sequence of SEQ ID NO: 411, a CDR-H2 comprising the amino acid sequence of SEQ ID NO: 412, and a CDR-H3 comprising the amino acid sequence of SEQ ID NO: 413; or (b) the VL domain comprises a CDR-L1 comprising the amino acid sequence of SEQ ID NO: 438, a CDR-L2 comprising the amino acid sequence of SEQ ID NO: 439, and a CDR-L3 comprising the amino acid sequence of SEQ ID NO: 440; and the VH domain comprises a CDR-H1 comprising the amino acid sequence of SEQ ID NO: 441, a CDR-H2 comprising the amino acid sequence of SEQ ID NO: 442, and a CDR-H3 comprising the amino acid sequence of SEQ ID NO: 443.

145. The masked antibody of embodiment 144, wherein the linker comprising a cleavable peptide comprises the amino acid sequence of SEQ ID NO: 455.

146. The masked antibody of embodiment 144 or 145, wherein the VL domain comprises the amino acid sequence of SEQ ID NO: 322, and the VH domain comprises the amino acid sequence of SEQ ID NO: 324.

147. The masked antibody of any one of embodiments 144-146, wherein the VL domain is contained in a light chain comprising the amino acid sequence of SEQ ID NO: 334, and the VH domain is contained in a heavy chain comprising the amino acid sequence of SEQ ID NO: 421.

148. The masked antibody of any one of embodiments 144-147, wherein the masked antibody comprises the amino acid sequence of SEQ ID NO: 422, and the amino acid sequence of SEQ ID NO: 421.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Production of Activatable Masked Anti-CTLA4 Antibodies

The anti-CTLA4 antibody, 9D9 muIgG2b mAb (9D9 mAb), was purchased from BioXcell for biopanning experiments. For all other experiments, parental anti-CTLA4 antibody (9D9), activatable masked anti-CTLA4 antibody (masked 9D9), and non-cleavable masked anti-CTLA4 antibody (non-cleavable masked 9D9) that are reactive against murine CTLA4 were generated and purified at ATUM.

Activatable masked anti-CTLA4 antibodies, parental anti-CTLA4 antibodies, and non-cleavable masked anti-CTLA4 antibodies were produced using HEK293 transient expression with expression plasmid pD2610-v5 (ATUM, Newark CA) and generated by gene synthesis (ATUM, Newark CA) using a murine IgG2a isotype. Seven days after transfection, supernatants from the transfected cells were harvested and masked anti-CTLA4 antibodies as well as parental anti-CTLA4 antibodies were purified with Kan-CapA resin (Kaneka) and buffer exchanged into phosphate buffered saline (PBS). The antibodies were then further purified by ion exchange using Source S or Capto S ImpAct (GE). Antibody concentrations were determined at an optical density of OD280 by spectrophotometer.

The masking peptide contained in both the masked 9D9 antibody and non-cleavable masked 9D antibody described above, was obtained by biopanning sterically occluding peptides from a phage display peptide library. The 9D9 muIgG2b mAb (BioXcell) was first captured on ProteinG Magnetic Beads (MB) (Thermo Fisher Scientific) at room temperature for 30 minutes. After blocking 9D9 muIgG2b mAb immobilized MB with skim milk, Ph.D.™-C7C phage peptide library (New England BioLabs) was added to screen sterically occluding peptides. After 30 minutes incubation at room temperature followed by washing unbound phages vigorously, bound phages were eluted with 0.2 M glycine pH 2.2 into a pH-neutralization solution. Eluted phages were amplified by infecting into E. coli K12 ER2738 (New England BioLabs) for the next round of biopanning. Three subsequent rounds of biopanning were done with an additional round of negative sorting using an isotype control (BioXcell) to eliminate peptides binding outside of 9D9 mAb CDRs. Identification and enrichment of peptides that specifically bound at the interface between 9D9 mAb and mouse CTLA4 was achieved.

After the final biopanning round, individual clones from the enriched population were evaluated for specific binding to 9D9 mAb by ELISA. The 9D9 mAb in the presence or absence of equimolar muCTLA4-hsIgG (R&D Systems) was coated on 96-well MaxiSorp plate (Thermo Fisher Scientific) overnight at 4° C. Individual phages displaying a unique peptide were added in triplicate to the plate blocked with skim milk and incubated for 1 hour at room temperature. After washing unbound phages vigorously, bound phages were detected using HRP-conjugated anti-M13 antibody (GE Healthcare) and HRP substrate (Sigma-Aldrich). Absorbance at 405 nm was measured in a microplate reader (Synergy HT, BioTek).

Clones that produced a high 9D9-binding signal and inhibited binding of murine CTLA4 to 9D9 mAb were selected and DNA was extracted for sequencing. The sequence from the phage encoding for the peptide CNLIVEGHC was chosen for subsequent representative experiments.

For design of the activatable masked anti-CTLA4 antibody (masked 9D9), the structural characteristics of 9D9 Fab in complex with peptide CNLIVEGHC (SEQ ID NO: 1) was determined at high resolution (1.8 Å, Table 3). 9D9 was cleaved with papain resin (Sigma) overnight at 37° C. Fab was purified with protein-A, cation-exchange (HiTrap SP-FF, GE Healthcare) and size exclusion (Superdex S75, GE Healthcare) column chromatography. Crystals of the purified Fab in 10 mM Tris-HCl pH 8.0, 25 mM NaCl, 1 mM EDTA were obtained using the hanging drop vapor diffusion method with 0.2 M Sodium Formate and 23% (w/v) PEG 3350 as the mother liquor. Crystals were harvested in cryoprotectant (1:1 mix of 35% (w/v) meso-erythritol and reservoir solution) and the data was collected on a Rigaku MicroMax007-HF rotating anode diffractometer with a Rigaku RAXIS IV++ detector. Native data was collected at 1.5418 Å at 100 K and processed using XDS, resulting in a 98.5% complete dataset to 1.8 Å. Molecular replacement with Phaser in the CCP4 suite and the trastuzumab Fab (PDB ID: 4IOI) as a search model was used to produce initial phases. See Donaldson J. M. et al., PNAS., 110: 17456-61, (2013). Several cycles of manual building in Coot followed by refinement with Phenix was used to produce the final model. Data collection and refinement statistics are listed in Table 3. The software PDBePISA was used to characterize the antibody-peptide interface in Table 4. It was determined that the CNLIVEGHC (SEQ ID NO: 1) peptide binds to the CDR loops at the interface between heavy and light chains of the 9D9 antibody. The peptide: 9D9 Fab interface consists of 5 hydrogen bonds (Table 4), resulting in an interaction surface area of 375 A2. An electrostatic surface representation of 9D9 Fab showed a large hydrophobic region at the antigen-binding site interface of the heavy and light chains. The central Leu-Ile-Val motif of the CNLIVEGHC (SEQ ID NO: 1) peptide is buried at this interface. The model indicated that the C-terminus of the CNLIVEGHC (SEQ ID NO: 1) peptide points towards the N-terminus of the light chain. The distance between the carboxy carbon of the peptide and the amide nitrogen of the light chain (residue Asp1) is 20.4 Å. A peptide that contains an MMP2/7/9 cleavage site was chosen to link the 9D9 antibody to the peptide. See Turk B. E. et al., Nat Biotech, 19:661-667, (2001). Glycine and serine amino acids were used to bridge the N- and C-termini gap. In addition, the MMP2/7/9 substrate sequence was mutated to create a 'non-cleavable' version of the masked anti-CTLA4 antibody (non-cleavable masked 9D9).

TABLE 3

| X-ray diffraction data and refinement statistics | |
|---|---|
| Space group | $P22_12_1$ |
| Unit cell dimensions (Å) | 37.0 × 88.5 × 128.7 |
| pH of crystallization condition | 8.5 |
| Protein/peptide concentration (μM) | 60/600 |
| Dataset | |
| Wavelength, Å | 1.5418 |
| Resolution range | 50-1.8 |
| Unique reflections (total) | 34911 (188519) |
| Completeness | 98.5 (91.1) |
| Redundancy | 5.4% (4.9%) |
| $R_{meas}$ | 0.073 (0.35) |
| CC(1/2) | 99.9 (93.0) |
| I/σ | 20.83 (5.14) |
| NCS copies | 1 |
| Model refinement | |
| Resolution range, Å | 33-1.88 |
| No. of reflections | 34,855 |
| No. of protein atoms | 3,936 |
| No. of water molecules | 561 |
| Residues in model | LC: 1-219, HC: 1-216, occluded peptide: 1-10 |
| Rwork/Rfree, % | 16.31/20.6 |
| Room mean square deviations | |
| Bond lengths, Å | 0.009 |
| Bond angles | 1 |
| Ramachandran plot | |
| Most favorable region, % | 99.08 |
| Additional allowed region, % | 0.92 |
| Disallowed region | 0 |

TABLE 4

| Hydrogen bonds between sterically occluded peptide and 9D9-Fab | | |
|---|---|---|
| Sterically occluded peptide | 9D9-Fab | Distance, Å |
| ASN 3 [ OD1 ] | LC: TYR 101 [ OH ] | 2.58 |
| ASN 3 [ ND2 ] | LC: GLY 96 [ O ] | 2.96 |
| ASN 3 [ ND2 ] | LC: SER 97 [ O ] | 3.16 |
| LEU 4 [ O ] | HC: TYR 33 [ OH ] | 3.53 |
| ILE 5 [ N ] | LC: TYR 101 [ OH ] | 3.78 |

Example 2: Determination of Binding Affinity Between Masking Peptides and Anti-CTLA4 Antibodies The binding affinity of the synthetic CNLIVEGHC (SEQ ID NO: 1) peptide to 9D9 antibody was determined.

Methods

Surface Plasmon Resonance was performed on a GE Biacore T200 instrument at 37° C. The 9D9 antibody and isotype control (reference channel) were coupled at 100 RU immobilization level to CM5 chip (GE Healthcare). Peptides were synthesized and diluted into HBS-EP+ running buffer (GE Healthcare). The binding data were analyzed using Biacore Evaluation Software, version 3.0.

Results

Figure 1A:
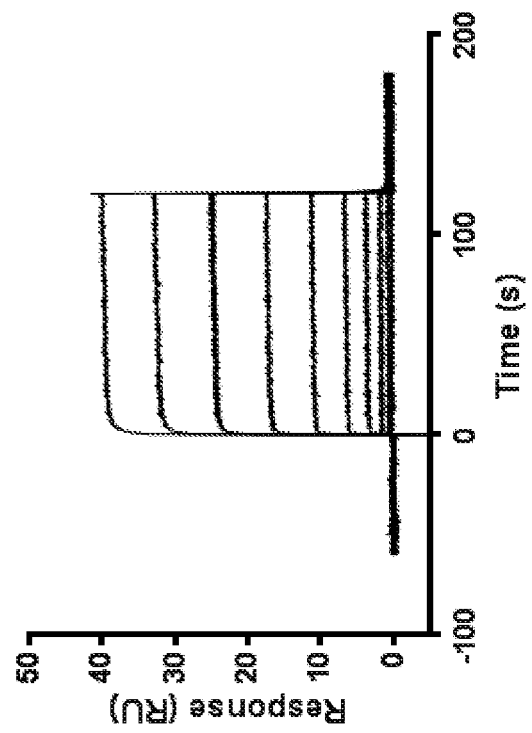

The binding affinity of the synthetic CNLIVEGHC (SEQ ID NO: 1) peptide to the 9D9 antibody as determined by SPR was 11 E-6±2.3E-6 M using a steady-state model (FIG. 1). A negative control peptide did not bind to the 9D9 antibody and the CNLIVEGHC (SEQ ID NO: 1) peptide did not bind to isotype control antibody. These results confirm that the selected peptide from phage library is specific to the 9D9 antibody.

Example 3A: In Vitro Characterization of Activatable Masked Anti-CTLA4 Antibodies Binding to Murine CTLA4

Methods

Assessment of Masked Antigen Binding Site

ELISA plates were coated overnight in TBS with murine CTLA4-Fc (R&D Systems) and then washed with TBS with 0.05% TWEEN® 20, and blocked with 1% BSA in PBS followed by washing with TBS with TWEEN® 20. Dilutions of parental anti-CTLA4 antibodies and masked anti-CTLA4 antibodies in PBS were allowed to bind to CTLA4 for 60 minutes before washing with TBS TWEEN® 20. Binding was detected with anti-muKappa-HRP (Abcam) and Super Signal Pico Chemiluminescent Substrate. Masked ratio was determined from the EC50 precleavage masked anti-CTLA4 antibody to the EC50 for parental anti-CTLA4 antibody.

Testing of Protease Cleavage

Parental anti-CTLA4 antibodies and masked anti-CTLA4 antibodies were incubated with 6 nM of MMP2 (R&D Systems) in 150 mM NaCl, 50 mM Tris, pH 7.5, 10 mM CaCl2, 0.02% NP-40) at 37° C. overnight. Antibody dilutions were tested for binding to murine CTLA4-Fc by the ELISA described above and by reduced-SDS-PAGE analysis, using "Any Kd Stain-Free pre-cast polyacrylamide gels" (Bio-Rad).

Results

Activatable masked anti-CTLA4 antibody exhibited 90-fold lower binding to murine CTLA4 (FIG. 2A). Protease activation of the masked anti-CTLA4 antibody fully restored binding of the antibody to murine CTLA4 at levels comparable to parental anti-CTLA4 antibody (FIG. 2A).

Example 3B: In Vitro Characterization of Activatable Masked Anti-CTLA4 Antibodies and Non-Cleavable Masked Anti-CTLA4 Antibodies Binding to Murine CTLA4

Methods

Low Density Antigen Binding ELISA

All ELISA were performed in a manner substantially similar to the description below or generally consistent with methods known in the art. Polysterene 96-well microplates (Thermo Fisher Scientific) were coated with 3 ng muCTLA4hsIgG protein (Abcam) per well and stored overnight at 4° C. Plates were washed with 0.1% TWEEN® in TBS (TBS-T), blocked with 1% BSA (Fisher) in PBS for 2 hours at 4° C., and washed with TBS-T. Serial dilutions of tested antibody in 0.05% TWEEN®+1% BSA in PBS (PBS-TB) were added to the plate and incubated at room temperature for 1 hour. After washing with TBS-T, HRP-conjugated goat anti-mouse Kappa light chain antibody (Abcam) diluted 1:4000 in PBS-TB was applied to the wells and incubated at room temperature for 1 hour. Plates were washed with TBS-T, chemiluminescent HRP substrate was applied to plate, and luminescence was recorded using a spectrophotometer (Synergy HT, BioTek). Data was analyzed with GraphPad Prism, version 7.02.

Enzymatic Activation of Masked Antibody

Parental anti-CTLA4 antibodies, masked anti-CTLA4 antibodies, and non-cleavable masked anti-CTLA4 antibodies were each diluted to 1 μM solution in cleavage buffer (150 mM NaCl: 50 mM Tris, pH 7.5:10 mM CaCl2; 0.02% NP-40). Recombinant MMP2 (R&D Systems) activated with 1 mM p-aminophenylmercuric acetate (AMPA) for 1 hour at 37° C. was added to each antibody solution to a final concentration of 4 nM and incubated overnight at 37° C. Antibody dilutions were tested for binding to murine CTLA4 (muCTLA4hsIgG protein: Abcam) by the low density antigen binding ELISA protocol as described above.

Results

The activatable masked anti-CTLA4 antibody and non-cleavable masked anti-CTLA4 antibody demonstrated ~156- and 218-fold lower binding to murine CTLA4 as compared to parental anti-CTLA4 antibody, respectively (FIG. 2B). The average EC50 for parental anti-CTLA4 antibody was 0.31±0.08 nM, activatable masked anti-CTLA4 antibody was 48.4±7.2 nM and non-cleavable masked anti-CTLA4 antibody was 67.7±16.3 nM as measured over three experiments (FIG. 2C). When treated with recombinant MMP2, binding comparable to parental anti-CTLA4 antibody was restored to the activatable masked anti-CTLA4 antibody (average EC50=0.29±0.03 nM, FIG. 2C) whereas binding by the non-cleavable masked anti-CTLA4 antibody was unchanged (average EC50=64.3±18.5 nM, FIG. 2C).

Example 4A: In Vivo Characterization of Activatable Masked Anti-CTLA4 Antibodies

Methods

Production of Activatable Masked Anti-CTLA4 Antibodies for In Vivo Studies

Masked anti-CTLA4 antibodies were produced using HEK293 transient expression with expression plasmid pD2610-v5 (ATUM, Newark CA). Seven days after transfection, supernatants from the transfected cells were harvested and masked anti-CTLA4 antibodies were purified with KanCapA resin (Kaneka), followed by purification by cation exchange using a Source S column (GE Healthcare) and eluted with a 0-1M NaCl gradient at pH 5. The antibodies were then buffer exchanged into PBS. Antibody concentrations were determined at an optical density of OD280 by spectrophotometer and endotoxin levels were determined using Charles River Endotoxin Kit.

Tumor Eradication by Activatable Masked Anti-CTLA4 Antibodies

C57Bl/6 mice with 50-100 mm$^3$ MC38 tumors were administered intraperitoneally a single dose of 200 µg of IgG2a control (BioXcel), parental anti-CTLA4 antibody reactive to murine CTLA4 (9D9.IgG2a, light chain comprising SEQ ID NO:237, heavy chain comprising SEQ ID NO:319), activatable masked anti-CTLA4 antibody reactive to murine CTLA4 (light chain comprising SEQ ID NO:238, heavy chain comprising SEQ ID NO: 319), masked anti-CTLA4 antibody 1005 reactive to murine CTLA4 (light chain comprising SEQ ID NO:240, heavy chain comprising SEQ ID NO:319), or anti-CTLA4 antibody 1 cross-reactive with human CTLA4 and murine CTLA4 (light chain comprising SEQ ID NO:327, heavy chain comprising SEQ ID NO:366). Body weight and tumor size were measured biweekly.

T Cell Population Analysis

C57Bl/6 mice with 50-100 mm$^3$ MC38 tumors were dosed with three 200 µg doses on day 1, 4, and 8 with IgG2a control (BioXcel), parental anti-CTLA4 antibody (9D9.IgG2a, light chain comprising SEQ ID NO:237, heavy chain comprising SEQ ID NO: 319 masked anti-CTLA4 antibody 2 (light chain comprising SEQ ID NO:238, heavy chain comprising SEQ ID NO:319), masked anti-CTLA4 antibody 1005 (light chain comprising SEQ ID NO:240, heavy chain comprising SEQ ID NO:319), or anti-CTLA4 antibody 1 cross-reactive with human CTLA4 and murine CTLA4 (light chain comprising SEQ ID NO:327, heavy chain comprising SEQ ID NO:366). On day 9, mice were sacrificed and tumors were dissociated using gentleMACS™ protocol "Tumor Dissociation Kit" (Milteni) and filtered through a 70 micron cell strainer and rinsed twice in PBS/2.5% FBS buffer to remove enzymatic buffer. Spleen cells were tumor infiltrate and spleen cells were dissociated by gently grinding the tissue across a mesh. Red blood cells were lysed with ACK buffer (Thermo Fisher) prior to staining of the cells. Staining of cells was with fluorescently labeled anti-CD45 (BioLegend), anti-CD3 (BioLegend), anti-CD4 (BioLegend), anti-CD8 (BD Biosciences), anti-CD25 (BioLegend). Prior to staining with anti-FoxP3 (eBioscience), and anti-Ki67 (eBioscience) the cells were permeabilized. Stained cells were analyzed by fluorescent activate cell sorting (FACS) for the percentages of CD4+, CD8+, and CD25 Foxp3+ (Tregs) cells of the live (Live/Dead Aqua purchased from Life) CD45 positive cells, as well as the percentage of these three cell populations that were Ki67 positive, a marker of cell proliferation.

Results

Figure 3A:
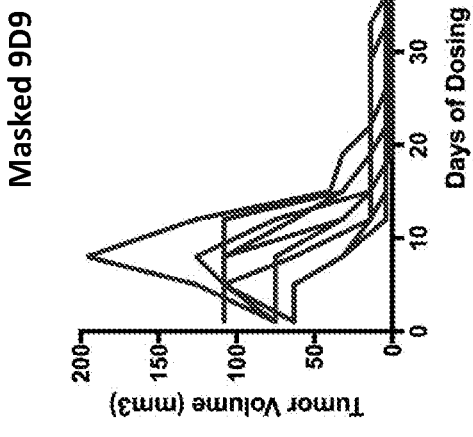
FIGS. 3A-3D is a series of graphs showing that efficacy of protease activated masked anti-CTLA4 antibody (Masked 9D9) in the reduction of tumor volume was equivalent to the efficacy of parental anti-CTLA4 antibody (9D9 IgG2a). MC38 syngeneic tumors were implanted in C57Bl/6 mice. A single 200 μg dose of FIG. 3A) muIgG2a control antibody, FIG. 3B) parental anti-CTLA4 antibody with IgG2a isotype (9D9.IgG2a), FIG. 3C) activatable masked anti-CTLA4 antibody (Masked 9D9) was administered intraperitoneally to a murine once tumors reached 60-120 mm3 in size, FIG. 3D) humanized IgG1 anti-CTLA4 antibody 1 (Antibody 1) demonstrated similar in vivo efficacy in reducing tumor volume in a MC38 murine tumor model as compared to mice treated with 3B) parental anti-CTLA4 antibody (9D9 IgG2a) or 3A) muIgG2a control antibody.
Figure 3B:
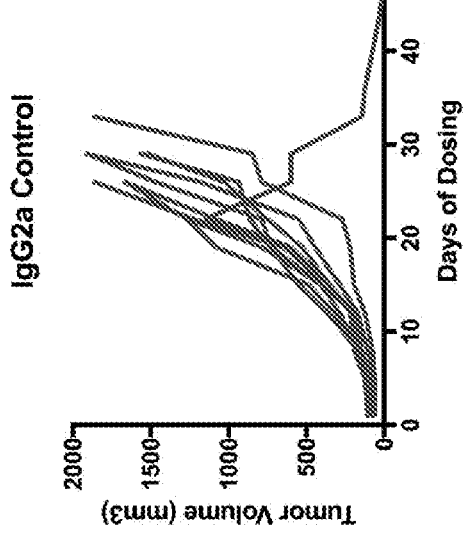
Figure 3C:
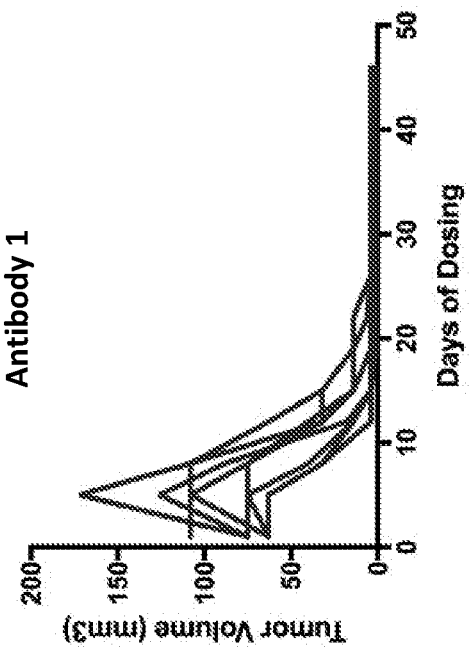
Figure 4:
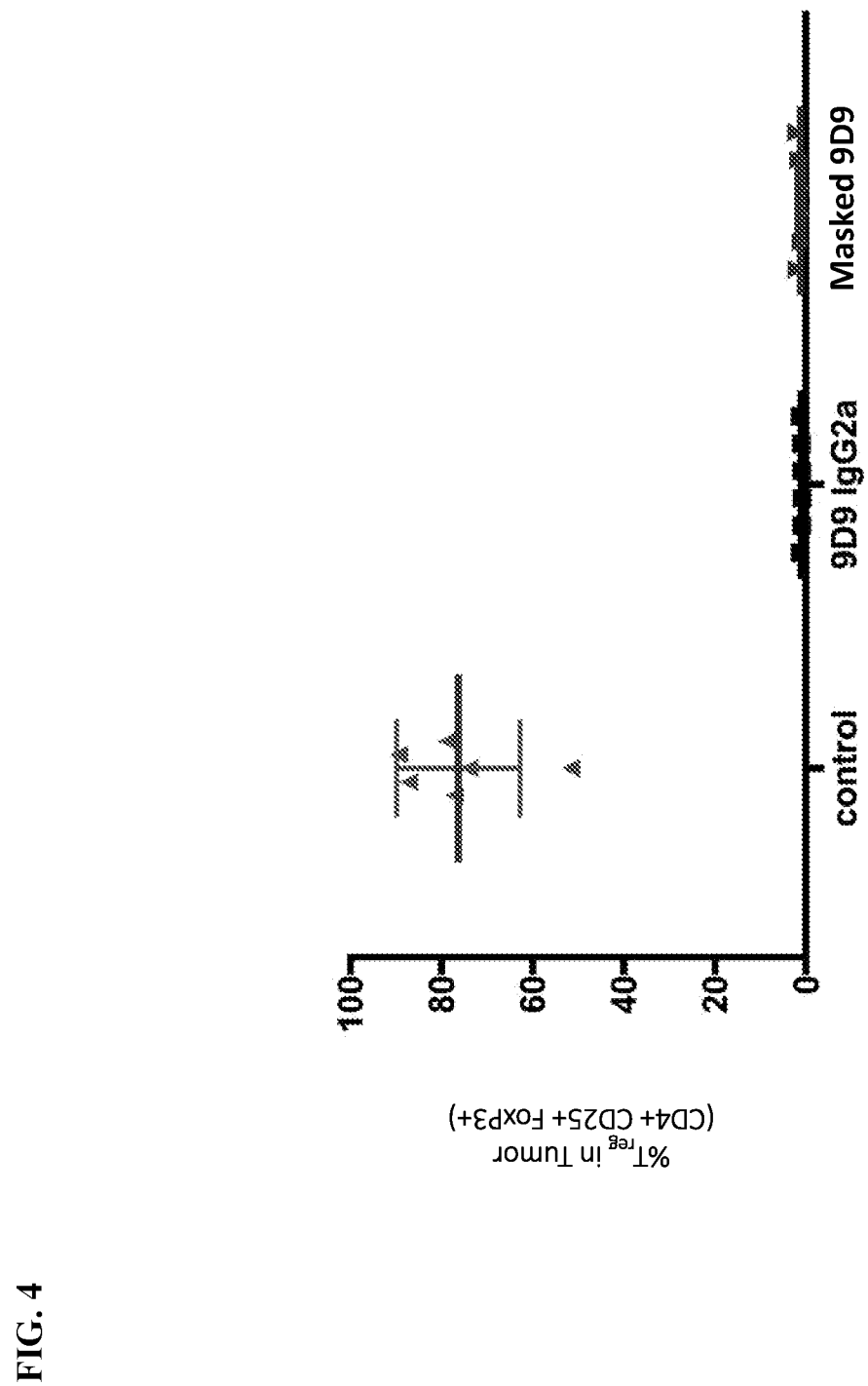
FIG. 4 is a graph showing equivalent depletion of regulatory T lymphocytes (Tregs) in the tumor infiltrate by protease activated masked anti-CTLA4 antibody (Masked 9D9) and parental anti-CTLA4 antibody (9D9 IgG2a). Control indicates treatment with muIgG2a control antibody.
Figure 5A:
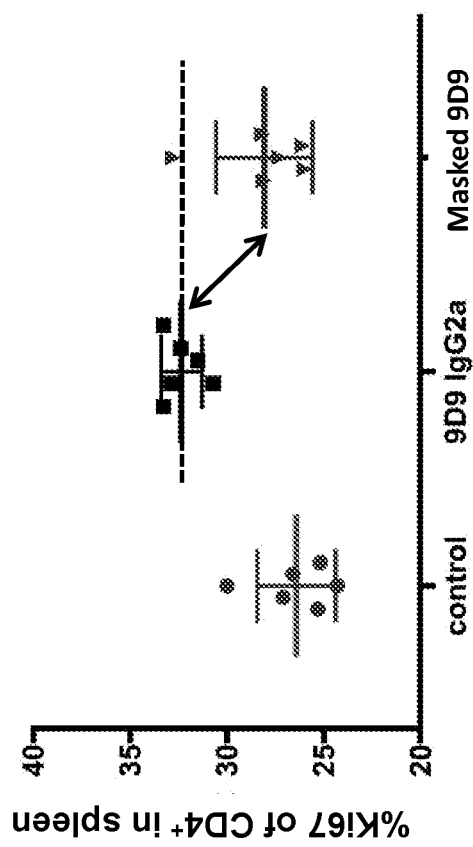
FIGS. 5A and 5B is a series of graphs showing that protease activated masked anti-CTLA4 antibody (Masked 9D9) markedly reduced proliferation of A) CD4+ T cells and B) CD8+ T cells in the spleens of treated mice. Arrow is pointing to mean values between treatment groups with parental anti-CTLA4 antibody (9D9 IgG2a) and protease activated masked anti-CTLA4 antibody (Masked 9D9).
Figure 5B:
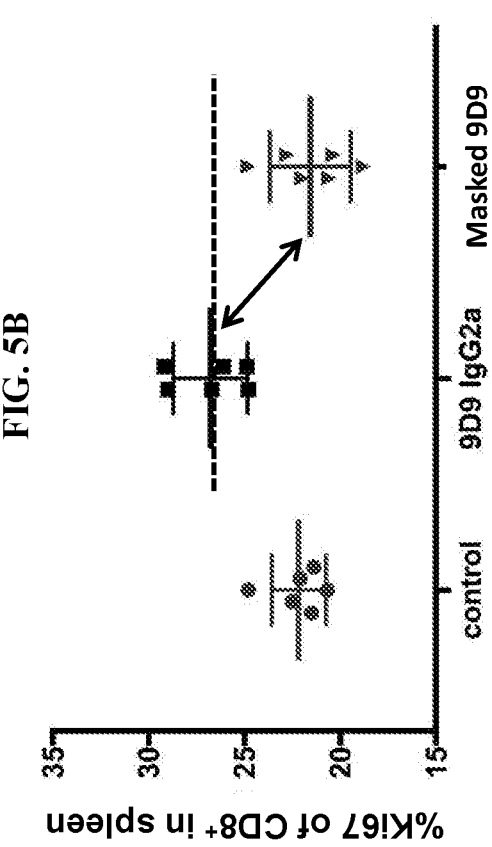

Parental anti-CTLA4 antibody (9D9.IgG2a) reduced tumor volume in mice as compared to tumor volume in mice treated with IgG2a control antibody (FIGS. 3A and 3B). Activatable masked anti-CTLA4 antibody showed equivalent efficacy in reducing tumor volume (FIG. 3C) as compared to parental anti-CTLA4 antibodies (FIG. 3B). Regulatory T lymphocytes (Tregs) in the TME are key to immune suppression. Both parental anti-CTLA4 antibody (9D9.IgG2a) and activatable masked anti-CTLA4 antibody 2 (Masked 9D9) preferentially depleted the regulatory T lymphocytes (Tregs) population in the tumor via effector function (FIG. 4). Blockade of CTLA4 on T cells in vivo results in proliferation of CD4+ and CD8+ T cells. Proliferation of T cells in the spleen after multi-dose administration of parental anti-CTLA4 antibody (9D9.IgG2a) or activatable masked anti-CTLA4 antibody 2 (Masked 9D9) were assessed by % Ki67+. Masked anti-CTLA4 antibodies showed reduced proliferation of CD4+ cells (FIG. 5A) and CD8+ T cells (FIG. 5B) in the periphery compared to the parental antibody (9D9.IgG2a).

Figure 3D:
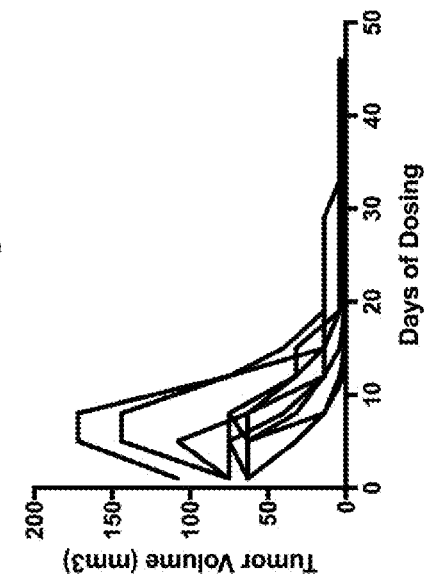

Humanized masked anti-CTLA4 antibody 1 has a higher affinity than ipilimumab for human CTLA4 (7-fold and 38-fold, respectively) and is cross-reactive with cynomolgus CTLA4 and murine CTLA4. Humanized masked anti-CTLA4 antibody 1 showed equivalent efficacy in reducing tumor volume (FIG. 3D) as compared to parental anti-CTLA4 antibodies (FIG. 3B).

Example 4B: In Vivo Characterization of Activatable Masked Anti-CTLA4 Antibodies The effects of activatable masked anti-CTLA4 antibodies on tumor growth as well as immune parameters in the tumor and in the periphery were investigated using a MC38 mouse colorectal carcinoma model, previously shown to respond to treatment with the 9D9 antibody. See Peggs K. S. et al., J Exp Med., 206:1717-1725, (2009) and Selby M. J., et al., Cancer Immunol Res., 1:32-42, (2013).

Methods

Tumor Eradication by Activatable Masked Anti-CTLA4 Antibodies

Female C57BL/6 aged between 8 and 12 weeks were injected subcutaneously with 0.5×106 MC38 tumor cells. When mean tumor volume reached 50-100 mm3, mice were randomized into treatment groups of comparable mean tumor volumes. To assess anti-tumor efficacy, antibodies formulated in PBS were administered intraperitoneally (i.p.) on day 1 post-randomization at 200 µg per dose in a volume of <250 µL. Tumor volumes were determined twice weekly. All mice were monitored individually and sacrificed upon either tumor volume reaching 1500 mm3 or 45 days post-randomization. To assess biological function of antibodies on regulatory T cells (Tregs) by FACS analysis as described below, tumor-bearing mice were administered antibody intraperitoneally on days 1, 4, and 8 post-randomization at 200 µg per dose in a volume of <250 µL. The control antibody was muIgG2a (BioXcell). All mice were sacrificed on day 9; tumor and spleen were harvested for FACS analysis.

T Cell Population Analysis

Mouse tumor samples were dissociated according to standard protocol by Tumor Dissociation Kit (gentleMACS) and passed through a 70 µm cell strainer. Spleen samples were dissociated with the back of a syringe in a 70 μm cell strainer. Red blood cells were lysed with ACK buffer (Lonza). Final cell suspensions were washed and resuspended in Staining Buffer (PBS pH 7.4, 2.5% FBS, 0.09% NaN3) at 2×107 cells/mL. Cells were treated with Mu Trustain fcX (BioLegend) to block Fc receptors prior to being stained with antibodies against CD45 (BioLegend), CD3 (BioLegend), CD4 (BioLegend), CD8 (BD Biosciences), CD25 (BioLegend), and Live/Dead Aqua (ThermoFisher). For intracellular staining, cells were fixed, permeabilized, and stained with antibodies against FoxP3 (eBioscience) and Ki-67 (eBioscience). Single color stains and FMOs were run for gating purposes.

Results

Figure 6A:
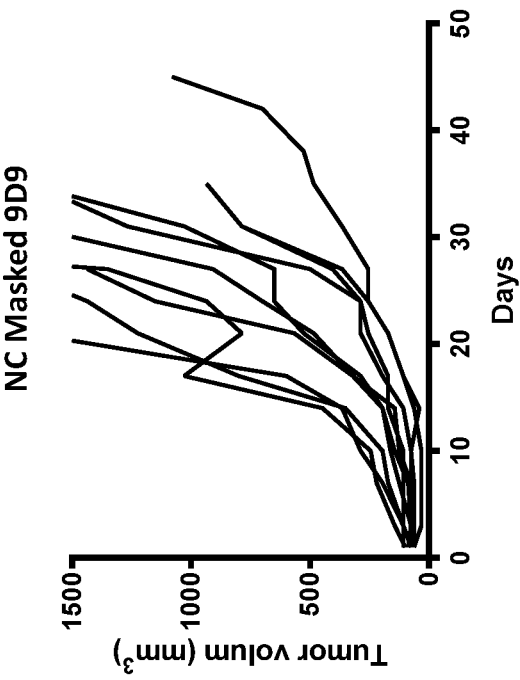
FIGS. 6A-6D is a series of graphs showing the efficacy and safety study of masked anti-CTLA4 antibodies. Tumor suppression activity of FIG. 6A) isotype control antibody (IgG2a Control), FIG. 6B) non-cleavable masked anti-CTLA4 antibody (NC Masked 9D9), FIG. 6C) parental anti-CTLA4 antibody (9D9), and FIG. 6D) activatable masked anti-CTLA4 antibody (Masked 9D9) was examined in MC38 tumor-bearing C57BL/6 mice (n=10).
Figure 6B:
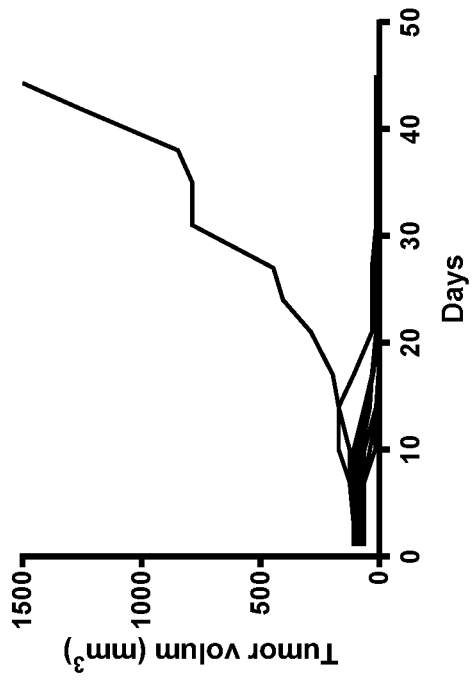
Figure 6C:
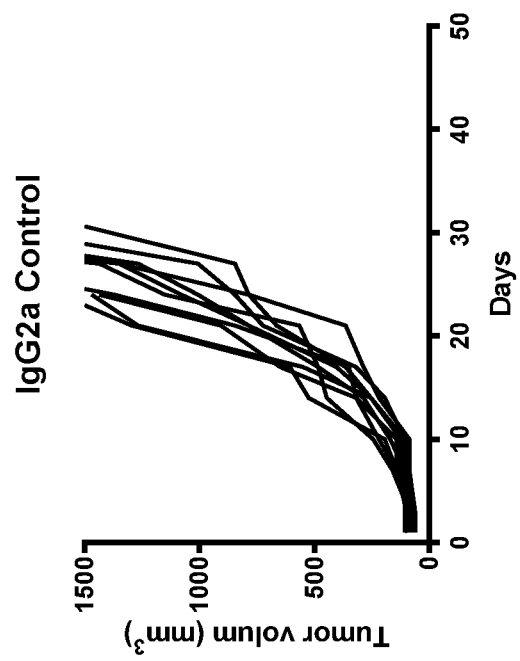
Figure 6D:
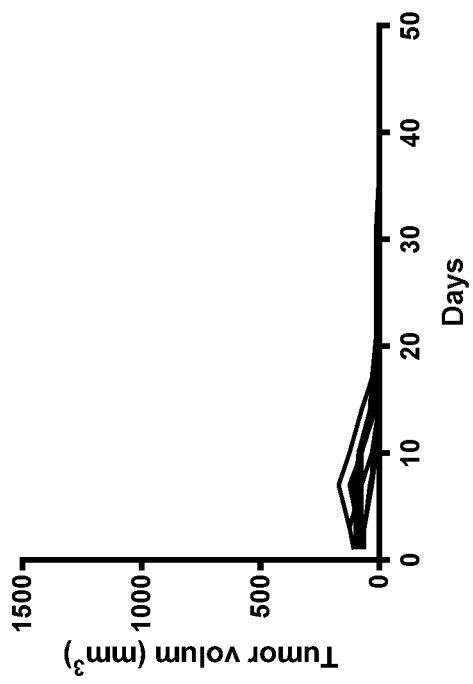

Administration of parental anti-CTLA4 antibody (FIG. 6C) and activatable masked anti-CTLA4 antibody (FIG. 6D) induced tumor regression of subcutaneously implanted MC38 tumors whereas tumors grew rapidly in mice treated with either isotype control antibody (FIG. 6A) or with the non-cleavable masked anti-CTLA4 antibody (FIG. 6B). These results demonstrate that activatable masked anti-CTLA4 antibody retained anti-tumor activity consistent with effective cleavage and dissociation of the masking peptide in the tumor microenvironment. In addition, full activity of activatable masked anti-CTLA4 antibody depended on protease cleavage as the non-cleavable masked anti-CTLA4 antibody failed to inhibit tumor growth. These results are consistent with the earlier observation indicating that local administration of anti-CTLA4 antibodies effectively induces tumor regressions in mice. See Marabelle, A., et al., JCI, 123:2447-2463, (2013).

Intratumoral and systemic immune activation by activatable masked anti-CTLA4 antibody administration was analyzed. Previous work established that muIgG2a anti-CTLA4 antibodies deplete Treg cells intratumorally in an FcγR-dependent fashion whereas they lead to activation and expansion of Tregs in the spleens of treated mice. See Selby M. J., et al., Cancer Immunol Res., 1:32-42, (2013). Therefore, to assess local and systemic activity of masked anti-CTLA4 antibodies, the abundance and proliferative states of Tregs intratumorally (FIG. 7A) and in the spleen (FIG. 7B) was assessed, respectively. Tumor and spleen samples were collected 24 hours after the last of three doses of the antibodies. Flow cytometric analysis revealed Tregs were significantly reduced in the tumors of mice treated with parental anti-CTLA4 antibody (FIG. 7A). Activatable masked anti-CTLA4 antibody was as effective in reducing Tregs as parental anti-CTLA4 antibody (FIG. 7A). In contrast, non-cleavable masked anti-CTLA4 antibody had no significant effect on intratumoral Treg abundance (FIG. 7A). These results indicate activatable masked anti-CTLA4 antibody has comparable activity in the tumor environment as parental anti-CTLA4 antibody in a manner that is dependent on the activity of tumor-associated proteases.

In contrast to the effects on Treg cells in tumor tissues, parental anti-CTLA4 antibody caused a marked increase in proliferating (Ki67+FOXP3+) Tregs in the spleens of treated mice (FIG. 7B). When compared to parental anti-CTLA4 antibody, activatable masked anti-CTLA4 antibody led to marginal increases in proliferating splenic Tregs, while non-cleavable masked anti-CTLA4 antibody had no effect on Treg proliferation when compared to isotype control antibody (FIG. 7B). Taken together, these results support the conclusion that tumor activation of activatable masked anti-CTLA4 antibody is largely confined to the tumor environment with reduced activity in normal tissues.

Example 5: In Vitro Characterization of Activatable Masked Anti-CTLA4 Antibodies Binding to Human CTLA4

Methods

Assessment of Masked Antigen Binding Site
ELISA plates were coated overnight in TBS with human CTLA4-Fc (R&D Systems) and then washed with TBS with 0.05% TWEEN® 20, and blocked with 1% BSA in PBS followed by washing with TBS with TWEEN® 20. Dilutions of parental anti-CTLA4 antibodies and masked anti-CTLA4 antibodies in PBS were allowed to bind to CTLA4 for 60 minutes before washing with TBS TWEEN® 20. Binding was detected with anti-huKappa-HRP (Abcam) and Super Signal Pico Chemiluminescent Substrate. Masked ratio was determined from the EC50 precleavage masked anti-CTLA4 antibody to the EC50 for parental anti-CTLA4 antibody.
Testing of Protease Cleavage
Parental anti-CTLA4 antibodies and masked anti-CTLA4 antibodies were incubated with 6 nM 1) Matriptase in 50 mM Tris, pH 9, 50 mM NaCl, 0.01% TWEEN®-20 at 37° C. overnight. Antibody dilutions were tested for binding to human CTLA4 by the ELISA described above and by reduced-SDS-PAGE analysis, using "Any Kd Stain-Free pre-cast polyacrylamide gels" (Bio-Rad).

Results

Figure 8:
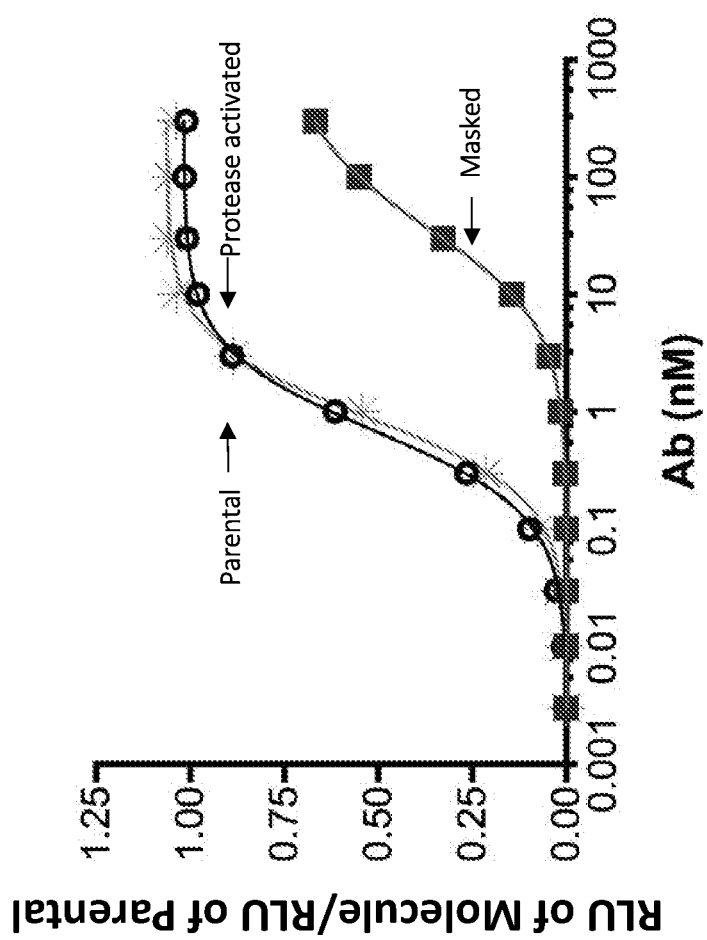
FIG. 8 is a graph showing protease activation of masked humanized anti-CTLA4 antibody 1. Masked humanized anti-CTLA4 antibody 1 exhibited lower binding to human CTLA4-Fc (Masked, filled squares) compared to parental humanized anti-CTLA4 antibody 1 (Parental, empty circles). Protease activation of the masked humanized anti-CTLA4 antibody fully restored binding to human CTLA4-Fc (Protease activated, asterisk) at levels comparable to parental humanized anti-CTLA4 antibody 1. X-axis indicates amount of antibody tested. RLU of molecule/RLU of parental on y-axis indicates the fraction of relative light units compared to parental humanized anti-CTLA4 antibody 1.

Humanized masked anti-CTLA4 antibody 1 exhibited 50 fold lower binding to human CTLA4 (FIG. 8). Protease activation of the humanized masked anti-CTLA4 antibody 1 fully restored binding of the antibody to human CTLA4 at levels comparable to parental anti-CTLA4 antibody (FIG. 8).

Example 6: Enzymatic Activation of Masked Antibodies

Masked antibodies were activated using a recombinant proteases with the protocol described below.

Masked antibodies were buffer exchanged into MMP cleavage buffer prior to incubation with the protease. For activation, protease (Anaspec, ProsecBio, and R&D Systems) was diluted to 100 ng/μL in MMP cleavage buffer (50 mM Tris pH 8.0, 150 mM NaCl, 10 mM CaCl2). APMA (10 mM in DMSO) was added to a final concentration of 1 mM. The enzyme was incubated at 37° C. for 1 hour. Activated protease was added to the masked antibodies at a ratio of 1:1000 antibody: protease (e.g., 1 μg MMP to 1 mg antibody) or an equal amount of buffer was added to negative control samples. Samples were incubated at 37° C. overnight.

Following incubation the treated antibodies were purified using Protein A resin. Briefly, 150 μL MabSure ProA slurry (GE Healthcare) was added to a 1.7 mL tube. The slurry was washed twice with 1 mL PBS by spinning for two minutes in a my Spin 6 centrifuge. Activated antibody (500 μL) was added to the slurry and incubated with rocking for thirty minutes at room temperature or three hours at 4° C. Antibody-slurry mixture was spun for two minutes in mySpin 6 centrifuge and the flow through was collected. The resin was washed twice with 1 mL of 1×PBS and the washes were collected. Antibodies were eluted using at least six times 100 µL of 25 mM Sodium Acetate pH 3.5 (into new 1.7 mL tube with 6 µL 1M Tris pH 8.0). The concentration of the eluates was measured.

All eluates and buffer exchanged samples were pooled into PBS. 500 µL of PBS was added to the pooled sample. The sample was added to a filter and spun three times. The pooled sample was collected by adding 100 µL of PBS to the top of the filter and mixing to remove exchanged protein. The concentration of purified antibodies was measured. Samples were diluted to 1 mg/mL in PBS.

Samples were analyzed for activation using SDS-PAGE. Briefly, 10 µL of sample (at 1 mg/mL) was mixed with 10 µL of loading buffer and boiled at 90° C. for ten minutes. 10 µL of sample was loaded onto a 15-well Any-kDa stain-free gel (BioRad) and run at 200V for thirty minutes. Proteins were imaged using BioRad imager to ensure complete activation by change in migration size.

Complete activation of masked antibodies was demonstrated by the change in migration size of the cleaved antibody.

Example 7: In Vitro Characterization of Anti-CTLA4 Antibodies Binding to Human CTLA4: Low Density Antigen Binding ELISA Methods Polystyrene 96-well microplates (Fisher #07-200-591) were coated with 1 µg/ml of human CTLA4-Fc (R&D #7268-CT) per well and stored overnight at 4° C. Plates were washed with 0.05% TWEEN® in TBS (TBS-T), blocked with 1% BSA (Sigma Aldrich #B4287-25G), and washed with TBS-T. Serial dilutions of samples containing anti-CTLA4 antibodies were made in assay buffer (PBS+ 0.05% TWEEN®+1% BSA), added to plate, and shaken orbitally at 100 RPM at room temperature for one hour. After washing with TBS-T, anti-human Kappa light chain [clone: SB81a]-HRP (Abcam #ab79115) diluted to 1:8000 in assay buffer was applied to the wells and shaken at room temperature for one hour. Plates were washed with TBS-T, HRP substrate (Super Signal Pico Chemiluminescent Substrate, Thermo #37069) was applied to plate, and luminescence was recorded using a spectrophotometer (BioTek). Data was analyzed with GraphPad Prism.

Antibodies tested include humanized anti-CTLA4 antibodies termed Antibody 1 and Antibody 2, and variants/forms/versions thereof. In accordance with a particular numbering scheme, Antibody 1 comprises a light chain variable region with a CDR-L1 comprising the amino acid sequence of SEQ ID NO: 402, a CDR-L2 comprising the amino acid sequence of SEQ ID NO: 403, and a CDR-L3 comprising the amino acid sequence of SEQ ID NO: 404, and comprises a heavy chain variable region comprising a CDR-H1 comprising the amino acid sequence of SEQ ID NO: 405, a CDR-H2 comprising the amino acid sequence of SEQ ID NO: 406, and a CDR-H3 comprising the amino acid sequence of SEQ ID NO: 407. Antibody 1 comprises a VL domain comprising the amino acid sequence of SEQ ID NO: 321, and a VH domain comprising the amino acid sequence of SEQ ID NO: 323. In accordance with the Kabat numbering scheme, Antibody 1 comprises a light chain variable region with a CDR-L1 comprising the amino acid sequence of SEQ ID NO: 432, a CDR-L2 comprising the amino acid sequence of SEQ ID NO: 433, and a CDR-L3 comprising the amino acid sequence of SEQ ID NO: 434, and comprises a heavy chain variable region comprising a CDR-H1 comprising the amino acid sequence of SEQ ID NO: 435, a CDR-H2 comprising the amino acid sequence of SEQ ID NO: 436, and a CDR-H3 comprising the amino acid sequence of SEQ ID NO: 437. In accordance with a particular numbering scheme, Antibody 2 comprises a light chain variable region with a CDR-L1 comprising the amino acid sequence of SEQ ID NO: 408, a CDR-L2 comprising the amino acid sequence of SEQ ID NO: 409, and a CDR-L3 comprising the amino acid sequence of SEQ ID NO: 410, and comprises a heavy chain variable region comprising a CDR-H1 comprising the amino acid sequence of SEQ ID NO: 411, a CDR-H2 comprising the amino acid sequence of SEQ ID NO: 412, and a CDR-H3 comprising the amino acid sequence of SEQ ID NO: 413. In accordance with Kabat numbering scheme, Antibody 2 comprises a light chain variable region with a CDR-L1 comprising the amino acid sequence of SEQ ID NO: 438, a CDR-L2 comprising the amino acid sequence of SEQ ID NO: 439, and a CDR-L3 comprising the amino acid sequence of SEQ ID NO: 440, and comprises a heavy chain variable region comprising a CDR-H1 comprising the amino acid sequence of SEQ ID NO: 441, a CDR-H2 comprising the amino acid sequence of SEQ ID NO: 442, and a CDR-H3 comprising the amino acid sequence of SEQ ID NO: 443. Various forms of Antibody 1 were generated, each with a nomenclature of "Antibody 1-#," and various forms of Antibody 2 were generated, each with a nomenclature of "Antibody 2-#."

Results

Figure 9A:
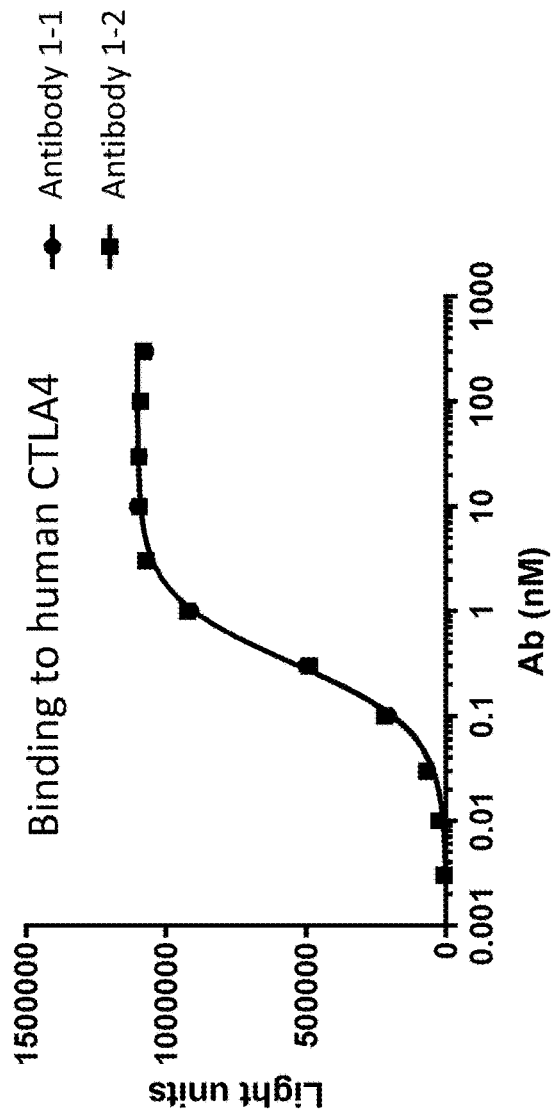
FIGS. 9A and 9B are graphs showing the binding of unmasked anti-CTLA4 antibodies to human CTLA4-Fc across a range of antibody concentrations.
Figure 9B:
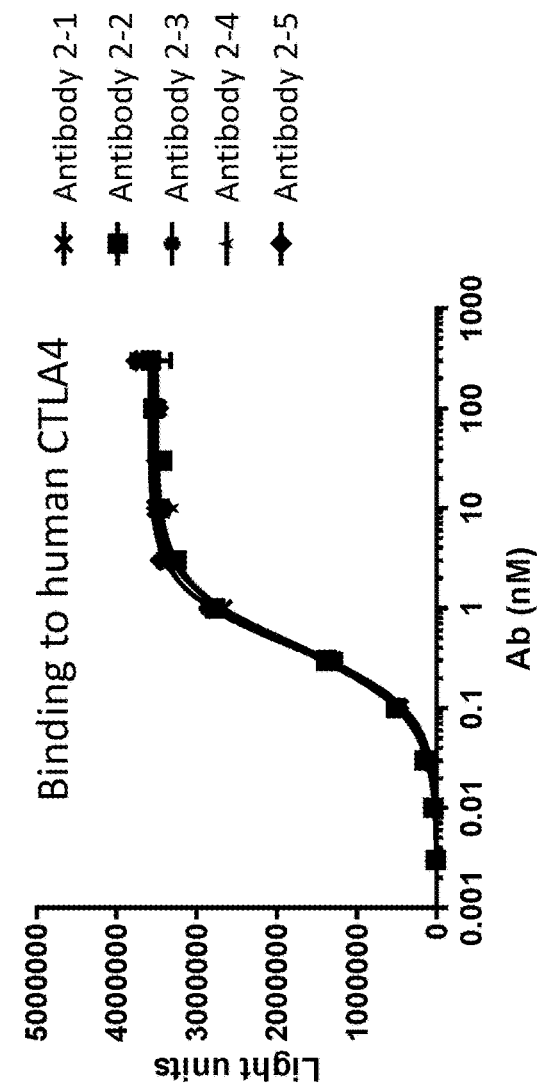

FIG. 9A and FIG. 9B show binding studies with the humanized anti-CTLA4 antibodies termed Antibody 1 and Antibody 2, or variants thereof. FIG. 9A shows no detectable difference between the binding of a version of Antibody 1 having a wild type Fc region (Antibody 1-1) and a version of Antibody 1 having a S239D mutation and an I332E mutation in the Fc region (Antibody 1-2) to human CTLA4-Fc. Antibody 1-2 comprises a VL domain comprising the amino acid sequence of SEQ ID NO: 327, and a VH domain comprising the amino acid sequence of SEQ ID NO: 478. FIG. 9B compares the CTLA4 binding of various forms of Antibody 2, including a version of Antibody 2 having a wild-type Fc region (Antibody 2-1), a version of Antibody 2 having a S239D mutation and an I332E mutation in the Fc region (Antibody 2-2), a version of Antibody 2 having a S239D mutation, an I332E mutation in the Fc region, and two hinge region mutations (Antibody 2-3), a version of Antibody 2 having S239D, I332E, and A330L mutations in the Fc region (Antibody 2-4), and a version of Antibody 2 having S239D, I332E, A330L mutations in the Fc region, and two hinge region mutations (Antibody 2-5). As shown in FIG. 9B, all forms of the antibodies bound to the human CTLA4-Fc similarly. The average $EC_{50}$ values for the antibodies tested are provided in Table 5 below.

TABLE 5

Antibody Binding to human CTLA4-Fc

| Antibody | $EC_{50}$ (nM) | $R^2$ |
|---|---|---|
| Antibody 1-1 | 0.32 ± 0.01 | 0.9984 |
| Antibody 1-2 | 0.32 ± 0.01 | 0.998 |
| Antibody 2-1 | 0.44 ± 0.02 | 0.9978 |
| Antibody 2-2 | 0.39 ± 0.01 | 0.9979 |

TABLE 5-continued

Antibody Binding to human CTLA4-Fc

| Antibody | EC$_{50}$ (nM) | R$^2$ |
|---|---|---|
| Antibody 2-3 | 0.40 ± 0.02 | 0.9967 |
| Antibody 2-4 | 0.40 ± 0.02 | 0.9962 |
| Antibody 2-5 | 0.41 ± 0.02 | 0.9968 |

Example 8: Impact of Protease Activation on Human CTLA4 Binding

Methods

Humanized anti-CTLA4 antibodies were used in low density antigen binding ELISA described in Example 7. For assessing activation of masked activatable forms of the humanized anti-CTLA4 antibodies, recombinant proteases were used as outlined in Example 6.

An unmasked version of Antibody 2 having a S239D mutation and an I332E mutation in the Fc region (Antibody 2-6) was used as an unmasked control for comparison to versions of the antibody having the same two mutations but also including a masking peptide that includes the amino sequence of SEQ ID NO: 19 or 5, as well as spacer linkers and a cleavable peptide. The parental unmasked Antibody 2-6 includes a variable heavy chain having the amino acid sequence of SEQ ID NO: 324, a variable light chain having the amino acid sequence of SEQ ID NO: 322, a heavy chain having the amino acid sequence of SEQ ID NO: 421, and a light chain having the amino acid sequence of SEQ ID NO: 334. The masked antibodies of Antibody 2-7 through Antibody 2-21 include the variable heavy chain, variable light chain, heavy chain, and light chain sequences of the parental unmasked Antibody 2-6 and further include a masking peptide, a spacer linker 1, a cleavable (or non-cleavable) peptide, and a spacer linker 2, as described in Table 6 and Table 9. Thus, each of Antibody 2-6, Antibody 2-7, Antibody 2-8, Antibody 2-9, Antibody 2-10, Antibody 2-11, Antibody 2-12, Antibody 2-13, Antibody 2-14, Antibody 2-15, Antibody 2-16, Antibody 2-17, Antibody 2-18, Antibody 2-19, Antibody 2-20, and Antibody 2-21 comprise a VH domain comprising the amino acid sequence of SEQ ID NO: 324, a VL domain comprising the amino acid sequence of SEQ ID NO: 322, a heavy chain comprising the amino acid sequence of SEQ ID NO: 421, and a light chain comprising the amino acid sequence of SEQ ID NO: 334. Unless otherwise indicated, the masked antibodies termed Antibody 2-7 through Antibody 2-21 are masked by linking the following components to the light chain of the parental unmasked Antibody 2-6 in an N-terminus to C-terminus direction as follows: 1) masking peptide: 2) spacer linker 1:3) cleavable peptide: 4) spacer linker 2: N-terminus of the light chain. Antibody 2-10 includes a cleavable peptide sequence that is non-cleavable, for use as a negative control. Examples of exemplary antibodies tested, including sequences of the spacer linkers and cleavable peptide in Antibody 2-7 through Antibody 2-13, are provided in Table 6.

TABLE 6

| Antibody | Masking Peptide | Spacer Linker 1 | Cleavable Peptide | Spacer Linker 2 | Heavy chain | Light chain + masking components |
|---|---|---|---|---|---|---|
| Antibody 2-7 | CPFPALELC (SEQ ID NO: 19) | GGSGGS (SEQ ID NO: 415) | VPLSLY (SEQ ID NO: 86) | SGG (SEQ ID NO: 102) | SEQ ID NO: 421 | SEQ ID NO: 424 |
| Antibody 2-8 | CPFPALELC (SEQ ID NO: 19) | GGPGSSP (SEQ ID NO: 416) | MPYDL YHP (SEQ ID NO: 47) | SGG (SEQ ID NO: 102) | SEQ ID NO: 421 | SEQ ID NO: 425 |
| Antibody 2-9 | CPFPALELC (SEQ ID NO: 19) | GGSSPP (SEQ ID NO: 417) | HEQLTV (SEQ ID NO: 57) | SGG (SEQ ID NO: 102) | SEQ ID NO: 421 | SEQ ID NO: 426 |
| Antibody 2-10 | CPFPALELC (SEQ ID NO: 19) | GGGSSGGSG (SEQ ID NO: 96) | GSGGSG (SEQ ID NO: 414) | SGG (SEQ ID NO: 102) | SEQ ID NO: 421 | SEQ ID NO: 427 |
| Antibody 2-11 | CPFPALELC (SEQ ID NO: 19) | SSPSPSGG (SEQ ID NO: 418) | GGIGQLTA (SEQ ID NO: 48) | SGG (SEQ ID NO: 102) | SEQ ID NO: 421 | SEQ ID NO: 428 |
| Antibody 2-12 | CPFPALELC (SEQ ID NO: 19) | GSPGSP (SEQ ID NO: 419) | KPILFFRL (SEQ ID NO: 54) | SGG (SEQ ID NO: 102) | SEQ ID NO: 421 | SEQ ID NO: 431 |
| Antibody 2-13 | CPFPALELC (SEQ ID NO: 19) | GGSSPP (SEQ ID NO: 417) | RAAAVKSP (SEQ ID NO: 72) | SGG (SEQ ID NO: 102) | SEQ ID NO: 421 | SEQ ID NO: 429 |

Serial dilutions of the antibodies were made in assay buffer, added to 96-well microplates coated with human CTLA4-Fc, and shaken at room temperature for one hour. Plates were washed with TBS-T, blocked with BSA, and washed again with TBS-T. The antibodies were added to plate and shaken. After washing, anti-human Kappa light chain (conjugated to HRP) in assay buffer was applied to the wells and shaken at room temperature. Plates were washed again before HRP substrate was added. Luminescence was recorded using a spectrophotometer and data analyzed with GraphPad Prism.

Results

Figure 10A:
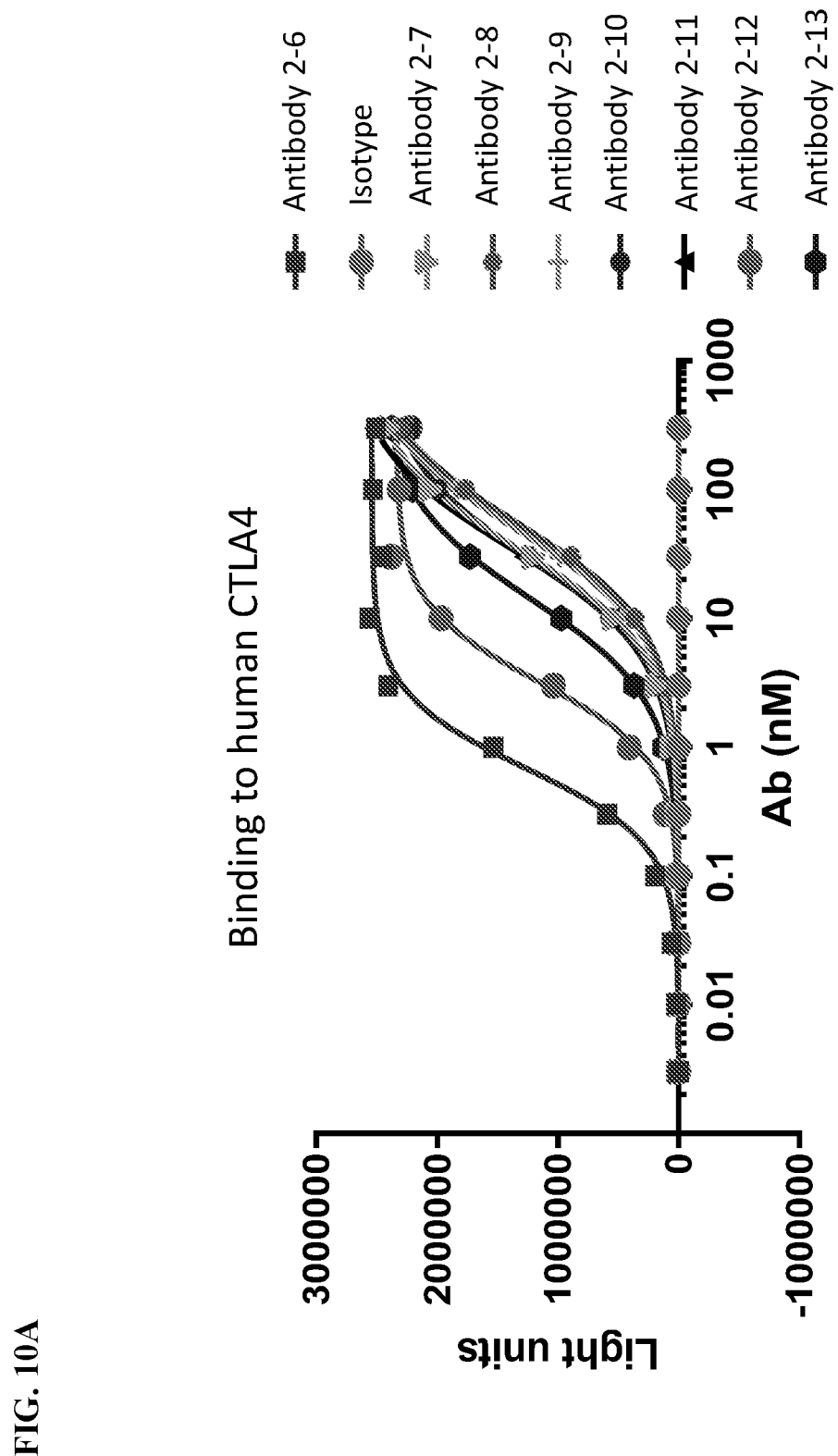
FIGS. 10A and 10B are graphs showing the binding of masked anti-CTLA4 antibodies to human CTLA4-Fc across a range of antibody concentrations.
Figure 10B:
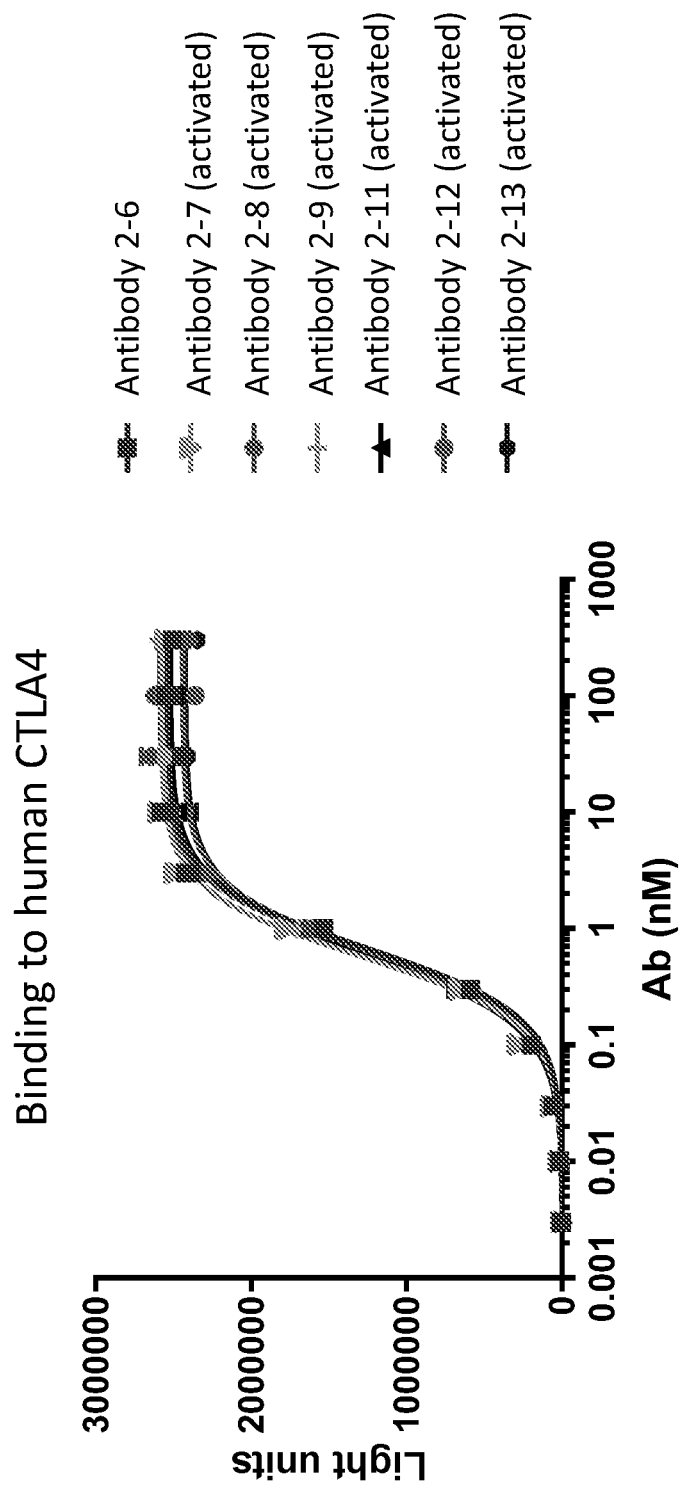

FIG. 10A and FIG. 10B show binding studies with masked and unmasked versions of Antibody 2 in the absence (FIG. 10A) or presence (FIG. 10B) of protease. FIG. 10A shows the binding of various versions of Antibody 2 and an IgG1 isotype in the absence of protease. Higher concentrations of antibodies are necessary to show binding as evidenced by the shift to the right of the unmasked Antibody 2-6 and the IgG1 isotype (FIG. 10A). Masked antibodies are considered occluded by masking peptide. The occlusion of each masked antibody is shown in Table 7, below, and is calculated by dividing the EC50 for the masked antibody by the EC50 of the unmasked parental antibody, Antibody 2-6. The variability in the amount of occlusion shows that the sequence of a spacer linker and/or cleavable peptide influences the ability of the masking peptide to block antigen binding. The EC50 and calculated occlusion for the antibodies are shown in Table 7 below.

TABLE 7

Table 2. Masked Antibody Binding to CTLA4

| Antibody | $EC_{50} \pm SE$ (nM) | $R^2$ | Occlusion |
|---|---|---|---|
| Antibody 2-6 | 0.69 ± 0.03 | 0.9967 | |
| Antibody 2-7 | 33.9 ± 0.7 | 0.9997 | 49 |
| Antibody 2-8 | 54.8 ± 1.0 | 0.9999 | 79 |
| Antibody 2-9 | 48.9 ± 1.0 | 0.9998 | 62 |
| Antibody 2-10 | 29.4 ± 1.5 | 0.9985 | 43 |
| Antibody 2-11 | 34.9 ± 0.5 | 0.9999 | 51 |
| Antibody 2-12 | 3.3 ± 0.2 | 0.9962 | 5 |
| Antibody 2-13 | 14.2 ± 0.2 | 0.9998 | 21 |

FIG. 10B shows the binding of various versions of Antibody 2, excluding Antibody 2-10 having the non-cleavable linker, in the presence of protease (i.e., activated). Unmasked parental Antibody 2-6 was included as a control and was not exposed to protease. Protease digestion was performed according to the protocol provided in Example 6. The data shown in FIG. 10B demonstrates that proteolytic cleavage of the cleavable peptide fully rescues the binding of the antibodies to human CTLA4 by restoring the binding of the antibodies to levels comparable to the unmasked parental antibody, Antibody 2-6. Binding data and activation data for the tested antibodies "activated" by the presence of prot TABLE 9-continued

| Antibody | Masking Peptide | Spacer Linker 1 | Cleavable Peptide | Spacer Linker 2 | Heavy chain | Light chain + masking components |
|---|---|---|---|---|---|---|
| Antibody 2-20 | CPFPALELC (SEQ ID NO: 19) | GGSSPP (SEQ ID NO: 417) | RAAAVKSP (SEQ ID NO: 72) | SGG (SEQ ID NO: 102) | SEQ ID NO: 421 | SEQ ID NO: 429 |
| Antibody 2-21 | CPFPALELC (SEQ ID NO: 19) | GGSSPP (SEQ ID NO: 417) | TSVLMAAP (SEQ ID NO: 51) | SGG (SEQ ID NO: 102) | SEQ ID NO: 421 | SEQ ID NO: 430 |

A comparison of the in vitro sensitivity of the cleavable peptide sequences to select proteases is shown as radar plots in FIG. 11A-H. Activation of each antibody by each protease on the radar plot is depicted using a radar plot, where activation is depicted as ranging from 0 (no activation) to 1.0 (full activation). Activation is calculated by the following formula: Activation=1−(EC50 of the activated masked antibody−EC50 of the unmasked parental antibody, Antibody 2-6)/(EC50 of the non-activated masked antibody−EC50 of the parental antibody, Antibody 2-6). The occlusion of each masked antibody is shown in Table 12, below, and is calculated by dividing the EC50 for the masked antibody by the EC50 of the unmasked parental antibody, Antibody 2-6. Binding was conducted according to the protocol provided in Example 7 and Example 8 and proteolytic treatment of the antibodies was conducted to according to the protocol provided in Example 6 and Example 8. A solution of masked anti-CTLA4 antibody (1000 nM) was made in appropriate cleavage buffer. Two antibody samples were aliquoted into two 0.5 mL Eppendorf tubes. A working solution of cleavage buffer (see Table 11) was added to corresponding antibody samples and cleavage buffer was added to control (no protease) samples.

TABLE 10

Proteases

| Protease | Source | Cleavage Buffer[1] | Protease per reaction (ng) | Working solution (ng/uL) | Time of reaction (min) |
|---|---|---|---|---|---|
| Adam17 | R&D Systems | A | 50 | 5 | 60 |
| MMP1 | Anaspec | B | 234 | 23.4 | 15 |
| MMP2 | R&D Systems | B | 8 | 0.8 | 15 |
| MMP7 | ProspecBio | B | 15 | 1.5 | 15 |
| MMP9 | ProspecBio | B | 50 | 5 | 15 |
| MMP10 | R&D Systems | B | 382 | 38.2 | 15 |
| MMP14 | R&D Systems | C | 201 | 20.1 | 15 |
| NapsinA | R&D Systems | B | 400 | 40 | 300 |

[1]see Table 11 for cleavage buffers.

TABLE 11

| Cleavage Buffer | Buffer chemistry |
|---|---|
| A | 100 mM NaOAc, 200 mM NaCl, pH 3.5 |
| B | 50 mM Tris, 50 mM NaCl, 0.01% TWEEN®-20, pH 9 |
| C | 50 mM Tris, 3 mM CaCl2, 1 uM ZnCl2, pH 8.5 |

Radar plots for antibodies having various cleavable peptide sequences are shown in FIGS. 11A-G. FIG. 11H shows that Antibody 2-15, which contains a cleavable peptide that is non-cleavable, for use as a negative control, was unaffected in its binding by the addition of various exemplary proteases. FIG. 11A shows a radar plot for Antibody 2-14.

Figure 11I:
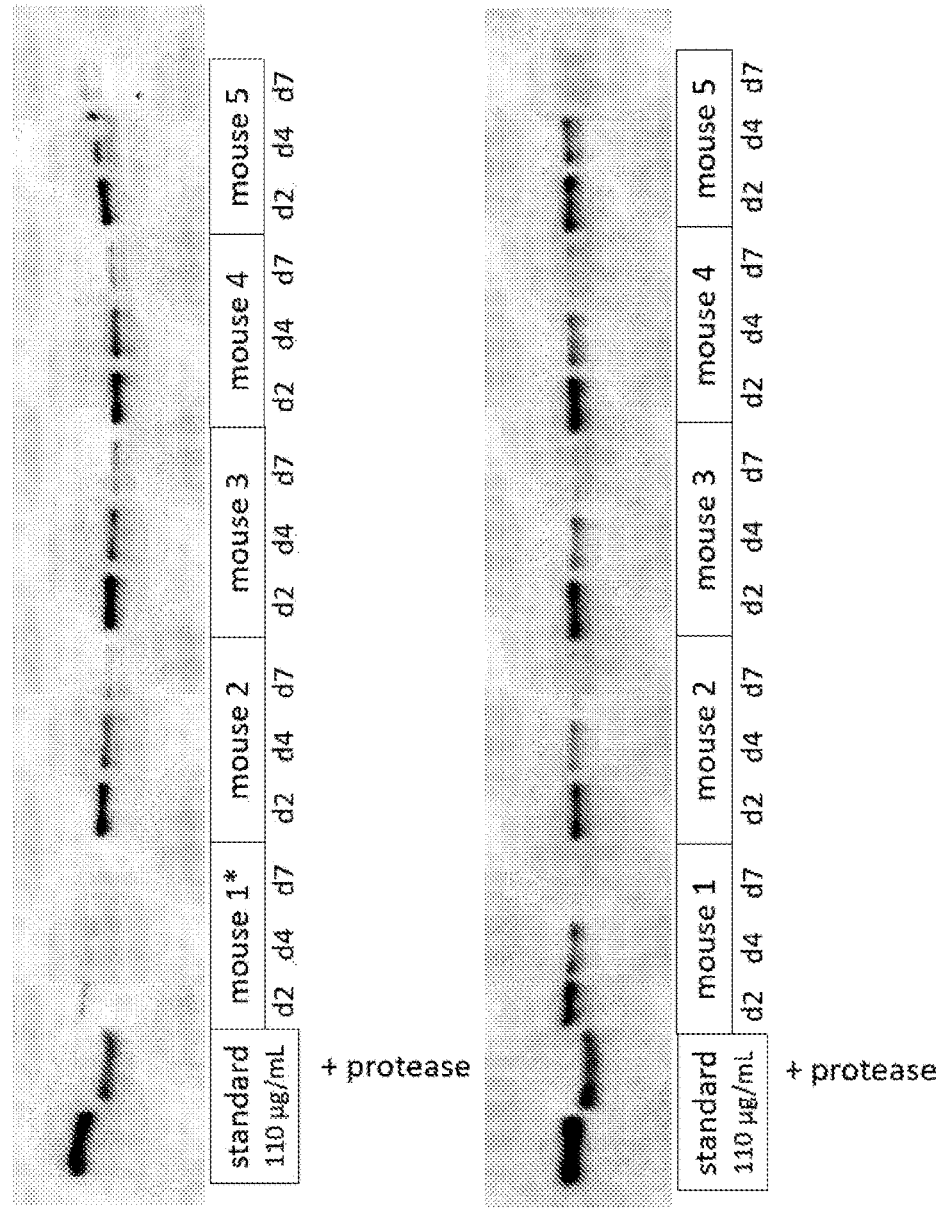
Figure 11J:
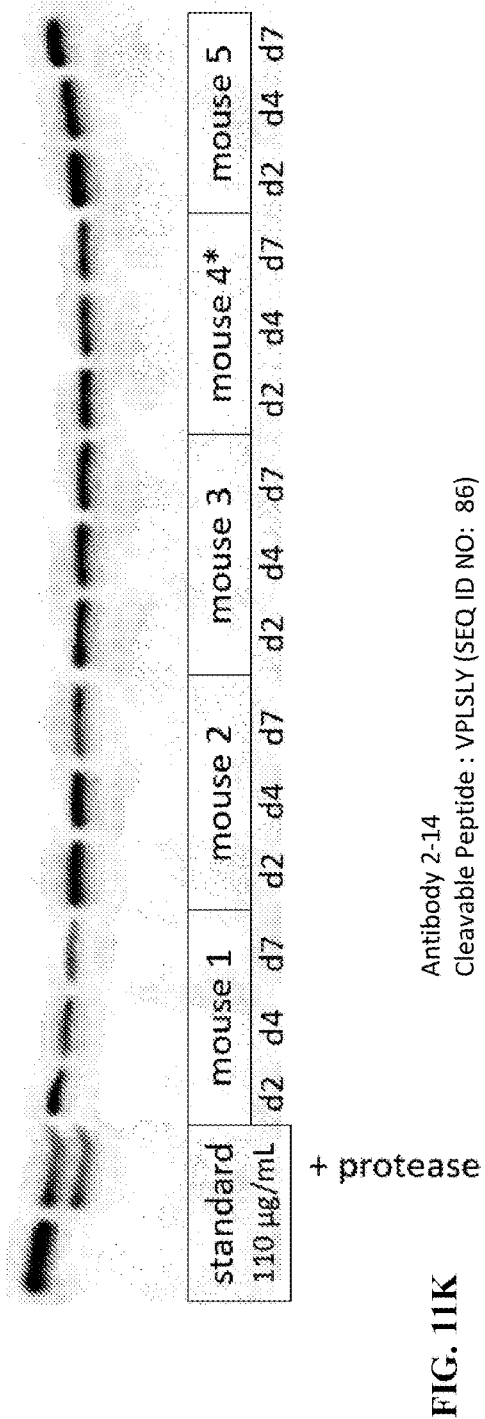

SDS-PAGE analysis of protease cleavage on day 2, (d2), day 4 (d4), or day 7 (d7) was assessed in healthy and MC38 tumor-bearing mice as previously described, and is shown in FIGS. 11I-11M. As shown in FIG. 11I, cleavage of the cleavable peptide in Antibody 2-14 was assessed in plasma of health mice. Groups of 5 healthy mice in each group were dosed with 200 μg of Antibody 2-14, except for mouse 1* (upper panel) which was dosed with 150 μg of Antibody 2-14. The standard was treated with (right lane) or without (left lane) protease. As shown in FIG. 11J, cleavage of the cleavable peptide in Antibody 2-16 was assessed in plasma of health mice. The standard used in FIG. 11J was Antibody 2-18. Healthy mice were dosed with 200 μg of Antibody 2-16, except for mouse 4* which was dosed with 150 μg of Antibody 2-14.

Figure 11K:
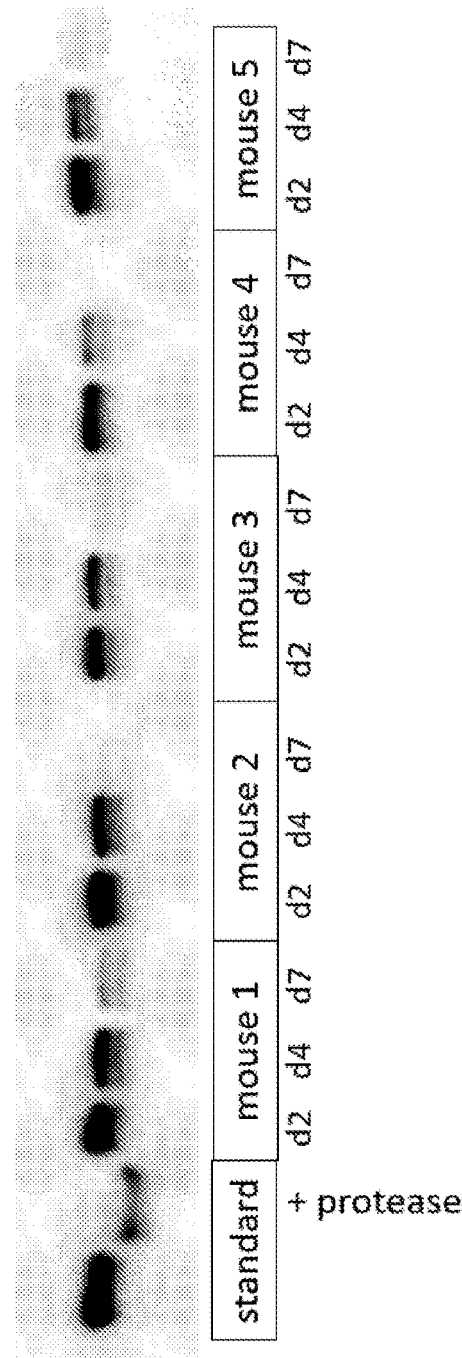

As shown in FIGS. 11K-11M, cleavage of the cleavable peptide in Antibody 2-14, the non-cleavable peptide in Antibody 2-15, and the cleavable peptide in Antibody 2-16 was assessed in the plasma of MC38 tumor-bearing mice. MC38 tumor-bearing mice were dosed with 200 μg of each antibody. In FIG. 11M, the day 2 (d2) sample for mouse 2 appears to be in error and should be disregarded.

Figure 12A:
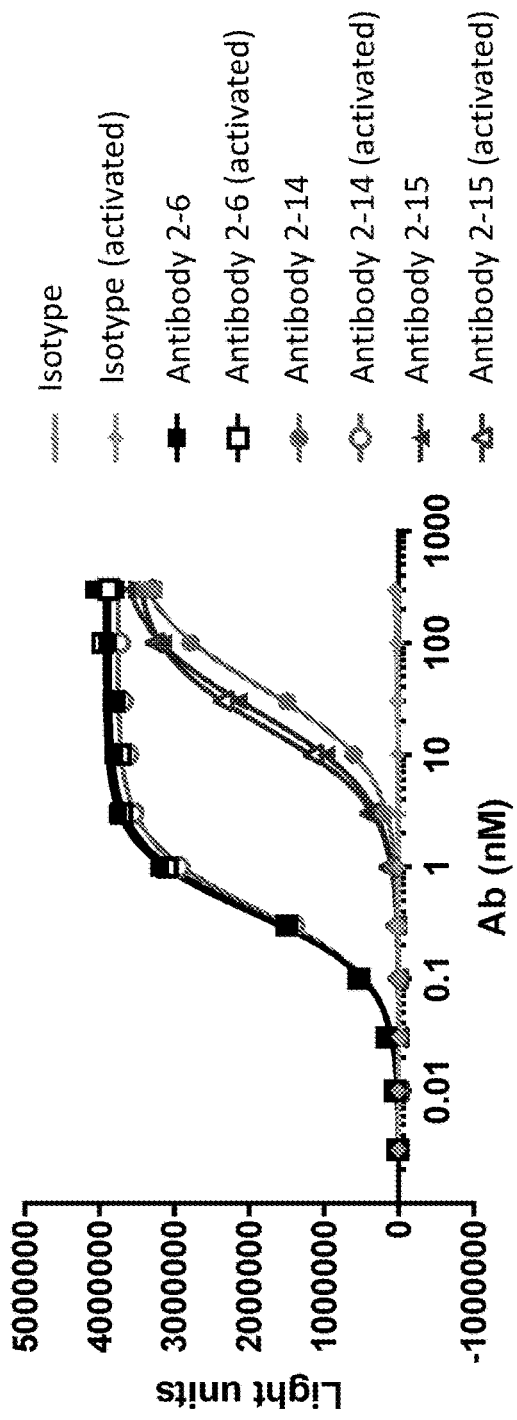
FIGS. 12A and 12B are graphs depicting the binding of masked anti-CTLA4 antibodies to human CTLA4-Fc in the presence or absence of protease activation. In the presence of protease, the masked antibody is "activated" by protease cleavage of the cleavable peptide.

The binding of Antibody 2-6, Antibody 2-14, and Antibody 2-15 to CTLA4 in the presence or absence of protease is shown in FIG. 12A, and EC50, occlusion, and activation are provided in Table 12. Antibody 2-6, which is unmasked, demonstrates binding that is unaffected by the presence of protease (FIG. 12A). Antibody 2-15, which is masked but includes a cleavable peptide sequence that is non-cleavable, demonstrates reduced binding affinity as compared to the unmasked parental Antibody 2-6 in the absence of protease that is not rescued by the addition of protease (FIG. 12A). Antibody 2-14, which is masked and includes a cleavable peptide, demonstrates reduced binding affinity with an occlusion value of 101 in the absence of protease, but this reduced binding affinity is rescued when activated by the addition of protease (FIG. 12A), with an activation value of 1.0 (Table 12). EC50s for Antibody 2-6, Antibody 2-14, and Antibody 2-15 in the presence or absence of protease are provided in Table 12 below.

TABLE 12

Masked and Activated Antibody Binding to CTLA4

| Antibody | Protease | EC$_{50}$ (nM) | R$^2$ | Occlusion | Activation |
|---|---|---|---|---|---|
| Antibody 2-6 | − | 0.39 ± 0.01 | 0.9979 | | |
| Antibody 2-6 | + | 0.39 ± 0.01 | 0.9981 | 1.0 | |
| Antibody 2-14 | − | 39.4 ± 1.8 | 0.9989 | 101 | |
| Antibody 2-14 | + | 0.41 ± 0.01 | 0.9982 | 1.1 | 1.00 |
| Antibody 2-15 | − | 24.3 ± 0.5 | 0.9997 | 62 | |
| Antibody 2-15 | + | 17.3 ± 0.7 | 0.9982 | 44 | 0.29 |

Figure 12B:
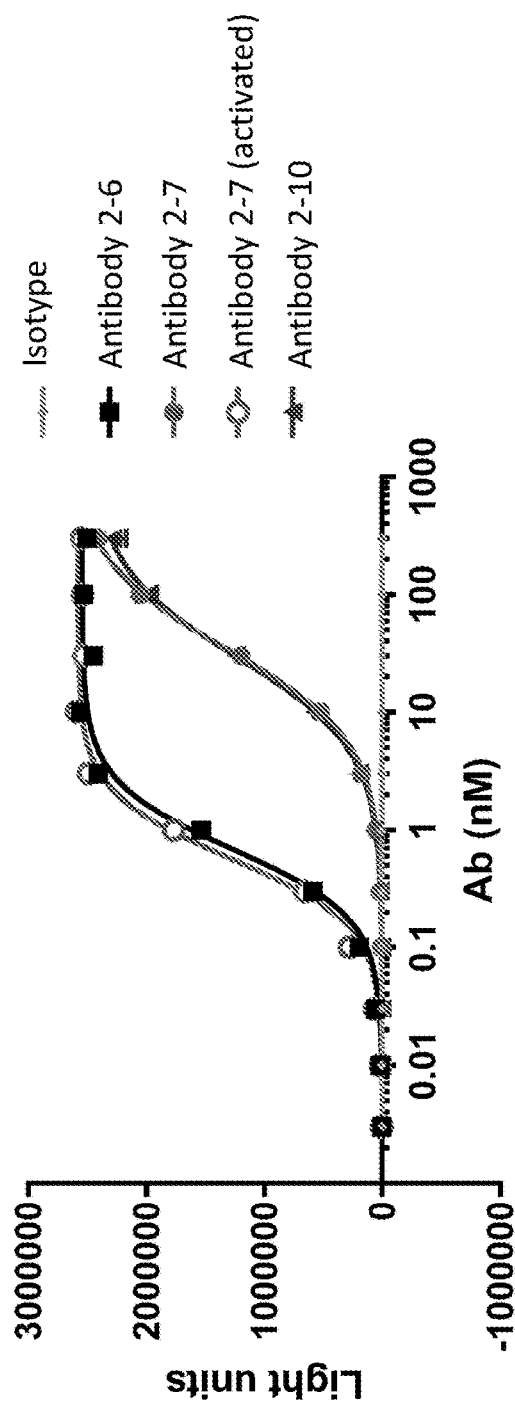

The binding of Antibody 2-6, Antibody 2-7, and Antibody 2-10 to CTLA4 in the presence or absence of protease is shown in FIG. 12B, and EC50, occlusion, and activation are provided in Table 13. Antibody 2-10 includes a cleavable peptide sequence that is non-cleavable, for use as a negative control. Antibody 2-7, which is masked and includes a cleavable peptide, demonstrates an occlusion value of 49 in the absence of protease, and an activation value of 1.0 upon activation using protease (FIG. 12B; Table 13). In the absence of protease, masked Antibody 2-7 demonstrates binding similar to masked Antibody 2-10, and, upon activation by addition of protease, Antibody 2-7 demonstrates binding similar to the unmasked parental Antibody 2-6. The EC50s for Antibody 2-6, Antibody 2-7, and Antibody 2-10 are provided in Table 13 below.

TABLE 13

Masked and Activated Antibody Binding to CTLA4

| Antibody | Protease | EC$_{50}$ (nM) | R$^2$ | Occlusion | Activation |
|---|---|---|---|---|---|
| Antibody 2-6 | − | 0.69 | 0.9967 | | |
| Antibody 2-7 | − | 33.9 | 0.9997 | 49 | |
| Antibody 2-7 | + | 0.58 | 0.9971 | 0.8 | 1.00 |
| Antibody 2-10 | − | 29.4 | 0.9985 | 43 | |

The data shown in FIG. 12A, FIG. 12B, Table 12, and Table 13 shows that the exemplary masking peptides included in Antibody 2-7 (SEQ ID NO: 19) and Antibody 2-14 (SEQ ID NO: 5) are each capable of masking binding activity in a reversible manner.

Example 10: Enterotoxin Analysis

Methods

SEB Assay

A Staphylococcal enterotoxin B (SEB) assay was used to examine the ability of various antibodies to promote IL-2 production from peripheral blood mononuclear cells (PBMCs). For the SEB Assay, dilutions of selected antibodies were prepared in pre-warmed media (RPMI+10% heat-inactivated FBS+1% HEPES+1% MEM NEAA+1% Na-pyruvate). Antibody solution was plated in triplicate and media only was added to "PBMC+SEB" wells, "PBMC only" wells, and outside border walls. SEB solution was prepared in pre-warmed media and added to all experimental wells except "PBMC only." PBMCs (BioIVT) were thawed in a water bath at 37° C. Cells were transferred, dropwise, to a conical tube and 20× pre-warmed medium was added to wash the cells. The cells were centrifuged and the media was aspirated. Cells were resuspended in 20 mL of pre-warmed media and an aliquot was taken for counting. The remaining cells were centrifuged and resuspended in volume to make the cells 1×10$^6$ cells/mL. The cells were plated 100 μL per well and the plate was incubated in 37° C., 5% CO$_2$ incubator for five days. On day five, the plate was spun for five minutes at 1000 RPM. From each well, 250 μL of cells were transferred to a new 96 well plate. The plate was spun again and 225 μL of cells were transferred to PCR strips. The samples were stored at −80° C. until analyzed by ELISA.

IL-2 ELISA

IL-2 levels of cell supernatant produced using the protocol described above was determined by analysis with Human IL-2 ELISA MAX Deluxe sets (BioLegend, Cat. #431806). Cell supernatant samples were diluted with assay buffer to fall within the standard curve. Samples were analyzed using GraphPad Prism and with Tukey's multiple comparisons test (one-way ANOVA) to determine the statistical significance between the treatment groups.

Results

Figure 13A:
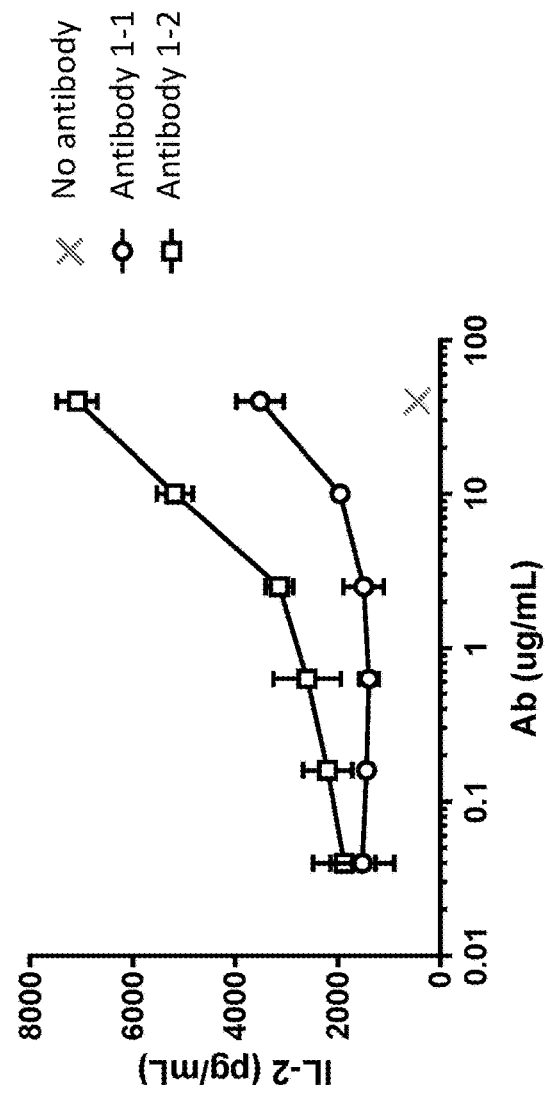
FIGS. 13A-13D are graphs depicting IL-2 levels (pg/mL) (FIGS. 13A and 13C) or fold changes in IL-2 levels (FIGS. 13B and 13D) as determined using a Staphylococcal enterotoxin B (SEB) assay, for unmasked forms of Antibody 1 and Antibody 2. Unmasked forms of Antibody 1 (Antibody 1-1 and 1-2) (FIGS. 13A and 13B) and unmasked forms of Antibody 2 (Antibody 2-1, Antibody 2-2, Antibody 2-3, Antibody 2-4, and Antibody 2-5) (FIGS. 13C and 13D) were tested for their ability to promote IL-2 production from peripheral mononuclear cells using an SEB assay. All tested forms of Antibody 1 and Antibody 2 demonstrated the ability to increase IL-2 levels as compared to a no-antibody control (FIGS. 13A and 13C).
Figure 13B:
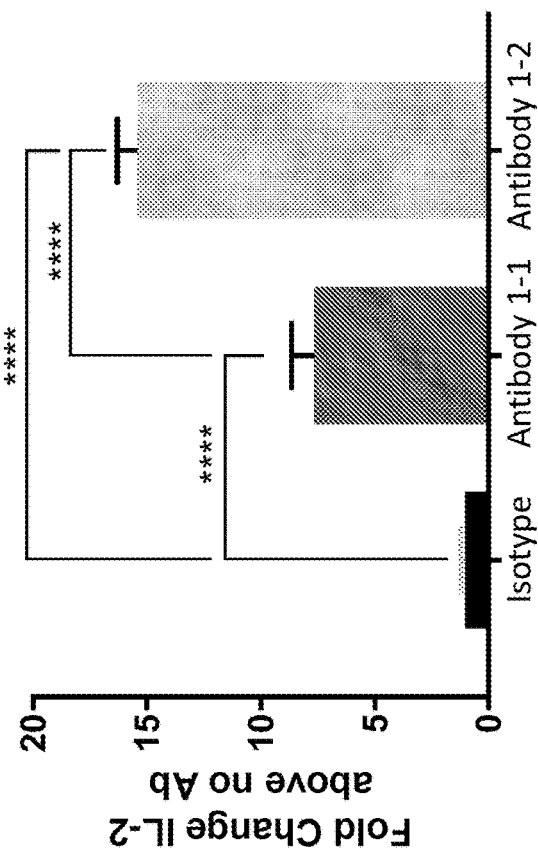
Figure 13C:
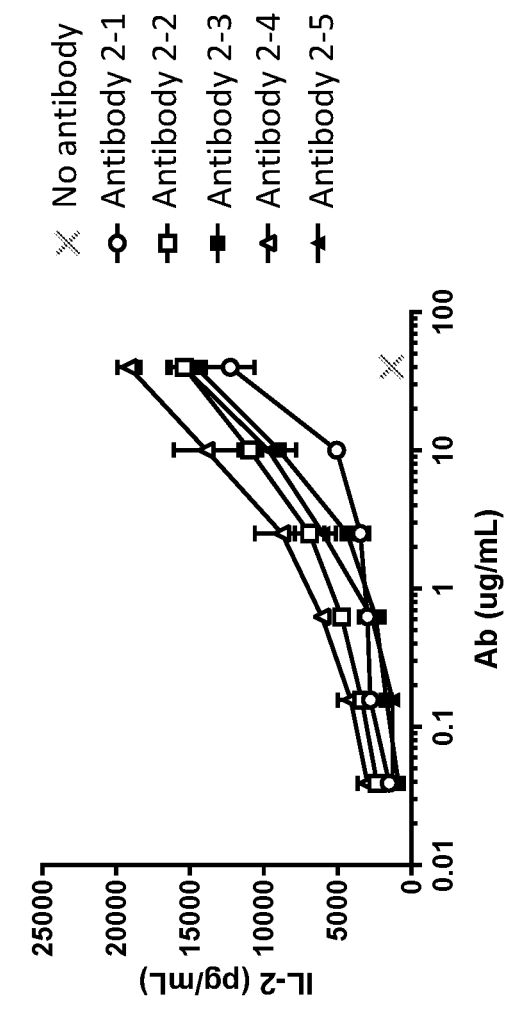
Figure 13D:
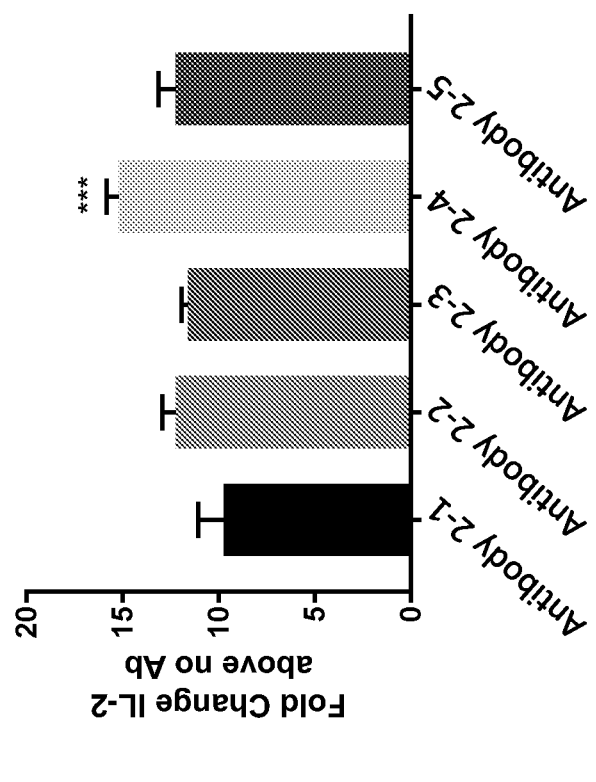

Various forms of Antibody 1 and Antibody 2 were tested in the SEB assay. Data showing the levels of IL-2 produced in the presence of Antibody 1-1 or Antibody 1-2, as described in Example 7, or no antibody, are shown in FIG. 13A. Data showing the levels of IL-2 produced in the presence of Antibody 2-1, Antibody 2-2, Antibody 2-3, Antibody 2-4, and Antibody 2-5, as described in Example 7, or no antibody, are shown in FIG. 13C. All tested antibodies demonstrated the ability to increase IL-2 levels as compared to a no-antibody control. Fold increases in IL-2 levels above the no antibody control for each antibody are shown in FIG. 13B and FIG. 13, along with comparison to an isotype control.

Example 11: Immune Function of Masked and Activated Anti-CTLA4 Antibodies

An SEB assay according to the protocol of Example 10 was conducted to test IL-2 production in response to treatment with various forms of Antibody 2. The assay was also run in the absence of an antibody (i.e., no antibody), or an isotype control antibody, as controls. The unmasked parental antibody, Antibody 2-6, was also tested for comparison.

Figure 14A:
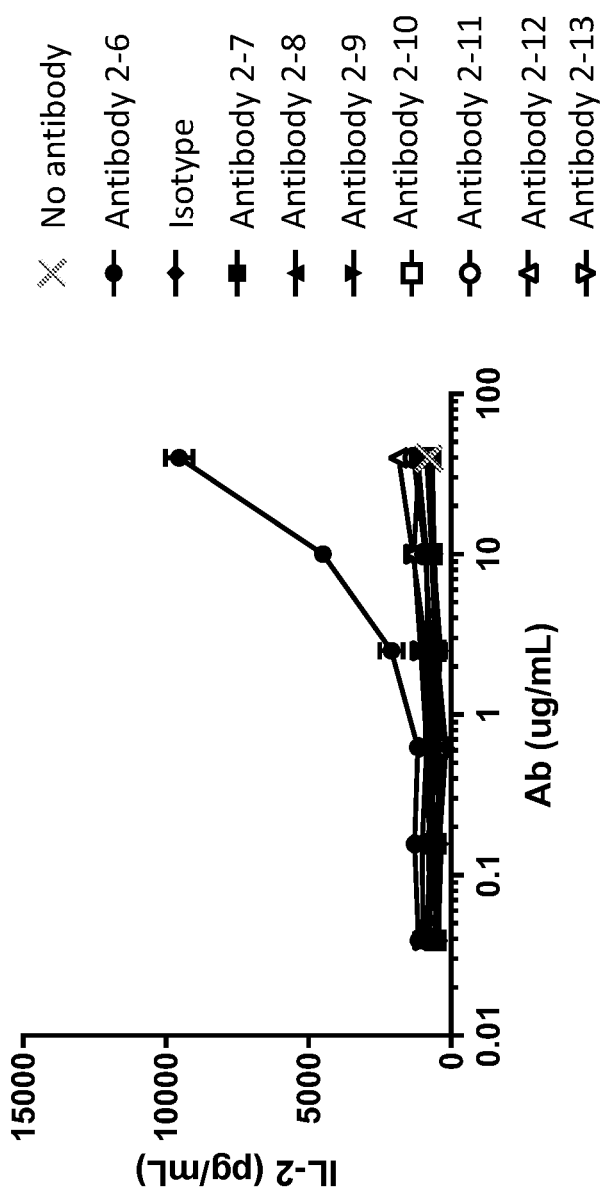
FIGS. 14A-14D are graphs depicting IL-2 levels (pg/mL) (FIGS. 14A and 14C) or fold changes in IL-2 levels (FIGS. 14B and 14D) as determined using a Staphylococcal enterotoxin B (SEB) assay, for masked forms of Antibody 2. An unmasked form of Antibody 2 (Antibody 2-6) was tested along with masked forms of Antibody 2-6 (Antibody 2-7, Antibody 2-8, Antibody 2-9, Antibody 2-10, Antibody 2-11, Antibody 2-12, and Antibody 2-13).
Figure 14B:
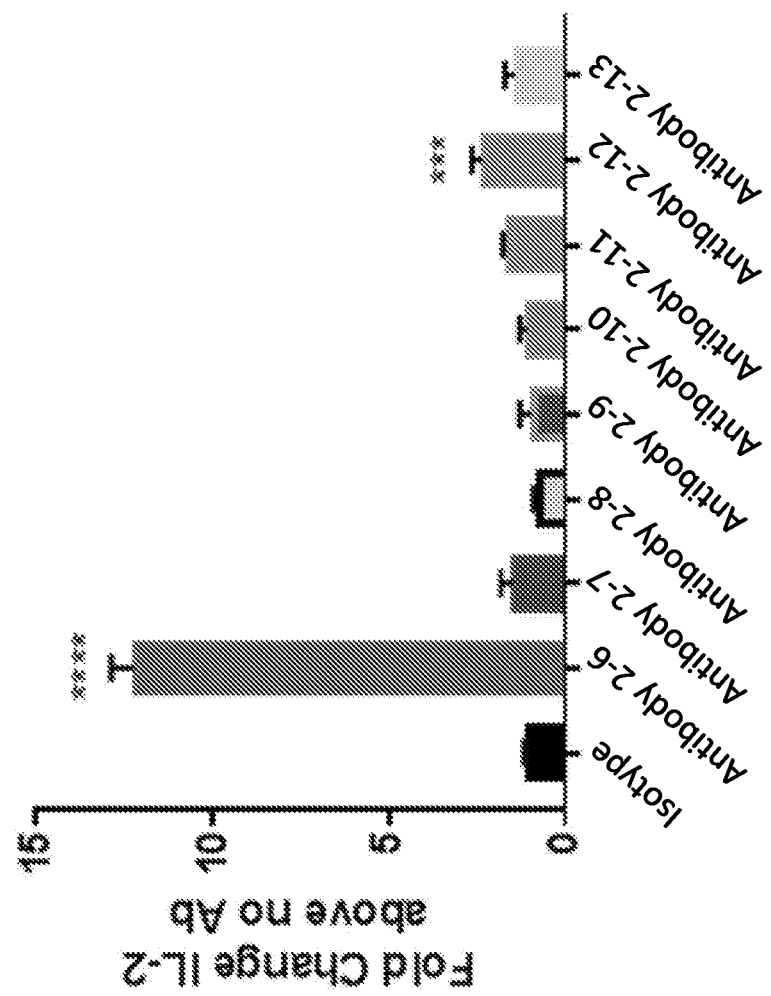

As shown in FIGS. 14A and 14B, in contrast to unmasked Antibody 2-6, which promoted strong IL-2 production, the masked forms of Antibody 2 were generally ineffective at promoting IL-2 production. As shown in FIG. 14B, Antibody 2-12 was the only masked antibody that resulted in a significant increase in IL-2 production as compared to an isotype control, although this increase was much less than the increase observed when using the unmasked Antibody 2-6 parental antibody. In contrast, Antibody 2-7, Antibody 2-8, Antibody 2-9, Antibody 2-10, Antibody 2-11, and Antibody 2-13 each did not promote a significant increase in IL-2 production as compared to an isotype control (FIG. 14B). Statistical analysis was performed using one-way ANOVA comparisons.

Figure 14C:
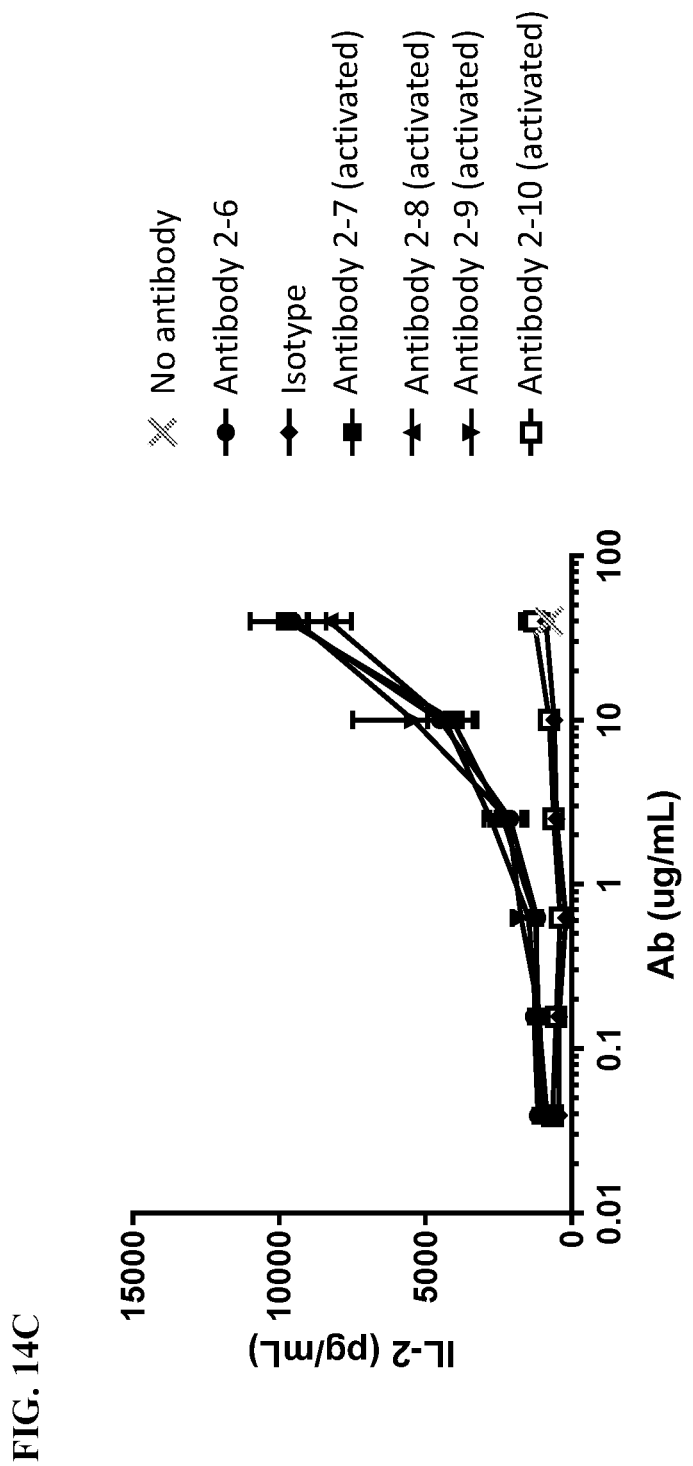
Figure 14D:
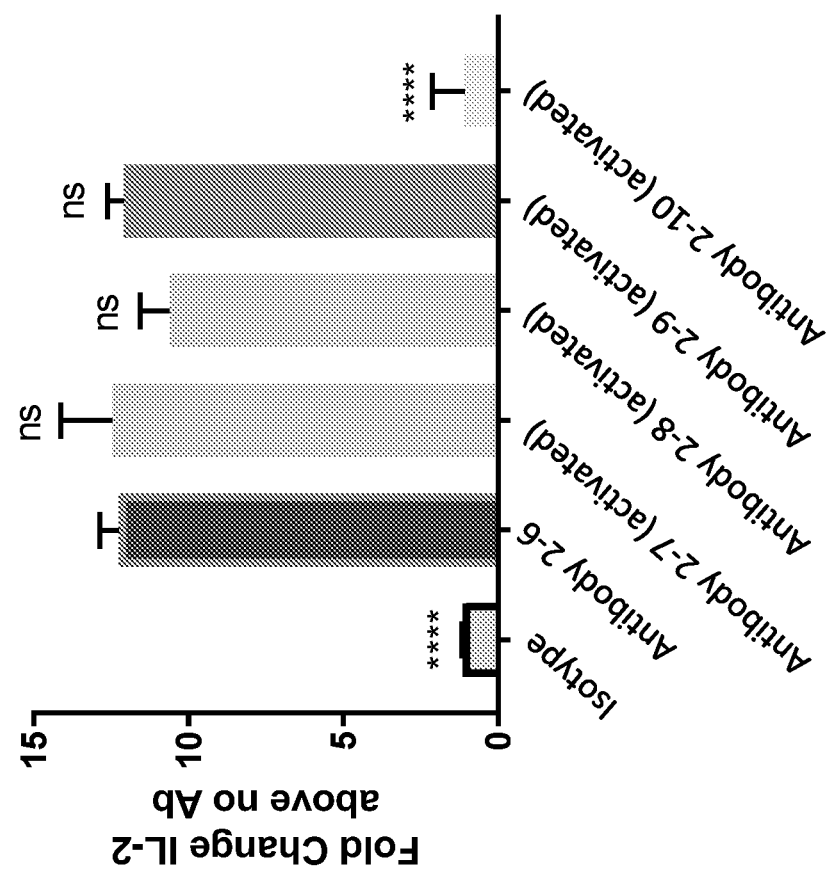

FIGS. 14C and 14D show the impact of protease treatment conducted according to the protocol of Example 6 on the ability of Antibody 2-7, Antibody 2-8, Antibody 2-9, and Antibody 2-10 to promote IL-2 production. Antibody 2-10 includes a cleavable peptide sequence that is non-cleavable, for use as a negative control. The unmasked parental Antibody 2-6 was tested as a positive control, and an isotype control antibody and a no antibody control were tested as negative controls. Statistical analysis shown in FIG. 14D was performed using one-way ANOVA comparisons vs. Antibody 2-6.

The results shown in FIG. 14C show that treatment with protease rescues the ability of Antibody 2-7, Antibody 2-8, and Antibody 2-9 to promote the production of IL-2 at levels similar to the unmasked parental Antibody 2-6. The graph shown in FIG. 14B compares the fold increases in IL-2 production above the no antibody control. Treatment with Antibody 2-10, which is masked but not activatable by protease, resulted in a similar level of IL-2 production, and a similar fold change above the no antibody control, as the isotype control (FIG. 14C and FIG. 14D).

Example 12: In Vivo Cleavage of Masked Anti-CTLA4 Antibodies

Methods

In Vivo Cleavage of Masked Anti-CTLA4 Antibodies in Plasma of Healthy Mice

Healthy, non-tumor bearing, seven-eight week old female C57BL/6J mice were injected intraperitoneally on day 0 with 200 µg of masked forms of Antibody 2. On days two and four, blood was collected via RO sinus and processed with LiHep for plasma isolation. On day seven, blood was collected via cardiac puncture and processed with LiHep for plasma isolation. Plasma was aliquoted and stored at −80° C. until Western blot analysis. Standard samples where the masked antibody was treated in the presence or absence of protease in vitro were included as positive controls. For Western blot analysis, plasma samples were diluted in PBS, then in Laemmli Sample Buffer and βME. Samples were heated at 95° C. then loaded on a Criterion TGX Stain-free Precast gel. SDS-PAGE was performed at 200 V for forty-two minutes. Protein was transferred to nitrocellulose membrane and blocked in 1×TBS with 1% Casein Blocker for one hour at room temperature shaking. The membrane was probed with HRP-conjugated Rb mAb to human Kappa Light Chain [clone EPR5367-8], diluted 1:10,000 in Casein Blocker, overnight at 4° C. shaking. The membrane was washed three times with PBS-TWEEN® and developed with SuperSignal ELISA Pico Chemiluminescent Substrate. Raw data was analyzed with ImageLab software. Activation percentage was calculated as follows: the intensity of the activated band/(intensity of the activated band+intensity of the masked non-activated band)*100%.

In vivo experiment was performed in two cohorts across two weeks, with Antibody 2-14 included in both cohorts. Antibodies that were tested include Antibody 2-14, Antibody 2-15, Antibody 2-16, Antibody 2-17, Antibody 2-18, Antibody 2-19, Antibody 2-20, and Antibody 2-21. Antibody 2-15 includes a cleavable peptide sequence that is non-cleavable, for use as a negative control.

Results

Figure 15A:
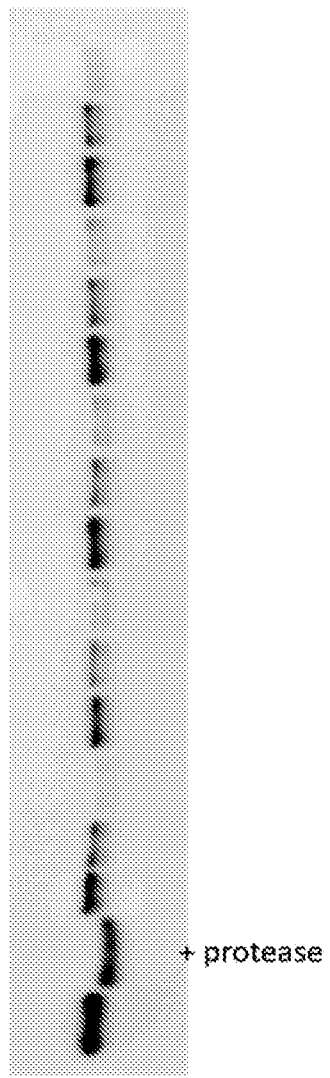
FIGS. 15A-15D depict the extent of in vivo cleavage of masked anti-CTLA4 antibodies in the plasma of health mice, as shown by Western blot analysis. The in vivo cleavage of masked forms of Antibody 2 (Antibody 2-14, Antibody 2-19, and Antibody 2-20) in health mice is shown at Days 2, 4, and 7 following intraperitoneal administration of the antibody. Standard samples where the masked antibody was treated in the presence or absence of protease in vitro was used as a control for cleavage. Antibody 2-14 (FIG. 15A) and Antibody 2-20 (FIG. 15C) were both activated in vivo.
Figure 15B:
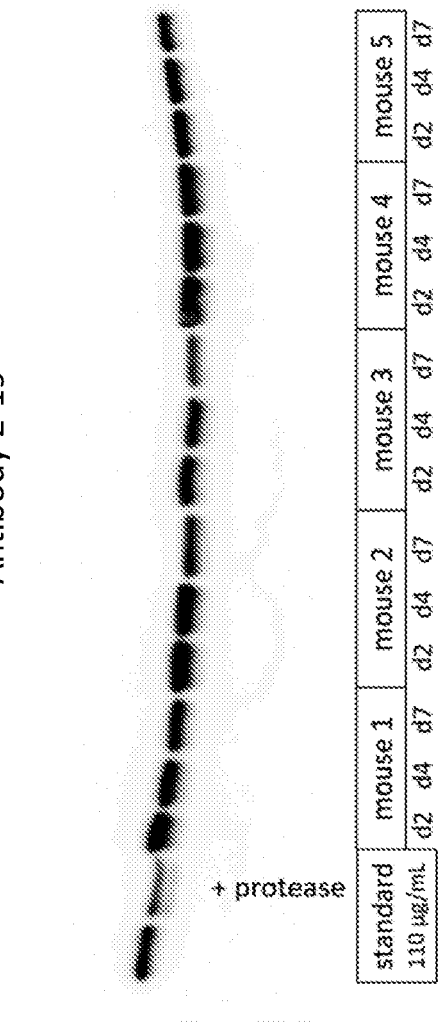
Figure 15C:
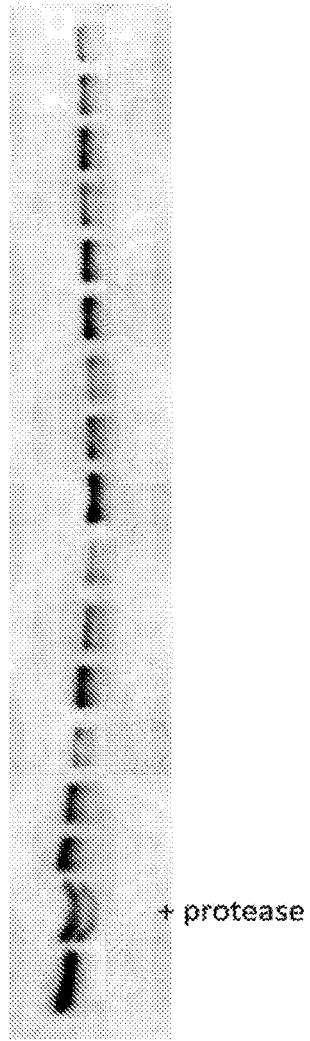
Figure 15D:
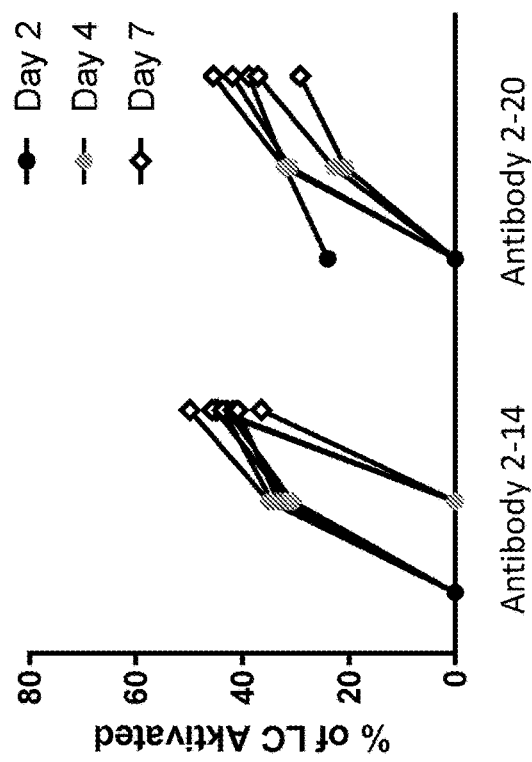

Antibody 2-14 (FIG. 15A) and Antibody 2-20 (FIG. 15C) were both activated in vivo. Activation of Antibody 2-19 was not detected in vivo (FIG. 15B). In vivo activation was also not detected for Antibody 2-16, Antibody 2-17, Antibody 2-18, and Antibody 2-21 (data not shown), nor was it detected for the negative control Antibody 2-15. The increase in the percentage of activation from Day 2 to Day 7 is shown in FIG. 15D for Antibody 2-14 and Antibody 2-20.

Example 13: In Vivo Cleavage of Masked Anti-CTLA4 Antibodies in Plasma of Tumor-Bearing Mice MC38 cells ($1 \times 10^6$) were injected subcutaneously into seven-eight week old female C57BL/6J mice subcutaneously. On day 0, the mice were randomized based on tumor volume measurements and injected intraperitoneally with 200 µg of Antibody 2 constructs. Blood was collected via RO sinus on days two and four and processed with LiHep for plasma isolation. On day seven, blood was collected via cardiac puncture and process with LiHep for plasma isolation. Plasma was aliquoted and stored at −80 C until Western blot analysis. Standard samples where the masked antibody was treated in the presence or absence of protease in vitro were included as positive controls. For Western blot analysis, plasma samples were diluted in PBS, then in Laemmli Sample Buffer and βME. Samples were heated at 95° C. then loaded on a Criterion TGX Stain-free Precast gel. SDS-PAGE was performed at 200 V for forty-two minutes. Protein was transferred to nitrocellulose membrane and blocked in 1×TBS with 1% Casein Blocker for one hour at room temperature shaking. The membrane was probed with HRP-conjugated Rb mAb to human Kappa Light Chain [clone EPR5367-8], diluted 1:10,000 in Casein Blocker, overnight at 4° C. shaking. The membrane was washed three times with PBS-TWEEN® and developed with SuperSignal ELISA Pico Chemiluminescent Substrate. Raw data was analyzed with ImageLab software.

In vivo experiment was performed in two cohorts across two weeks, with Antibody 2-14 included in both cohorts. Antibodies that were tested include Antibody 2-14, Antibody 2-15, Antibody 2-16, Antibody 2-17, Antibody 2-18, Antibody 2-19, Antibody 2-20, and Antibody 2-21. Antibody 2-15 includes a cleavable peptide sequence that is non-cleavable, for use as a negative control.

In another set of experiments, MC38 cells ($1 \times 10^6$) were injected subcutaneously into a mouse model with a knock-in with human CTLA4. MC38 tumor-beating mice were administered a single injection of 200 µg of a test antibody (e.g., IgG control, Antibody 2-1, Antibody 2-10, ipilimumab, or an afucosylated form of ipilimumab (ipilimumab-aFuc) and immunophenotyping was performed on CD45+ splenic cells and CD45+ intratumoral cells five days after injection. In some studies, tumor volume over time was measured following a single injection of 20 µg, 7 µg, or 2 µg of the test antibody. CD45+ cells were assessed for markers including those selective for CD3+/ICOS+, CD3+ T cells, CD4+/Ki67+, CD3+/Ki67+, CD4+/ICOS+, CD4+ T cells, CD8+/ICOS+, CD8+ T cells, Tregs+/ICOS+, CD8+/Ki67+, Tregs, Tregs+/Ki67+, with relative proportions of CD45+ cells having those markers identified.

Results

Figure 16A:
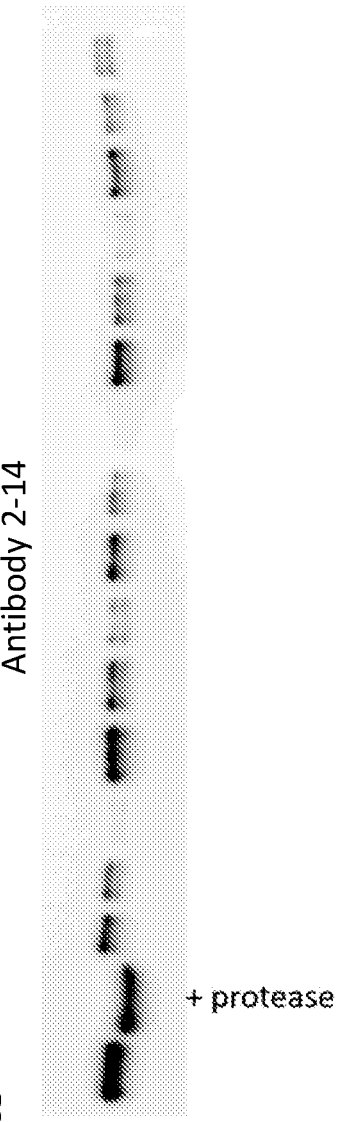
FIGS. 16A-16D depict the extent of in vivo cleavage of masked anti-CTLA4 antibodies in the plasma of tumor-bearing mice, as shown by Western blot analysis. The in vivo cleavage of masked forms of Antibody 2 (Antibody 2-14, Antibody 2-19, and Antibody 2-20) in MC38 tumor-bearing mice is shown at Days 2, 4, and 7 following intraperitoneal administration of the antibody. Standard samples where the masked antibody was treated in the presence or absence of protease in vitro was used as a control for cleavage. Antibody 2-14 (FIG. 16A) and Antibody 2-20 (FIG. 16C) were both activated in vivo.
Figure 16B:
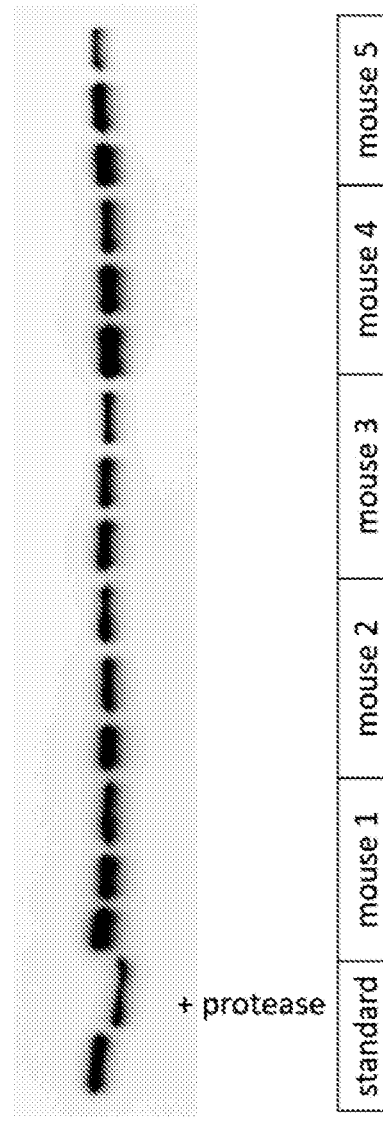
Figure 16C:
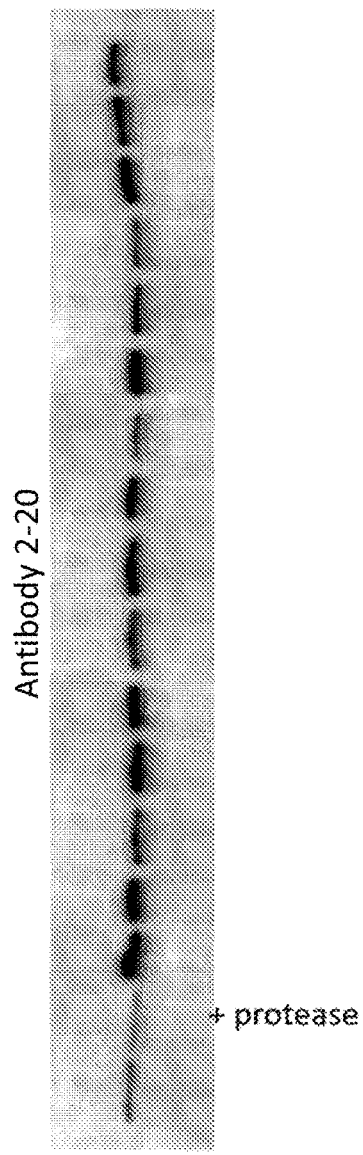
Figure 16D:
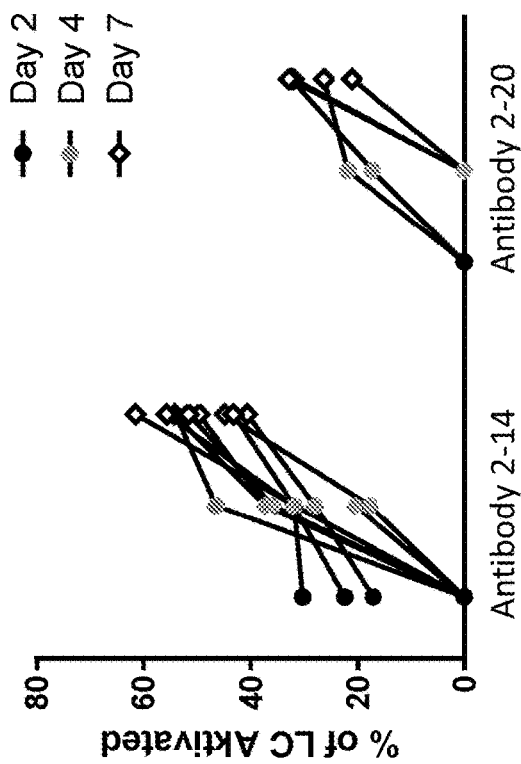

Antibody 2-14 and Antibody 2-20 were activated in vivo in the MC38-bearing mice (FIGS. 16A and 16C). Activation of Antibody 2-19 was not detected in vivo (FIG. 16B). Activation was also not detected for Antibody 2-16, Antibody 2-17, Antibody 2-18, and Antibody 2-21 (data not shown), nor was it detected for the negative control Antibody 2-15. The activation percentage of Antibody 2-14 was significantly greater in the MC38-bearing mice as compared to the healthy non-tumor-bearing mice, as determined by 2-way ANOVA (adjusted P value=0.0113) (FIG. 16D).

Results from studies using MC38 tumor-bearing mice are depicted in FIGS. 19A-19D, where relative proportion of CD45+ splenic (FIGS. 19A and 19B) or CD45+ intratumoral (FIGS. 19C and 19D) are provided for markers selective for CD3+/ICOS+, CD3+ T cells, CD4+/Ki67+, CD3+/Ki67+, CD4+/ICOS+, CD4+ T cells, CD8+/ICOS+, CD8+ T cells, Tregs+/ICOS+, CD8+/Ki67+, Tregs, Tregs+/Ki67+. Statistics are provided in FIGS. 19E (splenic cells) and 19F (intratumoral cells). Group 1: IgG, Group 2: Antibody 2-1; Group 3: Antibody 2-10: Group 4: Ipilimumab: Group 5: Ipilimumab-aFuc.

Figure 20A:
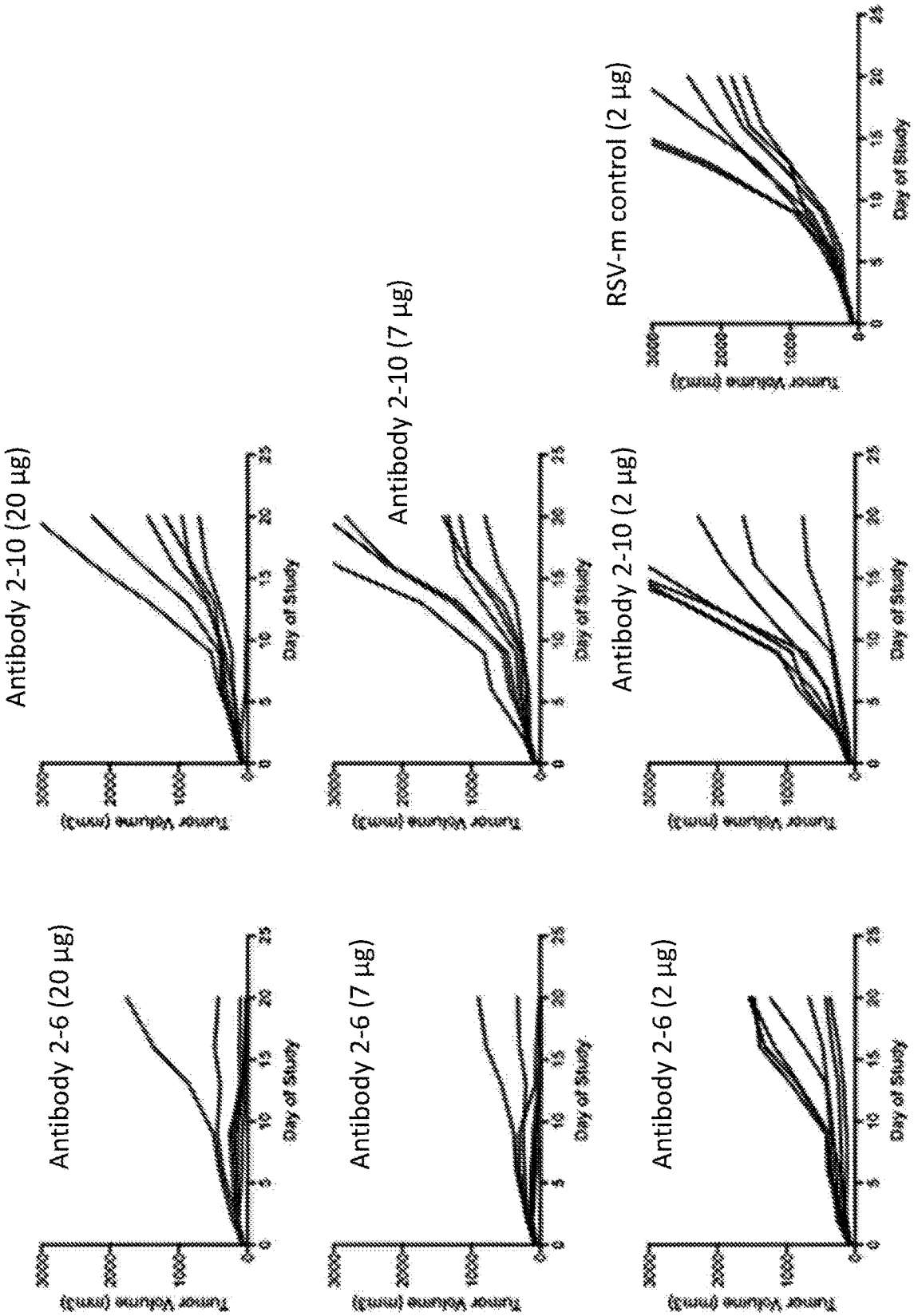
FIGS. 20A and 20B depict graphs showing tumor volume over time following administration of a single injection of 20 µg, 7 µg, or 2 µg of the test antibody.
Figure 20B:
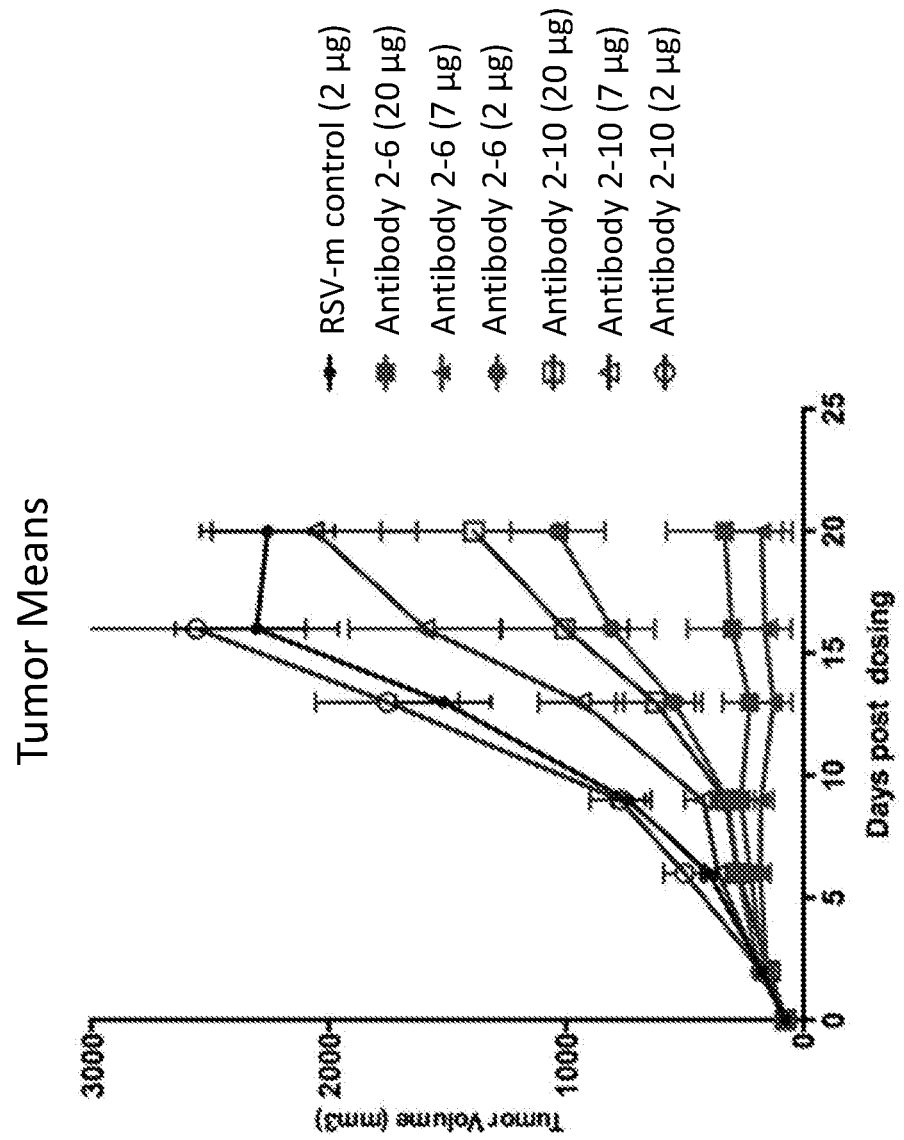

Results from studies using MC38 tumor-bearing mice that received a single injection of 20 µg. 7 µg, or 2 µg of the test antibody are depicted in FIGS. 20A and 20B. FIG. 20A shows tumor volume (mm$^3$) over time for Antibody 2-6, Antibody 2-10, and an RSV antibody having S239D and I332E mutations in the Fc domain (RSV-m). As shown in FIG. 20A, tumor growth is suppressed by the unmasked parental Antibody 2-6 as compared to the masked but non-cleavable Antibody 2-10. FIG. 20B depicts tumor means for tumor volume over time, which demonstrates slower tumor growth following administration of Antibody 2-6 as compared to Antibody 2-10 or the RSV-m control.

Example 14: ADCC Activity and CTLA4 Blockade by Anti-CTLA4 Antibodies

Methods

Reporter Bioassay

An FcγRIIIa reporter bioassay was performed using various anti-CTLA4 antibodies. Antibodies were diluted in pre-warmed complete medium (FBS with RPMI1640). CTLA4 effector cells (target cells: Promega J158A) were thawed and transferred to a conical tube containing complete medium. Cells were mixed and counted, and the density of the cells was adjusted to 1×10$^6$ cells/mL. Target cells were added to each well of a 96 well plate (Corning, Cat: #3917). Diluted antibodies were added to the appropriate wells and tested in duplicate. The content of each well was gently mixed and the plate was incubated at 37° C. for fifteen minutes. Effector cells (FcγRIIIa expressing Jurkat cells) were thawed and transferred to a conical tube containing complete medium. Cells were mixed and counted, and the density of the cells was adjusted to 3×10$^6$ cells/mL. Immediately, effector cells were dispensed into each well and mixed gently. The plate was covered with a lid and kept at 37° C. for six hours. One hour prior to measurement, Bio-Glo substrate and Bio-Glo buffer were removed from 4° C. Bio-Glo buffer was transferred to the bottle of Bio-Glo substrate to make Bio-Glo reagent, and was gently mixed by inversion. The bottle was kept at room temperature. After incubation, the assay plate was removed from the incubator and kept at room temperature for ten minutes. Bio-Glo reagent was added to each well, and the plate was incubated at room temperature for five-fifteen minute. The plate was then read with a luminometer.

The antibodies tested include Antibody 2-6, Antibody 2-14, and Antibody 2-15, as well as an isotype control. Antibody 2-6 is an unmasked parental antibody to Antibody 2-14 and Antibody 2-15. Antibody 2-15 includes a cleavable peptide sequence that is non-cleavable, for use as a negative control. Antibody 2-6, Antibody 2-14, and Antibody 2-15 were each tested without prior exposure to protease, and were also tested following exposure to protease, which allows for activation by cleavage of the cleavable peptide. The occlusion for each antibody is calculated by dividing the EC50 for the antibody by the EC50 of the unmasked parental antibody, Antibody 2-6.

Results

Figure 17:
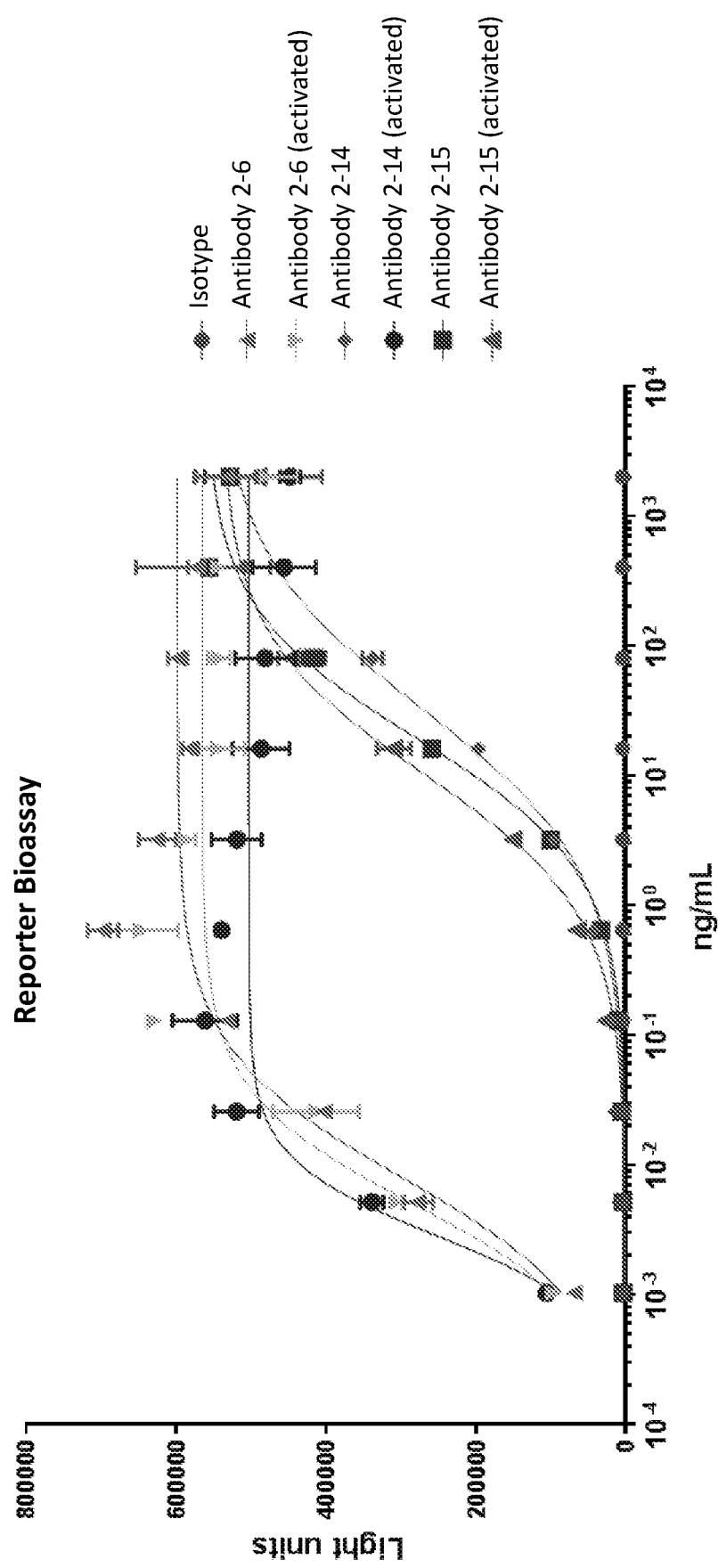
FIG. 17 is a graph showing the ability of masked anti-CTLA4 antibodies to promote ADCC activity, as determined using an ADCC reporter bioassay, in a masked state and in an "activated" state as a result of prior exposure to protease.

The unmasked parental Antibody 2-6 demonstrated a similar curve of reporter activation in the presence and absence of protease (FIG. 17). The masked antibodies, Antibody 2-14 and Antibody 2-15, demonstrated reduced reporter activation as compared to the unmasked parental Antibody 2-6 when tested without having prior exposure to protease (FIG. 17). The reporter activation of Antibody 2-15, which is non-activatable by protease, was not rescued (i.e., did not return to activation levels resembling those associated with the unmasked parental Antibody 2-6) by the prior addition of protease (FIG. 17). The reporter activation of Antibody 2-14, which is activatable by protease, was rescued to levels resembling those associated with the unmasked parental Antibody 2-6 (FIG. 17). EC50 values and the occlusion values for the antibodies tested are provided in Table 14.

TABLE 14

| Antibody | Protease | EC$_{50}$ (ng/mL) ± SE | R$^2$ | Occlusion |
|---|---|---|---|---|
| Antibody 2-6 | − | 8.0 × 10$^{-3}$ + 1.8 × 10$^{-3}$ | 0.927 | |
| Antibody 2-6 | + | 4.9 × 10$^{-3}$ + 1.3 × 10$^{-3}$ | 0.8759 | 0.6 |
| Antibody 2-14 | − | 33 + 6 | 0.9906 | 4,125 |
| Antibody 2-14 | + | 2.8 × 10$^{-3}$ + 0.5 × 10$^{-3}$ | 0.8953 | 0.4 |
| Antibody 2-15 | − | 19 + 2 | 0.9942 | 2,375 |
| Antibody 2-15 | + | 10 + 2 | 0.9722 | 1,250 |

CTLA4 Blockade Bioassay

The ability of anti-CTLA4 antibodies, including masked anti-CTLA4 antibodies, to block the interaction of CTLA4 with its ligands, CD80 and CD86, was tested using a CTLA4 blockade bioassay. Antibodies were diluted in pre-warmed complete medium. CTLA4 expressing Jurkat cells (effector cells) were thawed and transferred to a conical tube containing complete medium. The cells were mixed and counted. Cells were added to each well of a 96 well plate (Corning, #3917). Diluted antibodies were added to the appropriate wells and tested in duplicate. The plate was gently mixed and incubated at 37° C. for 15 minutes. APC cells (CD80/CD86 expressing Raji cells) were thawed and transferred to a conical tube containing complete medium. The cells were gently mixed, counted, and immediately dispensed to each well and mixed gently. The plate was covered and kept at 37° C. for 6 hours. Bio-Glo reagent was gently mixed by inversion and the bottle was kept at room temperature. After six hours of incubation the assay plate was removed from the incubator and kept at room temperature for ten minutes. Bio-Glo reagent was added to the wells and the plate was incubated at room temperature for five-fifteen minutes. The plate was then read with a luminometer and analyzed using GraphPad Prism. Statistical analysis of fold changes in the ability to block binding was performed using one-way ANOVA comparisons.

Antibodies tested include Antibody 2-2 and Antibody 2-14, as well as an isotype control. Antibody 2-2 is an unmasked form of Antibody 2. Antibody 2-14 was tested without prior exposure to protease (i.e., in a masked, non-activated form), and was also tested following exposure to protease (i.e., in an activated form). The assay was also run without using an antibody (i.e., as a no antibody control).

131

Results

Figure 18A:
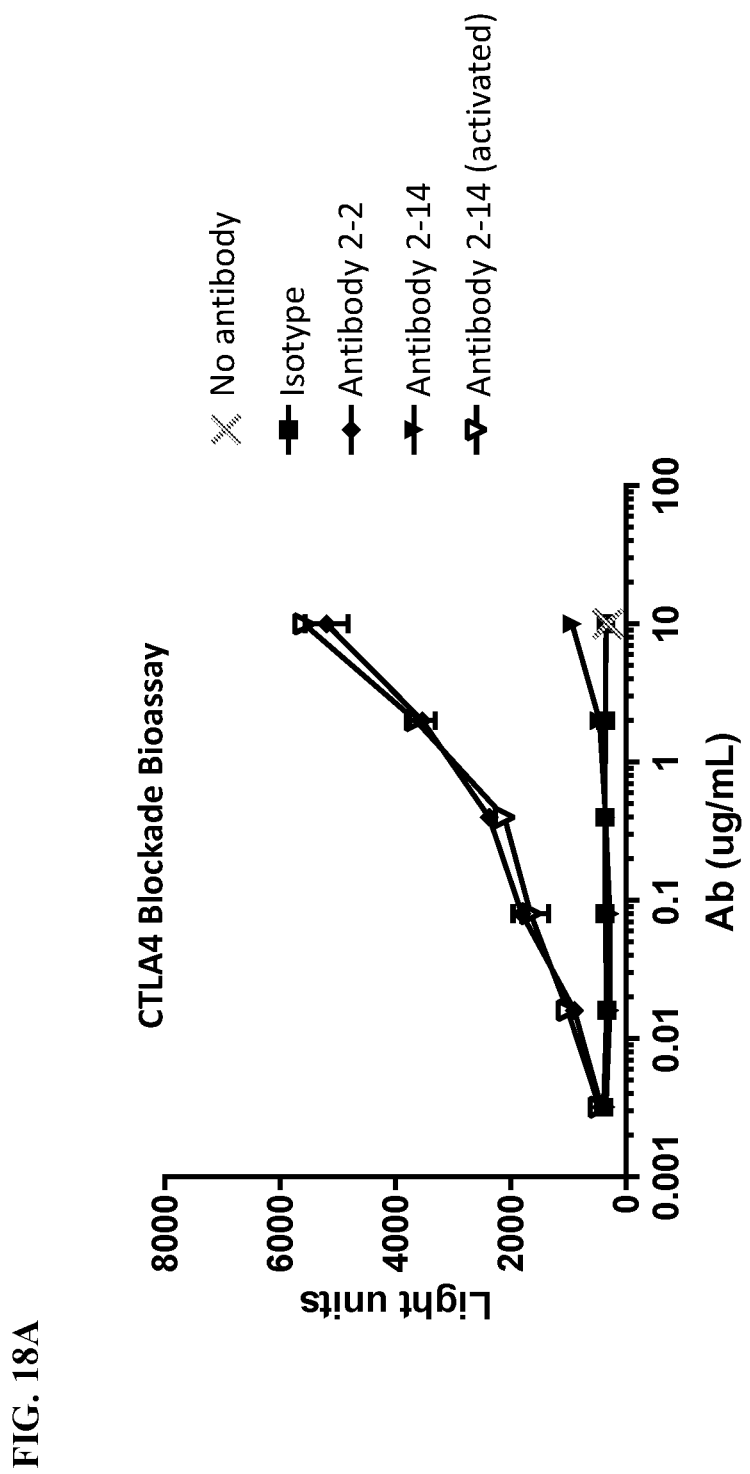
FIGS. 18A and 18B are graphs depicting the ability of anti-CTLA4 antibodies to block the interaction of CTLA4 with its ligands, CD80 and CD86, as determined using a CTLA4 blockade bioassay.
Figure 18B:
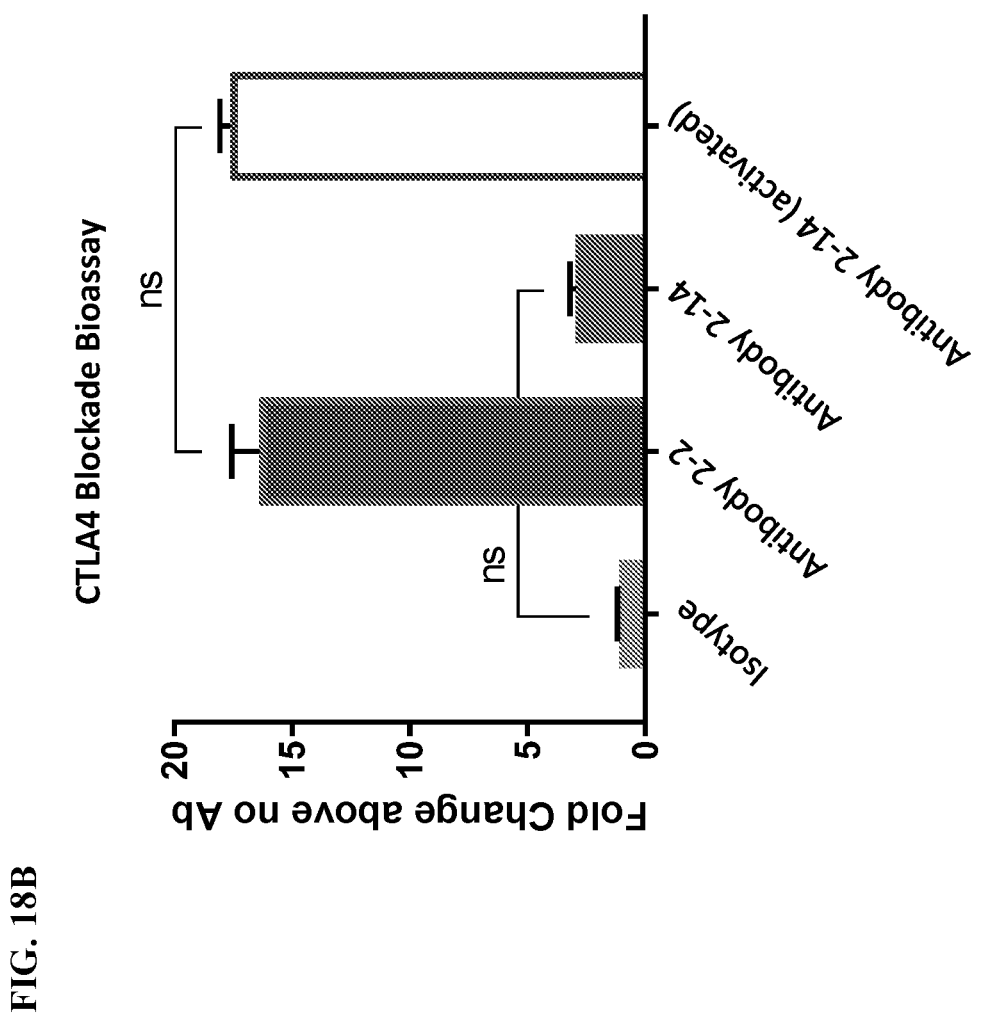
Figure 19A:
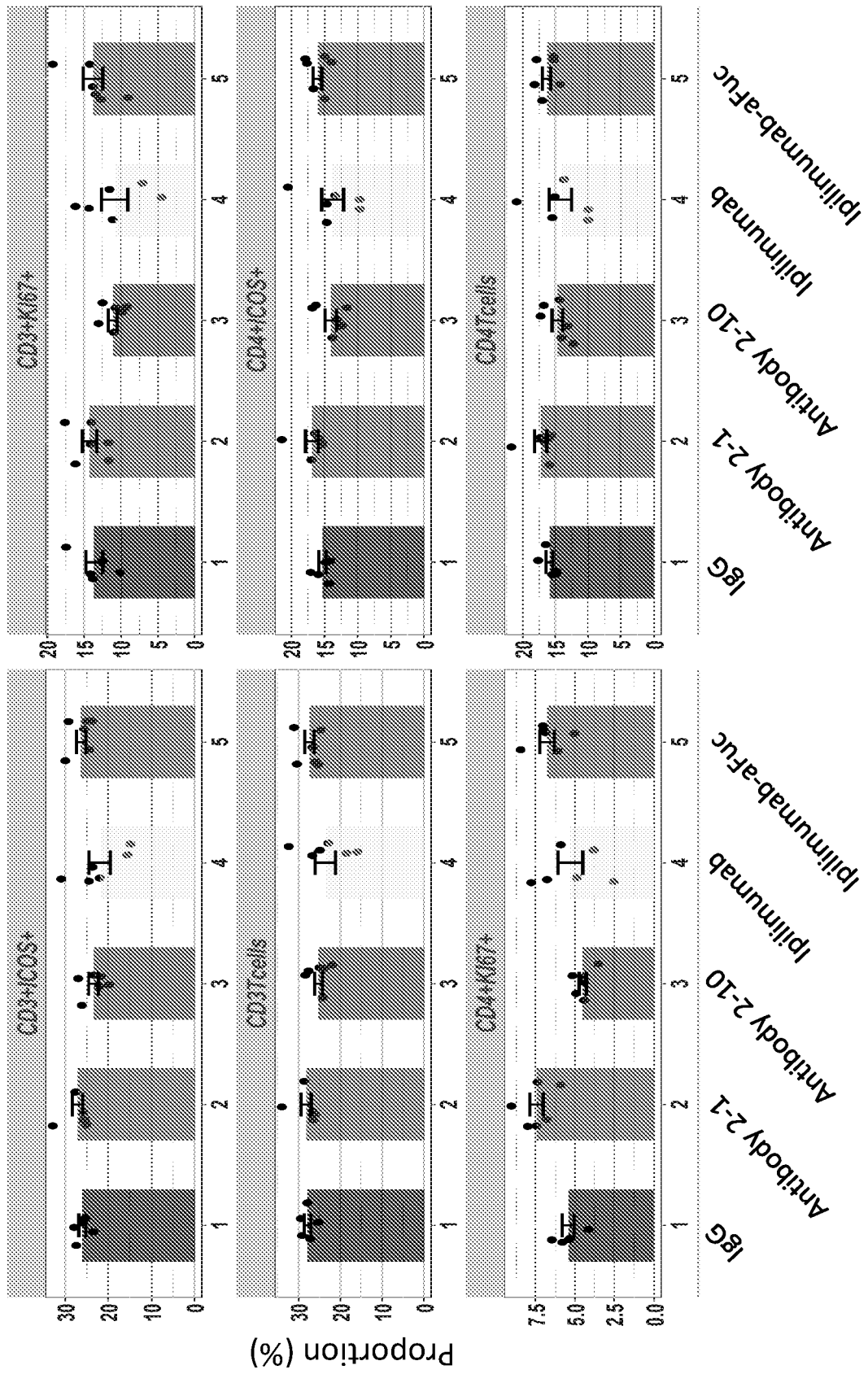
FIGS. 19A-19D depict the results from immunophenotyping studies that assessed the proportion of CD45+ cells that express markers including the following: CD3+/ICOS+, CD3+ T cells, CD4+/Ki67+, CD3+/Ki67+, CD4+/ICOS+, CD4+ T cells, CD8+/ICOS+, CD8+ T cells, Tregs+/ICOS+, CD8+/Ki67+, Tregs, Tregs+/Ki67+.
Figure 19B:
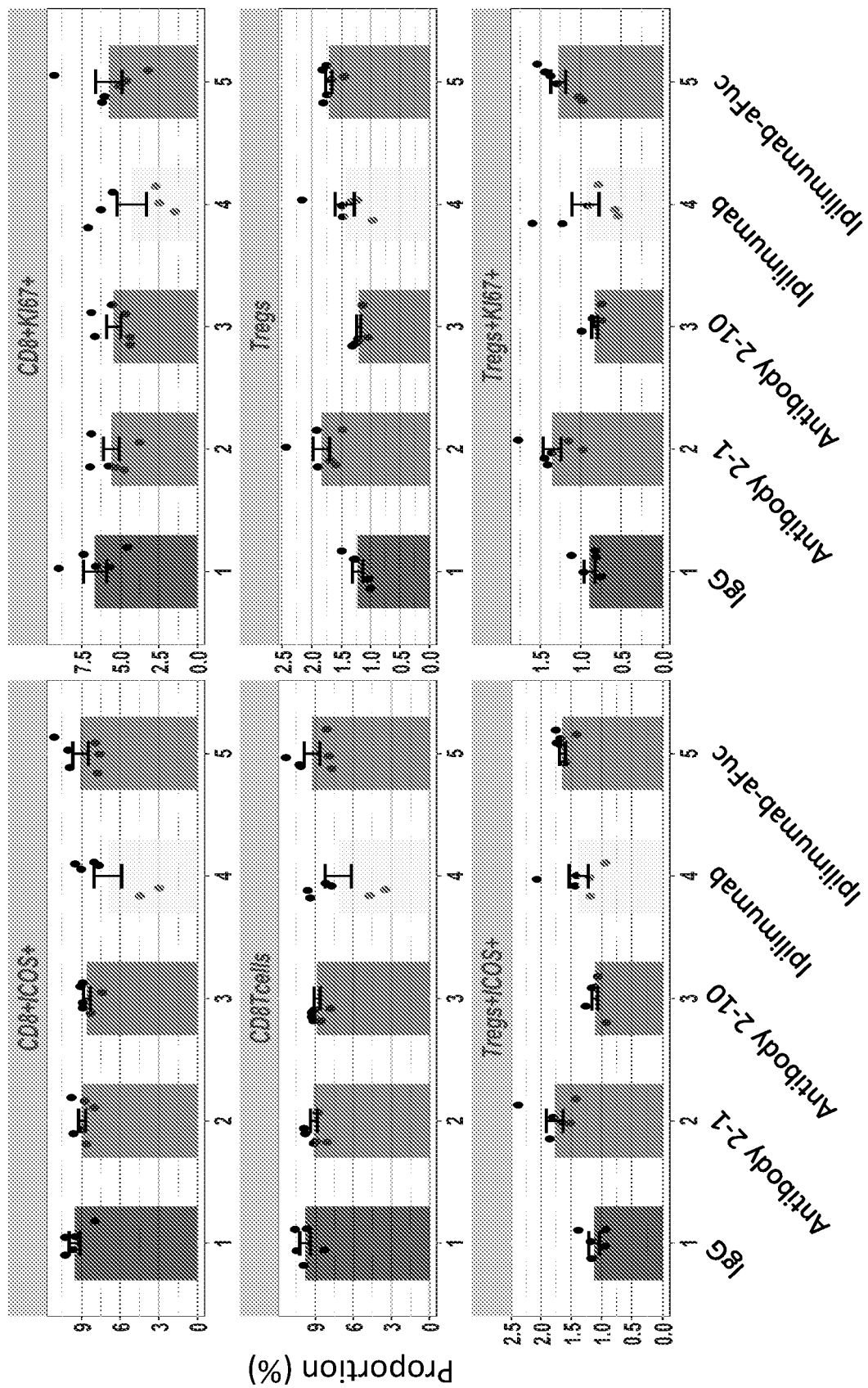
Figure 19C:
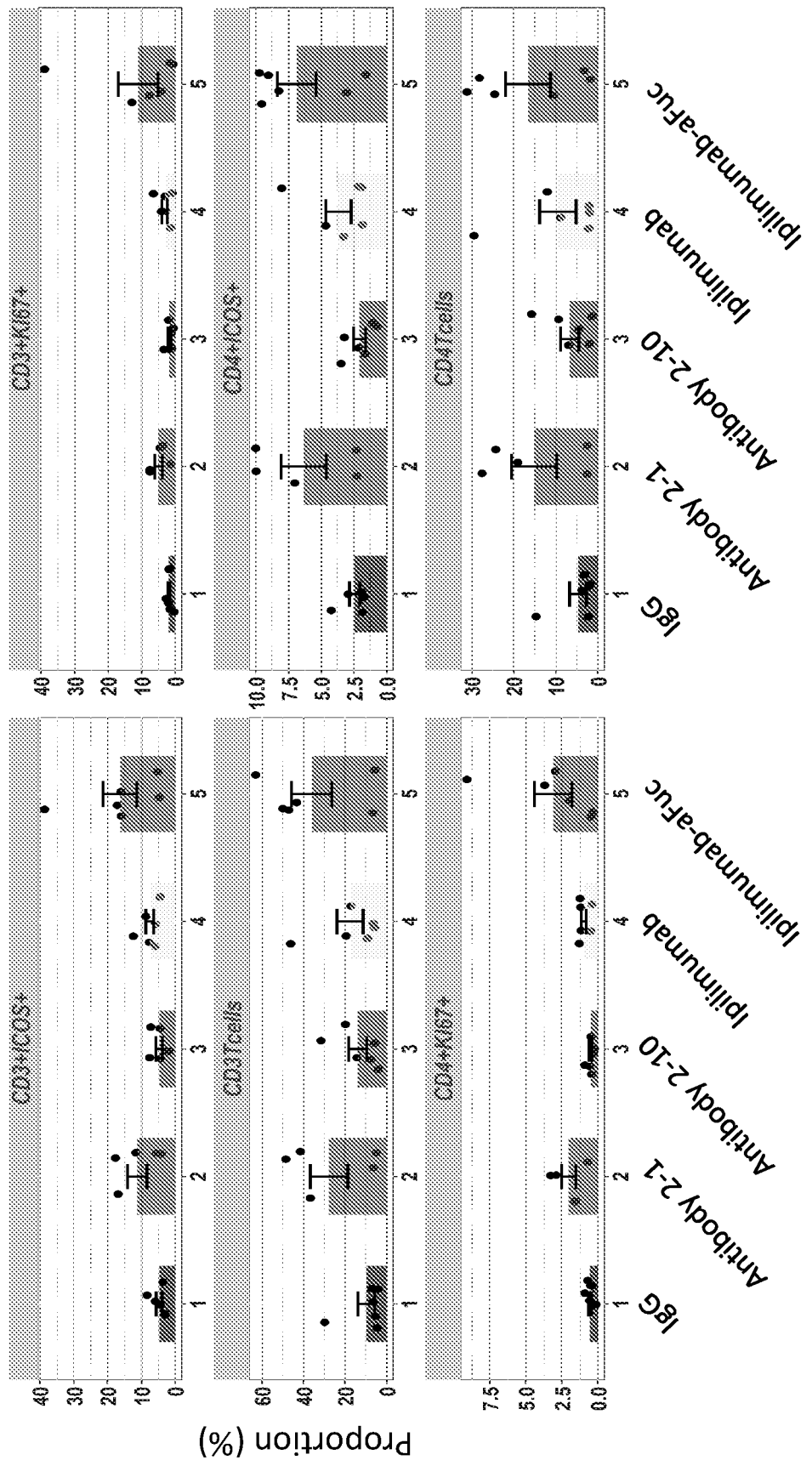
Figure 19D:
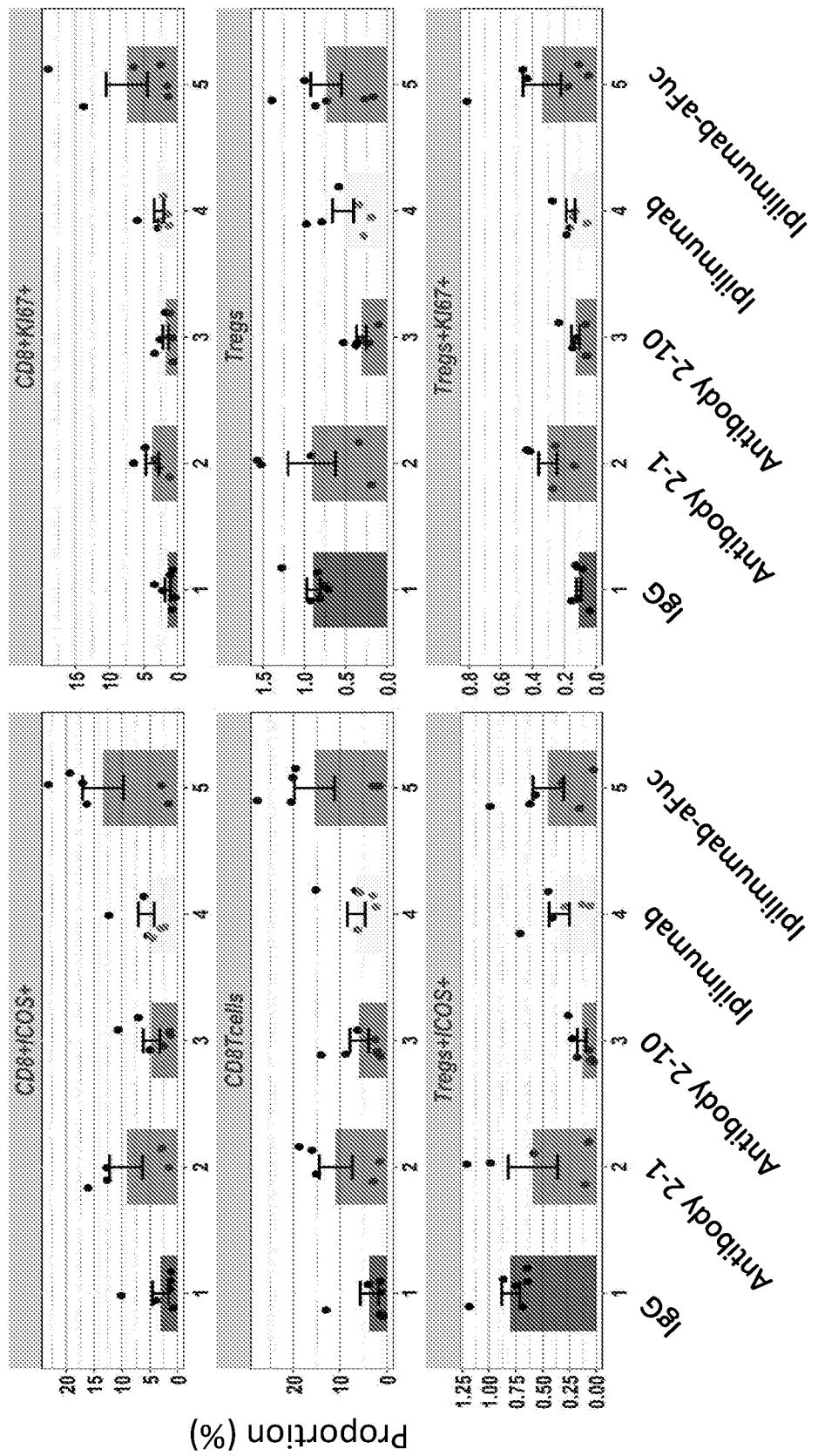

As shown in FIG. 18A, Antibody 2-14, when in a non-activated form due to the absence of protease, did not demonstrate an ability to effectively block the binding of CTLA4 to its ligands. An analysis of the fold change above the no antibody control revealed no significant difference between the ability of Antibody 2-14, when in a non-activated form, and the ability of an isotype control to block the binding of CTLA4 to its ligands (FIG. 18B). However, when Antibody 2-14 is in an activated form due to prior exposure to protease, it demonstrated an ability to effectively block the binding of CTLA4 to its ligands across a range of concentrations (FIG. 18A). The ability of activated Antibody 2-14 to block CTLA4 binding to its ligands was similar to that of unmasked Antibody 2-2 (FIGS. 18A and 18B). In fact, an analysis of the fold change above the no antibody control revealed no significant difference between the ability of activated Antibody 2-14 and unmasked Antibody 2-2 to block CTLA4 binding to its ligands (FIG. 18B).

Example 15: Efficacy and Pharmacodynamics of Anti-CTLA4 Antibodies in the MB49 Murine Bladder Tumor Model Methods Efficacy and pharmacodynamics (PD) of anti-CTLA4 antibodies were assessed using the MB49 murine bladder tumor model. Efficacy was assessed by administering each test antibody (RSV-m control antibody, ipilimumab, Antibody 2-6, Antibody 2-14, and Antibody 2-15) and then assessing tumor volume and body weight. The anti-RSV control antibody contains S239D and I332E mutations (RSV-m control antibody). Peripheral immunophenotyping was also carried out on day 5, which assessed the percentage of CD4+Ki67+ cells and the percentage of CD4+ICOS+ cells in the peripheral blood on day 5 following administration. Fourteen cohorts of mice were assessed for the efficacy studies, with dosing in mg/kg as shown in Table 15. As used herein, dosing in mg/kg is also referred to as "mpk." MB49 cells were inoculated subcutaneously into C57/BL6-huCTLA4 mice. Treatment started when the tumors reached approximately 350 mm$^3$. A One-way ANOVA with Dunnett's post-test was performed to determine the statistical significance of treatment vs control (RSV-m control). * P<0.05;  P<0.01; * P<0.001; **** P<0.0001.

TABLE 15

| Cohort | Antibody | Dosing (mg/kg) |
|---|---|---|
| 1 | RSV-m control | 10 |
| 2 | Ipilimumab | 0.3 |
| 3 | Ipilimumab | 1 |
| 4 | Ipilimumab | 3 |
| 5 | Antibody 2-6 | 0.3 |
| 6 | Antibody 2-6 | 1 |
| 7 | Antibody 2-6 | 3 |
| 8 | Antibody 2-6 | 10 |
| 9 | Antibody 2-14 | 1 |
| 10 | Antibody 2-14 | 3 |
| 11 | Antibody 2-14 | 10 |
| 12 | Antibody 2-15 | 1 |
| 13 | Antibody 2-15 | 3 |
| 14 | Antibody 2-15 | 10 |

Pharmacodynamics is assessed by administering antibody to each of five cohorts of mice, with dosing (mg/kg) as shown in Table 16. Immunophenotyping among other readouts are performed in the tumor, liver, spleen, and blood. T cells are assessed by measuring Foxp3+CD25+ cells as a percentage of CD4+ cells, and CD8+ cells are measured as a percentage of CD45+ cells. Cleavage and drug levels in tumors, liver, kidney, spleen, and plasma is also assessed.

TABLE 16

| Cohort | Antibody | Dosing (mg/kg) |
|---|---|---|
| 1 | RSV-m control | 10 |
| 2 | Ipilimumab | 3 |
| 3 | Antibody 2-6 | 3 |
| 4 | Antibody 2-14 | 3 |
| 5 | Antibody 2-15 | 3 |

Results

Figure 23A:
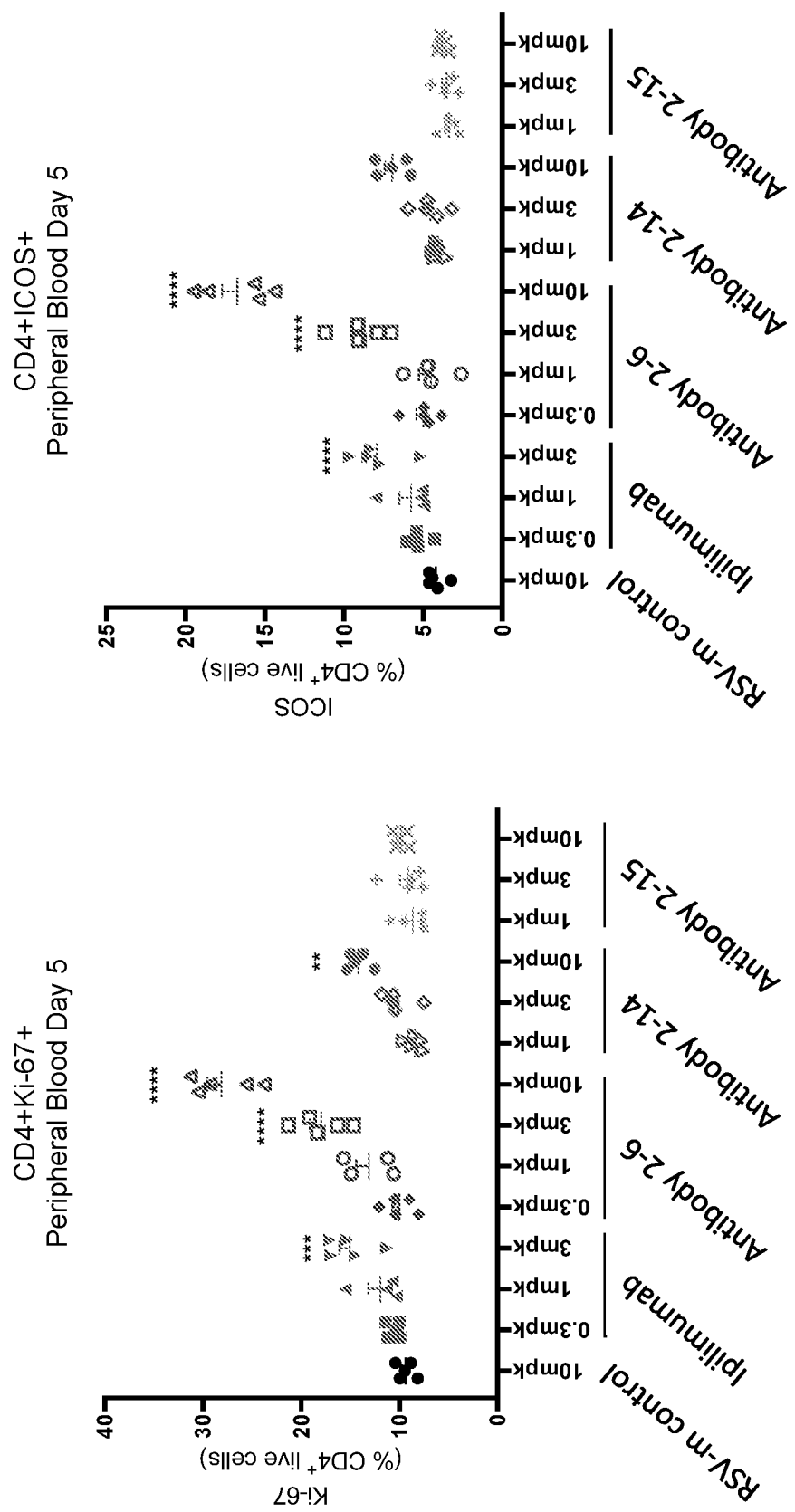
FIG. 23A depicts graphs with results from an efficacy study on the percentage of CD4+Ki67+ cells (left) and CD4+ICOS+ cells (right) in the peripheral blood on day 5 following administration, which represents the level of T-cell activation.

FIG. 23A shows results from efficacy studies on the percentage of CD4+Ki67+ cells (left) and CD4+ICOS+ cells (right) in the peripheral blood on day 5 following administration, which represents the level of T-cell activation. The results indicate that the masked anti-CTLA4 antibody Antibody 2-14 exhibited lower T-cell activation at a dosing of 10 mg/kg than the anti-CTLA4 antibody ipilimumab exhibited at a 3.3-fold lower dose of 3 mg/kg. This demonstrates that the masked Antibody 2-14 is safer than ipilimumab in the MB49 murine model.

Figure 23B:
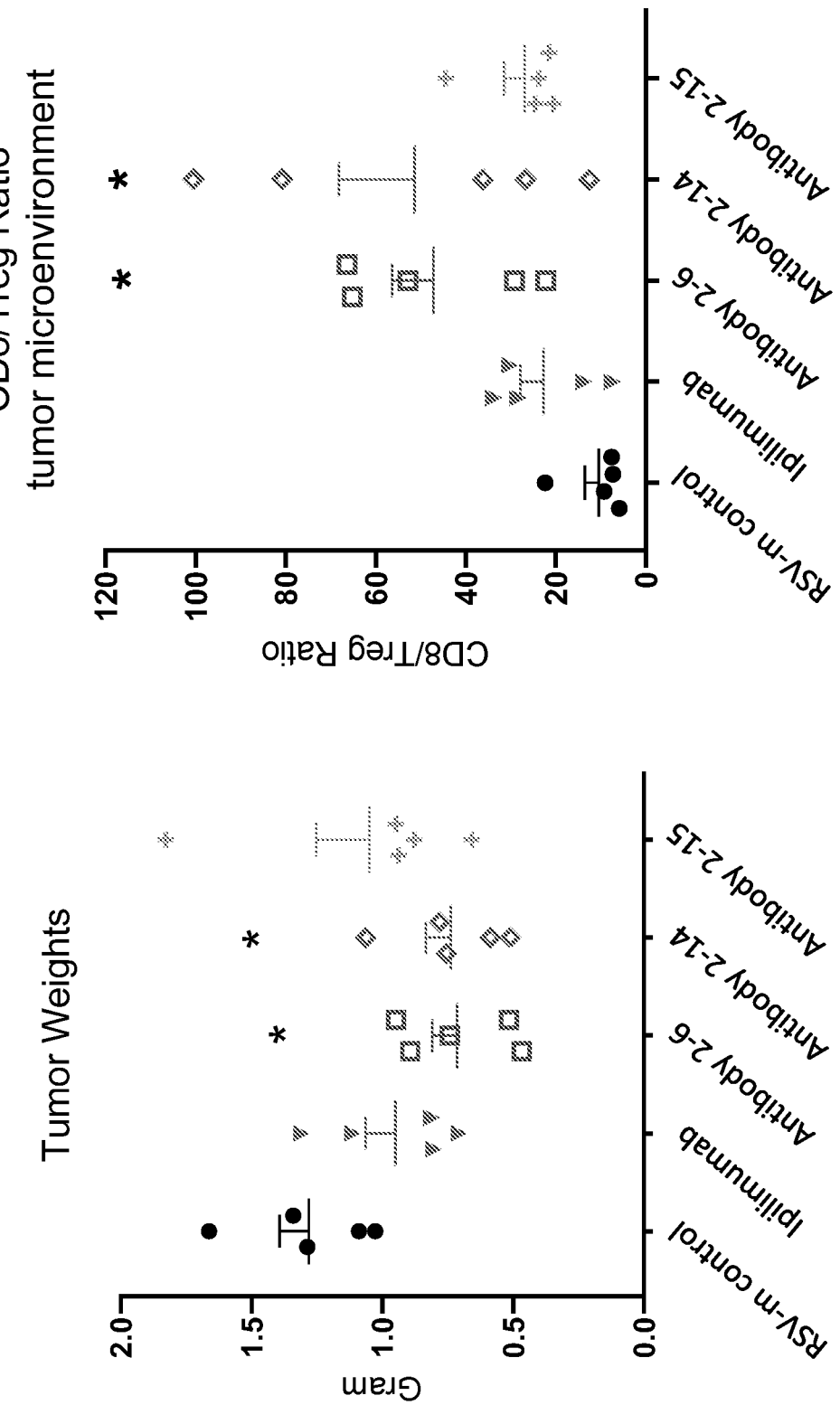
FIG. 23B depicts graphs showing tumor weight (left) and CD8/Treg ratios (right) as assessed on day 7 in mice treated with 10 mg/kg (RSV-m control) or 3 mg/kg (ipilimumab, Antibody 2-6, Antibody 2-14, Antibody 2-15).

As shown in FIG. 23B, tumor weight and CD8/Treg ratios were assessed on day 7 in mice treated with 10 mg/kg (RSV-m control) or 3 mg/kg (ipilimumab, Antibody 2-6, Antibody 2-14, Antibody 2-15). Mice treated with Antibody 2-6 or Antibody 2-14 exhibited the lowest tumor weights and the highest CD8/Treg ratios in tumors at 3 mg/kg on day 7. No change in body weight, spleen weight, kidney weight, or liver weight was observed with any of the therapies (data not shown).

As shown in FIG. 23C, Regulatory T cell depletion and CD8+ T cell activation is observed with Antibody 2-14, but not with ipilimumab.

Figure 23D:
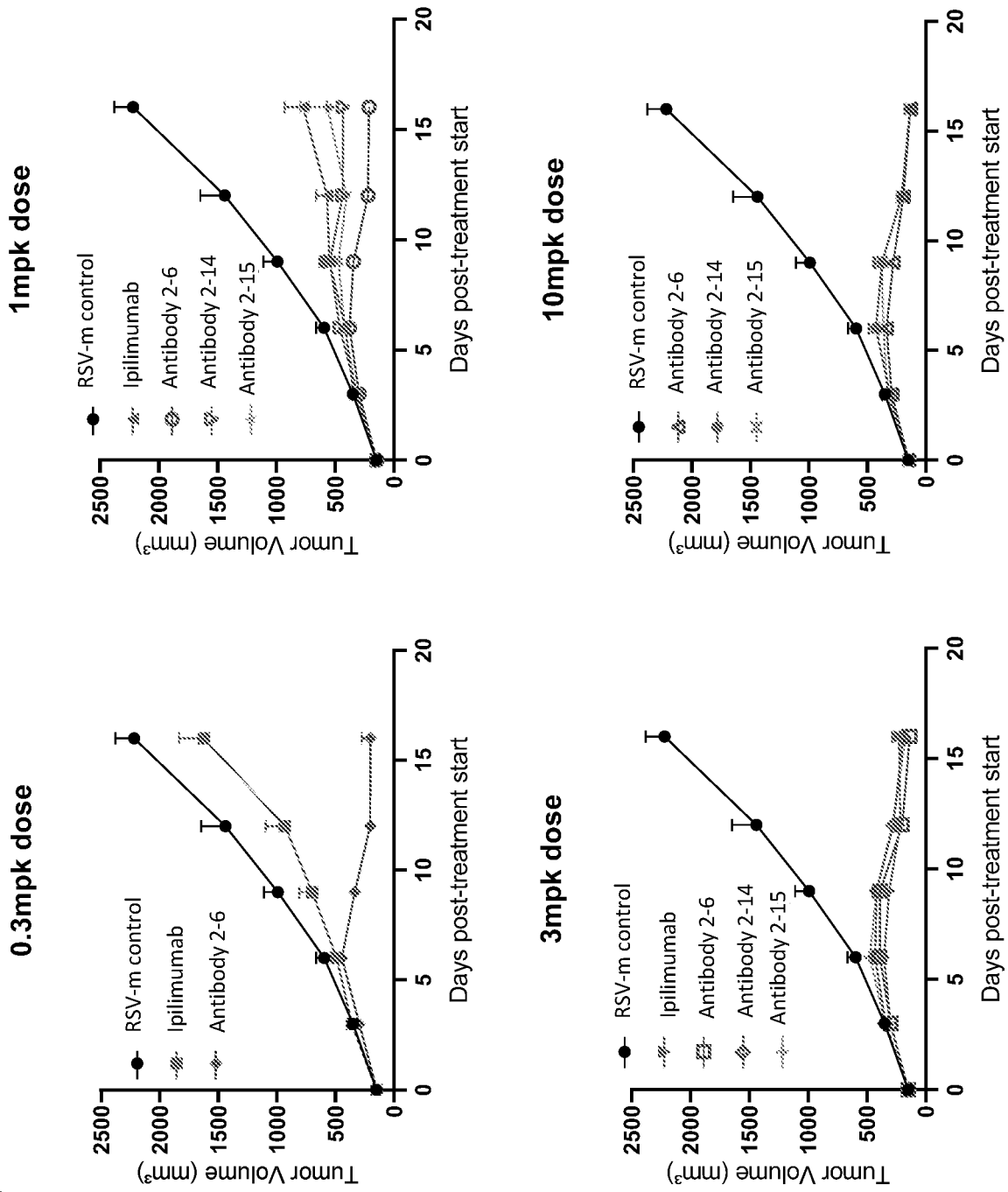
FIG. 23D depicts graphs showing tumor volume (mm$^3$) in mice over time following administration of 0.3 mg/kg, 1 mg/kg, 3 mg/kg, or 10 mg/kg for antibodies including RSV-m control, ipilimumab, Antibody 2-6, Antibody 2-14, and Antibody 2-15.

As shown in FIG. 23D, strong anti-tumor activity was observed following treatment with ani-CTLA4 antibodies. At a 0.3 mg/kg dose, Antibody 2-6 demonstrated superior anti-tumor activity as compared to ipilimumab.

Example 16: In Vivo Cleavage Detection of Anti-CTLA4 Antibodies in Tumor, Liver, Kidney, Spleen, and Plasma Methods B-hCTLA-4 transgenic female mice were purchased from Biocytogen and were 8-10 weeks old at the start of study. MC38 colorectal tumor cells ($5\times10^5$ cells per mouse), MB49 bladder cancer cells ($1\times10^6$ cells per mouse) or MCA205 fibrosarcoma cells ($1\times10^6$ cells per mouse) were subcutaneously into the right flank of each mouse. Upon reaching ~250-500 mm$^3$ sized tumors (day 0), the mice received a single 10 mg/kg intraperitoneal dose of indicated antibodies. Tumor, liver, kidney, spleen and plasma harvested on day 4 for analysis of cleavage by western blot.

For plasma samples, a direct western blot approach is utilized by separating equal volumes of denatured plasma (1-2 μL input) on a gradient criterion precast gel (BioRad). Separated proteins were then transferred into a nitrocellulose membrane using Turbo Transblot system (BioRad). Membranes were than developed using standard methods for anti-human kappa light chain reactivity with an HRP conjugated antibody (ab202549). Cleavage is assessed visually as the cleaved light chain migrates lower than the un-cleaved light chain with a mass difference of 2 kD.

Protein lysates from tumor, liver, spleen and kidney were generated using Tissue Lyser II (Qiagen) bead homogenizer in RIPA buffer (Pierce, 87788) supplemented with protease and phosphatase inhibitors (Thermo Fisher, 78442). Protein concentrations were determined by BCA assay and 3 mgs of tissue lysate was subjected to immunoprecipitation with biotin conjugated anti-human kappa light chain antibody (LSBio, LS-C351451-500) and streptavidin magnetic beads (Pierce, 88816). Proteins were eluted in 50 µL 10 mM Glycine (pH 2) and neutralized with 1M Tris (pH 8) prior to western blot detection of human kappa light chain as described above.

In another study, ex vivo cleavage of healthy monkey (cynomolgus) tissues (N=2) and plasma (N=3) was assessed using a CTLA4 ELISA assay. Tissues tested included kidney, spleen, liver, bladder, skin, colon, and lung.

In another study, in vivo cleavage was assessed in the plasma of healthy cynomolgus monkeys at 1 hour, 1 day, and 7 days after administration. Cleavage was identified by capillary electrophoresis (CE) and by mass spectrometry (MS). The abundance of cleavage products at expected cleavage site within Antibody 2-14 (VPLSLY) was calculated. Cleavage at another site (VPLSLYSGG) was also calculated for comparison. The abundance of cleavage for Antibody 2-16 was also calculated.

In another study, ex vivo cleavage in murine tumor, tissue, and plasma was assessed using a CTLA4 ELISA assay. This included the following murine models: C57/B16 (N=9), MC38 in wild type mice (N=9), MC38 in hCTLA4 mice (N=5), MB49 in wild type mice (N=6), MCA205 in wild type mice (N=4), and B16 in wild type mice (N=4). Cleavage in tumors, spleen, liver, kidney, and plasma was assessed. Plasma samples were pooled. Frequency of cleavage and the percentage of the molecule cleaved (median) were calculated.

In another study, ex vivo cleavage was performed using human conditioned media from human tumors (colon tumors, lung tumors). Protein A/G beads were used in two rounds of immunoprecipitation to remove human IgG from the human samples prior to analysis. SDS-PAGE analysis was performed using an anti-hkLC antibody to detect cleaved and uncleaved forms of the tested antibody. ELISA analysis was performed to calculate the percentage (%) of cleavage.

Results

Figure 24A:
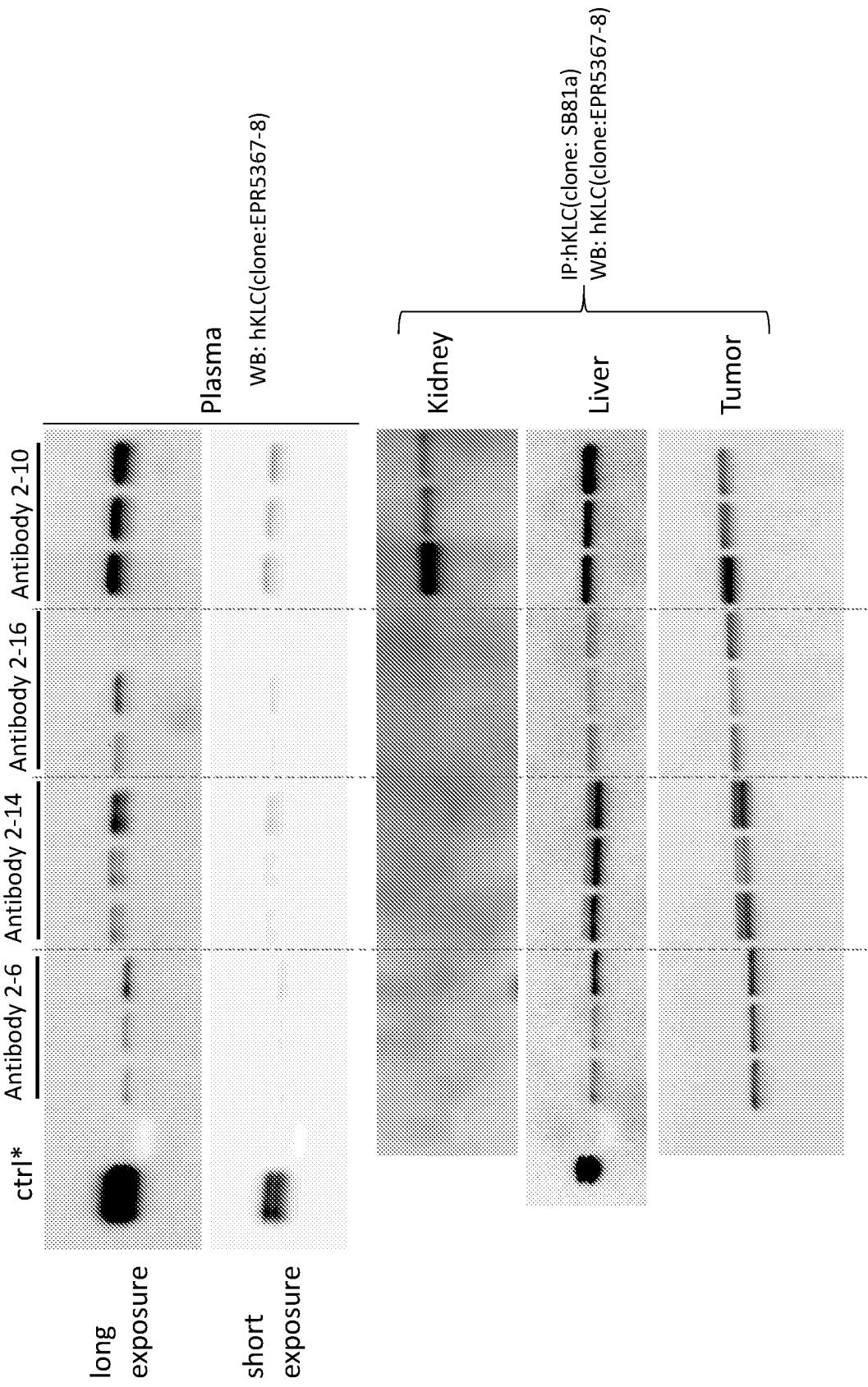
FIG. 24A depicts results from an SDS-PAGE Western blot analysis using MCA205 fibrosarcoma cells that assessed cleavage of Antibody 2-6, Antibody 2-14, Antibody 2-16, and Antibody 2-10, in plasma, kidney, liver, and tumor tissue.

As shown in FIG. 24A, for studies using MCA205 fibrosarcoma cells, cleavage products were strongly detected in tumors and in liver tissue with Antibody 2-14, but not with Antibody 2-16. The positive control (ctrl*) included a sample having 50% uncleaved and 50% cleaved product from Antibody 2-14.

Figure 24B:
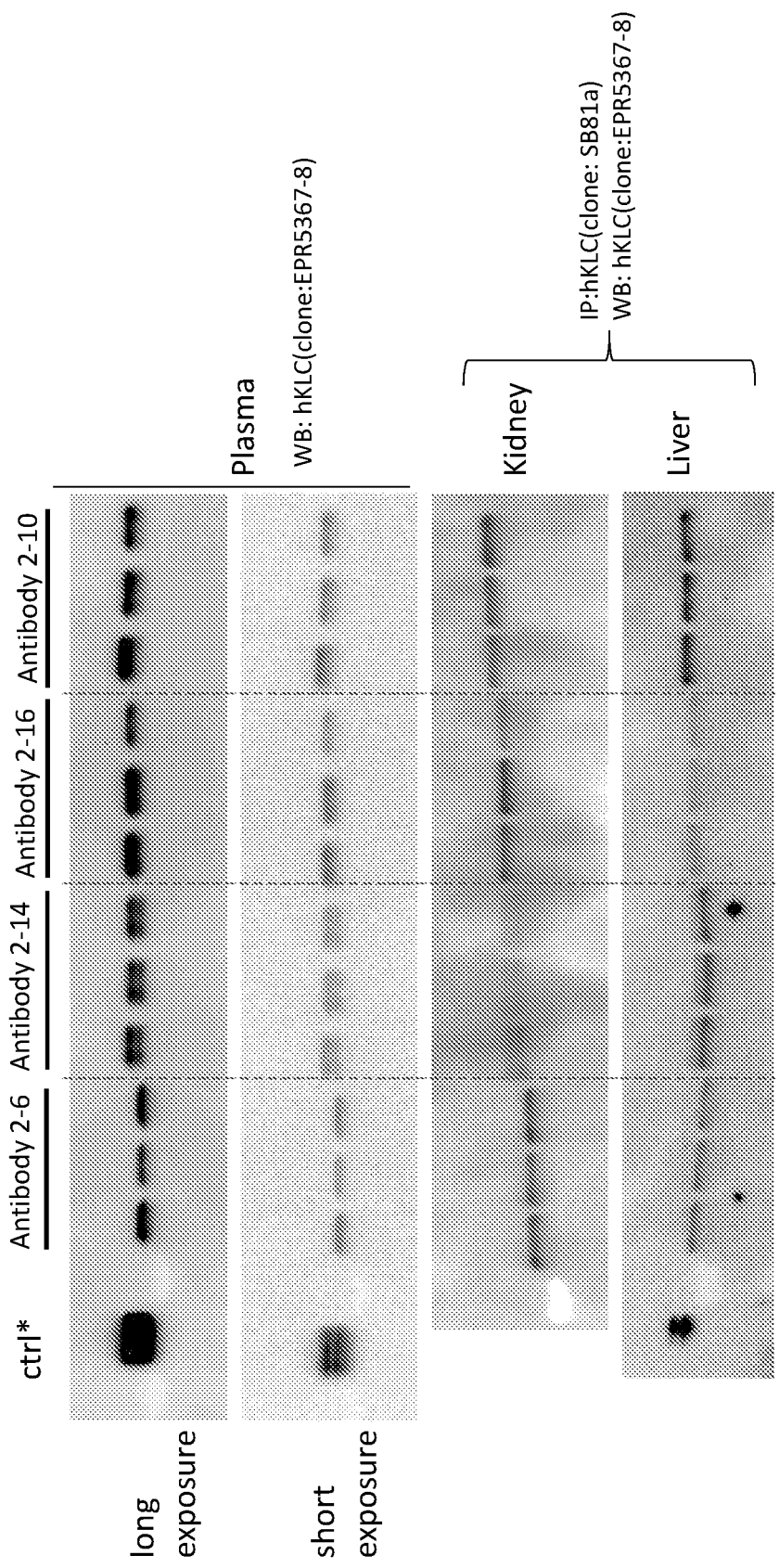
FIG. 24B depicts results from an SDS-PAGE Western blot analysis using MB49 cells that assessed cleavage of Antibody 2-6, Antibody 2-14, Antibody 2-16, and Antibody 2-10, in plasma, kidney, and liver tissue.

As shown in FIG. 24B, for studies using MB49 bladder cancer cells, cleavage products were strongly detected in liver tissue with Antibody 2-14, but not with Antibody 2-16. The positive control (ctrl*) included a sample having 50% uncleaved and 50% cleaved product from Antibody 2-14.

Figure 24C:
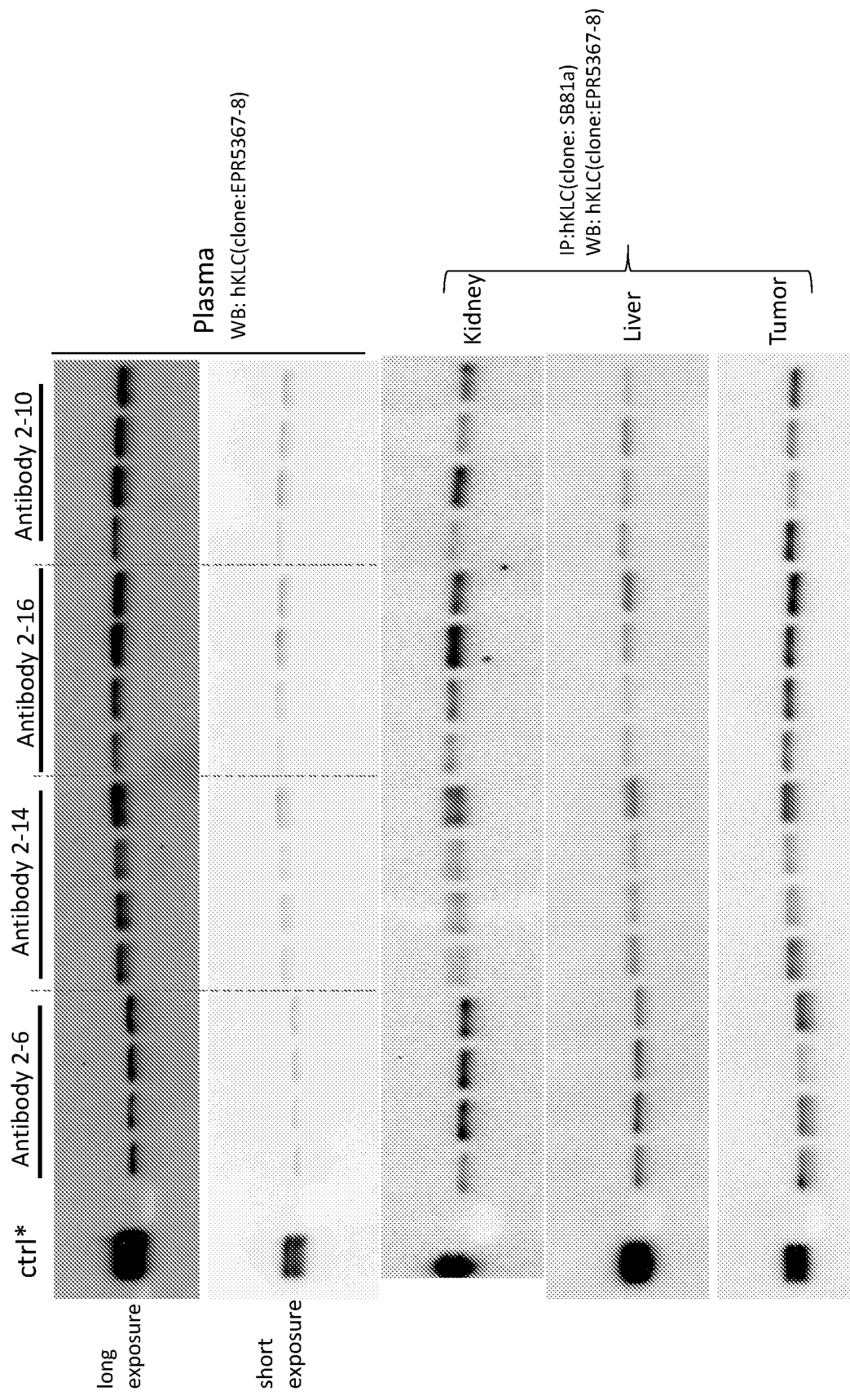
FIG. 24C depicts results from an SDS-PAGE Western blot analysis using MC38 cells that assessed cleavage of Antibody 2-6, Antibody 2-14, Antibody 2-16, and Antibody 2-10, in plasma, kidney, liver, and tumor tissue.

As shown in FIG. 24C, for studies using MC38 colorectal cancer cells, cleavage products were strongly detected in liver tissue with Antibody 2-14, but not with Antibody 2-16. The positive control (ctrl*) included a sample having 50% uncleaved and 50% cleaved product from Antibody 2-14.

Figure 24D:
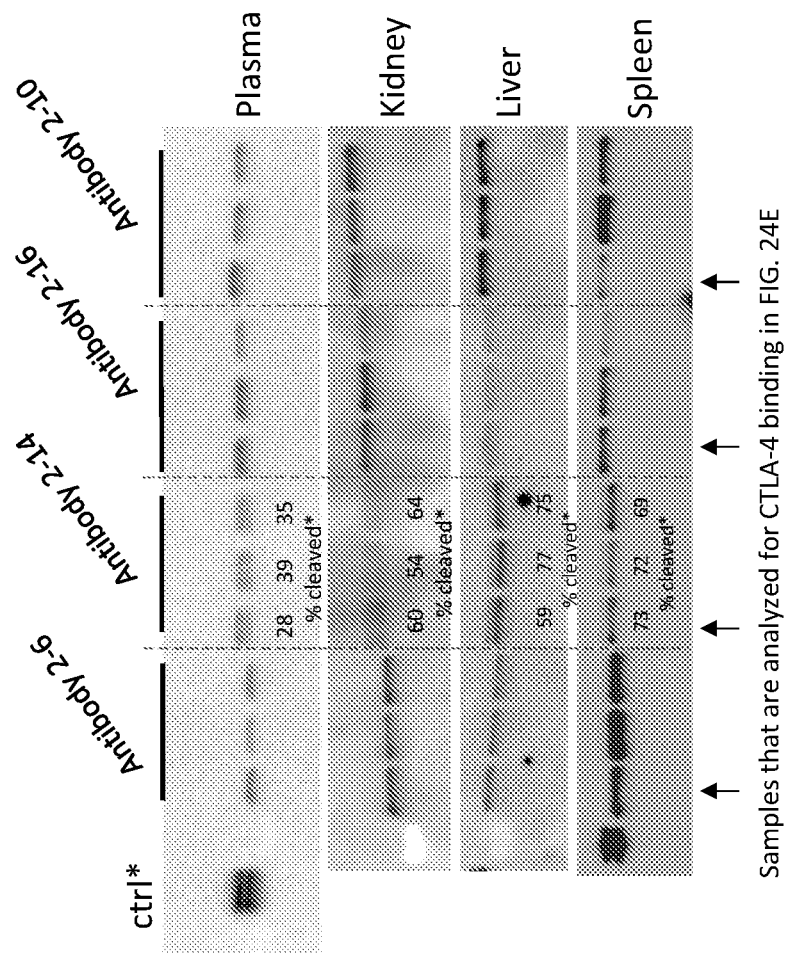
FIG. 24D depicts results from an SDS-PAGE Western blot analysis using MC38 cells that assessed cleavage, and provides a percentage of cleavage for select samples. Percentage of cleavage was calculated based on densometric intensity (cleavage %=lower band/(lower band+upper band).
Figure 24E:
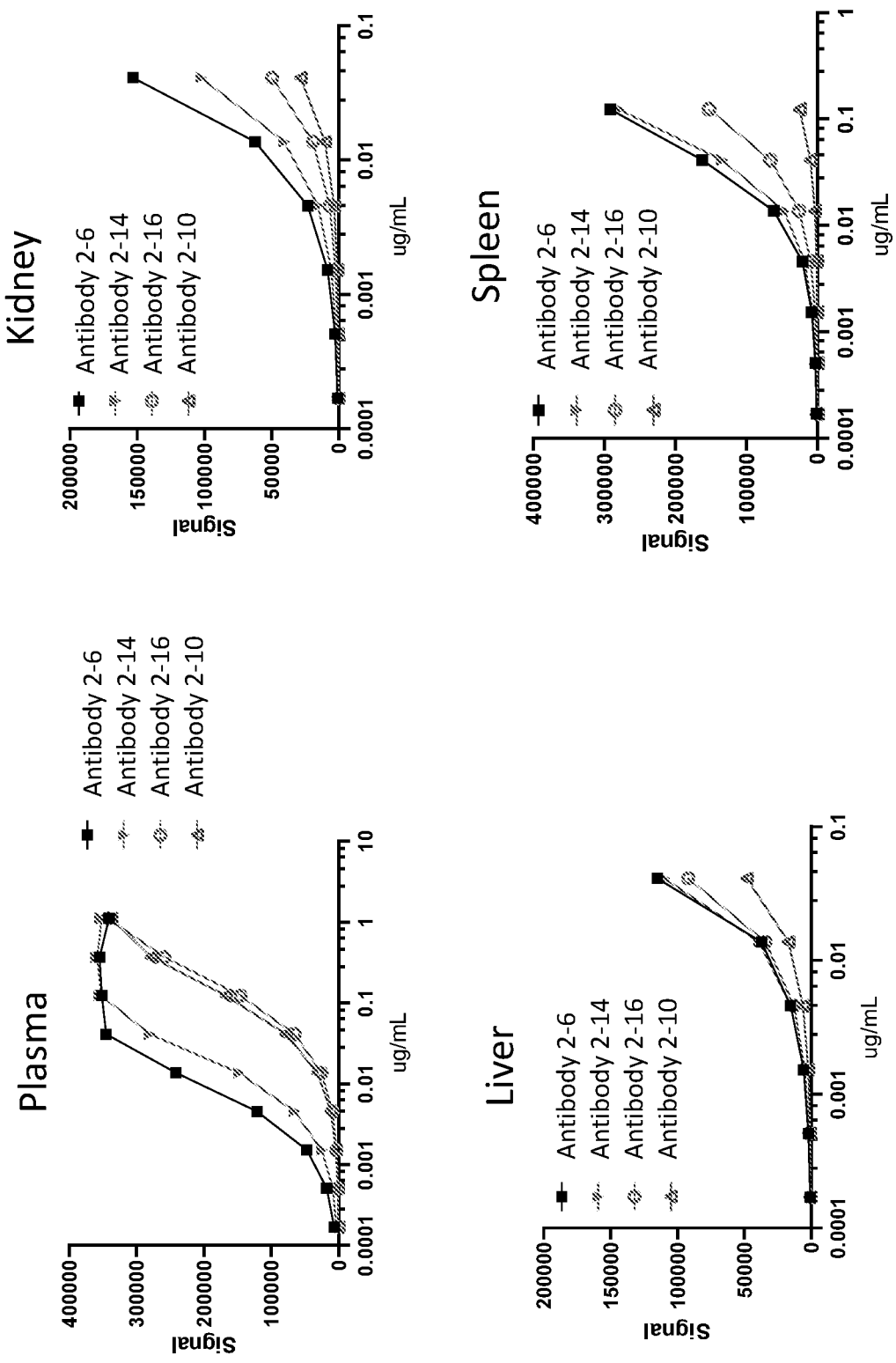
FIG. 24E depicts graphs showing binding between each antibody and CTLA4, where each antibody was isolated from plasma, kidney, liver, or spleen following administration to MB49-bearing B-hCTLA4 transgenic mice.
Figure 24F:
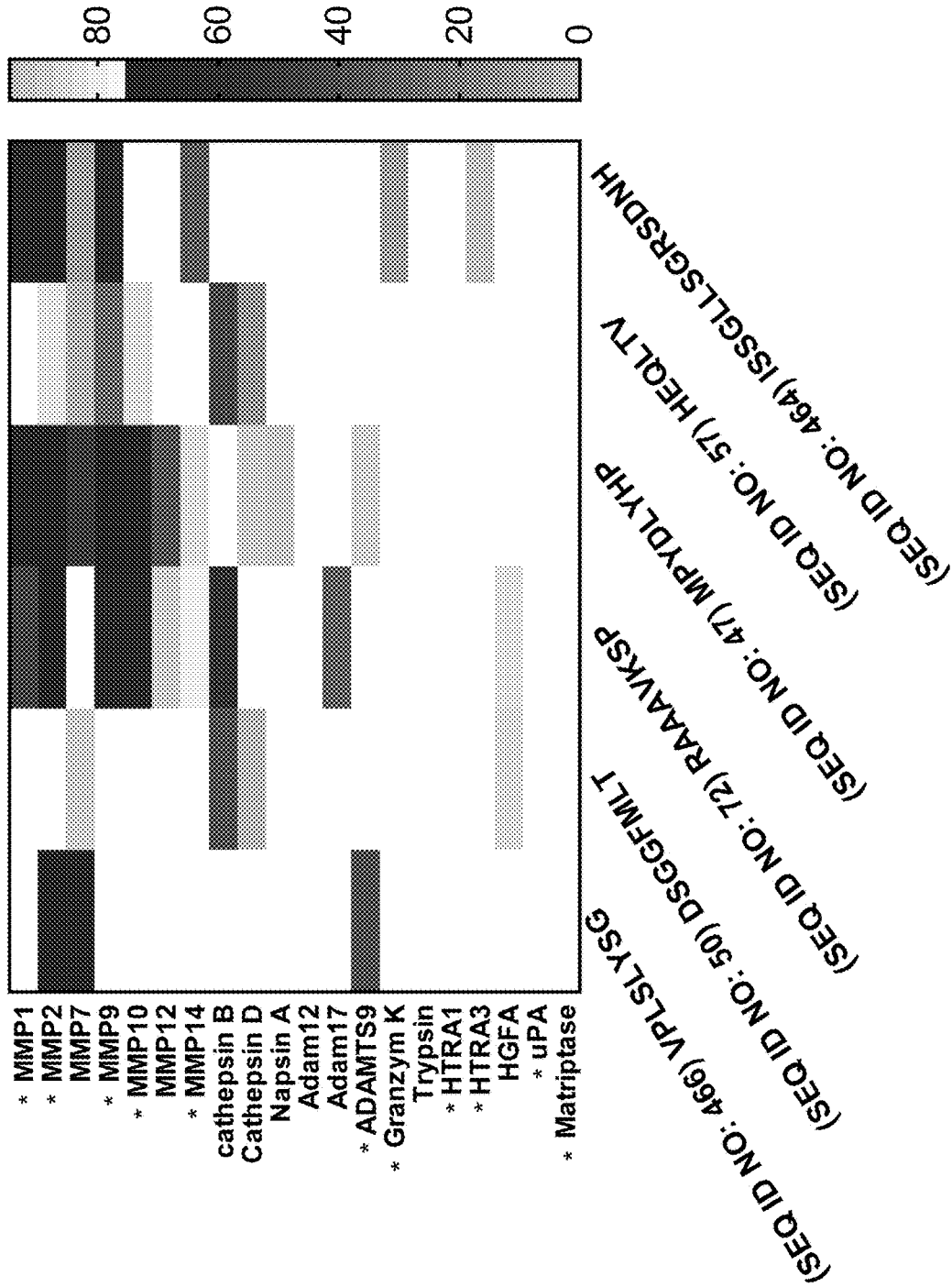
FIG. 24F depicts a heat map of the in vitro cleavage of cleavable peptide substrates by a panel of exemplary proteases.
Figure 25A:
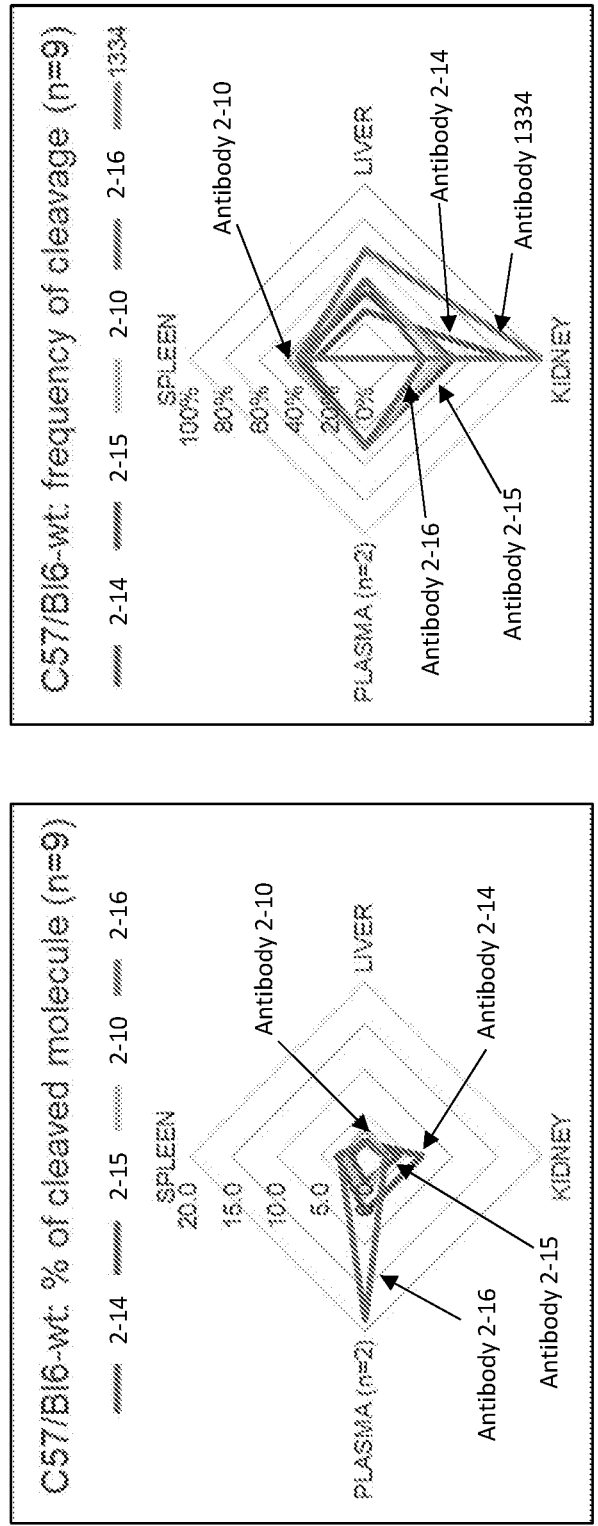
Figure 25B:
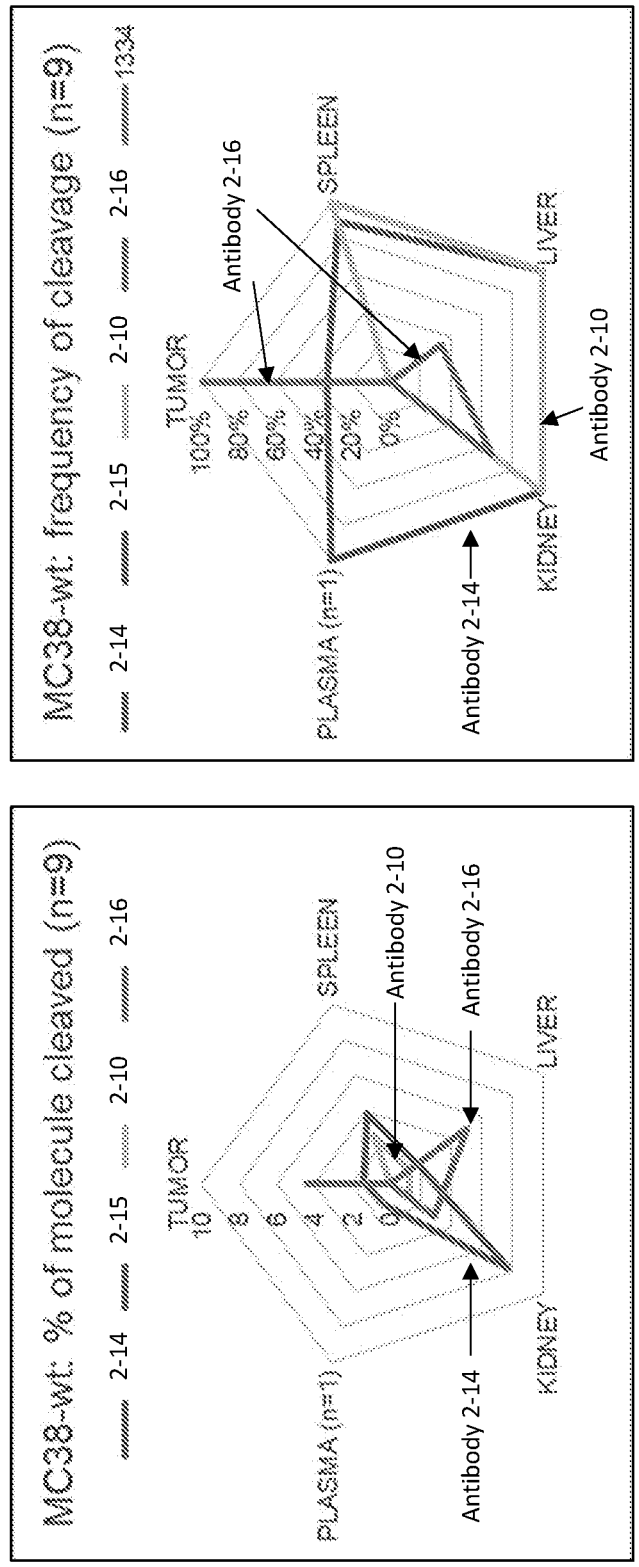
Figure 25D:
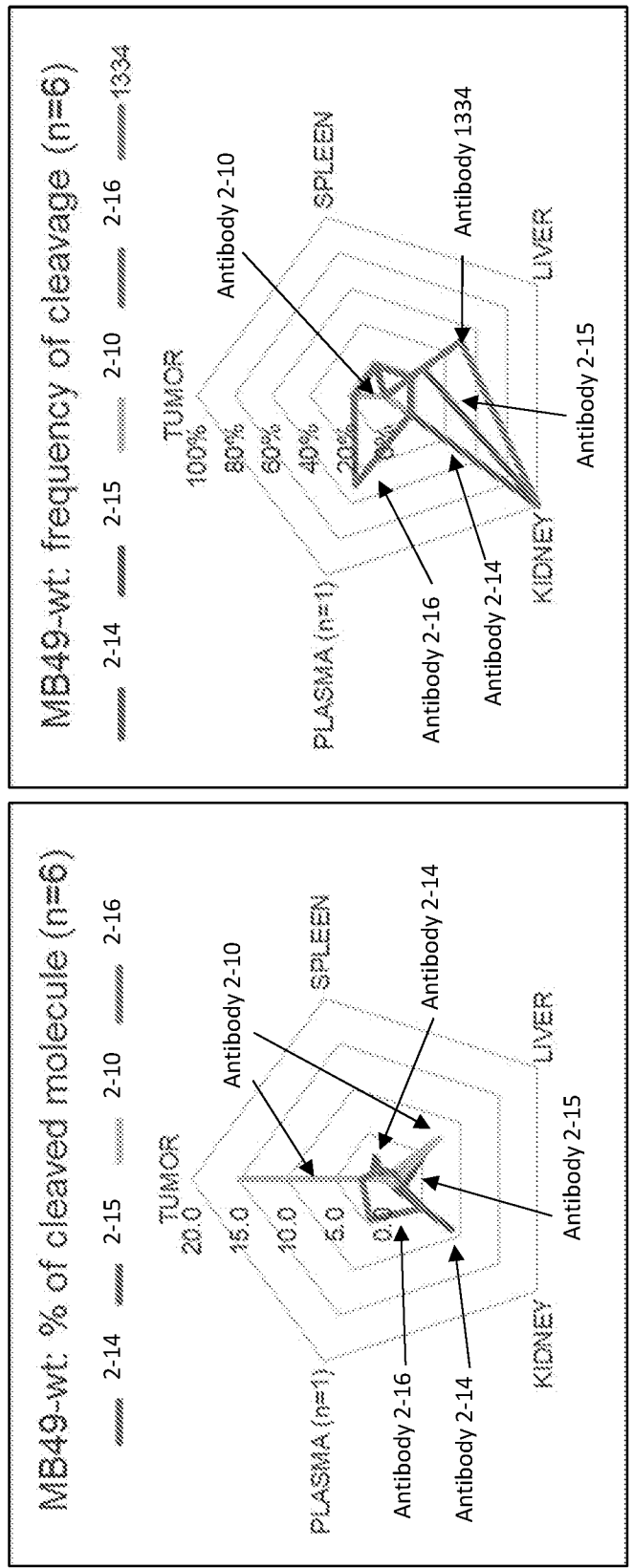
Figure 25E:
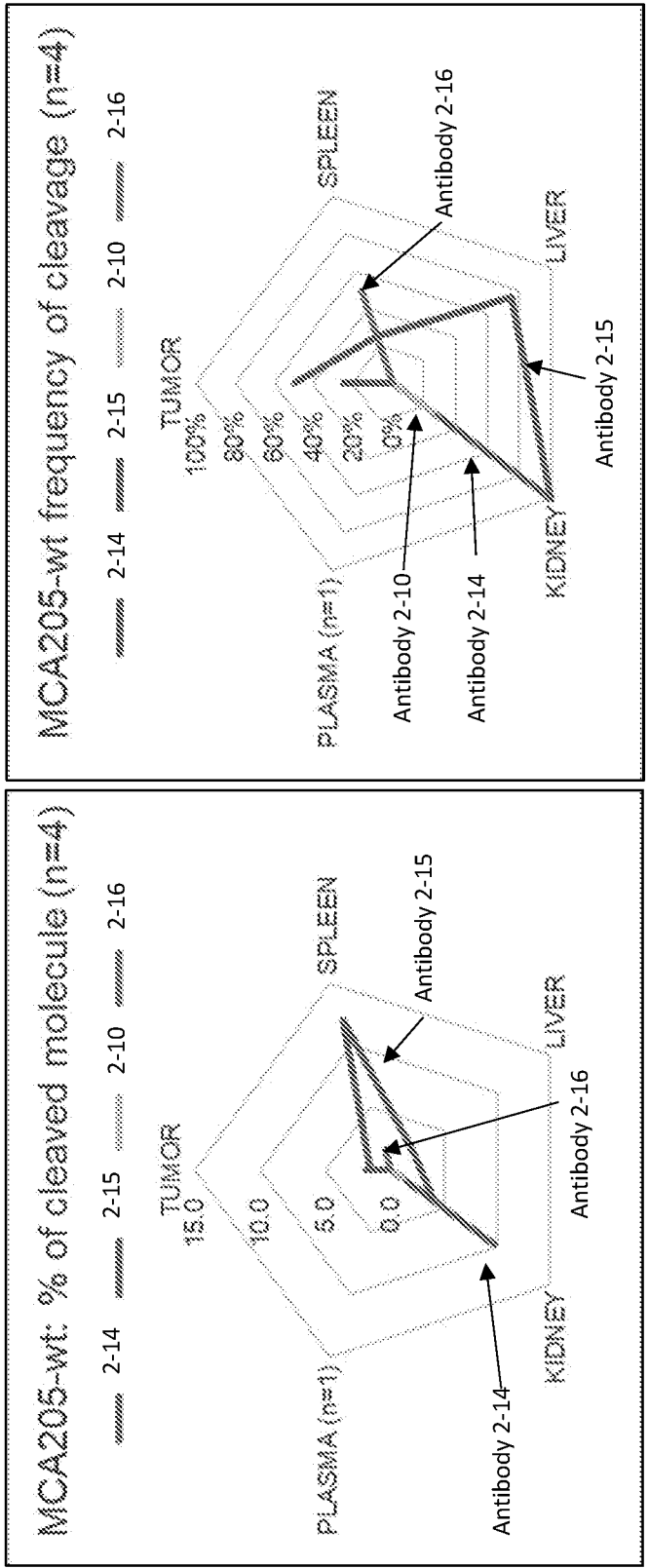

Studies were also carried out where IgG levels of each antibody administered to MB49-bearing mice was quantified by an ELISA assay and then each sample was assayed in a 3-fold dilution series starting at 1 µg/mL for spleen or 0.04 µg/mL for kidney and liver tissue, on a CTLA4-coated MSD plate to assess CTLA4 binding. These studies included a non-masked parental antibody (Antibody 2-6), masked and cleavable antibodies (e.g., Antibody 2-14 and Antibody 2-16), and a masked but non-cleavable antibody (Antibody 2-10). FIG. 24D is an SDS-PAGE analysis showing the percentage (%) of product cleaved for Antibody 2-14. The percentage of cleavage was calculated based on densometric intensity (cleavage %=lower band/(lower band+upper band). The first lane (left) shows 28% cleavage in plasma, 60% cleavage in kidney, 59% cleavage in liver, and 73% cleavage in spleen. The second lane (middle) shows 39% cleavage in plasma, 54% cleavage in kidney, 77% cleavage in liver, and 72% cleavage in spleen. The third lane (right) shows 35% cleavage in plasma, 64% cleavage in kidney, 75% cleavage in liver, and 69% cleavage in spleen. The arrows indicate which samples were utilized to assess binding to CTLA4, with results shown in FIG. 24E. FIG. 24E shows binding between each antibody and CTLA4, where each antibody was isolated from plasma, kidney, liver, or spleen following administration to MB49-bearing B-hCTLA4 transgenic mice. As shown in FIG. 24E, the non-cleavable masked Antibody 2-10 demonstrated reduced binding as compared to the unmasked parental Antibody 2-6, while the cleavable masked Antibody 2-14 demonstrated binding comparable to Antibody 2-6 in liver and spleen and greater binding than Antibody 2-10 in plasma, kidney, liver, and spleen. Antibody 2-16 demonstrated stronger binding compared to Antibody 2-10 in kidney, liver, and spleen. FIG. 24F depicts a heat map of the in vitro cleavage of cleavable peptide substrates by a panel of exemplary proteases.

Studies testing ex vivo cleavage of Antibody 2-14, Antibody 2-15, Antibody 2-10, Antibody 2-16, and Antibody 1334 in cyno organs and plasma by using a CTLA4 ELISA assay is summarized as follows. Antibody 2-14 demonstrated a high percentage of cleavage in the lung (88%), bladder (37%), and colon (36%). Antibody 2-16 demonstrated a moderate percentage of cleavage in the lung (30%) and spleen (15%). Antibody 1334 demonstrated a moderate percentage of cleavage in the lung (22%). Antibody 2-14 demonstrated a low percentage of cleavage in the plasma (4%). There was an absence of cleavage detected for Antibody 2-16 in the plasma. Antibody 1334 demonstrated a low percentage of cleavage in the plasma (5%).

Results for the studies testing ex vivo cleavage of certain antibodies (e.g., Antibody 2-14, Antibody 2-15, Antibody 2-10, Antibody 2-16, and Antibody 1334) in murine tumor, tissue, and plasma was assessed using a CTLA4 ELISA assay are shown in FIGS. 25A-25F for C57/B16-wt, MC38-wt, MC38-hCTLA4, M49-wt, MCA205-wt, and B16 mice. The percentage of cleaved molecules as calculated by the ELISA assay is summarized in Table 17.

TABLE 17

| | | Percentage (%) cleaved molecule. | | | | |
|---|---|---|---|---|---|---|
| Murine model | Tissue | Antibody 2-14 | Antibody 2-15 | Antibody 2-10 | Antibody 2-16 | Antibody 1334 |
| C57/B16-wt | Spleen (n = 9) | 3% | 2% | 2% | 3% | 4% |
| | Liver (n = 9) | 2% | 2% | 3% | 2% | 2% |
| | Kidney (n = 9) | 7% | 4% | 3% | 2% | 40% |
| | Plasma (n = 2) | 6% | 3% | 5% | 19% | 0% |
| MC38-wt | Tumor (n = 9) | 1% | | 0% | 4% | |
| | Spleen (n = 9) | 4% | | 3% | 0% | |
| | Liver (n = 9) | 2% | | 1% | 5% | |
| | Kidney (n = 9) | 8% | | 1% | 3% | |
| | Plasma (n = 1) | 1% | 0% | 0% | 0% | 0% |
| MC38-hCTLA4 | Tumor (n = 5) | 0% | 0% | 0% | 7% | 1% |
| | Spleen (n = 5) | 7% | 0% | 0% | 6% | 0% |
| | Liver (n = 5) | 2% | 0% | 2% | 2% | 6% |
| | Kidney (n = 5) | 25% | 4% | 3% | 5% | 72% |
| | Plasma (n = 1) | 1% | 0% | 0% | 0% | 30% |
| MB49-wt | Tumor (n = 6) | 1% | 5% | 15% | 2% | 0% |
| | Spleen (n = 6) | 3% | 0% | 0% | 1% | 0% |
| | Liver (n = 6) | 0% | 6% | 7% | 1% | 4% |
| | Kidney (n = 6) | 9% | 2% | 1% | 5% | 84% |
| | Plasma (n = 1) | | | 0% | 4% | |
| MCA205-wt | Tumor (n = 4) | 2% | 2% | 0% | 0% | |
| | Spleen (n = 4) | 0% | 12% | 0% | 2% | |
| | Liver (n = 4) | 0% | 2% | 0% | 0% | |
| | Kidney (n = 4) | 10% | 4% | 1% | 0% | |
| | Plasma (n = 1) | 0% | | 0% | 0% | |
| B16-wt | Tumor (n = 4) | 0% | 0% | 0% | 0% | 1% |
| | Spleen (n = 4) | 2% | 0% | 2% | 1% | 3% |
| | Liver (n = 4) | 2% | 0% | 1% | 1% | 0% |
| | Kidney (n = 4) | 16% | 3% | 3% | 2% | 38% |
| | Plasma (n = 1) | 0% | 0% | 0% | 0% | 1% |

Frequency of cleavage is shown in radar plots as shown in FIGS. 25A-25F. With respect to frequency of cleavage in tumor conditioned media, Antibody 2-14 exhibited 33% frequency in tumor conditioned media of MC38-wt, 17% frequency in tumor conditioned media of MB49-wt, and 25% frequency in tumor conditioned media of MCA205-wt; and Antibody 2-16 exhibited 100% frequency in tumor conditioned media of MC38-wt, 40% frequency in tumor conditioned media of MC38-hCTLA4, and 17% frequency in tumor conditioned media of MB49-wt. With respect to frequency of cleavage in kidney conditioned media, Antibody 2-14 exhibited 100% frequency in kidney conditioned media of MC38-wt, MC38-hCTLA4, MB49-wt, MCA205-wt, and B16-wt; and Antibody 2-16 exhibited 67% frequency in kidney conditioned media of MC38-wt, 80% frequency in kidney conditioned media of MC38-hCTLA4, 17% frequency in kidney conditioned media of MB49-wt, and 100% frequency in kidney conditioned media of B16-wt.

Figure 26A:
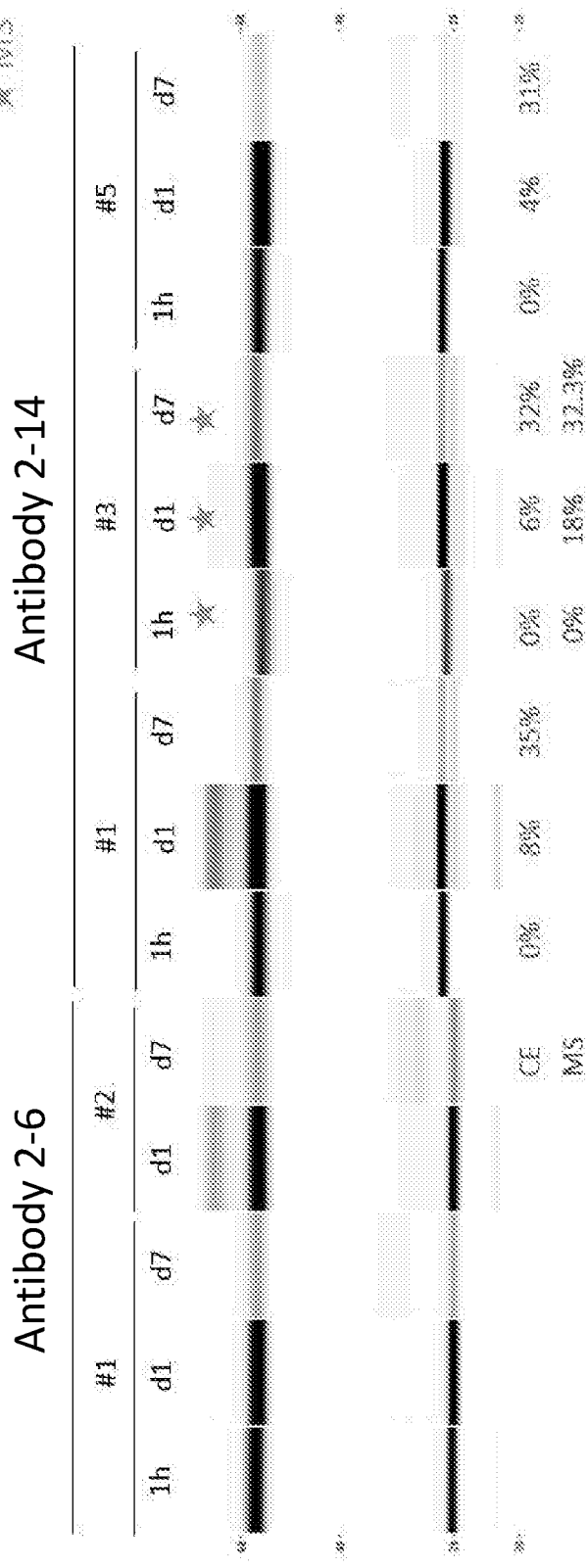
FIGS. 26A and 26B depict the results from in vivo cleavage studies in the plasma of healthy cynomolgus monkeys using Antibody 2-14.
Figure 26B:
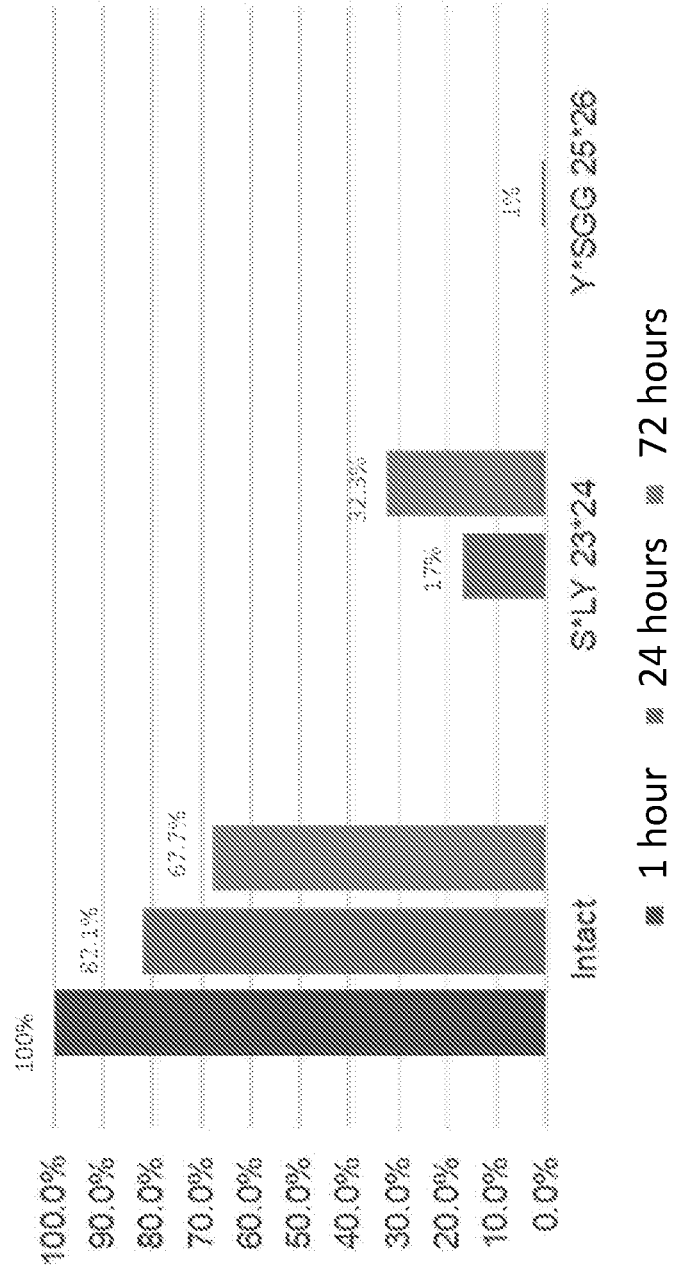

FIGS. 26A and 26B depict the results from in vivo cleavage studies in the plasma of healthy cynomolgus monkeys using Antibody 2-14. As shown in FIG. 26A, cleavage of Antibody 2-14 using capillary electrophoresis (CE) was calculated to be 0% at 1 hour for all three subjects, 8% at day 1 for subject #1, 6% at day 1 for subject #3, and 4% at day 1 for subject #5; and 35% at day 7 for subject #1, 32% at day 7 for subject #3, and 31% at day 7 for subject #5. Cleavage of Antibody 2-14 was also calculated using mass spectrometry (MS) for subject #3, which was calculated to be 0% at 1 hour, 18% at day 1, and 32.3% at day 7. The abundance of the intact (i.e., uncleaved) Antibody 2-14 as well as cleavage products at the expected cleavage site of (VPLSLY) or at another site (VPLSLYSGG) were quantified. The intact Antibody 2-14 was calculated to be at 100% abundance at 1 hour, 82.1% at 24 hours, and at 67.7% at 72 hours: the cleavage product VPLSLY was calculated to be at 0% abundance at 1 hour, 17% at 24 hours, and 32.3% abundance at 72 hours; and the cleavage product VPLSLYSGG was calculated to be at 0% abundance at 1 hour and 72 hours, and at 1% at 24 hours.

Figure 26C:
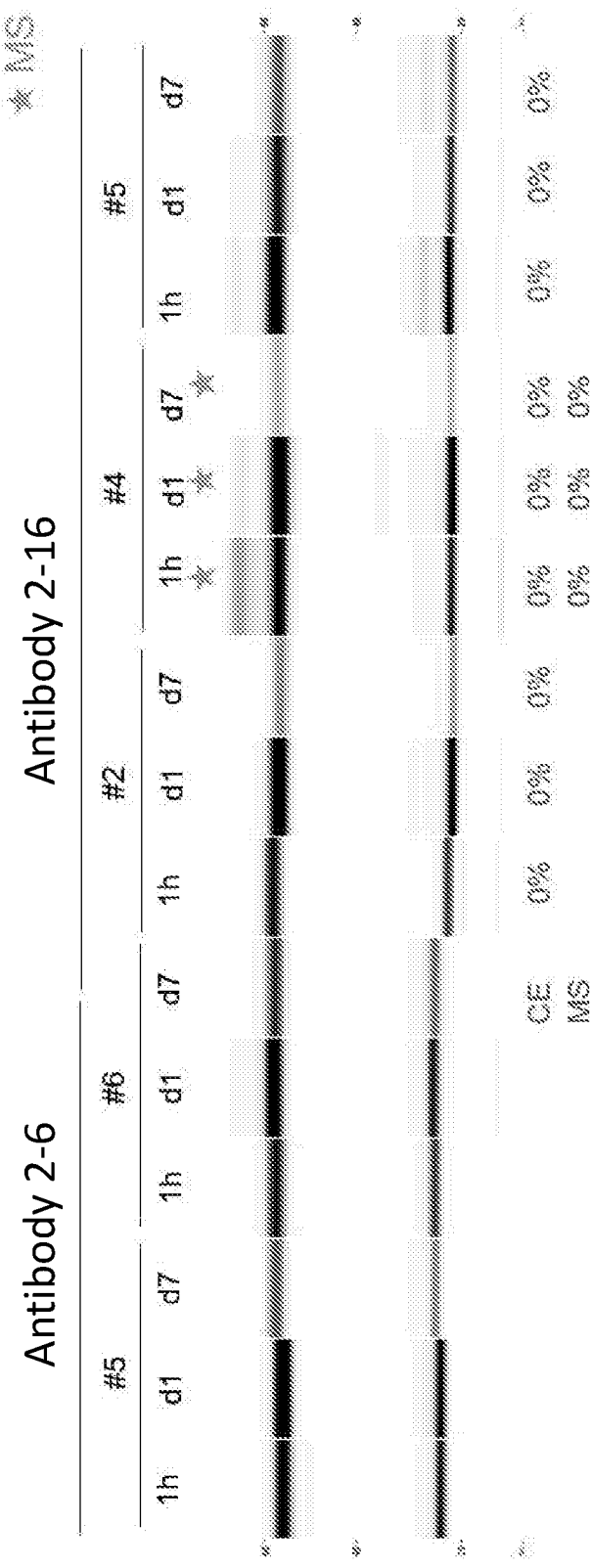
FIG. 26C depict the results from in vivo cleavage studies in the plasma of healthy cynomolgus monkeys using Antibody 2-16, including assessment of cleavage calculated using capillary electrophoresis (CE) and mass spectrometry (MS), as indicated.

FIG. 26C depicts the results from in vivo cleavage studies in the plasma of healthy cynomolgus monkeys using Antibody 2-16. As shown in FIG. 26C, no cleavage was identified for Antibody 2-16 using CE or MS under the conditions tested. The abundance of the intact (i.e., uncleaved) Antibody 2-16 was calculated to be at 100% abundance at 1 hour, 24 hours, and at 72 hours.

Figure 27A:
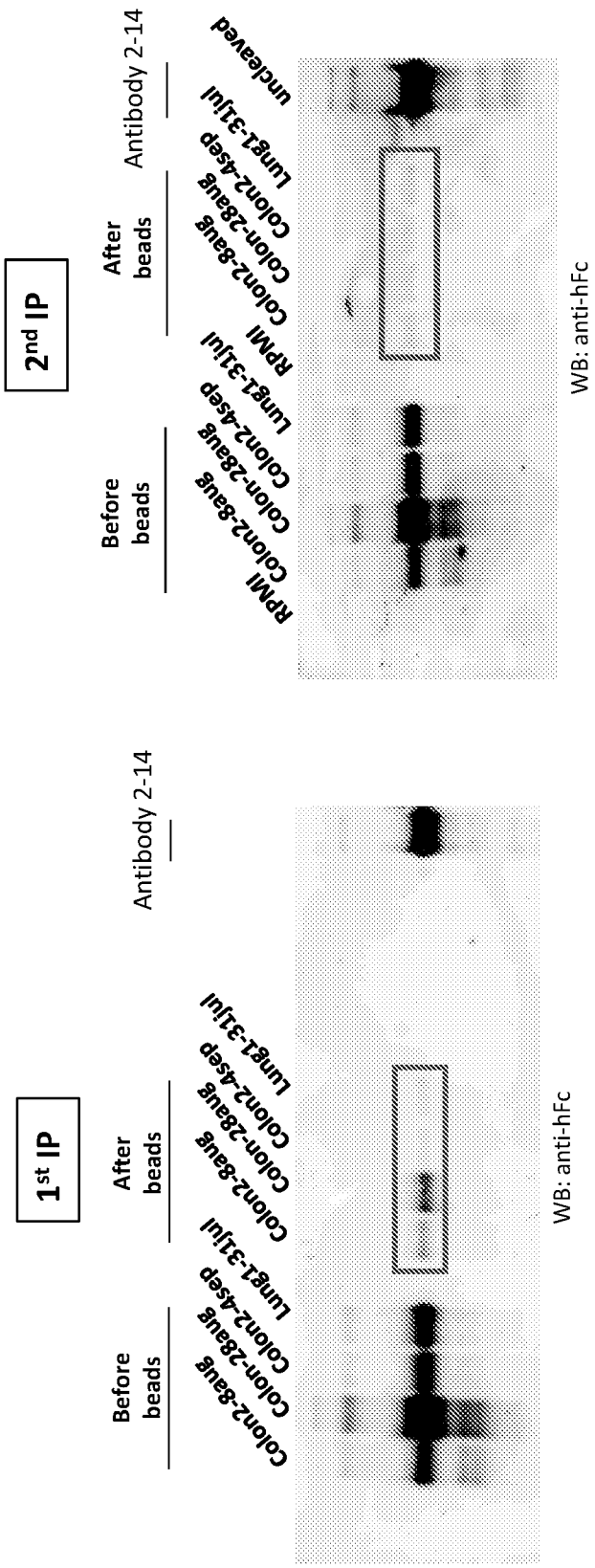
FIGS. 27A and 27B depict the results from ex vivo cleavage studies using media conditioned with human lung or colon tumor samples.
Figure 27B:
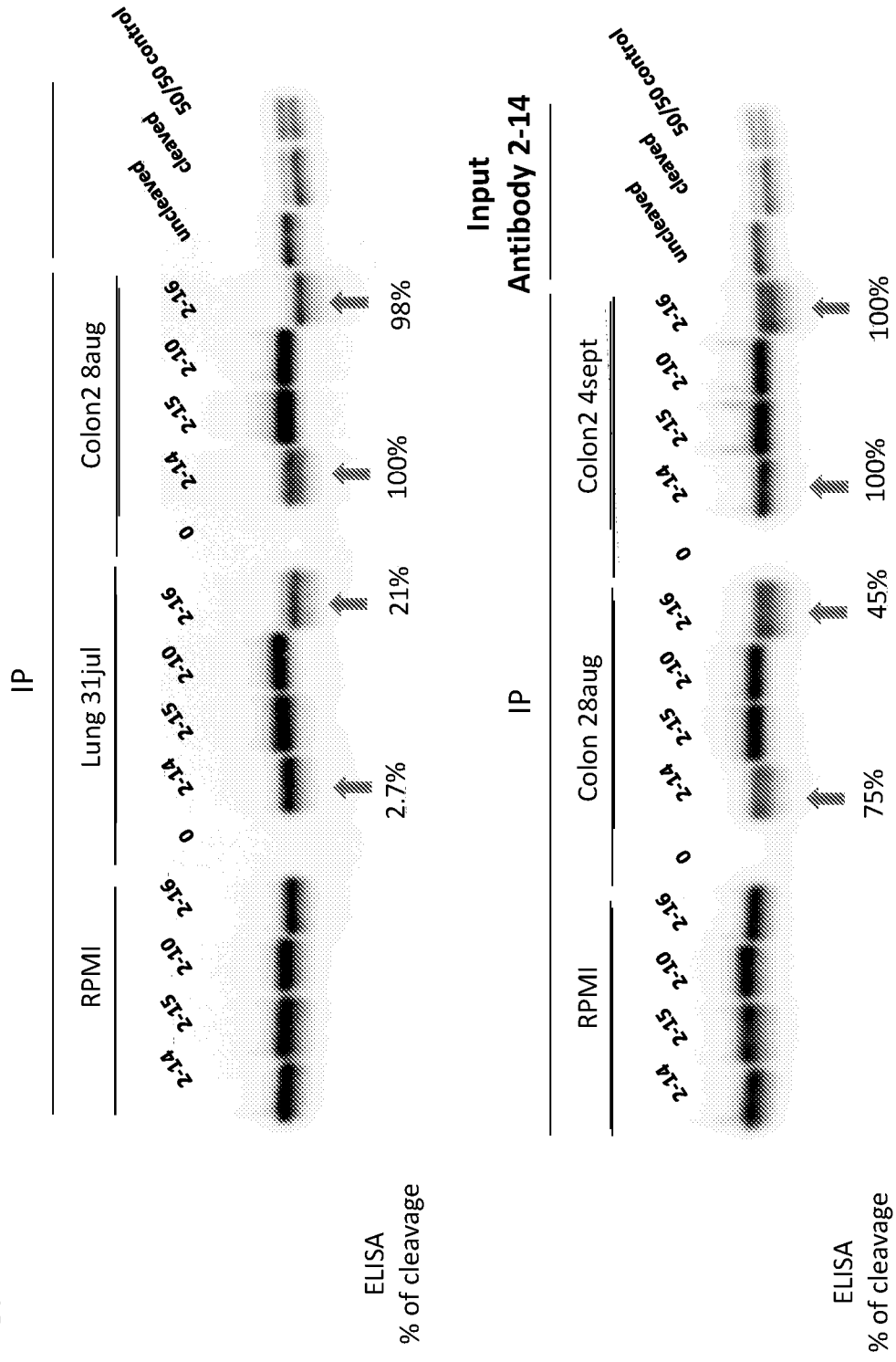

FIGS. 27A and 27B depict the results from ex vivo cleavage studies using media conditioned with human lung or colon tumor samples. FIG. 27A depicts SDS-PAGE analysis showing the removal of human IgG, thereby allowing for cleavage analysis, by performing two rounds of immunoprecipitation (IP). FIG. 27B depicts the results from SDS-PAGE analysis showing the presence of tested antibodies in a cleaved state, uncleaved state, or both states, following incubation in media conditioned with the human tumor sample. Results using ELISA assays (see FIG. 28E) were also calculated with the percentage (%) of cleavage shown for select samples depicting cleavage. As shown in FIG. 27B, Antibody 2-14 was shown to exhibit cleavage in the tumor samples, and was calculated to exhibit 2.7% of cleavage with the lung tumor sample, 100% of cleavage with the colon2 8aug colon tumor sample, 75% of cleavage for the colon 28aug colon tumor sample, and 100% of cleavage for the colon2 4sept colon tumor sample. As shown in FIG. 27B, Antibody 2-16 was shown to exhibit cleavage in the tumor samples, and was calculated to exhibit 21% of cleavage with the lung tumor sample, 98% of cleavage with the colon2 8aug colon tumor sample, 45% of cleavage for the colon 28aug colon tumor sample, and 100% of cleavage for the colon2 4sept colon tumor sample. This demonstrates that results from the ELISA binding assay correlated with cleavage as shown in the SDS-PAGE analysis for Antibody 2-14 and Antibody 2-16.

Figure 28A:
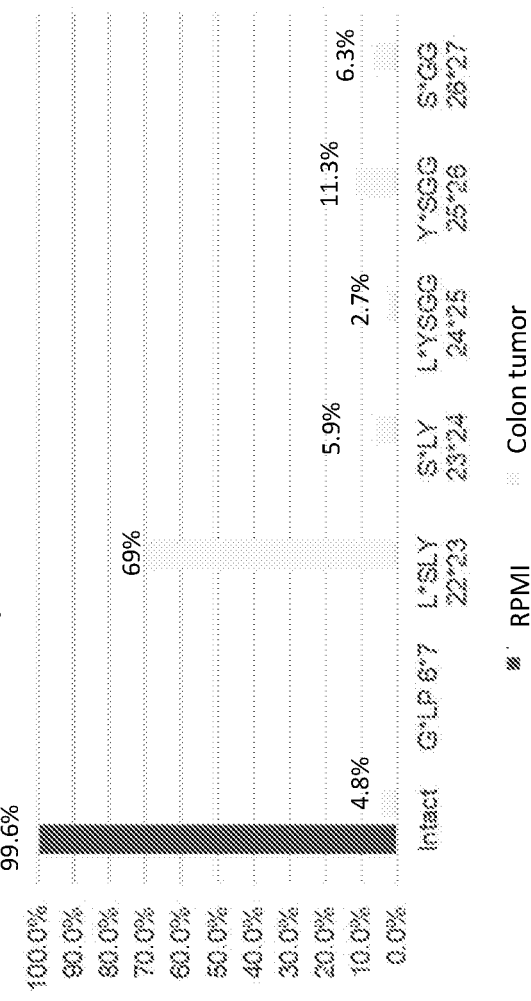
FIGS. 28A-28D depict the results from an analysis of the percentage (%) of the molecule cleaved (Antibody 2-14, FIG. 28A: Antibody 2-15, FIG. 28B: Antibody 2-16, FIG. 28C: Antibody 2-10, FIG. 28D) using mass spectrometry with colon tumor supernatant.
Figure 28B:
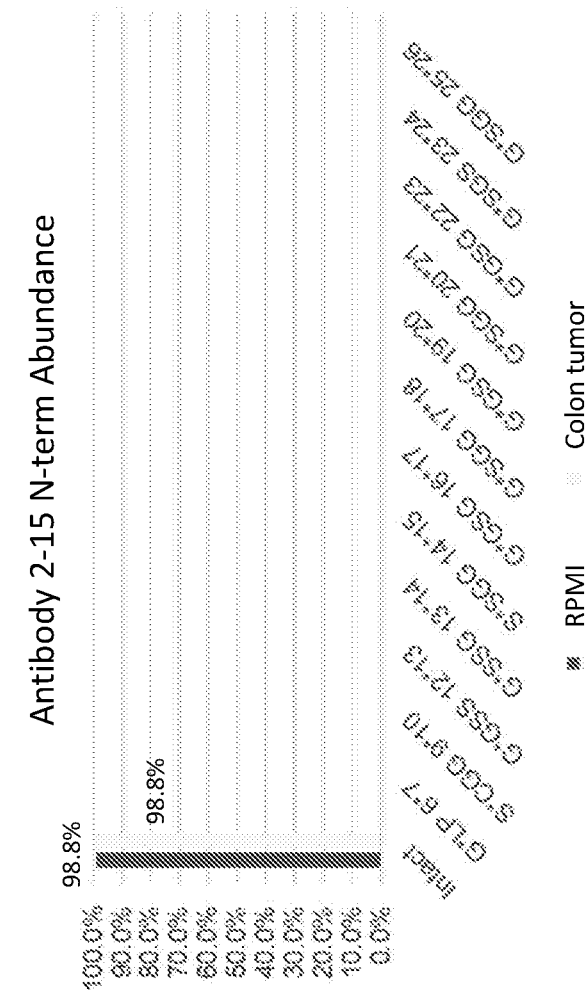
Figure 28C:
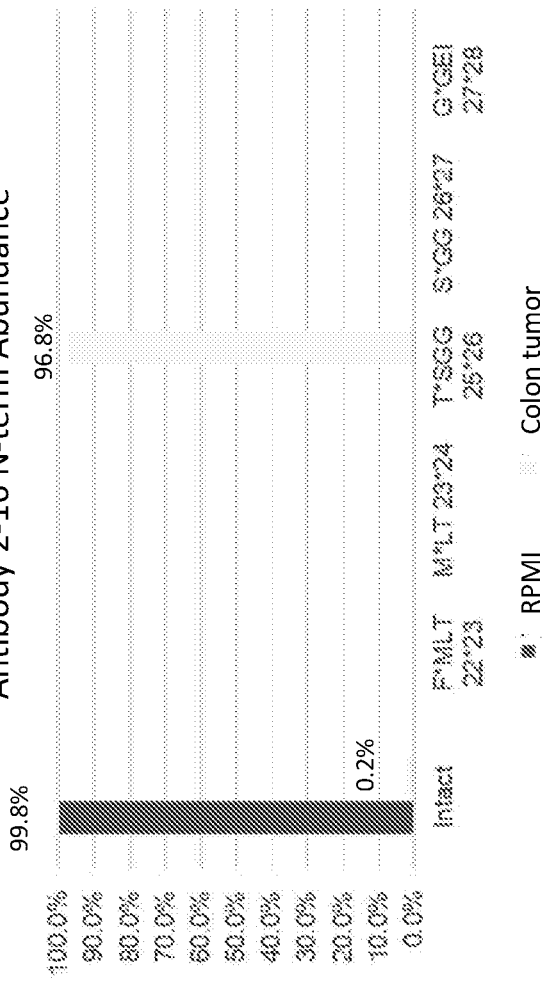
Figure 28D:
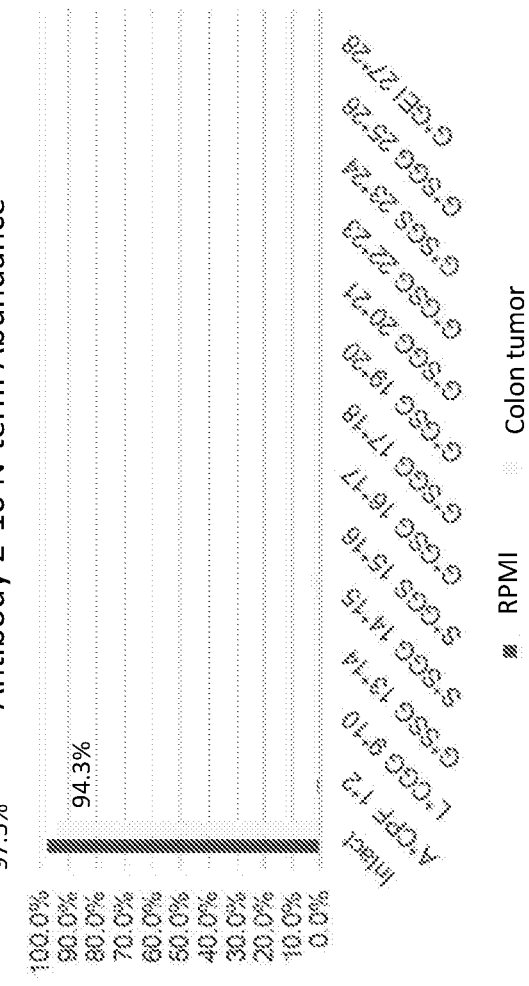

The percentage (%) of the molecule cleaved was also analyzed using mass spectrometry with colon tumor supernatant (colon2 4 sept colon tumor sample) and was compared with ELISA assay results. The abundance of the intact (i.e., uncleaved) antibody as well as cleavage products resulting from cleavage at various sites within the cleavable peptide was calculated. The results are shown in FIGS. 28A-28D. As shown in FIG. 28A, the abundance of intact Antibody 2-14 was 4.8% when cultured in colon tumor conditioned media, as compared to 99.6% abundance when cultured in RPMI as a control. When Antibody 2-14 was cultured in colon tumor conditioned media, the abundance of the L*SLY cleavage product was 69%, the abundance of the S*LY cleavage product was 5.9%, the abundance of the L*YSGG cleavage product was 2.7%, the abundance of the Y*SGG cleavage product was 11.3%, and the abundance of the S*GG cleavage product was 6.3%. As shown in FIG. 28B, the abundance of intact Antibody 2-15 was 98.8% when cultured in either colon tumor conditioned media or RMPI as a control. As shown in FIG. 28C, the abundance of intact Antibody 2-16 was 0.2% when cultured in colon tumor conditioned media, as compared to 99.8% when cultured in RMPI as a control. When Antibody 2-16 was cultured in colon tumor conditioned media, the abundance of the T*SGG cleavage product was 96.8%. As shown in FIG. 28D, the abundance of intact Antibody 2-10 was 94.3% when cultured in colon tumor conditioned media, as compared to 97.5% when cultured in RMPI as a control.

Figure 28E:
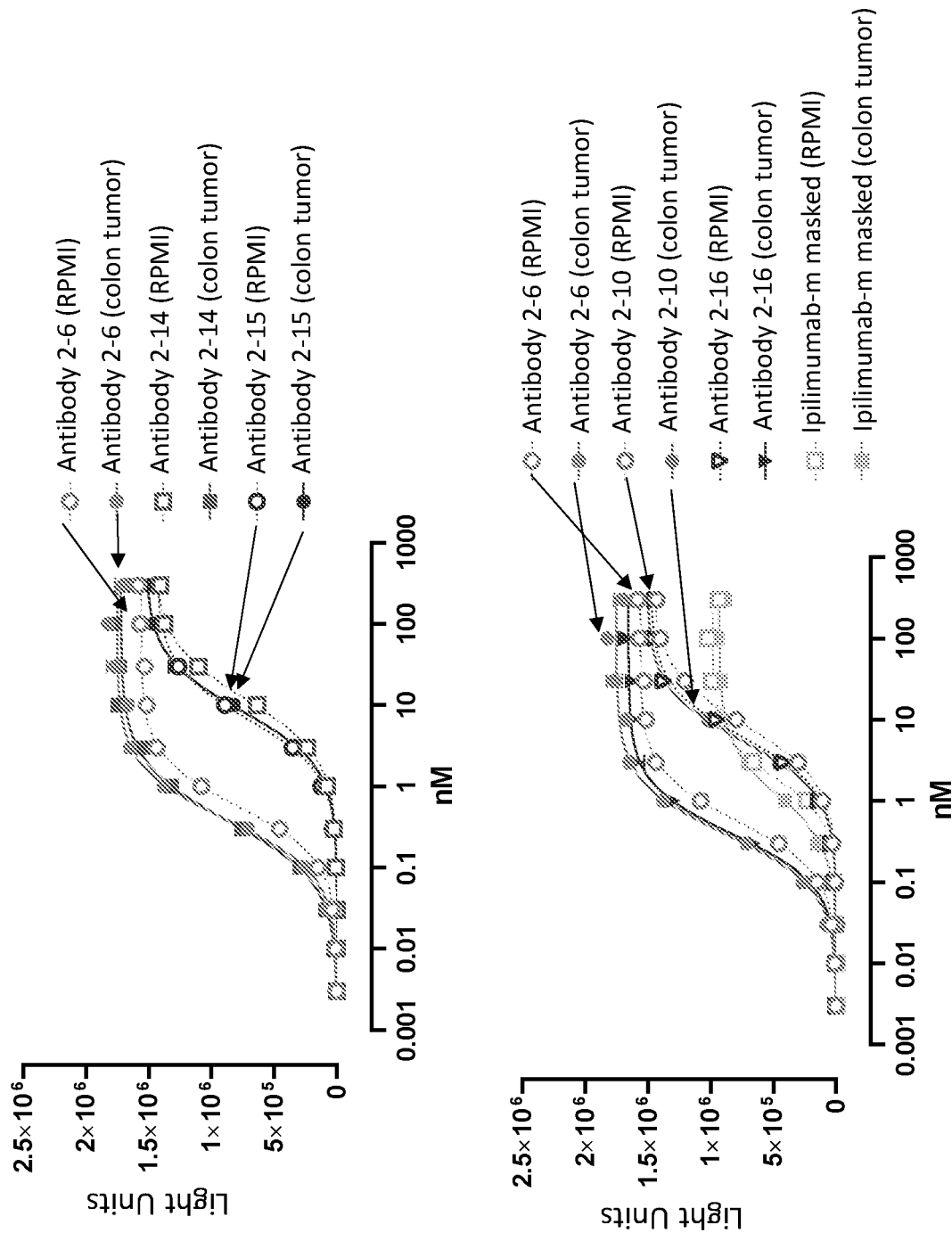
FIG. 28E depicts results from ELISA assays performed using Antibody 2-6, Antibody 2-14, Antibody 2-15, Antibody 2-10, Antibody 2-16, and masked ipilimumab-m, where each tested antibody was cultured in either colon tumor conditioned media (colon2 4 sept colon tumor sample) or in RPMI as a control.

ELISA assays were performed using Antibody 2-6, Antibody 2-14, Antibody 2-15, Antibody 2-10, Antibody 2-16, and a masked version of ipilimumab containing S239D and I332E mutations in the Fc domain (masked ipilimumab-m), where each tested antibody was cultured in either colon tumor conditioned media (colon2 4 sept colon tumor sample) or in RPMI as a control. The results are shown in FIG. 28E. Antibody 2-14 was calculated to exhibit 100% of molecules cleaved, Antibody 2-15 was calculated to exhibit 0% of molecules cleaved, Antibody 2-10 was calculated to exhibit 4% of molecules cleaved, and Antibody 2-16 was calculated to exhibit 100% of molecules cleaved.

The MS data shown in FIGS. 28A-28D correlates with the ELISA data for the percentage (%) of cleaved molecules. For Antibody 2-14, ELISA analysis showed 100% of cleavage with this colon tumor sample, as compared to 95.2% based on MS data. For Antibody 2-15, ELISA analysis showed 0% of cleavage with this colon tumor sample, as compared to 1.2% based on MS data. For Antibody 2-10, ELISA analysis showed 4% of cleavage with this colon tumor sample, as compared to 5.7% based on MS data. For Antibody 2-16, ELISA analysis showed 100% of cleavage with this colon tumor sample, as compared to 99.8% based on MS data.

Anti-CTLA4 ELISA analyses were performed using human tumor tissue and normal tissue adjacent to tumor tissue (NAT) obtained from the Cooperative Human Tissue Network (CHTN). The antibodies tested include Antibody 2-14, Antibody 2-16, and Antibody 1334. Table 18 summarizes the results. As shown in Table 18, the overall frequency of cleavage by human tumor tissue is higher for Antibody 2-14 (65%) than Antibody 2-16 (22%). The percentage of molecule cleaved by the tumor is slightly higher for Antibody 2-16 (26%) than Antibody 2-14 (22%). The overall percentage of molecule cleaved by the NAT is higher for Antibody 2-14 (24%) than Antibody 2-16 (7%).

TABLE 18

| Antibody | Tissue | Frequency of cleavage | | Percent (%) of cleavage | |
|---|---|---|---|---|---|
| | | NAT | Tumor | NAT | Tumor |
| Antibody 2-14 | Melanoma | 1/1 | 3/3 | 100% | 18% |
| | Renal cell | 19/25 | 15/26 | 10% | 25% |
| | Ovary | 1/1 | 4/9 | 4% | 5% |
| | Bladder | 3/3 | 4/5 | 56% | 7% |
| | Lymph node | | 1/1 | | 2% |
| | Colon | 8/8 | 7/7 | 34% | 46% |
| | Lung | 5/6 | 4/7 | 3% | 4% |
| | Breast | 3/4 | 3/4 | 64% | 37% |
| | Liver | 4/5 | 3/6 | 28% | 2% |
| | Total | 44/53 = 83% | 44/68 = 65% | 24% | 22% |
| Antibody 2-16 | Melanoma | 1/1 | 1/3 | 9% | 1% |
| | Renal cell | 9/25 | 4/26 | 2% | 26% |
| | Ovary | 0/1 | 2/9 | 0% | 5% |
| | Bladder | 0/3 | 0/5 | 0% | 0% |
| | Lymph node | | 0/1 | | 0% |
| | Colon | 3/8 | 5/7 | 3% | 50% |

TABLE 18-continued

| Antibody | Tissue | Frequency of cleavage | | Percent (%) of cleavage | |
|---|---|---|---|---|---|
| | | NAT | Tumor | NAT | Tumor |
| | Lung | 1/6 | 1/7 | 2% | 21% |
| | Breast | 1/4 | 1/4 | 5% | 6% |
| | Liver | 1/5 | 1/6 | 71% | 2% |
| | Total | 16/53 = 30% | 15/68 = 22% | 7% | 26% |
| Antibody 1334 | Melanoma | 1/1 | 2/3 | 32% | 4% |
| | Renal cell | 16/24 | 17/25 | 8% | 15% |
| | Ovary | 1/1 | 3/9 | 5% | 6% |
| | Bladder | 2/3 | 4/5 | 57% | 8% |
| | Lymph node | | 1/1 | | 14% |
| | Colon | 2/6 | 4/6 | 41% | 39% |
| | Lung | 1/6 | 1/7 | 18% | 6% |
| | Breast | 2/4 | 2/3 | 20% | 11% |
| | Liver | 4/5 | 2/6 | 28% | 4% |
| | Total | 26/50 = 52% | 33/65 = 51% | 18% | 14% |

Example 17: Enzymatic and Proteomic Profiling of MC38 and H228 Cell Lines with Patient Tumor and Normal Adjacent Tissue (NAT)

Total protein concentration in the samples was evaluated by bicinchoninic acid (BCA) assay following a standard protocol (Thermo Scientific #23225). The concentration of the Tumor/NAT pair samples was ~1 mg/mL, while the concentration of the cell line samples was generally 10× lower. Two of the replicate cell line samples (MC38-1 and H2228-1) were therefore concentrated 10× using a 10 kDa cut-off membrane. Samples were incubated with the AMSP-MS library at a final reaction concentration of 50 µg/mL protein.

A. Cell Cytotoxicity

The activity of Lactate Dehydrogenase (LDH) was measured in conditioned media samples to measure cytotoxicity using the LDH Assay (Thermo Scientific #88953) following the manufacturer's protocol. The background LDH activity was also measured in the serum-free DMEM medium as a control for MC38, and RPMI with or without serum as control for H2228, as well as NAT/Tumor samples. Cell cytotoxicity is expressed relative to that of the corresponding background medium control.

Figure 29:
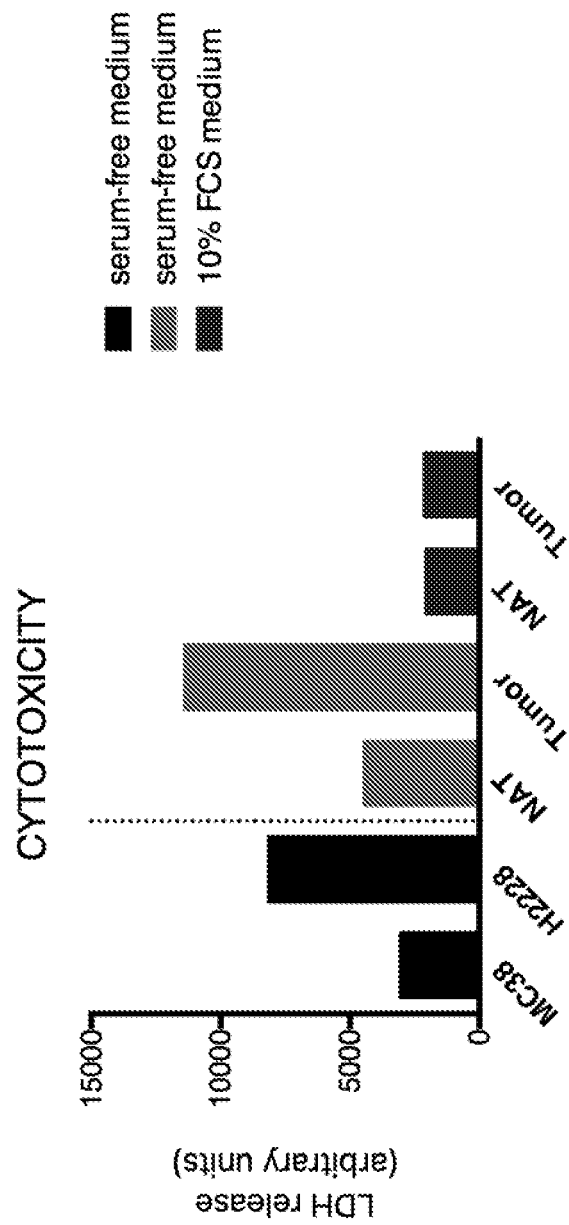
FIG. 29 depicts cell cytotoxicity measured using an LDH release assay completed in serum free or fetal calf serum (FCS) supplemented media conditioned from the indicated cell line or Tumor/NAT tissue.

The activity of LDH in conditioned media samples was used as a proxy for necrosis, as shown in FIG. 29. FIG. 29 shows cell cytotoxicity measured using an LDH release assay completed in serum free or fetal calf serum (FCS) supplemented media conditioned from the indicated cell line or Tumor/NAT tissue. Absorbance values are expressed as a percentage of the baseline activity measured in the corresponding medium for each sample. While MC38 cells had comparable LDH cytotoxicity with previous cell viability data, the H2228 cells had higher than expected cytotoxicity (~2.6 fold over MC38).

The tumor and NAT tissue showed increased cell death when cultured in serum-free medium. The tumor sample was more sensitive to a lack of serum than the NAT sample, potentially reflecting higher growth rates in the tumor sample. As shown in FIG. 29, the tissue samples cultured in complete media had the lowest cytotoxicity levels, compared to either tissue or cultured cell lines in serum-free media.

B. Protease Specificity Profiling

Protease specificity screening was performed with the Alaunus Multiplex Substrate Profiling by Mass Spectrometry (AMSP-MS) method. This method employs a physicochemically diverse peptide library as substrates for proteases, and reactions are monitored over time with mass spectrometric detection of cleaved products. The resulting cleavages are assessed for specific cleavage in the enzyme-treated sample by comparison with results from a no-enzyme control incubation.

For differential analysis of specificity profiles, a matrix of Z-scores was generated with iceLogo software (v.1.2) for each amino acid at each position. These Z-scores calculate how many times the frequency of a particular amino acid is deviated from the mean (i.e. the frequency of that specific amino acid at that specific position in the negative reference set). Differential Z-scores between sample pairs were then used to generate heatmaps in the R environment, using the gplot and RColorBrewer packages.

Time-dependent peptide cleavage products from the AMSP-MS library were identified through LC-MS/MS. The two cell line samples MC38 and H228 each showed a good level of activity against the library. The total number of cleavages observed during the time course was 40 (15 min), 107 (60 min) and 306 (240 min) for MC38; 149 (15 min), 170 (60 min) and 371 (240 min) for H2228. The profile of substrate specificity was extrapolated from the cumulative list of 453 (for MC38) and 690 (for H2228) cleavages observed across the entire time course, and is reported using iceLogo representation in FIG. 30. IceLogo considers both cleaved and uncleaved positions in the peptide library, and is employed to visualize the fold enrichment and de-enrichment of amino acids flanking the cleavage site at (P1-P1'). FIG. 30 shows substrate cleavages for MC38 and H2228 cell lines as an iceLogo graphic. Letter height measures the percent difference in amino acid frequency among cleaved peptides relative to all possible peptide cleavages in the library, plotted at each position P4 to P4'. Residues above the center line are favored: residues below the line are disfavored. Statistically significant residues ($p<0.05$) are colored by physicochemical property (black: hydrophobic; red: acidic, blue: basic, purple: amidic, green: small). Residues in grey were observed at $p>0.05$.

The specificity profile identified here by AMSP-MS shows endopeptidase activity, with a strong preference for hydrophobic and basic amino acids in P1 which is shared by both cell lines. MC38 cells showed a preference for R and Y in P1', as well as additional hydrophobic specificities at P3, P2, and P4'. H2228 cells showed a preference for H, S and Y at P1', as well as additional hydrophobic specificities at P2' and P4'.

C. NAT and Tumor Differential Analysis

Figure 2A:
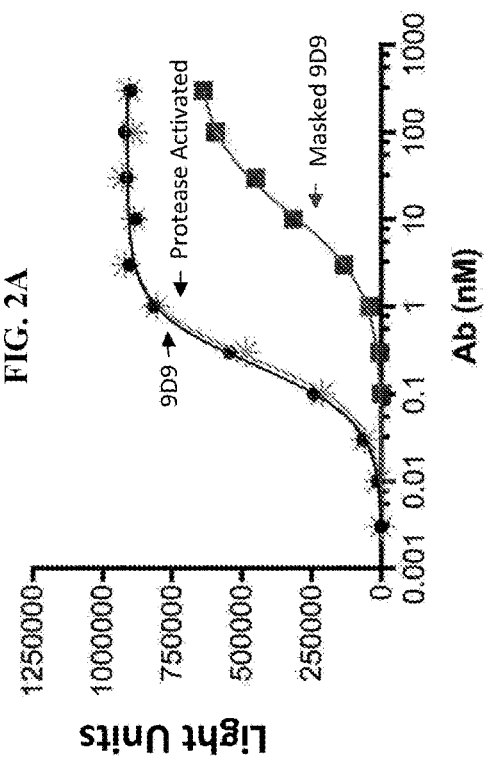
FIGS. 2A-2C is a series of graphs showing protease activation of masked murine anti-CTLA4 antibody.
Figure 2C:
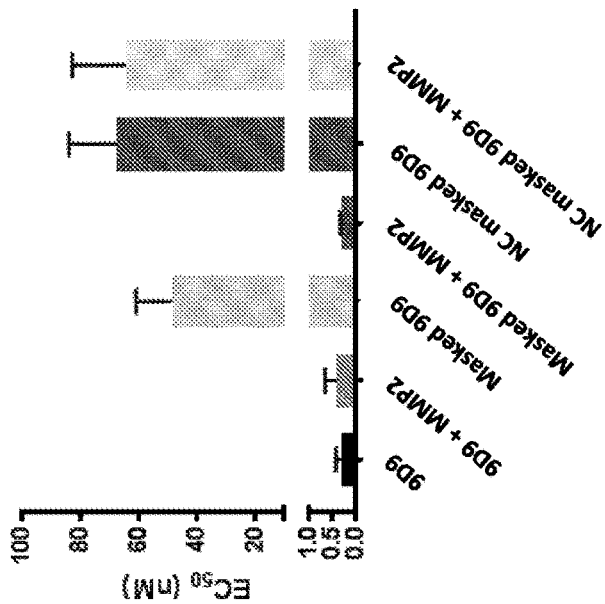
Figure 2B:
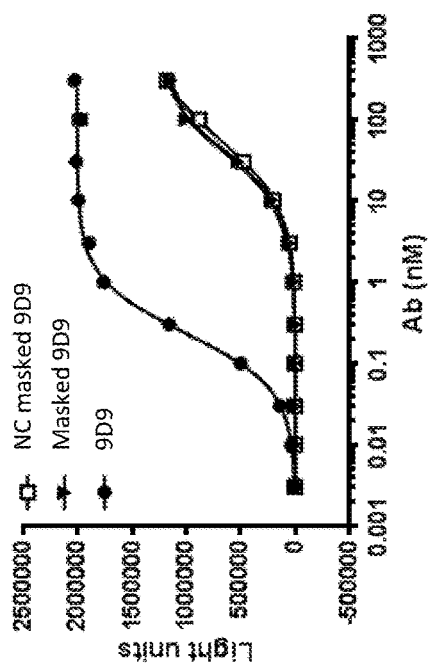
Figure 31A:
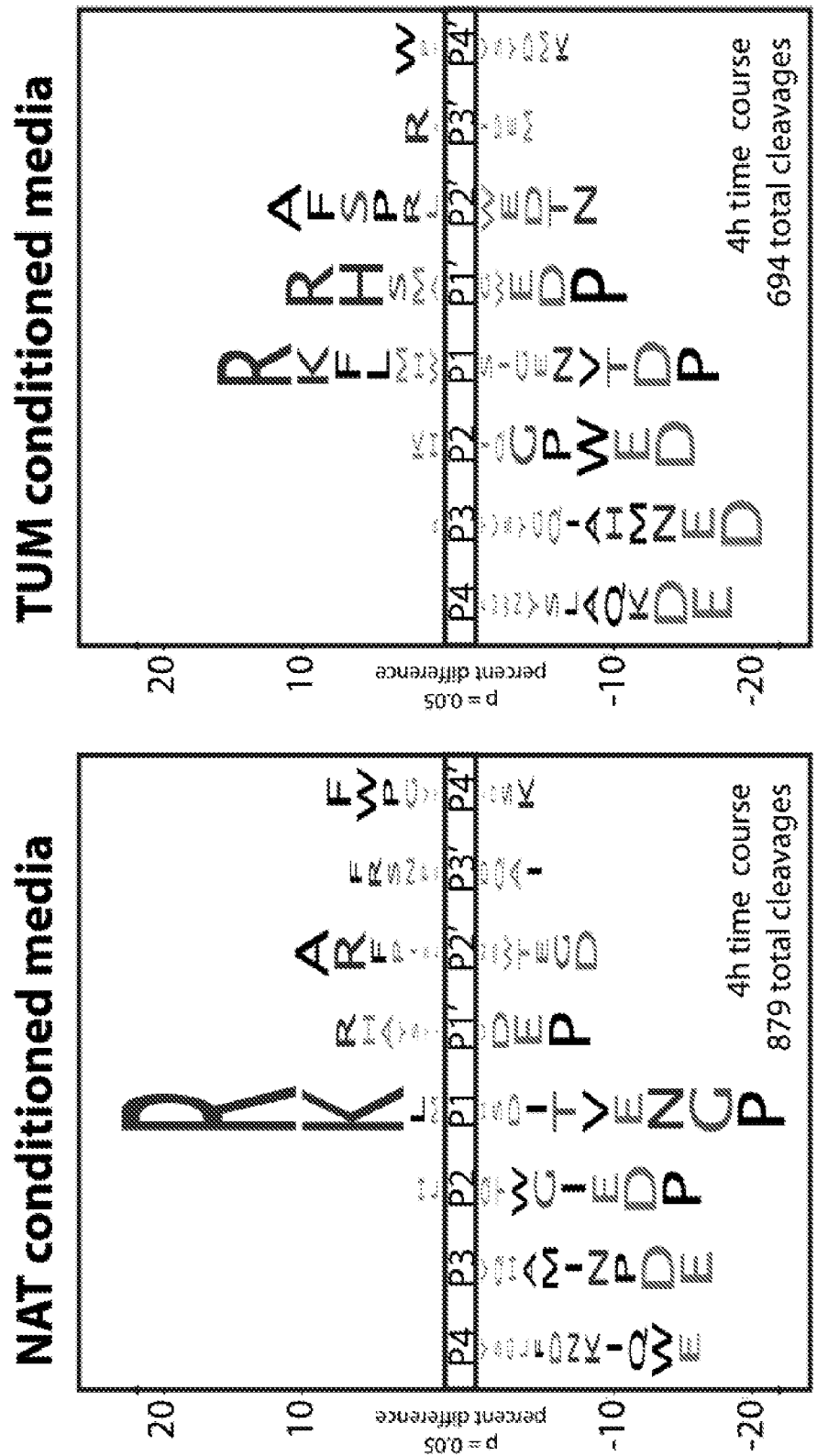
FIGS. 31A and 31B depict substrate cleavages for NAT and Tumor (TUM) tissues as an iceLogo.
Figure 31B:
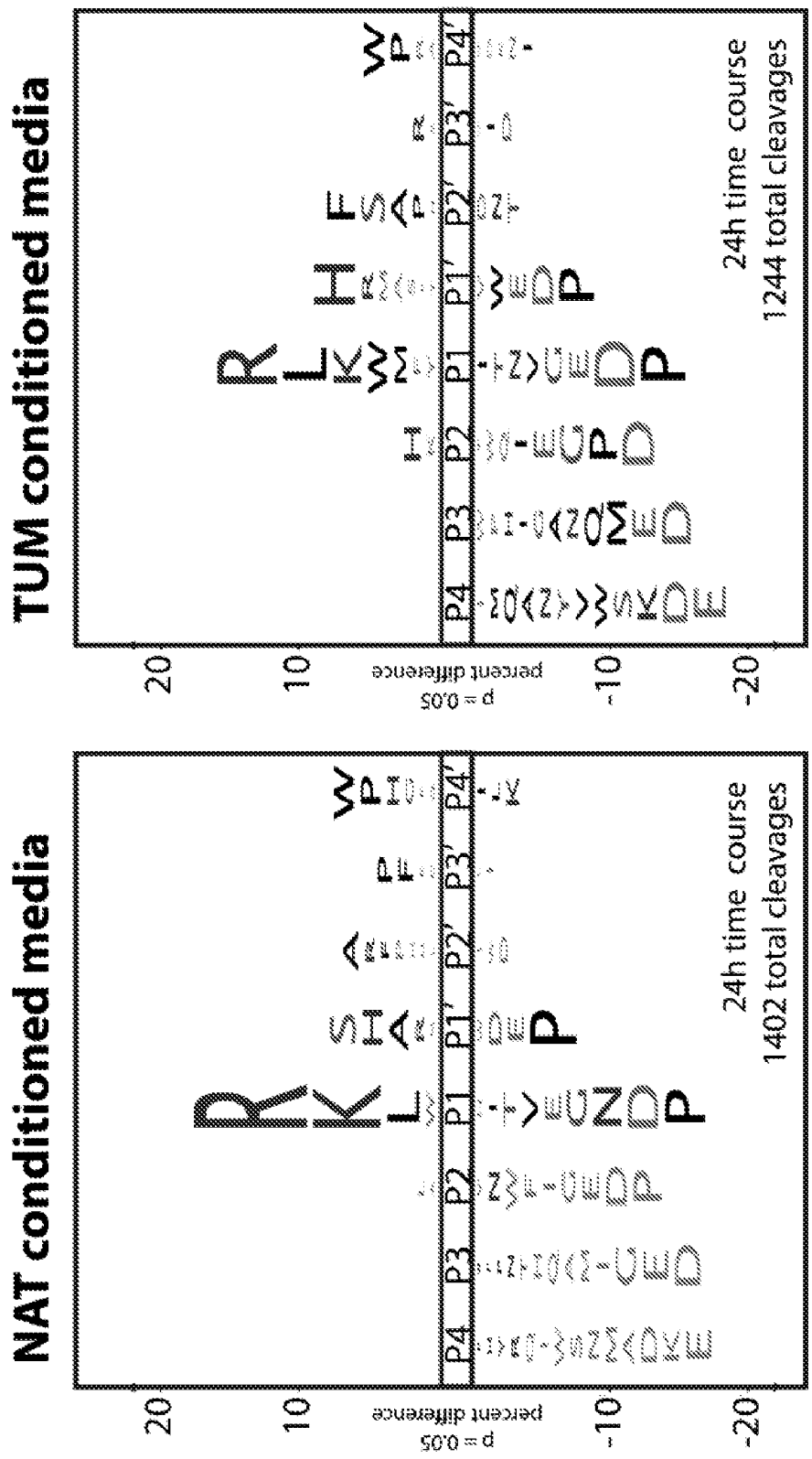

Time-dependent peptide cleavage products from the MSP-MS library were identified as described above in Example 17.B. The two patient tissue samples showed a high level of activity against the library. The total number of cleavages observed during the time course was 134 (15 min), 270 (60 min) and 475 (240 min) for NAT: 63 (15 min), 184 (60 min) and 447 (240 min) for tumor tissue. The profile of substrate specificity was extrapolated from the cumulative list of 879 (for NAT) and 694 (for tumor) cleavages observed across the entire time course, and is reported using iceLogo representation shown in FIG. 31A. As with FIG. 2, FIGS. 31A and 31B shows substrate cleavages for NAT and Tumor (TUM) tissues as an iceLogo.

Additionally, the activity of the two patient samples against the library was monitored at a longer 24 h time point to uncover additional differences in substrate specificities. The cleavages observed at this additional time point were 719 (for NAT) and 636 (for tumor). The profiles for the entire time course (including the 24 h time point) are shown in FIG. 31B. Norleucine (n) is a proxy for Met in the library. The NAT sample showed a strong preference for basic amino acids (mainly R and K) in P1, as well as R, H and S in P1'. The tumor sample showed a preference for both basic (R and K) and hydrophobic amino acids in P1, as well as a strong preference for H in P1'. The tumor sample also showed a preference for hydrophobic amino acids at P2', while both patient samples shared a preference for hydrophobic amino acids at P4'.

Figure 31C:
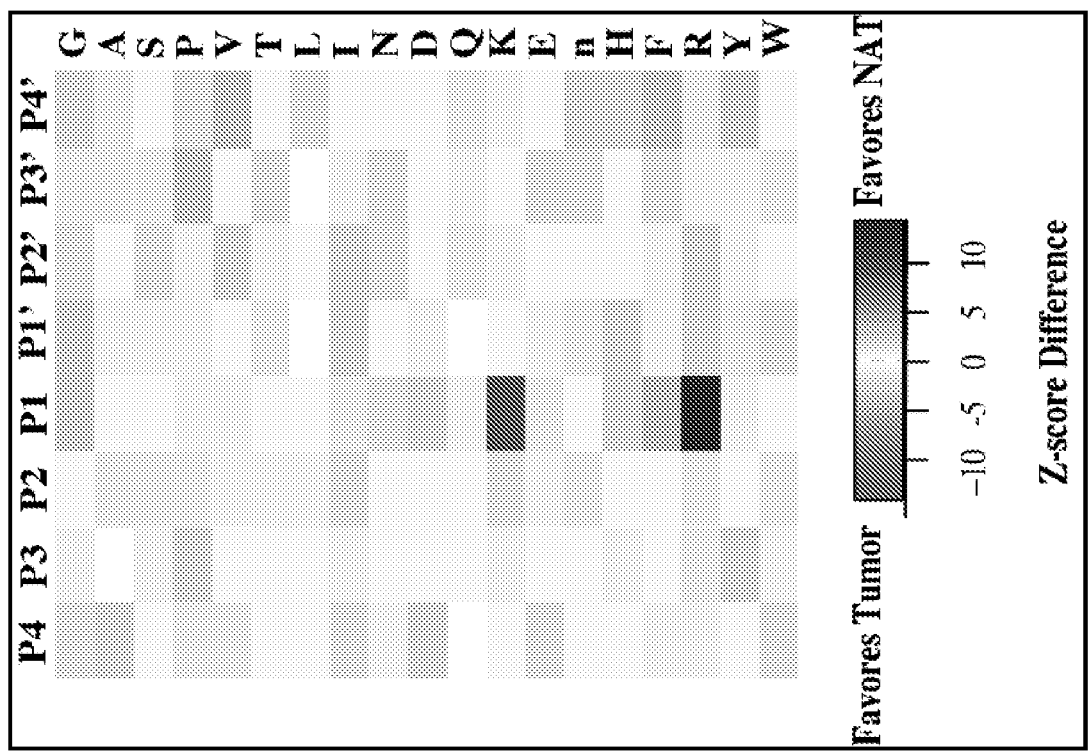
FIG. 31C depicts differences in Z-scores at the P4-P4' positions as a heatmap to highlight residues that are favored in NAT- or Tumor-specific cleavages. Norleucine (n) is a proxy for Met in the library.

To quantify differences in global substrate specificity between NAT and tumor samples, Z-scores from the cleavages in each sample were also used to generate a difference map derived from residue preferences at each subsite as is shown in FIG. 31C. FIG. 31C shows differences in Z-scores at the P4-P4' positions as a heatmap to highlight residues that are favored in NAT- or Tumor-specific cleavages. Norleucine (n) is a proxy for Met in the library. This confirmed the dominant specificity for lysine and arginine at P1 in the NAT sample, as well as highlighting additional minor preferences at other positions especially in the tumor sample (such as G and F in P1).

The inclusion of the cell line H2228 provided an opportunity to compare an immortalized cell line with primary tissue of similar origin in terms of specificity profiles, here Non-Small Cell Lung Carcinoma (NSCLC) was selected. The H2228 cells showed more pronounced differences in specificity with the NAT than the tumor sample. Furthermore, this differential analysis demonstrates some preferences in the H2228 cells when compared to NAT (left panel) that are similar to the profile of tumor tissue similarly compared to NAT, including G, H, and F at P1. Nonetheless, differences in specificity (although less prominent) were detected also between the H2228 cells and the tumor tissue shown in FIG. 31D, providing support for patient heterogeneity in terms of protease activity in the tumor microenvironment. FIG. 31D shows differences in Z-scores at the P4-P4' positions as a heat map to highlight residues that are favored in H2228-specific cleavages, compared to either NAT or tumor samples. Norleucine (n) is a proxy for Met in the library.

D. Kinetic Analysis of Peptide Sequences

Ten sequences (AK10) shown in Table 19 were analyzed via AMSP-MS. These sequences were slightly modified from the original sequences to generate mass spectrometry-compatible peptides (in some cases adding basic residues to add positive charge) and spacing residues (GG) to produce longer ~14-mer peptides. The peptides were prepared at a 500 nM final concentration in the AMSP-MS reaction. The AK10 library was also separately analyzed by LC-MS/MS for chemical validation of the peptide species.

TABLE 19

| Substrate Name | Sequence of Interest | Modified Sequence for Analysis |
|---|---|---|
| AK-01 | ISSGLLSGRSDNH (SEQ ID NO: 464) | KISSGLLSGRSDNH (SEQ ID NO: 470) |
| AK-02 | AVGLLAPPGGLSGRSDNH (SEQ ID NO: 465) | RAVGLLAPPGGLSGRSDNH (SEQ ID NO: 471) |
| AK-03 | VPLSLYSG (SEQ ID NO: 466) | RGGVPLSLYSGGGK (SEQ ID NO: 472) |
| AK-04 | MPYDLYHP (SEQ ID NO: 47) | RGGMPYDLYHPGGK (SEQ ID NO: 473) |
| AK-05 | DSGGFMLT (SEQ ID NO: 50) | RGGDSGGFMLTGGK (SEQ ID NO: 474) |
| AK-06 | HEQLTV (SEQ ID NO: 57) | RGSGHEQLTVGGSK (SEQ ID NO: 475) |
| AK-07 | RAAAVKSP (SEQ ID NO: 72) | GSGRAAAVKSPGSK (SEQ ID NO: 476) |
| AK-08 | RQARVVG (SEQ ID NO: 467) | GSGRQARVVGGGSK (SEQ ID NO: 477) |
| AK-09 | LSGRSNAMPYDLYHP (SEQ ID NO: 468) | N/A (not modified) |
| AK-10 | MPYDLYHPRQARVVG (SEQ ID NO: 469) | N/A (not modified) |

The AMSP-MS analysis was performed under standard substrate specificity profiling conditions, sampling time points during the reaction incubation at 0, 15, 60, 240 and 1200 min. Peptides were quantified by mass spectrometric label-free quantitation from the MSI precursor ion peak areas for each peptide species. Enzyme progress curves were modeled in GraphPad Prism software v 8.0 and data were fitted using non-linear least squares fitting to the first order kinetic equation:

$$Y = e^{(-[K_{obs}]t)}$$

where Y=percent product formation, $K_{obs}$ is the observed rate, and t=time. In Michaelis-Menten kinetics, the observed rate $K_{obs}$ is a function of the enzyme concentration and catalytic efficiency ($k_{cat}/K_M$). In this analysis of an enzyme mixture, $K_{obs}$ was used to rank product cleavages.

To represent the overall picture of the AK10 peptides in an AMSP-MS reaction, the normalized relative abundance of each substrate peptide was plotted over time. The relative abundance of substrate peptides in the AK10 library monitored via AMSP-MS with MC38 serum-free conditioned media. It was observed that for the MC38 serum-free conditioned media reaction, the abundance of each substrate decreased at different rates, due to a combination of enzymatic and non-enzymatic processes such as Met oxidation. To evaluate enzymatic cleavage, product formation analysis was also required.

Figure 32A:
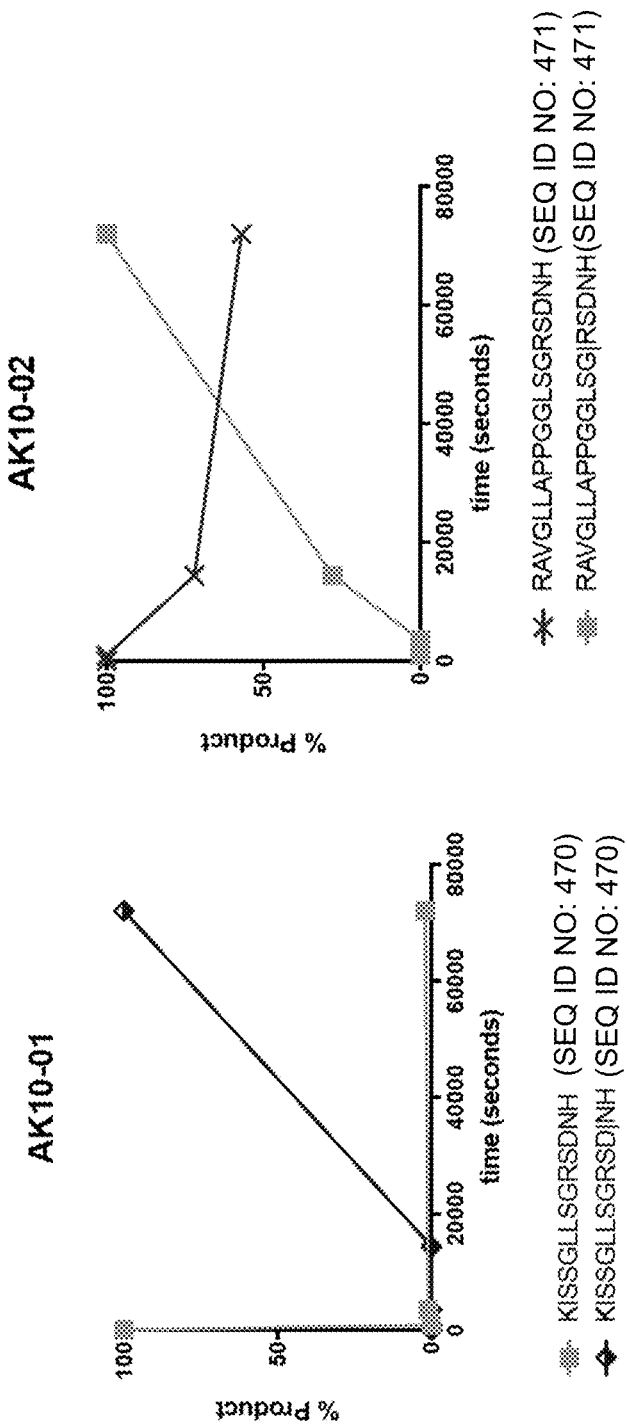

To evaluate whether a substrate is consumed by enzymatic processing, the rate of product formation was assessed for quality of fit to a one-phase decay model that ideally reaches saturation. FIGS. 32A and 32B show the individual progress curves for selected peptides with apparent degradation with the MC38 cell line. FIGS. 32A and 32B shows product formation curves for selected substrates with MC38 conditioned media: AK10-01 (FIG. 32A, left), AK10-02 (FIG. 32A, right); AK10-04 (FIG. 32B, left), and AK10-05 (FIG. 32B, right). In the case of AK10-02, clear product formation is apparent with a very slight curve, whereas the "products" formed from AK10-01, AK10-4 and AK10-05 are examples of unspecific degradation. AK10-01 is essentially linear, AK10-04 was present in the time zero point, and the product of AK10-05 continued to degrade due to chemical processes (some observed by LC-MS/MS).

Figure 33:
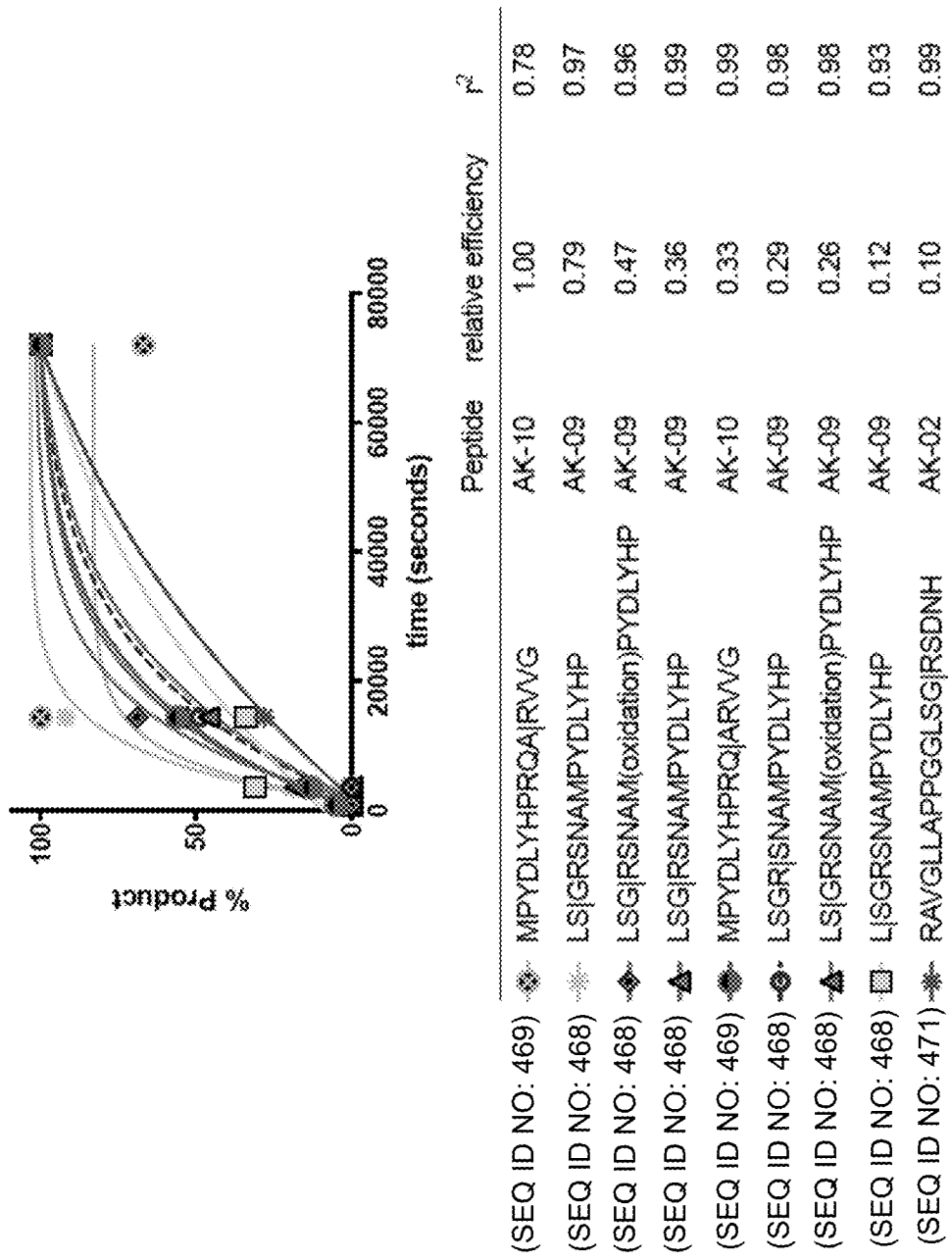
FIG. 33 depicts the relative efficiency of the major cleavage products from the MC38 AMSP-MS reaction with AK10 library peptides.

The best substrates for MC38 were AK-09 and AK-10 wherein multiple cleavage products were observed for these peptides. Their progress curves were fit to a first order kinetic rate, and then the cleavages were ranked by their relative efficiency, as shown in FIG. 33. FIG. 33 shows the relative efficiency of the major cleavage products from the MC38 AMSP-MS reaction with AK10 library peptides. The most rapid cleavage occurred in peptide AK-10 at PRQA|RVVG, where the "|" indicates the scissile bond. In peptide AK-09, multiple cleavages were observed within a narrow fold range of the top most efficient substrate, with cleavages at: LS|GRSNAM, LSG|RSNAM, and LSGR|SNAM. Low efficiency cleavage of AK-02 is also shown.

Figure 34A:
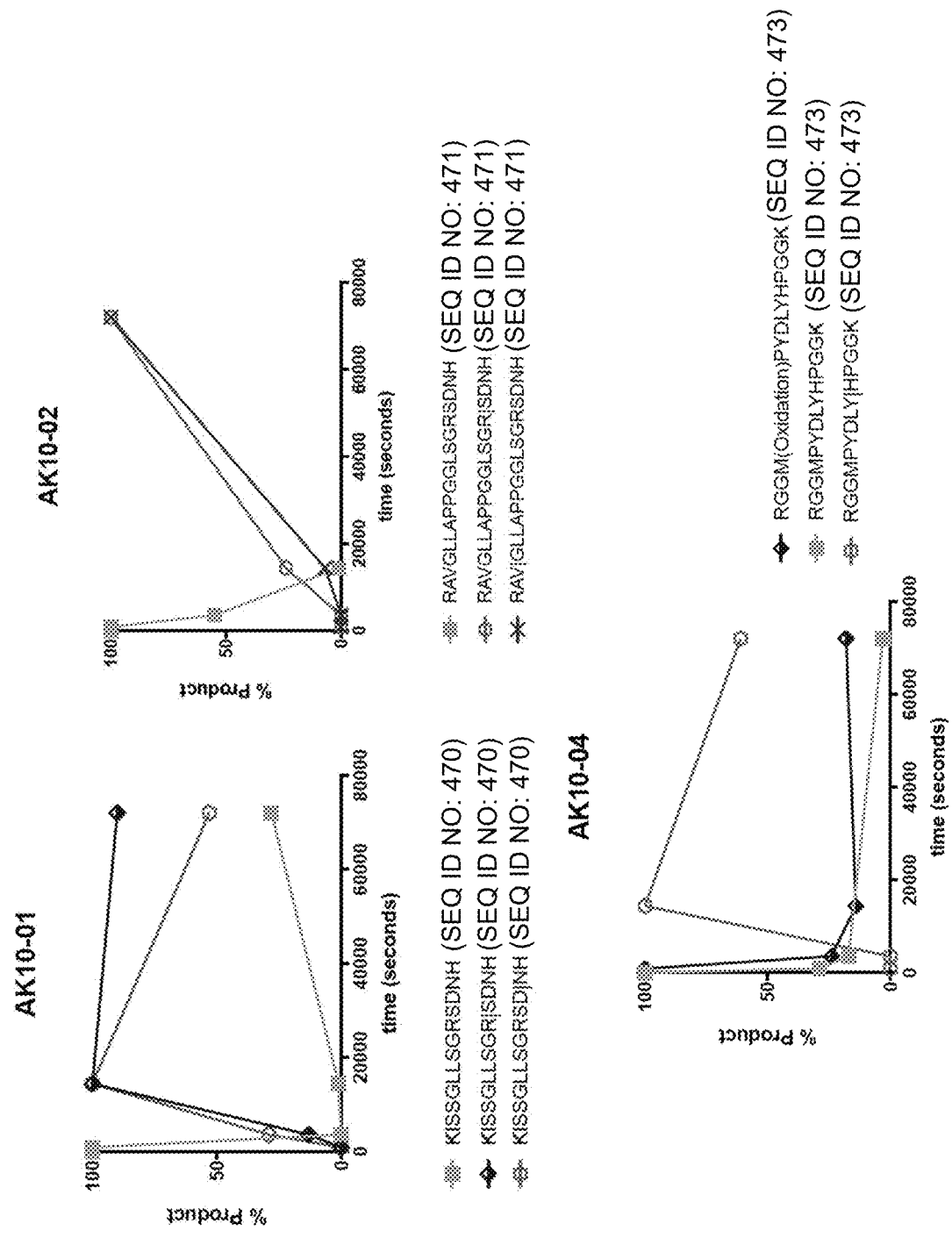
FIGS. 34A and 34B depict product formation curves for selected substrates with H2228 conditioned media: AK10-01 (FIG. 34A, top left), AK10-02 (FIG. 34A, top right), AK10-04 (FIG. 34A, lower), AK10-09 (FIG. 34B, left), and AK10-10 (FIG. 34B, right).
Figure 34B:
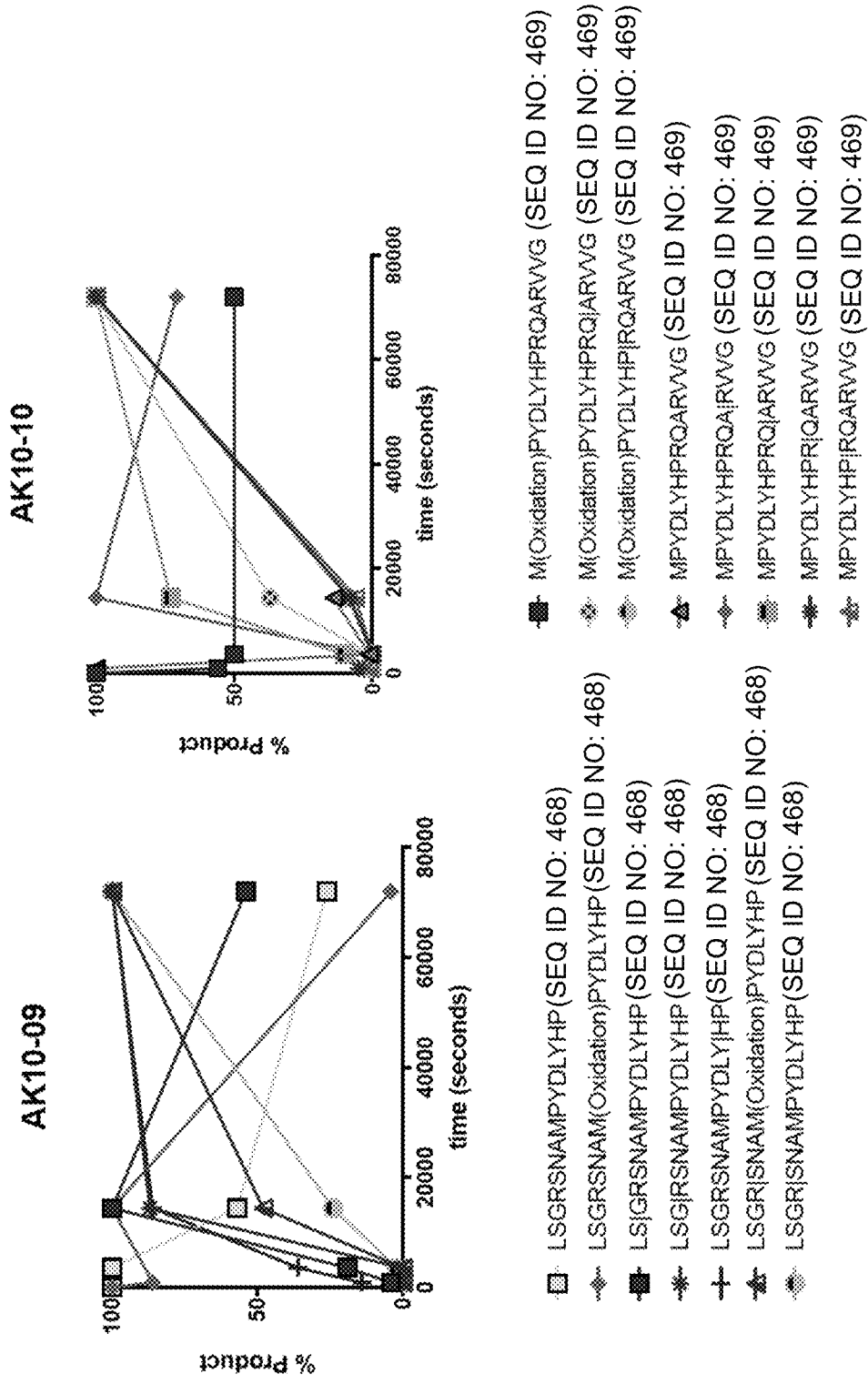
Figure 35:
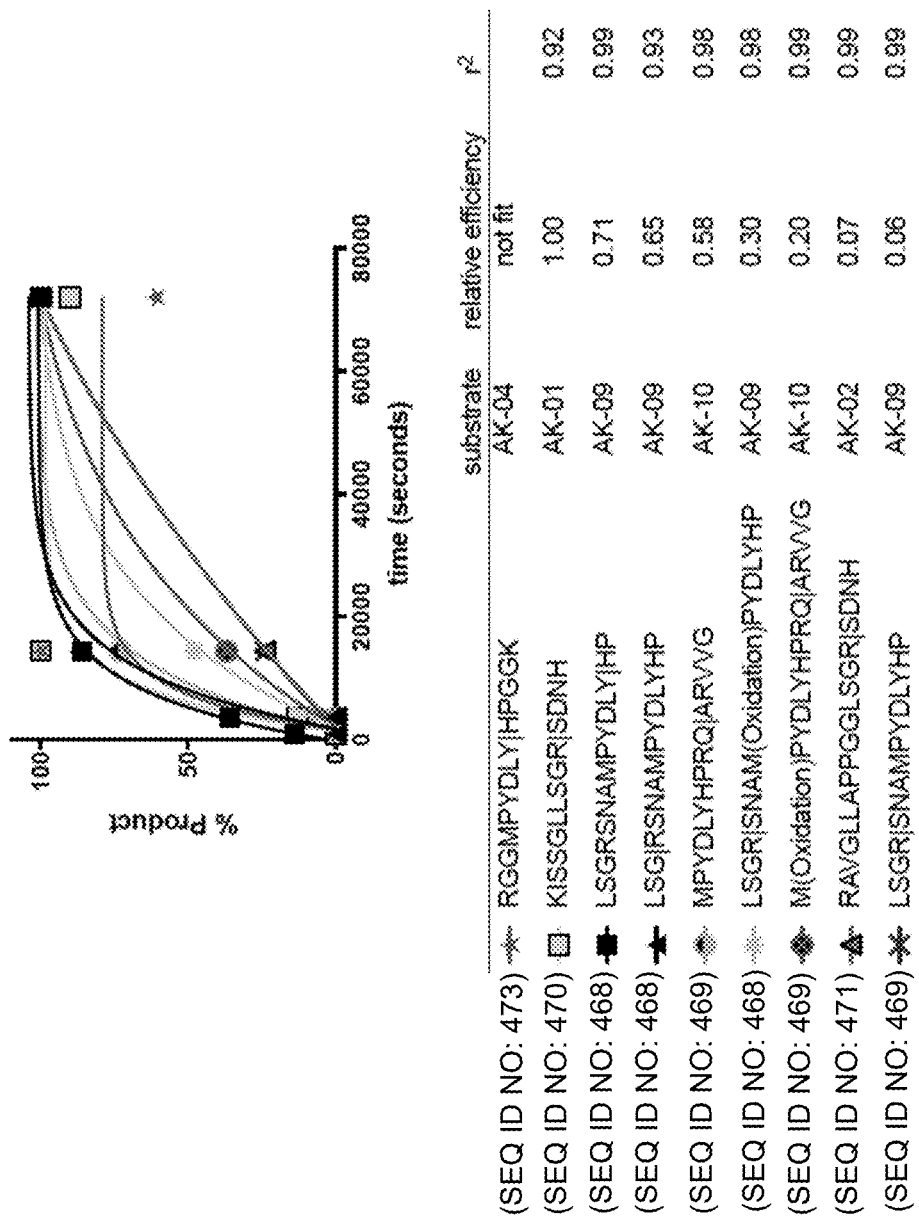
FIG. 35 depicts the top substrates cleaved by H2228 conditioned media monitored via AMSP-MS with their relative efficiencies.

The H2228 cell line produced cleavages in the peptides AK10-01, -02, -04, -09 and -10. Product formation for individual substrates are shown in FIGS. 34A and 34B. FIGS. 34A and 34B shows product formation curves for selected substrates with H2228 conditioned media: AK10-01 (FIG. 34A, top left), AK10-02 (FIG. 34A, top right), AK10-04 (FIG. 34A, lower), AK10-09 (FIG. 34B, left), and AK10-10 (FIG. 34B, right). The top substrates cleaved by H2228 conditioned media are shown in FIG. 35, with relative efficiencies calculated.

The top cleaved substrates in the AK10 library were fit to a first order kinetic rate, and the most efficiently cleaved motifs were: YDLY|HP and LSGR|S. The motif LSGR|S was cleaved in three peptides in the ranked order: AK-01>AK-09>AK-02. The YDLY|HP motif was cleaved in the context of two peptides in the ranked order: AK-04>AK-09. In peptide AK-10, the scissile bond was shifted to HPRQ|AR, but this peptide was still cleaved at within 5× efficiency of the top substrates.

Figure 36A:
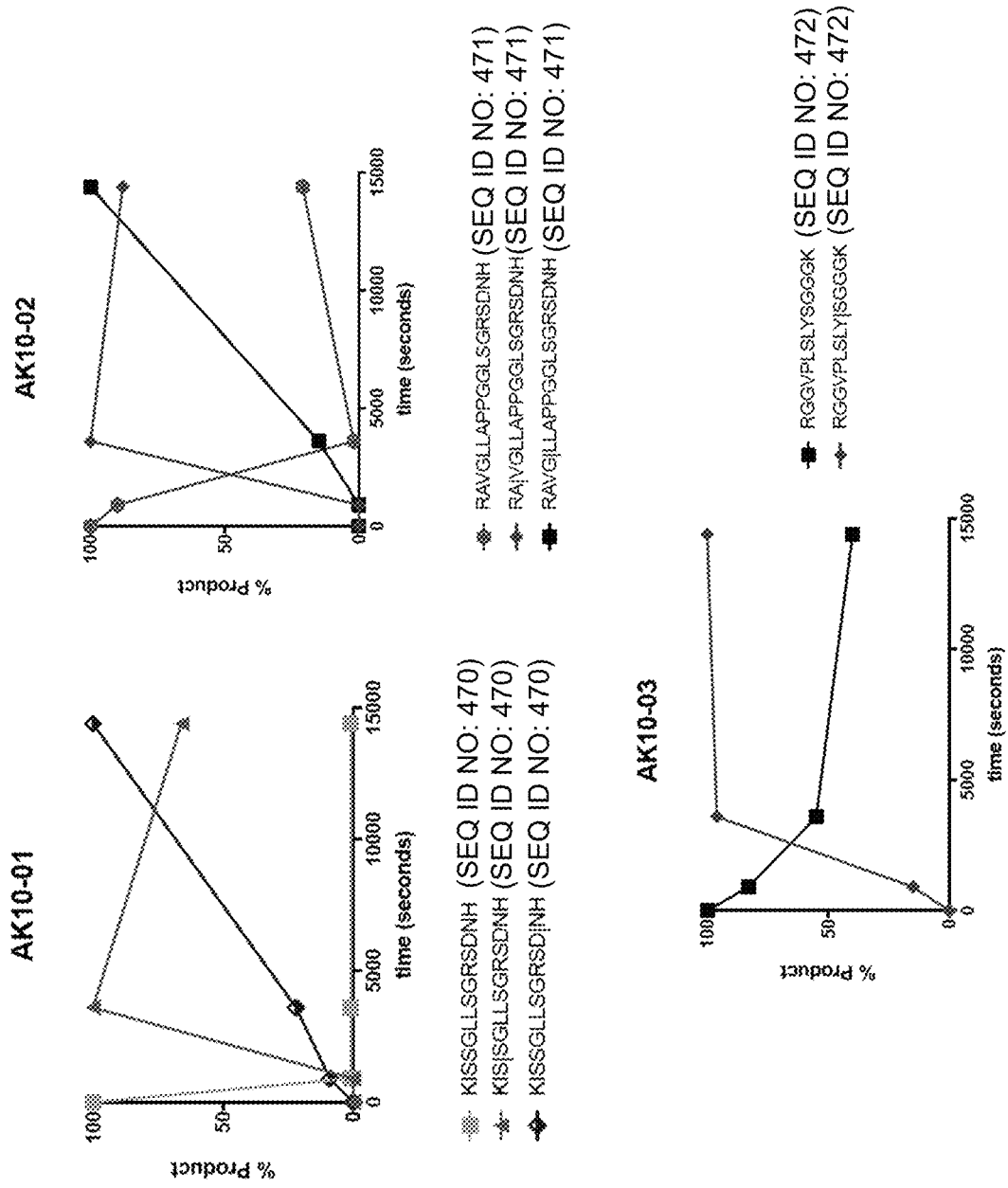
Figure 36C:
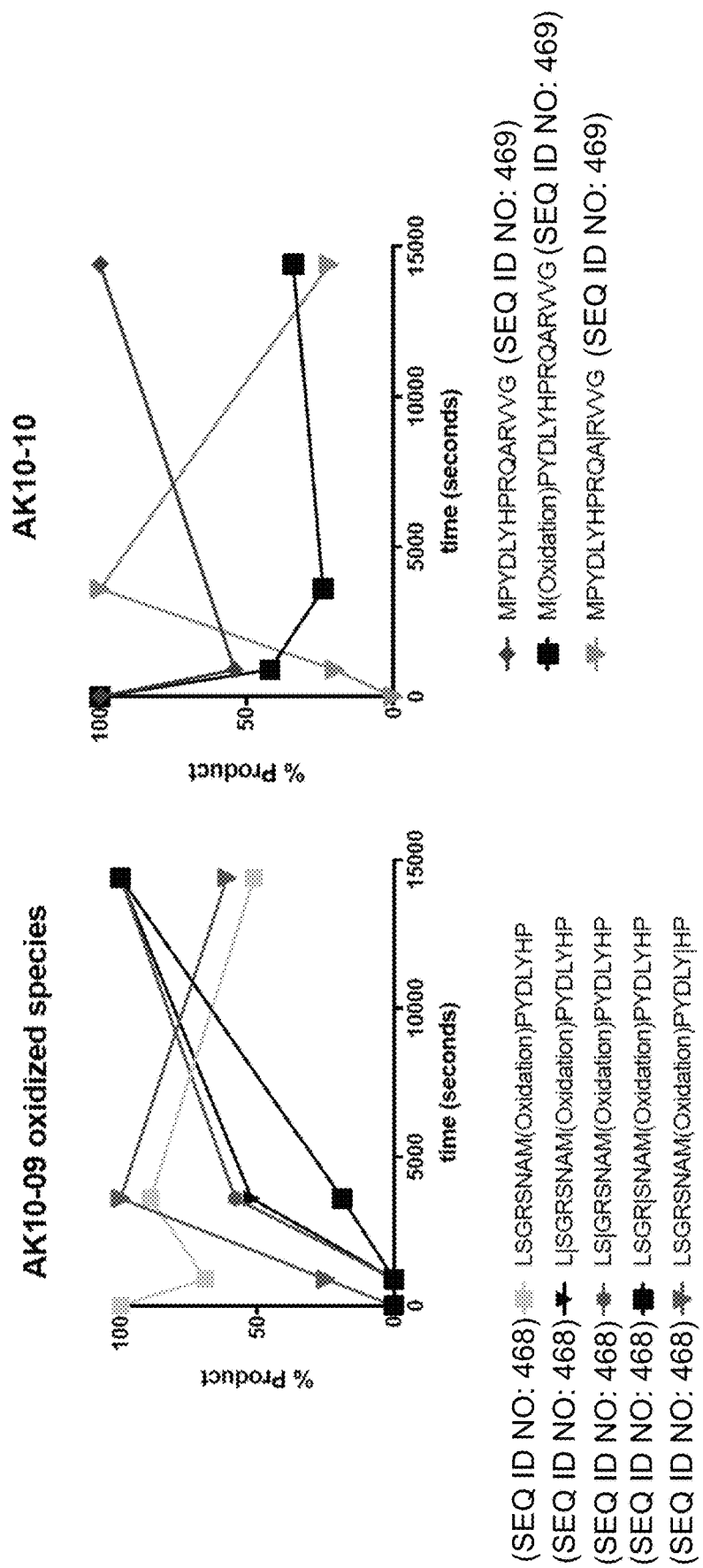

The patient tumor sample produced a broader set of cleavages than either the cell line samples in the AMSP-MS analysis of the AK10 library peptides. Individual product formation traces are shown in FIGS. 36A-36C. These figures depict the product formation curves for selected substrates with tumor conditioned media: AK10-01 (FIG. 36A, top left), AK10-02 (FIG. 36A, top middle), AK10-03 (FIG. 36A, bottom), AK10-04 (FIG. 36B, top left), and AK10-05 (FIG. 36B, top right), AK10-09 (FIG. 36B, bottom), AK10-09 oxidized peptides (FIG. 36C, left), and AK10-10 (FIG. 36C, right). As before, several degradation products were observed for peptide AK-09, both in the non-oxidized and oxidized peptide species. However, the only significant cleavage of the peptide AK-10 was at PRQA|RVV, and the product progress curve in FIG. 36C, right panel supported that secondary reactions were reducing the product signal.

Figure 36D:
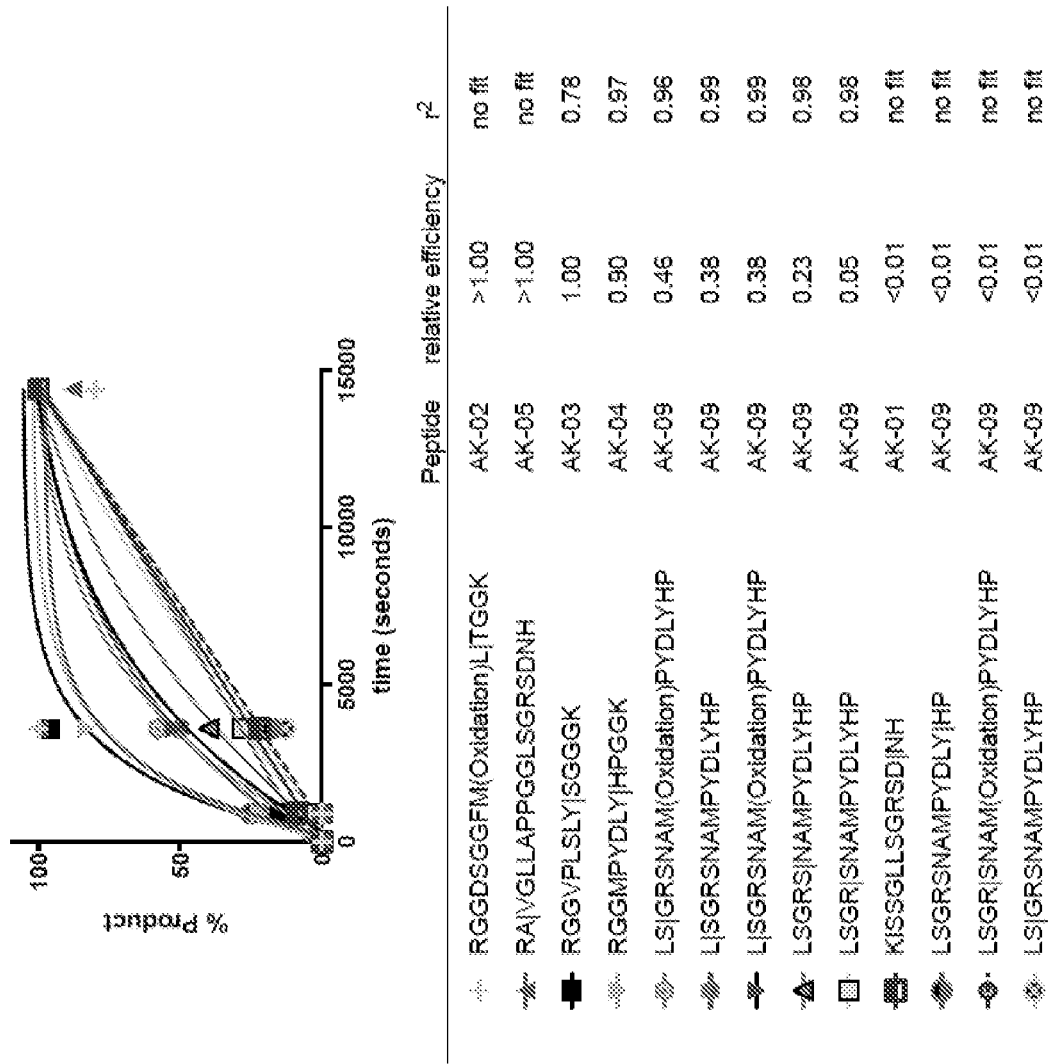
FIG. 36D depicts the top substrates cleaved by tumor conditioned media via AMSP-MS shown with their relative efficiencies.

The top substrates for the AK10 library in the tumor conditioned media are shown in FIG. 36D. The top cleavages were in the LSLY|SG motif of AK-03 and YDLY|HP of AK-04. NSCLC samples from H2228 and the tumor tissue shared significant cleavage of peptides AK-04 (at YDLY|HP) and AK-09 at multiple sites (LSG|R|SNAMPYDLY|HP).

Figure 37A:
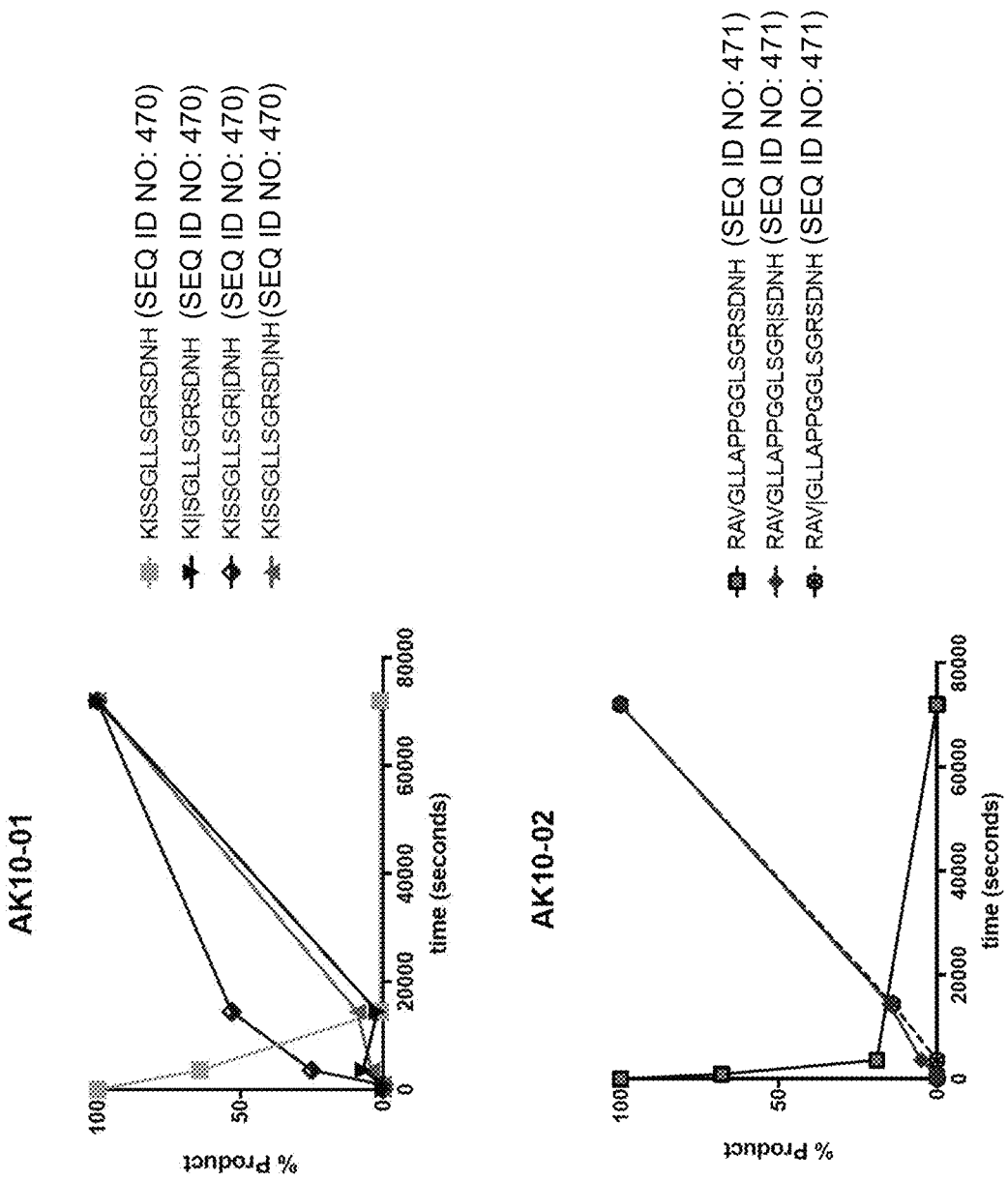
Figure 37B:
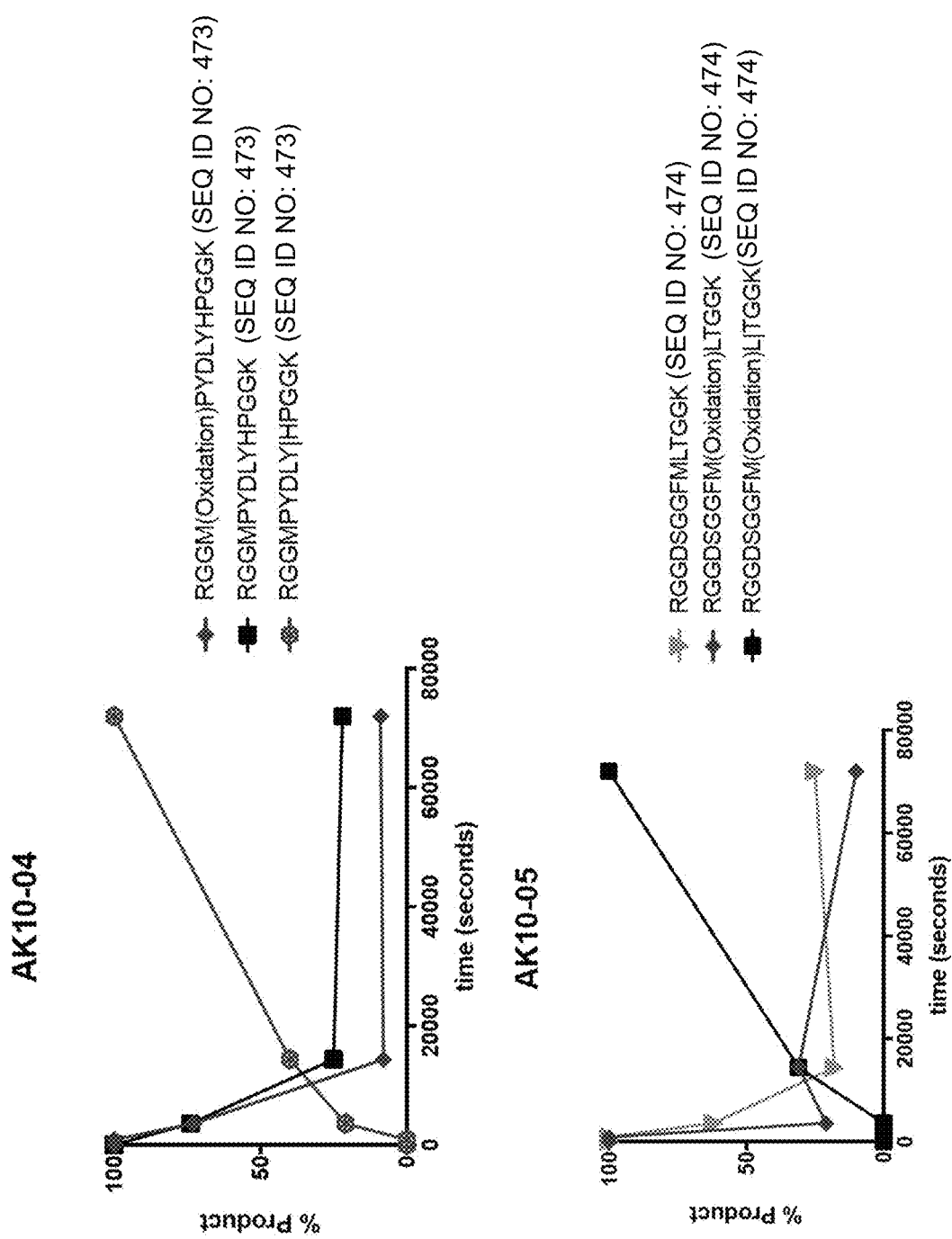
Figure 37C:
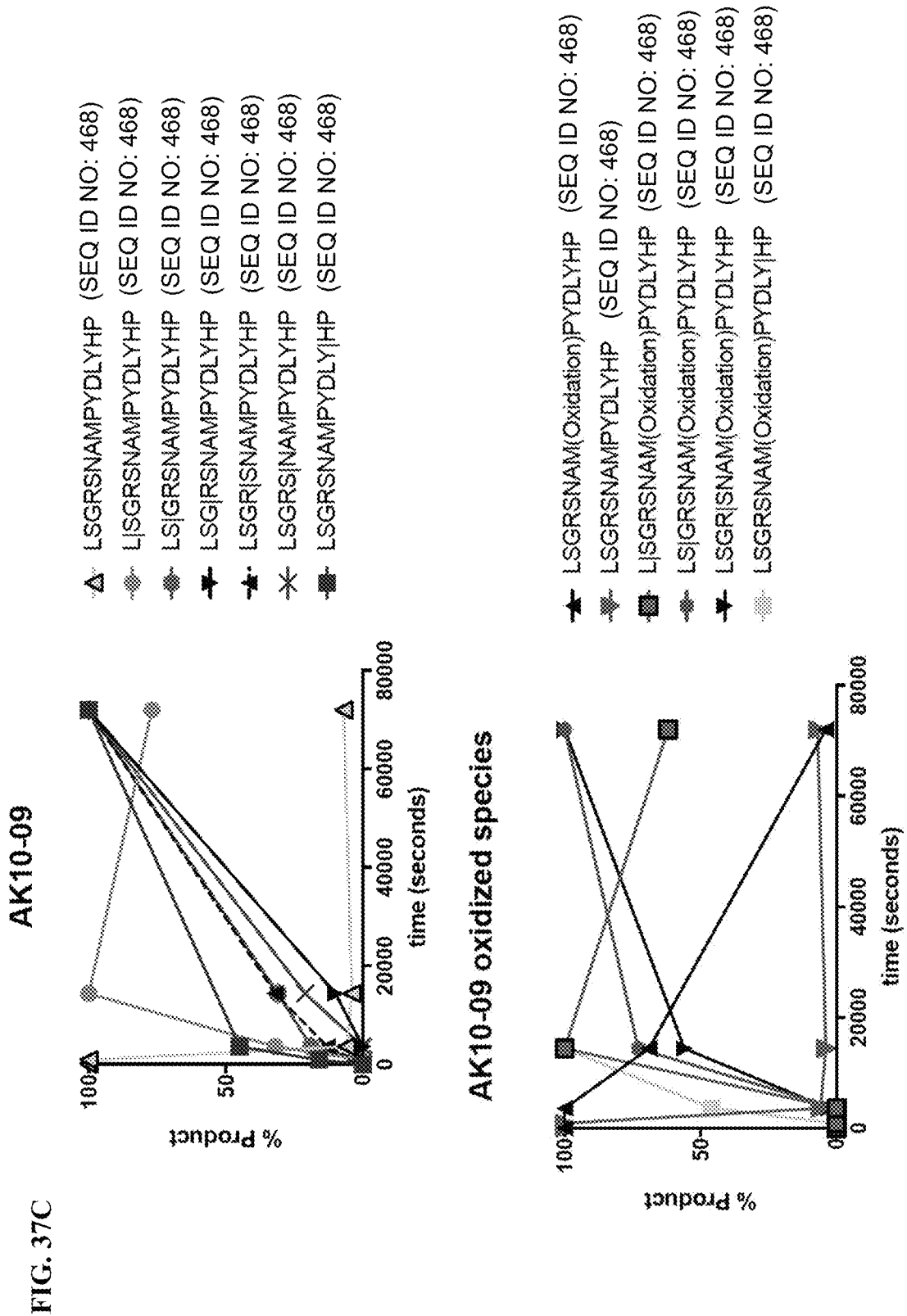

The NAT-conditioned media also produced specific cleavages. Substrate abundance monitoring revealed an overall trend for significant AK10 library degradation within the context of the experiment. Individual products showed a range of behaviors depicted in FIGS. 37A-37D. FIGS. 37A-37D depict the product formation curves for selected substrates with NAT conditioned media: AK10-01 (FIG. 37A, top), AK10-02 (FIG. 37A, bottom), AK10-04 (FIG. 37B, top), and AK10-05 (FIG. 37B, bottom), AK10-09 (FIG. 37C, top), AK10-09 oxidized peptides (FIG. 37C, bottom), and AK10-10 (FIG. 37D). The better performing substrates were AK-01, -04, -09, and -10, and the weaker substrates were AK-02 and AK-05.

Kinetic analysis of the most efficient NAT-catalyzed substrates is shown in FIG. 37E. The most efficient NAT substrate was AK-10 (LSGR|SDNH), a shared cleavage with H2228 but not the tumor sample. The other efficient substrates were AK-09 at multiple sites (LS|GR|SNAMPYDLY|HP), some of which were shared with H2228 and tumor, and AK-04 (at YDLY|HP).

This analysis demonstrated that normal adjacent tissue contains site-specific enzymatic activity that is shared with its matched tumor tissue. In particular, the YDLY|HP cleavages are apparent in the iceLogo motifs for Tumor conditioned media shown in FIG. 31A, right panel. The specificity toward LSGR|S motifs was also apparent in the tumor conditioned media iceLogo generated after 4 h reaction in FIG. 31A, right panel, and was detected even more clearly in the NAT sample given 24 h incubation time also in FIG. 31B, left panel.

MC38 only shared cleavages with the NSCLC samples within the LSGRS motif found in peptides AK-09 and AK-02. Cleavage of AK-10 by MC38 at the HPRQ|AR motif was shared with H2228 but not the tumor sample, or at the HPRQ|R site shared with NAT. MC38 cleavage of AK-02 at GLSG|RS was consistent with its strong P1' preference for Arg, as seen in its iceLogo motif depicted in FIG. 30, left panel.

In summary, Table 20 supports the conclusion that the AK10 library peptides had first order kinetic behavior consistent with enzymatic cleavage. Table 20 indicates (Yes/No/N.D.) whether the peptide substrate was cleaved by the conditioned media samples. N.D. indicates that it was not detected as an intact or cleaved species in the conditioned media-treated samples.

TABLE 20

| | Cleaved by conditioned media samples? | | | |
|---|---|---|---|---|
| Substrate | MC38 | H2228 | NAT | Tumor |
| AK-01 | No | Yes | Yes | Yes |
| AK-02 | No | Yes | No | Yes |
| AK-03 | No | No | No | Yes |
| AK-04 | No | Yes | Yes | Yes |
| AK-05 | No | No | No | Yes |
| AK-06 | No | No | No | No |
| AK-07 | No | No | No | No |
| AK-08 | N.D. | N.D. | N.D. | N.D. |
| AK-09 | Yes | Yes | Yes | Yes |
| AK-10 | Yes | Yes | Yes | Yes |

E. Proteomic Analysis

Protein concentration in samples was quantified by BCA assay, and 5 μg of total protein was used per digestion reaction. Samples were denatured with 4 M urea, reduced with 5 mM dithiothreitol (DTT) by reaction at 56° C. for 30 min. Samples were alkylated with iodoacetamide (IAM) at 10 mM by reaction in the dark at room temperature for 1 h. Excess IAM was quenched with 5 mM DTT, and then the reactions were diluted to 1M final urea. Samples were digested with sequencing grade porcine trypsin (Promega, V5111) at 1:50 mass ratio of trypsin to sample overnight at 37° C. The next day, the resulting peptide digest samples were desalted with C18 zip tips (Millipore-Sigma), and then freeze-dried. Samples were resuspended in 0.1% formic acid in HPLC-grade water for LC-MS/MS analysis.

Peptide sequencing by LC-MS/MS was performed on an QExactive Plus mass spectrometer (Thermo), equipped with a nanoACQUITY (Waters) ultraperformance LC (UPLC) system and an EASY-Spray ion source (Thermo). Reversed-phase chromatography was carried out with an EASY-Spray PepMap C18 column (Thermo, ES800; 3 µm bead size, 75 µm by 150 mm). Chromatography was performed at a 600-nl/min flow rate during sample loading for 14 min, and then at a 400-nl/min flow rate for peptide separation over 90 min with a linear gradient of 2 to 35% (vol/vol) acetonitrile in 0.1% formic acid. Peptide fragmentation was performed by higher-energy collisional dissociation (HCD) on the six most intense precursor ions, with a minimum of 2,000 counts, with an isolation width of 2.0 m z and a minimum normalized collision energy of 25.

MS peak lists were generated with MSConvert 6, and data were analyzed using Protein Prospector software, v.5.22.1 (UCSF). Data were searched against the SwissProt human or mouse library (downloaded Nov. 1, 2017) totaling 20,240 or 16,942 entries, respectively. MC38, a mouse cell line, was analyzed separately from the human NSCLC samples. The SwissProt bovine library was also searched to identify FCS proteins. A decoy database search approach was used to estimate the false-discovery rate (FDR), and score thresholds for reporting protein identifications were selected to obtain <1% FDR. Mass tolerances were set to 20 ppm for parent ions and 30 ppm for fragment ions, and trypsin specificity was selected with one non-specific cleavage and one missed cleavage allowed. Carbamidomethylation on Cys was used as a fixed modification. The following standard variable modifications were used: Protein N-term acetylation, Protein N-term acetylation+oxidation, N-terminal pyroglutamate formation from glutamine, Met-loss, and Met-oxidation. In addition, a minimum requirement of at least two unique peptides in a single LC-MS/MS run was required per protein identification in a given experiment across replicate samples.

Data were output with spectral counts (peptide counts) as an approximation of relative protein abundance. To correct for potential differences in protein loading between runs, peptide counts were normalized by the sum of total counts from that run. Searches were subsequently processed in Perseus, the data was log 2-normalized, then proteins were excluded if they didn't have a peptide count of >1 in at least 2 out of the 3 replicates. Then, missing values were replaced by random numbers imputed from the normal distribution. A Welch's t-test performed between the two replicate sets, and a volcano plot was generated in R.

Among the protein identifications were 47 proteases or protease inhibitors, including matrix metalloproteases (Mmp2, 7 and 12), the MMP inhibitor (Timp2), proteasome subunits (Psma), serpins and cystatins, carboxypeptidases (Cpe and Cpd), cathepsins (Ctsd, b, h, z, and l), aminopeptidases (Rnpep, Lap3), calpains (Cpns), prolyl-directed peptidases (Dpp3, Xpnpep1 and Pepd), a serine protease (Prss23), a tripeptidyl-peptidase (Tpp1), Adam10, and Casp3.

The abundance of proteases and inhibitors does not necessarily add up to observed activity, but the protein identifications provide insight into the motifs identified in activity data. The presence of cathepsins could account for P1 nLeu preference (Ctsd), or P1 Arg, Gly (Ctsb, Ctsl) for example. A strong preference for basic residues in the substrate specificity profiles at P1 could also be related to background serum proteins from the coagulation cascade, as bovine thrombin and plasmin were both detected in the proteomic data.

Analysis of the human NSCLC-related samples were combined to allow for comparison between samples: this included the H2228 cell line, patient tumor, and normal adjacent tissue. Here, the proteomic analysis resulted in the confident identification of 2243 unique proteins across all three samples.

Among the identifications were a similar list of proteases and their inhibitors: proteasome subunits, aminopeptidases B & N, calpain subunits, carboxypeptidases E and A, caspases 1,3,6,8, cathepsins B, D, E, L1, L2, S and Z, DPP1, 2 and 3: ADAM10, MMP14 and 9, MMP inhibitors 1 & 2: serpins, the serine protease HTRA1, prolyl endopeptidases including FAP, prolyl aminopeptidases, tripeptidyl peptidases TPP1 and TPP2, as well as coagulation factors and complement proteins.

Figure 38:
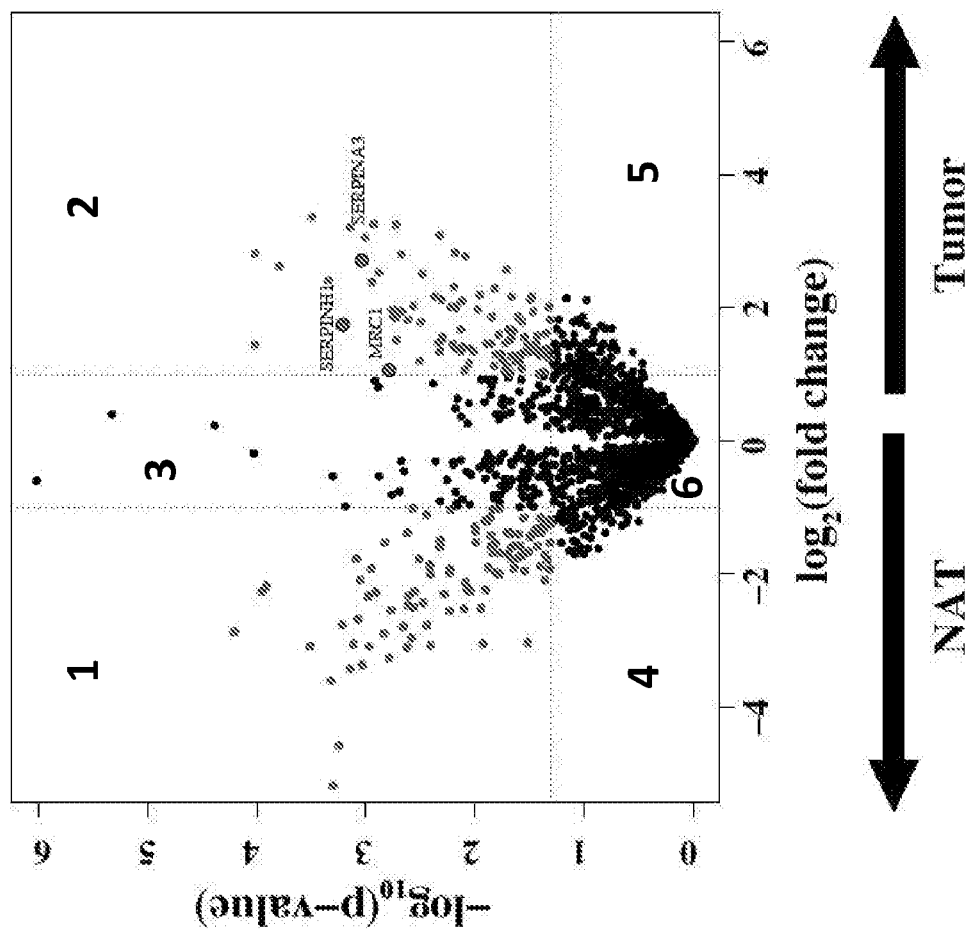
FIG. 38 depicts differentially expressed proteins in Tumor vs. NAT tissue samples as a volcano plot. Statistically significant proteins have a threshold fold difference of ≥2 fold change. Proteins significantly enriched in the tumor (upper right side, section 2) or NAT (upper left side, section 1) are present in these sections.

An example differential analysis was performed for the list of proteins detected in the conditioned media from NAT and Tumor samples using Perseus software, allowing for a two-sided Welch's t-test of differential expression between the two sets of replicate samples (based on peptide counts). The results are visualized in a volcano plot in FIG. 38, where proteins significantly enriched in the tumor (upper right side, section 2) or NAT (upper left side, section 1) are present in these sections. Three proteins of interest were identified in this list: Serpin H1, Alpha-1-antichymotrypsin (SERPINA3), and Macrophage mannose receptor 1 (MRC1).

In conclusion, unbiased activity profiling using AMSP-MS revealed cleavage profiles for each sample, with an overall strong preference for basic residues. The MC38 and H2228 cell lines had different protease specificity profiles while tumor and NAT tissues from the same patient shared similar protease specificities, but differential analysis revealed a stronger preference for P1 Arg/Lys in the NAT sample vs. P1 Leu, Phe or Gly in Tumor. Comparative kinetic analysis demonstrated two specific motifs were reliably cleaved across multiple samples and within individual substrates, including YDLY|HP and LSGR|S. The mouse MC38 cell line is of distinct biological origin from the other human NSCLC-related samples, yet the collection of proteases and inhibitors identified in MC38 conditioned media was remarkably similar to the NSCLC set. The proteases identified from proteomic analysis include candidates with specificity that is consistent with the observed AMSP-MS cleavages, including the cathepsins.

Example 18: In Vivo Assessment of Masked Anti-CTLA4 Antibodies in Cynomolgus Monkeys In a first set of experiments, cynomolgus monkeys were administered ipilimumab, Antibody 2-6, Antibody 2-10, or an isotype control, and pharmacodynamic (PD) effects were assessed by measuring the percentage (%) of Ki67+ cells in CD4+ cells. In a second set of experiments, cynomolgus monkeys were administered Antibody 2-6, Antibody 2-10, Antibody 2-14, Antibody 2-16, or an isotype control, and pharmacodynamic effects were assessed by measuring the percentage (%) of Ki67+ cells in CD4+ cells.

Figure 21:
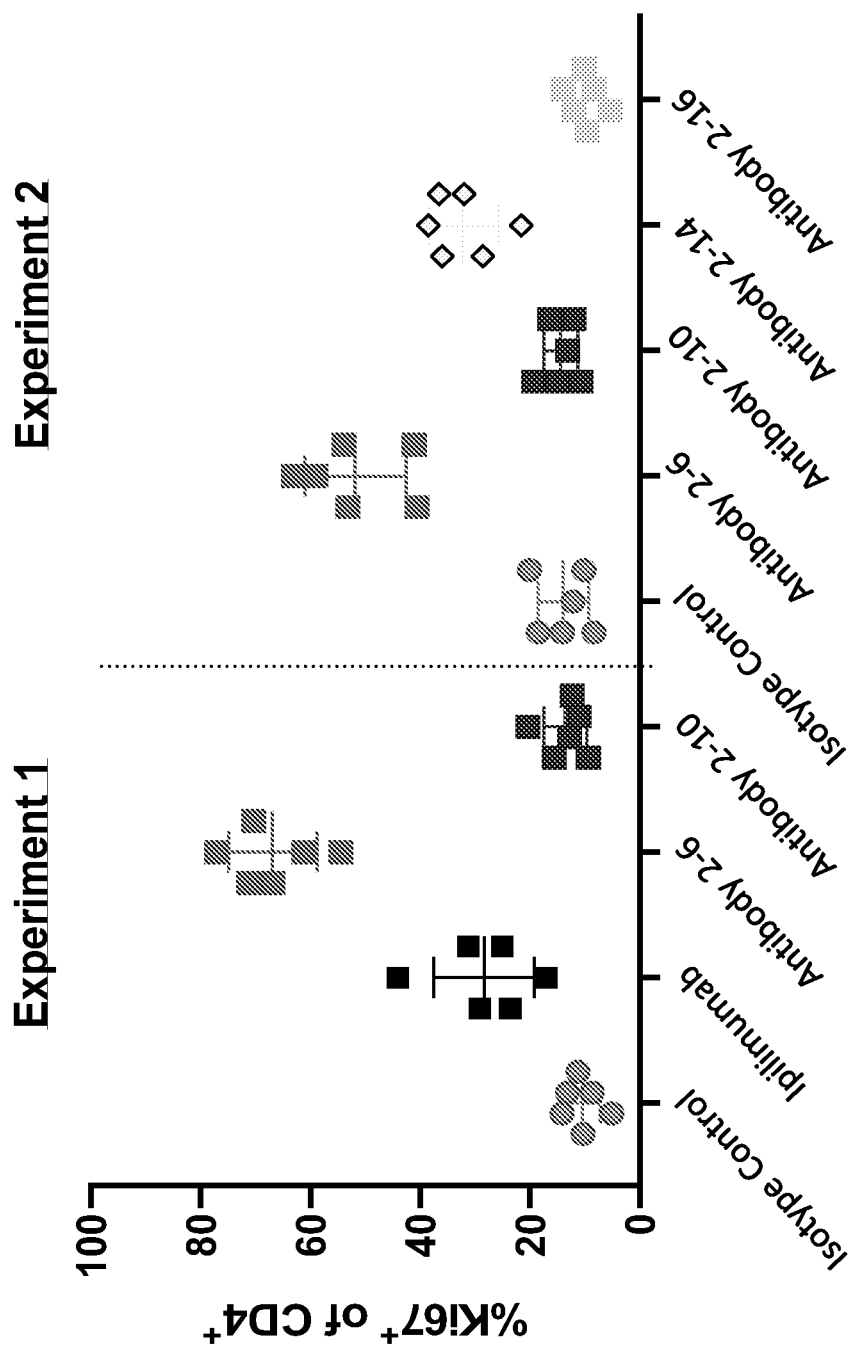
FIG. 21 depicts a graph showing the results from two sets of experiments (Experiment 1 and Experiment 2) that assessed pharmacodynamics effects in cynomolgus monkeys by evaluating the percentage of Ki67+ cells of total CD4+ cells following administration of Antibody 2-6, Antibody 2-10, Antibody 2-14, Antibody 2-16, or an isotype control.

Results from the first and second set of PD experiments are shown in FIG. 21. The parental unmasked Antibody 2-6 is more potent at inducing peripheral PD effects than ipilimumab as shown by an elevated percentage of Ki67+ cells in CD4+ cells as compared to ipilimumab. Antibody 2-10, which is a masked but non-cleavable version of Antibody 2-6, blocks the PD effects associated with Antibody 2-6. As shown in the second set of experiments (Experiment 2), the masked and cleavable antibodies Antibody 2-14 and Antibody 2-16 exhibits reduced PD effects as compared to the unmasked parental Antibody 2-6.

Pharmacokinetics were also assessed using cynomolgus monkeys following a 10 mg/kg intravenous dose of a test antibody (RSV-m control, ipilimumab, Antibody 2-6, Antibody 2-10, Antibody 2-14, Antibody 2-16, or a masked version of ipilimumab containing S239D and I332D mutations in the Fc domain (ipilimumab-m-masked). Levels of each antibody in plasma was measured, and half-life (days), Cmax (μg/mL), and area under the curve (AUC) (Day* μg/mL) were measured in two studies.

Figure 22:
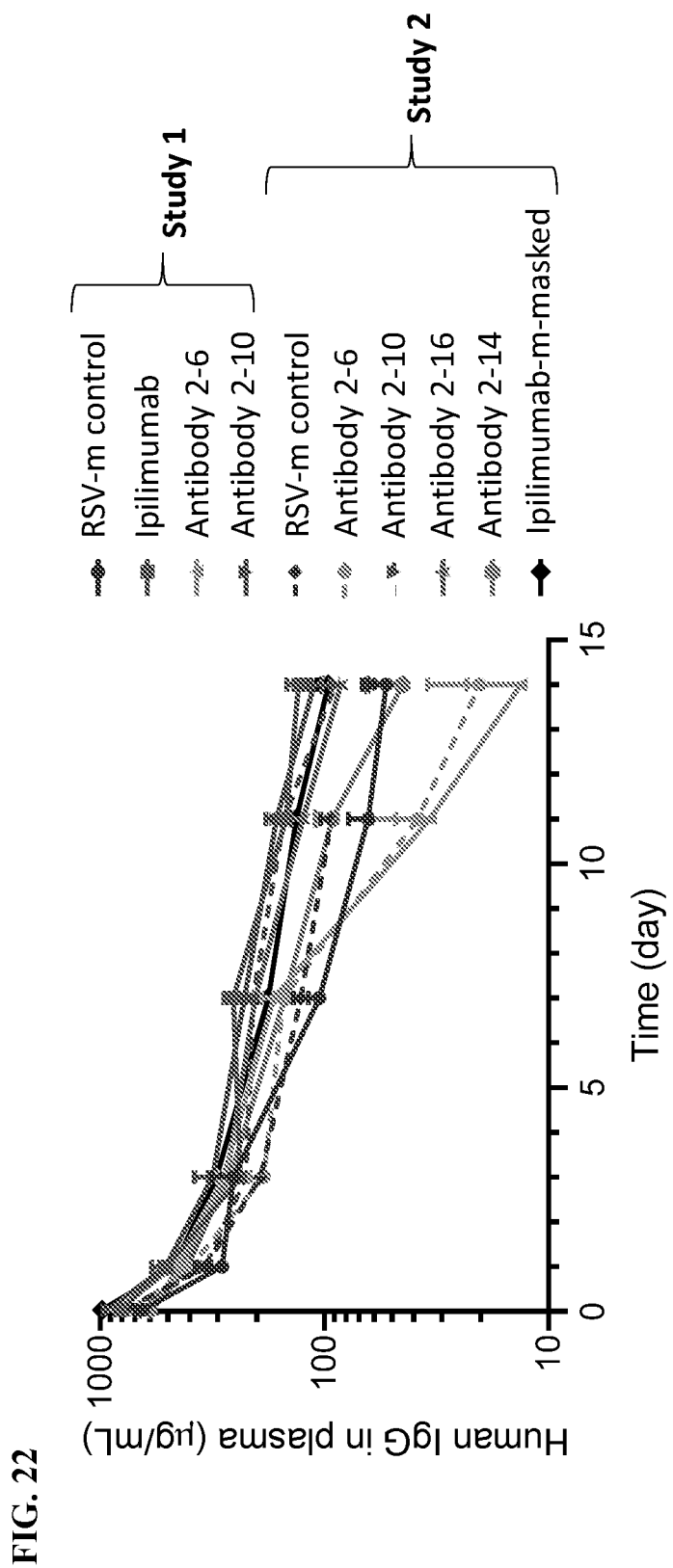
FIG. 22 depicts results from experiments that assessed pharmacokinetics in cynomolgus monkeys following administration of one of the following test antibodies: RSV-m control, ipilimumab, Antibody 2-6, Antibody 2-10, Antibody 2-14, Antibody 2-16, or ipilimumab-m-masked.

Results from the pharmacokinetic studies are shown in FIG. 22. FIG. 22 shows the level of each administered antibody over a period of 14 days. This data demonstrates that Antibody 2-14 and Antibody 2-16 display favorable pharmacokinetics in cynomolgus monkeys following a 10 mg/kg intravenous dose.

The invention claimed is:

1. A masked antibody, comprising:
   a) an anti-CTLA4 antibody or antigen-binding fragment thereof comprising a light chain variable (VL) domain and a heavy chain variable (VH) domain; and
   b) a masking peptide comprising the amino acid sequence of SEQ ID NO: 5; wherein the masking peptide is linked via a linker comprising a cleavable peptide to an amino-terminus of the VL domain;
   wherein the linker comprising a cleavable peptide comprises a cleavable peptide comprising the amino acid sequence of SEQ ID NO: 86;
   wherein (a) the VL domain comprises a CDR-L1 comprising the amino acid sequence of SEQ ID NO: 408, a CDR-L2 comprising the amino acid sequence of SEQ ID NO: 409, and a CDR-L3 comprising the amino acid sequence of SEQ ID NO: 410; and the VH domain comprises a CDR-H1 comprising the amino acid sequence of SEQ ID NO: 411, a CDR-H2 comprising the amino acid sequence of SEQ ID NO: 412, and a CDR-H3 comprising the amino acid sequence of SEQ ID NO: 413; or (b) the VL domain comprises a CDR-L1 comprising the amino acid sequence of SEQ ID NO: 438, a CDR-L2 comprising the amino acid sequence of SEQ ID NO: 439, and a CDR-L3 comprising the amino acid sequence of SEQ ID NO: 440; and the VH domain comprises a CDR-H1 comprising the amino acid sequence of SEQ ID NO: 441, a CDR-H2 comprising the amino acid sequence of SEQ ID NO: 442, and a CDR-H3 comprising the amino acid sequence of SEQ ID NO: 443.

2. The masked antibody of claim 1, wherein the cleavable peptide comprises an amino-terminus and a carboxy-terminus, and the linker comprising a cleavable peptide comprises a first spacer linker and a second spacer linker, wherein the first spacer linker is linked to the amino-terminus of the cleavable peptide and comprises the amino acid sequence of SEQ ID NO: 96, and the second spacer linker is linked to the carboxy-terminus of the cleavable peptide and comprises the amino acid sequence of SEQ ID NO: 102.

3. The masked antibody of claim 1, wherein the linker comprising a cleavable peptide comprises the amino acid sequence of SEQ ID NO: 454.

4. The masked antibody of claim 1, wherein the masked antibody comprises the amino acid sequence of SEQ ID NO: 228.

5. The masked antibody of claim 1, wherein the anti-CTLA4 antibody or antigen-binding fragment thereof is a humanized antibody, a chimeric antibody, or a human antibody.

6. The masked antibody of claim 1, wherein:
   the VL domain comprises the amino acid sequence of SEQ ID NO: 322, and the VH domain comprises the amino acid sequence of SEQ ID NO: 324.

7. The masked antibody of claim 1, wherein the VL domain is contained within a light chain comprising the amino acid sequence of SEQ ID NO: 334, and the VH domain is contained within a heavy chain comprising the amino acid sequence of SEQ ID NO: 421.

8. The masked antibody of claim 1, wherein the masked antibody comprises the amino acid sequence of SEQ ID NO: 421, and the amino acid sequence of SEQ ID NO: 358.

9. The masked antibody of claim 1, wherein the anti-CTLA4 antibody or antigen-binding fragment thereof is conjugated to an agent.

10. The masked antibody of claim 9, wherein the agent is an inhibitor of tubulin polymerization, a DNA damaging agent, or a DNA synthesis inhibitor.

11. A nucleic acid encoding the masked antibody of claim 1.

12. A host cell comprising the nucleic acid of claim 11.

13. A method of producing a masked antibody, comprising culturing the host cell of claim 12 under conditions that produce the masked antibody.

14. A method of treating a neoplastic disease in a subject, the method comprising administering to a subject an effective amount of the masked antibody of claim 1.

* * * * *

```
                        SEQUENCE LISTING

<160> NUMBER OF SEQ ID NOS: 508

<210> SEQ ID NO 1
    <211> LENGTH: 9
    <212> TYPE: PRT
    <213> ORGANISM: Artificial Sequence
    <220> FEATURE:
    <223> OTHER INFORMATION: Synthetic Construct

<400> SEQUENCE: 1

Cys Asn Leu Ile Val Glu Gly His Cys
    1               5

<210> SEQ ID NO 2
    <211> LENGTH: 16
    <212> TYPE: PRT
    <213> ORGANISM: Artificial Sequence
    <220> FEATURE:
    <223> OTHER INFORMATION: Synthetic Construct

<400> SEQUENCE: 2

Met Gln Thr Arg Cys Lys Glu Tyr Pro Arg Trp Cys Glu His Trp Leu
    1               5                   10                  15

<210> SEQ ID NO 3
    <211> LENGTH: 9
    <212> TYPE: PRT
    <213> ORGANISM: Artificial Sequence
    <220> FEATURE:
    <223> OTHER INFORMATION: Synthetic Construct

<400> SEQUENCE: 3

Cys Lys His Ala Pro Tyr Ala Leu Cys
    1               5

<210> SEQ ID NO 4
    <211> LENGTH: 9
    <212> TYPE: PRT
    <213> ORGANISM: Artificial Sequence
    <220> FEATURE:
    <223> OTHER INFORMATION: Synthetic Construct

<400> SEQUENCE: 4

Cys Pro Phe Pro Ala Lys Ile Leu Cys
    1               5

<210> SEQ ID NO 5
    <211> LENGTH: 9
    <212> TYPE: PRT
    <213> ORGANISM: Artificial Sequence
    <220> FEATURE:
    <223> OTHER INFORMATION: Synthetic Construct
```

```
<400> SEQUENCE: 5

Cys Pro Gly Lys Gly Leu Pro Ser Cys
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic Construct

<400> SEQUENCE: 6

Asn Trp Leu Gly Glu Trp Leu Pro Pro Gly Lys Val
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Synthetic Construct

<400> SEQUENCE: 7

Gln Phe Ile Glu Cys Pro Asn Phe Pro Arg Gln Cys Pro Gly Lys Asn
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic Construct

<400> SEQUENCE: 8

Val Arg Gln Gln Cys Ser Leu Asn Pro Gly Arg Cys Pro Tyr Leu Val
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic Construct

<400> SEQUENCE: 9

Val Trp Gln Glu Cys His Thr Ala Pro Gln Leu Cys Pro Gly Lys Ile
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic Construct

<400> SEQUENCE: 10

Asp Ser Tyr Thr Cys Arg Gly Pro Thr Trp Met Cys Ala Gly Asn Met
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Synthetic Construct

<400> SEQUENCE: 11
```

```
Phe Asn His Asp Cys Ser Gly His Trp Met Arg Cys Leu Asp Gln Gln
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic Construct

<400> SEQUENCE: 12

Asn Lys Ser Pro Cys Arg Pro Lys Met Val Ala Cys Tyr Gly Ile Leu
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic Construct

<400> SEQUENCE: 13

Pro Thr Pro Gln Cys Trp Asn Gln Tyr Tyr Glu Cys Trp Ile Pro Ser
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Ser Gln Lys Cys Pro Trp Thr Lys Glu Thr Cys Met His Tyr Met
1               5                   10              15

<210> SEQ ID NO 15
<211> LENGTH: 12
<212> TYPE: PRT
<213> ORGANISM: Artificial Sequence
<220> FEATURE:
<223> OTHER INFORMATION: Synthetic Construct

<400> SEQUENCE: 15

Trp His Leu Ser Met Tyr Pro Lys Pro Pro Ala Glu
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic Construct

<400> SEQUENCE: 16

Trp His Thr Asp Gly Phe Tyr Thr Arg Leu Pro Ala
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct

<400> SEQUENCE: 17
```

```
Cys Ile His Ala Pro Tyr Ala Lys Cys
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Cys Pro Ala Lys Ile Gly Gln Glu Cys
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Cys Pro Phe Pro Ala Leu Glu Leu Cys
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Cys Thr Lys Pro Ala Lys Ala Leu Cys
1               5

<210> SEQ ID NO 21
<211> LENGTH: 16
<212> TYPE: PRT
<213> ORGANISM: Artificial Sequence
<220> FEATURE:
<223> OTHER INFORMATION: Synthetic Construct

<400> SEQUENCE: 21

Asp Thr Ala Thr Cys Tyr Thr Thr Thr Gly Trp Cys Glu Gly Met Val
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic Construct

<400> SEQUENCE: 22

Asn Ser Asp Asn Cys Gly Pro Ala Lys Ser Thr Cys Met Tyr Asn Asp
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic Construct

<400> SEQUENCE: 23

Pro Pro Gly Lys Cys Thr Gln Pro His Arg Cys Pro Pro Leu Asn
```

```
<210> SEQ ID NO 24
<211> LENGTH: 16
<212> TYPE: PRT
<213> ORGANISM: Artificial Sequence
<220> FEATURE:
<223> OTHER INFORMATION: Synthetic Construct

<400> SEQUENCE: 24

Asp Asp Pro Val Cys Trp Asp Ser Asn Pro Thr Cys Gln Thr Ile Ala
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic Construct

<400> SEQUENCE: 25

Ile Ser Asp Gln Cys Ser Val Leu Phe Leu Ser Cys Asn Thr Arg Val
1               5                   10                  15

<210> SEQ ID NO 26
<211> LENGTH: 10
<212> TYPE: PRT
<213> ORGANISM: Artificial Sequence
<220> FEATURE:
<223> OTHER INFORMATION: Synthetic Construct

<400> SEQUENCE: 26

Ala Cys His Phe Pro His Pro Glu Gly Cys
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Cys Leu Pro Pro Phe Pro Thr Lys Cys
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Cys Pro Asp His Val Phe Pro Lys Cys
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

Cys Trp Leu Pro Lys Pro Asp Met Cys
1               5
```

```
<210> SEQ ID NO 30
<211> LENGTH: 9
<212> TYPE: PRT
<213> ORGANISM: Artificial Sequence
<220> FEATURE:
<223> OTHER INFORMATION: Synthetic Construct

<400> SEQUENCE: 30

Cys Trp Ser Trp Pro Ser Lys Ala Cys
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Construct

<400> SEQUENCE: 31

Cys Tyr Pro Phe Gly Lys Tyr Glu Cys
1               5

<210> SEQ ID NO 32
<211> LENGTH: 12
<212> TYPE: PRT
<213> ORGANISM: Artificial Sequence
<220> FEATURE:
<223> OTHER INFORMATION: Synthetic Construct

<400> SEQUENCE: 32

Ala Leu Thr Pro Ala Lys Trp Leu Pro Ala Asp Asp
1               5                   10

<210> SEQ ID NO 33
<211> LENGTH: 16
<212> TYPE: PRT
<213> ORGANISM: Artificial Sequence
<220> FEATURE:
<223> OTHER INFORMATION: Synthetic Construct

<400> SEQUENCE: 33

Asp Asp Lys Glu Cys Asp Trp Met His Phe Ala Cys Thr Gly Pro Gln
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Synthetic Construct

<400> SEQUENCE: 34

Asp Glu Met Lys Cys Ala Trp Ser Leu Glu Met Cys Val Arg Thr Ser
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetic Construct

<400> SEQUENCE: 35

Asp Pro Ile Leu Cys Pro Asn Thr Arg Met Ser Cys Asp Asn Gln Thr
1               5                   10                  15
```

```
<210> SEQ ID NO 36
<211> LENGTH: 12
<212> TYPE: PRT
<213> ORGANISM: Artificial Sequence
<220> FEATURE:
<223> OTHER INFORMATION: Synthetic Construct

<400> SEQUENCE: 36

Gly Asn Ala Leu Tyr Asp Ser Pro Gly Thr Met Leu
1               5                   10

<210> SEQ ID NO 37
<211> LENGTH: 16
<212> TYPE: PRT
<213> ORGANISM: Artificial Sequence
<220> FEATURE:
<223> OTHER INFORMATION: Synthetic Construct

<400> SEQUENCE: 37

Lys Asn Tyr Glu Cys Arg Glu Val Met Pro Pro Cys Glu Pro Asn Thr
1               5                   10                  15

<210> SEQ ID NO 38
<211> LENGTH: 12
<212> TYPE: PRT
<213> ORGANISM: Artificial Sequence
<220> FEATURE:
<223> OTHER INFORMATION: Synthetic Construct

<400> SEQUENCE: 38

Asn Ser Tyr Thr Ser Pro Tyr Trp Leu Pro Asp Ser
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Synthetic Construct

<400> SEQUENCE: 39

Ser Leu Thr Pro Pro Tyr Trp Ile Pro Arg Glu Trp
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic Construct

<400> SEQUENCE: 40

Ser Pro Leu Thr Pro His Asp Arg Pro Ser Phe Leu
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic Construct

<400> SEQUENCE: 41

Thr Ala Asp Val Phe Ser Ser Ser Arg Tyr Thr Arg
1               5                   10
```

```
<210> SEQ ID NO 42
<211> LENGTH: 16
<212> TYPE: PRT
<213> ORGANISM: Artificial Sequence
<220> FEATURE:
<223> OTHER INFORMATION: Synthetic Construct

<400> SEQUENCE: 42

Thr Asp Leu Gln Cys Pro Pro Ser Ser Pro Ile Cys Gln Ile Glu His
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Synthetic Construct

<400> SEQUENCE: 43

Thr Lys Cys His Cys Asp Gly Asn Cys Val Met Cys Tyr Gln Met Gln
1               5                   10                  15

<210> SEQ ID NO 44
<211> LENGTH: 12
<212> TYPE: PRT
<213> ORGANISM: Artificial Sequence
<220> FEATURE:
<223> OTHER INFORMATION: Synthetic Construct

<400> SEQUENCE: 44

Thr Leu Ala Tyr Glu Thr Pro Leu Leu Trp Leu Pro
1               5                   10

<210> SEQ ID NO 45
<211> LENGTH: 16
<212> TYPE: PRT
<213> ORGANISM: Artificial Sequence
<220> FEATURE:
<223> OTHER INFORMATION: Synthetic Construct

<400> SEQUENCE: 45

Thr Asn Trp His Cys Asn Asn Asp Gly Ser Ser Cys Asn Val Arg Ala
1               5                   10                  15

<210> SEQ ID NO 46
<211> LENGTH: 9
<212> TYPE: PRT
<213> ORGANISM: Artificial Sequence
<220> FEATURE:
<223> OTHER INFORMATION: Synthetic Construct

<400> SEQUENCE: 46

Cys Asn Leu Ile Val Gln Gly His Cys
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic Construct

<400> SEQUENCE: 47

Met Pro Tyr Asp Leu Tyr His Pro
1               5

<210> SEQ ID NO 48
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 48

Gly Gly Ile Gly Gln Leu Thr Ala
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic Construct

<400> SEQUENCE: 49

Asp Leu Gly Arg Phe Gln Thr Phe
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct

<400> SEQUENCE: 50

Asp Ser Gly Gly Phe Met Leu Thr
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic Construct

<400> SEQUENCE: 51

Thr Ser Val Leu Met Ala Ala Pro
1               5

<210> SEQ ID NO 52
<211> LENGTH: 10
<212> TYPE: PRT
<213> ORGANISM: Artificial Sequence
<220> FEATURE:
<223> OTHER INFORMATION: Synthetic Construct

<400> SEQUENCE: 52

Thr Ser Glu Phe Val Phe Ala Pro Asp Gln
1               5                   10

<210> SEQ ID NO 53
<211> LENGTH: 8
<212> TYPE: PRT
<213> ORGANISM: Artificial Sequence
<220> FEATURE:
<223> OTHER INFORMATION: Synthetic Construct

<400> SEQUENCE: 53

Lys Leu Val Leu Pro Val Leu Pro
1               5

<210> SEQ ID NO 54
<211> LENGTH: 8
```

```
<212> TYPE: PRT
<213> ORGANISM: Artificial Sequence
<220> FEATURE:
<223> OTHER INFORMATION: Synthetic Construct

<400> SEQUENCE: 54

Lys Pro Ile Leu Phe Phe Arg Leu
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic Construct

<400> SEQUENCE: 55

Ala Asn Gln Leu Lys Gly
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic Construct

<400> SEQUENCE: 56

Gln Ser Gln Leu Lys Glu
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic Construct

<400> SEQUENCE: 57

His Glu Gln Leu Thr Val
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Construct

<400> SEQUENCE: 58

Pro Ala Asn Leu Val Ala Pro Asp Pro
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic Construct

<400> SEQUENCE: 59

Pro Ala Pro Gly Val Tyr Pro Gly Pro
1               5

<210> SEQ ID NO 60
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 60

Ala Pro Ala Gly Leu Ile Val Pro Tyr Asn
1               5                   10

<210> SEQ ID NO 61
<211> LENGTH: 6
<212> TYPE: PRT
<213> ORGANISM: Artificial Sequence
<220> FEATURE:
<223> OTHER INFORMATION: Synthetic Construct

<400> SEQUENCE: 61

Pro Gln Ala Leu Val Ala
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic Construct

<400> SEQUENCE: 62

Val Gly Asn Leu Asn Phe
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic Construct

<400> SEQUENCE: 63

Val Ala Asn Leu Leu Tyr Glu
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic Construct

<400> SEQUENCE: 64

Val Tyr Asn Leu Met Asp
1               5

<210> SEQ ID NO 65
<211> LENGTH: 6
<212> TYPE: PRT
<213> ORGANISM: Artificial Sequence
<220> FEATURE:
<223> OTHER INFORMATION: Synthetic Construct

<400> SEQUENCE: 65

Thr Phe Asn Ile Lys Gln
1               5

<210> SEQ ID NO 66
<211> LENGTH: 7
<212> TYPE: PRT
<213> ORGANISM: Artificial Sequence
```

```
<220> FEATURE:
<223> OTHER INFORMATION: Synthetic Construct

<400> SEQUENCE: 66

Asp Leu Trp Lys Leu Leu Pro
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic Construct

<400> SEQUENCE: 67

Pro Gly Ser Thr Lys Arg Ala
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic Construct

<400> SEQUENCE: 68

Gln Gln Tyr Arg Ala Leu Lys Ser
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic Construct

<400> SEQUENCE: 69

Tyr Val Pro Arg Ala Val Leu
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic Construct

<400> SEQUENCE: 70

Gly Val Asn Lys Trp Pro Thr
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic Construct

<400> SEQUENCE: 71

Leu Ala Gln Ala Val Arg Ser Ser
1               5

<210> SEQ ID NO 72
<211> LENGTH: 8
<212> TYPE: PRT
<213> ORGANISM: Artificial Sequence
<220> FEATURE:
```

```
<223> OTHER INFORMATION: Synthetic Construct

<400> SEQUENCE: 72

Arg Ala Ala Ala Val Lys Ser Pro
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic Construct

<400> SEQUENCE: 73

Asp Leu Leu Ala Val Val Ala Ala Ser
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic Construct

<400> SEQUENCE: 74

Val Gln Thr Val Thr Trp Pro Asp
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic Construct

<400> SEQUENCE: 75

Ala Ile Pro Met Ser Ile Pro Pro
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic Construct

<400> SEQUENCE: 76

Gly Tyr Glu Val His His Gln Lys
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic Construct

<400> SEQUENCE: 77

Val His His Gln Lys Leu Val Phe
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 78

Ile Arg Arg Val Ser Tyr Ser Phe
1               5

<210> SEQ ID NO 79
<211> LENGTH: 14
<212> TYPE: PRT
<213> ORGANISM: Artificial Sequence
<220> FEATURE:
<223> OTHER INFORMATION: Synthetic Construct

<400> SEQUENCE: 79

Met Pro Tyr Asp Leu Tyr His Pro Ile Leu Phe Phe Arg Leu
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Synthetic Construct

<400> SEQUENCE: 80

Gly Gly Ile Gly Gln Leu Thr Ser Val Leu Met Ala Ala Pro
1               5                   10

<210> SEQ ID NO 81
<211> LENGTH: 15
<212> TYPE: PRT
<213> ORGANISM: Artificial Sequence
<220> FEATURE:
<223> OTHER INFORMATION: Synthetic Construct

<400> SEQUENCE: 81

Asp Ser Gly Gly Phe Met Leu Thr Leu Val Leu Pro Val Leu Pro
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Synthetic Construct

<400> SEQUENCE: 82

Thr Ser Glu Phe Val Phe Ala Pro Asp Leu Gly Arg Phe Gln Thr Phe
1               5                   10                  15

<210> SEQ ID NO 83
<211> LENGTH: 11
<212> TYPE: PRT
<213> ORGANISM: Artificial Sequence
<220> FEATURE:
<223> OTHER INFORMATION: Synthetic Construct

<400> SEQUENCE: 83

Thr Ser Thr Ser Gly Arg Ser Ala Asn Pro Arg
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Synthetic Construct
```

<400> SEQUENCE: 84

Thr Ser Thr Ser Gly Arg Ser Ala Asn Pro Gly
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic Construct

<400> SEQUENCE: 85

Thr Ser Thr Ser Gly Arg Ser Ala Asn Pro His
1               5                   10

<210> SEQ ID NO 86
<211> LENGTH: 6
<212> TYPE: PRT
<213> ORGANISM: Artificial Sequence
<220> FEATURE:
<223> OTHER INFORMATION: Synthetic Construct

<400> SEQUENCE: 86

Val Pro Leu Ser Leu Tyr
1               5

<210> SEQ ID NO 87
<211> LENGTH: 11
<212> TYPE: PRT
<213> ORGANISM: Artificial Sequence
<220> FEATURE:
<223> OTHER INFORMATION: Synthetic Construct

<400> SEQUENCE: 87

Thr Ser Ala Ser Gly Ala Ser Ala Ser Ala Ala
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthetic Construct

<400> SEQUENCE: 88

Pro Ser Ser Pro Gly Gly Gly Ser Ser Pro
1               5                   10

<210> SEQ ID NO 89
<211> LENGTH: 3
<212> TYPE: PRT
<213> ORGANISM: Artificial Sequence
<220> FEATURE:
<223> OTHER INFORMATION: Synthetic Construct

<400> SEQUENCE: 89

Gly Gly Ser
1

<210> SEQ ID NO 90
<211> LENGTH: 8
<212> TYPE: PRT
<213> ORGANISM: Artificial Sequence
<220> FEATURE:
<223> OTHER INFORMATION: Synthetic Construct

<400> SEQUENCE: 90

```
Gly Gly Gly Ser Ser Gly Gly Ser
1               5

<210> SEQ ID NO 91
<211> LENGTH: 5
<212> TYPE: PRT
<213> ORGANISM: Artificial Sequence
<220> FEATURE:
<223> OTHER INFORMATION: Synthetic Construct

<400> SEQUENCE: 91

Gly Gly Ser Gly Gly
1               5

<210> SEQ ID NO 92
<211> LENGTH: 4
<212> TYPE: PRT
<213> ORGANISM: Artificial Sequence
<220> FEATURE:
<223> OTHER INFORMATION: Synthetic Construct

<400> SEQUENCE: 92

Gly Gly Gly Ser
1

<210> SEQ ID NO 93
<211> LENGTH: 2
<212> TYPE: PRT
<213> ORGANISM: Artificial Sequence
<220> FEATURE:
<223> OTHER INFORMATION: Synthetic Construct

<400> SEQUENCE: 93

Gly Ser
1

<210> SEQ ID NO 94
<211> LENGTH: 10
<212> TYPE: PRT
<213> ORGANISM: Artificial Sequence
<220> FEATURE:
<223> OTHER INFORMATION: Synthetic Construct

<400> SEQUENCE: 94

Gly Ser Gly Gly Gly Ser Ser Gly Gly Ser
1               5                   10

<210> SEQ ID NO 95
<211> LENGTH: 6
<212> TYPE: PRT
<213> ORGANISM: Artificial Sequence
<220> FEATURE:
<223> OTHER INFORMATION: Synthetic Construct

<400> SEQUENCE: 95

Gly Ser Ser Gly Gly Ser
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic Construct

<400> SEQUENCE: 96
```

```
Gly Gly Gly Ser Ser Gly Gly Ser Gly
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic Construct

<400> SEQUENCE: 97

Gly Gly Ser Ala Gly Gly Ser
1               5

<210> SEQ ID NO 98
<211> LENGTH: 3
<212> TYPE: PRT
<213> ORGANISM: Artificial Sequence
<220> FEATURE:
<223> OTHER INFORMATION: Synthetic Construct

<400> SEQUENCE: 98

Gly His Ser
1

<210> SEQ ID NO 99
<211> LENGTH: 3
<212> TYPE: PRT
<213> ORGANISM: Artificial Sequence
<220> FEATURE:
<223> OTHER INFORMATION: Synthetic Construct

<400> SEQUENCE: 99

Gly Pro Ser
1

<210> SEQ ID NO 100
<211> LENGTH: 3
<212> TYPE: PRT
<213> ORGANISM: Artificial Sequence
<220> FEATURE:
<223> OTHER INFORMATION: Synthetic Construct

<400> SEQUENCE: 100

Gly Ala Ser
1

<210> SEQ ID NO 101
<211> LENGTH: 4
<212> TYPE: PRT
<213> ORGANISM: Artificial Sequence
<220> FEATURE:
<223> OTHER INFORMATION: Synthetic Construct

<400> SEQUENCE: 101

Ser Gly Gly Gly
1

<210> SEQ ID NO 102
<211> LENGTH: 3
<212> TYPE: PRT
<213> ORGANISM: Artificial Sequence
<220> FEATURE:
<223> OTHER INFORMATION: Synthetic Construct

<400> SEQUENCE: 102

Ser Gly Gly
1
```

```
<210> SEQ ID NO 103
<211> LENGTH: 6
<212> TYPE: PRT
<213> ORGANISM: Artificial Sequence
<220> FEATURE:
<223> OTHER INFORMATION: Synthetic Construct

<400> SEQUENCE: 103

Ser Gly Gly Ser Gly Gly
1               5

<210> SEQ ID NO 104
<211> LENGTH: 3
<212> TYPE: PRT
<213> ORGANISM: Artificial Sequence
<220> FEATURE:
<223> OTHER INFORMATION: Synthetic Construct

<400> SEQUENCE: 104

Ser Ser Gly
1

<210> SEQ ID NO 105
<211> LENGTH: 6
<212> TYPE: PRT
<213> ORGANISM: Artificial Sequence
<220> FEATURE:
<223> OTHER INFORMATION: Synthetic Construct

<400> SEQUENCE: 105

Gly Gly Gly Ser Gly Gly
1               5

<210> SEQ ID NO 106
<211> LENGTH: 2
<212> TYPE: PRT
<213> ORGANISM: Artificial Sequence
<220> FEATURE:
<223> OTHER INFORMATION: Synthetic Construct

<400> SEQUENCE: 106

Gly Gly
1

<210> SEQ ID NO 107
<211> LENGTH: 3
<212> TYPE: PRT
<213> ORGANISM: Artificial Sequence
<220> FEATURE:
<223> OTHER INFORMATION: Synthetic Construct

<400> SEQUENCE: 107

Gly Gly Gly
1

<210> SEQ ID NO 108
<211> LENGTH: 4
<212> TYPE: PRT
<213> ORGANISM: Artificial Sequence
<220> FEATURE:
<223> OTHER INFORMATION: Synthetic Construct

<400> SEQUENCE: 108

Gly Gly Gly Ser
1
```

```
<210> SEQ ID NO 109
<211> LENGTH: 4
<212> TYPE: PRT
<213> ORGANISM: Artificial Sequence
<220> FEATURE:
<223> OTHER INFORMATION: Synthetic Construct

<400> SEQUENCE: 109

Ser His Gly Gly
1

<210> SEQ ID NO 110
<211> LENGTH: 4
<212> TYPE: PRT
<213> ORGANISM: Artificial Sequence
<220> FEATURE:
<223> OTHER INFORMATION: Synthetic Construct

<400> SEQUENCE: 110

His Gly Gly Gly
1

<210> SEQ ID NO 111
<211> LENGTH: 4
<212> TYPE: PRT
<213> ORGANISM: Artificial Sequence
<220> FEATURE:
<223> OTHER INFORMATION: Synthetic Construct

<400> SEQUENCE: 111

Ser Gly Ala Ala
1

<210> SEQ ID NO 112
<211> LENGTH: 4
<212> TYPE: PRT
<213> ORGANISM: Artificial Sequence
<220> FEATURE:
<223> OTHER INFORMATION: Synthetic Construct

<400> SEQUENCE: 112

Ser Gly Pro Ala
1

<210> SEQ ID NO 113
<211> LENGTH: 23
<212> TYPE: PRT
<213> ORGANISM: Artificial Sequence
<220> FEATURE:
<223> OTHER INFORMATION: Synthetic Construct

<400> SEQUENCE: 113

Ala Cys Asn Leu Ile Val Glu Gly His Cys Gly Gly Ser Val Pro Leu
1               5                   10                  15

Ser Leu Tyr Ser Gly Gly Gly
            20

<210> SEQ ID NO 114
<211> LENGTH: 26
<212> TYPE: PRT
<213> ORGANISM: Artificial Sequence
<220> FEATURE:
<223> OTHER INFORMATION: Synthetic Construct

<400> SEQUENCE: 114
```

```
Ala Cys Asn Leu Ile Val Glu Gly His Cys Gly Gly Ser Ala Gly Gly
1               5                   10                  15

Ser Val Pro Leu Ser Leu Tyr Gly Gly Gly
            20                  25
```

<210> SEQ ID NO 115
<211> LENGTH: 26
<212> TYPE: PRT
<213> ORGANISM: Artificial Sequence
<220> FEATURE:
<223> OTHER INFORMATION: Synthetic Construct

<400> SEQUENCE: 115

```
Ala Cys Asn Leu Ile Val Glu Gly His Cys Gly Ser Thr Ser Thr Ser
1               5                   10                  15

Gly Arg Ser Ala Asn Pro Arg Gly Gly Ser
            20                  25
```

<210> SEQ ID NO 116
<211> LENGTH: 26
<212> TYPE: PRT
<213> ORGANISM: Artificial Sequence
<220> FEATURE:
<223> OTHER INFORMATION: Synthetic Construct

<400> SEQUENCE: 116

```
Ala Cys Asn Leu Ile Val Glu Gly His Cys Gly Ser Thr Ser Ala Ser
1               5                   10                  15

Gly Ala Ser Ala Ser Ala Ala Gly Gly Ser
            20                  25
```

<210> SEQ ID NO 117
<211> LENGTH: 23
<212> TYPE: PRT
<213> ORGANISM: Artificial Sequence
<220> FEATURE:
<223> OTHER INFORMATION: Synthetic Construct

<400> SEQUENCE: 117

```
Ala Cys Asn Leu Ile Val Glu Gly His Cys Gly Gly Ser Pro Ser Ser
1               5                   10                  15

Pro Gly Gly Gly Ser Ser Pro
            20
```

<210> SEQ ID NO 118
<211> LENGTH: 39
<212> TYPE: PRT
<213> ORGANISM: Artificial Sequence
<220> FEATURE:
<223> OTHER INFORMATION: Synthetic Construct

<400> SEQUENCE: 118

```
Asp Asp Pro Val Cys Trp Asp Ser Asn Pro Thr Cys Gln Thr Ile Ala
1               5                   10                  15

Gly Gly Gly Ser Ser Gly Gly Ser Thr Ser Thr Ser Gly Arg Ser Ala
            20                  25                  30

Asn Pro Arg Gly Gly Gly Ser
        35
```

<210> SEQ ID NO 119
<211> LENGTH: 39
<212> TYPE: PRT
<213> ORGANISM: Artificial Sequence
<220> FEATURE:

<223> OTHER INFORMATION: Synthetic Construct

<400> SEQUENCE: 119

Ile Ser Asp Gln Cys Ser Val Leu Phe Leu Ser Cys Asn Thr Arg Val
1               5                   10                  15

Gly Gly Gly Ser Ser Gly Gly Ser Thr Ser Thr Ser Gly Arg Ser Ala
                20                  25                  30

Asn Pro Arg Gly Gly Gly Ser
            35

<210> SEQ ID NO 120
<211> LENGTH: 33
<212> TYPE: PRT
<213> ORGANISM: Artificial Sequence
<220> FEATURE:
<223> OTHER INFORMATION: Synthetic Construct

<400> SEQUENCE: 120

Ala Cys His Phe Pro His Pro Glu Gly Cys Gly Gly Gly Ser Ser Gly
1               5                   10                  15

Gly Ser Thr Ser Thr Ser Gly Arg Ser Ala Asn Pro Arg Gly Gly Gly
                20                  25                  30

Ser

<210> SEQ ID NO 121
<211> LENGTH: 33
<212> TYPE: PRT
<213> ORGANISM: Artificial Sequence
<220> FEATURE:
<223> OTHER INFORMATION: Synthetic Construct

<400> SEQUENCE: 121

Ala Cys Leu Pro Pro Phe Pro Thr Lys Cys Gly Gly Gly Ser Ser Gly
1               5                   10                  15

Gly Ser Thr Ser Thr Ser Gly Arg Ser Ala Asn Pro Arg Gly Gly Gly
                20                  25                  30

Ser

<210> SEQ ID NO 122
<211> LENGTH: 33
<212> TYPE: PRT
<213> ORGANISM: Artificial Sequence
<220> FEATURE:
<223> OTHER INFORMATION: Synthetic Construct

<400> SEQUENCE: 122

Ala Cys Asn Leu Ile Val Glu Gly His Cys Gly Gly Gly Ser Ser Gly
1               5                   10                  15

Gly Ser Thr Ser Thr Ser Gly Arg Ser Ala Asn Pro Arg Gly Gly Gly
                20                  25                  30

Ser

<210> SEQ ID NO 123
<211> LENGTH: 33
<212> TYPE: PRT
<213> ORGANISM: Artificial Sequence
<220> FEATURE:
<223> OTHER INFORMATION: Synthetic Construct

<400> SEQUENCE: 123

Ala Cys Pro Asp His Val Phe Pro Lys Cys Gly Gly Gly Ser Ser Gly
1               5                   10                  15

Gly Ser Thr Ser Thr Ser Gly Arg Ser Ala Asn Pro Arg Gly Gly Gly
            20                  25                  30

Ser

<210> SEQ ID NO 124
<211> LENGTH: 33
<212> TYPE: PRT
<213> ORGANISM: Artificial Sequence
<220> FEATURE:
<223> OTHER INFORMATION: Synthetic Construct

<400> SEQUENCE: 124

Ala Cys Trp Leu Pro Lys Pro Asp Met Cys Gly Gly Gly Ser Ser Gly
1               5                   10                  15

Gly Ser Thr Ser Thr Ser Gly Arg Ser Ala Asn Pro Arg Gly Gly Gly
            20                  25                  30

Ser

<210> SEQ ID NO 125
<211> LENGTH: 33
<212> TYPE: PRT
<213> ORGANISM: Artificial Sequence
<220> FEATURE:
<223> OTHER INFORMATION: Synthetic Construct

<400> SEQUENCE: 125

Ala Cys Trp Ser Trp Pro Ser Lys Ala Cys Gly Gly Gly Ser Ser Gly
1               5                   10                  15

Gly Ser Thr Ser Thr Ser Gly Arg Ser Ala Asn Pro Arg Gly Gly Gly
            20                  25                  30

Ser

<210> SEQ ID NO 126
<211> LENGTH: 33
<212> TYPE: PRT
<213> ORGANISM: Artificial Sequence
<220> FEATURE:
<223> OTHER INFORMATION: Synthetic Construct

<400> SEQUENCE: 126

Ala Cys Tyr Pro Phe Gly Lys Tyr Glu Cys Gly Gly Gly Ser Ser Gly
1               5                   10                  15

Gly Ser Thr Ser Thr Ser Gly Arg Ser Ala Asn Pro Arg Gly Gly Gly
            20                  25                  30

Ser

<210> SEQ ID NO 127
<211> LENGTH: 35
<212> TYPE: PRT
<213> ORGANISM: Artificial Sequence
<220> FEATURE:
<223> OTHER INFORMATION: Synthetic Construct

<400> SEQUENCE: 127

Ala Leu Thr Pro Ala Lys Trp Leu Pro Ala Asp Asp Gly Gly Gly Ser
1               5                   10                  15

Ser Gly Gly Ser Thr Ser Thr Ser Gly Arg Ser Ala Asn Pro Arg Gly
            20                  25                  30

Gly Gly Ser
        35

<210> SEQ ID NO 128
<211> LENGTH: 39
<212> TYPE: PRT
<213> ORGANISM: Artificial Sequence
<220> FEATURE:
<223> OTHER INFORMATION: Synthetic Construct

<400> SEQUENCE: 128

Asp Asp Lys Glu Cys Asp Trp Met His Phe Ala Cys Thr Gly Pro Gln
1               5                   10                  15

Gly Gly Gly Ser Ser Gly Gly Ser Thr Ser Thr Ser Gly Arg Ser Ala
                20                  25                  30

Asn Pro Arg Gly Gly Gly Ser
            35

<210> SEQ ID NO 129
<211> LENGTH: 39
<212> TYPE: PRT
<213> ORGANISM: Artificial Sequence
<220> FEATURE:
<223> OTHER INFORMATION: Synthetic Construct

<400> SEQUENCE: 129

Asp Glu Met Lys Cys Ala Trp Ser Leu Glu Met Cys Val Arg Thr Ser
1               5                   10                  15

Gly Gly Gly Ser Ser Gly Gly Ser Thr Ser Thr Ser Gly Arg Ser Ala
                20                  25                  30

Asn Pro Arg Gly Gly Gly Ser
            35

<210> SEQ ID NO 130
<211> LENGTH: 39
<212> TYPE: PRT
<213> ORGANISM: Artificial Sequence
<220> FEATURE:
<223> OTHER INFORMATION: Synthetic Construct

<400> SEQUENCE: 130

Asp Pro Ile Leu Cys Pro Asn Thr Arg Met Ser Cys Asp Asn Gln Thr
1               5                   10                  15

Gly Gly Gly Ser Ser Gly Gly Ser Thr Ser Thr Ser Gly Arg Ser Ala
                20                  25                  30

Asn Pro Arg Gly Gly Gly Ser
            35

<210> SEQ ID NO 131
<211> LENGTH: 35
<212> TYPE: PRT
<213> ORGANISM: Artificial Sequence
<220> FEATURE:
<223> OTHER INFORMATION: Synthetic Construct

<400> SEQUENCE: 131

Gly Asn Ala Leu Tyr Asp Ser Pro Gly Thr Met Leu Gly Gly Gly Ser
1               5                   10                  15

Ser Gly Gly Ser Thr Ser Thr Ser Gly Arg Ser Ala Asn Pro Arg Gly
                20                  25                  30

Gly Gly Ser
        35

<210> SEQ ID NO 132
<211> LENGTH: 39

```
<212> TYPE: PRT
<213> ORGANISM: Artificial Sequence
<220> FEATURE:
<223> OTHER INFORMATION: Synthetic Construct

<400> SEQUENCE: 132

Lys Asn Tyr Glu Cys Arg Glu Val Met Pro Pro Cys Glu Pro Asn Thr
1               5                   10                  15

Gly Gly Gly Ser Ser Gly Gly Ser Thr Ser Thr Ser Gly Arg Ser Ala
            20                  25                  30

Asn Pro Arg Gly Gly Gly Ser
            35

<210> SEQ ID NO 133
<211> LENGTH: 35
<212> TYPE: PRT
<213> ORGANISM: Artificial Sequence
<220> FEATURE:
<223> OTHER INFORMATION: Synthetic Construct

<400> SEQUENCE: 133

Asn Ser Tyr Thr Ser Pro Tyr Trp Leu Pro Asp Ser Gly Gly Gly Ser
1               5                   10                  15

Ser Gly Gly Ser Thr Ser Thr Ser Gly Arg Ser Ala Asn Pro Arg Gly
            20                  25                  30

Gly Gly Ser
        35

<210> SEQ ID NO 134
<211> LENGTH: 35
<212> TYPE: PRT
<213> ORGANISM: Artificial Sequence
<220> FEATURE:
<223> OTHER INFORMATION: Synthetic Construct

<400> SEQUENCE: 134

Ser Leu Thr Pro Pro Tyr Trp Ile Pro Arg Glu Trp Gly Gly Gly Ser
1               5                   10                  15

Ser Gly Gly Ser Thr Ser Thr Ser Gly Arg Ser Ala Asn Pro Arg Gly
            20                  25                  30

Gly Gly Ser
        35

<210> SEQ ID NO 135
<211> LENGTH: 35
<212> TYPE: PRT
<213> ORGANISM: Artificial Sequence
<220> FEATURE:
<223> OTHER INFORMATION: Synthetic Construct

<400> SEQUENCE: 135

Ser Pro Leu Thr Pro His Asp Arg Pro Ser Phe Leu Gly Gly Gly Ser
1               5                   10                  15

Ser Gly Gly Ser Thr Ser Thr Ser Gly Arg Ser Ala Asn Pro Arg Gly
            20                  25                  30

Gly Gly Ser
        35

<210> SEQ ID NO 136
<211> LENGTH: 35
<212> TYPE: PRT
<213> ORGANISM: Artificial Sequence
<220> FEATURE:
```

<223> OTHER INFORMATION: Synthetic Construct

<400> SEQUENCE: 136

Thr Ala Asp Val Phe Ser Ser Arg Tyr Thr Arg Gly Gly Gly Ser
1               5                   10                  15

Ser Gly Gly Ser Thr Ser Thr Ser Gly Arg Ser Ala Asn Pro Arg Gly
            20                  25                  30

Gly Gly Ser
        35

<210> SEQ ID NO 137
<211> LENGTH: 39
<212> TYPE: PRT
<213> ORGANISM: Artificial Sequence
<220> FEATURE:
<223> OTHER INFORMATION: Synthetic Construct

<400> SEQUENCE: 137

Thr Asp Leu Gln Cys Pro Pro Ser Ser Pro Ile Cys Gln Ile Glu His
1               5                   10                  15

Gly Gly Gly Ser Ser Gly Gly Ser Thr Ser Thr Ser Gly Arg Ser Ala
            20                  25                  30

Asn Pro Arg Gly Gly Gly Ser
            35

<210> SEQ ID NO 138
<211> LENGTH: 39
<212> TYPE: PRT
<213> ORGANISM: Artificial Sequence
<220> FEATURE:
<223> OTHER INFORMATION: Synthetic Construct

<400> SEQUENCE: 138

Thr Lys Cys His Cys Asp Gly Asn Cys Val Met Cys Tyr Gln Met Gln
1               5                   10                  15

Gly Gly Gly Ser Ser Gly Gly Ser Thr Ser Thr Ser Gly Arg Ser Ala
            20                  25                  30

Asn Pro Arg Gly Gly Gly Ser
            35

<210> SEQ ID NO 139
<211> LENGTH: 35
<212> TYPE: PRT
<213> ORGANISM: Artificial Sequence
<220> FEATURE:
<223> OTHER INFORMATION: Synthetic Construct

<400> SEQUENCE: 139

Thr Leu Ala Tyr Glu Thr Pro Leu Leu Trp Leu Pro Gly Gly Gly Ser
1               5                   10                  15

Ser Gly Gly Ser Thr Ser Thr Ser Gly Arg Ser Ala Asn Pro Arg Gly
            20                  25                  30

Gly Gly Ser
        35

<210> SEQ ID NO 140
<211> LENGTH: 39
<212> TYPE: PRT
<213> ORGANISM: Artificial Sequence
<220> FEATURE:
<223> OTHER INFORMATION: Synthetic Construct

<400> SEQUENCE: 140

Thr Asn Trp His Cys Asn Asn Asp Gly Ser Ser Cys Asn Val Arg Ala
1               5                   10                  15

Gly Gly Gly Ser Ser Gly Gly Ser Thr Ser Thr Ser Gly Arg Ser Ala
                20                  25                  30

Asn Pro Arg Gly Gly Gly Ser
            35

<210> SEQ ID NO 141
<211> LENGTH: 33
<212> TYPE: PRT
<213> ORGANISM: Artificial Sequence
<220> FEATURE:
<223> OTHER INFORMATION: Synthetic Construct

<400> SEQUENCE: 141

Tyr Pro Tyr Asp Val Pro Asp Tyr Ala Gly Ala Cys Asn Leu Ile Val
1               5                   10                  15

Glu Gly His Cys Gly Gly Ser Val Pro Leu Ser Leu Tyr Ser Gly Gly
                20                  25                  30

Gly

<210> SEQ ID NO 142
<211> LENGTH: 32
<212> TYPE: PRT
<213> ORGANISM: Artificial Sequence
<220> FEATURE:
<223> OTHER INFORMATION: Synthetic Construct

<400> SEQUENCE: 142

Asp Tyr Lys Asp Asp Asp Lys Gly Ala Cys Asn Leu Ile Val Glu
1               5                   10                  15

Gly His Cys Gly Gly Ser Val Pro Leu Ser Leu Tyr Ser Gly Gly Gly
                20                  25                  30

<210> SEQ ID NO 143
<211> LENGTH: 34
<212> TYPE: PRT
<213> ORGANISM: Artificial Sequence
<220> FEATURE:
<223> OTHER INFORMATION: Synthetic Construct

<400> SEQUENCE: 143

Glu Gln Lys Leu Ile Ser Glu Glu Asp Leu Gly Ala Cys Asn Leu Ile
1               5                   10                  15

Val Glu Gly His Cys Gly Gly Ser Val Pro Leu Ser Leu Tyr Ser Gly
                20                  25                  30

Gly Gly

<210> SEQ ID NO 144
<211> LENGTH: 39
<212> TYPE: PRT
<213> ORGANISM: Artificial Sequence
<220> FEATURE:
<223> OTHER INFORMATION: Synthetic Construct

<400> SEQUENCE: 144

Gly Leu Asn Asp Ile Phe Glu Ala Gln Lys Ile Glu Trp His Glu Gly
1               5                   10                  15

Ala Cys Asn Leu Ile Val Glu Gly His Cys Gly Gly Ser Val Pro Leu
                20                  25                  30

Ser Leu Tyr Ser Gly Gly Gly

<210> SEQ ID NO 145
<211> LENGTH: 36
<212> TYPE: PRT
<213> ORGANISM: Artificial Sequence
<220> FEATURE:
<223> OTHER INFORMATION: Synthetic Construct

<400> SEQUENCE: 145

```
Tyr Pro Tyr Asp Val Pro Asp Tyr Ala Gly Ala Cys Asn Leu Ile Val
1               5                   10                  15

Glu Gly His Cys Gly Ser Thr Ser Thr Ser Gly Arg Ser Ala Asn Pro
            20                  25                  30

Arg Gly Gly Ser
        35
```

<210> SEQ ID NO 146
<211> LENGTH: 35
<212> TYPE: PRT
<213> ORGANISM: Artificial Sequence
<220> FEATURE:
<223> OTHER INFORMATION: Synthetic Construct

<400> SEQUENCE: 146

```
Asp Tyr Lys Asp Asp Asp Lys Gly Ala Cys Asn Leu Ile Val Glu
1               5                   10                  15

Gly His Cys Gly Ser Thr Ser Thr Ser Gly Arg Ser Ala Asn Pro Arg
            20                  25                  30

Gly Gly Ser
        35
```

<210> SEQ ID NO 147
<211> LENGTH: 37
<212> TYPE: PRT
<213> ORGANISM: Artificial Sequence
<220> FEATURE:
<223> OTHER INFORMATION: Synthetic Construct

<400> SEQUENCE: 147

```
Glu Gln Lys Leu Ile Ser Glu Glu Asp Leu Gly Ala Cys Asn Leu Ile
1               5                   10                  15

Val Glu Gly His Cys Gly Ser Thr Ser Thr Ser Gly Arg Ser Ala Asn
            20                  25                  30

Pro Arg Gly Gly Ser
        35
```

<210> SEQ ID NO 148
<211> LENGTH: 42
<212> TYPE: PRT
<213> ORGANISM: Artificial Sequence
<220> FEATURE:
<223> OTHER INFORMATION: Synthetic Construct

<400> SEQUENCE: 148

```
Gly Leu Asn Asp Ile Phe Glu Ala Gln Lys Ile Glu Trp His Glu Gly
1               5                   10                  15

Ala Cys Asn Leu Ile Val Glu Gly His Cys Gly Ser Thr Ser Thr Ser
            20                  25                  30

Gly Arg Ser Ala Asn Pro Arg Gly Gly Ser
        35                  40
```

```
<210> SEQ ID NO 149
<211> LENGTH: 25
<212> TYPE: PRT
<213> ORGANISM: Artificial Sequence
<220> FEATURE:
<223> OTHER INFORMATION: Synthetic Construct

<400> SEQUENCE: 149

Ala Cys Asn Leu Ile Val Glu Gly His Cys Gly Gly Ser Met Pro Tyr
1               5                   10                  15

Asp Leu Tyr His Pro Ser Gly Gly Gly
            20                  25

<210> SEQ ID NO 150
<211> LENGTH: 25
<212> TYPE: PRT
<213> ORGANISM: Artificial Sequence
<220> FEATURE:
<223> OTHER INFORMATION: Synthetic Construct

<400> SEQUENCE: 150

Ala Cys Asn Leu Ile Val Glu Gly His Cys Gly Gly Ser Gly Gly Ile
1               5                   10                  15

Gly Gln Leu Thr Ala Ser Gly Gly Gly
            20                  25

<210> SEQ ID NO 151
<211> LENGTH: 25
<212> TYPE: PRT
<213> ORGANISM: Artificial Sequence
<220> FEATURE:
<223> OTHER INFORMATION: Synthetic Construct

<400> SEQUENCE: 151

Ala Cys Asn Leu Ile Val Glu Gly His Cys Gly Gly Ser Asp Leu Gly
1               5                   10                  15

Arg Phe Gln Thr Phe Ser Gly Gly Gly
            20                  25

<210> SEQ ID NO 152
<211> LENGTH: 25
<212> TYPE: PRT
<213> ORGANISM: Artificial Sequence
<220> FEATURE:
<223> OTHER INFORMATION: Synthetic Construct

<400> SEQUENCE: 152

Ala Cys Asn Leu Ile Val Glu Gly His Cys Gly Gly Ser Asp Ser Gly
1               5                   10                  15

Gly Phe Met Leu Thr Ser Gly Gly Gly
            20                  25

<210> SEQ ID NO 153
<211> LENGTH: 25
<212> TYPE: PRT
<213> ORGANISM: Artificial Sequence
<220> FEATURE:
<223> OTHER INFORMATION: Synthetic Construct

<400> SEQUENCE: 153

Ala Cys Asn Leu Ile Val Glu Gly His Cys Gly Gly Ser Thr Ser Val
1               5                   10                  15

Leu Met Ala Ala Pro Ser Gly Gly Gly
            20                  25
```

<210> SEQ ID NO 154
<211> LENGTH: 27
<212> TYPE: PRT
<213> ORGANISM: Artificial Sequence
<220> FEATURE:
<223> OTHER INFORMATION: Synthetic Construct

<400> SEQUENCE: 154

Ala Cys Asn Leu Ile Val Glu Gly His Cys Gly Gly Ser Thr Ser Glu
1               5                   10                  15

Phe Val Phe Ala Pro Asp Gln Ser Gly Gly Gly
            20                  25

<210> SEQ ID NO 155
<211> LENGTH: 25
<212> TYPE: PRT
<213> ORGANISM: Artificial Sequence
<220> FEATURE:
<223> OTHER INFORMATION: Synthetic Construct

<400> SEQUENCE: 155

Ala Cys Asn Leu Ile Val Glu Gly His Cys Gly Gly Ser Lys Leu Val
1               5                   10                  15

Leu Pro Val Leu Pro Ser Gly Gly Gly
            20                  25

<210> SEQ ID NO 156
<211> LENGTH: 25
<212> TYPE: PRT
<213> ORGANISM: Artificial Sequence
<220> FEATURE:
<223> OTHER INFORMATION: Synthetic Construct

<400> SEQUENCE: 156

Ala Cys Asn Leu Ile Val Glu Gly His Cys Gly Gly Ser Lys Pro Ile
1               5                   10                  15

Leu Phe Phe Arg Leu Ser Gly Gly Gly
            20                  25

<210> SEQ ID NO 157
<211> LENGTH: 23
<212> TYPE: PRT
<213> ORGANISM: Artificial Sequence
<220> FEATURE:
<223> OTHER INFORMATION: Synthetic Construct

<400> SEQUENCE: 157

Ala Cys Asn Leu Ile Val Glu Gly His Cys Gly Gly Ser Ala Asn Gln
1               5                   10                  15

Leu Lys Gly Ser Gly Gly Gly
            20

<210> SEQ ID NO 158
<211> LENGTH: 23
<212> TYPE: PRT
<213> ORGANISM: Artificial Sequence
<220> FEATURE:
<223> OTHER INFORMATION: Synthetic Construct

<400> SEQUENCE: 158

Ala Cys Asn Leu Ile Val Glu Gly His Cys Gly Gly Ser Gln Ser Gln
1               5                   10                  15

Leu Lys Glu Ser Gly Gly Gly
            20

<210> SEQ ID NO 159
<211> LENGTH: 23
<212> TYPE: PRT
<213> ORGANISM: Artificial Sequence
<220> FEATURE:
<223> OTHER INFORMATION: Synthetic Construct

<400> SEQUENCE: 159

Ala Cys Asn Leu Ile Val Glu Gly His Cys Gly Gly Ser His Glu Gln
1               5                   10                  15

Leu Thr Val Ser Gly Gly Gly
            20

<210> SEQ ID NO 160
<211> LENGTH: 26
<212> TYPE: PRT
<213> ORGANISM: Artificial Sequence
<220> FEATURE:
<223> OTHER INFORMATION: Synthetic Construct

<400> SEQUENCE: 160

Ala Cys Asn Leu Ile Val Glu Gly His Cys Gly Gly Ser Pro Ala Asn
1               5                   10                  15

Leu Val Ala Pro Asp Pro Ser Gly Gly Gly
            20                  25

<210> SEQ ID NO 161
<211> LENGTH: 26
<212> TYPE: PRT
<213> ORGANISM: Artificial Sequence
<220> FEATURE:
<223> OTHER INFORMATION: Synthetic Construct

<400> SEQUENCE: 161

Ala Cys Asn Leu Ile Val Glu Gly His Cys Gly Gly Ser Pro Ala Pro
1               5                   10                  15

Gly Val Tyr Pro Gly Pro Ser Gly Gly Gly
            20                  25

<210> SEQ ID NO 162
<211> LENGTH: 27
<212> TYPE: PRT
<213> ORGANISM: Artificial Sequence
<220> FEATURE:
<223> OTHER INFORMATION: Synthetic Construct

<400> SEQUENCE: 162

Ala Cys Asn Leu Ile Val Glu Gly His Cys Gly Gly Ser Ala Pro Ala
1               5                   10                  15

Gly Leu Ile Val Pro Tyr Asn Ser Gly Gly Gly
            20                  25

<210> SEQ ID NO 163
<211> LENGTH: 23
<212> TYPE: PRT
<213> ORGANISM: Artificial Sequence
<220> FEATURE:
<223> OTHER INFORMATION: Synthetic Construct

<400> SEQUENCE: 163

Ala Cys Asn Leu Ile Val Glu Gly His Cys Gly Gly Ser Pro Gln Ala
1               5                   10                  15

Leu Val Ala Ser Gly Gly Gly

```
            20

<210> SEQ ID NO 164
<211> LENGTH: 23
<212> TYPE: PRT
<213> ORGANISM: Artificial Sequence
<220> FEATURE:
<223> OTHER INFORMATION: Synthetic Construct

<400> SEQUENCE: 164

Ala Cys Asn Leu Ile Val Glu Gly His Cys Gly Gly Ser Val Gly Asn
1               5                   10                  15

Leu Asn Phe Ser Gly Gly Gly
            20

<210> SEQ ID NO 165
<211> LENGTH: 24
<212> TYPE: PRT
<213> ORGANISM: Artificial Sequence
<220> FEATURE:
<223> OTHER INFORMATION: Synthetic Construct

<400> SEQUENCE: 165

Ala Cys Asn Leu Ile Val Glu Gly His Cys Gly Gly Ser Val Ala Asn
1               5                   10                  15

Leu Leu Tyr Glu Ser Gly Gly Gly
            20

<210> SEQ ID NO 166
<211> LENGTH: 23
<212> TYPE: PRT
<213> ORGANISM: Artificial Sequence
<220> FEATURE:
<223> OTHER INFORMATION: Synthetic Construct

<400> SEQUENCE: 166

Ala Cys Asn Leu Ile Val Glu Gly His Cys Gly Gly Ser Val Tyr Asn
1               5                   10                  15

Leu Met Asp Ser Gly Gly Gly
            20

<210> SEQ ID NO 167
<211> LENGTH: 23
<212> TYPE: PRT
<213> ORGANISM: Artificial Sequence
<220> FEATURE:
<223> OTHER INFORMATION: Synthetic Construct

<400> SEQUENCE: 167

Ala Cys Asn Leu Ile Val Glu Gly His Cys Gly Gly Ser Thr Phe Asn
1               5                   10                  15

Ile Lys Gln Ser Gly Gly Gly
            20

<210> SEQ ID NO 168
<211> LENGTH: 24
<212> TYPE: PRT
<213> ORGANISM: Artificial Sequence
<220> FEATURE:
<223> OTHER INFORMATION: Synthetic Construct

<400> SEQUENCE: 168

Ala Cys Asn Leu Ile Val Glu Gly His Cys Gly Gly Ser Asp Leu Trp
1               5                   10                  15
```

```
Lys Leu Leu Pro Ser Gly Gly Gly
            20

<210> SEQ ID NO 169
<211> LENGTH: 24
<212> TYPE: PRT
<213> ORGANISM: Artificial Sequence
<220> FEATURE:
<223> OTHER INFORMATION: Synthetic Construct

<400> SEQUENCE: 169

Ala Cys Asn Leu Ile Val Glu Gly His Cys Gly Gly Ser Pro Gly Ser
1               5                   10                  15

Thr Lys Arg Ala Ser Gly Gly Gly
            20

<210> SEQ ID NO 170
<211> LENGTH: 25
<212> TYPE: PRT
<213> ORGANISM: Artificial Sequence
<220> FEATURE:
<223> OTHER INFORMATION: Synthetic Construct

<400> SEQUENCE: 170

Ala Cys Asn Leu Ile Val Glu Gly His Cys Gly Gly Ser Gln Gln Tyr
1               5                   10                  15

Arg Ala Leu Lys Ser Ser Gly Gly Gly
            20                  25

<210> SEQ ID NO 171
<211> LENGTH: 24
<212> TYPE: PRT
<213> ORGANISM: Artificial Sequence
<220> FEATURE:
<223> OTHER INFORMATION: Synthetic Construct

<400> SEQUENCE: 171

Ala Cys Asn Leu Ile Val Glu Gly His Cys Gly Gly Ser Tyr Val Pro
1               5                   10                  15

Arg Ala Val Leu Ser Gly Gly Gly
            20

<210> SEQ ID NO 172
<211> LENGTH: 24
<212> TYPE: PRT
<213> ORGANISM: Artificial Sequence
<220> FEATURE:
<223> OTHER INFORMATION: Synthetic Construct

<400> SEQUENCE: 172

Ala Cys Asn Leu Ile Val Glu Gly His Cys Gly Gly Ser Gly Val Asn
1               5                   10                  15

Lys Trp Pro Thr Ser Gly Gly Gly
            20

<210> SEQ ID NO 173
<211> LENGTH: 25
<212> TYPE: PRT
<213> ORGANISM: Artificial Sequence
<220> FEATURE:
<223> OTHER INFORMATION: Synthetic Construct

<400> SEQUENCE: 173

Ala Cys Asn Leu Ile Val Glu Gly His Cys Gly Gly Ser Leu Ala Gln
1               5                   10                  15
```

```
Ala Val Arg Ser Ser Gly Gly Gly
            20                  25

<210> SEQ ID NO 174
<211> LENGTH: 25
<212> TYPE: PRT
<213> ORGANISM: Artificial Sequence
<220> FEATURE:
<223> OTHER INFORMATION: Synthetic Construct

<400> SEQUENCE: 174

Ala Cys Asn Leu Ile Val Glu Gly His Cys Gly Gly Ser Arg Ala Ala
1               5                   10                  15

Ala Val Lys Ser Pro Ser Gly Gly Gly
            20                  25

<210> SEQ ID NO 175
<211> LENGTH: 26
<212> TYPE: PRT
<213> ORGANISM: Artificial Sequence
<220> FEATURE:
<223> OTHER INFORMATION: Synthetic Construct

<400> SEQUENCE: 175

Ala Cys Asn Leu Ile Val Glu Gly His Cys Gly Gly Ser Asp Leu Leu
1               5                   10                  15

Ala Val Val Ala Ala Ser Ser Gly Gly Gly
            20                  25

<210> SEQ ID NO 176
<211> LENGTH: 25
<212> TYPE: PRT
<213> ORGANISM: Artificial Sequence
<220> FEATURE:
<223> OTHER INFORMATION: Synthetic Construct

<400> SEQUENCE: 176

Ala Cys Asn Leu Ile Val Glu Gly His Cys Gly Gly Ser Val Gln Thr
1               5                   10                  15

Val Thr Trp Pro Asp Ser Gly Gly Gly
            20                  25

<210> SEQ ID NO 177
<211> LENGTH: 25
<212> TYPE: PRT
<213> ORGANISM: Artificial Sequence
<220> FEATURE:
<223> OTHER INFORMATION: Synthetic Construct

<400> SEQUENCE: 177

Ala Cys Asn Leu Ile Val Glu Gly His Cys Gly Gly Ser Ala Ile Pro
1               5                   10                  15

Met Ser Ile Pro Pro Ser Gly Gly Gly
            20                  25

<210> SEQ ID NO 178
<211> LENGTH: 25
<212> TYPE: PRT
<213> ORGANISM: Artificial Sequence
<220> FEATURE:
<223> OTHER INFORMATION: Synthetic Construct

<400> SEQUENCE: 178

Ala Cys Asn Leu Ile Val Glu Gly His Cys Gly Gly Ser Gly Tyr Glu
```

```
                 1               5                  10                  15
Val His His Gln Lys Ser Gly Gly Gly
            20                  25

<210> SEQ ID NO 179
<211> LENGTH: 25
<212> TYPE: PRT
<213> ORGANISM: Artificial Sequence
<220> FEATURE:
<223> OTHER INFORMATION: Synthetic Construct

<400> SEQUENCE: 179

Ala Cys Asn Leu Ile Val Glu Gly His Cys Gly Gly Ser Val His His
1               5                  10                  15

Gln Lys Leu Val Phe Ser Gly Gly Gly
            20                  25

<210> SEQ ID NO 180
<211> LENGTH: 25
<212> TYPE: PRT
<213> ORGANISM: Artificial Sequence
<220> FEATURE:
<223> OTHER INFORMATION: Synthetic Construct

<400> SEQUENCE: 180

Ala Cys Asn Leu Ile Val Glu Gly His Cys Gly Gly Ser Ile Arg Arg
1               5                  10                  15

Val Ser Tyr Ser Phe Ser Gly Gly Gly
            20                  25

<210> SEQ ID NO 181
<211> LENGTH: 31
<212> TYPE: PRT
<213> ORGANISM: Artificial Sequence
<220> FEATURE:
<223> OTHER INFORMATION: Synthetic Construct

<400> SEQUENCE: 181

Ala Cys Asn Leu Ile Val Glu Gly His Cys Gly Gly Ser Met Pro Tyr
1               5                  10                  15

Asp Leu Tyr His Pro Ile Leu Phe Phe Arg Leu Ser Gly Gly Gly
            20                  25                  30

<210> SEQ ID NO 182
<211> LENGTH: 31
<212> TYPE: PRT
<213> ORGANISM: Artificial Sequence
<220> FEATURE:
<223> OTHER INFORMATION: Synthetic Construct

<400> SEQUENCE: 182

Ala Cys Asn Leu Ile Val Glu Gly His Cys Gly Gly Ser Gly Gly Ile
1               5                  10                  15

Gly Gln Leu Thr Ser Val Leu Met Ala Ala Pro Ser Gly Gly Gly
            20                  25                  30

<210> SEQ ID NO 183
<211> LENGTH: 32
<212> TYPE: PRT
<213> ORGANISM: Artificial Sequence
<220> FEATURE:
<223> OTHER INFORMATION: Synthetic Construct

<400> SEQUENCE: 183
```

```
Ala Cys Asn Leu Ile Val Glu Gly His Cys Gly Gly Ser Asp Ser Gly
1               5                   10                  15

Gly Phe Met Leu Thr Leu Val Leu Pro Val Leu Pro Ser Gly Gly Gly
            20                  25                  30
```

<210> SEQ ID NO 184
<211> LENGTH: 33
<212> TYPE: PRT
<213> ORGANISM: Artificial Sequence
<220> FEATURE:
<223> OTHER INFORMATION: Synthetic Construct

<400> SEQUENCE: 184

```
Ala Cys Asn Leu Ile Val Glu Gly His Cys Gly Gly Ser Thr Ser Glu
1               5                   10                  15

Phe Val Phe Ala Pro Asp Leu Gly Arg Phe Gln Thr Phe Ser Gly Gly
            20                  25                  30

Gly
```

<210> SEQ ID NO 185
<211> LENGTH: 23
<212> TYPE: PRT
<213> ORGANISM: Artificial Sequence
<220> FEATURE:
<223> OTHER INFORMATION: Synthetic Construct

<400> SEQUENCE: 185

```
Ala Cys Asn Leu Ile Val Gln Gly His Cys Gly Gly Ser Val Pro Leu
1               5                   10                  15

Ser Leu Tyr Ser Gly Gly Gly
            20
```

<210> SEQ ID NO 186
<211> LENGTH: 23
<212> TYPE: PRT
<213> ORGANISM: Artificial Sequence
<220> FEATURE:
<223> OTHER INFORMATION: Synthetic Construct

<400> SEQUENCE: 186

```
Ala Cys Asn Leu Ile Val Glu Gly His Cys Gly His Ser Val Pro Leu
1               5                   10                  15

Ser Leu Tyr Ser His Gly Gly
            20
```

<210> SEQ ID NO 187
<211> LENGTH: 23
<212> TYPE: PRT
<213> ORGANISM: Artificial Sequence
<220> FEATURE:
<223> OTHER INFORMATION: Synthetic Construct

<400> SEQUENCE: 187

```
Ala Cys Asn Leu Ile Val Glu Gly His Cys Gly Gly Ser Val Pro Leu
1               5                   10                  15

Ser Leu Tyr Ser His Gly Gly
            20
```

<210> SEQ ID NO 188
<211> LENGTH: 23
<212> TYPE: PRT
<213> ORGANISM: Artificial Sequence
<220> FEATURE:
<223> OTHER INFORMATION: Synthetic Construct

```
<400> SEQUENCE: 188

Ala Cys Asn Leu Ile Val Glu Gly His Cys Gly His Ser Val Pro Leu
1               5                   10                  15

Ser Leu Tyr Ser Gly Gly Gly
            20

<210> SEQ ID NO 189
<211> LENGTH: 23
<212> TYPE: PRT
<213> ORGANISM: Artificial Sequence
<220> FEATURE:
<223> OTHER INFORMATION: Synthetic Construct

<400> SEQUENCE: 189

Ala Cys Asn Leu Ile Val Glu Gly His Cys Gly Gly Ser Val Pro Leu
1               5                   10                  15

Ser Leu Tyr His Gly Gly Gly
            20

<210> SEQ ID NO 190
<211> LENGTH: 23
<212> TYPE: PRT
<213> ORGANISM: Artificial Sequence
<220> FEATURE:
<223> OTHER INFORMATION: Synthetic Construct

<400> SEQUENCE: 190

Ala Cys Asn Leu Ile Val Glu Gly His Cys Gly His Ser Val Pro Leu
1               5                   10                  15

Ser Leu Tyr His Gly Gly Gly
            20

<210> SEQ ID NO 191
<211> LENGTH: 23
<212> TYPE: PRT
<213> ORGANISM: Artificial Sequence
<220> FEATURE:
<223> OTHER INFORMATION: Synthetic Construct

<400> SEQUENCE: 191

Ala Cys Asn Leu Ile Val Glu Gly His Cys Gly Pro Ser Val Pro Leu
1               5                   10                  15

Ser Leu Tyr Ser Gly Ala Ala
            20

<210> SEQ ID NO 192
<211> LENGTH: 23
<212> TYPE: PRT
<213> ORGANISM: Artificial Sequence
<220> FEATURE:
<223> OTHER INFORMATION: Synthetic Construct

<400> SEQUENCE: 192

Ala Cys Asn Leu Ile Val Glu Gly His Cys Gly Ala Ser Val Pro Leu
1               5                   10                  15

Ser Leu Tyr Ser Gly Pro Ala
            20

<210> SEQ ID NO 193
<211> LENGTH: 23
<212> TYPE: PRT
<213> ORGANISM: Artificial Sequence
<220> FEATURE:
```

<223> OTHER INFORMATION: Synthetic Construct

<400> SEQUENCE: 193

Ala Cys Asn Leu Ile Val Glu Gly His Cys Gly Pro Ser Val Pro Leu
1               5                   10                  15

Ser Leu Tyr Ser Gly Pro Ala
            20

<210> SEQ ID NO 194
<211> LENGTH: 38
<212> TYPE: PRT
<213> ORGANISM: Artificial Sequence
<220> FEATURE:
<223> OTHER INFORMATION: Synthetic Construct

<400> SEQUENCE: 194

Met Gln Thr Arg Cys Lys Glu Tyr Pro Arg Trp Cys Glu His Trp Leu
1               5                   10                  15

Gly Gly Gly Ser Ser Gly Gly Ser Thr Ser Thr Ser Gly Arg Ser Ala
            20                  25                  30

Asn Pro Arg Ser Gly Gly
        35

<210> SEQ ID NO 195
<211> LENGTH: 35
<212> TYPE: PRT
<213> ORGANISM: Artificial Sequence
<220> FEATURE:
<223> OTHER INFORMATION: Synthetic Construct

<400> SEQUENCE: 195

Met Gln Thr Arg Cys Lys Glu Tyr Pro Arg Trp Cys Glu His Trp Leu
1               5                   10                  15

Gly Gly Ser Gly Gly Thr Ser Thr Ser Gly Arg Ser Ala Asn Pro Arg
            20                  25                  30

Ser Gly Gly
        35

<210> SEQ ID NO 196
<211> LENGTH: 34
<212> TYPE: PRT
<213> ORGANISM: Artificial Sequence
<220> FEATURE:
<223> OTHER INFORMATION: Synthetic Construct

<400> SEQUENCE: 196

Met Gln Thr Arg Cys Lys Glu Tyr Pro Arg Trp Cys Glu His Trp Leu
1               5                   10                  15

Gly Gly Gly Ser Thr Ser Thr Ser Gly Arg Ser Ala Asn Pro Arg Ser
            20                  25                  30

Gly Gly

<210> SEQ ID NO 197
<211> LENGTH: 33
<212> TYPE: PRT
<213> ORGANISM: Artificial Sequence
<220> FEATURE:
<223> OTHER INFORMATION: Synthetic Construct

<400> SEQUENCE: 197

Met Gln Thr Arg Cys Lys Glu Tyr Pro Arg Trp Cys Glu His Trp Leu
1               5                   10                  15

Gly Gly Ser Thr Ser Thr Ser Gly Arg Ser Ala Asn Pro Arg Ser Gly
            20                  25                  30

Gly

<210> SEQ ID NO 198
<211> LENGTH: 32
<212> TYPE: PRT
<213> ORGANISM: Artificial Sequence
<220> FEATURE:
<223> OTHER INFORMATION: Synthetic Construct

<400> SEQUENCE: 198

Met Gln Thr Arg Cys Lys Glu Tyr Pro Arg Trp Cys Glu His Trp Leu
1               5                   10                  15

Gly Ser Thr Ser Thr Ser Gly Arg Ser Ala Asn Pro Arg Ser Gly Gly
            20                  25                  30

<210> SEQ ID NO 199
<211> LENGTH: 35
<212> TYPE: PRT
<213> ORGANISM: Artificial Sequence
<220> FEATURE:
<223> OTHER INFORMATION: Synthetic Construct

<400> SEQUENCE: 199

Met Gln Thr Arg Cys Lys Glu Tyr Pro Arg Trp Cys Glu His Trp Leu
1               5                   10                  15

Gly Ser Thr Ser Thr Ser Gly Arg Ser Ala Asn Pro Arg Ser Gly Gly
            20                  25                  30

Ser Gly Gly
        35

<210> SEQ ID NO 200
<211> LENGTH: 32
<212> TYPE: PRT
<213> ORGANISM: Artificial Sequence
<220> FEATURE:
<223> OTHER INFORMATION: Synthetic Construct

<400> SEQUENCE: 200

Ala Cys Lys His Ala Pro Tyr Ala Leu Cys Gly Gly Ser Ser Gly
1               5                   10                  15

Gly Ser Thr Ser Thr Ser Gly Arg Ser Ala Asn Pro Arg Ser Gly Gly
            20                  25                  30

<210> SEQ ID NO 201
<211> LENGTH: 32
<212> TYPE: PRT
<213> ORGANISM: Artificial Sequence
<220> FEATURE:
<223> OTHER INFORMATION: Synthetic Construct

<400> SEQUENCE: 201

Ala Cys Pro Phe Pro Ala Lys Ile Leu Cys Gly Gly Gly Ser Ser Gly
1               5                   10                  15

Gly Ser Thr Ser Thr Ser Gly Arg Ser Ala Asn Pro Arg Ser Gly Gly
            20                  25                  30

<210> SEQ ID NO 202
<211> LENGTH: 32
<212> TYPE: PRT
<213> ORGANISM: Artificial Sequence
<220> FEATURE:
<223> OTHER INFORMATION: Synthetic Construct

<400> SEQUENCE: 202

Ala Cys Pro Gly Lys Gly Leu Pro Ser Cys Gly Gly Gly Ser Ser Gly
1               5                   10                  15

Gly Ser Thr Ser Thr Ser Gly Arg Ser Ala Asn Pro Arg Ser Gly Gly
                20                  25                  30

<210> SEQ ID NO 203
<211> LENGTH: 34
<212> TYPE: PRT
<213> ORGANISM: Artificial Sequence
<220> FEATURE:
<223> OTHER INFORMATION: Synthetic Construct

<400> SEQUENCE: 203

Asn Trp Leu Gly Glu Trp Leu Pro Pro Gly Lys Val Gly Gly Gly Ser
1               5                   10                  15

Ser Gly Gly Ser Thr Ser Thr Ser Gly Arg Ser Ala Asn Pro Arg Ser
                20                  25                  30

Gly Gly

<210> SEQ ID NO 204
<211> LENGTH: 38
<212> TYPE: PRT
<213> ORGANISM: Artificial Sequence
<220> FEATURE:
<223> OTHER INFORMATION: Synthetic Construct

<400> SEQUENCE: 204

Gln Phe Ile Glu Cys Pro Asn Phe Pro Arg Gln Cys Pro Gly Lys Asn
1               5                   10                  15

Gly Gly Gly Ser Ser Gly Gly Ser Thr Ser Thr Ser Gly Arg Ser Ala
                20                  25                  30

Asn Pro Arg Ser Gly Gly
        35

<210> SEQ ID NO 205
<211> LENGTH: 38
<212> TYPE: PRT
<213> ORGANISM: Artificial Sequence
<220> FEATURE:
<223> OTHER INFORMATION: Synthetic Construct

<400> SEQUENCE: 205

Val Arg Gln Gln Cys Ser Leu Asn Pro Gly Arg Cys Pro Tyr Leu Val
1               5                   10                  15

Gly Gly Gly Ser Ser Gly Gly Ser Thr Ser Thr Ser Gly Arg Ser Ala
                20                  25                  30

Asn Pro Arg Ser Gly Gly
        35

<210> SEQ ID NO 206
<211> LENGTH: 38
<212> TYPE: PRT
<213> ORGANISM: Artificial Sequence
<220> FEATURE:
<223> OTHER INFORMATION: Synthetic Construct

<400> SEQUENCE: 206

Val Trp Gln Glu Cys His Thr Ala Pro Gln Leu Cys Pro Gly Lys Ile
1               5                   10                  15

Gly Gly Gly Ser Ser Gly Gly Ser Thr Ser Thr Ser Gly Arg Ser Ala

```
                20                  25                  30

Asn Pro Arg Ser Gly Gly
            35

<210> SEQ ID NO 207
<211> LENGTH: 32
<212> TYPE: PRT
<213> ORGANISM: Artificial Sequence
<220> FEATURE:
<223> OTHER INFORMATION: Synthetic Construct

<400> SEQUENCE: 207

Met Gln Thr Arg Cys Lys Glu Tyr Pro Arg Trp Cys Glu His Trp Leu
1               5                   10                  15

Gly Ser Thr Ser Thr Ser Gly Arg Ser Ala Asn Pro Gly Ser Ser Gly
            20                  25                  30

<210> SEQ ID NO 208
<211> LENGTH: 32
<212> TYPE: PRT
<213> ORGANISM: Artificial Sequence
<220> FEATURE:
<223> OTHER INFORMATION: Synthetic Construct

<400> SEQUENCE: 208

Met Gln Thr Arg Cys Lys Glu Tyr Pro Arg Trp Cys Glu His Trp Leu
1               5                   10                  15

Gly Ser Thr Ser Thr Ser Gly Arg Ser Ala Asn Pro His Ser Gly Gly
            20                  25                  30

<210> SEQ ID NO 209
<211> LENGTH: 38
<212> TYPE: PRT
<213> ORGANISM: Artificial Sequence
<220> FEATURE:
<223> OTHER INFORMATION: Synthetic Construct

<400> SEQUENCE: 209

Asp Ser Tyr Thr Cys Arg Gly Pro Thr Trp Met Cys Ala Gly Asn Met
1               5                   10                  15

Gly Gly Gly Ser Ser Gly Gly Ser Thr Ser Thr Ser Gly Arg Ser Ala
            20                  25                  30

Asn Pro Arg Ser Gly Gly
            35

<210> SEQ ID NO 210
<211> LENGTH: 38
<212> TYPE: PRT
<213> ORGANISM: Artificial Sequence
<220> FEATURE:
<223> OTHER INFORMATION: Synthetic Construct

<400> SEQUENCE: 210

Phe Asn His Asp Cys Ser Gly His Trp Met Arg Cys Leu Asp Gln Gln
1               5                   10                  15

Gly Gly Gly Ser Ser Gly Gly Ser Thr Ser Thr Ser Gly Arg Ser Ala
            20                  25                  30

Asn Pro Arg Ser Gly Gly
            35

<210> SEQ ID NO 211
<211> LENGTH: 32
<212> TYPE: PRT
```

```
<213> ORGANISM: Artificial Sequence
<220> FEATURE:
<223> OTHER INFORMATION: Synthetic Construct

<400> SEQUENCE: 211

Met Gln Thr Arg Cys Lys Glu Tyr Pro Arg Trp Cys Glu His Trp Leu
1               5                   10                  15

Gly Gly Gly Ser Val Pro Leu Ser Leu Tyr Ser Gly Gly Ser Gly Gly
            20                  25                  30

<210> SEQ ID NO 212
<211> LENGTH: 38
<212> TYPE: PRT
<213> ORGANISM: Artificial Sequence
<220> FEATURE:
<223> OTHER INFORMATION: Synthetic Construct

<400> SEQUENCE: 212

Asn Lys Ser Pro Cys Arg Pro Lys Met Val Ala Cys Tyr Gly Ile Leu
1               5                   10                  15

Gly Gly Gly Ser Ser Gly Gly Ser Thr Ser Thr Ser Gly Arg Ser Ala
            20                  25                  30

Asn Pro Arg Ser Gly Gly
        35

<210> SEQ ID NO 213
<211> LENGTH: 38
<212> TYPE: PRT
<213> ORGANISM: Artificial Sequence
<220> FEATURE:
<223> OTHER INFORMATION: Synthetic Construct

<400> SEQUENCE: 213

Pro Thr Pro Gln Cys Trp Asn Gln Tyr Tyr Glu Cys Trp Ile Pro Ser
1               5                   10                  15

Gly Gly Gly Ser Ser Gly Gly Ser Thr Ser Thr Ser Gly Arg Ser Ala
            20                  25                  30

Asn Pro Arg Ser Gly Gly
        35

<210> SEQ ID NO 214
<211> LENGTH: 37
<212> TYPE: PRT
<213> ORGANISM: Artificial Sequence
<220> FEATURE:
<223> OTHER INFORMATION: Synthetic Construct

<400> SEQUENCE: 214

Ser Gln Lys Cys Pro Trp Thr Lys Glu Thr Cys Met His Tyr Met Gly
1               5                   10                  15

Gly Gly Ser Ser Gly Gly Ser Thr Ser Thr Ser Gly Arg Ser Ala Asn
            20                  25                  30

Pro Arg Ser Gly Gly
        35

<210> SEQ ID NO 215
<211> LENGTH: 34
<212> TYPE: PRT
<213> ORGANISM: Artificial Sequence
<220> FEATURE:
<223> OTHER INFORMATION: Synthetic Construct

<400> SEQUENCE: 215
```

```
Trp His Leu Ser Met Tyr Pro Lys Pro Pro Ala Glu Gly Gly Gly Ser
1               5                   10                  15

Ser Gly Gly Ser Thr Ser Thr Ser Gly Arg Ser Ala Asn Pro Arg Ser
            20                  25                  30

Gly Gly
```

<210> SEQ ID NO 216
<211> LENGTH: 34
<212> TYPE: PRT
<213> ORGANISM: Artificial Sequence
<220> FEATURE:
<223> OTHER INFORMATION: Synthetic Construct

<400> SEQUENCE: 216

```
Trp His Thr Asp Gly Phe Tyr Thr Arg Leu Pro Ala Gly Gly Gly Ser
1               5                   10                  15

Ser Gly Gly Ser Thr Ser Thr Ser Gly Arg Ser Ala Asn Pro Arg Ser
            20                  25                  30

Gly Gly
```

<210> SEQ ID NO 217
<211> LENGTH: 32
<212> TYPE: PRT
<213> ORGANISM: Artificial Sequence
<220> FEATURE:
<223> OTHER INFORMATION: Synthetic Construct

<400> SEQUENCE: 217

```
Ala Cys Ile His Ala Pro Tyr Ala Lys Cys Gly Gly Gly Ser Ser Gly
1               5                   10                  15

Gly Ser Thr Ser Thr Ser Gly Arg Ser Ala Asn Pro Arg Ser Gly Gly
            20                  25                  30
```

<210> SEQ ID NO 218
<211> LENGTH: 32
<212> TYPE: PRT
<213> ORGANISM: Artificial Sequence
<220> FEATURE:
<223> OTHER INFORMATION: Synthetic Construct

<400> SEQUENCE: 218

```
Ala Cys Pro Ala Lys Ile Gly Gln Glu Cys Gly Gly Gly Ser Ser Gly
1               5                   10                  15

Gly Ser Thr Ser Thr Ser Gly Arg Ser Ala Asn Pro Arg Ser Gly Gly
            20                  25                  30
```

<210> SEQ ID NO 219
<211> LENGTH: 32
<212> TYPE: PRT
<213> ORGANISM: Artificial Sequence
<220> FEATURE:
<223> OTHER INFORMATION: Synthetic Construct

<400> SEQUENCE: 219

```
Ala Cys Pro Phe Pro Ala Leu Glu Leu Cys Gly Gly Gly Ser Ser Gly
1               5                   10                  15

Gly Ser Thr Ser Thr Ser Gly Arg Ser Ala Asn Pro Arg Ser Gly Gly
            20                  25                  30
```

<210> SEQ ID NO 220
<211> LENGTH: 32
<212> TYPE: PRT
<213> ORGANISM: Artificial Sequence
<220> FEATURE:
<223> OTHER INFORMATION: Synthetic Construct

<400> SEQUENCE: 220

Ala Cys Thr Lys Pro Ala Lys Ala Leu Cys Gly Gly Ser Ser Gly
1               5                   10                  15

Gly Ser Thr Ser Thr Ser Gly Arg Ser Ala Asn Pro Arg Ser Gly Gly
            20                  25                  30

<210> SEQ ID NO 221
<211> LENGTH: 38
<212> TYPE: PRT
<213> ORGANISM: Artificial Sequence
<220> FEATURE:
<223> OTHER INFORMATION: Synthetic Construct

<400> SEQUENCE: 221

Asp Thr Ala Thr Cys Tyr Thr Thr Thr Gly Trp Cys Glu Gly Met Val
1               5                   10                  15

Gly Gly Gly Ser Ser Gly Gly Ser Thr Ser Thr Ser Gly Arg Ser Ala
            20                  25                  30

Asn Pro Arg Ser Gly Gly
        35

<210> SEQ ID NO 222
<211> LENGTH: 38
<212> TYPE: PRT
<213> ORGANISM: Artificial Sequence
<220> FEATURE:
<223> OTHER INFORMATION: Synthetic Construct

<400> SEQUENCE: 222

Asn Ser Asp Asn Cys Gly Pro Ala Lys Ser Thr Cys Met Tyr Asn Asp
1               5                   10                  15

Gly Gly Gly Ser Ser Gly Gly Ser Thr Ser Thr Ser Gly Arg Ser Ala
            20                  25                  30

Asn Pro Arg Ser Gly Gly
        35

<210> SEQ ID NO 223
<211> LENGTH: 37
<212> TYPE: PRT
<213> ORGANISM: Artificial Sequence
<220> FEATURE:
<223> OTHER INFORMATION: Synthetic Construct

<400> SEQUENCE: 223

Pro Pro Gly Lys Cys Thr Gln Pro His Arg Cys Pro Pro Leu Asn Gly
1               5                   10                  15

Gly Gly Ser Ser Gly Gly Ser Thr Ser Thr Ser Gly Arg Ser Ala Asn
            20                  25                  30

Pro Arg Ser Gly Gly
        35

<210> SEQ ID NO 224
<211> LENGTH: 34
<212> TYPE: PRT
<213> ORGANISM: Artificial Sequence
<220> FEATURE:
<223> OTHER INFORMATION: Synthetic Construct

<400> SEQUENCE: 224

Ala Cys Ile His Ala Pro Tyr Ala Lys Cys Gly Ser Gly Gly Gly Ser

```
1               5                   10                  15
Ser Gly Gly Ser Thr Ser Thr Ser Gly Arg Ser Ala Asn Pro Arg Ser
            20                  25                  30

Gly Gly

<210> SEQ ID NO 225
<211> LENGTH: 30
<212> TYPE: PRT
<213> ORGANISM: Artificial Sequence
<220> FEATURE:
<223> OTHER INFORMATION: Synthetic Construct

<400> SEQUENCE: 225

Ala Cys Pro Ala Lys Ile Gly Gln Glu Cys Gly Ser Ser Gly Gly Ser
1               5                   10                  15

Thr Ser Thr Ser Gly Arg Ser Ala Asn Pro Arg Ser Gly Gly
            20                  25                  30

<210> SEQ ID NO 226
<211> LENGTH: 35
<212> TYPE: PRT
<213> ORGANISM: Artificial Sequence
<220> FEATURE:
<223> OTHER INFORMATION: Synthetic Construct

<400> SEQUENCE: 226

Ala Cys Pro Gly Lys Gly Leu Pro Ser Cys Gly Gly Ser Ser Gly
1               5                   10                  15

Gly Ser Thr Ser Thr Ser Gly Arg Ser Ala Asn Pro Arg Gly Gly Gly
            20                  25                  30

Ser Gly Gly
        35

<210> SEQ ID NO 227
<211> LENGTH: 28
<212> TYPE: PRT
<213> ORGANISM: Artificial Sequence
<220> FEATURE:
<223> OTHER INFORMATION: Synthetic Construct

<400> SEQUENCE: 227

Ala Cys Pro Gly Lys Gly Leu Pro Ser Cys Gly Gly Gly Ser Thr Ser
1               5                   10                  15

Thr Ser Gly Arg Ser Ala Asn Pro Arg Ser Gly Gly
            20                  25

<210> SEQ ID NO 228
<211> LENGTH: 28
<212> TYPE: PRT
<213> ORGANISM: Artificial Sequence
<220> FEATURE:
<223> OTHER INFORMATION: Synthetic Construct

<400> SEQUENCE: 228

Ala Cys Pro Gly Lys Gly Leu Pro Ser Cys Gly Gly Gly Ser Ser Gly
1               5                   10                  15

Gly Ser Gly Val Pro Leu Ser Leu Tyr Ser Gly Gly
            20                  25

<210> SEQ ID NO 229
<211> LENGTH: 26
<212> TYPE: PRT
<213> ORGANISM: Artificial Sequence
```

```
<220> FEATURE:
<223> OTHER INFORMATION: Synthetic Construct

<400> SEQUENCE: 229

Ala Cys Pro Gly Lys Gly Leu Pro Ser Cys Gly Ser Thr Ser Thr Ser
1               5                   10                  15

Gly Arg Ser Ala Asn Pro Arg Ser Gly Gly
            20                  25

<210> SEQ ID NO 230
<211> LENGTH: 27
<212> TYPE: PRT
<213> ORGANISM: Artificial Sequence
<220> FEATURE:
<223> OTHER INFORMATION: Synthetic Construct

<400> SEQUENCE: 230

Ala Cys Pro Gly Lys Gly Leu Pro Ser Cys Gly Gly Ser Thr Ser Thr
1               5                   10                  15

Ser Gly Arg Ser Ala Asn Pro Arg Ser Gly Gly
            20                  25

<210> SEQ ID NO 231
<211> LENGTH: 27
<212> TYPE: PRT
<213> ORGANISM: Artificial Sequence
<220> FEATURE:
<223> OTHER INFORMATION: Synthetic Construct

<400> SEQUENCE: 231

Ala Cys Pro Gly Lys Gly Leu Pro Ser Cys Gly Gly Ser Thr Ser
1               5                   10                  15

Thr Ser Gly Arg Ser Ala Asn Pro Arg Gly Gly
            20                  25

<210> SEQ ID NO 232
<211> LENGTH: 100
<212> TYPE: PRT
<213> ORGANISM: Artificial Sequence
<220> FEATURE:
<223> OTHER INFORMATION: Synthetic Construct

<400> SEQUENCE: 232

Asp Ile Val Met Thr Gln Thr Thr Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro
            100

<210> SEQ ID NO 233
<211> LENGTH: 118
<212> TYPE: PRT
<213> ORGANISM: Artificial Sequence
```

<220> FEATURE:
<223> OTHER INFORMATION: Synthetic Construct

<400> SEQUENCE: 233

```
Glu Ala Lys Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Tyr Gly Ser Trp Phe Ala Tyr Trp Gly Gln Gly Thr Leu
            100                 105                 110

Ile Thr Val Ser Ser Ala
            115
```

<210> SEQ ID NO 234
<211> LENGTH: 119
<212> TYPE: PRT
<213> ORGANISM: Artificial Sequence
<220> FEATURE:
<223> OTHER INFORMATION: Synthetic Construct

<400> SEQUENCE: 234

```
Tyr Thr Phe Gly Gly Gly Thr Lys Leu Glu Ile Lys Arg Ala Asp Ala
1               5                   10                  15

Ala Pro Thr Val Ser Ile Phe Pro Pro Ser Ser Glu Gln Leu Thr Ser
            20                  25                  30

Gly Gly Ala Ser Val Val Cys Phe Leu Asn Asn Phe Tyr Pro Lys Asp
        35                  40                  45

Ile Asn Val Lys Trp Lys Ile Asp Gly Ser Glu Arg Gln Asn Gly Val
    50                  55                  60

Leu Asn Ser Trp Thr Asp Gln Asp Ser Lys Asp Ser Thr Tyr Ser Met
65                  70                  75                  80

Ser Ser Thr Leu Thr Leu Thr Lys Asp Glu Tyr Glu Arg His Asn Ser
                85                  90                  95

Tyr Thr Cys Glu Ala Thr His Lys Thr Ser Thr Ser Pro Ile Val Lys
            100                 105                 110

Ser Phe Asn Arg Asn Glu Cys
            115
```

<210> SEQ ID NO 235
<211> LENGTH: 329
<212> TYPE: PRT
<213> ORGANISM: Artificial Sequence
<220> FEATURE:
<223> OTHER INFORMATION: Synthetic Construct

<400> SEQUENCE: 235

```
Lys Thr Thr Ala Pro Ser Val Tyr Pro Leu Ala Pro Val Cys Gly Asp
1               5                   10                  15

Thr Thr Gly Ser Ser Val Thr Leu Gly Cys Leu Val Lys Gly Tyr Phe
            20                  25                  30
```

Pro Glu Pro Val Thr Leu Thr Trp Asn Ser Gly Ser Leu Ser Ser Gly
            35                  40                  45

Val His Thr Phe Pro Ala Val Leu Gln Ser Asp Leu Tyr Thr Leu Ser
    50                  55                  60

Ser Ser Val Thr Val Thr Ser Ser Thr Trp Pro Ser Gln Ser Ile Thr
65                  70                  75                  80

Cys Asn Val Ala His Pro Ala Ser Ser Thr Lys Val Asp Lys Lys Ile
                85                  90                  95

Glu Pro Arg Gly Pro Thr Ile Lys Pro Cys Pro Pro Cys Lys Cys Pro
            100                 105                 110

Ala Pro Asn Leu Leu Gly Gly Pro Ser Val Phe Ile Phe Pro Pro Lys
        115                 120                 125

Ile Lys Asp Val Leu Met Ile Ser Leu Ser Pro Ile Val Thr Cys Val
    130                 135                 140

Val Val Asp Val Ser Glu Asp Asp Pro Asp Val Gln Ile Ser Trp Phe
145                 150                 155                 160

Val Asn Asn Val Glu Val His Thr Ala Gln Thr Gln Thr His Arg Glu
                165                 170                 175

Asp Tyr Asn Ser Thr Leu Arg Val Val Ser Ala Leu Pro Ile Gln His
            180                 185                 190

Gln Asp Trp Met Ser Gly Lys Glu Phe Lys Cys Lys Val Asn Asn Lys
        195                 200                 205

Asp Leu Pro Ala Pro Ile Glu Arg Thr Ile Ser Lys Pro Lys Gly Ser
    210                 215                 220

Val Arg Ala Pro Gln Val Tyr Val Leu Pro Pro Pro Glu Glu Glu Met
225                 230                 235                 240

Thr Lys Lys Gln Val Thr Leu Thr Cys Met Val Thr Asp Phe Met Pro
                245                 250                 255

Glu Asp Ile Tyr Val Glu Trp Thr Asn Asn Gly Lys Thr Glu Leu Asn
            260                 265                 270

Tyr Lys Asn Thr Glu Pro Val Leu Asp Ser Asp Gly Ser Tyr Phe Met
        275                 280                 285

Tyr Ser Lys Leu Arg Val Glu Lys Lys Asn Trp Val Glu Arg Asn Ser
    290                 295                 300

Tyr Ser Cys Ser Val Val His Glu Gly Leu His Asn His His Thr Thr
305                 310                 315                 320

Lys Ser Phe Ser Arg Thr Pro Gly Lys
                325

<210> SEQ ID NO 236
<211> LENGTH: 335
<212> TYPE: PRT
<213> ORGANISM: Artificial Sequence
<220> FEATURE:
<223> OTHER INFORMATION: Synthetic Construct

<400> SEQUENCE: 236

Lys Thr Thr Pro Pro Ser Val Tyr Pro Leu Ala Pro Gly Cys Gly Asp
1               5                   10                  15

Thr Thr Gly Ser Ser Val Thr Leu Gly Cys Leu Val Lys Gly Tyr Phe
            20                  25                  30

Pro Glu Ser Val Thr Val Thr Trp Asn Ser Gly Ser Leu Ser Ser Ser
        35                  40                  45

Val His Thr Phe Pro Ala Leu Leu Gln Ser Gly Leu Tyr Thr Met Ser
    50                  55                  60

Ser Ser Val Thr Val Pro Ser Ser Thr Trp Pro Ser Gln Thr Val Thr
65                  70                  75                  80

Cys Ser Val Ala His Pro Ala Ser Ser Thr Thr Val Asp Lys Lys Leu
                85                  90                  95

Glu Pro Ser Gly Pro Ile Ser Thr Ile Asn Pro Cys Pro Cys Lys
            100                 105                 110

Glu Cys His Lys Cys Pro Ala Pro Asn Leu Glu Gly Gly Pro Ser Val
            115                 120                 125

Phe Ile Phe Pro Pro Asn Ile Lys Asp Val Leu Met Ile Ser Leu Thr
        130                 135                 140

Pro Lys Val Thr Cys Val Val Asp Val Ser Glu Asp Asp Pro Asp
145                 150                 155                 160

Val Gln Ile Ser Trp Phe Val Asn Asn Val Glu Val His Thr Ala Gln
                165                 170                 175

Thr Gln Thr His Arg Glu Asp Tyr Asn Ser Thr Ile Arg Val Val Ser
            180                 185                 190

Thr Leu Pro Ile Gln His Gln Asp Trp Met Ser Gly Lys Glu Phe Lys
        195                 200                 205

Cys Lys Val Asn Asn Lys Asp Leu Pro Ser Pro Ile Glu Arg Thr Ile
210                 215                 220

Ser Lys Ile Lys Gly Leu Val Arg Ala Pro Gln Val Tyr Ile Leu Pro
225                 230                 235                 240

Pro Pro Ala Glu Gln Leu Ser Arg Lys Asp Val Ser Leu Thr Cys Leu
                245                 250                 255

Val Val Gly Phe Asn Pro Gly Asp Ile Ser Val Glu Trp Thr Ser Asn
            260                 265                 270

Gly His Thr Glu Glu Asn Tyr Lys Asp Thr Ala Pro Val Leu Asp Ser
        275                 280                 285

Asp Gly Ser Tyr Phe Ile Tyr Ser Lys Leu Asn Met Lys Thr Ser Lys
        290                 295                 300

Trp Glu Lys Thr Asp Ser Phe Ser Cys Asn Val Arg His Glu Gly Leu
305                 310                 315                 320

Lys Asn Tyr Tyr Leu Lys Lys Thr Ile Ser Arg Ser Pro Gly Lys
                325                 330                 335

<210> SEQ ID NO 237
<211> LENGTH: 219
<212> TYPE: PRT
<213> ORGANISM: Artificial Sequence
<220> FEATURE:
<223> OTHER INFORMATION: Synthetic Construct

<400> SEQUENCE: 237

Asp Ile Val Met Thr Gln Thr Thr Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

```
Ser His Val Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
            130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
            210                 215
```

<210> SEQ ID NO 238
<211> LENGTH: 242
<212> TYPE: PRT
<213> ORGANISM: Artificial Sequence
<220> FEATURE:
<223> OTHER INFORMATION: Synthetic Construct

<400> SEQUENCE: 238

```
Ala Cys Asn Leu Ile Val Glu Gly His Cys Gly Gly Ser Val Pro Leu
1               5                   10                  15

Ser Leu Tyr Ser Gly Gly Gly Asp Ile Val Met Thr Gln Thr Thr Leu
                20                  25                  30

Ser Leu Pro Val Ser Leu Gly Asp Gln Ala Ser Ile Ser Cys Arg Ser
            35                  40                  45

Ser Gln Ser Ile Val His Ser Asn Gly Asn Thr Tyr Leu Glu Trp Tyr
        50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
        115                 120                 125

Gly Thr Lys Leu Glu Ile Lys Arg Ala Asp Ala Ala Pro Thr Val Ser
    130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
                165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
        195                 200                 205

Leu Thr Lys Asp Glu Tyr Glu Arg His Asn Ser Tyr Thr Cys Glu Ala
    210                 215                 220

Thr His Lys Thr Ser Thr Ser Pro Ile Val Lys Ser Phe Asn Arg Asn
225                 230                 235                 240
```

-continued

Glu Cys

<210> SEQ ID NO 239
<211> LENGTH: 245
<212> TYPE: PRT
<213> ORGANISM: Artificial Sequence
<220> FEATURE:
<223> OTHER INFORMATION: Synthetic Construct

<400> SEQUENCE: 239

Ala Cys Asn Leu Ile Val Glu Gly His Cys Gly Gly Ser Ala Gly Gly
1               5                   10                  15

Ser Val Pro Leu Ser Leu Tyr Gly Gly Gly Asp Ile Val Met Thr Gln
            20                  25                  30

Thr Thr Leu Ser Leu Pro Val Ser Leu Gly Asp Gln Ala Ser Ile Ser
        35                  40                  45

Cys Arg Ser Ser Gln Ser Ile Val His Ser Asn Gly Asn Thr Tyr Leu
    50                  55                  60

Glu Trp Tyr Leu Gln Lys Pro Gly Gln Ser Pro Lys Leu Leu Ile Tyr
65                  70                  75                  80

Lys Val Ser Asn Arg Phe Ser Gly Val Pro Asp Arg Phe Ser Gly Ser
                85                  90                  95

Gly Ser Gly Thr Asp Phe Thr Leu Lys Ile Ser Arg Val Glu Ala Glu
            100                 105                 110

Asp Leu Gly Val Tyr Tyr Cys Phe Gln Gly Ser His Val Pro Tyr Thr
        115                 120                 125

Phe Gly Gly Gly Thr Lys Leu Glu Ile Lys Arg Ala Asp Ala Ala Pro
    130                 135                 140

Thr Val Ser Ile Phe Pro Pro Ser Ser Glu Gln Leu Thr Ser Gly Gly
145                 150                 155                 160

Ala Ser Val Val Cys Phe Leu Asn Asn Phe Tyr Pro Lys Asp Ile Asn
                165                 170                 175

Val Lys Trp Lys Ile Asp Gly Ser Glu Arg Gln Asn Gly Val Leu Asn
            180                 185                 190

Ser Trp Thr Asp Gln Asp Ser Lys Asp Ser Thr Tyr Ser Met Ser Ser
        195                 200                 205

Thr Leu Thr Leu Thr Lys Asp Glu Tyr Glu Arg His Asn Ser Tyr Thr
    210                 215                 220

Cys Glu Ala Thr His Lys Thr Ser Thr Ser Pro Ile Val Lys Ser Phe
225                 230                 235                 240

Asn Arg Asn Glu Cys
                245

<210> SEQ ID NO 240
<211> LENGTH: 245
<212> TYPE: PRT
<213> ORGANISM: Artificial Sequence
<220> FEATURE:
<223> OTHER INFORMATION: Synthetic Construct

<400> SEQUENCE: 240

Ala Cys Asn Leu Ile Val Glu Gly His Cys Gly Ser Thr Ser Thr Ser
1               5                   10                  15

Gly Arg Ser Ala Asn Pro Arg Gly Gly Ser Asp Ile Val Met Thr Gln
            20                  25                  30

Thr Thr Leu Ser Leu Pro Val Ser Leu Gly Asp Gln Ala Ser Ile Ser
        35                  40                  45

Cys Arg Ser Ser Gln Ser Ile Val His Ser Asn Gly Asn Thr Tyr Leu
 50                  55                  60

Glu Trp Tyr Leu Gln Lys Pro Gly Gln Ser Pro Lys Leu Leu Ile Tyr
 65                  70                  75                  80

Lys Val Ser Asn Arg Phe Ser Gly Val Pro Asp Arg Phe Ser Gly Ser
                 85                  90                  95

Gly Ser Gly Thr Asp Phe Thr Leu Lys Ile Ser Arg Val Glu Ala Glu
            100                 105                 110

Asp Leu Gly Val Tyr Tyr Cys Phe Gln Gly Ser His Val Pro Tyr Thr
        115                 120                 125

Phe Gly Gly Gly Thr Lys Leu Glu Ile Lys Arg Ala Asp Ala Ala Pro
130                 135                 140

Thr Val Ser Ile Phe Pro Pro Ser Ser Glu Gln Leu Thr Ser Gly Gly
145                 150                 155                 160

Ala Ser Val Val Cys Phe Leu Asn Asn Phe Tyr Pro Lys Asp Ile Asn
                165                 170                 175

Val Lys Trp Lys Ile Asp Gly Ser Glu Arg Gln Asn Gly Val Leu Asn
            180                 185                 190

Ser Trp Thr Asp Gln Asp Ser Lys Asp Ser Thr Tyr Ser Met Ser Ser
        195                 200                 205

Thr Leu Thr Leu Thr Lys Asp Glu Tyr Glu Arg His Asn Ser Tyr Thr
210                 215                 220

Cys Glu Ala Thr His Lys Thr Ser Thr Ser Pro Ile Val Lys Ser Phe
225                 230                 235                 240

Asn Arg Asn Glu Cys
            245

<210> SEQ ID NO 241
<211> LENGTH: 245
<212> TYPE: PRT
<213> ORGANISM: Artificial Sequence
<220> FEATURE:
<223> OTHER INFORMATION: Synthetic Construct

<400> SEQUENCE: 241

Ala Cys Asn Leu Ile Val Glu Gly His Cys Gly Ser Thr Ser Ala Ser
 1               5                  10                  15

Gly Ala Ser Ala Ser Ala Ala Gly Gly Ser Asp Ile Val Met Thr Gln
             20                  25                  30

Thr Thr Leu Ser Leu Pro Val Ser Leu Gly Asp Gln Ala Ser Ile Ser
         35                  40                  45

Cys Arg Ser Ser Gln Ser Ile Val His Ser Asn Gly Asn Thr Tyr Leu
 50                  55                  60

Glu Trp Tyr Leu Gln Lys Pro Gly Gln Ser Pro Lys Leu Leu Ile Tyr
 65                  70                  75                  80

Lys Val Ser Asn Arg Phe Ser Gly Val Pro Asp Arg Phe Ser Gly Ser
                 85                  90                  95

Gly Ser Gly Thr Asp Phe Thr Leu Lys Ile Ser Arg Val Glu Ala Glu
            100                 105                 110

Asp Leu Gly Val Tyr Tyr Cys Phe Gln Gly Ser His Val Pro Tyr Thr
        115                 120                 125

Phe Gly Gly Gly Thr Lys Leu Glu Ile Lys Arg Ala Asp Ala Ala Pro
130                 135                 140

Thr Val Ser Ile Phe Pro Pro Ser Ser Glu Gln Leu Thr Ser Gly Gly
145                 150                 155                 160

Ala Ser Val Val Cys Phe Leu Asn Asn Phe Tyr Pro Lys Asp Ile Asn
                165                 170                 175

Val Lys Trp Lys Ile Asp Gly Ser Glu Arg Gln Asn Gly Val Leu Asn
            180                 185                 190

Ser Trp Thr Asp Gln Asp Ser Lys Asp Ser Thr Tyr Ser Met Ser Ser
        195                 200                 205

Thr Leu Thr Leu Thr Lys Asp Glu Tyr Glu Arg His Asn Ser Tyr Thr
    210                 215                 220

Cys Glu Ala Thr His Lys Thr Ser Thr Ser Pro Ile Val Lys Ser Phe
225                 230                 235                 240

Asn Arg Asn Glu Cys
                245

<210> SEQ ID NO 242
<211> LENGTH: 242
<212> TYPE: PRT
<213> ORGANISM: Artificial Sequence
<220> FEATURE:
<223> OTHER INFORMATION: Synthetic Construct

<400> SEQUENCE: 242

Ala Cys Asn Leu Ile Val Glu Gly His Cys Gly Gly Ser Pro Ser Ser
1               5                   10                  15

Pro Gly Gly Gly Ser Ser Pro Asp Ile Val Met Thr Gln Thr Thr Leu
            20                  25                  30

Ser Leu Pro Val Ser Leu Gly Asp Gln Ala Ser Ile Ser Cys Arg Ser
        35                  40                  45

Ser Gln Ser Ile Val His Ser Asn Gly Asn Thr Tyr Leu Glu Trp Tyr
    50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
        115                 120                 125

Gly Thr Lys Leu Glu Ile Lys Arg Ala Asp Ala Ala Pro Thr Val Ser
    130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
                165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
        195                 200                 205

Leu Thr Lys Asp Glu Tyr Glu Arg His Asn Ser Tyr Thr Cys Glu Ala
    210                 215                 220

Thr His Lys Thr Ser Thr Ser Pro Ile Val Lys Ser Phe Asn Arg Asn
225                 230                 235                 240

Glu Cys

<210> SEQ ID NO 243
<211> LENGTH: 258
<212> TYPE: PRT

```
<213> ORGANISM: Artificial Sequence
<220> FEATURE:
<223> OTHER INFORMATION: Synthetic Construct

<400> SEQUENCE: 243

Asp Asp Pro Val Cys Trp Asp Ser Asn Pro Thr Cys Gln Thr Ile Ala
1               5                   10                  15

Gly Gly Gly Ser Ser Gly Gly Ser Thr Ser Thr Ser Gly Arg Ser Ala
                20                  25                  30

Asn Pro Arg Gly Gly Gly Ser Asp Ile Val Met Thr Gln Thr Thr Leu
            35                  40                  45

Ser Leu Pro Val Ser Leu Gly Asp Gln Ala Ser Ile Ser Cys Arg Ser
50                  55                  60

Ser Gln Ser Ile Val His Ser Asn Gly Asn Thr Tyr Leu Glu Trp Tyr
65                  70                  75                  80

Leu Gln Lys Pro Gly Gln Ser Pro Lys Leu Leu Ile Tyr Lys Val Ser
                85                  90                  95

Asn Arg Phe Ser Gly Val Pro Asp Arg Phe Ser Gly Ser Gly Ser Gly
            100                 105                 110

Thr Asp Phe Thr Leu Lys Ile Ser Arg Val Glu Ala Glu Asp Leu Gly
        115                 120                 125

Val Tyr Tyr Cys Phe Gln Gly Ser His Val Pro Tyr Thr Phe Gly Gly
    130                 135                 140

Gly Thr Lys Leu Glu Ile Lys Arg Ala Asp Ala Ala Pro Thr Val Ser
145                 150                 155                 160

Ile Phe Pro Pro Ser Ser Glu Gln Leu Thr Ser Gly Gly Ala Ser Val
                165                 170                 175

Val Cys Phe Leu Asn Asn Phe Tyr Pro Lys Asp Ile Asn Val Lys Trp
            180                 185                 190

Lys Ile Asp Gly Ser Glu Arg Gln Asn Gly Val Leu Asn Ser Trp Thr
        195                 200                 205

Asp Gln Asp Ser Lys Asp Ser Thr Tyr Ser Met Ser Ser Thr Leu Thr
    210                 215                 220

Leu Thr Lys Asp Glu Tyr Glu Arg His Asn Ser Tyr Thr Cys Glu Ala
225                 230                 235                 240

Thr His Lys Thr Ser Thr Ser Pro Ile Val Lys Ser Phe Asn Arg Asn
                245                 250                 255

Glu Cys

<210> SEQ ID NO 244
<211> LENGTH: 258
<212> TYPE: PRT
<213> ORGANISM: Artificial Sequence
<220> FEATURE:
<223> OTHER INFORMATION: Synthetic Construct

<400> SEQUENCE: 244

Ile Ser Asp Gln Cys Ser Val Leu Phe Leu Ser Cys Asn Thr Arg Val
1               5                   10                  15

Gly Gly Gly Ser Ser Gly Gly Ser Thr Ser Thr Ser Gly Arg Ser Ala
                20                  25                  30

Asn Pro Arg Gly Gly Gly Ser Asp Ile Val Met Thr Gln Thr Thr Leu
            35                  40                  45

Ser Leu Pro Val Ser Leu Gly Asp Gln Ala Ser Ile Ser Cys Arg Ser
50                  55                  60

Ser Gln Ser Ile Val His Ser Asn Gly Asn Thr Tyr Leu Glu Trp Tyr
```

```
                65                  70                  75                  80
Leu Gln Lys Pro Gly Gln Ser Pro Lys Leu Leu Ile Tyr Lys Val Ser
                    85                  90                  95

Asn Arg Phe Ser Gly Val Pro Asp Arg Phe Ser Gly Ser Gly Ser Gly
                100                 105                 110

Thr Asp Phe Thr Leu Lys Ile Ser Arg Val Glu Ala Glu Asp Leu Gly
                115                 120                 125

Val Tyr Tyr Cys Phe Gln Gly Ser His Val Pro Tyr Thr Phe Gly Gly
        130                 135                 140

Gly Thr Lys Leu Glu Ile Lys Arg Ala Asp Ala Ala Pro Thr Val Ser
145                 150                 155                 160

Ile Phe Pro Pro Ser Ser Glu Gln Leu Thr Ser Gly Gly Ala Ser Val
                165                 170                 175

Val Cys Phe Leu Asn Asn Phe Tyr Pro Lys Asp Ile Asn Val Lys Trp
                180                 185                 190

Lys Ile Asp Gly Ser Glu Arg Gln Asn Gly Val Leu Asn Ser Trp Thr
            195                 200                 205

Asp Gln Asp Ser Lys Asp Ser Thr Tyr Ser Met Ser Ser Thr Leu Thr
        210                 215                 220

Leu Thr Lys Asp Glu Tyr Glu Arg His Asn Ser Tyr Thr Cys Glu Ala
225                 230                 235                 240

Thr His Lys Thr Ser Thr Ser Pro Ile Val Lys Ser Phe Asn Arg Asn
                245                 250                 255

Glu Cys

<210> SEQ ID NO 245
<211> LENGTH: 252
<212> TYPE: PRT
<213> ORGANISM: Artificial Sequence
<220> FEATURE:
<223> OTHER INFORMATION: Synthetic Construct

<400> SEQUENCE: 245

Ala Cys His Phe Pro His Pro Glu Gly Cys Gly Gly Ser Ser Gly
1               5                   10                  15

Gly Ser Thr Ser Thr Ser Gly Arg Ser Ala Asn Pro Arg Gly Gly Gly
                20                  25                  30

Ser Asp Ile Val Met Thr Gln Thr Leu Ser Leu Pro Val Ser Leu
            35                  40                  45

Gly Asp Gln Ala Ser Ile Ser Cys Arg Ser Ser Gln Ser Ile Val His
        50                  55                  60

Ser Asn Gly Asn Thr Tyr Leu Glu Trp Tyr Leu Gln Lys Pro Gly Gln
65                  70                  75                  80

Ser Pro Lys Leu Leu Ile Tyr Lys Val Ser Asn Arg Phe Ser Gly Val
                85                  90                  95

Pro Asp Arg Phe Ser Gly Ser Gly Ser Gly Thr Asp Phe Thr Leu Lys
                100                 105                 110

Ile Ser Arg Val Glu Ala Glu Asp Leu Gly Val Tyr Tyr Cys Phe Gln
            115                 120                 125

Gly Ser His Val Pro Tyr Thr Phe Gly Gly Thr Lys Leu Glu Ile
        130                 135                 140

Lys Arg Ala Asp Ala Ala Pro Thr Val Ser Ile Phe Pro Pro Ser Ser
145                 150                 155                 160

Glu Gln Leu Thr Ser Gly Gly Ala Ser Val Val Cys Phe Leu Asn Asn
                165                 170                 175
```

```
Phe Tyr Pro Lys Asp Ile Asn Val Lys Trp Lys Ile Asp Gly Ser Glu
            180                 185                 190

Arg Gln Asn Gly Val Leu Asn Ser Trp Thr Asp Gln Asp Ser Lys Asp
        195                 200                 205

Ser Thr Tyr Ser Met Ser Ser Thr Leu Thr Leu Thr Lys Asp Glu Tyr
    210                 215                 220

Glu Arg His Asn Ser Tyr Thr Cys Glu Ala Thr His Lys Thr Ser Thr
225                 230                 235                 240

Ser Pro Ile Val Lys Ser Phe Asn Arg Asn Glu Cys
            245                 250

<210> SEQ ID NO 246
<211> LENGTH: 252
<212> TYPE: PRT
<213> ORGANISM: Artificial Sequence
<220> FEATURE:
<223> OTHER INFORMATION: Synthetic Construct

<400> SEQUENCE: 246

Ala Cys Leu Pro Pro Phe Pro Thr Lys Cys Gly Gly Gly Ser Ser Gly
1               5                   10                  15

Gly Ser Thr Ser Thr Ser Gly Arg Ser Ala Asn Pro Arg Gly Gly Gly
            20                  25                  30

Ser Asp Ile Val Met Thr Gln Thr Thr Leu Ser Leu Pro Val Ser Leu
        35                  40                  45

Gly Asp Gln Ala Ser Ile Ser Cys Arg Ser Ser Gln Ser Ile Val His
    50                  55                  60

Ser Asn Gly Asn Thr Tyr Leu Glu Trp Tyr Leu Gln Lys Pro Gly Gln
65                  70                  75                  80

Ser Pro Lys Leu Leu Ile Tyr Lys Val Ser Asn Arg Phe Ser Gly Val
                85                  90                  95

Pro Asp Arg Phe Ser Gly Ser Gly Ser Gly Thr Asp Phe Thr Leu Lys
            100                 105                 110

Ile Ser Arg Val Glu Ala Glu Asp Leu Gly Val Tyr Tyr Cys Phe Gln
        115                 120                 125

Gly Ser His Val Pro Tyr Thr Phe Gly Gly Gly Thr Lys Leu Glu Ile
    130                 135                 140

Lys Arg Ala Asp Ala Ala Pro Thr Val Ser Ile Phe Pro Pro Ser Ser
145                 150                 155                 160

Glu Gln Leu Thr Ser Gly Gly Ala Ser Val Val Cys Phe Leu Asn Asn
                165                 170                 175

Phe Tyr Pro Lys Asp Ile Asn Val Lys Trp Lys Ile Asp Gly Ser Glu
            180                 185                 190

Arg Gln Asn Gly Val Leu Asn Ser Trp Thr Asp Gln Asp Ser Lys Asp
        195                 200                 205

Ser Thr Tyr Ser Met Ser Ser Thr Leu Thr Leu Thr Lys Asp Glu Tyr
    210                 215                 220

Glu Arg His Asn Ser Tyr Thr Cys Glu Ala Thr His Lys Thr Ser Thr
225                 230                 235                 240

Ser Pro Ile Val Lys Ser Phe Asn Arg Asn Glu Cys
            245                 250

<210> SEQ ID NO 247
<211> LENGTH: 252
<212> TYPE: PRT
<213> ORGANISM: Artificial Sequence
```

```
<220> FEATURE:
<223> OTHER INFORMATION: Synthetic Construct

<400> SEQUENCE: 247

Ala Cys Asn Leu Ile Val Glu Gly His Cys Gly Gly Ser Ser Gly
1               5                   10                  15

Gly Ser Thr Ser Thr Ser Gly Arg Ser Ala Asn Pro Arg Gly Gly
                20                  25                  30

Ser Asp Ile Val Met Thr Gln Thr Thr Leu Ser Leu Pro Val Ser Leu
            35                  40                  45

Gly Asp Gln Ala Ser Ile Ser Cys Arg Ser Ser Gln Ser Ile Val His
        50                  55                  60

Ser Asn Gly Asn Thr Tyr Leu Glu Trp Tyr Leu Gln Lys Pro Gly Gln
65                  70                  75                  80

Ser Pro Lys Leu Leu Ile Tyr Lys Val Ser Asn Arg Phe Ser Gly Val
                85                  90                  95

Pro Asp Arg Phe Ser Gly Ser Gly Ser Gly Thr Asp Phe Thr Leu Lys
                100                 105                 110

Ile Ser Arg Val Glu Ala Glu Asp Leu Gly Val Tyr Tyr Cys Phe Gln
            115                 120                 125

Gly Ser His Val Pro Tyr Thr Phe Gly Gly Gly Thr Lys Leu Glu Ile
        130                 135                 140

Lys Arg Ala Asp Ala Ala Pro Thr Val Ser Ile Phe Pro Pro Ser Ser
145                 150                 155                 160

Glu Gln Leu Thr Ser Gly Gly Ala Ser Val Val Cys Phe Leu Asn Asn
                165                 170                 175

Phe Tyr Pro Lys Asp Ile Asn Val Lys Trp Lys Ile Asp Gly Ser Glu
                180                 185                 190

Arg Gln Asn Gly Val Leu Asn Ser Trp Thr Asp Gln Asp Ser Lys Asp
            195                 200                 205

Ser Thr Tyr Ser Met Ser Ser Thr Leu Thr Leu Thr Lys Asp Glu Tyr
        210                 215                 220

Glu Arg His Asn Ser Tyr Thr Cys Glu Ala Thr His Lys Thr Ser Thr
225                 230                 235                 240

Ser Pro Ile Val Lys Ser Phe Asn Arg Asn Glu Cys
                245                 250

<210> SEQ ID NO 248
<211> LENGTH: 252
<212> TYPE: PRT
<213> ORGANISM: Artificial Sequence
<220> FEATURE:
<223> OTHER INFORMATION: Synthetic Construct

<400> SEQUENCE: 248

Ala Cys Pro Asp His Val Phe Pro Lys Cys Gly Gly Ser Ser Gly
1               5                   10                  15

Gly Ser Thr Ser Thr Ser Gly Arg Ser Ala Asn Pro Arg Gly Gly
                20                  25                  30

Ser Asp Ile Val Met Thr Gln Thr Thr Leu Ser Leu Pro Val Ser Leu
            35                  40                  45

Gly Asp Gln Ala Ser Ile Ser Cys Arg Ser Ser Gln Ser Ile Val His
        50                  55                  60

Ser Asn Gly Asn Thr Tyr Leu Glu Trp Tyr Leu Gln Lys Pro Gly Gln
65                  70                  75                  80

Ser Pro Lys Leu Leu Ile Tyr Lys Val Ser Asn Arg Phe Ser Gly Val
```

```
            85                   90                   95
Pro Asp Arg Phe Ser Gly Ser Gly Ser Gly Thr Asp Phe Thr Leu Lys
                100                 105                 110

Ile Ser Arg Val Glu Ala Glu Asp Leu Gly Val Tyr Tyr Cys Phe Gln
            115                 120                 125

Gly Ser His Val Pro Tyr Thr Phe Gly Gly Gly Thr Lys Leu Glu Ile
        130                 135                 140

Lys Arg Ala Asp Ala Ala Pro Thr Val Ser Ile Phe Pro Pro Ser Ser
145                 150                 155                 160

Glu Gln Leu Thr Ser Gly Gly Ala Ser Val Val Cys Phe Leu Asn Asn
                165                 170                 175

Phe Tyr Pro Lys Asp Ile Asn Val Lys Trp Lys Ile Asp Gly Ser Glu
            180                 185                 190

Arg Gln Asn Gly Val Leu Asn Ser Trp Thr Asp Gln Asp Ser Lys Asp
        195                 200                 205

Ser Thr Tyr Ser Met Ser Ser Thr Leu Thr Leu Thr Lys Asp Glu Tyr
    210                 215                 220

Glu Arg His Asn Ser Tyr Thr Cys Glu Ala Thr His Lys Thr Ser Thr
225                 230                 235                 240

Ser Pro Ile Val Lys Ser Phe Asn Arg Asn Glu Cys
                245                 250

<210> SEQ ID NO 249
<211> LENGTH: 252
<212> TYPE: PRT
<213> ORGANISM: Artificial Sequence
<220> FEATURE:
<223> OTHER INFORMATION: Synthetic Construct

<400> SEQUENCE: 249

Ala Cys Trp Leu Pro Lys Pro Asp Met Cys Gly Gly Ser Ser Gly
1               5                  10                  15

Gly Ser Thr Ser Thr Ser Gly Arg Ser Ala Asn Pro Arg Gly Gly Gly
            20                  25                  30

Ser Asp Ile Val Met Thr Gln Thr Thr Leu Ser Leu Pro Val Ser Leu
        35                  40                  45

Gly Asp Gln Ala Ser Ile Ser Cys Arg Ser Ser Gln Ser Ile Val His
    50                  55                  60

Ser Asn Gly Asn Thr Tyr Leu Glu Trp Tyr Leu Gln Lys Pro Gly Gln
65                  70                  75                  80

Ser Pro Lys Leu Leu Ile Tyr Lys Val Ser Asn Arg Phe Ser Gly Val
                85                  90                  95

Pro Asp Arg Phe Ser Gly Ser Gly Ser Gly Thr Asp Phe Thr Leu Lys
                100                 105                 110

Ile Ser Arg Val Glu Ala Glu Asp Leu Gly Val Tyr Tyr Cys Phe Gln
            115                 120                 125

Gly Ser His Val Pro Tyr Thr Phe Gly Gly Gly Thr Lys Leu Glu Ile
        130                 135                 140

Lys Arg Ala Asp Ala Ala Pro Thr Val Ser Ile Phe Pro Pro Ser Ser
145                 150                 155                 160

Glu Gln Leu Thr Ser Gly Gly Ala Ser Val Val Cys Phe Leu Asn Asn
                165                 170                 175

Phe Tyr Pro Lys Asp Ile Asn Val Lys Trp Lys Ile Asp Gly Ser Glu
            180                 185                 190

Arg Gln Asn Gly Val Leu Asn Ser Trp Thr Asp Gln Asp Ser Lys Asp
```

```
                195                 200                 205
Ser Thr Tyr Ser Met Ser Ser Thr Leu Thr Leu Thr Lys Asp Glu Tyr
210                 215                 220

Glu Arg His Asn Ser Tyr Thr Cys Glu Ala Thr His Lys Thr Ser Thr
225                 230                 235                 240

Ser Pro Ile Val Lys Ser Phe Asn Arg Asn Glu Cys
                245                 250

<210> SEQ ID NO 250
<211> LENGTH: 252
<212> TYPE: PRT
<213> ORGANISM: Artificial Sequence
<220> FEATURE:
<223> OTHER INFORMATION: Synthetic Construct

<400> SEQUENCE: 250

Ala Cys Trp Ser Trp Pro Ser Lys Ala Cys Gly Gly Ser Ser Gly
1               5                   10                  15

Gly Ser Thr Ser Thr Ser Gly Arg Ser Ala Asn Pro Arg Gly Gly Gly
                20                  25                  30

Ser Asp Ile Val Met Thr Gln Thr Thr Leu Ser Leu Pro Val Ser Leu
                35                  40                  45

Gly Asp Gln Ala Ser Ile Ser Cys Arg Ser Ser Gln Ser Ile Val His
50                  55                  60

Ser Asn Gly Asn Thr Tyr Leu Glu Trp Tyr Leu Gln Lys Pro Gly Gln
65                  70                  75                  80

Ser Pro Lys Leu Leu Ile Tyr Lys Val Ser Asn Arg Phe Ser Gly Val
                85                  90                  95

Pro Asp Arg Phe Ser Gly Ser Gly Ser Gly Thr Asp Phe Thr Leu Lys
                100                 105                 110

Ile Ser Arg Val Glu Ala Glu Asp Leu Gly Val Tyr Tyr Cys Phe Gln
                115                 120                 125

Gly Ser His Val Pro Tyr Thr Phe Gly Gly Gly Thr Lys Leu Glu Ile
                130                 135                 140

Lys Arg Ala Asp Ala Ala Pro Thr Val Ser Ile Phe Pro Pro Ser Ser
145                 150                 155                 160

Glu Gln Leu Thr Ser Gly Gly Ala Ser Val Val Cys Phe Leu Asn Asn
                165                 170                 175

Phe Tyr Pro Lys Asp Ile Asn Val Lys Trp Lys Ile Asp Gly Ser Glu
                180                 185                 190

Arg Gln Asn Gly Val Leu Asn Ser Trp Thr Asp Gln Asp Ser Lys Asp
                195                 200                 205

Ser Thr Tyr Ser Met Ser Ser Thr Leu Thr Leu Thr Lys Asp Glu Tyr
210                 215                 220

Glu Arg His Asn Ser Tyr Thr Cys Glu Ala Thr His Lys Thr Ser Thr
225                 230                 235                 240

Ser Pro Ile Val Lys Ser Phe Asn Arg Asn Glu Cys
                245                 250

<210> SEQ ID NO 251
<211> LENGTH: 252
<212> TYPE: PRT
<213> ORGANISM: Artificial Sequence
<220> FEATURE:
<223> OTHER INFORMATION: Synthetic Construct

<400> SEQUENCE: 251
```

Ala Cys Tyr Pro Phe Gly Lys Tyr Glu Cys Gly Gly Ser Ser Gly
1               5                   10                  15

Gly Ser Thr Ser Thr Ser Gly Arg Ser Ala Asn Pro Arg Gly Gly
                20                  25                  30

Ser Asp Ile Val Met Thr Gln Thr Thr Leu Ser Leu Pro Val Ser Leu
                35                  40                  45

Gly Asp Gln Ala Ser Ile Ser Cys Arg Ser Ser Gln Ser Ile Val His
50                  55                  60

Ser Asn Gly Asn Thr Tyr Leu Glu Trp Tyr Leu Gln Lys Pro Gly Gln
65                  70                  75                  80

Ser Pro Lys Leu Leu Ile Tyr Lys Val Ser Asn Arg Phe Ser Gly Val
                85                  90                  95

Pro Asp Arg Phe Ser Gly Ser Gly Ser Gly Thr Asp Phe Thr Leu Lys
                100                 105                 110

Ile Ser Arg Val Glu Ala Glu Asp Leu Gly Val Tyr Tyr Cys Phe Gln
                115                 120                 125

Gly Ser His Val Pro Tyr Thr Phe Gly Gly Gly Thr Lys Leu Glu Ile
                130                 135                 140

Lys Arg Ala Asp Ala Ala Pro Thr Val Ser Ile Phe Pro Pro Ser Ser
145                 150                 155                 160

Glu Gln Leu Thr Ser Gly Gly Ala Ser Val Val Cys Phe Leu Asn Asn
                165                 170                 175

Phe Tyr Pro Lys Asp Ile Asn Val Lys Trp Lys Ile Asp Gly Ser Glu
                180                 185                 190

Arg Gln Asn Gly Val Leu Asn Ser Trp Thr Asp Gln Asp Ser Lys Asp
                195                 200                 205

Ser Thr Tyr Ser Met Ser Ser Thr Leu Thr Leu Thr Lys Asp Glu Tyr
210                 215                 220

Glu Arg His Asn Ser Tyr Thr Cys Glu Ala Thr His Lys Thr Ser Thr
225                 230                 235                 240

Ser Pro Ile Val Lys Ser Phe Asn Arg Asn Glu Cys
                245                 250

<210> SEQ ID NO 252
<211> LENGTH: 254
<212> TYPE: PRT
<213> ORGANISM: Artificial Sequence
<220> FEATURE:
<223> OTHER INFORMATION: Synthetic Construct

<400> SEQUENCE: 252

Ala Leu Thr Pro Ala Lys Trp Leu Pro Ala Asp Asp Gly Gly Gly Ser
1               5                   10                  15

Ser Gly Gly Ser Thr Ser Thr Ser Gly Arg Ser Ala Asn Pro Arg Gly
                20                  25                  30

Gly Gly Ser Asp Ile Val Met Thr Gln Thr Thr Leu Ser Leu Pro Val
                35                  40                  45

Ser Leu Gly Asp Gln Ala Ser Ile Ser Cys Arg Ser Ser Gln Ser Ile
50                  55                  60

Val His Ser Asn Gly Asn Thr Tyr Leu Glu Trp Tyr Leu Gln Lys Pro
65                  70                  75                  80

Gly Gln Ser Pro Lys Leu Leu Ile Tyr Lys Val Ser Asn Arg Phe Ser
                85                  90                  95

Gly Val Pro Asp Arg Phe Ser Gly Ser Gly Ser Gly Thr Asp Phe Thr
                100                 105                 110

```
Leu Lys Ile Ser Arg Val Glu Ala Glu Asp Leu Gly Val Tyr Tyr Cys
            115                 120                 125

Phe Gln Gly Ser His Val Pro Tyr Thr Phe Gly Gly Gly Thr Lys Leu
        130                 135                 140

Glu Ile Lys Arg Ala Asp Ala Ala Pro Thr Val Ser Ile Phe Pro Pro
145                 150                 155                 160

Ser Ser Glu Gln Leu Thr Ser Gly Gly Ala Ser Val Val Cys Phe Leu
                165                 170                 175

Asn Asn Phe Tyr Pro Lys Asp Ile Asn Val Lys Trp Lys Ile Asp Gly
            180                 185                 190

Ser Glu Arg Gln Asn Gly Val Leu Asn Ser Trp Thr Asp Gln Asp Ser
        195                 200                 205

Lys Asp Ser Thr Tyr Ser Met Ser Ser Thr Leu Thr Leu Thr Lys Asp
210                 215                 220

Glu Tyr Glu Arg His Asn Ser Tyr Thr Cys Glu Ala Thr His Lys Thr
225                 230                 235                 240

Ser Thr Ser Pro Ile Val Lys Ser Phe Asn Arg Asn Glu Cys
                245                 250

<210> SEQ ID NO 253
<211> LENGTH: 258
<212> TYPE: PRT
<213> ORGANISM: Artificial Sequence
<220> FEATURE:
<223> OTHER INFORMATION: Synthetic Construct

<400> SEQUENCE: 253

Asp Asp Lys Glu Cys Asp Trp Met His Phe Ala Cys Thr Gly Pro Gln
1               5                   10                  15

Gly Gly Gly Ser Ser Gly Gly Ser Thr Ser Thr Ser Gly Arg Ser Ala
            20                  25                  30

Asn Pro Arg Gly Gly Gly Ser Asp Ile Val Met Thr Gln Thr Thr Leu
        35                  40                  45

Ser Leu Pro Val Ser Leu Gly Asp Gln Ala Ser Ile Ser Cys Arg Ser
    50                  55                  60

Ser Gln Ser Ile Val His Ser Asn Gly Asn Thr Tyr Leu Glu Trp Tyr
65                  70                  75                  80

Leu Gln Lys Pro Gly Gln Ser Pro Lys Leu Leu Ile Tyr Lys Val Ser
                85                  90                  95

Asn Arg Phe Ser Gly Val Pro Asp Arg Phe Ser Gly Ser Gly Ser Gly
            100                 105                 110

Thr Asp Phe Thr Leu Lys Ile Ser Arg Val Glu Ala Glu Asp Leu Gly
        115                 120                 125

Val Tyr Tyr Cys Phe Gln Gly Ser His Val Pro Tyr Thr Phe Gly Gly
    130                 135                 140

Gly Thr Lys Leu Glu Ile Lys Arg Ala Asp Ala Ala Pro Thr Val Ser
145                 150                 155                 160

Ile Phe Pro Pro Ser Ser Glu Gln Leu Thr Ser Gly Gly Ala Ser Val
                165                 170                 175

Val Cys Phe Leu Asn Asn Phe Tyr Pro Lys Asp Ile Asn Val Lys Trp
            180                 185                 190

Lys Ile Asp Gly Ser Glu Arg Gln Asn Gly Val Leu Asn Ser Trp Thr
        195                 200                 205

Asp Gln Asp Ser Lys Asp Ser Thr Tyr Ser Met Ser Ser Thr Leu Thr
    210                 215                 220
```

```
Leu Thr Lys Asp Glu Tyr Glu Arg His Asn Ser Tyr Thr Cys Glu Ala
225                 230                 235                 240

Thr His Lys Thr Ser Thr Ser Pro Ile Val Lys Ser Phe Asn Arg Asn
                245                 250                 255

Glu Cys
```

<210> SEQ ID NO 254
<211> LENGTH: 258
<212> TYPE: PRT
<213> ORGANISM: Artificial Sequence
<220> FEATURE:
<223> OTHER INFORMATION: Synthetic Construct

<400> SEQUENCE: 254

```
Asp Glu Met Lys Cys Ala Trp Ser Leu Glu Met Cys Val Arg Thr Ser
1               5                   10                  15

Gly Gly Gly Ser Ser Gly Gly Ser Thr Ser Thr Ser Gly Arg Ser Ala
                20                  25                  30

Asn Pro Arg Gly Gly Gly Ser Asp Ile Val Met Thr Gln Thr Thr Leu
            35                  40                  45

Ser Leu Pro Val Ser Leu Gly Asp Gln Ala Ser Ile Ser Cys Arg Ser
50                  55                  60

Ser Gln Ser Ile Val His Ser Asn Gly Asn Thr Tyr Leu Glu Trp Tyr
65                  70                  75                  80

Leu Gln Lys Pro Gly Gln Ser Pro Lys Leu Leu Ile Tyr Lys Val Ser
                85                  90                  95

Asn Arg Phe Ser Gly Val Pro Asp Arg Phe Ser Gly Ser Gly Ser Gly
            100                 105                 110

Thr Asp Phe Thr Leu Lys Ile Ser Arg Val Glu Ala Glu Asp Leu Gly
        115                 120                 125

Val Tyr Tyr Cys Phe Gln Gly Ser His Val Pro Tyr Thr Phe Gly Gly
    130                 135                 140

Gly Thr Lys Leu Glu Ile Lys Arg Ala Asp Ala Ala Pro Thr Val Ser
145                 150                 155                 160

Ile Phe Pro Pro Ser Ser Glu Gln Leu Thr Ser Gly Gly Ala Ser Val
                165                 170                 175

Val Cys Phe Leu Asn Asn Phe Tyr Pro Lys Asp Ile Asn Val Lys Trp
            180                 185                 190

Lys Ile Asp Gly Ser Glu Arg Gln Asn Gly Val Leu Asn Ser Trp Thr
        195                 200                 205

Asp Gln Asp Ser Lys Asp Ser Thr Tyr Ser Met Ser Ser Thr Leu Thr
    210                 215                 220

Leu Thr Lys Asp Glu Tyr Glu Arg His Asn Ser Tyr Thr Cys Glu Ala
225                 230                 235                 240

Thr His Lys Thr Ser Thr Ser Pro Ile Val Lys Ser Phe Asn Arg Asn
                245                 250                 255

Glu Cys
```

<210> SEQ ID NO 255
<211> LENGTH: 258
<212> TYPE: PRT
<213> ORGANISM: Artificial Sequence
<220> FEATURE:
<223> OTHER INFORMATION: Synthetic Construct

<400> SEQUENCE: 255

Asp Pro Ile Leu Cys Pro Asn Thr Arg Met Ser Cys Asp Asn Gln Thr

```
            1               5                  10                 15
Gly Gly Gly Ser Ser Gly Gly Ser Thr Ser Thr Ser Gly Arg Ser Ala
                20                  25                 30
Asn Pro Arg Gly Gly Gly Ser Asp Ile Val Met Thr Gln Thr Thr Leu
                35                  40                 45
Ser Leu Pro Val Ser Leu Gly Asp Gln Ala Ser Ile Ser Cys Arg Ser
 50                      55                  60
Ser Gln Ser Ile Val His Ser Asn Gly Asn Thr Tyr Leu Glu Trp Tyr
 65                  70                  75                  80
Leu Gln Lys Pro Gly Gln Ser Pro Lys Leu Leu Ile Tyr Lys Val Ser
                85                  90                  95
Asn Arg Phe Ser Gly Val Pro Asp Arg Phe Ser Gly Ser Gly Ser Gly
                100                 105                110
Thr Asp Phe Thr Leu Lys Ile Ser Arg Val Glu Ala Glu Asp Leu Gly
                115                 120                125
Val Tyr Tyr Cys Phe Gln Gly Ser His Val Pro Tyr Thr Phe Gly Gly
                130                 135                140
Gly Thr Lys Leu Glu Ile Lys Arg Ala Asp Ala Ala Pro Thr Val Ser
145                 150                 155                 160
Ile Phe Pro Pro Ser Ser Glu Gln Leu Thr Ser Gly Gly Ala Ser Val
                165                 170                 175
Val Cys Phe Leu Asn Asn Phe Tyr Pro Lys Asp Ile Asn Val Lys Trp
                180                 185                 190
Lys Ile Asp Gly Ser Glu Arg Gln Asn Gly Val Leu Asn Ser Trp Thr
                195                 200                 205
Asp Gln Asp Ser Lys Asp Ser Thr Tyr Ser Met Ser Ser Thr Leu Thr
                210                 215                 220
Leu Thr Lys Asp Glu Tyr Glu Arg His Asn Ser Tyr Thr Cys Glu Ala
225                 230                 235                 240
Thr His Lys Thr Ser Thr Ser Pro Ile Val Lys Ser Phe Asn Arg Asn
                245                 250                 255
Glu Cys

<210> SEQ ID NO 256
<211> LENGTH: 254
<212> TYPE: PRT
<213> ORGANISM: Artificial Sequence
<220> FEATURE:
<223> OTHER INFORMATION: Synthetic Construct

<400> SEQUENCE: 256

Gly Asn Ala Leu Tyr Asp Ser Pro Gly Thr Met Leu Gly Gly Gly Ser
 1               5                  10                 15
Ser Gly Gly Ser Thr Ser Thr Ser Gly Arg Ser Ala Asn Pro Arg Gly
                20                  25                 30
Gly Gly Ser Asp Ile Val Met Thr Gln Thr Thr Leu Ser Leu Pro Val
                35                  40                 45
Ser Leu Gly Asp Gln Ala Ser Ile Ser Cys Arg Ser Ser Gln Ser Ile
 50                      55                  60
Val His Ser Asn Gly Asn Thr Tyr Leu Glu Trp Tyr Leu Gln Lys Pro
 65                  70                  75                  80
Gly Gln Ser Pro Lys Leu Leu Ile Tyr Lys Val Ser Asn Arg Phe Ser
                85                  90                  95
Gly Val Pro Asp Arg Phe Ser Gly Ser Gly Ser Gly Thr Asp Phe Thr
                100                 105                110
```

```
Leu Lys Ile Ser Arg Val Glu Ala Glu Asp Leu Gly Val Tyr Tyr Cys
            115                 120                 125
Phe Gln Gly Ser His Val Pro Tyr Thr Phe Gly Gly Gly Thr Lys Leu
    130                 135                 140
Glu Ile Lys Arg Ala Asp Ala Ala Pro Thr Val Ser Ile Phe Pro Pro
145                 150                 155                 160
Ser Ser Glu Gln Leu Thr Ser Gly Gly Ala Ser Val Val Cys Phe Leu
                165                 170                 175
Asn Asn Phe Tyr Pro Lys Asp Ile Asn Val Lys Trp Lys Ile Asp Gly
                180                 185                 190
Ser Glu Arg Gln Asn Gly Val Leu Asn Ser Trp Thr Asp Gln Asp Ser
            195                 200                 205
Lys Asp Ser Thr Tyr Ser Met Ser Ser Thr Leu Thr Leu Thr Lys Asp
210                 215                 220
Glu Tyr Glu Arg His Asn Ser Tyr Thr Cys Glu Ala Thr His Lys Thr
225                 230                 235                 240
Ser Thr Ser Pro Ile Val Lys Ser Phe Asn Arg Asn Glu Cys
                245                 250

<210> SEQ ID NO 257
<211> LENGTH: 258
<212> TYPE: PRT
<213> ORGANISM: Artificial Sequence
<220> FEATURE:
<223> OTHER INFORMATION: Synthetic Construct

<400> SEQUENCE: 257

Lys Asn Tyr Glu Cys Arg Glu Val Met Pro Pro Cys Glu Pro Asn Thr
1               5                   10                  15
Gly Gly Gly Ser Ser Gly Gly Ser Thr Ser Thr Ser Gly Arg Ser Ala
                20                  25                  30
Asn Pro Arg Gly Gly Gly Ser Asp Ile Val Met Thr Gln Thr Thr Leu
            35                  40                  45
Ser Leu Pro Val Ser Leu Gly Asp Gln Ala Ser Ile Ser Cys Arg Ser
50                  55                  60
Ser Gln Ser Ile Val His Ser Asn Gly Asn Thr Tyr Leu Glu Trp Tyr
65                  70                  75                  80
Leu Gln Lys Pro Gly Gln Ser Pro Lys Leu Leu Ile Tyr Lys Val Ser
                85                  90                  95
Asn Arg Phe Ser Gly Val Pro Asp Arg Phe Ser Gly Ser Gly Ser Gly
                100                 105                 110
Thr Asp Phe Thr Leu Lys Ile Ser Arg Val Glu Ala Glu Asp Leu Gly
            115                 120                 125
Val Tyr Tyr Cys Phe Gln Gly Ser His Val Pro Tyr Thr Phe Gly Gly
    130                 135                 140
Gly Thr Lys Leu Glu Ile Lys Arg Ala Asp Ala Ala Pro Thr Val Ser
145                 150                 155                 160
Ile Phe Pro Pro Ser Ser Glu Gln Leu Thr Ser Gly Gly Ala Ser Val
                165                 170                 175
Val Cys Phe Leu Asn Asn Phe Tyr Pro Lys Asp Ile Asn Val Lys Trp
                180                 185                 190
Lys Ile Asp Gly Ser Glu Arg Gln Asn Gly Val Leu Asn Ser Trp Thr
            195                 200                 205
Asp Gln Asp Ser Lys Asp Ser Thr Tyr Ser Met Ser Ser Thr Leu Thr
210                 215                 220
```

```
Leu Thr Lys Asp Glu Tyr Glu Arg His Asn Ser Tyr Thr Cys Glu Ala
225                 230                 235                 240

Thr His Lys Thr Ser Thr Ser Pro Ile Val Lys Ser Phe Asn Arg Asn
                245                 250                 255

Glu Cys

<210> SEQ ID NO 258
<211> LENGTH: 254
<212> TYPE: PRT
<213> ORGANISM: Artificial Sequence
<220> FEATURE:
<223> OTHER INFORMATION: Synthetic Construct

<400> SEQUENCE: 258

Asn Ser Tyr Thr Ser Pro Tyr Trp Leu Pro Asp Ser Gly Gly Gly Ser
1               5                   10                  15

Ser Gly Gly Ser Thr Ser Thr Ser Gly Arg Ser Ala Asn Pro Arg Gly
                20                  25                  30

Gly Gly Ser Asp Ile Val Met Thr Gln Thr Thr Leu Ser Leu Pro Val
            35                  40                  45

Ser Leu Gly Asp Gln Ala Ser Ile Ser Cys Arg Ser Ser Gln Ser Ile
    50                  55                  60

Val His Ser Asn Gly Asn Thr Tyr Leu Glu Trp Tyr Leu Gln Lys Pro
65                  70                  75                  80

Gly Gln Ser Pro Lys Leu Leu Ile Tyr Lys Val Ser Asn Arg Phe Ser
                85                  90                  95

Gly Val Pro Asp Arg Phe Ser Gly Ser Gly Ser Gly Thr Asp Phe Thr
            100                 105                 110

Leu Lys Ile Ser Arg Val Glu Ala Glu Asp Leu Gly Val Tyr Tyr Cys
        115                 120                 125

Phe Gln Gly Ser His Val Pro Tyr Thr Phe Gly Gly Gly Thr Lys Leu
    130                 135                 140

Glu Ile Lys Arg Ala Asp Ala Ala Pro Thr Val Ser Ile Phe Pro Pro
145                 150                 155                 160

Ser Ser Glu Gln Leu Thr Ser Gly Gly Ala Ser Val Val Cys Phe Leu
                165                 170                 175

Asn Asn Phe Tyr Pro Lys Asp Ile Asn Val Lys Trp Lys Ile Asp Gly
            180                 185                 190

Ser Glu Arg Gln Asn Gly Val Leu Asn Ser Trp Thr Asp Gln Asp Ser
        195                 200                 205

Lys Asp Ser Thr Tyr Ser Met Ser Ser Thr Leu Thr Leu Thr Lys Asp
    210                 215                 220

Glu Tyr Glu Arg His Asn Ser Tyr Thr Cys Glu Ala Thr His Lys Thr
225                 230                 235                 240

Ser Thr Ser Pro Ile Val Lys Ser Phe Asn Arg Asn Glu Cys
                245                 250

<210> SEQ ID NO 259
<211> LENGTH: 254
<212> TYPE: PRT
<213> ORGANISM: Artificial Sequence
<220> FEATURE:
<223> OTHER INFORMATION: Synthetic Construct

<400> SEQUENCE: 259

Ser Leu Thr Pro Pro Tyr Trp Ile Pro Arg Glu Trp Gly Gly Gly Ser
1               5                   10                  15
```

Ser Gly Gly Ser Thr Ser Thr Ser Gly Arg Ser Ala Asn Pro Arg Gly
            20                  25                  30

Gly Gly Ser Asp Ile Val Met Thr Gln Thr Thr Leu Ser Leu Pro Val
        35                  40                  45

Ser Leu Gly Asp Gln Ala Ser Ile Ser Cys Arg Ser Ser Gln Ser Ile
    50                  55                  60

Val His Ser Asn Gly Asn Thr Tyr Leu Glu Trp Tyr Leu Gln Lys Pro
65                  70                  75                  80

Gly Gln Ser Pro Lys Leu Leu Ile Tyr Lys Val Ser Asn Arg Phe Ser
                85                  90                  95

Gly Val Pro Asp Arg Phe Ser Gly Ser Gly Ser Gly Thr Asp Phe Thr
            100                 105                 110

Leu Lys Ile Ser Arg Val Glu Ala Glu Asp Leu Gly Val Tyr Tyr Cys
        115                 120                 125

Phe Gln Gly Ser His Val Pro Tyr Thr Phe Gly Gly Gly Thr Lys Leu
130                 135                 140

Glu Ile Lys Arg Ala Asp Ala Ala Pro Thr Val Ser Ile Phe Pro Pro
145                 150                 155                 160

Ser Ser Glu Gln Leu Thr Ser Gly Gly Ala Ser Val Val Cys Phe Leu
                165                 170                 175

Asn Asn Phe Tyr Pro Lys Asp Ile Asn Val Lys Trp Lys Ile Asp Gly
            180                 185                 190

Ser Glu Arg Gln Asn Gly Val Leu Asn Ser Trp Thr Asp Gln Asp Ser
        195                 200                 205

Lys Asp Ser Thr Tyr Ser Met Ser Ser Thr Leu Thr Leu Thr Lys Asp
210                 215                 220

Glu Tyr Glu Arg His Asn Ser Tyr Thr Cys Glu Ala Thr His Lys Thr
225                 230                 235                 240

Ser Thr Ser Pro Ile Val Lys Ser Phe Asn Arg Asn Glu Cys
                245                 250

<210> SEQ ID NO 260
<211> LENGTH: 254
<212> TYPE: PRT
<213> ORGANISM: Artificial Sequence
<220> FEATURE:
<223> OTHER INFORMATION: Synthetic Construct

<400> SEQUENCE: 260

Ser Pro Leu Thr Pro His Asp Arg Pro Ser Phe Leu Gly Gly Gly Ser
1               5                   10                  15

Ser Gly Gly Ser Thr Ser Thr Ser Gly Arg Ser Ala Asn Pro Arg Gly
            20                  25                  30

Gly Gly Ser Asp Ile Val Met Thr Gln Thr Thr Leu Ser Leu Pro Val
        35                  40                  45

Ser Leu Gly Asp Gln Ala Ser Ile Ser Cys Arg Ser Ser Gln Ser Ile
    50                  55                  60

Val His Ser Asn Gly Asn Thr Tyr Leu Glu Trp Tyr Leu Gln Lys Pro
65                  70                  75                  80

Gly Gln Ser Pro Lys Leu Leu Ile Tyr Lys Val Ser Asn Arg Phe Ser
                85                  90                  95

Gly Val Pro Asp Arg Phe Ser Gly Ser Gly Ser Gly Thr Asp Phe Thr
            100                 105                 110

Leu Lys Ile Ser Arg Val Glu Ala Glu Asp Leu Gly Val Tyr Tyr Cys
        115                 120                 125

```
Phe Gln Gly Ser His Val Pro Tyr Thr Phe Gly Gly Thr Lys Leu
    130                 135                 140

Glu Ile Lys Arg Ala Asp Ala Ala Pro Thr Val Ser Ile Phe Pro Pro
145                 150                 155                 160

Ser Ser Glu Gln Leu Thr Ser Gly Gly Ala Ser Val Val Cys Phe Leu
                165                 170                 175

Asn Asn Phe Tyr Pro Lys Asp Ile Asn Val Lys Trp Lys Ile Asp Gly
                180                 185                 190

Ser Glu Arg Gln Asn Gly Val Leu Asn Ser Trp Thr Asp Gln Asp Ser
                195                 200                 205

Lys Asp Ser Thr Tyr Ser Met Ser Ser Thr Leu Thr Leu Thr Lys Asp
                210                 215                 220

Glu Tyr Glu Arg His Asn Ser Tyr Thr Cys Glu Ala Thr His Lys Thr
225                 230                 235                 240

Ser Thr Ser Pro Ile Val Lys Ser Phe Asn Arg Asn Glu Cys
                245                 250
```

<210> SEQ ID NO 261
<211> LENGTH: 254
<212> TYPE: PRT
<213> ORGANISM: Artificial Sequence
<220> FEATURE:
<223> OTHER INFORMATION: Synthetic Construct

<400> SEQUENCE: 261

```
Thr Ala Asp Val Phe Ser Ser Arg Tyr Thr Arg Gly Gly Gly Ser
1               5                   10                  15

Ser Gly Gly Ser Thr Ser Thr Ser Gly Arg Ser Ala Asn Pro Arg Gly
                20                  25                  30

Gly Gly Ser Asp Ile Val Met Thr Gln Thr Thr Leu Ser Leu Pro Val
                35                  40                  45

Ser Leu Gly Asp Gln Ala Ser Ile Ser Cys Arg Ser Ser Gln Ser Ile
            50                  55                  60

Val His Ser Asn Gly Asn Thr Tyr Leu Glu Trp Tyr Leu Gln Lys Pro
65                  70                  75                  80

Gly Gln Ser Pro Lys Leu Leu Ile Tyr Lys Val Ser Asn Arg Phe Ser
                85                  90                  95

Gly Val Pro Asp Arg Phe Ser Gly Ser Gly Ser Gly Thr Asp Phe Thr
                100                 105                 110

Leu Lys Ile Ser Arg Val Glu Ala Glu Asp Leu Gly Val Tyr Tyr Cys
            115                 120                 125

Phe Gln Gly Ser His Val Pro Tyr Thr Phe Gly Gly Gly Thr Lys Leu
    130                 135                 140

Glu Ile Lys Arg Ala Asp Ala Ala Pro Thr Val Ser Ile Phe Pro Pro
145                 150                 155                 160

Ser Ser Glu Gln Leu Thr Ser Gly Gly Ala Ser Val Val Cys Phe Leu
                165                 170                 175

Asn Asn Phe Tyr Pro Lys Asp Ile Asn Val Lys Trp Lys Ile Asp Gly
                180                 185                 190

Ser Glu Arg Gln Asn Gly Val Leu Asn Ser Trp Thr Asp Gln Asp Ser
                195                 200                 205

Lys Asp Ser Thr Tyr Ser Met Ser Ser Thr Leu Thr Leu Thr Lys Asp
                210                 215                 220

Glu Tyr Glu Arg His Asn Ser Tyr Thr Cys Glu Ala Thr His Lys Thr
225                 230                 235                 240
```

```
Ser Thr Ser Pro Ile Val Lys Ser Phe Asn Arg Asn Glu Cys
            245                 250
```

<210> SEQ ID NO 262
<211> LENGTH: 258
<212> TYPE: PRT
<213> ORGANISM: Artificial Sequence
<220> FEATURE:
<223> OTHER INFORMATION: Synthetic Construct

<400> SEQUENCE: 262

```
Thr Asp Leu Gln Cys Pro Pro Ser Ser Ile Cys Gln Ile Glu His
1               5                   10                  15

Gly Gly Gly Ser Ser Gly Gly Ser Thr Ser Thr Ser Gly Arg Ser Ala
                20                  25                  30

Asn Pro Arg Gly Gly Ser Asp Ile Val Met Thr Gln Thr Thr Leu
            35                  40                  45

Ser Leu Pro Val Ser Leu Gly Asp Gln Ala Ser Ile Ser Cys Arg Ser
    50                  55                  60

Ser Gln Ser Ile Val His Ser Asn Gly Asn Thr Tyr Leu Glu Trp Tyr
65              70                  75                  80

Leu Gln Lys Pro Gly Gln Ser Pro Lys Leu Leu Ile Tyr Lys Val Ser
                85                  90                  95

Asn Arg Phe Ser Gly Val Pro Asp Arg Phe Ser Gly Ser Gly Ser Gly
            100                 105                 110

Thr Asp Phe Thr Leu Lys Ile Ser Arg Val Glu Ala Glu Asp Leu Gly
        115                 120                 125

Val Tyr Tyr Cys Phe Gln Gly Ser His Val Pro Tyr Thr Phe Gly Gly
    130                 135                 140

Gly Thr Lys Leu Glu Ile Lys Arg Ala Asp Ala Ala Pro Thr Val Ser
145             150                 155                 160

Ile Phe Pro Pro Ser Ser Glu Gln Leu Thr Ser Gly Gly Ala Ser Val
                165                 170                 175

Val Cys Phe Leu Asn Asn Phe Tyr Pro Lys Asp Ile Asn Val Lys Trp
            180                 185                 190

Lys Ile Asp Gly Ser Glu Arg Gln Asn Gly Val Leu Asn Ser Trp Thr
        195                 200                 205

Asp Gln Asp Ser Lys Asp Ser Thr Tyr Ser Met Ser Ser Thr Leu Thr
    210                 215                 220

Leu Thr Lys Asp Glu Tyr Glu Arg His Asn Ser Tyr Thr Cys Glu Ala
225             230                 235                 240

Thr His Lys Thr Ser Thr Ser Pro Ile Val Lys Ser Phe Asn Arg Asn
                245                 250                 255

Glu Cys
```

<210> SEQ ID NO 263
<211> LENGTH: 258
<212> TYPE: PRT
<213> ORGANISM: Artificial Sequence
<220> FEATURE:
<223> OTHER INFORMATION: Synthetic Construct

<400> SEQUENCE: 263

```
Thr Lys Cys His Cys Asp Gly Asn Cys Val Met Cys Tyr Gln Met Gln
1               5                   10                  15

Gly Gly Gly Ser Ser Gly Gly Ser Thr Ser Thr Ser Gly Arg Ser Ala
                20                  25                  30
```

Asn Pro Arg Gly Gly Gly Ser Asp Ile Val Met Thr Gln Thr Thr Leu
                35                  40                  45

Ser Leu Pro Val Ser Leu Gly Asp Gln Ala Ser Ile Ser Cys Arg Ser
    50                  55                  60

Ser Gln Ser Ile Val His Ser Asn Gly Asn Thr Tyr Leu Glu Trp Tyr
65                  70                  75                  80

Leu Gln Lys Pro Gly Gln Ser Pro Lys Leu Leu Ile Tyr Lys Val Ser
                85                  90                  95

Asn Arg Phe Ser Gly Val Pro Asp Arg Phe Ser Gly Ser Gly Ser Gly
            100                 105                 110

Thr Asp Phe Thr Leu Lys Ile Ser Arg Val Glu Ala Glu Asp Leu Gly
            115                 120                 125

Val Tyr Tyr Cys Phe Gln Gly Ser His Val Pro Tyr Thr Phe Gly Gly
        130                 135                 140

Gly Thr Lys Leu Glu Ile Lys Arg Ala Asp Ala Ala Pro Thr Val Ser
145                 150                 155                 160

Ile Phe Pro Pro Ser Ser Glu Gln Leu Thr Ser Gly Gly Ala Ser Val
                165                 170                 175

Val Cys Phe Leu Asn Asn Phe Tyr Pro Lys Asp Ile Asn Val Lys Trp
            180                 185                 190

Lys Ile Asp Gly Ser Glu Arg Gln Asn Gly Val Leu Asn Ser Trp Thr
        195                 200                 205

Asp Gln Asp Ser Lys Asp Ser Thr Tyr Ser Met Ser Ser Thr Leu Thr
    210                 215                 220

Leu Thr Lys Asp Glu Tyr Glu Arg His Asn Ser Tyr Thr Cys Glu Ala
225                 230                 235                 240

Thr His Lys Thr Ser Thr Ser Pro Ile Val Lys Ser Phe Asn Arg Asn
                245                 250                 255

Glu Cys

<210> SEQ ID NO 264
<211> LENGTH: 254
<212> TYPE: PRT
<213> ORGANISM: Artificial Sequence
<220> FEATURE:
<223> OTHER INFORMATION: Synthetic Construct

<400> SEQUENCE: 264

Thr Leu Ala Tyr Glu Thr Pro Leu Leu Trp Leu Pro Gly Gly Gly Ser
1               5                   10                  15

Ser Gly Gly Ser Thr Ser Thr Ser Gly Arg Ser Ala Asn Pro Arg Gly
            20                  25                  30

Gly Gly Ser Asp Ile Val Met Thr Gln Thr Thr Leu Ser Leu Pro Val
        35                  40                  45

Ser Leu Gly Asp Gln Ala Ser Ile Ser Cys Arg Ser Ser Gln Ser Ile
    50                  55                  60

Val His Ser Asn Gly Asn Thr Tyr Leu Glu Trp Tyr Leu Gln Lys Pro
65                  70                  75                  80

Gly Gln Ser Pro Lys Leu Leu Ile Tyr Lys Val Ser Asn Arg Phe Ser
                85                  90                  95

Gly Val Pro Asp Arg Phe Ser Gly Ser Gly Ser Gly Thr Asp Phe Thr
            100                 105                 110

Leu Lys Ile Ser Arg Val Glu Ala Glu Asp Leu Gly Val Tyr Tyr Cys
        115                 120                 125

Phe Gln Gly Ser His Val Pro Tyr Thr Phe Gly Gly Gly Thr Lys Leu
130                 135                 140

Glu Ile Lys Arg Ala Asp Ala Ala Pro Thr Val Ser Ile Phe Pro Pro
145                 150                 155                 160

Ser Ser Glu Gln Leu Thr Ser Gly Gly Ala Ser Val Val Cys Phe Leu
            165                 170                 175

Asn Asn Phe Tyr Pro Lys Asp Ile Asn Val Lys Trp Lys Ile Asp Gly
            180                 185                 190

Ser Glu Arg Gln Asn Gly Val Leu Asn Ser Trp Thr Asp Gln Asp Ser
        195                 200                 205

Lys Asp Ser Thr Tyr Ser Met Ser Ser Thr Leu Thr Leu Thr Lys Asp
210                 215                 220

Glu Tyr Glu Arg His Asn Ser Tyr Thr Cys Glu Ala Thr His Lys Thr
225                 230                 235                 240

Ser Thr Ser Pro Ile Val Lys Ser Phe Asn Arg Asn Glu Cys
            245                 250

<210> SEQ ID NO 265
<211> LENGTH: 258
<212> TYPE: PRT
<213> ORGANISM: Artificial Sequence
<220> FEATURE:
<223> OTHER INFORMATION: Synthetic Construct

<400> SEQUENCE: 265

Thr Asn Trp His Cys Asn Asn Asp Gly Ser Ser Cys Asn Val Arg Ala
1               5                   10                  15

Gly Gly Gly Ser Ser Gly Gly Ser Thr Ser Thr Ser Gly Arg Ser Ala
            20                  25                  30

Asn Pro Arg Gly Gly Gly Ser Asp Ile Val Met Thr Gln Thr Thr Leu
            35                  40                  45

Ser Leu Pro Val Ser Leu Gly Asp Gln Ala Ser Ile Ser Cys Arg Ser
50                  55                  60

Ser Gln Ser Ile Val His Ser Asn Gly Asn Thr Tyr Leu Glu Trp Tyr
65                  70                  75                  80

Leu Gln Lys Pro Gly Gln Ser Pro Lys Leu Leu Ile Tyr Lys Val Ser
                85                  90                  95

Asn Arg Phe Ser Gly Val Pro Asp Arg Phe Ser Gly Ser Gly Ser Gly
            100                 105                 110

Thr Asp Phe Thr Leu Lys Ile Ser Arg Val Glu Ala Glu Asp Leu Gly
            115                 120                 125

Val Tyr Tyr Cys Phe Gln Gly Ser His Val Pro Tyr Thr Phe Gly Gly
130                 135                 140

Gly Thr Lys Leu Glu Ile Lys Arg Ala Asp Ala Ala Pro Thr Val Ser
145                 150                 155                 160

Ile Phe Pro Pro Ser Ser Glu Gln Leu Thr Ser Gly Gly Ala Ser Val
            165                 170                 175

Val Cys Phe Leu Asn Asn Phe Tyr Pro Lys Asp Ile Asn Val Lys Trp
            180                 185                 190

Lys Ile Asp Gly Ser Glu Arg Gln Asn Gly Val Leu Asn Ser Trp Thr
        195                 200                 205

Asp Gln Asp Ser Lys Asp Ser Thr Tyr Ser Met Ser Ser Thr Leu Thr
        210                 215                 220

Leu Thr Lys Asp Glu Tyr Glu Arg His Asn Ser Tyr Thr Cys Glu Ala
225                 230                 235                 240

```
Thr His Lys Thr Ser Thr Ser Pro Ile Val Lys Ser Phe Asn Arg Asn
                245                 250                 255

Glu Cys

<210> SEQ ID NO 266
<211> LENGTH: 252
<212> TYPE: PRT
<213> ORGANISM: Artificial Sequence
<220> FEATURE:
<223> OTHER INFORMATION: Synthetic Construct

<400> SEQUENCE: 266

Tyr Pro Tyr Asp Val Pro Asp Tyr Ala Gly Ala Cys Asn Leu Ile Val
1               5                   10                  15

Glu Gly His Cys Gly Gly Ser Val Pro Leu Ser Leu Tyr Ser Gly Gly
            20                  25                  30

Gly Asp Ile Val Met Thr Gln Thr Leu Ser Leu Pro Val Ser Leu
        35                  40                  45

Gly Asp Gln Ala Ser Ile Ser Cys Arg Ser Ser Gln Ser Ile Val His
    50                  55                  60

Ser Asn Gly Asn Thr Tyr Leu Glu Trp Tyr Leu Gln Lys Pro Gly Gln
65                  70                  75                  80

Ser Pro Lys Leu Leu Ile Tyr Lys Val Ser Asn Arg Phe Ser Gly Val
                85                  90                  95

Pro Asp Arg Phe Ser Gly Ser Gly Ser Gly Thr Asp Phe Thr Leu Lys
            100                 105                 110

Ile Ser Arg Val Glu Ala Glu Asp Leu Gly Val Tyr Tyr Cys Phe Gln
        115                 120                 125

Gly Ser His Val Pro Tyr Thr Phe Gly Gly Gly Thr Lys Leu Glu Ile
    130                 135                 140

Lys Arg Ala Asp Ala Ala Pro Thr Val Ser Ile Phe Pro Pro Ser Ser
145                 150                 155                 160

Glu Gln Leu Thr Ser Gly Gly Ala Ser Val Val Cys Phe Leu Asn Asn
                165                 170                 175

Phe Tyr Pro Lys Asp Ile Asn Val Lys Trp Lys Ile Asp Gly Ser Glu
            180                 185                 190

Arg Gln Asn Gly Val Leu Asn Ser Trp Thr Asp Gln Asp Ser Lys Asp
        195                 200                 205

Ser Thr Tyr Ser Met Ser Ser Thr Leu Thr Leu Thr Lys Asp Glu Tyr
    210                 215                 220

Glu Arg His Asn Ser Tyr Thr Cys Glu Ala Thr His Lys Thr Ser Thr
225                 230                 235                 240

Ser Pro Ile Val Lys Ser Phe Asn Arg Asn Glu Cys
                245                 250

<210> SEQ ID NO 267
<211> LENGTH: 251
<212> TYPE: PRT
<213> ORGANISM: Artificial Sequence
<220> FEATURE:
<223> OTHER INFORMATION: Synthetic Construct

<400> SEQUENCE: 267

Asp Tyr Lys Asp Asp Asp Lys Gly Ala Cys Asn Leu Ile Val Glu
1               5                   10                  15

Gly His Cys Gly Gly Ser Val Pro Leu Ser Leu Tyr Ser Gly Gly Gly
            20                  25                  30
```

```
Asp Ile Val Met Thr Gln Thr Thr Leu Ser Leu Pro Val Ser Leu Gly
            35                  40                  45

Asp Gln Ala Ser Ile Ser Cys Arg Ser Ser Gln Ser Ile Val His Ser
 50                  55                  60

Asn Gly Asn Thr Tyr Leu Glu Trp Tyr Leu Gln Lys Pro Gly Gln Ser
 65                  70                  75                  80

Pro Lys Leu Leu Ile Tyr Lys Val Ser Asn Arg Phe Ser Gly Val Pro
                85                  90                  95

Asp Arg Phe Ser Gly Ser Gly Ser Gly Thr Asp Phe Thr Leu Lys Ile
            100                 105                 110

Ser Arg Val Glu Ala Glu Asp Leu Gly Val Tyr Tyr Cys Phe Gln Gly
            115                 120                 125

Ser His Val Pro Tyr Thr Phe Gly Gly Gly Thr Lys Leu Glu Ile Lys
    130                 135                 140

Arg Ala Asp Ala Ala Pro Thr Val Ser Ile Phe Pro Pro Ser Ser Glu
145                 150                 155                 160

Gln Leu Thr Ser Gly Gly Ala Ser Val Val Cys Phe Leu Asn Asn Phe
                165                 170                 175

Tyr Pro Lys Asp Ile Asn Val Lys Trp Lys Ile Asp Gly Ser Glu Arg
            180                 185                 190

Gln Asn Gly Val Leu Asn Ser Trp Thr Asp Gln Asp Ser Lys Asp Ser
        195                 200                 205

Thr Tyr Ser Met Ser Ser Thr Leu Thr Leu Thr Lys Asp Glu Tyr Glu
    210                 215                 220

Arg His Asn Ser Tyr Thr Cys Glu Ala Thr His Lys Thr Ser Thr Ser
225                 230                 235                 240

Pro Ile Val Lys Ser Phe Asn Arg Asn Glu Cys
                245                 250

<210> SEQ ID NO 268
<211> LENGTH: 253
<212> TYPE: PRT
<213> ORGANISM: Artificial Sequence
<220> FEATURE:
<223> OTHER INFORMATION: Synthetic Construct

<400> SEQUENCE: 268

Glu Gln Lys Leu Ile Ser Glu Glu Asp Leu Gly Ala Cys Asn Leu Ile
1               5                   10                  15

Val Glu Gly His Cys Gly Gly Ser Val Pro Leu Ser Leu Tyr Ser Gly
            20                  25                  30

Gly Gly Asp Ile Val Met Thr Gln Thr Thr Leu Ser Leu Pro Val Ser
        35                  40                  45

Leu Gly Asp Gln Ala Ser Ile Ser Cys Arg Ser Ser Gln Ser Ile Val
    50                  55                  60

His Ser Asn Gly Asn Thr Tyr Leu Glu Trp Tyr Leu Gln Lys Pro Gly
 65                  70                  75                  80

Gln Ser Pro Lys Leu Leu Ile Tyr Lys Val Ser Asn Arg Phe Ser Gly
                85                  90                  95

Val Pro Asp Arg Phe Ser Gly Ser Gly Ser Gly Thr Asp Phe Thr Leu
            100                 105                 110

Lys Ile Ser Arg Val Glu Ala Glu Asp Leu Gly Val Tyr Tyr Cys Phe
        115                 120                 125

Gln Gly Ser His Val Pro Tyr Thr Phe Gly Gly Gly Thr Lys Leu Glu
    130                 135                 140
```

```
Ile Lys Arg Ala Asp Ala Ala Pro Thr Val Ser Ile Phe Pro Pro Ser
145                 150                 155                 160

Ser Glu Gln Leu Thr Ser Gly Gly Ala Ser Val Val Cys Phe Leu Asn
            165                 170                 175

Asn Phe Tyr Pro Lys Asp Ile Asn Val Lys Trp Lys Ile Asp Gly Ser
        180                 185                 190

Glu Arg Gln Asn Gly Val Leu Asn Ser Trp Thr Asp Gln Asp Ser Lys
    195                 200                 205

Asp Ser Thr Tyr Ser Met Ser Ser Thr Leu Thr Leu Thr Lys Asp Glu
        210                 215                 220

Tyr Glu Arg His Asn Ser Tyr Thr Cys Glu Ala Thr His Lys Thr Ser
225                 230                 235                 240

Thr Ser Pro Ile Val Lys Ser Phe Asn Arg Asn Glu Cys
                245                 250
```

<210> SEQ ID NO 269
<211> LENGTH: 258
<212> TYPE: PRT
<213> ORGANISM: Artificial Sequence
<220> FEATURE:
<223> OTHER INFORMATION: Synthetic Construct

<400> SEQUENCE: 269

```
Gly Leu Asn Asp Ile Phe Glu Ala Gln Lys Ile Glu Trp His Glu Gly
1               5                   10                  15

Ala Cys Asn Leu Ile Val Glu Gly His Cys Gly Gly Ser Val Pro Leu
                20                  25                  30

Ser Leu Tyr Ser Gly Gly Asp Ile Val Met Thr Gln Thr Thr Leu
            35                  40                  45

Ser Leu Pro Val Ser Leu Gly Asp Gln Ala Ser Ile Ser Cys Arg Ser
        50                  55                  60

Ser Gln Ser Ile Val His Ser Asn Gly Asn Thr Tyr Leu Glu Trp Tyr
65                  70                  75                  80

Leu Gln Lys Pro Gly Gln Ser Pro Lys Leu Leu Ile Tyr Lys Val Ser
                85                  90                  95

Asn Arg Phe Ser Gly Val Pro Asp Arg Phe Ser Gly Ser Gly Ser Gly
            100                 105                 110

Thr Asp Phe Thr Leu Lys Ile Ser Arg Val Glu Ala Glu Asp Leu Gly
        115                 120                 125

Val Tyr Tyr Cys Phe Gln Gly Ser His Val Pro Tyr Thr Phe Gly Gly
    130                 135                 140

Gly Thr Lys Leu Glu Ile Lys Arg Ala Asp Ala Ala Pro Thr Val Ser
145                 150                 155                 160

Ile Phe Pro Pro Ser Ser Glu Gln Leu Thr Ser Gly Gly Ala Ser Val
                165                 170                 175

Val Cys Phe Leu Asn Asn Phe Tyr Pro Lys Asp Ile Asn Val Lys Trp
            180                 185                 190

Lys Ile Asp Gly Ser Glu Arg Gln Asn Gly Val Leu Asn Ser Trp Thr
        195                 200                 205

Asp Gln Asp Ser Lys Asp Ser Thr Tyr Ser Met Ser Ser Thr Leu Thr
    210                 215                 220

Leu Thr Lys Asp Glu Tyr Glu Arg His Asn Ser Tyr Thr Cys Glu Ala
225                 230                 235                 240

Thr His Lys Thr Ser Thr Ser Pro Ile Val Lys Ser Phe Asn Arg Asn
                245                 250                 255
```

Glu Cys

<210> SEQ ID NO 270
<211> LENGTH: 255
<212> TYPE: PRT
<213> ORGANISM: Artificial Sequence
<220> FEATURE:
<223> OTHER INFORMATION: Synthetic Construct

<400> SEQUENCE: 270

Tyr Pro Tyr Asp Val Pro Asp Tyr Ala Gly Ala Cys Asn Leu Ile Val
1               5                   10                  15

Glu Gly His Cys Gly Ser Thr Ser Thr Ser Gly Arg Ser Ala Asn Pro
            20                  25                  30

Arg Gly Gly Ser Asp Ile Val Met Thr Gln Thr Thr Leu Ser Leu Pro
        35                  40                  45

Val Ser Leu Gly Asp Gln Ala Ser Ile Ser Cys Arg Ser Ser Gln Ser
    50                  55                  60

Ile Val His Ser Asn Gly Asn Thr Tyr Leu Glu Trp Tyr Leu Gln Lys
65                  70                  75                  80

Pro Gly Gln Ser Pro Lys Leu Leu Ile Tyr Lys Val Ser Asn Arg Phe
                85                  90                  95

Ser Gly Val Pro Asp Arg Phe Ser Gly Ser Gly Ser Gly Thr Asp Phe
            100                 105                 110

Thr Leu Lys Ile Ser Arg Val Glu Ala Glu Asp Leu Gly Val Tyr Tyr
        115                 120                 125

Cys Phe Gln Gly Ser His Val Pro Tyr Thr Phe Gly Gly Gly Thr Lys
    130                 135                 140

Leu Glu Ile Lys Arg Ala Asp Ala Ala Pro Thr Val Ser Ile Phe Pro
145                 150                 155                 160

Pro Ser Ser Glu Gln Leu Thr Ser Gly Gly Ala Ser Val Val Cys Phe
                165                 170                 175

Leu Asn Asn Phe Tyr Pro Lys Asp Ile Asn Val Lys Trp Lys Ile Asp
            180                 185                 190

Gly Ser Glu Arg Gln Asn Gly Val Leu Asn Ser Trp Thr Asp Gln Asp
        195                 200                 205

Ser Lys Asp Ser Thr Tyr Ser Met Ser Ser Thr Leu Thr Leu Thr Lys
    210                 215                 220

Asp Glu Tyr Glu Arg His Asn Ser Tyr Thr Cys Glu Ala Thr His Lys
225                 230                 235                 240

Thr Ser Thr Ser Pro Ile Val Lys Ser Phe Asn Arg Asn Glu Cys
                245                 250                 255

<210> SEQ ID NO 271
<211> LENGTH: 254
<212> TYPE: PRT
<213> ORGANISM: Artificial Sequence
<220> FEATURE:
<223> OTHER INFORMATION: Synthetic Construct

<400> SEQUENCE: 271

Asp Tyr Lys Asp Asp Asp Asp Lys Gly Ala Cys Asn Leu Ile Val Glu
1               5                   10                  15

Gly His Cys Gly Ser Thr Ser Thr Ser Gly Arg Ser Ala Asn Pro Arg
            20                  25                  30

Gly Gly Ser Asp Ile Val Met Thr Gln Thr Thr Leu Ser Leu Pro Val
        35                  40                  45

```
Ser Leu Gly Asp Gln Ala Ser Ile Ser Cys Arg Ser Gln Ser Ile
    50                  55                  60

Val His Ser Asn Gly Asn Thr Tyr Leu Glu Trp Tyr Leu Gln Lys Pro
 65                  70                  75                  80

Gly Gln Ser Pro Lys Leu Leu Ile Tyr Lys Val Ser Asn Arg Phe Ser
                 85                  90                  95

Gly Val Pro Asp Arg Phe Ser Gly Ser Gly Ser Gly Thr Asp Phe Thr
            100                 105                 110

Leu Lys Ile Ser Arg Val Glu Ala Glu Asp Leu Gly Val Tyr Tyr Cys
        115                 120                 125

Phe Gln Gly Ser His Val Pro Tyr Thr Phe Gly Gly Gly Thr Lys Leu
130                 135                 140

Glu Ile Lys Arg Ala Asp Ala Ala Pro Thr Val Ser Ile Phe Pro Pro
145                 150                 155                 160

Ser Ser Glu Gln Leu Thr Ser Gly Gly Ala Ser Val Val Cys Phe Leu
                165                 170                 175

Asn Asn Phe Tyr Pro Lys Asp Ile Asn Val Lys Trp Lys Ile Asp Gly
            180                 185                 190

Ser Glu Arg Gln Asn Gly Val Leu Asn Ser Trp Thr Asp Gln Asp Ser
        195                 200                 205

Lys Asp Ser Thr Tyr Ser Met Ser Ser Thr Leu Thr Leu Thr Lys Asp
210                 215                 220

Glu Tyr Glu Arg His Asn Ser Tyr Thr Cys Glu Ala Thr His Lys Thr
225                 230                 235                 240

Ser Thr Ser Pro Ile Val Lys Ser Phe Asn Arg Asn Glu Cys
                245                 250

<210> SEQ ID NO 272
<211> LENGTH: 256
<212> TYPE: PRT
<213> ORGANISM: Artificial Sequence
<220> FEATURE:
<223> OTHER INFORMATION: Synthetic Construct

<400> SEQUENCE: 272

Glu Gln Lys Leu Ile Ser Glu Glu Asp Leu Gly Ala Cys Asn Leu Ile
 1               5                  10                  15

Val Glu Gly His Cys Gly Ser Thr Ser Thr Ser Gly Arg Ser Ala Asn
             20                  25                  30

Pro Arg Gly Gly Ser Asp Ile Val Met Thr Gln Thr Leu Ser Leu
         35                  40                  45

Pro Val Ser Leu Gly Asp Gln Ala Ser Ile Ser Cys Arg Ser Ser Gln
 50                  55                  60

Ser Ile Val His Ser Asn Gly Asn Thr Tyr Leu Glu Trp Tyr Leu Gln
 65                  70                  75                  80

Lys Pro Gly Gln Ser Pro Lys Leu Leu Ile Tyr Lys Val Ser Asn Arg
                 85                  90                  95

Phe Ser Gly Val Pro Asp Arg Phe Ser Gly Ser Gly Ser Gly Thr Asp
            100                 105                 110

Phe Thr Leu Lys Ile Ser Arg Val Glu Ala Glu Asp Leu Gly Val Tyr
        115                 120                 125

Tyr Cys Phe Gln Gly Ser His Val Pro Tyr Thr Phe Gly Gly Gly Thr
130                 135                 140

Lys Leu Glu Ile Lys Arg Ala Asp Ala Ala Pro Thr Val Ser Ile Phe
145                 150                 155                 160
```

```
Pro Pro Ser Ser Glu Gln Leu Thr Ser Gly Gly Ala Ser Val Val Cys
            165                 170                 175

Phe Leu Asn Asn Phe Tyr Pro Lys Asp Ile Asn Val Lys Trp Lys Ile
        180                 185                 190

Asp Gly Ser Glu Arg Gln Asn Gly Val Leu Asn Ser Trp Thr Asp Gln
        195                 200                 205

Asp Ser Lys Asp Ser Thr Tyr Ser Met Ser Thr Leu Thr Leu Thr
210                 215                 220

Lys Asp Glu Tyr Glu Arg His Asn Ser Tyr Thr Cys Glu Ala Thr His
225                 230                 235                 240

Lys Thr Ser Thr Ser Pro Ile Val Lys Ser Phe Asn Arg Asn Glu Cys
            245                 250                 255

<210> SEQ ID NO 273
<211> LENGTH: 261
<212> TYPE: PRT
<213> ORGANISM: Artificial Sequence
<220> FEATURE:
<223> OTHER INFORMATION: Synthetic Construct

<400> SEQUENCE: 273

Gly Leu Asn Asp Ile Phe Glu Ala Gln Lys Ile Glu Trp His Glu Gly
1               5                   10                  15

Ala Cys Asn Leu Ile Val Glu Gly His Cys Gly Ser Thr Ser Thr Ser
            20                  25                  30

Gly Arg Ser Ala Asn Pro Arg Gly Gly Ser Asp Ile Val Met Thr Gln
        35                  40                  45

Thr Thr Leu Ser Leu Pro Val Ser Leu Gly Asp Gln Ala Ser Ile Ser
    50                  55                  60

Cys Arg Ser Ser Gln Ser Ile Val His Ser Asn Gly Asn Thr Tyr Leu
65                  70                  75                  80

Glu Trp Tyr Leu Gln Lys Pro Gly Gln Ser Pro Lys Leu Leu Ile Tyr
                85                  90                  95

Lys Val Ser Asn Arg Phe Ser Gly Val Pro Asp Arg Phe Ser Gly Ser
            100                 105                 110

Gly Ser Gly Thr Asp Phe Thr Leu Lys Ile Ser Arg Val Glu Ala Glu
        115                 120                 125

Asp Leu Gly Val Tyr Tyr Cys Phe Gln Gly Ser His Val Pro Tyr Thr
    130                 135                 140

Phe Gly Gly Gly Thr Lys Leu Glu Ile Lys Arg Ala Asp Ala Ala Pro
145                 150                 155                 160

Thr Val Ser Ile Phe Pro Pro Ser Ser Glu Gln Leu Thr Ser Gly Gly
                165                 170                 175

Ala Ser Val Val Cys Phe Leu Asn Asn Phe Tyr Pro Lys Asp Ile Asn
            180                 185                 190

Val Lys Trp Lys Ile Asp Gly Ser Glu Arg Gln Asn Gly Val Leu Asn
        195                 200                 205

Ser Trp Thr Asp Gln Asp Ser Lys Asp Ser Thr Tyr Ser Met Ser Ser
    210                 215                 220

Thr Leu Thr Leu Thr Lys Asp Glu Tyr Glu Arg His Asn Ser Tyr Thr
225                 230                 235                 240

Cys Glu Ala Thr His Lys Thr Ser Thr Ser Pro Ile Val Lys Ser Phe
                245                 250                 255

Asn Arg Asn Glu Cys
            260
```

```
<210> SEQ ID NO 274
<211> LENGTH: 244
<212> TYPE: PRT
<213> ORGANISM: Artificial Sequence
<220> FEATURE:
<223> OTHER INFORMATION: Synthetic Construct

<400> SEQUENCE: 274

Ala Cys Asn Leu Ile Val Glu Gly His Cys Gly Gly Ser Met Pro Tyr
1               5                   10                  15

Asp Leu Tyr His Pro Ser Gly Gly Asp Ile Val Met Thr Gln Thr
            20                  25                  30

Thr Leu Ser Leu Pro Val Ser Leu Gly Asp Gln Ala Ser Ile Ser Cys
        35                  40                  45

Arg Ser Ser Gln Ser Ile Val His Ser Asn Gly Asn Thr Tyr Leu Glu
    50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
        115                 120                 125

Gly Gly Gly Thr Lys Leu Glu Ile Lys Arg Ala Asp Ala Ala Pro Thr
    130                 135                 140

Val Ser Ile Phe Pro Pro Ser Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
            180                 185                 190

Trp Thr Asp Gln Asp Ser Lys Asp Ser Thr Tyr Ser Met Ser Ser Thr
        195                 200                 205

Leu Thr Leu Thr Lys Asp Glu Tyr Glu Arg His Asn Ser Tyr Thr Cys
    210                 215                 220

Glu Ala Thr His Lys Thr Ser Thr Ser Pro Ile Val Lys Ser Phe Asn
225                 230                 235                 240

Arg Asn Glu Cys

<210> SEQ ID NO 275
<211> LENGTH: 244
<212> TYPE: PRT
<213> ORGANISM: Artificial Sequence
<220> FEATURE:
<223> OTHER INFORMATION: Synthetic Construct

<400> SEQUENCE: 275

Ala Cys Asn Leu Ile Val Glu Gly His Cys Gly Gly Ser Gly Gly Ile
1               5                   10                  15

Gly Gln Leu Thr Ala Ser Gly Gly Asp Ile Val Met Thr Gln Thr
            20                  25                  30

Thr Leu Ser Leu Pro Val Ser Leu Gly Asp Gln Ala Ser Ile Ser Cys
        35                  40                  45

Arg Ser Ser Gln Ser Ile Val His Ser Asn Gly Asn Thr Tyr Leu Glu
    50                  55                  60
```

```
Trp Tyr Leu Gln Lys Pro Gly Gln Ser Pro Lys Leu Leu Ile Tyr Lys
 65                  70                  75                  80

Val Ser Asn Arg Phe Ser Gly Val Pro Asp Arg Phe Ser Gly Ser Gly
                 85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
            115                 120                 125

Gly Gly Gly Thr Lys Leu Glu Ile Lys Arg Ala Asp Ala Ala Pro Thr
            130                 135                 140

Val Ser Ile Phe Pro Pro Ser Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
                180                 185                 190

Trp Thr Asp Gln Asp Ser Lys Asp Ser Thr Tyr Ser Met Ser Ser Thr
                195                 200                 205

Leu Thr Leu Thr Lys Asp Glu Tyr Glu Arg His Asn Ser Tyr Thr Cys
            210                 215                 220

Glu Ala Thr His Lys Thr Ser Thr Ser Pro Ile Val Lys Ser Phe Asn
225                 230                 235                 240

Arg Asn Glu Cys

<210> SEQ ID NO 276
<211> LENGTH: 244
<212> TYPE: PRT
<213> ORGANISM: Artificial Sequence
<220> FEATURE:
<223> OTHER INFORMATION: Synthetic Construct

<400> SEQUENCE: 276

Ala Cys Asn Leu Ile Val Glu Gly His Cys Gly Gly Ser Asp Leu Gly
 1               5                  10                  15

Arg Phe Gln Thr Phe Ser Gly Gly Gly Asp Ile Val Met Thr Gln Thr
                 20                  25                  30

Thr Leu Ser Leu Pro Val Ser Leu Gly Asp Gln Ala Ser Ile Ser Cys
             35                  40                  45

Arg Ser Ser Gln Ser Ile Val His Ser Asn Gly Asn Thr Tyr Leu Glu
 50                  55                  60

Trp Tyr Leu Gln Lys Pro Gly Gln Ser Pro Lys Leu Leu Ile Tyr Lys
 65                  70                  75                  80

Val Ser Asn Arg Phe Ser Gly Val Pro Asp Arg Phe Ser Gly Ser Gly
                 85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
            115                 120                 125

Gly Gly Gly Thr Lys Leu Glu Ile Lys Arg Ala Asp Ala Ala Pro Thr
            130                 135                 140

Val Ser Ile Phe Pro Pro Ser Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
```

```
                        180              185              190

Trp Thr Asp Gln Asp Ser Lys Asp Ser Thr Tyr Ser Met Ser Ser Thr
            195                 200                 205

Leu Thr Leu Thr Lys Asp Glu Tyr Glu Arg His Asn Ser Tyr Thr Cys
            210                 215                 220

Glu Ala Thr His Lys Thr Ser Thr Ser Pro Ile Val Lys Ser Phe Asn
225                 230                 235                 240

Arg Asn Glu Cys

<210> SEQ ID NO 277
<211> LENGTH: 244
<212> TYPE: PRT
<213> ORGANISM: Artificial Sequence
<220> FEATURE:
<223> OTHER INFORMATION: Synthetic Construct

<400> SEQUENCE: 277

Ala Cys Asn Leu Ile Val Glu Gly His Cys Gly Gly Ser Asp Ser Gly
1               5                   10                  15

Gly Phe Met Leu Thr Ser Gly Gly Asp Ile Val Met Thr Gln Thr
            20                  25                  30

Thr Leu Ser Leu Pro Val Ser Leu Gly Asp Gln Ala Ser Ile Ser Cys
            35                  40                  45

Arg Ser Ser Gln Ser Ile Val His Ser Asn Gly Asn Thr Tyr Leu Glu
        50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
            115                 120                 125

Gly Gly Gly Thr Lys Leu Glu Ile Lys Arg Ala Asp Ala Ala Pro Thr
        130                 135                 140

Val Ser Ile Phe Pro Pro Ser Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
            180                 185                 190

Trp Thr Asp Gln Asp Ser Lys Asp Ser Thr Tyr Ser Met Ser Ser Thr
            195                 200                 205

Leu Thr Leu Thr Lys Asp Glu Tyr Glu Arg His Asn Ser Tyr Thr Cys
            210                 215                 220

Glu Ala Thr His Lys Thr Ser Thr Ser Pro Ile Val Lys Ser Phe Asn
225                 230                 235                 240

Arg Asn Glu Cys

<210> SEQ ID NO 278
<211> LENGTH: 244
<212> TYPE: PRT
<213> ORGANISM: Artificial Sequence
<220> FEATURE:
<223> OTHER INFORMATION: Synthetic Construct

<400> SEQUENCE: 278
```

Ala Cys Asn Leu Ile Val Glu Gly His Cys Gly Gly Ser Thr Ser Val
1               5                   10                  15

Leu Met Ala Ala Pro Ser Gly Gly Gly Asp Ile Val Met Thr Gln Thr
            20                  25                  30

Thr Leu Ser Leu Pro Val Ser Leu Gly Asp Gln Ala Ser Ile Ser Cys
            35                  40                  45

Arg Ser Ser Gln Ser Ile Val His Ser Asn Gly Asn Thr Tyr Leu Glu
        50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
            115                 120                 125

Gly Gly Gly Thr Lys Leu Glu Ile Lys Arg Ala Asp Ala Ala Pro Thr
    130                 135                 140

Val Ser Ile Phe Pro Pro Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
            180                 185                 190

Trp Thr Asp Gln Asp Ser Lys Asp Ser Thr Tyr Ser Met Ser Ser Thr
        195                 200                 205

Leu Thr Leu Thr Lys Asp Glu Tyr Glu Arg His Asn Ser Tyr Thr Cys
        210                 215                 220

Glu Ala Thr His Lys Thr Ser Thr Ser Pro Ile Val Lys Ser Phe Asn
225                 230                 235                 240

Arg Asn Glu Cys

<210> SEQ ID NO 279
<211> LENGTH: 246
<212> TYPE: PRT
<213> ORGANISM: Artificial Sequence
<220> FEATURE:
<223> OTHER INFORMATION: Synthetic Construct

<400> SEQUENCE: 279

Ala Cys Asn Leu Ile Val Glu Gly His Cys Gly Gly Ser Thr Ser Glu
1               5                   10                  15

Phe Val Phe Ala Pro Asp Gln Ser Gly Gly Gly Asp Ile Val Met Thr
            20                  25                  30

Gln Thr Thr Leu Ser Leu Pro Val Ser Leu Gly Asp Gln Ala Ser Ile
            35                  40                  45

Ser Cys Arg Ser Ser Gln Ser Ile Val His Ser Asn Gly Asn Thr Tyr
        50                  55                  60

Leu Glu Trp Tyr Leu Gln Lys Pro Gly Gln Ser Pro Lys Leu Leu Ile
65                  70                  75                  80

Tyr Lys Val Ser Asn Arg Phe Ser Gly Val Pro Asp Arg Phe Ser Gly
                85                  90                  95

Ser Gly Ser Gly Thr Asp Phe Thr Leu Lys Ile Ser Arg Val Glu Ala
            100                 105                 110

```
Glu Asp Leu Gly Val Tyr Tyr Cys Phe Gln Gly Ser His Val Pro Tyr
            115                 120                 125

Thr Phe Gly Gly Gly Thr Lys Leu Glu Ile Lys Arg Ala Asp Ala Ala
130                 135                 140

Pro Thr Val Ser Ile Phe Pro Pro Ser Ser Glu Gln Leu Thr Ser Gly
145                 150                 155                 160

Gly Ala Ser Val Val Cys Phe Leu Asn Asn Phe Tyr Pro Lys Asp Ile
                165                 170                 175

Asn Val Lys Trp Lys Ile Asp Gly Ser Glu Arg Gln Asn Gly Val Leu
            180                 185                 190

Asn Ser Trp Thr Asp Gln Asp Ser Lys Asp Ser Thr Tyr Ser Met Ser
        195                 200                 205

Ser Thr Leu Thr Leu Thr Lys Asp Glu Tyr Glu Arg His Asn Ser Tyr
210                 215                 220

Thr Cys Glu Ala Thr His Lys Thr Ser Thr Ser Pro Ile Val Lys Ser
225                 230                 235                 240

Phe Asn Arg Asn Glu Cys
                245

<210> SEQ ID NO 280
<211> LENGTH: 244
<212> TYPE: PRT
<213> ORGANISM: Artificial Sequence
<220> FEATURE:
<223> OTHER INFORMATION: Synthetic Construct

<400> SEQUENCE: 280

Ala Cys Asn Leu Ile Val Glu Gly His Cys Gly Gly Ser Lys Leu Val
1               5                   10                  15

Leu Pro Val Leu Pro Ser Gly Gly Asp Ile Val Met Thr Gln Thr
            20                  25                  30

Thr Leu Ser Leu Pro Val Ser Leu Gly Asp Gln Ala Ser Ile Ser Cys
        35                  40                  45

Arg Ser Ser Gln Ser Ile Val His Ser Asn Gly Asn Thr Tyr Leu Glu
    50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
        115                 120                 125

Gly Gly Gly Thr Lys Leu Glu Ile Lys Arg Ala Asp Ala Ala Pro Thr
130                 135                 140

Val Ser Ile Phe Pro Pro Ser Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
            180                 185                 190

Trp Thr Asp Gln Asp Ser Lys Asp Ser Thr Tyr Ser Met Ser Ser Thr
        195                 200                 205

Leu Thr Leu Thr Lys Asp Glu Tyr Glu Arg His Asn Ser Tyr Thr Cys
    210                 215                 220
```

```
Glu Ala Thr His Lys Thr Ser Thr Ser Pro Ile Val Lys Ser Phe Asn
225                 230                 235                 240

Arg Asn Glu Cys

<210> SEQ ID NO 281
<211> LENGTH: 244
<212> TYPE: PRT
<213> ORGANISM: Artificial Sequence
<220> FEATURE:
<223> OTHER INFORMATION: Synthetic Construct

<400> SEQUENCE: 281

Ala Cys Asn Leu Ile Val Glu Gly His Cys Gly Gly Ser Lys Pro Ile
1               5                   10                  15

Leu Phe Phe Arg Leu Ser Gly Gly Asp Ile Val Met Thr Gln Thr
                20                  25                  30

Thr Leu Ser Leu Pro Val Ser Leu Gly Asp Gln Ala Ser Ile Ser Cys
            35                  40                  45

Arg Ser Ser Gln Ser Ile Val His Ser Asn Gly Asn Thr Tyr Leu Glu
        50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
        115                 120                 125

Gly Gly Gly Thr Lys Leu Glu Ile Lys Arg Ala Asp Ala Ala Pro Thr
    130                 135                 140

Val Ser Ile Phe Pro Pro Ser Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
            180                 185                 190

Trp Thr Asp Gln Asp Ser Lys Asp Ser Thr Tyr Ser Met Ser Ser Thr
        195                 200                 205

Leu Thr Leu Thr Lys Asp Glu Tyr Glu Arg His Asn Ser Tyr Thr Cys
    210                 215                 220

Glu Ala Thr His Lys Thr Ser Thr Ser Pro Ile Val Lys Ser Phe Asn
225                 230                 235                 240

Arg Asn Glu Cys

<210> SEQ ID NO 282
<211> LENGTH: 242
<212> TYPE: PRT
<213> ORGANISM: Artificial Sequence
<220> FEATURE:
<223> OTHER INFORMATION: Synthetic Construct

<400> SEQUENCE: 282

Ala Cys Asn Leu Ile Val Glu Gly His Cys Gly Gly Ser Ala Asn Gln
1               5                   10                  15

Leu Lys Gly Ser Gly Gly Asp Ile Val Met Thr Gln Thr Thr Leu
                20                  25                  30

Ser Leu Pro Val Ser Leu Gly Asp Gln Ala Ser Ile Ser Cys Arg Ser
```

```
            35                  40                  45
Ser Gln Ser Ile Val His Ser Asn Gly Asn Thr Tyr Leu Glu Trp Tyr
 50                  55                  60

Leu Gln Lys Pro Gly Gln Ser Pro Lys Leu Leu Ile Tyr Lys Val Ser
 65                  70                  75                  80

Asn Arg Phe Ser Gly Val Pro Asp Arg Phe Ser Gly Ser Gly Ser Gly
                 85                  90                  95

Thr Asp Phe Thr Leu Lys Ile Ser Arg Val Glu Ala Glu Asp Leu Gly
                100                 105                 110

Val Tyr Tyr Cys Phe Gln Gly Ser His Val Pro Tyr Thr Phe Gly Gly
                115                 120                 125

Gly Thr Lys Leu Glu Ile Lys Arg Ala Asp Ala Ala Pro Thr Val Ser
                130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
                165                 170                 175

Lys Ile Asp Gly Ser Glu Arg Gln Asn Gly Val Leu Asn Ser Trp Thr
                180                 185                 190

Asp Gln Asp Ser Lys Asp Ser Thr Tyr Ser Met Ser Ser Thr Leu Thr
                195                 200                 205

Leu Thr Lys Asp Glu Tyr Glu Arg His Asn Ser Tyr Thr Cys Glu Ala
210                 215                 220

Thr His Lys Thr Ser Thr Ser Pro Ile Val Lys Ser Phe Asn Arg Asn
225                 230                 235                 240

Glu Cys

<210> SEQ ID NO 283
<211> LENGTH: 242
<212> TYPE: PRT
<213> ORGANISM: Artificial Sequence
<220> FEATURE:
<223> OTHER INFORMATION: Synthetic Construct

<400> SEQUENCE: 283

Ala Cys Asn Leu Ile Val Glu Gly His Cys Gly Gly Ser Gln Ser Gln
 1               5                  10                  15

Leu Lys Glu Ser Gly Gly Gly Asp Ile Val Met Thr Gln Thr Thr Leu
                20                  25                  30

Ser Leu Pro Val Ser Leu Gly Asp Gln Ala Ser Ile Ser Cys Arg Ser
                35                  40                  45

Ser Gln Ser Ile Val His Ser Asn Gly Asn Thr Tyr Leu Glu Trp Tyr
 50                  55                  60

Leu Gln Lys Pro Gly Gln Ser Pro Lys Leu Leu Ile Tyr Lys Val Ser
 65                  70                  75                  80

Asn Arg Phe Ser Gly Val Pro Asp Arg Phe Ser Gly Ser Gly Ser Gly
                 85                  90                  95

Thr Asp Phe Thr Leu Lys Ile Ser Arg Val Glu Ala Glu Asp Leu Gly
                100                 105                 110

Val Tyr Tyr Cys Phe Gln Gly Ser His Val Pro Tyr Thr Phe Gly Gly
                115                 120                 125

Gly Thr Lys Leu Glu Ile Lys Arg Ala Asp Ala Ala Pro Thr Val Ser
                130                 135                 140

Ile Phe Pro Pro Ser Ser Glu Gln Leu Thr Ser Gly Gly Ala Ser Val
145                 150                 155                 160
```

Val Cys Phe Leu Asn Asn Phe Tyr Pro Lys Asp Ile Asn Val Lys Trp
            165                 170                 175

Lys Ile Asp Gly Ser Glu Arg Gln Asn Gly Val Leu Asn Ser Trp Thr
            180                 185                 190

Asp Gln Asp Ser Lys Ser Thr Tyr Ser Met Ser Ser Thr Leu Thr
            195                 200                 205

Leu Thr Lys Asp Glu Tyr Glu Arg His Asn Ser Tyr Thr Cys Glu Ala
        210                 215                 220

Thr His Lys Thr Ser Thr Ser Pro Ile Val Lys Ser Phe Asn Arg Asn
225                 230                 235                 240

Glu Cys

<210> SEQ ID NO 284
<211> LENGTH: 242
<212> TYPE: PRT
<213> ORGANISM: Artificial Sequence
<220> FEATURE:
<223> OTHER INFORMATION: Synthetic Construct

<400> SEQUENCE: 284

Ala Cys Asn Leu Ile Val Glu Gly His Cys Gly Gly Ser His Glu Gln
1               5                   10                  15

Leu Thr Val Ser Gly Gly Gly Asp Ile Val Met Thr Gln Thr Thr Leu
            20                  25                  30

Ser Leu Pro Val Ser Leu Gly Asp Gln Ala Ser Ile Ser Cys Arg Ser
        35                  40                  45

Ser Gln Ser Ile Val His Ser Asn Gly Asn Thr Tyr Leu Glu Trp Tyr
    50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
        115                 120                 125

Gly Thr Lys Leu Glu Ile Lys Arg Ala Asp Ala Ala Pro Thr Val Ser
    130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
                165                 170                 175

Lys Ile Asp Gly Ser Glu Arg Gln Asn Gly Val Leu Asn Ser Trp Thr
            180                 185                 190

Asp Gln Asp Ser Lys Ser Thr Tyr Ser Met Ser Ser Thr Leu Thr
            195                 200                 205

Leu Thr Lys Asp Glu Tyr Glu Arg His Asn Ser Tyr Thr Cys Glu Ala
        210                 215                 220

Thr His Lys Thr Ser Thr Ser Pro Ile Val Lys Ser Phe Asn Arg Asn
225                 230                 235                 240

Glu Cys

<210> SEQ ID NO 285
<211> LENGTH: 245
<212> TYPE: PRT

```
<213> ORGANISM: Artificial Sequence
<220> FEATURE:
<223> OTHER INFORMATION: Synthetic Construct

<400> SEQUENCE: 285

Ala Cys Asn Leu Ile Val Glu Gly His Cys Gly Gly Ser Pro Ala Asn
1               5                   10                  15

Leu Val Ala Pro Asp Pro Ser Gly Gly Asp Ile Val Met Thr Gln
            20                  25                  30

Thr Thr Leu Ser Leu Pro Val Ser Leu Gly Asp Gln Ala Ser Ile Ser
                35                  40                  45

Cys Arg Ser Ser Gln Ser Ile Val His Ser Asn Gly Asn Thr Tyr Leu
50                  55                  60

Glu Trp Tyr Leu Gln Lys Pro Gly Gln Ser Pro Lys Leu Leu Ile Tyr
65                  70                  75                  80

Lys Val Ser Asn Arg Phe Ser Gly Val Pro Asp Arg Phe Ser Gly Ser
                85                  90                  95

Gly Ser Gly Thr Asp Phe Thr Leu Lys Ile Ser Arg Val Glu Ala Glu
            100                 105                 110

Asp Leu Gly Val Tyr Tyr Cys Phe Gln Gly Ser His Val Pro Tyr Thr
        115                 120                 125

Phe Gly Gly Gly Thr Lys Leu Glu Ile Lys Arg Ala Asp Ala Ala Pro
130                 135                 140

Thr Val Ser Ile Phe Pro Pro Ser Ser Glu Gln Leu Thr Ser Gly Gly
145                 150                 155                 160

Ala Ser Val Val Cys Phe Leu Asn Asn Phe Tyr Pro Lys Asp Ile Asn
                165                 170                 175

Val Lys Trp Lys Ile Asp Gly Ser Glu Arg Gln Asn Gly Val Leu Asn
            180                 185                 190

Ser Trp Thr Asp Gln Asp Ser Lys Asp Ser Thr Tyr Ser Met Ser Ser
        195                 200                 205

Thr Leu Thr Leu Thr Lys Asp Glu Tyr Glu Arg His Asn Ser Tyr Thr
210                 215                 220

Cys Glu Ala Thr His Lys Thr Ser Thr Ser Pro Ile Val Lys Ser Phe
225                 230                 235                 240

Asn Arg Asn Glu Cys
                245

<210> SEQ ID NO 286
<211> LENGTH: 245
<212> TYPE: PRT
<213> ORGANISM: Artificial Sequence
<220> FEATURE:
<223> OTHER INFORMATION: Synthetic Construct

<400> SEQUENCE: 286

Ala Cys Asn Leu Ile Val Glu Gly His Cys Gly Gly Ser Pro Ala Pro
1               5                   10                  15

Gly Val Tyr Pro Gly Pro Ser Gly Gly Asp Ile Val Met Thr Gln
            20                  25                  30

Thr Thr Leu Ser Leu Pro Val Ser Leu Gly Asp Gln Ala Ser Ile Ser
                35                  40                  45

Cys Arg Ser Ser Gln Ser Ile Val His Ser Asn Gly Asn Thr Tyr Leu
50                  55                  60

Glu Trp Tyr Leu Gln Lys Pro Gly Gln Ser Pro Lys Leu Leu Ile Tyr
65                  70                  75                  80
```

```
Lys Val Ser Asn Arg Phe Ser Gly Val Pro Asp Arg Phe Ser Gly Ser
                85                  90                  95

Gly Ser Gly Thr Asp Phe Thr Leu Lys Ile Ser Arg Val Glu Ala Glu
            100                 105                 110

Asp Leu Gly Val Tyr Tyr Cys Phe Gln Gly Ser His Val Pro Tyr Thr
        115                 120                 125

Phe Gly Gly Gly Thr Lys Leu Glu Ile Lys Arg Ala Asp Ala Ala Pro
    130                 135                 140

Thr Val Ser Ile Phe Pro Pro Ser Ser Glu Gln Leu Thr Ser Gly Gly
145                 150                 155                 160

Ala Ser Val Val Cys Phe Leu Asn Asn Phe Tyr Pro Lys Asp Ile Asn
                165                 170                 175

Val Lys Trp Lys Ile Asp Gly Ser Glu Arg Gln Asn Gly Val Leu Asn
            180                 185                 190

Ser Trp Thr Asp Gln Asp Ser Lys Asp Ser Thr Tyr Ser Met Ser Ser
            195                 200                 205

Thr Leu Thr Leu Thr Lys Asp Glu Tyr Glu Arg His Asn Ser Tyr Thr
        210                 215                 220

Cys Glu Ala Thr His Lys Thr Ser Thr Ser Pro Ile Val Lys Ser Phe
225                 230                 235                 240

Asn Arg Asn Glu Cys
                245

<210> SEQ ID NO 287
<211> LENGTH: 246
<212> TYPE: PRT
<213> ORGANISM: Artificial Sequence
<220> FEATURE:
<223> OTHER INFORMATION: Synthetic Construct

<400> SEQUENCE: 287

Ala Cys Asn Leu Ile Val Glu Gly His Cys Gly Gly Ser Ala Pro Ala
1               5                   10                  15

Gly Leu Ile Val Pro Tyr Asn Ser Gly Gly Asp Ile Val Met Thr
            20                  25                  30

Gln Thr Thr Leu Ser Leu Pro Val Ser Leu Gly Asp Gln Ala Ser Ile
            35                  40                  45

Ser Cys Arg Ser Ser Gln Ser Ile Val His Ser Asn Gly Asn Thr Tyr
    50                  55                  60

Leu Glu Trp Tyr Leu Gln Lys Pro Gly Gln Ser Pro Lys Leu Leu Ile
65                  70                  75                  80

Tyr Lys Val Ser Asn Arg Phe Ser Gly Val Pro Asp Arg Phe Ser Gly
                85                  90                  95

Ser Gly Ser Gly Thr Asp Phe Thr Leu Lys Ile Ser Arg Val Glu Ala
            100                 105                 110

Glu Asp Leu Gly Val Tyr Tyr Cys Phe Gln Gly Ser His Val Pro Tyr
        115                 120                 125

Thr Phe Gly Gly Gly Thr Lys Leu Glu Ile Lys Arg Ala Asp Ala Ala
    130                 135                 140

Pro Thr Val Ser Ile Phe Pro Pro Ser Ser Glu Gln Leu Thr Ser Gly
145                 150                 155                 160

Gly Ala Ser Val Val Cys Phe Leu Asn Asn Phe Tyr Pro Lys Asp Ile
                165                 170                 175

Asn Val Lys Trp Lys Ile Asp Gly Ser Glu Arg Gln Asn Gly Val Leu
            180                 185                 190
```

Asn Ser Trp Thr Asp Gln Asp Ser Lys Asp Ser Thr Tyr Ser Met Ser
            195                 200                 205

Ser Thr Leu Thr Leu Thr Lys Asp Glu Tyr Glu Arg His Asn Ser Tyr
    210                 215                 220

Thr Cys Glu Ala Thr His Lys Thr Ser Thr Ser Pro Ile Val Lys Ser
225                 230                 235                 240

Phe Asn Arg Asn Glu Cys
                245

<210> SEQ ID NO 288
<211> LENGTH: 242
<212> TYPE: PRT
<213> ORGANISM: Artificial Sequence
<220> FEATURE:
<223> OTHER INFORMATION: Synthetic Construct

<400> SEQUENCE: 288

Ala Cys Asn Leu Ile Val Glu Gly His Cys Gly Gly Ser Pro Gln Ala
1               5                   10                  15

Leu Val Ala Ser Gly Gly Asp Ile Val Met Thr Gln Thr Thr Leu
            20                  25                  30

Ser Leu Pro Val Ser Leu Gly Asp Gln Ala Ser Ile Ser Cys Arg Ser
            35                  40                  45

Ser Gln Ser Ile Val His Ser Asn Gly Asn Thr Tyr Leu Glu Trp Tyr
        50                  55                  60

Leu Gln Lys Pro Gly Gln Ser Pro Lys Leu Leu Ile Tyr Lys Val Ser
65              70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
        115                 120                 125

Gly Thr Lys Leu Glu Ile Lys Arg Ala Asp Ala Ala Pro Thr Val Ser
130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
                165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
        195                 200                 205

Leu Thr Lys Asp Glu Tyr Glu Arg His Asn Ser Tyr Thr Cys Glu Ala
    210                 215                 220

Thr His Lys Thr Ser Thr Ser Pro Ile Val Lys Ser Phe Asn Arg Asn
225                 230                 235                 240

Glu Cys

<210> SEQ ID NO 289
<211> LENGTH: 242
<212> TYPE: PRT
<213> ORGANISM: Artificial Sequence
<220> FEATURE:
<223> OTHER INFORMATION: Synthetic Construct

<400> SEQUENCE: 289

```
Ala Cys Asn Leu Ile Val Glu Gly His Cys Gly Gly Ser Val Gly Asn
1               5                   10                  15

Leu Asn Phe Ser Gly Gly Gly Asp Ile Val Met Thr Gln Thr Thr Leu
            20                  25                  30

Ser Leu Pro Val Ser Leu Gly Asp Gln Ala Ser Ile Ser Cys Arg Ser
        35                  40                  45

Ser Gln Ser Ile Val His Ser Asn Gly Asn Thr Tyr Leu Glu Trp Tyr
    50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
            115                 120                 125

Gly Thr Lys Leu Glu Ile Lys Arg Ala Asp Ala Ala Pro Thr Val Ser
        130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
                165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
        195                 200                 205

Leu Thr Lys Asp Glu Tyr Glu Arg His Asn Ser Tyr Thr Cys Glu Ala
210                 215                 220

Thr His Lys Thr Ser Thr Ser Pro Ile Val Lys Ser Phe Asn Arg Asn
225                 230                 235                 240

Glu Cys

<210> SEQ ID NO 290
<211> LENGTH: 243
<212> TYPE: PRT
<213> ORGANISM: Artificial Sequence
<220> FEATURE:
<223> OTHER INFORMATION: Synthetic Construct

<400> SEQUENCE: 290

Ala Cys Asn Leu Ile Val Glu Gly His Cys Gly Gly Ser Val Ala Asn
1               5                   10                  15

Leu Leu Tyr Glu Ser Gly Gly Gly Asp Ile Val Met Thr Gln Thr Thr
            20                  25                  30

Leu Ser Leu Pro Val Ser Leu Gly Asp Gln Ala Ser Ile Ser Cys Arg
        35                  40                  45

Ser Ser Gln Ser Ile Val His Ser Asn Gly Asn Thr Tyr Leu Glu Trp
    50                  55                  60

Tyr Leu Gln Lys Pro Gly Gln Ser Pro Lys Leu Leu Ile Tyr Lys Val
65                  70                  75                  80

Ser Asn Arg Phe Ser Gly Val Pro Asp Arg Phe Ser Gly Ser Gly Ser
                85                  90                  95

Gly Thr Asp Phe Thr Leu Lys Ile Ser Arg Val Glu Ala Glu Asp Leu
            100                 105                 110

Gly Val Tyr Tyr Cys Phe Gln Gly Ser His Val Pro Tyr Thr Phe Gly
```

```
            115                 120                 125
Gly Gly Thr Lys Leu Glu Ile Lys Arg Ala Asp Ala Ala Pro Thr Val
    130                 135                 140

Ser Ile Phe Pro Pro Ser Ser Glu Gln Leu Thr Ser Gly Gly Ala Ser
145                 150                 155                 160

Val Val Cys Phe Leu Asn Asn Phe Tyr Pro Lys Asp Ile Asn Val Lys
                165                 170                 175

Trp Lys Ile Asp Gly Ser Glu Arg Gln Asn Gly Val Leu Asn Ser Trp
            180                 185                 190

Thr Asp Gln Asp Ser Lys Asp Ser Thr Tyr Ser Met Ser Ser Thr Leu
        195                 200                 205

Thr Leu Thr Lys Asp Glu Tyr Glu Arg His Asn Ser Tyr Thr Cys Glu
    210                 215                 220

Ala Thr His Lys Thr Ser Thr Ser Pro Ile Val Lys Ser Phe Asn Arg
225                 230                 235                 240

Asn Glu Cys

<210> SEQ ID NO 291
<211> LENGTH: 242
<212> TYPE: PRT
<213> ORGANISM: Artificial Sequence
<220> FEATURE:
<223> OTHER INFORMATION: Synthetic Construct

<400> SEQUENCE: 291

Ala Cys Asn Leu Ile Val Glu Gly His Cys Gly Gly Ser Val Tyr Asn
1               5                   10                  15

Leu Met Asp Ser Gly Gly Gly Asp Ile Val Met Thr Gln Thr Thr Leu
            20                  25                  30

Ser Leu Pro Val Ser Leu Gly Asp Gln Ala Ser Ile Ser Cys Arg Ser
        35                  40                  45

Ser Gln Ser Ile Val His Ser Asn Gly Asn Thr Tyr Leu Glu Trp Tyr
    50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
        115                 120                 125

Gly Thr Lys Leu Glu Ile Lys Arg Ala Asp Ala Ala Pro Thr Val Ser
    130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
                165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
        195                 200                 205

Leu Thr Lys Asp Glu Tyr Glu Arg His Asn Ser Tyr Thr Cys Glu Ala
    210                 215                 220

Thr His Lys Thr Ser Thr Ser Pro Ile Val Lys Ser Phe Asn Arg Asn
225                 230                 235                 240
```

Glu Cys

<210> SEQ ID NO 292
<211> LENGTH: 242
<212> TYPE: PRT
<213> ORGANISM: Artificial Sequence
<220> FEATURE:
<223> OTHER INFORMATION: Synthetic Construct

<400> SEQUENCE: 292

Ala Cys Asn Leu Ile Val Glu Gly His Cys Gly Gly Ser Thr Phe Asn
1               5                   10                  15

Ile Lys Gln Ser Gly Gly Gly Asp Ile Val Met Thr Gln Thr Thr Leu
            20                  25                  30

Ser Leu Pro Val Ser Leu Gly Asp Gln Ala Ser Ile Ser Cys Arg Ser
        35                  40                  45

Ser Gln Ser Ile Val His Ser Asn Gly Asn Thr Tyr Leu Glu Trp Tyr
    50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
        115                 120                 125

Gly Thr Lys Leu Glu Ile Lys Arg Ala Asp Ala Ala Pro Thr Val Ser
    130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
                165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
        195                 200                 205

Leu Thr Lys Asp Glu Tyr Glu Arg His Asn Ser Tyr Thr Cys Glu Ala
    210                 215                 220

Thr His Lys Thr Ser Thr Ser Pro Ile Val Lys Ser Phe Asn Arg Asn
225                 230                 235                 240

Glu Cys

<210> SEQ ID NO 293
<211> LENGTH: 243
<212> TYPE: PRT
<213> ORGANISM: Artificial Sequence
<220> FEATURE:
<223> OTHER INFORMATION: Synthetic Construct

<400> SEQUENCE: 293

Ala Cys Asn Leu Ile Val Glu Gly His Cys Gly Gly Ser Asp Leu Trp
1               5                   10                  15

Lys Leu Leu Pro Ser Gly Gly Gly Asp Ile Val Met Thr Gln Thr Thr
            20                  25                  30

Leu Ser Leu Pro Val Ser Leu Gly Asp Gln Ala Ser Ile Ser Cys Arg
        35                  40                  45

Ser Ser Gln Ser Ile Val His Ser Asn Gly Asn Thr Tyr Leu Glu Trp
50                      55                      60

Tyr Leu Gln Lys Pro Gly Gln Ser Pro Lys Leu Leu Ile Tyr Lys Val
65                      70                      75                      80

Ser Asn Arg Phe Ser Gly Val Pro Asp Arg Phe Ser Gly Ser Gly Ser
                85                      90                      95

Gly Thr Asp Phe Thr Leu Lys Ile Ser Arg Val Glu Ala Glu Asp Leu
                100                     105                     110

Gly Val Tyr Tyr Cys Phe Gln Gly Ser His Val Pro Tyr Thr Phe Gly
                115                     120                     125

Gly Gly Thr Lys Leu Glu Ile Lys Arg Ala Asp Ala Ala Pro Thr Val
                130                     135                     140

Ser Ile Phe Pro Pro Ser Ser Glu Gln Leu Thr Ser Gly Gly Ala Ser
145                     150                     155                     160

Val Val Cys Phe Leu Asn Asn Phe Tyr Pro Lys Asp Ile Asn Val Lys
                165                     170                     175

Trp Lys Ile Asp Gly Ser Glu Arg Gln Asn Gly Val Leu Asn Ser Trp
                180                     185                     190

Thr Asp Gln Asp Ser Lys Asp Ser Thr Tyr Ser Met Ser Ser Thr Leu
                195                     200                     205

Thr Leu Thr Lys Asp Glu Tyr Glu Arg His Asn Ser Tyr Thr Cys Glu
                210                     215                     220

Ala Thr His Lys Thr Ser Thr Ser Pro Ile Val Lys Ser Phe Asn Arg
225                     230                     235                     240

Asn Glu Cys

<210> SEQ ID NO 294
<211> LENGTH: 243
<212> TYPE: PRT
<213> ORGANISM: Artificial Sequence
<220> FEATURE:
<223> OTHER INFORMATION: Synthetic Construct

<400> SEQUENCE: 294

Ala Cys Asn Leu Ile Val Glu Gly His Cys Gly Gly Ser Pro Gly Ser
1                       5                       10                      15

Thr Lys Arg Ala Ser Gly Gly Gly Asp Ile Val Met Thr Gln Thr Thr
                20                      25                      30

Leu Ser Leu Pro Val Ser Leu Gly Asp Gln Ala Ser Ile Ser Cys Arg
                35                      40                      45

Ser Ser Gln Ser Ile Val His Ser Asn Gly Asn Thr Tyr Leu Glu Trp
50                      55                      60

Tyr Leu Gln Lys Pro Gly Gln Ser Pro Lys Leu Leu Ile Tyr Lys Val
65                      70                      75                      80

Ser Asn Arg Phe Ser Gly Val Pro Asp Arg Phe Ser Gly Ser Gly Ser
                85                      90                      95

Gly Thr Asp Phe Thr Leu Lys Ile Ser Arg Val Glu Ala Glu Asp Leu
                100                     105                     110

Gly Val Tyr Tyr Cys Phe Gln Gly Ser His Val Pro Tyr Thr Phe Gly
                115                     120                     125

Gly Gly Thr Lys Leu Glu Ile Lys Arg Ala Asp Ala Ala Pro Thr Val
                130                     135                     140

Ser Ile Phe Pro Pro Ser Ser Glu Gln Leu Thr Ser Gly Gly Ala Ser
145                     150                     155                     160

Val Val Cys Phe Leu Asn Asn Phe Tyr Pro Lys Asp Ile Asn Val Lys

```
                  165                 170                 175

Trp Lys Ile Asp Gly Ser Glu Arg Gln Asn Gly Val Leu Asn Ser Trp
            180                 185                 190

Thr Asp Gln Asp Ser Lys Asp Ser Thr Tyr Ser Met Ser Ser Thr Leu
        195                 200                 205

Thr Leu Thr Lys Asp Glu Tyr Glu Arg His Asn Ser Tyr Thr Cys Glu
    210                 215                 220

Ala Thr His Lys Thr Ser Thr Ser Pro Ile Val Lys Ser Phe Asn Arg
225                 230                 235                 240

Asn Glu Cys

<210> SEQ ID NO 295
<211> LENGTH: 244
<212> TYPE: PRT
<213> ORGANISM: Artificial Sequence
<220> FEATURE:
<223> OTHER INFORMATION: Synthetic Construct

<400> SEQUENCE: 295

Ala Cys Asn Leu Ile Val Glu Gly His Cys Gly Gly Ser Gln Gln Tyr
1               5                   10                  15

Arg Ala Leu Lys Ser Ser Gly Gly Asp Ile Val Met Thr Gln Thr
            20                  25                  30

Thr Leu Ser Leu Pro Val Ser Leu Gly Asp Gln Ala Ser Ile Ser Cys
        35                  40                  45

Arg Ser Ser Gln Ser Ile Val His Ser Asn Gly Asn Thr Tyr Leu Glu
    50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
        115                 120                 125

Gly Gly Gly Thr Lys Leu Glu Ile Lys Arg Ala Asp Ala Ala Pro Thr
    130                 135                 140

Val Ser Ile Phe Pro Pro Ser Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
            180                 185                 190

Trp Thr Asp Gln Asp Ser Lys Asp Ser Thr Tyr Ser Met Ser Ser Thr
        195                 200                 205

Leu Thr Leu Thr Lys Asp Glu Tyr Glu Arg His Asn Ser Tyr Thr Cys
    210                 215                 220

Glu Ala Thr His Lys Thr Ser Thr Ser Pro Ile Val Lys Ser Phe Asn
225                 230                 235                 240

Arg Asn Glu Cys

<210> SEQ ID NO 296
<211> LENGTH: 243
<212> TYPE: PRT
<213> ORGANISM: Artificial Sequence
<220> FEATURE:
```

<223> OTHER INFORMATION: Synthetic Construct

<400> SEQUENCE: 296

```
Ala Cys Asn Leu Ile Val Glu Gly His Cys Gly Gly Ser Tyr Val Pro
1               5                   10                  15

Arg Ala Val Leu Ser Gly Gly Gly Asp Ile Val Met Thr Gln Thr Thr
            20                  25                  30

Leu Ser Leu Pro Val Ser Leu Gly Asp Gln Ala Ser Ile Ser Cys Arg
        35                  40                  45

Ser Ser Gln Ser Ile Val His Ser Asn Gly Asn Thr Tyr Leu Glu Trp
    50                  55                  60

Tyr Leu Gln Lys Pro Gly Gln Ser Pro Lys Leu Leu Ile Tyr Lys Val
65                  70                  75                  80

Ser Asn Arg Phe Ser Gly Val Pro Asp Arg Phe Ser Gly Ser Gly Ser
                85                  90                  95

Gly Thr Asp Phe Thr Leu Lys Ile Ser Arg Val Glu Ala Glu Asp Leu
            100                 105                 110

Gly Val Tyr Tyr Cys Phe Gln Gly Ser His Val Pro Tyr Thr Phe Gly
        115                 120                 125

Gly Gly Thr Lys Leu Glu Ile Lys Arg Ala Asp Ala Ala Pro Thr Val
    130                 135                 140

Ser Ile Phe Pro Pro Ser Ser Glu Gln Leu Thr Ser Gly Gly Ala Ser
145                 150                 155                 160

Val Val Cys Phe Leu Asn Asn Phe Tyr Pro Lys Asp Ile Asn Val Lys
                165                 170                 175

Trp Lys Ile Asp Gly Ser Glu Arg Gln Asn Gly Val Leu Asn Ser Trp
            180                 185                 190

Thr Asp Gln Asp Ser Lys Asp Ser Thr Tyr Ser Met Ser Ser Thr Leu
        195                 200                 205

Thr Leu Thr Lys Asp Glu Tyr Glu Arg His Asn Ser Tyr Thr Cys Glu
    210                 215                 220

Ala Thr His Lys Thr Ser Thr Ser Pro Ile Val Lys Ser Phe Asn Arg
225                 230                 235                 240

Asn Glu Cys
```

<210> SEQ ID NO 297
<211> LENGTH: 243
<212> TYPE: PRT
<213> ORGANISM: Artificial Sequence
<220> FEATURE:
<223> OTHER INFORMATION: Synthetic Construct

<400> SEQUENCE: 297

```
Ala Cys Asn Leu Ile Val Glu Gly His Cys Gly Gly Ser Gly Val Asn
1               5                   10                  15

Lys Trp Pro Thr Ser Gly Gly Gly Asp Ile Val Met Thr Gln Thr Thr
            20                  25                  30

Leu Ser Leu Pro Val Ser Leu Gly Asp Gln Ala Ser Ile Ser Cys Arg
        35                  40                  45

Ser Ser Gln Ser Ile Val His Ser Asn Gly Asn Thr Tyr Leu Glu Trp
    50                  55                  60

Tyr Leu Gln Lys Pro Gly Gln Ser Pro Lys Leu Leu Ile Tyr Lys Val
65                  70                  75                  80

Ser Asn Arg Phe Ser Gly Val Pro Asp Arg Phe Ser Gly Ser Gly Ser
                85                  90                  95
```

```
Gly Thr Asp Phe Thr Leu Lys Ile Ser Arg Val Glu Ala Glu Asp Leu
            100                 105                 110

Gly Val Tyr Tyr Cys Phe Gln Gly Ser His Val Pro Tyr Thr Phe Gly
        115                 120                 125

Gly Gly Thr Lys Leu Glu Ile Lys Arg Ala Asp Ala Ala Pro Thr Val
    130                 135                 140

Ser Ile Phe Pro Pro Ser Ser Glu Gln Leu Thr Ser Gly Gly Ala Ser
145                 150                 155                 160

Val Val Cys Phe Leu Asn Asn Phe Tyr Pro Lys Asp Ile Asn Val Lys
                165                 170                 175

Trp Lys Ile Asp Gly Ser Glu Arg Gln Asn Gly Val Leu Asn Ser Trp
            180                 185                 190

Thr Asp Gln Asp Ser Lys Asp Ser Thr Tyr Ser Met Ser Ser Thr Leu
        195                 200                 205

Thr Leu Thr Lys Asp Glu Tyr Glu Arg His Asn Ser Tyr Thr Cys Glu
    210                 215                 220

Ala Thr His Lys Thr Ser Thr Ser Pro Ile Val Lys Ser Phe Asn Arg
225                 230                 235                 240

Asn Glu Cys

<210> SEQ ID NO 298
<211> LENGTH: 244
<212> TYPE: PRT
<213> ORGANISM: Artificial Sequence
<220> FEATURE:
<223> OTHER INFORMATION: Synthetic Construct

<400> SEQUENCE: 298

Ala Cys Asn Leu Ile Val Glu Gly His Cys Gly Gly Ser Leu Ala Gln
1               5                   10                  15

Ala Val Arg Ser Ser Gly Gly Asp Ile Val Met Thr Gln Thr
            20                  25                  30

Thr Leu Ser Leu Pro Val Ser Leu Gly Asp Gln Ala Ser Ile Ser Cys
        35                  40                  45

Arg Ser Ser Gln Ser Ile Val His Ser Asn Gly Asn Thr Tyr Leu Glu
    50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
        115                 120                 125

Gly Gly Gly Thr Lys Leu Glu Ile Lys Arg Ala Asp Ala Ala Pro Thr
    130                 135                 140

Val Ser Ile Phe Pro Pro Ser Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
            180                 185                 190

Trp Thr Asp Gln Asp Ser Lys Asp Ser Thr Tyr Ser Met Ser Ser Thr
        195                 200                 205

Leu Thr Leu Thr Lys Asp Glu Tyr Glu Arg His Asn Ser Tyr Thr Cys
```

```
                210                 215                 220
Glu Ala Thr His Lys Thr Ser Thr Ser Pro Ile Val Lys Ser Phe Asn
225                 230                 235                 240

Arg Asn Glu Cys

<210> SEQ ID NO 299
<211> LENGTH: 244
<212> TYPE: PRT
<213> ORGANISM: Artificial Sequence
<220> FEATURE:
<223> OTHER INFORMATION: Synthetic Construct

<400> SEQUENCE: 299

Ala Cys Asn Leu Ile Val Glu Gly His Cys Gly Gly Ser Arg Ala Ala
1               5                   10                  15

Ala Val Lys Ser Pro Ser Gly Gly Gly Asp Ile Val Met Thr Gln Thr
                20                  25                  30

Thr Leu Ser Leu Pro Val Ser Leu Gly Asp Gln Ala Ser Ile Ser Cys
            35                  40                  45

Arg Ser Ser Gln Ser Ile Val His Ser Asn Gly Asn Thr Tyr Leu Glu
        50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
        115                 120                 125

Gly Gly Gly Thr Lys Leu Glu Ile Lys Arg Ala Asp Ala Ala Pro Thr
    130                 135                 140

Val Ser Ile Phe Pro Pro Ser Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
            180                 185                 190

Trp Thr Asp Gln Asp Ser Lys Asp Ser Thr Tyr Ser Met Ser Ser Thr
        195                 200                 205

Leu Thr Leu Thr Lys Asp Glu Tyr Glu Arg His Asn Ser Tyr Thr Cys
    210                 215                 220

Glu Ala Thr His Lys Thr Ser Thr Ser Pro Ile Val Lys Ser Phe Asn
225                 230                 235                 240

Arg Asn Glu Cys

<210> SEQ ID NO 300
<211> LENGTH: 245
<212> TYPE: PRT
<213> ORGANISM: Artificial Sequence
<220> FEATURE:
<223> OTHER INFORMATION: Synthetic Construct

<400> SEQUENCE: 300

Ala Cys Asn Leu Ile Val Glu Gly His Cys Gly Gly Ser Asp Leu Leu
1               5                   10                  15

Ala Val Val Ala Ala Ser Ser Gly Gly Gly Asp Ile Val Met Thr Gln
                20                  25                  30
```

Thr Thr Leu Ser Leu Pro Val Ser Leu Gly Asp Gln Ala Ser Ile Ser
                35                  40                  45

Cys Arg Ser Ser Gln Ser Ile Val His Ser Asn Gly Asn Thr Tyr Leu
         50                  55                  60

Glu Trp Tyr Leu Gln Lys Pro Gly Gln Ser Pro Lys Leu Leu Ile Tyr
 65                  70                  75                  80

Lys Val Ser Asn Arg Phe Ser Gly Val Pro Asp Arg Phe Ser Gly Ser
                 85                  90                  95

Gly Ser Gly Thr Asp Phe Thr Leu Lys Ile Ser Arg Val Glu Ala Glu
            100                 105                 110

Asp Leu Gly Val Tyr Tyr Cys Phe Gln Gly Ser His Val Pro Tyr Thr
             115                 120                 125

Phe Gly Gly Gly Thr Lys Leu Glu Ile Lys Arg Ala Asp Ala Ala Pro
130                 135                 140

Thr Val Ser Ile Phe Pro Pro Ser Ser Glu Gln Leu Thr Ser Gly Gly
145                 150                 155                 160

Ala Ser Val Val Cys Phe Leu Asn Asn Phe Tyr Pro Lys Asp Ile Asn
                165                 170                 175

Val Lys Trp Lys Ile Asp Gly Ser Glu Arg Gln Asn Gly Val Leu Asn
            180                 185                 190

Ser Trp Thr Asp Gln Asp Ser Lys Asp Ser Thr Tyr Ser Met Ser Ser
        195                 200                 205

Thr Leu Thr Leu Thr Lys Asp Glu Tyr Glu Arg His Asn Ser Tyr Thr
    210                 215                 220

Cys Glu Ala Thr His Lys Thr Ser Thr Ser Pro Ile Val Lys Ser Phe
225                 230                 235                 240

Asn Arg Asn Glu Cys
                245

<210> SEQ ID NO 301
<211> LENGTH: 244
<212> TYPE: PRT
<213> ORGANISM: Artificial Sequence
<220> FEATURE:
<223> OTHER INFORMATION: Synthetic Construct

<400> SEQUENCE: 301

Ala Cys Asn Leu Ile Val Glu Gly His Cys Gly Gly Ser Val Gln Thr
 1               5                  10                  15

Val Thr Trp Pro Asp Ser Gly Gly Asp Ile Val Met Thr Gln Thr
                 20                  25                  30

Thr Leu Ser Leu Pro Val Ser Leu Gly Asp Gln Ala Ser Ile Ser Cys
            35                  40                  45

Arg Ser Ser Gln Ser Ile Val His Ser Asn Gly Asn Thr Tyr Leu Glu
        50                  55                  60

Trp Tyr Leu Gln Lys Pro Gly Gln Ser Pro Lys Leu Leu Ile Tyr Lys
 65                  70                  75                  80

Val Ser Asn Arg Phe Ser Gly Val Pro Asp Arg Phe Ser Gly Ser Gly
                 85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
        115                 120                 125

Gly Gly Gly Thr Lys Leu Glu Ile Lys Arg Ala Asp Ala Ala Pro Thr
130                 135                 140

```
Val Ser Ile Phe Pro Pro Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
            180                 185                 190

Trp Thr Asp Gln Asp Ser Lys Asp Ser Thr Tyr Ser Met Ser Ser Thr
        195                 200                 205

Leu Thr Leu Thr Lys Asp Glu Tyr Glu Arg His Asn Ser Tyr Thr Cys
    210                 215                 220

Glu Ala Thr His Lys Thr Ser Thr Ser Pro Ile Val Lys Ser Phe Asn
225                 230                 235                 240

Arg Asn Glu Cys

<210> SEQ ID NO 302
<211> LENGTH: 244
<212> TYPE: PRT
<213> ORGANISM: Artificial Sequence
<220> FEATURE:
<223> OTHER INFORMATION: Synthetic Construct

<400> SEQUENCE: 302

Ala Cys Asn Leu Ile Val Glu Gly His Cys Gly Gly Ser Ala Ile Pro
1               5                   10                  15

Met Ser Ile Pro Pro Ser Gly Gly Asp Ile Val Met Thr Gln Thr
            20                  25                  30

Thr Leu Ser Leu Pro Val Ser Leu Gly Asp Gln Ala Ser Ile Ser Cys
        35                  40                  45

Arg Ser Ser Gln Ser Ile Val His Ser Asn Gly Asn Thr Tyr Leu Glu
    50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
        115                 120                 125

Gly Gly Gly Thr Lys Leu Glu Ile Lys Arg Ala Asp Ala Ala Pro Thr
    130                 135                 140

Val Ser Ile Phe Pro Pro Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
            180                 185                 190

Trp Thr Asp Gln Asp Ser Lys Asp Ser Thr Tyr Ser Met Ser Ser Thr
        195                 200                 205

Leu Thr Leu Thr Lys Asp Glu Tyr Glu Arg His Asn Ser Tyr Thr Cys
    210                 215                 220

Glu Ala Thr His Lys Thr Ser Thr Ser Pro Ile Val Lys Ser Phe Asn
225                 230                 235                 240

Arg Asn Glu Cys
```

```
<210> SEQ ID NO 303
<211> LENGTH: 244
<212> TYPE: PRT
<213> ORGANISM: Artificial Sequence
<220> FEATURE:
<223> OTHER INFORMATION: Synthetic Construct

<400> SEQUENCE: 303

Ala Cys Asn Leu Ile Val Glu Gly His Cys Gly Gly Ser Gly Tyr Glu
1               5                   10                  15

Val His His Gln Lys Ser Gly Gly Gly Asp Ile Val Met Thr Gln Thr
                20                  25                  30

Thr Leu Ser Leu Pro Val Ser Leu Gly Asp Gln Ala Ser Ile Ser Cys
            35                  40                  45

Arg Ser Ser Gln Ser Ile Val His Ser Asn Gly Asn Thr Tyr Leu Glu
        50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
            100                 105                 110

Leu Gly Val Tyr Tyr Cys Phe Gln Gly Ser His Val Pro Tyr Thr Phe
        115                 120                 125

Gly Gly Gly Thr Lys Leu Glu Ile Lys Arg Ala Asp Ala Ala Pro Thr
    130                 135                 140

Val Ser Ile Phe Pro Pro Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
            180                 185                 190

Trp Thr Asp Gln Asp Ser Lys Asp Ser Thr Tyr Ser Met Ser Ser Thr
        195                 200                 205

Leu Thr Leu Thr Lys Asp Glu Tyr Glu Arg His Asn Ser Tyr Thr Cys
    210                 215                 220

Glu Ala Thr His Lys Thr Ser Thr Ser Pro Ile Val Lys Ser Phe Asn
225                 230                 235                 240

Arg Asn Glu Cys

<210> SEQ ID NO 304
<211> LENGTH: 244
<212> TYPE: PRT
<213> ORGANISM: Artificial Sequence
<220> FEATURE:
<223> OTHER INFORMATION: Synthetic Construct

<400> SEQUENCE: 304

Ala Cys Asn Leu Ile Val Glu Gly His Cys Gly Gly Ser Val His His
1               5                   10                  15

Gln Lys Leu Val Phe Ser Gly Gly Gly Asp Ile Val Met Thr Gln Thr
                20                  25                  30

Thr Leu Ser Leu Pro Val Ser Leu Gly Asp Gln Ala Ser Ile Ser Cys
            35                  40                  45

Arg Ser Ser Gln Ser Ile Val His Ser Asn Gly Asn Thr Tyr Leu Glu
        50                  55                  60

Trp Tyr Leu Gln Lys Pro Gly Gln Ser Pro Lys Leu Leu Ile Tyr Lys
```

```
                65                  70                  75                  80
Val Ser Asn Arg Phe Ser Gly Val Pro Asp Arg Phe Ser Gly Ser Gly
                    85                  90                  95

Ser Gly Thr Asp Phe Thr Leu Lys Ile Ser Arg Val Glu Ala Glu Asp
                100                 105                 110

Leu Gly Val Tyr Tyr Cys Phe Gln Gly Ser His Val Pro Tyr Thr Phe
                115                 120                 125

Gly Gly Gly Thr Lys Leu Glu Ile Lys Arg Ala Asp Ala Ala Pro Thr
            130                 135                 140

Val Ser Ile Phe Pro Pro Ser Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
                180                 185                 190

Trp Thr Asp Gln Asp Ser Lys Asp Ser Thr Tyr Ser Met Ser Ser Thr
                195                 200                 205

Leu Thr Leu Thr Lys Asp Glu Tyr Glu Arg His Asn Ser Tyr Thr Cys
            210                 215                 220

Glu Ala Thr His Lys Thr Ser Thr Ser Pro Ile Val Lys Ser Phe Asn
225                 230                 235                 240

Arg Asn Glu Cys

<210> SEQ ID NO 305
<211> LENGTH: 244
<212> TYPE: PRT
<213> ORGANISM: Artificial Sequence
<220> FEATURE:
<223> OTHER INFORMATION: Synthetic Construct

<400> SEQUENCE: 305

Ala Cys Asn Leu Ile Val Glu Gly His Cys Gly Gly Ser Ile Arg Arg
1               5                   10                  15

Val Ser Tyr Ser Phe Ser Gly Gly Asp Ile Val Met Thr Gln Thr
                20                  25                  30

Thr Leu Ser Leu Pro Val Ser Leu Gly Asp Gln Ala Ser Ile Ser Cys
            35                  40                  45

Arg Ser Ser Gln Ser Ile Val His Ser Asn Gly Asn Thr Tyr Leu Glu
        50                  55                  60

Trp Tyr Leu Gln Lys Pro Gly Gln Ser Pro Lys Leu Leu Ile Tyr Lys
65                  70                  75                  80

Val Ser Asn Arg Phe Ser Gly Val Pro Asp Arg Phe Ser Gly Ser Gly
                85                  90                  95

Ser Gly Thr Asp Phe Thr Leu Lys Ile Ser Arg Val Glu Ala Glu Asp
                100                 105                 110

Leu Gly Val Tyr Tyr Cys Phe Gln Gly Ser His Val Pro Tyr Thr Phe
                115                 120                 125

Gly Gly Gly Thr Lys Leu Glu Ile Lys Arg Ala Asp Ala Ala Pro Thr
            130                 135                 140

Val Ser Ile Phe Pro Pro Ser Ser Glu Gln Leu Thr Ser Gly Gly Ala
145                 150                 155                 160

Ser Val Val Cys Phe Leu Asn Asn Phe Tyr Pro Lys Asp Ile Asn Val
                165                 170                 175

Lys Trp Lys Ile Asp Gly Ser Glu Arg Gln Asn Gly Val Leu Asn Ser
                180                 185                 190
```

```
Trp Thr Asp Gln Asp Ser Lys Asp Ser Thr Tyr Ser Met Ser Ser Thr
        195                 200                 205
Leu Thr Leu Thr Lys Asp Glu Tyr Glu Arg His Asn Ser Tyr Thr Cys
    210                 215                 220
Glu Ala Thr His Lys Thr Ser Thr Ser Pro Ile Val Lys Ser Phe Asn
225                 230                 235                 240
Arg Asn Glu Cys

<210> SEQ ID NO 306
<211> LENGTH: 250
<212> TYPE: PRT
<213> ORGANISM: Artificial Sequence
<220> FEATURE:
<223> OTHER INFORMATION: Synthetic Construct

<400> SEQUENCE: 306

Ala Cys Asn Leu Ile Val Glu Gly His Cys Gly Gly Ser Met Pro Tyr
1               5                   10                  15
Asp Leu Tyr His Pro Ile Leu Phe Phe Arg Leu Ser Gly Gly Gly Asp
                20                  25                  30
Ile Val Met Thr Gln Thr Thr Leu Ser Leu Pro Val Ser Leu Gly Asp
            35                  40                  45
Gln Ala Ser Ile Ser Cys Arg Ser Ser Gln Ser Ile Val His Ser Asn
50                  55                  60
Gly Asn Thr Tyr Leu Glu Trp Tyr Leu Gln Lys Pro Gly Gln Ser Pro
65                  70                  75                  80
Lys Leu Leu Ile Tyr Lys Val Ser Asn Arg Phe Ser Gly Val Pro Asp
                85                  90                  95
Arg Phe Ser Gly Ser Gly Ser Gly Thr Asp Phe Thr Leu Lys Ile Ser
            100                 105                 110
Arg Val Glu Ala Glu Asp Leu Gly Val Tyr Tyr Cys Phe Gln Gly Ser
        115                 120                 125
His Val Pro Tyr Thr Phe Gly Gly Gly Thr Lys Leu Glu Ile Lys Arg
    130                 135                 140
Ala Asp Ala Ala Pro Thr Val Ser Ile Phe Pro Pro Ser Ser Glu Gln
145                 150                 155                 160
Leu Thr Ser Gly Gly Ala Ser Val Val Cys Phe Leu Asn Asn Phe Tyr
                165                 170                 175
Pro Lys Asp Ile Asn Val Lys Trp Lys Ile Asp Gly Ser Glu Arg Gln
            180                 185                 190
Asn Gly Val Leu Asn Ser Trp Thr Asp Gln Asp Ser Lys Asp Ser Thr
        195                 200                 205
Tyr Ser Met Ser Ser Thr Leu Thr Leu Thr Lys Asp Glu Tyr Glu Arg
    210                 215                 220
His Asn Ser Tyr Thr Cys Glu Ala Thr His Lys Thr Ser Thr Ser Pro
225                 230                 235                 240
Ile Val Lys Ser Phe Asn Arg Asn Glu Cys
                245                 250

<210> SEQ ID NO 307
<211> LENGTH: 250
<212> TYPE: PRT
<213> ORGANISM: Artificial Sequence
<220> FEATURE:
<223> OTHER INFORMATION: Synthetic Construct

<400> SEQUENCE: 307
```

Ala Cys Asn Leu Ile Val Glu Gly His Cys Gly Gly Ser Gly Gly Ile
1               5                   10                  15

Gly Gln Leu Thr Ser Val Leu Met Ala Ala Pro Ser Gly Gly Gly Asp
            20                  25                  30

Ile Val Met Thr Gln Thr Thr Leu Ser Leu Pro Val Ser Leu Gly Asp
        35                  40                  45

Gln Ala Ser Ile Ser Cys Arg Ser Ser Gln Ser Ile Val His Ser Asn
    50                  55                  60

Gly Asn Thr Tyr Leu Glu Trp Tyr Leu Gln Lys Pro Gly Gln Ser Pro
65                  70                  75                  80

Lys Leu Leu Ile Tyr Lys Val Ser Asn Arg Phe Ser Gly Val Pro Asp
                85                  90                  95

Arg Phe Ser Gly Ser Gly Ser Gly Thr Asp Phe Thr Leu Lys Ile Ser
            100                 105                 110

Arg Val Glu Ala Glu Asp Leu Gly Val Tyr Tyr Cys Phe Gln Gly Ser
        115                 120                 125

His Val Pro Tyr Thr Phe Gly Gly Gly Thr Lys Leu Glu Ile Lys Arg
    130                 135                 140

Ala Asp Ala Ala Pro Thr Val Ser Ile Phe Pro Pro Ser Ser Glu Gln
145                 150                 155                 160

Leu Thr Ser Gly Gly Ala Ser Val Val Cys Phe Leu Asn Asn Phe Tyr
                165                 170                 175

Pro Lys Asp Ile Asn Val Lys Trp Lys Ile Asp Gly Ser Glu Arg Gln
            180                 185                 190

Asn Gly Val Leu Asn Ser Trp Thr Asp Gln Asp Ser Lys Asp Ser Thr
        195                 200                 205

Tyr Ser Met Ser Ser Thr Leu Thr Leu Thr Lys Asp Glu Tyr Glu Arg
    210                 215                 220

His Asn Ser Tyr Thr Cys Glu Ala Thr His Lys Thr Ser Thr Ser Pro
225                 230                 235                 240

Ile Val Lys Ser Phe Asn Arg Asn Glu Cys
                245                 250

<210> SEQ ID NO 308
<211> LENGTH: 251
<212> TYPE: PRT
<213> ORGANISM: Artificial Sequence
<220> FEATURE:
<223> OTHER INFORMATION: Synthetic Construct

<400> SEQUENCE: 308

Ala Cys Asn Leu Ile Val Glu Gly His Cys Gly Gly Ser Asp Ser Gly
1               5                   10                  15

Gly Phe Met Leu Thr Leu Val Leu Pro Val Leu Pro Ser Gly Gly Gly
            20                  25                  30

Asp Ile Val Met Thr Gln Thr Thr Leu Ser Leu Pro Val Ser Leu Gly
        35                  40                  45

Asp Gln Ala Ser Ile Ser Cys Arg Ser Ser Gln Ser Ile Val His Ser
    50                  55                  60

Asn Gly Asn Thr Tyr Leu Glu Trp Tyr Leu Gln Lys Pro Gly Gln Ser
65                  70                  75                  80

Pro Lys Leu Leu Ile Tyr Lys Val Ser Asn Arg Phe Ser Gly Val Pro
                85                  90                  95

Asp Arg Phe Ser Gly Ser Gly Ser Gly Thr Asp Phe Thr Leu Lys Ile
            100                 105                 110

Ser Arg Val Glu Ala Glu Asp Leu Gly Val Tyr Tyr Cys Phe Gln Gly
            115                 120                 125

Ser His Val Pro Tyr Thr Phe Gly Gly Gly Thr Lys Leu Glu Ile Lys
            130                 135                 140

Arg Ala Asp Ala Ala Pro Thr Val Ser Ile Phe Pro Pro Ser Ser Glu
145                 150                 155                 160

Gln Leu Thr Ser Gly Gly Ala Ser Val Val Cys Phe Leu Asn Asn Phe
            165                 170                 175

Tyr Pro Lys Asp Ile Asn Val Lys Trp Lys Ile Asp Gly Ser Glu Arg
            180                 185                 190

Gln Asn Gly Val Leu Asn Ser Trp Thr Asp Gln Asp Ser Lys Asp Ser
            195                 200                 205

Thr Tyr Ser Met Ser Ser Thr Leu Thr Leu Thr Lys Asp Glu Tyr Glu
            210                 215                 220

Arg His Asn Ser Tyr Thr Cys Glu Ala Thr His Lys Thr Ser Thr Ser
225                 230                 235                 240

Pro Ile Val Lys Ser Phe Asn Arg Asn Glu Cys
            245                 250

<210> SEQ ID NO 309
<211> LENGTH: 252
<212> TYPE: PRT
<213> ORGANISM: Artificial Sequence
<220> FEATURE:
<223> OTHER INFORMATION: Synthetic Construct

<400> SEQUENCE: 309

Ala Cys Asn Leu Ile Val Glu Gly His Cys Gly Gly Ser Thr Ser Glu
1               5                   10                  15

Phe Val Phe Ala Pro Asp Leu Gly Arg Phe Gln Thr Phe Ser Gly Gly
            20                  25                  30

Gly Asp Ile Val Met Thr Gln Thr Thr Leu Ser Leu Pro Val Ser Leu
            35                  40                  45

Gly Asp Gln Ala Ser Ile Ser Cys Arg Ser Ser Gln Ser Ile Val His
50                  55                  60

Ser Asn Gly Asn Thr Tyr Leu Glu Trp Tyr Leu Gln Lys Pro Gly Gln
65                  70                  75                  80

Ser Pro Lys Leu Leu Ile Tyr Lys Val Ser Asn Arg Phe Ser Gly Val
            85                  90                  95

Pro Asp Arg Phe Ser Gly Ser Gly Ser Gly Thr Asp Phe Thr Leu Lys
            100                 105                 110

Ile Ser Arg Val Glu Ala Glu Asp Leu Gly Val Tyr Tyr Cys Phe Gln
            115                 120                 125

Gly Ser His Val Pro Tyr Thr Phe Gly Gly Gly Thr Lys Leu Glu Ile
            130                 135                 140

Lys Arg Ala Asp Ala Ala Pro Thr Val Ser Ile Phe Pro Pro Ser Ser
145                 150                 155                 160

Glu Gln Leu Thr Ser Gly Gly Ala Ser Val Val Cys Phe Leu Asn Asn
            165                 170                 175

Phe Tyr Pro Lys Asp Ile Asn Val Lys Trp Lys Ile Asp Gly Ser Glu
            180                 185                 190

Arg Gln Asn Gly Val Leu Asn Ser Trp Thr Asp Gln Asp Ser Lys Asp
            195                 200                 205

Ser Thr Tyr Ser Met Ser Ser Thr Leu Thr Leu Thr Lys Asp Glu Tyr
            210                 215                 220

Glu Arg His Asn Ser Tyr Thr Cys Glu Ala Thr His Lys Thr Ser Thr
225                 230                 235                 240

Ser Pro Ile Val Lys Ser Phe Asn Arg Asn Glu Cys
                245                 250

<210> SEQ ID NO 310
<211> LENGTH: 242
<212> TYPE: PRT
<213> ORGANISM: Artificial Sequence
<220> FEATURE:
<223> OTHER INFORMATION: Synthetic Construct

<400> SEQUENCE: 310

Ala Cys Asn Leu Ile Val Gln Gly His Cys Gly Gly Ser Val Pro Leu
1               5                   10                  15

Ser Leu Tyr Ser Gly Gly Gly Asp Ile Val Met Thr Gln Thr Thr Leu
            20                  25                  30

Ser Leu Pro Val Ser Leu Gly Asp Gln Ala Ser Ile Ser Cys Arg Ser
        35                  40                  45

Ser Gln Ser Ile Val His Ser Asn Gly Asn Thr Tyr Leu Glu Trp Tyr
    50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
        115                 120                 125

Gly Thr Lys Leu Glu Ile Lys Arg Ala Asp Ala Ala Pro Thr Val Ser
    130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
                165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
        195                 200                 205

Leu Thr Lys Asp Glu Tyr Glu Arg His Asn Ser Tyr Thr Cys Glu Ala
    210                 215                 220

Thr His Lys Thr Ser Thr Ser Pro Ile Val Lys Ser Phe Asn Arg Asn
225                 230                 235                 240

Glu Cys

<210> SEQ ID NO 311
<211> LENGTH: 242
<212> TYPE: PRT
<213> ORGANISM: Artificial Sequence
<220> FEATURE:
<223> OTHER INFORMATION: Synthetic Construct

<400> SEQUENCE: 311

Ala Cys Asn Leu Ile Val Glu Gly His Cys Gly His Ser Val Pro Leu
1               5                   10                  15

Ser Leu Tyr Ser His Gly Gly Asp Ile Val Met Thr Gln Thr Thr Leu
            20                  25                  30

```
Ser Leu Pro Val Ser Leu Gly Asp Gln Ala Ser Ile Ser Cys Arg Ser
        35                  40                  45

Ser Gln Ser Ile Val His Ser Asn Gly Asn Thr Tyr Leu Glu Trp Tyr
    50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
        115                 120                 125

Gly Thr Lys Leu Glu Ile Lys Arg Ala Asp Ala Ala Pro Thr Val Ser
    130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
                165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
        195                 200                 205

Leu Thr Lys Asp Glu Tyr Glu Arg His Asn Ser Tyr Thr Cys Glu Ala
    210                 215                 220

Thr His Lys Thr Ser Thr Ser Pro Ile Val Lys Ser Phe Asn Arg Asn
225                 230                 235                 240

Glu Cys

<210> SEQ ID NO 312
<211> LENGTH: 242
<212> TYPE: PRT
<213> ORGANISM: Artificial Sequence
<220> FEATURE:
<223> OTHER INFORMATION: Synthetic Construct

<400> SEQUENCE: 312

Ala Cys Asn Leu Ile Val Glu Gly His Cys Gly Gly Ser Val Pro Leu
1               5                   10                  15

Ser Leu Tyr Ser His Gly Gly Asp Ile Val Met Thr Gln Thr Thr Leu
                20                  25                  30

Ser Leu Pro Val Ser Leu Gly Asp Gln Ala Ser Ile Ser Cys Arg Ser
        35                  40                  45

Ser Gln Ser Ile Val His Ser Asn Gly Asn Thr Tyr Leu Glu Trp Tyr
    50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
        115                 120                 125

Gly Thr Lys Leu Glu Ile Lys Arg Ala Asp Ala Ala Pro Thr Val Ser
    130                 135                 140
```

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
            165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
            195                 200                 205

Leu Thr Lys Asp Glu Tyr Glu Arg His Asn Ser Tyr Thr Cys Glu Ala
            210                 215                 220

Thr His Lys Thr Ser Thr Ser Pro Ile Val Lys Ser Phe Asn Arg Asn
225                 230                 235                 240

Glu Cys

<210> SEQ ID NO 313
<211> LENGTH: 242
<212> TYPE: PRT
<213> ORGANISM: Artificial Sequence
<220> FEATURE:
<223> OTHER INFORMATION: Synthetic Construct

<400> SEQUENCE: 313

Ala Cys Asn Leu Ile Val Glu Gly His Cys Gly His Ser Val Pro Leu
1               5                   10                  15

Ser Leu Tyr Ser Gly Gly Gly Asp Ile Val Met Thr Gln Thr Thr Leu
            20                  25                  30

Ser Leu Pro Val Ser Leu Gly Asp Gln Ala Ser Ile Ser Cys Arg Ser
            35                  40                  45

Ser Gln Ser Ile Val His Ser Asn Gly Asn Thr Tyr Leu Glu Trp Tyr
        50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
            115                 120                 125

Gly Thr Lys Leu Glu Ile Lys Arg Ala Asp Ala Ala Pro Thr Val Ser
        130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
            165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
            195                 200                 205

Leu Thr Lys Asp Glu Tyr Glu Arg His Asn Ser Tyr Thr Cys Glu Ala
            210                 215                 220

Thr His Lys Thr Ser Thr Ser Pro Ile Val Lys Ser Phe Asn Arg Asn
225                 230                 235                 240

Glu Cys

<210> SEQ ID NO 314

```
<211> LENGTH: 242
<212> TYPE: PRT
<213> ORGANISM: Artificial Sequence
<220> FEATURE:
<223> OTHER INFORMATION: Synthetic Construct

<400> SEQUENCE: 314

Ala Cys Asn Leu Ile Val Glu Gly His Cys Gly Gly Ser Val Pro Leu
1               5                   10                  15

Ser Leu Tyr His Gly Gly Gly Asp Ile Val Met Thr Gln Thr Thr Leu
            20                  25                  30

Ser Leu Pro Val Ser Leu Gly Asp Gln Ala Ser Ile Ser Cys Arg Ser
        35                  40                  45

Ser Gln Ser Ile Val His Ser Asn Gly Asn Thr Tyr Leu Glu Trp Tyr
    50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
        115                 120                 125

Gly Thr Lys Leu Glu Ile Lys Arg Ala Asp Ala Ala Pro Thr Val Ser
    130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
                165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
        195                 200                 205

Leu Thr Lys Asp Glu Tyr Glu Arg His Asn Ser Tyr Thr Cys Glu Ala
    210                 215                 220

Thr His Lys Thr Ser Thr Ser Pro Ile Val Lys Ser Phe Asn Arg Asn
225                 230                 235                 240

Glu Cys

<210> SEQ ID NO 315
<211> LENGTH: 242
<212> TYPE: PRT
<213> ORGANISM: Artificial Sequence
<220> FEATURE:
<223> OTHER INFORMATION: Synthetic Construct

<400> SEQUENCE: 315

Ala Cys Asn Leu Ile Val Glu Gly His Cys Gly His Ser Val Pro Leu
1               5                   10                  15

Ser Leu Tyr His Gly Gly Gly Asp Ile Val Met Thr Gln Thr Thr Leu
            20                  25                  30

Ser Leu Pro Val Ser Leu Gly Asp Gln Ala Ser Ile Ser Cys Arg Ser
        35                  40                  45

Ser Gln Ser Ile Val His Ser Asn Gly Asn Thr Tyr Leu Glu Trp Tyr
    50                  55                  60

Leu Gln Lys Pro Gly Gln Ser Pro Lys Leu Leu Ile Tyr Lys Val Ser
65                  70                  75                  80
```

```
Asn Arg Phe Ser Gly Val Pro Asp Arg Phe Ser Gly Ser Gly
            85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
            115                 120                 125

Gly Thr Lys Leu Glu Ile Lys Arg Ala Asp Ala Ala Pro Thr Val Ser
130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
            165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
            195                 200                 205

Leu Thr Lys Asp Glu Tyr Glu Arg His Asn Ser Tyr Thr Cys Glu Ala
            210                 215                 220

Thr His Lys Thr Ser Thr Ser Pro Ile Val Lys Ser Phe Asn Arg Asn
225                 230                 235                 240

Glu Cys

<210> SEQ ID NO 316
<211> LENGTH: 242
<212> TYPE: PRT
<213> ORGANISM: Artificial Sequence
<220> FEATURE:
<223> OTHER INFORMATION: Synthetic Construct

<400> SEQUENCE: 316

Ala Cys Asn Leu Ile Val Glu Gly His Cys Gly Pro Ser Val Pro Leu
1               5                   10                  15

Ser Leu Tyr Ser Gly Ala Ala Asp Ile Val Met Thr Gln Thr Thr Leu
            20                  25                  30

Ser Leu Pro Val Ser Leu Gly Asp Gln Ala Ser Ile Ser Cys Arg Ser
            35                  40                  45

Ser Gln Ser Ile Val His Ser Asn Gly Asn Thr Tyr Leu Glu Trp Tyr
            50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
            85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
            115                 120                 125

Gly Thr Lys Leu Glu Ile Lys Arg Ala Asp Ala Ala Pro Thr Val Ser
130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
            165                 170                 175

Lys Ile Asp Gly Ser Glu Arg Gln Asn Gly Val Leu Asn Ser Trp Thr
            180                 185                 190
```

Asp Gln Asp Ser Lys Asp Ser Thr Tyr Ser Met Ser Ser Thr Leu Thr
            195                 200                 205

Leu Thr Lys Asp Glu Tyr Glu Arg His Asn Ser Tyr Thr Cys Glu Ala
        210                 215                 220

Thr His Lys Thr Ser Thr Ser Pro Ile Val Lys Ser Phe Asn Arg Asn
225                 230                 235                 240

Glu Cys

<210> SEQ ID NO 317
<211> LENGTH: 242
<212> TYPE: PRT
<213> ORGANISM: Artificial Sequence
<220> FEATURE:
<223> OTHER INFORMATION: Synthetic Construct

<400> SEQUENCE: 317

Ala Cys Asn Leu Ile Val Glu Gly His Cys Gly Ala Ser Val Pro Leu
1               5                   10                  15

Ser Leu Tyr Ser Gly Pro Ala Asp Ile Val Met Thr Gln Thr Thr Leu
            20                  25                  30

Ser Leu Pro Val Ser Leu Gly Asp Gln Ala Ser Ile Ser Cys Arg Ser
        35                  40                  45

Ser Gln Ser Ile Val His Ser Asn Gly Asn Thr Tyr Leu Glu Trp Tyr
    50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
            100                 105                 110

Val Tyr Tyr Cys Phe Gln Gly Ser His Val Pro Tyr Thr Phe Gly Gly
        115                 120                 125

Gly Thr Lys Leu Glu Ile Lys Arg Ala Asp Ala Ala Pro Thr Val Ser
    130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
                165                 170                 175

Lys Ile Asp Gly Ser Glu Arg Gln Asn Gly Val Leu Asn Ser Trp Thr
            180                 185                 190

Asp Gln Asp Ser Lys Asp Ser Thr Tyr Ser Met Ser Ser Thr Leu Thr
        195                 200                 205

Leu Thr Lys Asp Glu Tyr Glu Arg His Asn Ser Tyr Thr Cys Glu Ala
    210                 215                 220

Thr His Lys Thr Ser Thr Ser Pro Ile Val Lys Ser Phe Asn Arg Asn
225                 230                 235                 240

Glu Cys

<210> SEQ ID NO 318
<211> LENGTH: 242
<212> TYPE: PRT
<213> ORGANISM: Artificial Sequence
<220> FEATURE:
<223> OTHER INFORMATION: Synthetic Construct

<400> SEQUENCE: 318

Ala Cys Asn Leu Ile Val Glu Gly His Cys Gly Pro Ser Val Pro Leu

-continued

```
1               5                   10                  15
Ser Leu Tyr Ser Gly Pro Ala Asp Ile Val Met Thr Gln Thr Thr Leu
                20                  25                  30

Ser Leu Pro Val Ser Leu Gly Asp Gln Ala Ser Ile Ser Cys Arg Ser
                35                  40                  45

Ser Gln Ser Ile Val His Ser Asn Gly Asn Thr Tyr Leu Glu Trp Tyr
            50                  55                  60

Leu Gln Lys Pro Gly Gln Ser Pro Lys Leu Leu Ile Tyr Lys Val Ser
65                  70                  75                  80

Asn Arg Phe Ser Gly Val Pro Asp Arg Phe Ser Gly Ser Gly Ser Gly
                85                  90                  95

Thr Asp Phe Thr Leu Lys Ile Ser Arg Val Glu Ala Glu Asp Leu Gly
                100                 105                 110

Val Tyr Tyr Cys Phe Gln Gly Ser His Val Pro Tyr Thr Phe Gly Gly
                115                 120                 125

Gly Thr Lys Leu Glu Ile Lys Arg Ala Asp Ala Ala Pro Thr Val Ser
            130                 135                 140

Ile Phe Pro Pro Ser Ser Glu Gln Leu Thr Ser Gly Gly Ala Ser Val
145                 150                 155                 160

Val Cys Phe Leu Asn Asn Phe Tyr Pro Lys Asp Ile Asn Val Lys Trp
                165                 170                 175

Lys Ile Asp Gly Ser Glu Arg Gln Asn Gly Val Leu Asn Ser Trp Thr
                180                 185                 190

Asp Gln Asp Ser Lys Asp Ser Thr Tyr Ser Met Ser Ser Thr Leu Thr
                195                 200                 205

Leu Thr Lys Asp Glu Tyr Glu Arg His Asn Ser Tyr Thr Cys Glu Ala
            210                 215                 220

Thr His Lys Thr Ser Thr Ser Pro Ile Val Lys Ser Phe Asn Arg Asn
225                 230                 235                 240

Glu Cys
```

<210> SEQ ID NO 319
<211> LENGTH: 447
<212> TYPE: PRT
<213> ORGANISM: Artificial Sequence
<220> FEATURE:
<223> OTHER INFORMATION: Synthetic Construct

<400> SEQUENCE: 319

```
Glu Ala Lys Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
                35                  40                  45

Gly Val Ile Asn Pro Tyr Asn Gly Asp Thr Ser Tyr Asn Gln Lys Phe
            50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Tyr Gly Ser Trp Phe Ala Tyr Trp Gly Gln Gly Thr Leu
                100                 105                 110

Ile Thr Val Ser Ser Ala Lys Thr Thr Ala Pro Ser Val Tyr Pro Leu
                115                 120                 125
```

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
    370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
        435                 440                 445

<210> SEQ ID NO 320
<211> LENGTH: 453
<212> TYPE: PRT
<213> ORGANISM: Artificial Sequence
<220> FEATURE:
<223> OTHER INFORMATION: Synthetic Construct

<400> SEQUENCE: 320

Glu Ala Lys Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

-continued

```
Gly Val Ile Asn Pro Tyr Asn Gly Asp Thr Ser Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Glu Leu Asn Ser Leu Thr Ser Glu Asp Ser Ala Val Tyr Tyr Cys
                 85                  90                  95

Ala Arg Tyr Tyr Gly Ser Trp Phe Ala Tyr Trp Gly Gln Gly Thr Leu
                100                 105                 110

Ile Thr Val Ser Ser Ala Lys Thr Thr Pro Pro Ser Val Tyr Pro Leu
            115                 120                 125

Ala Pro Gly Cys Gly Asp Thr Thr Gly Ser Ser Val Thr Leu Gly Cys
    130                 135                 140

Leu Val Lys Gly Tyr Phe Pro Glu Ser Val Thr Val Thr Trp Asn Ser
145                 150                 155                 160

Gly Ser Leu Ser Ser Ser Val His Thr Phe Pro Ala Leu Leu Gln Ser
                165                 170                 175

Gly Leu Tyr Thr Met Ser Ser Ser Val Thr Val Pro Ser Ser Thr Trp
                180                 185                 190

Pro Ser Gln Thr Val Thr Cys Ser Val Ala His Pro Ala Ser Ser Thr
            195                 200                 205

Thr Val Asp Lys Lys Leu Glu Pro Ser Gly Pro Ile Ser Thr Ile Asn
    210                 215                 220

Pro Cys Pro Pro Cys Lys Glu Cys His Lys Cys Pro Ala Pro Asn Leu
225                 230                 235                 240

Glu Gly Gly Pro Ser Val Phe Ile Phe Pro Pro Asn Ile Lys Asp Val
                245                 250                 255

Leu Met Ile Ser Leu Thr Pro Lys Val Thr Cys Val Val Val Asp Val
                260                 265                 270

Ser Glu Asp Asp Pro Asp Val Gln Ile Ser Trp Phe Val Asn Asn Val
            275                 280                 285

Glu Val His Thr Ala Gln Thr Gln Thr His Arg Glu Asp Tyr Asn Ser
    290                 295                 300

Thr Ile Arg Val Val Ser Thr Leu Pro Ile Gln His Gln Asp Trp Met
305                 310                 315                 320

Ser Gly Lys Glu Phe Lys Cys Lys Val Asn Asn Lys Asp Leu Pro Ser
                325                 330                 335

Pro Ile Glu Arg Thr Ile Ser Lys Ile Lys Gly Leu Val Arg Ala Pro
                340                 345                 350

Gln Val Tyr Ile Leu Pro Pro Pro Ala Glu Gln Leu Ser Arg Lys Asp
            355                 360                 365

Val Ser Leu Thr Cys Leu Val Val Gly Phe Asn Pro Gly Asp Ile Ser
    370                 375                 380

Val Glu Trp Thr Ser Asn Gly His Thr Glu Glu Asn Tyr Lys Asp Thr
385                 390                 395                 400

Ala Pro Val Leu Asp Ser Asp Gly Ser Tyr Phe Ile Tyr Ser Lys Leu
                405                 410                 415

Asn Met Lys Thr Ser Lys Trp Glu Lys Thr Asp Ser Phe Ser Cys Asn
                420                 425                 430

Val Arg His Glu Gly Leu Lys Asn Tyr Tyr Leu Lys Lys Thr Ile Ser
            435                 440                 445

Arg Ser Pro Gly Lys
    450
```

```
<210> SEQ ID NO 321
<211> LENGTH: 113
<212> TYPE: PRT
<213> ORGANISM: Artificial Sequence
<220> FEATURE:
<223> OTHER INFORMATION: Synthetic Construct

<400> SEQUENCE: 321

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Leu Asn Ser
            20                  25                  30

Asp Gly Asn Thr Tyr Leu Tyr Trp Tyr Leu Gln Lys Pro Gly Gln Ser
        35                  40                  45

Pro Gln Leu Leu Ile Tyr Leu Val Ser Lys Leu Gly Ser Gly Val Pro
    50                  55                  60

Asn Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Asp Pro Trp Thr Phe Gly Gly Gly Thr Lys Val Glu Ile Lys
            100                 105                 110

Arg

<210> SEQ ID NO 322
<211> LENGTH: 107
<212> TYPE: PRT
<213> ORGANISM: Artificial Sequence
<220> FEATURE:
<223> OTHER INFORMATION: Synthetic Construct

<400> SEQUENCE: 322

Glu Ile Val Leu Thr Gln Ser Pro Asp Phe Gln Ser Val Thr Pro Lys
1               5                   10                  15

Glu Lys Val Thr Ile Thr Cys Ser Ala Asn Ser Ala Leu Ser Tyr Met
            20                  25                  30

Tyr Trp Tyr Gln Gln Lys Pro Asp Gln Ser Pro Lys Leu Trp Val His
        35                  40                  45

Gly Thr Ser Asn Leu Ala Ser Gly Val Pro Ser Arg Phe Ser Gly Ser
    50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys His His Trp Ser Asn Thr Gln Trp Thr
                85                  90                  95

Phe Gly Gly Gly Thr Lys Val Glu Ile Lys Arg
            100                 105

<210> SEQ ID NO 323
<211> LENGTH: 121
<212> TYPE: PRT
<213> ORGANISM: Artificial Sequence
<220> FEATURE:
<223> OTHER INFORMATION: Synthetic Construct

<400> SEQUENCE: 323

Gln Val Gln Leu Gln Glu Ser Gly Pro Gly Leu Val Lys Pro Ser Glu
1               5                   10                  15

Thr Leu Ser Leu Thr Cys Ser Val Thr Tyr His Thr Ile Thr Ser Gly
            20                  25                  30
```

```
Tyr Asp Trp Thr Trp Ile Arg Lys Pro Pro Gly Lys Gly Met Glu Trp
         35                  40                  45

Ile Gly Tyr Ile Ser Tyr Ser Gly Asn Thr Asn Tyr Asn Pro Ser Leu
 50                  55                  60

Lys Ser Arg Val Thr Ile Ser Arg Asp Thr Ser Lys Asn Gln Phe Phe
 65                  70                  75                  80

Leu Lys Leu Ser Ser Val Thr Ala Ala Asp Thr Ala Val Tyr Tyr Cys
                 85                  90                  95

Ala Ser Met Met Val Pro His Tyr Tyr Val Met Asp Ala Trp Gly Gln
                100                 105                 110

Gly Thr Leu Val Thr Val Ser Ser Ala
                115                 120
```

<210> SEQ ID NO 324
<211> LENGTH: 120
<212> TYPE: PRT
<213> ORGANISM: Artificial Sequence
<220> FEATURE:
<223> OTHER INFORMATION: Synthetic Construct

<400> SEQUENCE: 324

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr Asn Tyr
                 20                  25                  30

Phe Met Asn Trp Val Arg Gln Ala Pro Gly Gln Gly Leu Glu Trp Met
             35                  40                  45

Gly Arg Val Asp Pro Glu Gln Gly Arg Ala Asp Tyr Ala Glu Lys Phe
 50                  55                  60

Lys Lys Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Ala Met Asp Asn Tyr Gly Phe Ala Tyr Trp Gly Gln Gly
                100                 105                 110

Thr Leu Val Thr Val Ser Ser Ala
             115                 120
```

<210> SEQ ID NO 325
<211> LENGTH: 106
<212> TYPE: PRT
<213> ORGANISM: Artificial Sequence
<220> FEATURE:
<223> OTHER INFORMATION: Synthetic Construct

<400> SEQUENCE: 325

```
Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
                 20                  25                  30

Pro Arg Glu Ala Lys Val Gln Trp Lys Val Asp Asn Ala Leu Gln Ser
             35                  40                  45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
```

```
                        85                  90                  95

Val Thr Lys Ser Phe Asn Arg Gly Glu Cys
            100                 105

<210> SEQ ID NO 326
<211> LENGTH: 329
<212> TYPE: PRT
<213> ORGANISM: Artificial Sequence
<220> FEATURE:
<223> OTHER INFORMATION: Synthetic Construct

<400> SEQUENCE: 326

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 327
<211> LENGTH: 219
<212> TYPE: PRT
<213> ORGANISM: Artificial Sequence
<220> FEATURE:
<223> OTHER INFORMATION: Synthetic Construct

<400> SEQUENCE: 327

```
Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Leu Asn Ser
            20                  25                  30

Asp Gly Asn Thr Tyr Leu Tyr Trp Tyr Leu Gln Lys Pro Gly Gln Ser
        35                  40                  45

Pro Gln Leu Leu Ile Tyr Leu Val Ser Lys Leu Gly Ser Gly Val Pro
    50                  55                  60

Asn Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Asp Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 328
<211> LENGTH: 257
<212> TYPE: PRT
<213> ORGANISM: Artificial Sequence
<220> FEATURE:
<223> OTHER INFORMATION: Synthetic Construct

<400> SEQUENCE: 328

```
Met Gln Thr Arg Cys Lys Glu Tyr Pro Arg Trp Cys Glu His Trp Leu
1               5                   10                  15

Gly Gly Gly Ser Ser Gly Gly Ser Thr Ser Thr Ser Gly Arg Ser Ala
            20                  25                  30

Asn Pro Arg Ser Gly Gly Asp Ile Val Met Thr Gln Thr Pro Leu Ser
        35                  40                  45

Leu Ser Val Thr Pro Gly Gln Pro Ala Ser Ile Ser Cys Arg Ser Ser
    50                  55                  60

Gln Ser Leu Leu Asn Ser Asp Gly Asn Thr Tyr Leu Tyr Trp Tyr Leu
65                  70                  75                  80

Gln Lys Pro Gly Gln Ser Pro Gln Leu Leu Ile Tyr Leu Val Ser Lys
                85                  90                  95
```

```
Leu Gly Ser Gly Val Pro Asn Arg Phe Ser Gly Ser Gly Ser Gly Thr
            100                 105                 110

Asp Phe Thr Leu Lys Ile Ser Arg Val Glu Ala Glu Asp Val Gly Val
        115                 120                 125

Tyr Tyr Cys Val Gln Gly Thr His Asp Pro Trp Thr Phe Gly Gly Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys

<210> SEQ ID NO 329
<211> LENGTH: 254
<212> TYPE: PRT
<213> ORGANISM: Artificial Sequence
<220> FEATURE:
<223> OTHER INFORMATION: Synthetic Construct

<400> SEQUENCE: 329

Met Gln Thr Arg Cys Lys Glu Tyr Pro Arg Trp Cys Glu His Trp Leu
1               5                   10                  15

Gly Gly Ser Gly Gly Thr Ser Thr Ser Gly Arg Ser Ala Asn Pro Arg
            20                  25                  30

Ser Gly Gly Asp Ile Val Met Thr Gln Thr Pro Leu Ser Leu Ser Val
        35                  40                  45

Thr Pro Gly Gln Pro Ala Ser Ile Ser Cys Arg Ser Ser Gln Ser Leu
    50                  55                  60

Leu Asn Ser Asp Gly Asn Thr Tyr Leu Tyr Trp Tyr Leu Gln Lys Pro
65                  70                  75                  80

Gly Gln Ser Pro Gln Leu Leu Ile Tyr Leu Val Ser Lys Leu Gly Ser
                85                  90                  95

Gly Val Pro Asn Arg Phe Ser Gly Ser Gly Ser Gly Thr Asp Phe Thr
            100                 105                 110

Leu Lys Ile Ser Arg Val Glu Ala Glu Asp Val Gly Val Tyr Tyr Cys
        115                 120                 125

Val Gln Gly Thr His Asp Pro Trp Thr Phe Gly Gly Gly Thr Lys Val
    130                 135                 140

Glu Ile Lys Arg Thr Val Ala Ala Pro Ser Val Phe Ile Phe Pro Pro
145                 150                 155                 160

Ser Asp Glu Gln Leu Lys Ser Gly Thr Ala Ser Val Val Cys Leu Leu
                165                 170                 175

Asn Asn Phe Tyr Pro Arg Glu Ala Lys Val Gln Trp Lys Val Asp Asn
            180                 185                 190

Ala Leu Gln Ser Gly Asn Ser Gln Glu Ser Val Thr Glu Gln Asp Ser
```

```
              195                 200                 205
Lys Asp Ser Thr Tyr Ser Leu Ser Ser Thr Leu Thr Leu Ser Lys Ala
    210                 215                 220

Asp Tyr Glu Lys His Lys Val Tyr Ala Cys Glu Val Thr His Gln Gly
225                 230                 235                 240

Leu Ser Ser Pro Val Thr Lys Ser Phe Asn Arg Gly Glu Cys
                245                 250

<210> SEQ ID NO 330
<211> LENGTH: 253
<212> TYPE: PRT
<213> ORGANISM: Artificial Sequence
<220> FEATURE:
<223> OTHER INFORMATION: Synthetic Construct

<400> SEQUENCE: 330

Met Gln Thr Arg Cys Lys Glu Tyr Pro Arg Trp Cys Glu His Trp Leu
1               5                   10                  15

Gly Gly Gly Ser Thr Ser Thr Ser Gly Arg Ser Ala Asn Pro Arg Ser
                20                  25                  30

Gly Gly Asp Ile Val Met Thr Gln Thr Pro Leu Ser Leu Ser Val Thr
            35                  40                  45

Pro Gly Gln Pro Ala Ser Ile Ser Cys Arg Ser Ser Gln Ser Leu Leu
    50                  55                  60

Asn Ser Asp Gly Asn Thr Tyr Leu Tyr Trp Tyr Leu Gln Lys Pro Gly
65                  70                  75                  80

Gln Ser Pro Gln Leu Leu Ile Tyr Leu Val Ser Lys Leu Gly Ser Gly
                85                  90                  95

Val Pro Asn Arg Phe Ser Gly Ser Gly Ser Gly Thr Asp Phe Thr Leu
            100                 105                 110

Lys Ile Ser Arg Val Glu Ala Glu Asp Val Gly Val Tyr Tyr Cys Val
    115                 120                 125

Gln Gly Thr His Asp Pro Trp Thr Phe Gly Gly Gly Thr Lys Val Glu
130                 135                 140

Ile Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
    195                 200                 205

Asp Ser Thr Tyr Ser Leu Ser Ser Thr Leu Thr Leu Ser Lys Ala Asp
210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250

<210> SEQ ID NO 331
<211> LENGTH: 252
<212> TYPE: PRT
<213> ORGANISM: Artificial Sequence
<220> FEATURE:
<223> OTHER INFORMATION: Synthetic Construct

<400> SEQUENCE: 331
```

```
Met Gln Thr Arg Cys Lys Glu Tyr Pro Arg Trp Cys Glu His Trp Leu
1               5                   10                  15

Gly Gly Ser Thr Ser Thr Ser Gly Arg Ser Ala Asn Pro Arg Ser Gly
            20                  25                  30

Gly Asp Ile Val Met Thr Gln Thr Pro Leu Ser Leu Ser Val Thr Pro
            35                  40                  45

Gly Gln Pro Ala Ser Ile Ser Cys Arg Ser Ser Gln Ser Leu Leu Asn
50                  55                  60

Ser Asp Gly Asn Thr Tyr Leu Tyr Trp Tyr Leu Gln Lys Pro Gly Gln
65                  70                  75                  80

Ser Pro Gln Leu Leu Ile Tyr Leu Val Ser Lys Leu Gly Ser Gly Val
                85                  90                  95

Pro Asn Arg Phe Ser Gly Ser Gly Ser Gly Thr Asp Phe Thr Leu Lys
                100                 105                 110

Ile Ser Arg Val Glu Ala Glu Asp Val Gly Val Tyr Tyr Cys Val Gln
                115                 120                 125

Gly Thr His Asp Pro Trp Thr Phe Gly Gly Gly Thr Lys Val Glu Ile
            130                 135                 140

Lys Arg Thr Val Ala Ala Pro Ser Val Phe Ile Phe Pro Pro Ser Asp
145                 150                 155                 160

Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
                180                 185                 190

Gln Ser Gly Asn Ser Gln Glu Ser Val Thr Glu Gln Asp Ser Lys Asp
            195                 200                 205

Ser Thr Tyr Ser Leu Ser Ser Thr Leu Thr Leu Ser Lys Ala Asp Tyr
210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250

<210> SEQ ID NO 332
<211> LENGTH: 251
<212> TYPE: PRT
<213> ORGANISM: Artificial Sequence
<220> FEATURE:
<223> OTHER INFORMATION: Synthetic Construct

<400> SEQUENCE: 332

Met Gln Thr Arg Cys Lys Glu Tyr Pro Arg Trp Cys Glu His Trp Leu
1               5                   10                  15

Gly Ser Thr Ser Thr Ser Gly Arg Ser Ala Asn Pro Arg Ser Gly Gly
            20                  25                  30

Asp Ile Val Met Thr Gln Thr Pro Leu Ser Leu Ser Val Thr Pro Gly
            35                  40                  45

Gln Pro Ala Ser Ile Ser Cys Arg Ser Ser Gln Ser Leu Leu Asn Ser
    50                  55                  60

Asp Gly Asn Thr Tyr Leu Tyr Trp Tyr Leu Gln Lys Pro Gly Gln Ser
65                  70                  75                  80

Pro Gln Leu Leu Ile Tyr Leu Val Ser Lys Leu Gly Ser Gly Val Pro
                85                  90                  95

Asn Arg Phe Ser Gly Ser Gly Ser Gly Thr Asp Phe Thr Leu Lys Ile
                100                 105                 110
```

Ser Arg Val Glu Ala Glu Asp Val Gly Val Tyr Tyr Cys Val Gln Gly
            115                 120                 125

Thr His Asp Pro Trp Thr Phe Gly Gly Gly Thr Lys Val Glu Ile Lys
130                 135                 140

Arg Thr Val Ala Ala Pro Ser Val Phe Ile Phe Pro Pro Ser Asp Glu
145                 150                 155                 160

Gln Leu Lys Ser Gly Thr Ala Ser Val Val Cys Leu Leu Asn Asn Phe
            165                 170                 175

Tyr Pro Arg Glu Ala Lys Val Gln Trp Lys Val Asp Asn Ala Leu Gln
            180                 185                 190

Ser Gly Asn Ser Gln Glu Ser Val Thr Glu Gln Asp Ser Lys Asp Ser
            195                 200                 205

Thr Tyr Ser Leu Ser Ser Thr Leu Thr Leu Ser Lys Ala Asp Tyr Glu
            210                 215                 220

Lys His Lys Val Tyr Ala Cys Glu Val Thr His Gln Gly Leu Ser Ser
225                 230                 235                 240

Pro Val Thr Lys Ser Phe Asn Arg Gly Glu Cys
            245                 250

<210> SEQ ID NO 333
<211> LENGTH: 254
<212> TYPE: PRT
<213> ORGANISM: Artificial Sequence
<220> FEATURE:
<223> OTHER INFORMATION: Synthetic Construct

<400> SEQUENCE: 333

Met Gln Thr Arg Cys Lys Glu Tyr Pro Arg Trp Cys Glu His Trp Leu
1               5                   10                  15

Gly Ser Thr Ser Thr Ser Gly Arg Ser Ala Asn Pro Arg Ser Gly Gly
            20                  25                  30

Ser Gly Gly Asp Ile Val Met Thr Gln Thr Pro Leu Ser Leu Ser Val
            35                  40                  45

Thr Pro Gly Gln Pro Ala Ser Ile Ser Cys Arg Ser Ser Gln Ser Leu
50                  55                  60

Leu Asn Ser Asp Gly Asn Thr Tyr Leu Tyr Trp Tyr Leu Gln Lys Pro
65                  70                  75                  80

Gly Gln Ser Pro Gln Leu Leu Ile Tyr Leu Val Ser Lys Leu Gly Ser
            85                  90                  95

Gly Val Pro Asn Arg Phe Ser Gly Ser Gly Ser Gly Thr Asp Phe Thr
            100                 105                 110

Leu Lys Ile Ser Arg Val Glu Ala Glu Asp Val Gly Val Tyr Tyr Cys
            115                 120                 125

Val Gln Gly Thr His Asp Pro Trp Thr Phe Gly Gly Gly Thr Lys Val
            130                 135                 140

Glu Ile Lys Arg Thr Val Ala Ala Pro Ser Val Phe Ile Phe Pro Pro
145                 150                 155                 160

Ser Asp Glu Gln Leu Lys Ser Gly Thr Ala Ser Val Val Cys Leu Leu
            165                 170                 175

Asn Asn Phe Tyr Pro Arg Glu Ala Lys Val Gln Trp Lys Val Asp Asn
            180                 185                 190

Ala Leu Gln Ser Gly Asn Ser Gln Glu Ser Val Thr Glu Gln Asp Ser
            195                 200                 205

Lys Asp Ser Thr Tyr Ser Leu Ser Ser Thr Leu Thr Leu Ser Lys Ala
            210                 215                 220

```
Asp Tyr Glu Lys His Lys Val Tyr Ala Cys Glu Val Thr His Gln Gly
225                 230                 235                 240

Leu Ser Ser Pro Val Thr Lys Ser Phe Asn Arg Gly Glu Cys
                245                 250
```

<210> SEQ ID NO 334
<211> LENGTH: 213
<212> TYPE: PRT
<213> ORGANISM: Artificial Sequence
<220> FEATURE:
<223> OTHER INFORMATION: Synthetic Construct

<400> SEQUENCE: 334

```
Glu Ile Val Leu Thr Gln Ser Pro Asp Phe Gln Ser Val Thr Pro Lys
1               5                   10                  15

Glu Lys Val Thr Ile Thr Cys Ser Ala Asn Ser Ala Leu Ser Tyr Met
            20                  25                  30

Tyr Trp Tyr Gln Gln Lys Pro Asp Gln Ser Pro Lys Leu Trp Val His
        35                  40                  45

Gly Thr Ser Asn Leu Ala Ser Gly Val Pro Ser Arg Phe Ser Gly Ser
    50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys His His Trp Ser Asn Thr Gln Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 335
<211> LENGTH: 245
<212> TYPE: PRT
<213> ORGANISM: Artificial Sequence
<220> FEATURE:
<223> OTHER INFORMATION: Synthetic Construct

<400> SEQUENCE: 335

```
Ala Cys Lys His Ala Pro Tyr Ala Leu Cys Gly Gly Gly Ser Ser Gly
1               5                   10                  15

Gly Ser Thr Ser Thr Ser Gly Arg Ser Ala Asn Pro Arg Ser Gly Gly
            20                  25                  30

Glu Ile Val Leu Thr Gln Ser Pro Asp Phe Gln Ser Val Thr Pro Lys
        35                  40                  45

Glu Lys Val Thr Ile Thr Cys Ser Ala Asn Ser Ala Leu Ser Tyr Met
    50                  55                  60
```

```
Tyr Trp Tyr Gln Gln Lys Pro Asp Gln Ser Pro Lys Leu Trp Val His
 65                  70                  75                  80

Gly Thr Ser Asn Leu Ala Ser Gly Val Pro Ser Arg Phe Ser Gly Ser
                 85                  90                  95

Gly Ser Gly Thr Asp Phe Thr Leu Thr Ile Asn Ser Leu Glu Ala Glu
            100                 105                 110

Asp Ala Ala Thr Tyr Tyr Cys His His Trp Ser Asn Thr Gln Trp Thr
            115                 120                 125

Phe Gly Gly Gly Thr Lys Val Glu Ile Lys Arg Thr Val Ala Ala Pro
            130                 135                 140

Ser Val Phe Ile Phe Pro Pro Ser Asp Glu Gln Leu Lys Ser Gly Thr
145                 150                 155                 160

Ala Ser Val Val Cys Leu Leu Asn Asn Phe Tyr Pro Arg Glu Ala Lys
                165                 170                 175

Val Gln Trp Lys Val Asp Asn Ala Leu Gln Ser Gly Asn Ser Gln Glu
                180                 185                 190

Ser Val Thr Glu Gln Asp Ser Lys Asp Ser Thr Tyr Ser Leu Ser Ser
            195                 200                 205

Thr Leu Thr Leu Ser Lys Ala Asp Tyr Glu Lys His Lys Val Tyr Ala
    210                 215                 220

Cys Glu Val Thr His Gln Gly Leu Ser Ser Pro Val Thr Lys Ser Phe
225                 230                 235                 240

Asn Arg Gly Glu Cys
                245

<210> SEQ ID NO 336
<211> LENGTH: 245
<212> TYPE: PRT
<213> ORGANISM: Artificial Sequence
<220> FEATURE:
<223> OTHER INFORMATION: Synthetic Construct

<400> SEQUENCE: 336

Ala Cys Pro Phe Pro Ala Lys Ile Leu Cys Gly Gly Ser Ser Gly
1                5                  10                  15

Gly Ser Thr Ser Thr Ser Gly Arg Ser Ala Asn Pro Arg Ser Gly Gly
                 20                  25                  30

Glu Ile Val Leu Thr Gln Ser Pro Asp Phe Gln Ser Val Thr Pro Lys
             35                  40                  45

Glu Lys Val Thr Ile Thr Cys Ser Ala Asn Ser Ala Leu Ser Tyr Met
         50                  55                  60

Tyr Trp Tyr Gln Gln Lys Pro Asp Gln Ser Pro Lys Leu Trp Val His
 65                  70                  75                  80

Gly Thr Ser Asn Leu Ala Ser Gly Val Pro Ser Arg Phe Ser Gly Ser
                 85                  90                  95

Gly Ser Gly Thr Asp Phe Thr Leu Thr Ile Asn Ser Leu Glu Ala Glu
            100                 105                 110

Asp Ala Ala Thr Tyr Tyr Cys His His Trp Ser Asn Thr Gln Trp Thr
            115                 120                 125

Phe Gly Gly Gly Thr Lys Val Glu Ile Lys Arg Thr Val Ala Ala Pro
            130                 135                 140

Ser Val Phe Ile Phe Pro Pro Ser Asp Glu Gln Leu Lys Ser Gly Thr
145                 150                 155                 160

Ala Ser Val Val Cys Leu Leu Asn Asn Phe Tyr Pro Arg Glu Ala Lys
                165                 170                 175
```

Val Gln Trp Lys Val Asp Asn Ala Leu Gln Ser Gly Asn Ser Gln Glu
            180                 185                 190

Ser Val Thr Glu Gln Asp Ser Lys Asp Ser Thr Tyr Ser Leu Ser Ser
            195                 200                 205

Thr Leu Thr Leu Ser Lys Ala Asp Tyr Glu Lys His Lys Val Tyr Ala
            210                 215                 220

Cys Glu Val Thr His Gln Gly Leu Ser Ser Pro Val Thr Lys Ser Phe
225                 230                 235                 240

Asn Arg Gly Glu Cys
            245

<210> SEQ ID NO 337
<211> LENGTH: 245
<212> TYPE: PRT
<213> ORGANISM: Artificial Sequence
<220> FEATURE:
<223> OTHER INFORMATION: Synthetic Construct

<400> SEQUENCE: 337

Ala Cys Pro Gly Lys Gly Leu Pro Ser Cys Gly Gly Ser Ser Gly
1               5                   10                  15

Gly Ser Thr Ser Thr Ser Gly Arg Ser Ala Asn Pro Arg Ser Gly Gly
            20                  25                  30

Glu Ile Val Leu Thr Gln Ser Pro Asp Phe Gln Ser Val Thr Pro Lys
            35                  40                  45

Glu Lys Val Thr Ile Thr Cys Ser Ala Asn Ser Ala Leu Ser Tyr Met
        50                  55                  60

Tyr Trp Tyr Gln Gln Lys Pro Asp Gln Ser Pro Lys Leu Trp Val His
65                  70                  75                  80

Gly Thr Ser Asn Leu Ala Ser Gly Val Pro Ser Arg Phe Ser Gly Ser
                85                  90                  95

Gly Ser Gly Thr Asp Phe Thr Leu Thr Ile Asn Ser Leu Glu Ala Glu
            100                 105                 110

Asp Ala Ala Thr Tyr Tyr Cys His His Trp Ser Asn Thr Gln Trp Thr
            115                 120                 125

Phe Gly Gly Gly Thr Lys Val Glu Ile Lys Arg Thr Val Ala Ala Pro
    130                 135                 140

Ser Val Phe Ile Phe Pro Pro Ser Asp Glu Gln Leu Lys Ser Gly Thr
145                 150                 155                 160

Ala Ser Val Val Cys Leu Leu Asn Asn Phe Tyr Pro Arg Glu Ala Lys
                165                 170                 175

Val Gln Trp Lys Val Asp Asn Ala Leu Gln Ser Gly Asn Ser Gln Glu
            180                 185                 190

Ser Val Thr Glu Gln Asp Ser Lys Asp Ser Thr Tyr Ser Leu Ser Ser
            195                 200                 205

Thr Leu Thr Leu Ser Lys Ala Asp Tyr Glu Lys His Lys Val Tyr Ala
            210                 215                 220

Cys Glu Val Thr His Gln Gly Leu Ser Ser Pro Val Thr Lys Ser Phe
225                 230                 235                 240

Asn Arg Gly Glu Cys
            245

<210> SEQ ID NO 338
<211> LENGTH: 247
<212> TYPE: PRT
<213> ORGANISM: Artificial Sequence

```
<220> FEATURE:
<223> OTHER INFORMATION: Synthetic Construct

<400> SEQUENCE: 338

Asn Trp Leu Gly Glu Trp Leu Pro Pro Gly Lys Val Gly Gly Ser
1               5                   10                  15

Ser Gly Gly Ser Thr Ser Thr Ser Gly Arg Ser Ala Asn Pro Arg Ser
            20                  25                  30

Gly Gly Glu Ile Val Leu Thr Gln Ser Pro Asp Phe Gln Ser Val Thr
        35                  40                  45

Pro Lys Glu Lys Val Thr Ile Thr Cys Ser Ala Asn Ser Ala Leu Ser
50                  55                  60

Tyr Met Tyr Trp Tyr Gln Gln Lys Pro Asp Gln Ser Pro Lys Leu Trp
65                  70                  75                  80

Val His Gly Thr Ser Asn Leu Ala Ser Gly Val Pro Ser Arg Phe Ser
                85                  90                  95

Gly Ser Gly Ser Gly Thr Asp Phe Thr Leu Thr Ile Asn Ser Leu Glu
            100                 105                 110

Ala Glu Asp Ala Ala Thr Tyr Tyr Cys His His Trp Ser Asn Thr Gln
        115                 120                 125

Trp Thr Phe Gly Gly Gly Thr Lys Val Glu Ile Lys Arg Thr Val Ala
130                 135                 140

Ala Pro Ser Val Phe Ile Phe Pro Pro Ser Asp Glu Gln Leu Lys Ser
145                 150                 155                 160

Gly Thr Ala Ser Val Val Cys Leu Leu Asn Asn Phe Tyr Pro Arg Glu
                165                 170                 175

Ala Lys Val Gln Trp Lys Val Asp Asn Ala Leu Gln Ser Gly Asn Ser
            180                 185                 190

Gln Glu Ser Val Thr Glu Gln Asp Ser Lys Asp Ser Thr Tyr Ser Leu
        195                 200                 205

Ser Ser Thr Leu Thr Leu Ser Lys Ala Asp Tyr Glu Lys His Lys Val
210                 215                 220

Tyr Ala Cys Glu Val Thr His Gln Gly Leu Ser Ser Pro Val Thr Lys
225                 230                 235                 240

Ser Phe Asn Arg Gly Glu Cys
                245

<210> SEQ ID NO 339
<211> LENGTH: 251
<212> TYPE: PRT
<213> ORGANISM: Artificial Sequence
<220> FEATURE:
<223> OTHER INFORMATION: Synthetic Construct

<400> SEQUENCE: 339

Gln Phe Ile Glu Cys Pro Asn Phe Pro Arg Gln Cys Pro Gly Lys Asn
1               5                   10                  15

Gly Gly Gly Ser Ser Gly Gly Ser Thr Ser Thr Ser Gly Arg Ser Ala
            20                  25                  30

Asn Pro Arg Ser Gly Gly Glu Ile Val Leu Thr Gln Ser Pro Asp Phe
        35                  40                  45

Gln Ser Val Thr Pro Lys Glu Lys Val Thr Ile Thr Cys Ser Ala Asn
    50                  55                  60

Ser Ala Leu Ser Tyr Met Tyr Trp Tyr Gln Gln Lys Pro Asp Gln Ser
65                  70                  75                  80

Pro Lys Leu Trp Val His Gly Thr Ser Asn Leu Ala Ser Gly Val Pro
```

```
            85                  90                  95
Ser Arg Phe Ser Gly Ser Gly Ser Gly Thr Asp Phe Thr Leu Thr Ile
            100                 105                 110

Asn Ser Leu Glu Ala Glu Asp Ala Ala Thr Tyr Tyr Cys His His Trp
            115                 120                 125

Ser Asn Thr Gln Trp Thr Phe Gly Gly Gly Thr Lys Val Glu Ile Lys
            130                 135                 140

Arg Thr Val Ala Ala Pro Ser Val Phe Ile Phe Pro Pro Ser Asp Glu
145                 150                 155                 160

Gln Leu Lys Ser Gly Thr Ala Ser Val Val Cys Leu Leu Asn Asn Phe
                165                 170                 175

Tyr Pro Arg Glu Ala Lys Val Gln Trp Lys Val Asp Asn Ala Leu Gln
                180                 185                 190

Ser Gly Asn Ser Gln Glu Ser Val Thr Glu Gln Asp Ser Lys Asp Ser
                195                 200                 205

Thr Tyr Ser Leu Ser Ser Thr Leu Thr Leu Ser Lys Ala Asp Tyr Glu
            210                 215                 220

Lys His Lys Val Tyr Ala Cys Glu Val Thr His Gln Gly Leu Ser Ser
225                 230                 235                 240

Pro Val Thr Lys Ser Phe Asn Arg Gly Glu Cys
                245                 250
```

<210> SEQ ID NO 340
<211> LENGTH: 251
<212> TYPE: PRT
<213> ORGANISM: Artificial Sequence
<220> FEATURE:
<223> OTHER INFORMATION: Synthetic Construct

<400> SEQUENCE: 340

```
Val Arg Gln Gln Cys Ser Leu Asn Pro Gly Arg Cys Pro Tyr Leu Val
1               5                   10                  15

Gly Gly Gly Ser Ser Gly Gly Ser Thr Ser Thr Ser Gly Arg Ser Ala
            20                  25                  30

Asn Pro Arg Ser Gly Gly Glu Ile Val Leu Thr Gln Ser Pro Asp Phe
            35                  40                  45

Gln Ser Val Thr Pro Lys Glu Lys Val Thr Ile Thr Cys Ser Ala Asn
        50                  55                  60

Ser Ala Leu Ser Tyr Met Tyr Trp Tyr Gln Gln Lys Pro Asp Gln Ser
65                  70                  75                  80

Pro Lys Leu Trp Val His Gly Thr Ser Asn Leu Ala Ser Gly Val Pro
                85                  90                  95

Ser Arg Phe Ser Gly Ser Gly Ser Gly Thr Asp Phe Thr Leu Thr Ile
            100                 105                 110

Asn Ser Leu Glu Ala Glu Asp Ala Ala Thr Tyr Tyr Cys His His Trp
            115                 120                 125

Ser Asn Thr Gln Trp Thr Phe Gly Gly Gly Thr Lys Val Glu Ile Lys
            130                 135                 140

Arg Thr Val Ala Ala Pro Ser Val Phe Ile Phe Pro Pro Ser Asp Glu
145                 150                 155                 160

Gln Leu Lys Ser Gly Thr Ala Ser Val Val Cys Leu Leu Asn Asn Phe
                165                 170                 175

Tyr Pro Arg Glu Ala Lys Val Gln Trp Lys Val Asp Asn Ala Leu Gln
                180                 185                 190

Ser Gly Asn Ser Gln Glu Ser Val Thr Glu Gln Asp Ser Lys Asp Ser
```

```
                    195                 200                 205
Thr Tyr Ser Leu Ser Ser Thr Leu Thr Leu Ser Lys Ala Asp Tyr Glu
    210                 215                 220
Lys His Lys Val Tyr Ala Cys Glu Val Thr His Gln Gly Leu Ser Ser
225                 230                 235                 240
Pro Val Thr Lys Ser Phe Asn Arg Gly Glu Cys
                245                 250
```

<210> SEQ ID NO 341
<211> LENGTH: 251
<212> TYPE: PRT
<213> ORGANISM: Artificial Sequence
<220> FEATURE:
<223> OTHER INFORMATION: Synthetic Construct

<400> SEQUENCE: 341

```
Val Trp Gln Glu Cys His Thr Ala Pro Gln Leu Cys Pro Gly Lys Ile
1               5                   10                  15
Gly Gly Gly Ser Ser Gly Gly Ser Thr Ser Thr Ser Gly Arg Ser Ala
                20                  25                  30
Asn Pro Arg Ser Gly Gly Glu Ile Val Leu Thr Gln Ser Pro Asp Phe
            35                  40                  45
Gln Ser Val Thr Pro Lys Glu Lys Val Thr Ile Thr Cys Ser Ala Asn
    50                  55                  60
Ser Ala Leu Ser Tyr Met Tyr Trp Tyr Gln Gln Lys Pro Asp Gln Ser
65                  70                  75                  80
Pro Lys Leu Trp Val His Gly Thr Ser Asn Leu Ala Ser Gly Val Pro
                85                  90                  95
Ser Arg Phe Ser Gly Ser Gly Ser Gly Thr Asp Phe Thr Leu Thr Ile
            100                 105                 110
Asn Ser Leu Glu Ala Glu Asp Ala Ala Thr Tyr Tyr Cys His His Trp
    115                 120                 125
Ser Asn Thr Gln Trp Thr Phe Gly Gly Gly Thr Lys Val Glu Ile Lys
130                 135                 140
Arg Thr Val Ala Ala Pro Ser Val Phe Ile Phe Pro Pro Ser Asp Glu
145                 150                 155                 160
Gln Leu Lys Ser Gly Thr Ala Ser Val Val Cys Leu Leu Asn Asn Phe
                165                 170                 175
Tyr Pro Arg Glu Ala Lys Val Gln Trp Lys Val Asp Asn Ala Leu Gln
            180                 185                 190
Ser Gly Asn Ser Gln Glu Ser Val Thr Glu Gln Asp Ser Lys Asp Ser
    195                 200                 205
Thr Tyr Ser Leu Ser Ser Thr Leu Thr Leu Ser Lys Ala Asp Tyr Glu
    210                 215                 220
Lys His Lys Val Tyr Ala Cys Glu Val Thr His Gln Gly Leu Ser Ser
225                 230                 235                 240
Pro Val Thr Lys Ser Phe Asn Arg Gly Glu Cys
                245                 250
```

<210> SEQ ID NO 342
<211> LENGTH: 257
<212> TYPE: PRT
<213> ORGANISM: Artificial Sequence
<220> FEATURE:
<223> OTHER INFORMATION: Synthetic Construct

<400> SEQUENCE: 342

```
Asp Ser Tyr Thr Cys Arg Gly Pro Thr Trp Met Cys Ala Gly Asn Met
1               5                   10                  15

Gly Gly Gly Ser Ser Gly Gly Ser Thr Ser Thr Ser Gly Arg Ser Ala
            20                  25                  30

Asn Pro Arg Ser Gly Gly Asp Ile Val Met Thr Gln Thr Pro Leu Ser
        35                  40                  45

Leu Ser Val Thr Pro Gly Gln Pro Ala Ser Ile Ser Cys Arg Ser Ser
    50                  55                  60

Gln Ser Leu Leu Asn Ser Asp Gly Asn Thr Tyr Leu Tyr Trp Tyr Leu
65                  70                  75                  80

Gln Lys Pro Gly Gln Ser Pro Gln Leu Leu Ile Tyr Leu Val Ser Lys
                85                  90                  95

Leu Gly Ser Gly Val Pro Asn Arg Phe Ser Gly Ser Gly Ser Gly Thr
            100                 105                 110

Asp Phe Thr Leu Lys Ile Ser Arg Val Glu Ala Glu Asp Val Gly Val
        115                 120                 125

Tyr Tyr Cys Val Gln Gly Thr His Asp Pro Trp Thr Phe Gly Gly Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys

<210> SEQ ID NO 343
<211> LENGTH: 257
<212> TYPE: PRT
<213> ORGANISM: Artificial Sequence
<220> FEATURE:
<223> OTHER INFORMATION: Synthetic Construct

<400> SEQUENCE: 343

Phe Asn His Asp Cys Ser Gly His Trp Met Arg Cys Leu Asp Gln Gln
1               5                   10                  15

Gly Gly Gly Ser Ser Gly Gly Ser Thr Ser Thr Ser Gly Arg Ser Ala
            20                  25                  30

Asn Pro Arg Ser Gly Gly Asp Ile Val Met Thr Gln Thr Pro Leu Ser
        35                  40                  45

Leu Ser Val Thr Pro Gly Gln Pro Ala Ser Ile Ser Cys Arg Ser Ser
    50                  55                  60

Gln Ser Leu Leu Asn Ser Asp Gly Asn Thr Tyr Leu Tyr Trp Tyr Leu
65                  70                  75                  80

Gln Lys Pro Gly Gln Ser Pro Gln Leu Leu Ile Tyr Leu Val Ser Lys
                85                  90                  95

Leu Gly Ser Gly Val Pro Asn Arg Phe Ser Gly Ser Gly Ser Gly Thr
```

```
                        100                 105                 110
Asp Phe Thr Leu Lys Ile Ser Arg Val Glu Ala Glu Asp Val Gly Val
            115                 120                 125
Tyr Tyr Cys Val Gln Gly Thr His Asp Pro Trp Thr Phe Gly Gly Gly
    130                 135                 140
Thr Lys Val Glu Ile Lys Arg Thr Val Ala Ala Pro Ser Val Phe Ile
145                 150                 155                 160
Phe Pro Pro Ser Asp Glu Gln Leu Lys Ser Gly Thr Ala Ser Val Val
                165                 170                 175
Cys Leu Leu Asn Asn Phe Tyr Pro Arg Glu Ala Lys Val Gln Trp Lys
            180                 185                 190
Val Asp Asn Ala Leu Gln Ser Gly Asn Ser Gln Glu Ser Val Thr Glu
    195                 200                 205
Gln Asp Ser Lys Asp Ser Thr Tyr Ser Leu Ser Ser Thr Leu Thr Leu
210                 215                 220
Ser Lys Ala Asp Tyr Glu Lys His Lys Val Tyr Ala Cys Glu Val Thr
225                 230                 235                 240
His Gln Gly Leu Ser Ser Pro Val Thr Lys Ser Phe Asn Arg Gly Glu
                245                 250                 255
Cys

<210> SEQ ID NO 344
<211> LENGTH: 251
<212> TYPE: PRT
<213> ORGANISM: Artificial Sequence
<220> FEATURE:
<223> OTHER INFORMATION: Synthetic Construct

<400> SEQUENCE: 344

Met Gln Thr Arg Cys Lys Glu Tyr Pro Arg Trp Cys Glu His Trp Leu
1               5                   10                  15
Gly Gly Gly Ser Val Pro Leu Ser Leu Tyr Ser Gly Gly Ser Gly Gly
            20                  25                  30
Asp Ile Val Met Thr Gln Thr Pro Leu Ser Leu Ser Val Thr Pro Gly
        35                  40                  45
Gln Pro Ala Ser Ile Ser Cys Arg Ser Ser Gln Ser Leu Leu Asn Ser
    50                  55                  60
Asp Gly Asn Thr Tyr Leu Tyr Trp Tyr Leu Gln Lys Pro Gly Gln Ser
65                  70                  75                  80
Pro Gln Leu Leu Ile Tyr Leu Val Ser Lys Leu Gly Ser Gly Val Pro
                85                  90                  95
Asn Arg Phe Ser Gly Ser Gly Ser Gly Thr Asp Phe Thr Leu Lys Ile
            100                 105                 110
Ser Arg Val Glu Ala Glu Asp Val Gly Val Tyr Tyr Cys Val Gln Gly
        115                 120                 125
Thr His Asp Pro Trp Thr Phe Gly Gly Gly Thr Lys Val Glu Ile Lys
    130                 135                 140
Arg Thr Val Ala Ala Pro Ser Val Phe Ile Phe Pro Pro Ser Asp Glu
145                 150                 155                 160
Gln Leu Lys Ser Gly Thr Ala Ser Val Val Cys Leu Leu Asn Asn Phe
                165                 170                 175
Tyr Pro Arg Glu Ala Lys Val Gln Trp Lys Val Asp Asn Ala Leu Gln
            180                 185                 190
Ser Gly Asn Ser Gln Glu Ser Val Thr Glu Gln Asp Ser Lys Asp Ser
        195                 200                 205
```

```
Thr Tyr Ser Leu Ser Ser Thr Leu Thr Leu Ser Lys Ala Asp Tyr Glu
        210                 215                 220

Lys His Lys Val Tyr Ala Cys Glu Val Thr His Gln Gly Leu Ser Ser
225                 230                 235                 240

Pro Val Thr Lys Ser Phe Asn Arg Gly Glu Cys
                245                 250

<210> SEQ ID NO 345
<211> LENGTH: 257
<212> TYPE: PRT
<213> ORGANISM: Artificial Sequence
<220> FEATURE:
<223> OTHER INFORMATION: Synthetic Construct

<400> SEQUENCE: 345

Asn Lys Ser Pro Cys Arg Pro Lys Met Val Ala Cys Tyr Gly Ile Leu
1               5                   10                  15

Gly Gly Gly Ser Ser Gly Gly Ser Thr Ser Thr Ser Gly Arg Ser Ala
                20                  25                  30

Asn Pro Arg Ser Gly Gly Asp Ile Val Met Thr Gln Thr Pro Leu Ser
            35                  40                  45

Leu Ser Val Thr Pro Gly Gln Pro Ala Ser Ile Ser Cys Arg Ser Ser
        50                  55                  60

Gln Ser Leu Leu Asn Ser Asp Gly Asn Thr Tyr Leu Tyr Trp Tyr Leu
65                  70                  75                  80

Gln Lys Pro Gly Gln Ser Pro Gln Leu Leu Ile Tyr Leu Val Ser Lys
                85                  90                  95

Leu Gly Ser Gly Val Pro Asn Arg Phe Ser Gly Ser Gly Ser Gly Thr
            100                 105                 110

Asp Phe Thr Leu Lys Ile Ser Arg Val Glu Ala Glu Asp Val Gly Val
        115                 120                 125

Tyr Tyr Cys Val Gln Gly Thr His Asp Pro Trp Thr Phe Gly Gly Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys

<210> SEQ ID NO 346
<211> LENGTH: 257
<212> TYPE: PRT
<213> ORGANISM: Artificial Sequence
<220> FEATURE:
<223> OTHER INFORMATION: Synthetic Construct

<400> SEQUENCE: 346
```

Pro Thr Pro Gln Cys Trp Asn Gln Tyr Tyr Glu Cys Trp Ile Pro Ser
1               5                   10                  15

Gly Gly Gly Ser Ser Gly Gly Ser Thr Ser Thr Ser Gly Arg Ser Ala
                20                  25                  30

Asn Pro Arg Ser Gly Gly Asp Ile Val Met Thr Gln Thr Pro Leu Ser
            35                  40                  45

Leu Ser Val Thr Pro Gly Gln Pro Ala Ser Ile Ser Cys Arg Ser Ser
        50                  55                  60

Gln Ser Leu Leu Asn Ser Asp Gly Asn Thr Tyr Leu Tyr Trp Tyr Leu
65              70                  75                  80

Gln Lys Pro Gly Gln Ser Pro Gln Leu Leu Ile Tyr Leu Val Ser Lys
                85                  90                  95

Leu Gly Ser Gly Val Pro Asn Arg Phe Ser Gly Ser Gly Ser Gly Thr
            100                 105                 110

Asp Phe Thr Leu Lys Ile Ser Arg Val Glu Ala Glu Asp Val Gly Val
        115                 120                 125

Tyr Tyr Cys Val Gln Gly Thr His Asp Pro Trp Thr Phe Gly Gly Gly
    130                 135                 140

Thr Lys Val Glu Ile Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
            165                 170                 175

Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
            195                 200                 205

Gln Asp Ser Lys Asp Ser Thr Tyr Ser Leu Ser Ser Thr Leu Thr Leu
        210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
            245                 250                 255

Cys

<210> SEQ ID NO 347
<211> LENGTH: 256
<212> TYPE: PRT
<213> ORGANISM: Artificial Sequence
<220> FEATURE:
<223> OTHER INFORMATION: Synthetic Construct

<400> SEQUENCE: 347

Ser Gln Lys Cys Pro Trp Thr Lys Glu Thr Cys Met His Tyr Met Gly
1               5                   10                  15

Gly Gly Ser Ser Gly Gly Ser Thr Ser Thr Ser Gly Arg Ser Ala Asn
                20                  25                  30

Pro Arg Ser Gly Gly Asp Ile Val Met Thr Gln Thr Pro Leu Ser Leu
            35                  40                  45

Ser Val Thr Pro Gly Gln Pro Ala Ser Ile Ser Cys Arg Ser Ser Gln
        50                  55                  60

Ser Leu Leu Asn Ser Asp Gly Asn Thr Tyr Leu Tyr Trp Tyr Leu Gln
65              70                  75                  80

Lys Pro Gly Gln Ser Pro Gln Leu Leu Ile Tyr Leu Val Ser Lys Leu
                85                  90                  95

```
Gly Ser Gly Val Pro Asn Arg Phe Ser Gly Ser Gly Ser Gly Thr Asp
            100                 105                 110

Phe Thr Leu Lys Ile Ser Arg Val Glu Ala Glu Asp Val Gly Val Tyr
        115                 120                 125

Tyr Cys Val Gln Gly Thr His Asp Pro Trp Thr Phe Gly Gly Gly Thr
    130                 135                 140

Lys Val Glu Ile Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255

<210> SEQ ID NO 348
<211> LENGTH: 253
<212> TYPE: PRT
<213> ORGANISM: Artificial Sequence
<220> FEATURE:
<223> OTHER INFORMATION: Synthetic Construct

<400> SEQUENCE: 348

Trp His Leu Ser Met Tyr Pro Lys Pro Pro Ala Glu Gly Gly Gly Ser
1               5                   10                  15

Ser Gly Gly Ser Thr Ser Thr Ser Gly Arg Ser Ala Asn Pro Arg Ser
            20                  25                  30

Gly Gly Asp Ile Val Met Thr Gln Thr Pro Leu Ser Leu Ser Val Thr
        35                  40                  45

Pro Gly Gln Pro Ala Ser Ile Ser Cys Arg Ser Ser Gln Ser Leu Leu
    50                  55                  60

Asn Ser Asp Gly Asn Thr Tyr Leu Tyr Trp Tyr Leu Gln Lys Pro Gly
65                  70                  75                  80

Gln Ser Pro Gln Leu Leu Ile Tyr Leu Val Ser Lys Leu Gly Ser Gly
                85                  90                  95

Val Pro Asn Arg Phe Ser Gly Ser Gly Ser Gly Thr Asp Phe Thr Leu
            100                 105                 110

Lys Ile Ser Arg Val Glu Ala Glu Asp Val Gly Val Tyr Tyr Cys Val
        115                 120                 125

Gln Gly Thr His Asp Pro Trp Thr Phe Gly Gly Gly Thr Lys Val Glu
    130                 135                 140

Ile Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205
```

Asp Ser Thr Tyr Ser Leu Ser Ser Thr Leu Thr Leu Ser Lys Ala Asp
         210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250

<210> SEQ ID NO 349
<211> LENGTH: 253
<212> TYPE: PRT
<213> ORGANISM: Artificial Sequence
<220> FEATURE:
<223> OTHER INFORMATION: Synthetic Construct

<400> SEQUENCE: 349

Trp His Thr Asp Gly Phe Tyr Thr Arg Leu Pro Ala Gly Gly Gly Ser
1               5                   10                  15

Ser Gly Gly Ser Thr Ser Thr Ser Gly Arg Ser Ala Asn Pro Arg Ser
                20                  25                  30

Gly Gly Asp Ile Val Met Thr Gln Thr Pro Leu Ser Leu Ser Val Thr
            35                  40                  45

Pro Gly Gln Pro Ala Ser Ile Ser Cys Arg Ser Ser Gln Ser Leu Leu
50                  55                  60

Asn Ser Asp Gly Asn Thr Tyr Leu Tyr Trp Tyr Leu Gln Lys Pro Gly
65                  70                  75                  80

Gln Ser Pro Gln Leu Leu Ile Tyr Leu Val Ser Lys Leu Gly Ser Gly
                85                  90                  95

Val Pro Asn Arg Phe Ser Gly Ser Gly Ser Gly Thr Asp Phe Thr Leu
            100                 105                 110

Lys Ile Ser Arg Val Glu Ala Glu Asp Val Gly Val Tyr Tyr Cys Val
        115                 120                 125

Gln Gly Thr His Asp Pro Trp Thr Phe Gly Gly Gly Thr Lys Val Glu
    130                 135                 140

Ile Lys Arg Thr Val Ala Ala Pro Ser Val Phe Ile Phe Pro Pro Ser
145                 150                 155                 160

Asp Glu Gln Leu Lys Ser Gly Thr Ala Ser Val Val Cys Leu Leu Asn
                165                 170                 175

Asn Phe Tyr Pro Arg Glu Ala Lys Val Gln Trp Lys Val Asp Asn Ala
            180                 185                 190

Leu Gln Ser Gly Asn Ser Gln Glu Ser Val Thr Glu Gln Asp Ser Lys
        195                 200                 205

Asp Ser Thr Tyr Ser Leu Ser Ser Thr Leu Thr Leu Ser Lys Ala Asp
    210                 215                 220

Tyr Glu Lys His Lys Val Tyr Ala Cys Glu Val Thr His Gln Gly Leu
225                 230                 235                 240

Ser Ser Pro Val Thr Lys Ser Phe Asn Arg Gly Glu Cys
                245                 250

<210> SEQ ID NO 350
<211> LENGTH: 213
<212> TYPE: PRT
<213> ORGANISM: Artificial Sequence
<220> FEATURE:
<223> OTHER INFORMATION: Synthetic Construct

<400> SEQUENCE: 350

Glu Ile Val Leu Thr Gln Ser Pro Asp Phe Gln Ser Val Thr Pro Lys
1               5                   10                  15

```
Glu Lys Val Thr Ile Thr Cys Ser Ala Asn Ser Ala Leu Ser Tyr Met
             20                  25                  30

Tyr Trp Tyr Gln Gln Lys Pro Asp Gln Ser Pro Lys Leu Trp Val His
         35                  40                  45

Gly Thr Ser Asn Leu Ala Ser Gly Val Pro Ser Arg Phe Ser Gly Ser
 50                  55                  60

Gly Ser Gly Thr Asp Phe Thr Leu Thr Ile Asn Ser Leu Glu Ala Glu
 65                  70                  75                  80

Asp Ala Ala Thr Tyr Tyr Cys His His Trp Ser Asn Thr Gln Trp Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 351
<211> LENGTH: 245
<212> TYPE: PRT
<213> ORGANISM: Artificial Sequence
<220> FEATURE:
<223> OTHER INFORMATION: Synthetic Construct

<400> SEQUENCE: 351

Ala Cys Ile His Ala Pro Tyr Ala Lys Cys Gly Gly Ser Ser Gly
 1               5                  10                  15

Gly Ser Thr Ser Thr Ser Gly Arg Ser Ala Asn Pro Arg Ser Gly Gly
             20                  25                  30

Glu Ile Val Leu Thr Gln Ser Pro Asp Phe Gln Ser Val Thr Pro Lys
         35                  40                  45

Glu Lys Val Thr Ile Thr Cys Ser Ala Asn Ser Ala Leu Ser Tyr Met
 50                  55                  60

Tyr Trp Tyr Gln Gln Lys Pro Asp Gln Ser Pro Lys Leu Trp Val His
 65                  70                  75                  80

Gly Thr Ser Asn Leu Ala Ser Gly Val Pro Ser Arg Phe Ser Gly Ser
                 85                  90                  95

Gly Ser Gly Thr Asp Phe Thr Leu Thr Ile Asn Ser Leu Glu Ala Glu
            100                 105                 110

Asp Ala Ala Thr Tyr Tyr Cys His His Trp Ser Asn Thr Gln Trp Thr
            115                 120                 125

Phe Gly Gly Gly Thr Lys Val Glu Ile Lys Arg Thr Val Ala Ala Pro
130                 135                 140

Ser Val Phe Ile Phe Pro Pro Ser Asp Glu Gln Leu Lys Ser Gly Thr
145                 150                 155                 160
```

Ala Ser Val Val Cys Leu Leu Asn Asn Phe Tyr Pro Arg Glu Ala Lys
            165                 170                 175

Val Gln Trp Lys Val Asp Asn Ala Leu Gln Ser Gly Asn Ser Gln Glu
        180                 185                 190

Ser Val Thr Glu Gln Asp Ser Lys Asp Ser Thr Tyr Ser Leu Ser Ser
    195                 200                 205

Thr Leu Thr Leu Ser Lys Ala Asp Tyr Glu Lys His Lys Val Tyr Ala
    210                 215                 220

Cys Glu Val Thr His Gln Gly Leu Ser Ser Pro Val Thr Lys Ser Phe
225                 230                 235                 240

Asn Arg Gly Glu Cys
            245

<210> SEQ ID NO 352
<211> LENGTH: 247
<212> TYPE: PRT
<213> ORGANISM: Artificial Sequence
<220> FEATURE:
<223> OTHER INFORMATION: Synthetic Construct

<400> SEQUENCE: 352

Ala Cys Ile His Ala Pro Tyr Ala Lys Cys Gly Ser Gly Gly Gly Ser
1               5                   10                  15

Ser Gly Gly Ser Thr Ser Thr Ser Gly Arg Ser Ala Asn Pro Arg Ser
            20                  25                  30

Gly Gly Glu Ile Val Leu Thr Gln Ser Pro Asp Phe Gln Ser Val Thr
        35                  40                  45

Pro Lys Glu Lys Val Thr Ile Thr Cys Ser Ala Asn Ser Ala Leu Ser
    50                  55                  60

Tyr Met Tyr Trp Tyr Gln Gln Lys Pro Asp Gln Ser Pro Lys Leu Trp
65                  70                  75                  80

Val His Gly Thr Ser Asn Leu Ala Ser Gly Val Pro Ser Arg Phe Ser
            85                  90                  95

Gly Ser Gly Ser Gly Thr Asp Phe Thr Leu Thr Ile Asn Ser Leu Glu
            100                 105                 110

Ala Glu Asp Ala Ala Thr Tyr Tyr Cys His His Trp Ser Asn Thr Gln
        115                 120                 125

Trp Thr Phe Gly Gly Gly Thr Lys Val Glu Ile Lys Arg Thr Val Ala
    130                 135                 140

Ala Pro Ser Val Phe Ile Phe Pro Pro Ser Asp Glu Gln Leu Lys Ser
145                 150                 155                 160

Gly Thr Ala Ser Val Val Cys Leu Leu Asn Asn Phe Tyr Pro Arg Glu
            165                 170                 175

Ala Lys Val Gln Trp Lys Val Asp Asn Ala Leu Gln Ser Gly Asn Ser
            180                 185                 190

Gln Glu Ser Val Thr Glu Gln Asp Ser Lys Asp Ser Thr Tyr Ser Leu
        195                 200                 205

Ser Ser Thr Leu Thr Leu Ser Lys Ala Asp Tyr Glu Lys His Lys Val
    210                 215                 220

Tyr Ala Cys Glu Val Thr His Gln Gly Leu Ser Ser Pro Val Thr Lys
225                 230                 235                 240

Ser Phe Asn Arg Gly Glu Cys
            245

<210> SEQ ID NO 353

```
<211> LENGTH: 245
<212> TYPE: PRT
<213> ORGANISM: Artificial Sequence
<220> FEATURE:
<223> OTHER INFORMATION: Synthetic Construct

<400> SEQUENCE: 353

Ala Cys Pro Ala Lys Ile Gly Gln Glu Cys Gly Gly Ser Ser Gly
1               5                   10                  15

Gly Ser Thr Ser Thr Ser Gly Arg Ser Ala Asn Pro Arg Ser Gly Gly
            20                  25                  30

Glu Ile Val Leu Thr Gln Ser Pro Asp Phe Gln Ser Val Thr Pro Lys
                35                  40                  45

Glu Lys Val Thr Ile Thr Cys Ser Ala Asn Ser Ala Leu Ser Tyr Met
50                  55                  60

Tyr Trp Tyr Gln Gln Lys Pro Asp Gln Ser Pro Lys Leu Trp Val His
65                  70                  75                  80

Gly Thr Ser Asn Leu Ala Ser Gly Val Pro Ser Arg Phe Ser Gly Ser
                85                  90                  95

Gly Ser Gly Thr Asp Phe Thr Leu Thr Ile Asn Ser Leu Glu Ala Glu
            100                 105                 110

Asp Ala Ala Thr Tyr Tyr Cys His His Trp Ser Asn Thr Gln Trp Thr
                115                 120                 125

Phe Gly Gly Gly Thr Lys Val Glu Ile Lys Arg Thr Val Ala Ala Pro
130                 135                 140

Ser Val Phe Ile Phe Pro Pro Ser Asp Glu Gln Leu Lys Ser Gly Thr
145                 150                 155                 160

Ala Ser Val Val Cys Leu Leu Asn Asn Phe Tyr Pro Arg Glu Ala Lys
                165                 170                 175

Val Gln Trp Lys Val Asp Asn Ala Leu Gln Ser Gly Asn Ser Gln Glu
            180                 185                 190

Ser Val Thr Glu Gln Asp Ser Lys Asp Ser Thr Tyr Ser Leu Ser Ser
        195                 200                 205

Thr Leu Thr Leu Ser Lys Ala Asp Tyr Glu Lys His Lys Val Tyr Ala
    210                 215                 220

Cys Glu Val Thr His Gln Gly Leu Ser Ser Pro Val Thr Lys Ser Phe
225                 230                 235                 240

Asn Arg Gly Glu Cys
                245

<210> SEQ ID NO 354
<211> LENGTH: 243
<212> TYPE: PRT
<213> ORGANISM: Artificial Sequence
<220> FEATURE:
<223> OTHER INFORMATION: Synthetic Construct

<400> SEQUENCE: 354

Ala Cys Pro Ala Lys Ile Gly Gln Glu Cys Gly Ser Ser Gly Gly Ser
1               5                   10                  15

Thr Ser Thr Ser Gly Arg Ser Ala Asn Pro Arg Ser Gly Gly Glu Ile
            20                  25                  30

Val Leu Thr Gln Ser Pro Asp Phe Gln Ser Val Thr Pro Lys Glu Lys
                35                  40                  45

Val Thr Ile Thr Cys Ser Ala Asn Ser Ala Leu Ser Tyr Met Tyr Trp
50                  55                  60

Tyr Gln Gln Lys Pro Asp Gln Ser Pro Lys Leu Trp Val His Gly Thr
```

```
                65                  70                  75                  80
        Ser Asn Leu Ala Ser Gly Val Pro Ser Arg Phe Ser Gly Ser
                        85                  90                  95

Gly Thr Asp Phe Thr Leu Thr Ile Asn Ser Leu Glu Ala Glu Asp Ala
                        100                 105                 110

Ala Thr Tyr Tyr Cys His His Trp Ser Asn Thr Gln Trp Thr Phe Gly
                        115                 120                 125

Gly Gly Thr Lys Val Glu Ile Lys Arg Thr Val Ala Ala Pro Ser Val
                130                 135                 140

Phe Ile Phe Pro Pro Ser Asp Glu Gln Leu Lys Ser Gly Thr Ala Ser
        145                 150                 155                 160

Val Val Cys Leu Leu Asn Asn Phe Tyr Pro Arg Glu Ala Lys Val Gln
                        165                 170                 175

Trp Lys Val Asp Asn Ala Leu Gln Ser Gly Asn Ser Gln Glu Ser Val
                        180                 185                 190

Thr Glu Gln Asp Ser Lys Asp Ser Thr Tyr Ser Leu Ser Ser Thr Leu
                        195                 200                 205

Thr Leu Ser Lys Ala Asp Tyr Glu Lys His Lys Val Tyr Ala Cys Glu
                210                 215                 220

Val Thr His Gln Gly Leu Ser Ser Pro Val Thr Lys Ser Phe Asn Arg
        225                 230                 235                 240

Gly Glu Cys

<210> SEQ ID NO 355
<211> LENGTH: 245
<212> TYPE: PRT
<213> ORGANISM: Artificial Sequence
<220> FEATURE:
<223> OTHER INFORMATION: Synthetic Construct

<400> SEQUENCE: 355

Ala Cys Pro Phe Pro Ala Leu Glu Leu Cys Gly Gly Gly Ser Ser Gly
        1               5                   10                  15

Gly Ser Thr Ser Thr Ser Gly Arg Ser Ala Asn Pro Arg Ser Gly Gly
                        20                  25                  30

Glu Ile Val Leu Thr Gln Ser Pro Asp Phe Gln Ser Val Thr Pro Lys
                        35                  40                  45

Glu Lys Val Thr Ile Thr Cys Ser Ala Asn Ser Ala Leu Ser Tyr Met
                50                  55                  60

Tyr Trp Tyr Gln Gln Lys Pro Asp Gln Ser Pro Lys Leu Trp Val His
        65                  70                  75                  80

Gly Thr Ser Asn Leu Ala Ser Gly Val Pro Ser Arg Phe Ser Gly Ser
                        85                  90                  95

Gly Ser Gly Thr Asp Phe Thr Leu Thr Ile Asn Ser Leu Glu Ala Glu
                        100                 105                 110

Asp Ala Ala Thr Tyr Tyr Cys His His Trp Ser Asn Thr Gln Trp Thr
                        115                 120                 125

Phe Gly Gly Gly Thr Lys Val Glu Ile Lys Arg Thr Val Ala Ala Pro
                130                 135                 140

Ser Val Phe Ile Phe Pro Pro Ser Asp Glu Gln Leu Lys Ser Gly Thr
        145                 150                 155                 160

Ala Ser Val Val Cys Leu Leu Asn Asn Phe Tyr Pro Arg Glu Ala Lys
                        165                 170                 175

Val Gln Trp Lys Val Asp Asn Ala Leu Gln Ser Gly Asn Ser Gln Glu
                        180                 185                 190
```

```
Ser Val Thr Glu Gln Asp Ser Lys Asp Ser Thr Tyr Ser Leu Ser Ser
        195                 200                 205

Thr Leu Thr Leu Ser Lys Ala Asp Tyr Glu Lys His Lys Val Tyr Ala
        210                 215                 220

Cys Glu Val Thr His Gln Gly Leu Ser Ser Pro Val Thr Lys Ser Phe
225                 230                 235                 240

Asn Arg Gly Glu Cys
                245

<210> SEQ ID NO 356
<211> LENGTH: 248
<212> TYPE: PRT
<213> ORGANISM: Artificial Sequence
<220> FEATURE:
<223> OTHER INFORMATION: Synthetic Construct

<400> SEQUENCE: 356

Ala Cys Pro Gly Lys Gly Leu Pro Ser Cys Gly Gly Ser Ser Gly
1               5                   10                  15

Gly Ser Thr Ser Thr Ser Gly Arg Ser Ala Asn Pro Arg Gly Gly Gly
        20                  25                  30

Ser Gly Gly Glu Ile Val Leu Thr Gln Ser Pro Asp Phe Gln Ser Val
        35                  40                  45

Thr Pro Lys Glu Lys Val Thr Ile Thr Cys Ser Ala Asn Ser Ala Leu
50                  55                  60

Ser Tyr Met Tyr Trp Tyr Gln Gln Lys Pro Asp Gln Ser Pro Lys Leu
65                  70                  75                  80

Trp Val His Gly Thr Ser Asn Leu Ala Ser Gly Val Pro Ser Arg Phe
                85                  90                  95

Ser Gly Ser Gly Ser Gly Thr Asp Phe Thr Leu Thr Ile Asn Ser Leu
            100                 105                 110

Glu Ala Glu Asp Ala Ala Thr Tyr Tyr Cys His His Trp Ser Asn Thr
        115                 120                 125

Gln Trp Thr Phe Gly Gly Gly Thr Lys Val Glu Ile Lys Arg Thr Val
    130                 135                 140

Ala Ala Pro Ser Val Phe Ile Phe Pro Pro Ser Asp Glu Gln Leu Lys
145                 150                 155                 160

Ser Gly Thr Ala Ser Val Val Cys Leu Leu Asn Asn Phe Tyr Pro Arg
                165                 170                 175

Glu Ala Lys Val Gln Trp Lys Val Asp Asn Ala Leu Gln Ser Gly Asn
            180                 185                 190

Ser Gln Glu Ser Val Thr Glu Gln Asp Ser Lys Asp Ser Thr Tyr Ser
        195                 200                 205

Leu Ser Ser Thr Leu Thr Leu Ser Lys Ala Asp Tyr Glu Lys His Lys
        210                 215                 220

Val Tyr Ala Cys Glu Val Thr His Gln Gly Leu Ser Ser Pro Val Thr
225                 230                 235                 240

Lys Ser Phe Asn Arg Gly Glu Cys
                245

<210> SEQ ID NO 357
<211> LENGTH: 241
<212> TYPE: PRT
<213> ORGANISM: Artificial Sequence
<220> FEATURE:
<223> OTHER INFORMATION: Synthetic Construct
```

<400> SEQUENCE: 357

```
Ala Cys Pro Gly Lys Gly Leu Pro Ser Cys Gly Gly Gly Ser Thr Ser
1               5                   10                  15
Thr Ser Gly Arg Ser Ala Asn Pro Arg Ser Gly Gly Glu Ile Val Leu
            20                  25                  30
Thr Gln Ser Pro Asp Phe Gln Ser Val Thr Pro Lys Glu Lys Val Thr
        35                  40                  45
Ile Thr Cys Ser Ala Asn Ser Ala Leu Ser Tyr Met Tyr Trp Tyr Gln
    50                  55                  60
Gln Lys Pro Asp Gln Ser Pro Lys Leu Trp Val His Gly Thr Ser Asn
65                  70                  75                  80
Leu Ala Ser Gly Val Pro Ser Arg Phe Ser Gly Ser Gly Ser Gly Thr
                85                  90                  95
Asp Phe Thr Leu Thr Ile Asn Ser Leu Glu Ala Glu Asp Ala Ala Thr
            100                 105                 110
Tyr Tyr Cys His His Trp Ser Asn Thr Gln Trp Thr Phe Gly Gly Gly
        115                 120                 125
Thr Lys Val Glu Ile Lys Arg Thr Val Ala Ala Pro Ser Val Phe Ile
    130                 135                 140
Phe Pro Pro Ser Asp Glu Gln Leu Lys Ser Gly Thr Ala Ser Val Val
145                 150                 155                 160
Cys Leu Leu Asn Asn Phe Tyr Pro Arg Glu Ala Lys Val Gln Trp Lys
                165                 170                 175
Val Asp Asn Ala Leu Gln Ser Gly Asn Ser Gln Glu Ser Val Thr Glu
            180                 185                 190
Gln Asp Ser Lys Asp Ser Thr Tyr Ser Leu Ser Ser Thr Leu Thr Leu
        195                 200                 205
Ser Lys Ala Asp Tyr Glu Lys His Lys Val Tyr Ala Cys Glu Val Thr
    210                 215                 220
His Gln Gly Leu Ser Ser Pro Val Thr Lys Ser Phe Asn Arg Gly Glu
225                 230                 235                 240
Cys
```

<210> SEQ ID NO 358
<211> LENGTH: 241
<212> TYPE: PRT
<213> ORGANISM: Artificial Sequence
<220> FEATURE:
<223> OTHER INFORMATION: Synthetic Construct

<400> SEQUENCE: 358

```
Ala Cys Pro Gly Lys Gly Leu Pro Ser Cys Gly Gly Gly Ser Ser Gly
1               5                   10                  15
Gly Ser Gly Val Pro Leu Ser Leu Tyr Ser Gly Gly Glu Ile Val Leu
            20                  25                  30
Thr Gln Ser Pro Asp Phe Gln Ser Val Thr Pro Lys Glu Lys Val Thr
        35                  40                  45
Ile Thr Cys Ser Ala Asn Ser Ala Leu Ser Tyr Met Tyr Trp Tyr Gln
    50                  55                  60
Gln Lys Pro Asp Gln Ser Pro Lys Leu Trp Val His Gly Thr Ser Asn
65                  70                  75                  80
Leu Ala Ser Gly Val Pro Ser Arg Phe Ser Gly Ser Gly Ser Gly Thr
                85                  90                  95
Asp Phe Thr Leu Thr Ile Asn Ser Leu Glu Ala Glu Asp Ala Ala Thr
            100                 105                 110
```

```
Tyr Tyr Cys His His Trp Ser Asn Thr Gln Trp Thr Phe Gly Gly Gly
            115                 120                 125

Thr Lys Val Glu Ile Lys Arg Thr Val Ala Ala Pro Ser Val Phe Ile
130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 359
<211> LENGTH: 239
<212> TYPE: PRT
<213> ORGANISM: Artificial Sequence
<220> FEATURE:
<223> OTHER INFORMATION: Synthetic Construct

<400> SEQUENCE: 359

Ala Cys Pro Gly Lys Gly Leu Pro Ser Cys Gly Ser Thr Ser Thr Ser
1               5                   10                  15

Gly Arg Ser Ala Asn Pro Arg Ser Gly Gly Glu Ile Val Leu Thr Gln
            20                  25                  30

Ser Pro Asp Phe Gln Ser Val Thr Pro Lys Glu Lys Val Thr Ile Thr
        35                  40                  45

Cys Ser Ala Asn Ser Ala Leu Ser Tyr Met Tyr Trp Tyr Gln Gln Lys
    50                  55                  60

Pro Asp Gln Ser Pro Lys Leu Trp Val His Gly Thr Ser Asn Leu Ala
65                  70                  75                  80

Ser Gly Val Pro Ser Arg Phe Ser Gly Ser Gly Ser Gly Thr Asp Phe
                85                  90                  95

Thr Leu Thr Ile Asn Ser Leu Glu Ala Glu Asp Ala Ala Thr Tyr Tyr
            100                 105                 110

Cys His His Trp Ser Asn Thr Gln Trp Thr Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220
```

```
Gly Leu Ser Ser Pro Val Thr Lys Ser Phe Asn Arg Gly Glu Cys
225                 230                 235
```

<210> SEQ ID NO 360
<211> LENGTH: 240
<212> TYPE: PRT
<213> ORGANISM: Artificial Sequence
<220> FEATURE:
<223> OTHER INFORMATION: Synthetic Construct

<400> SEQUENCE: 360

```
Ala Cys Pro Gly Lys Gly Leu Pro Ser Cys Gly Gly Ser Thr Ser
1               5                   10                  15

Ser Gly Arg Ser Ala Asn Pro Arg Gly Gly Glu Ile Val Leu Thr
                20                  25                  30

Gln Ser Pro Asp Phe Gln Ser Val Thr Pro Lys Glu Lys Val Thr Ile
        35                  40                  45

Thr Cys Ser Ala Asn Ser Ala Leu Ser Tyr Met Tyr Trp Tyr Gln Gln
    50                  55                  60

Lys Pro Asp Gln Ser Pro Lys Leu Trp Val His Gly Thr Ser Asn Leu
65                  70                  75                  80

Ala Ser Gly Val Pro Ser Arg Phe Ser Gly Ser Gly Ser Gly Thr Asp
                85                  90                  95

Phe Thr Leu Thr Ile Asn Ser Leu Glu Ala Glu Asp Ala Ala Thr Tyr
            100                 105                 110

Tyr Cys His His Trp Ser Asn Thr Gln Trp Thr Phe Gly Gly Gly Thr
        115                 120                 125

Lys Val Glu Ile Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240
```

<210> SEQ ID NO 361
<211> LENGTH: 240
<212> TYPE: PRT
<213> ORGANISM: Artificial Sequence
<220> FEATURE:
<223> OTHER INFORMATION: Synthetic Construct

<400> SEQUENCE: 361

```
Ala Cys Pro Gly Lys Gly Leu Pro Ser Cys Gly Gly Gly Ser Thr Ser
1               5                   10                  15

Thr Ser Gly Arg Ser Ala Asn Pro Arg Gly Gly Glu Ile Val Leu Thr
                20                  25                  30

Gln Ser Pro Asp Phe Gln Ser Val Thr Pro Lys Glu Lys Val Thr Ile
        35                  40                  45

Thr Cys Ser Ala Asn Ser Ala Leu Ser Tyr Met Tyr Trp Tyr Gln Gln
    50                  55                  60
```

```
Lys Pro Asp Gln Ser Pro Lys Leu Trp Val His Gly Thr Ser Asn Leu
 65                  70                  75                  80

Ala Ser Gly Val Pro Ser Arg Phe Ser Gly Ser Gly Ser Gly Thr Asp
                 85                  90                  95

Phe Thr Leu Thr Ile Asn Ser Leu Glu Ala Glu Asp Ala Ala Thr Tyr
            100                 105                 110

Tyr Cys His His Trp Ser Asn Thr Gln Trp Thr Phe Gly Gly Gly Thr
            115                 120                 125

Lys Val Glu Ile Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
210                 215                 220

Gln Gly Leu Ser Ser Pro Val Thr Lys Ser Phe Asn Arg Gly Glu Cys
225                 230                 235                 240

<210> SEQ ID NO 362
<211> LENGTH: 245
<212> TYPE: PRT
<213> ORGANISM: Artificial Sequence
<220> FEATURE:
<223> OTHER INFORMATION: Synthetic Construct

<400> SEQUENCE: 362

Ala Cys Thr Lys Pro Ala Lys Ala Leu Cys Gly Gly Gly Ser Ser Gly
1               5                   10                  15

Gly Ser Thr Ser Thr Ser Gly Arg Ser Ala Asn Pro Arg Ser Gly Gly
            20                  25                  30

Glu Ile Val Leu Thr Gln Ser Pro Asp Phe Gln Ser Val Thr Pro Lys
        35                  40                  45

Glu Lys Val Thr Ile Thr Cys Ser Ala Asn Ser Ala Leu Ser Tyr Met
    50                  55                  60

Tyr Trp Tyr Gln Gln Lys Pro Asp Gln Ser Pro Lys Leu Trp Val His
 65                  70                  75                  80

Gly Thr Ser Asn Leu Ala Ser Gly Val Pro Ser Arg Phe Ser Gly Ser
                 85                  90                  95

Gly Ser Gly Thr Asp Phe Thr Leu Thr Ile Asn Ser Leu Glu Ala Glu
            100                 105                 110

Asp Ala Ala Thr Tyr Tyr Cys His His Trp Ser Asn Thr Gln Trp Thr
        115                 120                 125

Phe Gly Gly Gly Thr Lys Val Glu Ile Lys Arg Thr Val Ala Ala Pro
    130                 135                 140

Ser Val Phe Ile Phe Pro Pro Ser Asp Glu Gln Leu Lys Ser Gly Thr
145                 150                 155                 160

Ala Ser Val Val Cys Leu Leu Asn Asn Phe Tyr Pro Arg Glu Ala Lys
                165                 170                 175

Val Gln Trp Lys Val Asp Asn Ala Leu Gln Ser Gly Asn Ser Gln Glu
            180                 185                 190
```

```
Ser Val Thr Glu Gln Asp Ser Lys Asp Ser Thr Tyr Ser Leu Ser Ser
        195                 200                 205

Thr Leu Thr Leu Ser Lys Ala Asp Tyr Glu Lys His Lys Val Tyr Ala
    210                 215                 220

Cys Glu Val Thr His Gln Gly Leu Ser Ser Pro Val Thr Lys Ser Phe
225                 230                 235                 240

Asn Arg Gly Glu Cys
                245

<210> SEQ ID NO 363
<211> LENGTH: 251
<212> TYPE: PRT
<213> ORGANISM: Artificial Sequence
<220> FEATURE:
<223> OTHER INFORMATION: Synthetic Construct

<400> SEQUENCE: 363

Asp Thr Ala Thr Cys Tyr Thr Thr Thr Gly Trp Cys Glu Gly Met Val
1               5                   10                  15

Gly Gly Gly Ser Ser Gly Gly Ser Thr Ser Thr Ser Gly Arg Ser Ala
            20                  25                  30

Asn Pro Arg Ser Gly Gly Glu Ile Val Leu Thr Gln Ser Pro Asp Phe
        35                  40                  45

Gln Ser Val Thr Pro Lys Glu Lys Val Thr Ile Thr Cys Ser Ala Asn
    50                  55                  60

Ser Ala Leu Ser Tyr Met Tyr Trp Tyr Gln Gln Lys Pro Asp Gln Ser
65                  70                  75                  80

Pro Lys Leu Trp Val His Gly Thr Ser Asn Leu Ala Ser Gly Val Pro
                85                  90                  95

Ser Arg Phe Ser Gly Ser Gly Ser Gly Thr Asp Phe Thr Leu Thr Ile
            100                 105                 110

Asn Ser Leu Glu Ala Glu Asp Ala Ala Thr Tyr Tyr Cys His His Trp
        115                 120                 125

Ser Asn Thr Gln Trp Thr Phe Gly Gly Gly Thr Lys Val Glu Ile Lys
    130                 135                 140

Arg Thr Val Ala Ala Pro Ser Val Phe Ile Phe Pro Pro Ser Asp Glu
145                 150                 155                 160

Gln Leu Lys Ser Gly Thr Ala Ser Val Val Cys Leu Leu Asn Asn Phe
                165                 170                 175

Tyr Pro Arg Glu Ala Lys Val Gln Trp Lys Val Asp Asn Ala Leu Gln
            180                 185                 190

Ser Gly Asn Ser Gln Glu Ser Val Thr Glu Gln Asp Ser Lys Asp Ser
        195                 200                 205

Thr Tyr Ser Leu Ser Ser Thr Leu Thr Leu Ser Lys Ala Asp Tyr Glu
    210                 215                 220

Lys His Lys Val Tyr Ala Cys Glu Val Thr His Gln Gly Leu Ser Ser
225                 230                 235                 240

Pro Val Thr Lys Ser Phe Asn Arg Gly Glu Cys
                245                 250

<210> SEQ ID NO 364
<211> LENGTH: 251
<212> TYPE: PRT
<213> ORGANISM: Artificial Sequence
<220> FEATURE:
<223> OTHER INFORMATION: Synthetic Construct
```

<400> SEQUENCE: 364

Asn Ser Asp Asn Cys Gly Pro Ala Lys Ser Thr Cys Met Tyr Asn Asp
1               5                   10                  15

Gly Gly Gly Ser Ser Gly Gly Ser Thr Ser Thr Ser Gly Arg Ser Ala
            20                  25                  30

Asn Pro Arg Ser Gly Gly Glu Ile Val Leu Thr Gln Ser Pro Asp Phe
        35                  40                  45

Gln Ser Val Thr Pro Lys Glu Lys Val Thr Ile Thr Cys Ser Ala Asn
    50                  55                  60

Ser Ala Leu Ser Tyr Met Tyr Trp Tyr Gln Gln Lys Pro Asp Gln Ser
65                  70                  75                  80

Pro Lys Leu Trp Val His Gly Thr Ser Asn Leu Ala Ser Gly Val Pro
                85                  90                  95

Ser Arg Phe Ser Gly Ser Gly Ser Gly Thr Asp Phe Thr Leu Thr Ile
            100                 105                 110

Asn Ser Leu Glu Ala Glu Asp Ala Ala Thr Tyr Tyr Cys His His Trp
        115                 120                 125

Ser Asn Thr Gln Trp Thr Phe Gly Gly Gly Thr Lys Val Glu Ile Lys
    130                 135                 140

Arg Thr Val Ala Ala Pro Ser Val Phe Ile Phe Pro Pro Ser Asp Glu
145                 150                 155                 160

Gln Leu Lys Ser Gly Thr Ala Ser Val Val Cys Leu Leu Asn Asn Phe
            165                 170                 175

Tyr Pro Arg Glu Ala Lys Val Gln Trp Lys Val Asp Asn Ala Leu Gln
        180                 185                 190

Ser Gly Asn Ser Gln Glu Ser Val Thr Glu Gln Asp Ser Lys Asp Ser
    195                 200                 205

Thr Tyr Ser Leu Ser Ser Thr Leu Thr Leu Ser Lys Ala Asp Tyr Glu
210                 215                 220

Lys His Lys Val Tyr Ala Cys Glu Val Thr His Gln Gly Leu Ser Ser
225                 230                 235                 240

Pro Val Thr Lys Ser Phe Asn Arg Gly Glu Cys
            245                 250

<210> SEQ ID NO 365
<211> LENGTH: 250
<212> TYPE: PRT
<213> ORGANISM: Artificial Sequence
<220> FEATURE:
<223> OTHER INFORMATION: Synthetic Construct

<400> SEQUENCE: 365

Pro Pro Gly Lys Cys Thr Gln Pro His Arg Cys Pro Pro Leu Asn Gly
1               5                   10                  15

Gly Gly Ser Ser Gly Gly Ser Thr Ser Thr Ser Gly Arg Ser Ala Asn
            20                  25                  30

Pro Arg Ser Gly Gly Glu Ile Val Leu Thr Gln Ser Pro Asp Phe Gln
        35                  40                  45

Ser Val Thr Pro Lys Glu Lys Val Thr Ile Thr Cys Ser Ala Asn Ser
    50                  55                  60

Ala Leu Ser Tyr Met Tyr Trp Tyr Gln Gln Lys Pro Asp Gln Ser Pro
65                  70                  75                  80

Lys Leu Trp Val His Gly Thr Ser Asn Leu Ala Ser Gly Val Pro Ser
                85                  90                  95

Arg Phe Ser Gly Ser Gly Ser Gly Thr Asp Phe Thr Leu Thr Ile Asn

```
                100                 105                 110
Ser Leu Glu Ala Glu Asp Ala Ala Thr Tyr Tyr Cys His His Trp Ser
            115                 120                 125
Asn Thr Gln Trp Thr Phe Gly Gly Gly Thr Lys Val Glu Ile Lys Arg
            130                 135                 140
Thr Val Ala Ala Pro Ser Val Phe Ile Phe Pro Pro Ser Asp Glu Gln
145                 150                 155                 160
Leu Lys Ser Gly Thr Ala Ser Val Val Cys Leu Leu Asn Asn Phe Tyr
                165                 170                 175
Pro Arg Glu Ala Lys Val Gln Trp Lys Val Asp Asn Ala Leu Gln Ser
                180                 185                 190
Gly Asn Ser Gln Glu Ser Val Thr Glu Gln Asp Ser Lys Asp Ser Thr
                195                 200                 205
Tyr Ser Leu Ser Ser Thr Leu Thr Leu Ser Lys Ala Asp Tyr Glu Lys
                210                 215                 220
His Lys Val Tyr Ala Cys Glu Val Thr His Gln Gly Leu Ser Ser Pro
225                 230                 235                 240
Val Thr Lys Ser Phe Asn Arg Gly Glu Cys
                245                 250

<210> SEQ ID NO 366
<211> LENGTH: 450
<212> TYPE: PRT
<213> ORGANISM: Artificial Sequence
<220> FEATURE:
<223> OTHER INFORMATION: Synthetic Construct

<400> SEQUENCE: 366

Gln Val Gln Leu Gln Glu Ser Gly Pro Gly Leu Val Lys Pro Ser Glu
1               5                   10                  15
Thr Leu Ser Leu Thr Cys Ser Val Thr Tyr His Thr Ile Thr Ser Gly
            20                  25                  30
Tyr Asp Trp Thr Trp Ile Arg Lys Pro Pro Gly Lys Gly Met Glu Trp
        35                  40                  45
Ile Gly Tyr Ile Ser Tyr Ser Gly Asn Thr Asn Tyr Asn Pro Ser Leu
    50                  55                  60
Lys Ser Arg Val Thr Ile Ser Arg Asp Thr Ser Lys Asn Gln Phe Phe
65                  70                  75                  80
Leu Lys Leu Ser Ser Val Thr Ala Ala Asp Thr Ala Val Tyr Tyr Cys
                85                  90                  95
Ala Ser Met Met Val Pro His Tyr Tyr Val Met Asp Ala Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
```

```
            210                 215                 220
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 367
<211> LENGTH: 488
<212> TYPE: PRT
<213> ORGANISM: Artificial Sequence
<220> FEATURE:
<223> OTHER INFORMATION: Synthetic Construct

<400> SEQUENCE: 367

Met Gln Thr Arg Cys Lys Glu Tyr Pro Arg Trp Cys Glu His Trp Leu
1               5                   10                  15

Gly Gly Gly Ser Ser Gly Gly Ser Thr Ser Thr Ser Gly Arg Ser Ala
                20                  25                  30

Asn Pro Arg Ser Gly Gly Gln Val Gln Leu Gln Glu Ser Gly Pro Gly
            35                  40                  45

Leu Val Lys Pro Ser Glu Thr Leu Ser Leu Thr Cys Ser Val Thr Tyr
        50                  55                  60

His Thr Ile Thr Ser Gly Tyr Asp Trp Thr Trp Ile Arg Lys Pro Pro
65                  70                  75                  80

Gly Lys Gly Met Glu Trp Ile Gly Tyr Ile Ser Tyr Ser Gly Asn Thr
                85                  90                  95

Asn Tyr Asn Pro Ser Leu Lys Ser Arg Val Thr Ile Ser Arg Asp Thr
            100                 105                 110

Ser Lys Asn Gln Phe Phe Leu Lys Leu Ser Ser Val Thr Ala Ala Asp
```

115                 120                 125
Thr Ala Val Tyr Tyr Cys Ala Ser Met Met Val Pro His Tyr Tyr Val
130                 135                 140

Met Asp Ala Trp Gly Gln Gly Thr Leu Val Thr Val Ser Ser Ala Ser
145                 150                 155                 160

Thr Lys Gly Pro Ser Val Phe Pro Leu Ala Pro Ser Ser Lys Ser Thr
                165                 170                 175

Ser Gly Gly Thr Ala Ala Leu Gly Cys Leu Val Lys Asp Tyr Phe Pro
            180                 185                 190

Glu Pro Val Thr Val Ser Trp Asn Ser Gly Ala Leu Thr Ser Gly Val
        195                 200                 205

His Thr Phe Pro Ala Val Leu Gln Ser Ser Gly Leu Tyr Ser Leu Ser
210                 215                 220

Ser Val Val Thr Val Pro Ser Ser Ser Leu Gly Thr Gln Thr Tyr Ile
225                 230                 235                 240

Cys Asn Val Asn His Lys Pro Ser Asn Thr Lys Val Asp Lys Lys Val
                245                 250                 255

Glu Pro Lys Ser Cys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485

<210> SEQ ID NO 368
<211> LENGTH: 485
<212> TYPE: PRT
<213> ORGANISM: Artificial Sequence
<220> FEATURE:
<223> OTHER INFORMATION: Synthetic Construct

<400> SEQUENCE: 368

```
Met Gln Thr Arg Cys Lys Glu Tyr Pro Arg Trp Cys Glu His Trp Leu
1               5                   10                  15

Gly Gly Ser Gly Gly Thr Ser Thr Ser Gly Arg Ser Ala Asn Pro Arg
            20                  25                  30

Ser Gly Gly Gln Val Gln Leu Gln Glu Ser Gly Pro Gly Leu Val Lys
        35                  40                  45

Pro Ser Glu Thr Leu Ser Leu Thr Cys Ser Val Thr Tyr His Thr Ile
    50                  55                  60

Thr Ser Gly Tyr Asp Trp Thr Trp Ile Arg Lys Pro Pro Gly Lys Gly
65                  70                  75                  80

Met Glu Trp Ile Gly Tyr Ile Ser Tyr Ser Gly Asn Thr Asn Tyr Asn
                85                  90                  95

Pro Ser Leu Lys Ser Arg Val Thr Ile Ser Arg Asp Thr Ser Lys Asn
            100                 105                 110

Gln Phe Phe Leu Lys Leu Ser Ser Val Thr Ala Ala Asp Thr Ala Val
        115                 120                 125

Tyr Tyr Cys Ala Ser Met Met Val Pro His Tyr Tyr Val Met Asp Ala
    130                 135                 140

Trp Gly Gln Gly Thr Leu Val Thr Val Ser Ser Ala Ser Thr Lys Gly
145                 150                 155                 160

Pro Ser Val Phe Pro Leu Ala Pro Ser Ser Lys Ser Thr Ser Gly Gly
                165                 170                 175

Thr Ala Ala Leu Gly Cys Leu Val Lys Asp Tyr Phe Pro Glu Pro Val
            180                 185                 190

Thr Val Ser Trp Asn Ser Gly Ala Leu Thr Ser Gly Val His Thr Phe
        195                 200                 205

Pro Ala Val Leu Gln Ser Ser Gly Leu Tyr Ser Leu Ser Ser Val Val
    210                 215                 220

Thr Val Pro Ser Ser Ser Leu Gly Thr Gln Thr Tyr Ile Cys Asn Val
225                 230                 235                 240

Asn His Lys Pro Ser Asn Thr Lys Val Asp Lys Lys Val Glu Pro Lys
                245                 250                 255

Ser Cys Asp Lys Thr His Thr Cys Pro Pro Cys Pro Ala Pro Glu Leu
            260                 265                 270

Leu Gly Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
    290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
    370                 375                 380

Gln Val Tyr Thr Leu Pro Pro Ser Arg Asp Glu Leu Thr Lys Asn Gln
385                 390                 395                 400

Val Ser Leu Thr Cys Leu Val Lys Gly Phe Tyr Pro Ser Asp Ile Ala
                405                 410                 415
```

-continued

Val Glu Trp Glu Ser Asn Gly Gln Pro Glu Asn Asn Tyr Lys Thr Thr
                420                 425                 430

Pro Pro Val Leu Asp Ser Asp Gly Ser Phe Phe Leu Tyr Ser Lys Leu
            435                 440                 445

Thr Val Asp Lys Ser Arg Trp Gln Gln Gly Asn Val Phe Ser Cys Ser
        450                 455                 460

Val Met His Glu Ala Leu His Asn His Tyr Thr Gln Lys Ser Leu Ser
465                 470                 475                 480

Leu Ser Pro Gly Lys
                485

<210> SEQ ID NO 369
<211> LENGTH: 484
<212> TYPE: PRT
<213> ORGANISM: Artificial Sequence
<220> FEATURE:
<223> OTHER INFORMATION: Synthetic Construct

<400> SEQUENCE: 369

Met Gln Thr Arg Cys Lys Glu Tyr Pro Arg Trp Cys Glu His Trp Leu
1               5                   10                  15

Gly Gly Gly Ser Thr Ser Thr Ser Gly Arg Ser Ala Asn Pro Arg Ser
            20                  25                  30

Gly Gly Gln Val Gln Leu Gln Glu Ser Gly Pro Gly Leu Val Lys Pro
        35                  40                  45

Ser Glu Thr Leu Ser Leu Thr Cys Ser Val Thr Tyr His Thr Ile Thr
    50                  55                  60

Ser Gly Tyr Asp Trp Thr Trp Ile Arg Lys Pro Pro Gly Lys Gly Met
65                  70                  75                  80

Glu Trp Ile Gly Tyr Ile Ser Tyr Ser Gly Asn Thr Asn Tyr Asn Pro
                85                  90                  95

Ser Leu Lys Ser Arg Val Thr Ile Ser Arg Asp Thr Ser Lys Asn Gln
            100                 105                 110

Phe Phe Leu Lys Leu Ser Ser Val Thr Ala Ala Asp Thr Ala Val Tyr
        115                 120                 125

Tyr Cys Ala Ser Met Met Val Pro His Tyr Tyr Val Met Asp Ala Trp
    130                 135                 140

Gly Gln Gly Thr Leu Val Thr Val Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255

Cys Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

```
Met Ile Ser Arg Thr Pro Glu Val Thr Cys Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Lys

<210> SEQ ID NO 370
<211> LENGTH: 483
<212> TYPE: PRT
<213> ORGANISM: Artificial Sequence
<220> FEATURE:
<223> OTHER INFORMATION: Synthetic Construct

<400> SEQUENCE: 370

Met Gln Thr Arg Cys Lys Glu Tyr Pro Arg Trp Cys Glu His Trp Leu
1               5                   10                  15

Gly Gly Ser Thr Ser Thr Ser Gly Arg Ser Ala Asn Pro Arg Ser Gly
            20                  25                  30

Gly Gln Val Gln Leu Gln Glu Ser Gly Pro Gly Leu Val Lys Pro Ser
        35                  40                  45

Glu Thr Leu Ser Leu Thr Cys Ser Val Thr Tyr His Thr Ile Thr Ser
50                  55                  60

Gly Tyr Asp Trp Thr Trp Ile Arg Lys Pro Pro Gly Lys Gly Met Glu
65                  70                  75                  80

Trp Ile Gly Tyr Ile Ser Tyr Ser Gly Asn Thr Asn Tyr Asn Pro Ser
                85                  90                  95

Leu Lys Ser Arg Val Thr Ile Ser Arg Asp Thr Ser Lys Asn Gln Phe
            100                 105                 110

Phe Leu Lys Leu Ser Ser Val Thr Ala Ala Asp Thr Ala Val Tyr Tyr
        115                 120                 125

Cys Ala Ser Met Met Val Pro His Tyr Tyr Val Met Asp Ala Trp Gly
    130                 135                 140

Gln Gly Thr Leu Val Thr Val Ser Ser Ala Ser Thr Lys Gly Pro Ser
145                 150                 155                 160
```

-continued

```
Val Phe Pro Leu Ala Pro Ser Ser Lys Ser Thr Ser Gly Gly Thr Ala
            165                 170                 175
Ala Leu Gly Cys Leu Val Lys Asp Tyr Phe Pro Glu Pro Val Thr Val
        180                 185                 190
Ser Trp Asn Ser Gly Ala Leu Thr Ser Gly Val His Thr Phe Pro Ala
        195                 200                 205
Val Leu Gln Ser Ser Gly Leu Tyr Ser Leu Ser Ser Val Val Thr Val
    210                 215                 220
Pro Ser Ser Ser Leu Gly Thr Gln Thr Tyr Ile Cys Asn Val Asn His
225                 230                 235                 240
Lys Pro Ser Asn Thr Lys Val Asp Lys Lys Val Glu Pro Lys Ser Cys
                245                 250                 255
Asp Lys Thr His Thr Cys Pro Pro Cys Pro Ala Pro Glu Leu Leu Gly
            260                 265                 270
Gly Pro Ser Val Phe Leu Phe Pro Pro Lys Pro Lys Asp Thr Leu Met
        275                 280                 285
Ile Ser Arg Thr Pro Glu Val Thr Cys Val Val Val Asp Val Ser His
    290                 295                 300
Glu Asp Pro Glu Val Lys Phe Asn Trp Tyr Val Asp Gly Val Glu Val
305                 310                 315                 320
His Asn Ala Lys Thr Lys Pro Arg Glu Glu Gln Tyr Asn Ser Thr Tyr
                325                 330                 335
Arg Val Val Ser Val Leu Thr Val Leu His Gln Asp Trp Leu Asn Gly
            340                 345                 350
Lys Glu Tyr Lys Cys Lys Val Ser Asn Lys Ala Leu Pro Ala Pro Ile
        355                 360                 365
Glu Lys Thr Ile Ser Lys Ala Lys Gly Gln Pro Arg Glu Pro Gln Val
    370                 375                 380
Tyr Thr Leu Pro Pro Ser Arg Asp Glu Leu Thr Lys Asn Gln Val Ser
385                 390                 395                 400
Leu Thr Cys Leu Val Lys Gly Phe Tyr Pro Ser Asp Ile Ala Val Glu
                405                 410                 415
Trp Glu Ser Asn Gly Gln Pro Glu Asn Asn Tyr Lys Thr Thr Pro Pro
            420                 425                 430
Val Leu Asp Ser Asp Gly Ser Phe Phe Leu Tyr Ser Lys Leu Thr Val
        435                 440                 445
Asp Lys Ser Arg Trp Gln Gln Gly Asn Val Phe Ser Cys Ser Val Met
    450                 455                 460
His Glu Ala Leu His Asn His Tyr Thr Gln Lys Ser Leu Ser Leu Ser
465                 470                 475                 480
Pro Gly Lys

<210> SEQ ID NO 371
<211> LENGTH: 482
<212> TYPE: PRT
<213> ORGANISM: Artificial Sequence
<220> FEATURE:
<223> OTHER INFORMATION: Synthetic Construct

<400> SEQUENCE: 371

Met Gln Thr Arg Cys Lys Glu Tyr Pro Arg Trp Cys Glu His Trp Leu
1               5                   10                  15
Gly Ser Thr Ser Thr Ser Gly Arg Ser Ala Asn Pro Arg Ser Gly Gly
            20                  25                  30
Gln Val Gln Leu Gln Glu Ser Gly Pro Gly Leu Val Lys Pro Ser Glu
```

-continued

```
            35                  40                  45
Thr Leu Ser Leu Thr Cys Ser Val Thr Tyr His Thr Ile Thr Ser Gly
 50                  55                  60

Tyr Asp Trp Thr Trp Ile Arg Lys Pro Pro Gly Lys Gly Met Glu Trp
 65                  70                  75                  80

Ile Gly Tyr Ile Ser Tyr Ser Gly Asn Thr Asn Tyr Asn Pro Ser Leu
                 85                  90                  95

Lys Ser Arg Val Thr Ile Ser Arg Asp Thr Ser Lys Asn Gln Phe Phe
                100                 105                 110

Leu Lys Leu Ser Ser Val Thr Ala Ala Asp Thr Ala Val Tyr Tyr Cys
                115                 120                 125

Ala Ser Met Met Val Pro His Tyr Tyr Val Met Asp Ala Trp Gly Gln
130                 135                 140

Gly Thr Leu Val Thr Val Ser Ser Ala Ser Thr Lys Gly Pro Ser Val
145                 150                 155                 160

Phe Pro Leu Ala Pro Ser Ser Lys Ser Thr Ser Gly Gly Thr Ala Ala
                165                 170                 175

Leu Gly Cys Leu Val Lys Asp Tyr Phe Pro Glu Pro Val Thr Val Ser
                180                 185                 190

Trp Asn Ser Gly Ala Leu Thr Ser Gly Val His Thr Phe Pro Ala Val
                195                 200                 205

Leu Gln Ser Ser Gly Leu Tyr Ser Leu Ser Ser Val Val Thr Val Pro
                210                 215                 220

Ser Ser Ser Leu Gly Thr Gln Thr Tyr Ile Cys Asn Val Asn His Lys
225                 230                 235                 240

Pro Ser Asn Thr Lys Val Asp Lys Lys Val Glu Pro Lys Ser Cys Asp
                245                 250                 255

Lys Thr His Thr Cys Pro Pro Cys Pro Ala Pro Glu Leu Leu Gly Gly
                260                 265                 270

Pro Ser Val Phe Leu Phe Pro Pro Lys Pro Lys Asp Thr Leu Met Ile
                275                 280                 285

Ser Arg Thr Pro Glu Val Thr Cys Val Val Val Asp Val Ser His Glu
290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
                340                 345                 350

Glu Tyr Lys Cys Lys Val Ser Asn Lys Ala Leu Pro Ala Pro Ile Glu
                355                 360                 365

Lys Thr Ile Ser Lys Ala Lys Gly Gln Pro Arg Glu Pro Gln Val Tyr
                370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
                420                 425                 430

Leu Asp Ser Asp Gly Ser Phe Phe Leu Tyr Ser Lys Leu Thr Val Asp
                435                 440                 445

Lys Ser Arg Trp Gln Gln Gly Asn Val Phe Ser Cys Ser Val Met His
                450                 455                 460
```

Glu Ala Leu His Asn His Tyr Thr Gln Lys Ser Leu Ser Leu Ser Pro
465                 470                 475                 480

Gly Lys

<210> SEQ ID NO 372
<211> LENGTH: 485
<212> TYPE: PRT
<213> ORGANISM: Artificial Sequence
<220> FEATURE:
<223> OTHER INFORMATION: Synthetic Construct

<400> SEQUENCE: 372

Met Gln Thr Arg Cys Lys Glu Tyr Pro Arg Trp Cys Glu His Trp Leu
1               5                   10                  15

Gly Ser Thr Ser Thr Ser Gly Arg Ser Ala Asn Pro Arg Ser Gly Gly
            20                  25                  30

Ser Gly Gly Gln Val Gln Leu Gln Glu Ser Gly Pro Gly Leu Val Lys
        35                  40                  45

Pro Ser Glu Thr Leu Ser Leu Thr Cys Ser Val Thr Tyr His Thr Ile
    50                  55                  60

Thr Ser Gly Tyr Asp Trp Thr Trp Ile Arg Lys Pro Pro Gly Lys Gly
65                  70                  75                  80

Met Glu Trp Ile Gly Tyr Ile Ser Tyr Ser Gly Asn Thr Asn Tyr Asn
                85                  90                  95

Pro Ser Leu Lys Ser Arg Val Thr Ile Ser Arg Asp Thr Ser Lys Asn
            100                 105                 110

Gln Phe Phe Leu Lys Leu Ser Ser Val Thr Ala Ala Asp Thr Ala Val
        115                 120                 125

Tyr Tyr Cys Ala Ser Met Met Val Pro His Tyr Tyr Val Met Asp Ala
    130                 135                 140

Trp Gly Gln Gly Thr Leu Val Thr Val Ser Ser Ala Ser Thr Lys Gly
145                 150                 155                 160

Pro Ser Val Phe Pro Leu Ala Pro Ser Ser Lys Ser Thr Ser Gly Gly
                165                 170                 175

Thr Ala Ala Leu Gly Cys Leu Val Lys Asp Tyr Phe Pro Glu Pro Val
            180                 185                 190

Thr Val Ser Trp Asn Ser Gly Ala Leu Thr Ser Gly Val His Thr Phe
        195                 200                 205

Pro Ala Val Leu Gln Ser Ser Gly Leu Tyr Ser Leu Ser Ser Val Val
    210                 215                 220

Thr Val Pro Ser Ser Ser Leu Gly Thr Gln Thr Tyr Ile Cys Asn Val
225                 230                 235                 240

Asn His Lys Pro Ser Asn Thr Lys Val Asp Lys Lys Val Glu Pro Lys
                245                 250                 255

Ser Cys Asp Lys Thr His Thr Cys Pro Pro Cys Pro Ala Pro Glu Leu
            260                 265                 270

Leu Gly Gly Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
    290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Lys Val Ser Asn Lys Ala Leu Pro Ala
        355                 360                 365

Pro Ile Glu Lys Thr Ile Ser Lys Ala Lys Gly Gln Pro Arg Glu Pro
370                 375                 380

Gln Val Tyr Thr Leu Pro Pro Ser Arg Asp Glu Leu Thr Lys Asn Gln
385                 390                 395                 400

Val Ser Leu Thr Cys Leu Val Lys Gly Phe Tyr Pro Ser Asp Ile Ala
                405                 410                 415

Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
450                 455                 460

Val Met His Glu Ala Leu His Asn His Tyr Thr Gln Lys Ser Leu Ser
465                 470                 475                 480

Leu Ser Pro Gly Lys
            485

<210> SEQ ID NO 373
<211> LENGTH: 481
<212> TYPE: PRT
<213> ORGANISM: Artificial Sequence
<220> FEATURE:
<223> OTHER INFORMATION: Synthetic Construct

<400> SEQUENCE: 373

Ala Cys Lys His Ala Pro Tyr Ala Leu Cys Gly Gly Gly Ser Ser Gly
1               5                   10                  15

Gly Ser Thr Ser Thr Ser Gly Arg Ser Ala Asn Pro Arg Ser Gly Gly
            20                  25                  30

Gln Val Gln Leu Val Gln Ser Gly Ala Glu Val Lys Lys Pro Gly Ser
        35                  40                  45

Ser Val Lys Val Ser Cys Lys Ala Ser Gly Tyr Thr Phe Thr Asn Tyr
    50                  55                  60

Phe Met Asn Trp Val Arg Gln Ala Pro Gly Gln Gly Leu Glu Trp Met
65                  70                  75                  80

Gly Arg Val Asp Pro Glu Gln Gly Arg Ala Asp Tyr Ala Glu Lys Phe
                85                  90                  95

Lys Lys Arg Val Thr Ile Thr Ala Asp Lys Ser Thr Ser Thr Ala Tyr
            100                 105                 110

Met Glu Leu Ser Ser Leu Arg Ser Glu Asp Thr Ala Val Tyr Tyr Cys
        115                 120                 125

Ala Arg Arg Ala Met Asp Asn Tyr Gly Phe Ala Tyr Trp Gly Gln Gly
    130                 135                 140

Thr Leu Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
            245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
            325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
            405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
450                 455                 460

Ala Leu His Asn His Tyr Thr Gln Lys Ser Leu Ser Leu Ser Pro Gly
465                 470                 475                 480

Lys

```
<210> SEQ ID NO 374
<211> LENGTH: 481
<212> TYPE: PRT
<213> ORGANISM: Artificial Sequence
<220> FEATURE:
<223> OTHER INFORMATION: Synthetic Construct

<400> SEQUENCE: 374
```

Ala Cys Pro Phe Pro Ala Lys Ile Leu Cys Gly Gly Ser Ser Gly
1               5                   10                  15

Gly Ser Thr Ser Thr Ser Gly Arg Ser Ala Asn Pro Arg Ser Gly Gly
            20                  25                  30

Gln Val Gln Leu Val Gln Ser Gly Ala Glu Val Lys Lys Pro Gly Ser
        35                  40                  45

Ser Val Lys Val Ser Cys Lys Ala Ser Gly Tyr Thr Phe Thr Asn Tyr
    50                  55                  60

Phe Met Asn Trp Val Arg Gln Ala Pro Gly Gln Gly Leu Glu Trp Met
65                  70                  75                  80

Gly Arg Val Asp Pro Glu Gln Gly Arg Ala Asp Tyr Ala Glu Lys Phe

```
                    85                  90                  95
Lys Lys Arg Val Thr Ile Thr Ala Asp Lys Ser Thr Ser Thr Ala Tyr
            100                 105                 110
Met Glu Leu Ser Ser Leu Arg Ser Glu Asp Thr Ala Val Tyr Tyr Cys
            115                 120                 125
Ala Arg Arg Ala Met Asp Asn Tyr Gly Phe Ala Tyr Trp Gly Gln Gly
            130                 135                 140
Thr Leu Val Thr Val Ser Ser Ala Ser Thr Lys Gly Pro Ser Val Phe
145                 150                 155                 160
Pro Leu Ala Pro Ser Ser Lys Ser Thr Ser Gly Gly Thr Ala Ala Leu
                    165                 170                 175
Gly Cys Leu Val Lys Asp Tyr Phe Pro Glu Pro Val Thr Val Ser Trp
                    180                 185                 190
Asn Ser Gly Ala Leu Thr Ser Gly Val His Thr Phe Pro Ala Val Leu
                    195                 200                 205
Gln Ser Ser Gly Leu Tyr Ser Leu Ser Ser Val Val Thr Val Pro Ser
            210                 215                 220
Ser Ser Leu Gly Thr Gln Thr Tyr Ile Cys Asn Val Asn His Lys Pro
225                 230                 235                 240
Ser Asn Thr Lys Val Asp Lys Lys Val Glu Pro Lys Ser Cys Asp Lys
                    245                 250                 255
Thr His Thr Cys Pro Pro Cys Pro Ala Pro Glu Leu Leu Gly Gly Pro
                    260                 265                 270
Ser Val Phe Leu Phe Pro Pro Lys Pro Lys Asp Thr Leu Met Ile Ser
            275                 280                 285
Arg Thr Pro Glu Val Thr Cys Val Val Val Asp Val Ser His Glu Asp
            290                 295                 300
Pro Glu Val Lys Phe Asn Trp Tyr Val Asp Gly Val Glu Val His Asn
305                 310                 315                 320
Ala Lys Thr Lys Pro Arg Glu Glu Gln Tyr Asn Ser Thr Tyr Arg Val
                    325                 330                 335
Val Ser Val Leu Thr Val Leu His Gln Asp Trp Leu Asn Gly Lys Glu
            340                 345                 350
Tyr Lys Cys Lys Val Ser Asn Lys Ala Leu Pro Ala Pro Ile Glu Lys
            355                 360                 365
Thr Ile Ser Lys Ala Lys Gly Gln Pro Arg Glu Pro Gln Val Tyr Thr
            370                 375                 380
Leu Pro Pro Ser Arg Asp Glu Leu Thr Lys Asn Gln Val Ser Leu Thr
385                 390                 395                 400
Cys Leu Val Lys Gly Phe Tyr Pro Ser Asp Ile Ala Val Glu Trp Glu
                    405                 410                 415
Ser Asn Gly Gln Pro Glu Asn Asn Tyr Lys Thr Thr Pro Pro Val Leu
                    420                 425                 430
Asp Ser Asp Gly Ser Phe Phe Leu Tyr Ser Lys Leu Thr Val Asp Lys
                    435                 440                 445
Ser Arg Trp Gln Gln Gly Asn Val Phe Ser Cys Ser Val Met His Glu
            450                 455                 460
Ala Leu His Asn His Tyr Thr Gln Lys Ser Leu Ser Leu Ser Pro Gly
465                 470                 475                 480
Lys

<210> SEQ ID NO 375
<211> LENGTH: 481
```

```
<212> TYPE: PRT
<213> ORGANISM: Artificial Sequence
<220> FEATURE:
<223> OTHER INFORMATION: Synthetic Construct

<400> SEQUENCE: 375

Ala Cys Pro Gly Lys Gly Leu Pro Ser Cys Gly Gly Ser Ser Gly
1               5                   10                  15

Gly Ser Thr Ser Thr Ser Gly Arg Ser Ala Asn Pro Arg Ser Gly Gly
            20                  25                  30

Gln Val Gln Leu Val Gln Ser Gly Ala Glu Val Lys Lys Pro Gly Ser
        35                  40                  45

Ser Val Lys Val Ser Cys Lys Ala Ser Gly Tyr Thr Phe Thr Asn Tyr
50                  55                  60

Phe Met Asn Trp Val Arg Gln Ala Pro Gly Gln Gly Leu Glu Trp Met
65                  70                  75                  80

Gly Arg Val Asp Pro Glu Gln Gly Arg Ala Asp Tyr Ala Glu Lys Phe
                85                  90                  95

Lys Lys Arg Val Thr Ile Thr Ala Asp Lys Ser Thr Ser Thr Ala Tyr
                100                 105                 110

Met Glu Leu Ser Ser Leu Arg Ser Glu Asp Thr Ala Val Tyr Tyr Cys
            115                 120                 125

Ala Arg Arg Ala Met Asp Asn Tyr Gly Phe Ala Tyr Trp Gly Gln Gly
        130                 135                 140

Thr Leu Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
                180                 185                 190

Asn Ser Gly Ala Leu Thr Ser Gly Val His Thr Phe Pro Ala Val Leu
            195                 200                 205

Gln Ser Ser Gly Leu Tyr Ser Leu Ser Ser Val Val Thr Val Pro Ser
        210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
                260                 265                 270

Ser Val Phe Leu Phe Pro Pro Lys Pro Lys Asp Thr Leu Met Ile Ser
            275                 280                 285

Arg Thr Pro Glu Val Thr Cys Val Val Val Asp Val Ser His Glu Asp
        290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
                340                 345                 350

Tyr Lys Cys Lys Val Ser Asn Lys Ala Leu Pro Ala Pro Ile Glu Lys
            355                 360                 365

Thr Ile Ser Lys Ala Lys Gly Gln Pro Arg Glu Pro Gln Val Tyr Thr
        370                 375                 380
```

```
Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
            405                 410                 415

Ser Asn Gly Gln Pro Glu Asn Asn Tyr Lys Thr Thr Pro Pro Val Leu
        420                 425                 430

Asp Ser Asp Gly Ser Phe Phe Leu Tyr Ser Lys Leu Thr Val Asp Lys
    435                 440                 445

Ser Arg Trp Gln Gln Gly Asn Val Phe Ser Cys Ser Val Met His Glu
450                 455                 460

Ala Leu His Asn His Tyr Thr Gln Lys Ser Leu Ser Leu Ser Pro Gly
465                 470                 475                 480

Lys

<210> SEQ ID NO 376
<211> LENGTH: 483
<212> TYPE: PRT
<213> ORGANISM: Artificial Sequence
<220> FEATURE:
<223> OTHER INFORMATION: Synthetic Construct

<400> SEQUENCE: 376

Asn Trp Leu Gly Glu Trp Leu Pro Pro Gly Lys Val Gly Gly Ser
1               5                   10                  15

Ser Gly Gly Ser Thr Ser Thr Ser Gly Arg Ser Ala Asn Pro Arg Ser
                20                  25                  30

Gly Gly Gln Val Gln Leu Val Gln Ser Gly Ala Glu Val Lys Lys Pro
            35                  40                  45

Gly Ser Ser Val Lys Val Ser Cys Lys Ala Ser Gly Tyr Thr Phe Thr
        50                  55                  60

Asn Tyr Phe Met Asn Trp Val Arg Gln Ala Pro Gly Gln Gly Leu Glu
65                  70                  75                  80

Trp Met Gly Arg Val Asp Pro Glu Gln Gly Arg Ala Asp Tyr Ala Glu
                85                  90                  95

Lys Phe Lys Lys Arg Val Thr Ile Thr Ala Asp Lys Ser Thr Ser Thr
            100                 105                 110

Ala Tyr Met Glu Leu Ser Ser Leu Arg Ser Glu Asp Thr Ala Val Tyr
        115                 120                 125

Tyr Cys Ala Arg Arg Ala Met Asp Asn Tyr Gly Phe Ala Tyr Trp Gly
130                 135                 140

Gln Gly Thr Leu Val Thr Val Ser Ser Ala Ser Thr Lys Gly Pro Ser
145                 150                 155                 160

Val Phe Pro Leu Ala Pro Ser Ser Lys Ser Thr Ser Gly Gly Thr Ala
                165                 170                 175

Ala Leu Gly Cys Leu Val Lys Asp Tyr Phe Pro Glu Pro Val Thr Val
            180                 185                 190

Ser Trp Asn Ser Gly Ala Leu Thr Ser Gly Val His Thr Phe Pro Ala
        195                 200                 205

Val Leu Gln Ser Ser Gly Leu Tyr Ser Leu Ser Ser Val Val Thr Val
    210                 215                 220

Pro Ser Ser Ser Leu Gly Thr Gln Thr Tyr Ile Cys Asn Val Asn His
225                 230                 235                 240

Lys Pro Ser Asn Thr Lys Val Asp Lys Lys Val Glu Pro Lys Ser Cys
                245                 250                 255

Asp Lys Thr His Thr Cys Pro Pro Cys Pro Ala Pro Glu Leu Leu Gly
```

```
                    260                 265                 270
Gly Pro Ser Val Phe Leu Phe Pro Pro Lys Pro Lys Asp Thr Leu Met
                275                 280                 285
Ile Ser Arg Thr Pro Glu Val Thr Cys Val Val Val Asp Val Ser His
            290                 295                 300
Glu Asp Pro Glu Val Lys Phe Asn Trp Tyr Val Asp Gly Val Glu Val
305                 310                 315                 320
His Asn Ala Lys Thr Lys Pro Arg Glu Glu Gln Tyr Asn Ser Thr Tyr
                325                 330                 335
Arg Val Val Ser Val Leu Thr Val Leu His Gln Asp Trp Leu Asn Gly
            340                 345                 350
Lys Glu Tyr Lys Cys Lys Val Ser Asn Lys Ala Leu Pro Ala Pro Ile
        355                 360                 365
Glu Lys Thr Ile Ser Lys Ala Lys Gly Gln Pro Arg Glu Pro Gln Val
    370                 375                 380
Tyr Thr Leu Pro Pro Ser Arg Asp Glu Leu Thr Lys Asn Gln Val Ser
385                 390                 395                 400
Leu Thr Cys Leu Val Lys Gly Phe Tyr Pro Ser Asp Ile Ala Val Glu
                405                 410                 415
Trp Glu Ser Asn Gly Gln Pro Glu Asn Asn Tyr Lys Thr Thr Pro Pro
            420                 425                 430
Val Leu Asp Ser Asp Gly Ser Phe Phe Leu Tyr Ser Lys Leu Thr Val
        435                 440                 445
Asp Lys Ser Arg Trp Gln Gln Gly Asn Val Phe Ser Cys Ser Val Met
    450                 455                 460
His Glu Ala Leu His Asn His Tyr Thr Gln Lys Ser Leu Ser Leu Ser
465                 470                 475                 480
Pro Gly Lys

<210> SEQ ID NO 377
<211> LENGTH: 487
<212> TYPE: PRT
<213> ORGANISM: Artificial Sequence
<220> FEATURE:
<223> OTHER INFORMATION: Synthetic Construct

<400> SEQUENCE: 377

Gln Phe Ile Glu Cys Pro Asn Phe Pro Arg Gln Cys Pro Gly Lys Asn
1               5                   10                  15
Gly Gly Gly Ser Ser Gly Gly Ser Thr Ser Thr Ser Gly Arg Ser Ala
            20                  25                  30
Asn Pro Arg Ser Gly Gly Gln Val Gln Leu Val Gln Ser Gly Ala Glu
        35                  40                  45
Val Lys Lys Pro Gly Ser Ser Val Lys Val Ser Cys Lys Ala Ser Gly
    50                  55                  60
Tyr Thr Phe Thr Asn Tyr Phe Met Asn Trp Val Arg Gln Ala Pro Gly
65                  70                  75                  80
Gln Gly Leu Glu Trp Met Gly Arg Val Asp Pro Glu Gln Gly Arg Ala
                85                  90                  95
Asp Tyr Ala Glu Lys Phe Lys Arg Val Thr Ile Thr Ala Asp Lys
            100                 105                 110
Ser Thr Ser Thr Ala Tyr Met Glu Leu Ser Ser Leu Arg Ser Glu Asp
        115                 120                 125
Thr Ala Val Tyr Tyr Cys Ala Arg Arg Ala Met Asp Asn Tyr Gly Phe
    130                 135                 140
```

Ala Tyr Trp Gly Gln Gly Thr Leu Val Thr Val Ser Ser Ala Ser Thr
145                 150                 155                 160

Lys Gly Pro Ser Val Phe Pro Leu Ala Pro Ser Ser Lys Ser Thr Ser
            165                 170                 175

Gly Gly Thr Ala Ala Leu Gly Cys Leu Val Lys Asp Tyr Phe Pro Glu
                180                 185                 190

Pro Val Thr Val Ser Trp Asn Ser Gly Ala Leu Thr Ser Gly Val His
            195                 200                 205

Thr Phe Pro Ala Val Leu Gln Ser Ser Gly Leu Tyr Ser Leu Ser Ser
210                 215                 220

Val Val Thr Val Pro Ser Ser Leu Gly Thr Gln Thr Tyr Ile Cys
225                 230                 235                 240

Asn Val Asn His Lys Pro Ser Asn Thr Lys Val Asp Lys Lys Val Glu
                245                 250                 255

Pro Lys Ser Cys Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
            275                 280                 285

Asp Thr Leu Met Ile Ser Arg Thr Pro Glu Val Thr Cys Val Val Val
290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
            355                 360                 365

Pro Ala Pro Ile Glu Lys Thr Ile Ser Lys Ala Lys Gly Gln Pro Arg
370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
            435                 440                 445

Lys Leu Thr Val Asp Lys Ser Arg Trp Gln Gln Gly Asn Val Phe Ser
            450                 455                 460

Cys Ser Val Met His Glu Ala Leu His Asn His Tyr Thr Gln Lys Ser
465                 470                 475                 480

Leu Ser Leu Ser Pro Gly Lys
                485

<210> SEQ ID NO 378
<211> LENGTH: 487
<212> TYPE: PRT
<213> ORGANISM: Artificial Sequence
<220> FEATURE:
<223> OTHER INFORMATION: Synthetic Construct

<400> SEQUENCE: 378

Val Arg Gln Gln Cys Ser Leu Asn Pro Gly Arg Cys Pro Tyr Leu Val
1               5                   10                  15

-continued

```
Gly Gly Gly Ser Ser Gly Gly Ser Thr Ser Thr Ser Gly Arg Ser Ala
            20                  25                  30
Asn Pro Arg Ser Gly Gly Gln Val Gln Leu Val Gln Ser Gly Ala Glu
            35                  40                  45
Val Lys Lys Pro Gly Ser Ser Val Lys Val Ser Cys Lys Ala Ser Gly
 50                  55                  60
Tyr Thr Phe Thr Asn Tyr Phe Met Asn Trp Val Arg Gln Ala Pro Gly
 65                  70                  75                  80
Gln Gly Leu Glu Trp Met Gly Arg Val Asp Pro Glu Gln Gly Arg Ala
                 85                  90                  95
Asp Tyr Ala Glu Lys Phe Lys Lys Arg Val Thr Ile Thr Ala Asp Lys
                100                 105                 110
Ser Thr Ser Thr Ala Tyr Met Glu Leu Ser Ser Leu Arg Ser Glu Asp
            115                 120                 125
Thr Ala Val Tyr Tyr Cys Ala Arg Arg Ala Met Asp Asn Tyr Gly Phe
130                 135                 140
Ala Tyr Trp Gly Gln Gly Thr Leu Val Thr Val Ser Ser Ala Ser Thr
145                 150                 155                 160
Lys Gly Pro Ser Val Phe Pro Leu Ala Pro Ser Ser Lys Ser Thr Ser
                165                 170                 175
Gly Gly Thr Ala Ala Leu Gly Cys Leu Val Lys Asp Tyr Phe Pro Glu
            180                 185                 190
Pro Val Thr Val Ser Trp Asn Ser Gly Ala Leu Thr Ser Gly Val His
            195                 200                 205
Thr Phe Pro Ala Val Leu Gln Ser Ser Gly Leu Tyr Ser Leu Ser Ser
        210                 215                 220
Val Val Thr Val Pro Ser Ser Ser Leu Gly Thr Gln Thr Tyr Ile Cys
225                 230                 235                 240
Asn Val Asn His Lys Pro Ser Asn Thr Lys Val Asp Lys Lys Val Glu
                245                 250                 255
Pro Lys Ser Cys Asp Lys Thr His Thr Cys Pro Pro Cys Pro Ala Pro
            260                 265                 270
Glu Leu Leu Gly Gly Pro Ser Val Phe Leu Phe Pro Pro Lys Pro Lys
        275                 280                 285
Asp Thr Leu Met Ile Ser Arg Thr Pro Glu Val Thr Cys Val Val Val
        290                 295                 300
Asp Val Ser His Glu Asp Pro Glu Val Lys Phe Asn Trp Tyr Val Asp
305                 310                 315                 320
Gly Val Glu Val His Asn Ala Lys Thr Lys Pro Arg Glu Glu Gln Tyr
                325                 330                 335
Asn Ser Thr Tyr Arg Val Val Ser Val Leu Thr Val Leu His Gln Asp
            340                 345                 350
Trp Leu Asn Gly Lys Glu Tyr Lys Cys Lys Val Ser Asn Lys Ala Leu
        355                 360                 365
Pro Ala Pro Ile Glu Lys Thr Ile Ser Lys Ala Lys Gly Gln Pro Arg
        370                 375                 380
Glu Pro Gln Val Tyr Thr Leu Pro Pro Ser Arg Asp Glu Leu Thr Lys
385                 390                 395                 400
Asn Gln Val Ser Leu Thr Cys Leu Val Lys Gly Phe Tyr Pro Ser Asp
                405                 410                 415
Ile Ala Val Glu Trp Glu Ser Asn Gly Gln Pro Glu Asn Asn Tyr Lys
            420                 425                 430
```

```
Thr Thr Pro Pro Val Leu Asp Ser Asp Gly Ser Phe Phe Leu Tyr Ser
            435                 440                 445

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Gly Lys
                485

<210> SEQ ID NO 379
<211> LENGTH: 487
<212> TYPE: PRT
<213> ORGANISM: Artificial Sequence
<220> FEATURE:
<223> OTHER INFORMATION: Synthetic Construct

<400> SEQUENCE: 379

Val Trp Gln Glu Cys His Thr Ala Pro Gln Leu Cys Pro Gly Lys Ile
1               5                   10                  15

Gly Gly Gly Ser Ser Gly Gly Ser Thr Ser Thr Ser Gly Arg Ser Ala
                20                  25                  30

Asn Pro Arg Ser Gly Gly Gln Val Gln Leu Val Gln Ser Gly Ala Glu
            35                  40                  45

Val Lys Lys Pro Gly Ser Ser Val Lys Val Ser Cys Lys Ala Ser Gly
    50                  55                  60

Tyr Thr Phe Thr Asn Tyr Phe Met Asn Trp Val Arg Gln Ala Pro Gly
65                  70                  75                  80

Gln Gly Leu Glu Trp Met Gly Arg Val Asp Pro Glu Gln Gly Arg Ala
                85                  90                  95

Asp Tyr Ala Glu Lys Phe Lys Lys Arg Val Thr Ile Thr Ala Asp Lys
            100                 105                 110

Ser Thr Ser Thr Ala Tyr Met Glu Leu Ser Ser Leu Arg Ser Glu Asp
    115                 120                 125

Thr Ala Val Tyr Tyr Cys Ala Arg Arg Ala Met Asp Asn Tyr Gly Phe
130                 135                 140

Ala Tyr Trp Gly Gln Gly Thr Leu Val Thr Val Ser Ser Ala Ser Thr
145                 150                 155                 160

Lys Gly Pro Ser Val Phe Pro Leu Ala Pro Ser Ser Lys Ser Thr Ser
                165                 170                 175

Gly Gly Thr Ala Ala Leu Gly Cys Leu Val Lys Asp Tyr Phe Pro Glu
            180                 185                 190

Pro Val Thr Val Ser Trp Asn Ser Gly Ala Leu Thr Ser Gly Val His
    195                 200                 205

Thr Phe Pro Ala Val Leu Gln Ser Ser Gly Leu Tyr Ser Leu Ser Ser
210                 215                 220

Val Val Thr Val Pro Ser Ser Ser Leu Gly Thr Gln Thr Tyr Ile Cys
225                 230                 235                 240

Asn Val Asn His Lys Pro Ser Asn Thr Lys Val Asp Lys Lys Val Glu
                245                 250                 255

Pro Lys Ser Cys Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
    275                 280                 285

Asp Thr Leu Met Ile Ser Arg Thr Pro Glu Val Thr Cys Val Val Val
290                 295                 300
```

```
Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
            325                 330                 335

Asn Ser Thr Tyr Arg Val Val Ser Val Leu Thr Val Leu His Gln Asp
        340                 345                 350

Trp Leu Asn Gly Lys Glu Tyr Lys Cys Lys Val Ser Asn Lys Ala Leu
    355                 360                 365

Pro Ala Pro Ile Glu Lys Thr Ile Ser Lys Ala Lys Gly Gln Pro Arg
370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
            405                 410                 415

Ile Ala Val Glu Trp Glu Ser Asn Gly Gln Pro Glu Asn Asn Tyr Lys
        420                 425                 430

Thr Thr Pro Pro Val Leu Asp Ser Asp Gly Ser Phe Phe Leu Tyr Ser
    435                 440                 445

Lys Leu Thr Val Asp Lys Ser Arg Trp Gln Gln Gly Asn Val Phe Ser
450                 455                 460

Cys Ser Val Met His Glu Ala Leu His Asn His Tyr Thr Gln Lys Ser
465                 470                 475                 480

Leu Ser Leu Ser Pro Gly Lys
            485

<210> SEQ ID NO 380
<211> LENGTH: 449
<212> TYPE: PRT
<213> ORGANISM: Artificial Sequence
<220> FEATURE:
<223> OTHER INFORMATION: Synthetic Construct

<400> SEQUENCE: 380

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Phe Met Asn Trp Val Arg Gln Ala Pro Gly Gln Gly Leu Glu Trp Met
        35                  40                  45

Gly Arg Val Asp Pro Glu Gln Gly Arg Ala Asp Tyr Ala Glu Lys Phe
    50                  55                  60

Lys Lys Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Arg Ala Met Asp Asn Tyr Gly Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175
```

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 381
<211> LENGTH: 482
<212> TYPE: PRT
<213> ORGANISM: Artificial Sequence
<220> FEATURE:
<223> OTHER INFORMATION: Synthetic Construct

<400> SEQUENCE: 381

Met Gln Thr Arg Cys Lys Glu Tyr Pro Arg Trp Cys Glu His Trp Leu
1               5                   10                  15

Gly Ser Thr Ser Thr Ser Gly Arg Ser Ala Asn Pro Gly Ser Ser Gly
            20                  25                  30

Gln Val Gln Leu Gln Glu Ser Gly Pro Gly Leu Val Lys Pro Ser Glu
        35                  40                  45

Thr Leu Ser Leu Thr Cys Ser Val Thr Tyr His Thr Ile Thr Ser Gly
    50                  55                  60

Tyr Asp Trp Thr Trp Ile Arg Lys Pro Pro Gly Lys Gly Met Glu Trp
65                  70                  75                  80

Ile Gly Tyr Ile Ser Tyr Ser Gly Asn Thr Asn Tyr Asn Pro Ser Leu

```
                   85                  90                  95
Lys Ser Arg Val Thr Ile Ser Arg Asp Thr Ser Lys Asn Gln Phe Phe
                100                 105                 110
Leu Lys Leu Ser Ser Val Thr Ala Ala Asp Thr Ala Val Tyr Tyr Cys
                115                 120                 125
Ala Ser Met Met Val Pro His Tyr Tyr Val Met Asp Ala Trp Gly Gln
                130                 135                 140
Gly Thr Leu Val Thr Val Ser Ser Ala Ser Thr Lys Gly Pro Ser Val
145                 150                 155                 160
Phe Pro Leu Ala Pro Ser Ser Lys Ser Thr Ser Gly Gly Thr Ala Ala
                165                 170                 175
Leu Gly Cys Leu Val Lys Asp Tyr Phe Pro Glu Pro Val Thr Val Ser
                180                 185                 190
Trp Asn Ser Gly Ala Leu Thr Ser Gly Val His Thr Phe Pro Ala Val
                195                 200                 205
Leu Gln Ser Ser Gly Leu Tyr Ser Leu Ser Ser Val Val Thr Val Pro
                210                 215                 220
Ser Ser Ser Leu Gly Thr Gln Thr Tyr Ile Cys Asn Val Asn His Lys
225                 230                 235                 240
Pro Ser Asn Thr Lys Val Asp Lys Lys Val Glu Pro Lys Ser Cys Asp
                245                 250                 255
Lys Thr His Thr Cys Pro Pro Cys Pro Ala Pro Glu Leu Leu Gly Gly
                260                 265                 270
Pro Ser Val Phe Leu Phe Pro Pro Lys Pro Lys Asp Thr Leu Met Ile
                275                 280                 285
Ser Arg Thr Pro Glu Val Thr Cys Val Val Val Asp Val Ser His Glu
290                 295                 300
Asp Pro Glu Val Lys Phe Asn Trp Tyr Val Asp Gly Val Glu Val His
305                 310                 315                 320
Asn Ala Lys Thr Lys Pro Arg Glu Glu Gln Tyr Asn Ser Thr Tyr Arg
                325                 330                 335
Val Val Ser Val Leu Thr Val Leu His Gln Asp Trp Leu Asn Gly Lys
                340                 345                 350
Glu Tyr Lys Cys Lys Val Ser Asn Lys Ala Leu Pro Ala Pro Ile Glu
                355                 360                 365
Lys Thr Ile Ser Lys Ala Lys Gly Gln Pro Arg Glu Pro Gln Val Tyr
                370                 375                 380
Thr Leu Pro Pro Ser Arg Asp Glu Leu Thr Lys Asn Gln Val Ser Leu
385                 390                 395                 400
Thr Cys Leu Val Lys Gly Phe Tyr Pro Ser Asp Ile Ala Val Glu Trp
                405                 410                 415
Glu Ser Asn Gly Gln Pro Glu Asn Asn Tyr Lys Thr Thr Pro Pro Val
                420                 425                 430
Leu Asp Ser Asp Gly Ser Phe Phe Leu Tyr Ser Lys Leu Thr Val Asp
                435                 440                 445
Lys Ser Arg Trp Gln Gln Gly Asn Val Phe Ser Cys Ser Val Met His
                450                 455                 460
Glu Ala Leu His Asn His Tyr Thr Gln Lys Ser Leu Ser Leu Ser Pro
465                 470                 475                 480
Gly Lys

<210> SEQ ID NO 382
<211> LENGTH: 482
```

```
<212> TYPE: PRT
<213> ORGANISM: Artificial Sequence
<220> FEATURE:
<223> OTHER INFORMATION: Synthetic Construct

<400> SEQUENCE: 382

Met Gln Thr Arg Cys Lys Glu Tyr Pro Arg Trp Cys Glu His Trp Leu
1               5                   10                  15

Gly Ser Thr Ser Thr Ser Gly Arg Ser Ala Asn Pro His Ser Gly Gly
            20                  25                  30

Gln Val Gln Leu Gln Glu Ser Gly Pro Gly Leu Val Lys Pro Ser Glu
        35                  40                  45

Thr Leu Ser Leu Thr Cys Ser Val Thr Tyr His Thr Ile Thr Ser Gly
    50                  55                  60

Tyr Asp Trp Thr Trp Ile Arg Lys Pro Pro Gly Lys Gly Met Glu Trp
65                  70                  75                  80

Ile Gly Tyr Ile Ser Tyr Ser Gly Asn Thr Asn Tyr Asn Pro Ser Leu
                85                  90                  95

Lys Ser Arg Val Thr Ile Ser Arg Asp Thr Ser Lys Asn Gln Phe Phe
            100                 105                 110

Leu Lys Leu Ser Ser Val Thr Ala Ala Asp Thr Ala Val Tyr Tyr Cys
        115                 120                 125

Ala Ser Met Met Val Pro His Tyr Tyr Val Met Asp Ala Trp Gly Gln
    130                 135                 140

Gly Thr Leu Val Thr Val Ser Ser Ala Ser Thr Lys Gly Pro Ser Val
145                 150                 155                 160

Phe Pro Leu Ala Pro Ser Ser Lys Ser Thr Ser Gly Gly Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
        195                 200                 205

Leu Gln Ser Ser Gly Leu Tyr Ser Leu Ser Ser Val Val Thr Val Pro
    210                 215                 220

Ser Ser Ser Leu Gly Thr Gln Thr Tyr Ile Cys Asn Val Asn His Lys
225                 230                 235                 240

Pro Ser Asn Thr Lys Val Asp Lys Lys Val Glu Pro Lys Ser Cys Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380
```

```
Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys

<210> SEQ ID NO 383
<211> LENGTH: 488
<212> TYPE: PRT
<213> ORGANISM: Artificial Sequence
<220> FEATURE:
<223> OTHER INFORMATION: Synthetic Construct

<400> SEQUENCE: 383

Asp Ser Tyr Thr Cys Arg Gly Pro Thr Trp Met Cys Ala Gly Asn Met
1               5                   10                  15

Gly Gly Gly Ser Ser Gly Gly Ser Thr Ser Thr Ser Gly Arg Ser Ala
            20                  25                  30

Asn Pro Arg Ser Gly Gln Val Gln Leu Gln Glu Ser Gly Pro Gly
        35                  40                  45

Leu Val Lys Pro Ser Glu Thr Leu Ser Leu Thr Cys Ser Val Thr Tyr
    50                  55                  60

His Thr Ile Thr Ser Gly Tyr Asp Trp Thr Trp Ile Arg Lys Pro Pro
65                  70                  75                  80

Gly Lys Gly Met Glu Trp Ile Gly Tyr Ile Ser Tyr Ser Gly Asn Thr
                85                  90                  95

Asn Tyr Asn Pro Ser Leu Lys Ser Arg Val Thr Ile Ser Arg Asp Thr
            100                 105                 110

Ser Lys Asn Gln Phe Phe Leu Lys Leu Ser Ser Val Thr Ala Ala Asp
        115                 120                 125

Thr Ala Val Tyr Tyr Cys Ala Ser Met Met Val Pro His Tyr Tyr Val
    130                 135                 140

Met Asp Ala Trp Gly Gln Gly Thr Leu Val Thr Val Ser Ser Ala Ser
145                 150                 155                 160

Thr Lys Gly Pro Ser Val Phe Pro Leu Ala Pro Ser Ser Lys Ser Thr
                165                 170                 175

Ser Gly Gly Thr Ala Ala Leu Gly Cys Leu Val Lys Asp Tyr Phe Pro
            180                 185                 190

Glu Pro Val Thr Val Ser Trp Asn Ser Gly Ala Leu Thr Ser Gly Val
        195                 200                 205

His Thr Phe Pro Ala Val Leu Gln Ser Ser Gly Leu Tyr Ser Leu Ser
    210                 215                 220

Ser Val Val Thr Val Pro Ser Ser Ser Leu Gly Thr Gln Thr Tyr Ile
225                 230                 235                 240

Cys Asn Val Asn His Lys Pro Ser Asn Thr Lys Val Asp Lys Lys Val
                245                 250                 255

Glu Pro Lys Ser Cys Asp Lys Thr His Thr Cys Pro Pro Cys Pro Ala
```

```
                260                 265                 270
Pro Glu Leu Leu Gly Gly Pro Ser Val Phe Leu Phe Pro Pro Lys Pro
            275                 280                 285

Lys Asp Thr Leu Met Ile Ser Arg Thr Pro Glu Val Thr Cys Val Val
290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
            355                 360                 365

Leu Pro Ala Pro Ile Glu Lys Thr Ile Ser Lys Ala Lys Gly Gln Pro
            370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
            435                 440                 445

Ser Lys Leu Thr Val Asp Lys Ser Arg Trp Gln Gln Gly Asn Val Phe
            450                 455                 460

Ser Cys Ser Val Met His Glu Ala Leu His Asn His Tyr Thr Gln Lys
465                 470                 475                 480

Ser Leu Ser Leu Ser Pro Gly Lys
                485

<210> SEQ ID NO 384
<211> LENGTH: 488
<212> TYPE: PRT
<213> ORGANISM: Artificial Sequence
<220> FEATURE:
<223> OTHER INFORMATION: Synthetic Construct

<400> SEQUENCE: 384

Phe Asn His Asp Cys Ser Gly His Trp Met Arg Cys Leu Asp Gln Gln
1               5                   10                  15

Gly Gly Gly Ser Ser Gly Ser Thr Ser Thr Ser Gly Arg Ser Ala
            20                  25                  30

Asn Pro Arg Ser Gly Gly Gln Val Gln Leu Gln Glu Ser Gly Pro Gly
            35                  40                  45

Leu Val Lys Pro Ser Glu Thr Leu Ser Leu Thr Cys Ser Val Thr Tyr
50                  55                  60

His Thr Ile Thr Ser Gly Tyr Asp Trp Thr Trp Ile Arg Lys Pro Pro
65                  70                  75                  80

Gly Lys Gly Met Glu Trp Ile Gly Tyr Ile Ser Tyr Ser Gly Asn Thr
                85                  90                  95

Asn Tyr Asn Pro Ser Leu Lys Ser Arg Val Thr Ile Ser Arg Asp Thr
            100                 105                 110

Ser Lys Asn Gln Phe Phe Leu Lys Leu Ser Ser Val Thr Ala Ala Asp
            115                 120                 125

Thr Ala Val Tyr Tyr Cys Ala Ser Met Met Val Pro His Tyr Tyr Val
```

```
             130                 135                 140
Met Asp Ala Trp Gly Gln Gly Thr Leu Val Thr Val Ser Ser Ala Ser
145                 150                 155                 160

Thr Lys Gly Pro Ser Val Phe Pro Leu Ala Pro Ser Ser Lys Ser Thr
                165                 170                 175

Ser Gly Gly Thr Ala Ala Leu Gly Cys Leu Val Lys Asp Tyr Phe Pro
            180                 185                 190

Glu Pro Val Thr Val Ser Trp Asn Ser Gly Ala Leu Thr Ser Gly Val
        195                 200                 205

His Thr Phe Pro Ala Val Leu Gln Ser Ser Gly Leu Tyr Ser Leu Ser
    210                 215                 220

Ser Val Val Thr Val Pro Ser Ser Ser Leu Gly Thr Gln Thr Tyr Ile
225                 230                 235                 240

Cys Asn Val Asn His Lys Pro Ser Asn Thr Lys Val Asp Lys Lys Val
                245                 250                 255

Glu Pro Lys Ser Cys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys
                485

<210> SEQ ID NO 385
<211> LENGTH: 482
<212> TYPE: PRT
<213> ORGANISM: Artificial Sequence
<220> FEATURE:
<223> OTHER INFORMATION: Synthetic Construct

<400> SEQUENCE: 385

Met Gln Thr Arg Cys Lys Glu Tyr Pro Arg Trp Cys Glu His Trp Leu
```

-continued

```
1               5                   10                  15
Gly Gly Gly Ser Val Pro Leu Ser Leu Tyr Ser Gly Gly Ser Gly Gly
                20                  25                  30
Gln Val Gln Leu Gln Glu Ser Gly Pro Gly Leu Val Lys Pro Ser Glu
                35                  40                  45
Thr Leu Ser Leu Thr Cys Ser Val Thr Tyr His Thr Ile Thr Ser Gly
                50                  55                  60
Tyr Asp Trp Thr Trp Ile Arg Lys Pro Pro Gly Lys Gly Met Glu Trp
65                              70                  75              80
Ile Gly Tyr Ile Ser Tyr Ser Gly Asn Thr Asn Tyr Asn Pro Ser Leu
                85                  90                  95
Lys Ser Arg Val Thr Ile Ser Arg Asp Thr Ser Lys Asn Gln Phe Phe
                100                 105                 110
Leu Lys Leu Ser Ser Val Thr Ala Ala Asp Thr Ala Val Tyr Tyr Cys
                115                 120                 125
Ala Ser Met Met Val Pro His Tyr Tyr Val Met Asp Ala Trp Gly Gln
                130                 135                 140
Gly Thr Leu Val Thr Val Ser Ser Ala Ser Thr Lys Gly Pro Ser Val
145                 150                 155                 160
Phe Pro Leu Ala Pro Ser Ser Lys Ser Thr Ser Gly Gly Thr Ala Ala
                165                 170                 175
Leu Gly Cys Leu Val Lys Asp Tyr Phe Pro Glu Pro Val Thr Val Ser
                180                 185                 190
Trp Asn Ser Gly Ala Leu Thr Ser Gly Val His Thr Phe Pro Ala Val
                195                 200                 205
Leu Gln Ser Ser Gly Leu Tyr Ser Leu Ser Ser Val Val Thr Val Pro
                210                 215                 220
Ser Ser Ser Leu Gly Thr Gln Thr Tyr Ile Cys Asn Val Asn His Lys
225                 230                 235                 240
Pro Ser Asn Thr Lys Val Asp Lys Lys Val Glu Pro Lys Ser Cys Asp
                245                 250                 255
Lys Thr His Thr Cys Pro Pro Cys Pro Ala Pro Glu Leu Leu Gly Gly
                260                 265                 270
Pro Ser Val Phe Leu Phe Pro Pro Lys Pro Lys Asp Thr Leu Met Ile
                275                 280                 285
Ser Arg Thr Pro Glu Val Thr Cys Val Val Val Asp Val Ser His Glu
                290                 295                 300
Asp Pro Glu Val Lys Phe Asn Trp Tyr Val Asp Gly Val Glu Val His
305                 310                 315                 320
Asn Ala Lys Thr Lys Pro Arg Glu Glu Gln Tyr Asn Ser Thr Tyr Arg
                325                 330                 335
Val Val Ser Val Leu Thr Val Leu His Gln Asp Trp Leu Asn Gly Lys
                340                 345                 350
Glu Tyr Lys Cys Lys Val Ser Asn Lys Ala Leu Pro Ala Pro Ile Glu
                355                 360                 365
Lys Thr Ile Ser Lys Ala Lys Gly Gln Pro Arg Glu Pro Gln Val Tyr
                370                 375                 380
Thr Leu Pro Pro Ser Arg Asp Glu Leu Thr Lys Asn Gln Val Ser Leu
385                 390                 395                 400
Thr Cys Leu Val Lys Gly Phe Tyr Pro Ser Asp Ile Ala Val Glu Trp
                405                 410                 415
Glu Ser Asn Gly Gln Pro Glu Asn Asn Tyr Lys Thr Thr Pro Pro Val
                420                 425                 430
```

-continued

Leu Asp Ser Asp Gly Ser Phe Phe Leu Tyr Ser Lys Leu Thr Val Asp
          435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys

<210> SEQ ID NO 386
<211> LENGTH: 488
<212> TYPE: PRT
<213> ORGANISM: Artificial Sequence
<220> FEATURE:
<223> OTHER INFORMATION: Synthetic Construct

<400> SEQUENCE: 386

Asn Lys Ser Pro Cys Arg Pro Lys Met Val Ala Cys Tyr Gly Ile Leu
1               5                   10                  15

Gly Gly Gly Ser Ser Gly Gly Ser Thr Ser Thr Ser Gly Arg Ser Ala
                20                  25                  30

Asn Pro Arg Ser Gly Gly Gln Val Gln Leu Gln Glu Ser Gly Pro Gly
            35                  40                  45

Leu Val Lys Pro Ser Glu Thr Leu Ser Leu Thr Cys Ser Val Thr Tyr
50                  55                  60

His Thr Ile Thr Ser Gly Tyr Asp Trp Thr Trp Ile Arg Lys Pro Pro
65                  70                  75                  80

Gly Lys Gly Met Glu Trp Ile Gly Tyr Ile Ser Tyr Ser Gly Asn Thr
                85                  90                  95

Asn Tyr Asn Pro Ser Leu Lys Ser Arg Val Thr Ile Ser Arg Asp Thr
            100                 105                 110

Ser Lys Asn Gln Phe Phe Leu Lys Leu Ser Ser Val Thr Ala Ala Asp
        115                 120                 125

Thr Ala Val Tyr Tyr Cys Ala Ser Met Met Val Pro His Tyr Tyr Val
    130                 135                 140

Met Asp Ala Trp Gly Gln Gly Thr Leu Val Thr Val Ser Ser Ala Ser
145                 150                 155                 160

Thr Lys Gly Pro Ser Val Phe Pro Leu Ala Pro Ser Ser Lys Ser Thr
                165                 170                 175

Ser Gly Gly Thr Ala Ala Leu Gly Cys Leu Val Lys Asp Tyr Phe Pro
            180                 185                 190

Glu Pro Val Thr Val Ser Trp Asn Ser Gly Ala Leu Thr Ser Gly Val
        195                 200                 205

His Thr Phe Pro Ala Val Leu Gln Ser Ser Gly Leu Tyr Ser Leu Ser
    210                 215                 220

Ser Val Val Thr Val Pro Ser Ser Ser Leu Gly Thr Gln Thr Tyr Ile
225                 230                 235                 240

Cys Asn Val Asn His Lys Pro Ser Asn Thr Lys Val Asp Lys Lys Val
                245                 250                 255

Glu Pro Lys Ser Cys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

```
Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
            325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
            355                 360                 365

Leu Pro Ala Pro Ile Glu Lys Thr Ile Ser Lys Ala Lys Gly Gln Pro
            370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
                420                 425                 430

Lys Thr Thr Pro Pro Val Leu Asp Ser Asp Gly Ser Phe Phe Leu Tyr
            435                 440                 445

Ser Lys Leu Thr Val Asp Lys Ser Arg Trp Gln Gln Gly Asn Val Phe
450                 455                 460

Ser Cys Ser Val Met His Glu Ala Leu His Asn His Tyr Thr Gln Lys
465                 470                 475                 480

Ser Leu Ser Leu Ser Pro Gly Lys
                485

<210> SEQ ID NO 387
<211> LENGTH: 488
<212> TYPE: PRT
<213> ORGANISM: Artificial Sequence
<220> FEATURE:
<223> OTHER INFORMATION: Synthetic Construct

<400> SEQUENCE: 387

Pro Thr Pro Gln Cys Trp Asn Gln Tyr Tyr Glu Cys Trp Ile Pro Ser
1               5                   10                  15

Gly Gly Gly Ser Ser Gly Gly Ser Thr Ser Thr Ser Gly Arg Ser Ala
            20                  25                  30

Asn Pro Arg Ser Gly Gly Gln Val Gln Leu Gln Glu Ser Gly Pro Gly
            35                  40                  45

Leu Val Lys Pro Ser Glu Thr Leu Ser Leu Thr Cys Ser Val Thr Tyr
50                  55                  60

His Thr Ile Thr Ser Gly Tyr Asp Trp Thr Trp Ile Arg Lys Pro Pro
65                  70                  75                  80

Gly Lys Gly Met Glu Trp Ile Gly Tyr Ile Ser Tyr Ser Gly Asn Thr
            85                  90                  95

Asn Tyr Asn Pro Ser Leu Lys Ser Arg Val Thr Ile Ser Arg Asp Thr
            100                 105                 110

Ser Lys Asn Gln Phe Phe Leu Lys Leu Ser Ser Val Thr Ala Ala Asp
        115                 120                 125

Thr Ala Val Tyr Tyr Cys Ala Ser Met Met Val Pro His Tyr Tyr Val
        130                 135                 140

Met Asp Ala Trp Gly Gln Gly Thr Leu Val Thr Val Ser Ser Ala Ser
145                 150                 155                 160

Thr Lys Gly Pro Ser Val Phe Pro Leu Ala Pro Ser Ser Lys Ser Thr
                165                 170                 175
```

```
Ser Gly Gly Thr Ala Ala Leu Gly Cys Leu Val Lys Asp Tyr Phe Pro
            180                 185                 190

Glu Pro Val Thr Val Ser Trp Asn Ser Gly Ala Leu Thr Ser Gly Val
        195                 200                 205

His Thr Phe Pro Ala Val Leu Gln Ser Ser Gly Leu Tyr Ser Leu Ser
    210                 215                 220

Ser Val Val Thr Val Pro Ser Ser Ser Leu Gly Thr Gln Thr Tyr Ile
225                 230                 235                 240

Cys Asn Val Asn His Lys Pro Ser Asn Thr Lys Val Asp Lys Lys Val
                245                 250                 255

Glu Pro Lys Ser Cys Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
450                 455                 460

Ser Cys Ser Val Met His Glu Ala Leu His Asn His Tyr Thr Gln Lys
465                 470                 475                 480

Ser Leu Ser Leu Ser Pro Gly Lys
            485

<210> SEQ ID NO 388
<211> LENGTH: 487
<212> TYPE: PRT
<213> ORGANISM: Artificial Sequence
<220> FEATURE:
<223> OTHER INFORMATION: Synthetic Construct

<400> SEQUENCE: 388

Ser Gln Lys Cys Pro Trp Thr Lys Glu Thr Cys Met His Tyr Met Gly
1               5                   10                  15

Gly Gly Ser Ser Gly Gly Ser Thr Ser Thr Ser Gly Arg Ser Ala Asn
            20                  25                  30

Pro Arg Ser Gly Gly Gln Val Gln Leu Gln Glu Ser Gly Pro Gly Leu
        35                  40                  45
```

```
Val Lys Pro Ser Glu Thr Leu Ser Leu Thr Cys Ser Val Thr Tyr His
    50                  55                  60

Thr Ile Thr Ser Gly Tyr Asp Trp Thr Trp Ile Arg Lys Pro Pro Gly
65                  70                  75                  80

Lys Gly Met Glu Trp Ile Gly Tyr Ile Ser Tyr Ser Gly Asn Thr Asn
                85                  90                  95

Tyr Asn Pro Ser Leu Lys Ser Arg Val Thr Ile Ser Arg Asp Thr Ser
            100                 105                 110

Lys Asn Gln Phe Phe Leu Lys Leu Ser Ser Val Thr Ala Ala Asp Thr
            115                 120                 125

Ala Val Tyr Tyr Cys Ala Ser Met Met Val Pro His Tyr Tyr Val Met
        130                 135                 140

Asp Ala Trp Gly Gln Gly Thr Leu Val Thr Val Ser Ser Ala Ser Thr
145                 150                 155                 160

Lys Gly Pro Ser Val Phe Pro Leu Ala Pro Ser Ser Lys Ser Thr Ser
                165                 170                 175

Gly Gly Thr Ala Ala Leu Gly Cys Leu Val Lys Asp Tyr Phe Pro Glu
            180                 185                 190

Pro Val Thr Val Ser Trp Asn Ser Gly Ala Leu Thr Ser Gly Val His
            195                 200                 205

Thr Phe Pro Ala Val Leu Gln Ser Ser Gly Leu Tyr Ser Leu Ser Ser
    210                 215                 220

Val Val Thr Val Pro Ser Ser Ser Leu Gly Thr Gln Thr Tyr Ile Cys
225                 230                 235                 240

Asn Val Asn His Lys Pro Ser Asn Thr Lys Val Asp Lys Lys Val Glu
                245                 250                 255

Pro Lys Ser Cys Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
        355                 360                 365

Pro Ala Pro Ile Glu Lys Thr Ile Ser Lys Ala Lys Gly Gln Pro Arg
    370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
            435                 440                 445

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
```

```
                        465                 470                 475                 480
Leu Ser Leu Ser Pro Gly Lys
                        485

<210> SEQ ID NO 389
<211> LENGTH: 484
<212> TYPE: PRT
<213> ORGANISM: Artificial Sequence
<220> FEATURE:
<223> OTHER INFORMATION: Synthetic Construct

<400> SEQUENCE: 389

Trp His Leu Ser Met Tyr Pro Lys Pro Pro Ala Glu Gly Gly Ser
1               5                   10                  15

Ser Gly Gly Ser Thr Ser Thr Ser Gly Arg Ser Ala Asn Pro Arg Ser
                20                  25                  30

Gly Gly Gln Val Gln Leu Gln Glu Ser Gly Pro Gly Leu Val Lys Pro
            35                  40                  45

Ser Glu Thr Leu Ser Leu Thr Cys Ser Val Thr Tyr His Thr Ile Thr
    50                  55                  60

Ser Gly Tyr Asp Trp Thr Trp Ile Arg Lys Pro Pro Gly Lys Gly Met
65                  70                  75                  80

Glu Trp Ile Gly Tyr Ile Ser Tyr Ser Gly Asn Thr Asn Tyr Asn Pro
                85                  90                  95

Ser Leu Lys Ser Arg Val Thr Ile Ser Arg Asp Thr Ser Lys Asn Gln
                100                 105                 110

Phe Phe Leu Lys Leu Ser Ser Val Thr Ala Ala Asp Thr Ala Val Tyr
            115                 120                 125

Tyr Cys Ala Ser Met Met Val Pro His Tyr Tyr Val Met Asp Ala Trp
130                 135                 140

Gly Gln Gly Thr Leu Val Thr Val Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255

Cys Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
```

```
               340                 345                 350
Gly Lys Glu Tyr Lys Cys Lys Val Ser Asn Lys Ala Leu Pro Ala Pro
            355                 360                 365

Ile Glu Lys Thr Ile Ser Lys Ala Lys Gly Gln Pro Arg Glu Pro Gln
        370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Lys

<210> SEQ ID NO 390
<211> LENGTH: 484
<212> TYPE: PRT
<213> ORGANISM: Artificial Sequence
<220> FEATURE:
<223> OTHER INFORMATION: Synthetic Construct

<400> SEQUENCE: 390

Trp His Thr Asp Gly Phe Tyr Thr Arg Leu Pro Ala Gly Gly Gly Ser
1               5                   10                  15

Ser Gly Gly Ser Thr Ser Thr Ser Gly Arg Ser Ala Asn Pro Arg Ser
                20                  25                  30

Gly Gly Gln Val Gln Leu Gln Glu Ser Gly Pro Gly Leu Val Lys Pro
            35                  40                  45

Ser Glu Thr Leu Ser Leu Thr Cys Ser Val Thr Tyr His Thr Ile Thr
        50                  55                  60

Ser Gly Tyr Asp Trp Thr Trp Ile Arg Lys Pro Pro Gly Lys Gly Met
65                  70                  75                  80

Glu Trp Ile Gly Tyr Ile Ser Tyr Ser Gly Asn Thr Asn Tyr Asn Pro
                85                  90                  95

Ser Leu Lys Ser Arg Val Thr Ile Ser Arg Asp Thr Ser Lys Asn Gln
                100                 105                 110

Phe Phe Leu Lys Leu Ser Ser Val Thr Ala Ala Asp Thr Ala Val Tyr
            115                 120                 125

Tyr Cys Ala Ser Met Met Val Pro His Tyr Tyr Val Met Asp Ala Trp
        130                 135                 140

Gly Gln Gly Thr Leu Val Thr Val Ser Ser Ala Ser Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220
```

```
Val Pro Ser Ser Leu Gly Thr Gln Thr Tyr Ile Cys Asn Val Asn
225                 230                 235                 240

His Lys Pro Ser Asn Thr Lys Val Asp Lys Val Glu Pro Lys Ser
            245                 250                 255

Cys Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
            275                 280                 285

Met Ile Ser Arg Thr Pro Glu Val Thr Cys Val Val Val Asp Val Ser
            290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
            325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
            355                 360                 365

Ile Glu Lys Thr Ile Ser Lys Ala Lys Gly Gln Pro Arg Glu Pro Gln
370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
            405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
            435                 440                 445

Val Asp Lys Ser Arg Trp Gln Gln Gly Asn Val Phe Ser Cys Ser Val
            450                 455                 460

Met His Glu Ala Leu His Asn His Tyr Thr Gln Lys Ser Leu Ser Leu
465                 470                 475                 480

Ser Pro Gly Lys

<210> SEQ ID NO 391
<211> LENGTH: 481
<212> TYPE: PRT
<213> ORGANISM: Artificial Sequence
<220> FEATURE:
<223> OTHER INFORMATION: Synthetic Construct

<400> SEQUENCE: 391

Ala Cys Ile His Ala Pro Tyr Ala Lys Cys Gly Gly Gly Ser Ser Gly
1               5                   10                  15

Gly Ser Thr Ser Thr Ser Gly Arg Ser Ala Asn Pro Arg Ser Gly Gly
            20                  25                  30

Gln Val Gln Leu Val Gln Ser Gly Ala Glu Val Lys Lys Pro Gly Ser
            35                  40                  45

Ser Val Lys Val Ser Cys Lys Ala Ser Gly Tyr Thr Phe Thr Asn Tyr
        50                  55                  60

Phe Met Asn Trp Val Arg Gln Ala Pro Gly Gln Gly Leu Glu Trp Met
65                  70                  75                  80

Gly Arg Val Asp Pro Glu Gln Gly Arg Ala Asp Tyr Ala Glu Lys Phe
                85                  90                  95
```

-continued

```
Lys Lys Arg Val Thr Ile Thr Ala Asp Lys Ser Thr Ser Thr Ala Tyr
            100                 105                 110

Met Glu Leu Ser Ser Leu Arg Ser Glu Asp Thr Ala Val Tyr Tyr Cys
        115                 120                 125

Ala Arg Arg Ala Met Asp Asn Tyr Gly Phe Ala Tyr Trp Gly Gln Gly
    130                 135                 140

Thr Leu Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys

<210> SEQ ID NO 392
<211> LENGTH: 481
<212> TYPE: PRT
<213> ORGANISM: Artificial Sequence
```

<220> FEATURE:
<223> OTHER INFORMATION: Synthetic Construct

<400> SEQUENCE: 392

```
Ala Cys Pro Ala Lys Ile Gly Gln Glu Cys Gly Gly Ser Ser Gly
1               5                   10                  15

Gly Ser Thr Ser Thr Ser Gly Arg Ser Ala Asn Pro Arg Ser Gly Gly
            20                  25                  30

Gln Val Gln Leu Val Gln Ser Gly Ala Glu Val Lys Lys Pro Gly Ser
        35                  40                  45

Ser Val Lys Val Ser Cys Lys Ala Ser Gly Tyr Thr Phe Thr Asn Tyr
    50                  55                  60

Phe Met Asn Trp Val Arg Gln Ala Pro Gly Gln Gly Leu Glu Trp Met
65                  70                  75                  80

Gly Arg Val Asp Pro Glu Gln Gly Arg Ala Asp Tyr Ala Glu Lys Phe
                85                  90                  95

Lys Lys Arg Val Thr Ile Thr Ala Asp Lys Ser Thr Ser Thr Ala Tyr
            100                 105                 110

Met Glu Leu Ser Ser Leu Arg Ser Glu Asp Thr Ala Val Tyr Tyr Cys
        115                 120                 125

Ala Arg Arg Ala Met Asp Asn Tyr Gly Phe Ala Tyr Trp Gly Gln Gly
    130                 135                 140

Thr Leu Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400
```

Cys Leu Val Lys Gly Phe Tyr Pro Ser Asp Ile Ala Val Glu Trp Glu
            405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
            435                 440                 445

Ser Arg Trp Gln Gln Gly Asn Val Phe Ser Cys Ser Val Met His Glu
        450                 455                 460

Ala Leu His Asn His Tyr Thr Gln Lys Ser Leu Ser Leu Ser Pro Gly
465                 470                 475                 480

Lys

<210> SEQ ID NO 393
<211> LENGTH: 481
<212> TYPE: PRT
<213> ORGANISM: Artificial Sequence
<220> FEATURE:
<223> OTHER INFORMATION: Synthetic Construct

<400> SEQUENCE: 393

Ala Cys Pro Phe Pro Ala Leu Glu Leu Cys Gly Gly Gly Ser Ser Gly
1               5                   10                  15

Gly Ser Thr Ser Thr Ser Gly Arg Ser Ala Asn Pro Arg Ser Gly Gly
            20                  25                  30

Gln Val Gln Leu Val Gln Ser Gly Ala Glu Val Lys Lys Pro Gly Ser
        35                  40                  45

Ser Val Lys Val Ser Cys Lys Ala Ser Gly Tyr Thr Phe Thr Asn Tyr
    50                  55                  60

Phe Met Asn Trp Val Arg Gln Ala Pro Gly Gln Gly Leu Glu Trp Met
65                  70                  75                  80

Gly Arg Val Asp Pro Glu Gln Gly Arg Ala Asp Tyr Ala Glu Lys Phe
                85                  90                  95

Lys Lys Arg Val Thr Ile Thr Ala Asp Lys Ser Thr Ser Thr Ala Tyr
            100                 105                 110

Met Glu Leu Ser Ser Leu Arg Ser Glu Asp Thr Ala Val Tyr Tyr Cys
        115                 120                 125

Ala Arg Arg Ala Met Asp Asn Tyr Gly Phe Ala Tyr Trp Gly Gln Gly
    130                 135                 140

Thr Leu Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Glu Leu Leu Gly Gly Pro
            260                 265                 270

```
Ser Val Phe Leu Phe Pro Pro Lys Pro Lys Asp Thr Leu Met Ile Ser
            275                 280                 285

Arg Thr Pro Glu Val Thr Cys Val Val Val Asp Val Ser His Glu Asp
        290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys

<210> SEQ ID NO 394
<211> LENGTH: 481
<212> TYPE: PRT
<213> ORGANISM: Artificial Sequence
<220> FEATURE:
<223> OTHER INFORMATION: Synthetic Construct

<400> SEQUENCE: 394

Ala Cys Thr Lys Pro Ala Lys Ala Leu Cys Gly Gly Gly Ser Ser Gly
1               5                   10                  15

Gly Ser Thr Ser Thr Ser Gly Arg Ser Ala Asn Pro Arg Ser Gly Gly
            20                  25                  30

Gln Val Gln Leu Val Gln Ser Gly Ala Glu Val Lys Lys Pro Gly Ser
        35                  40                  45

Ser Val Lys Val Ser Cys Lys Ala Ser Gly Tyr Thr Phe Thr Asn Tyr
    50                  55                  60

Phe Met Asn Trp Val Arg Gln Ala Pro Gly Gln Gly Leu Glu Trp Met
65                  70                  75                  80

Gly Arg Val Asp Pro Glu Gln Gly Arg Ala Asp Tyr Ala Glu Lys Phe
                85                  90                  95

Lys Lys Arg Val Thr Ile Thr Ala Asp Lys Ser Thr Ser Thr Ala Tyr
            100                 105                 110

Met Glu Leu Ser Ser Leu Arg Ser Glu Asp Thr Ala Val Tyr Tyr Cys
        115                 120                 125

Ala Arg Arg Ala Met Asp Asn Tyr Gly Phe Ala Tyr Trp Gly Gln Gly
    130                 135                 140

Thr Leu Val Thr Val Ser Ser Ala Ser Thr Lys Gly Pro Ser Val Phe
```

```
                145                 150                 155                 160
Pro Leu Ala Pro Ser Ser Lys Ser Thr Ser Gly Gly Thr Ala Ala Leu
                    165                 170                 175

Gly Cys Leu Val Lys Asp Tyr Phe Pro Glu Pro Val Thr Val Ser Trp
                    180                 185                 190

Asn Ser Gly Ala Leu Thr Ser Gly Val His Thr Phe Pro Ala Val Leu
                    195                 200                 205

Gln Ser Ser Gly Leu Tyr Ser Leu Ser Ser Val Val Thr Val Pro Ser
                    210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                    245                 250                 255

Thr His Thr Cys Pro Pro Cys Pro Ala Pro Glu Leu Leu Gly Gly Pro
                    260                 265                 270

Ser Val Phe Leu Phe Pro Pro Lys Pro Lys Asp Thr Leu Met Ile Ser
                    275                 280                 285

Arg Thr Pro Glu Val Thr Cys Val Val Val Asp Val Ser His Glu Asp
                    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                    325                 330                 335

Val Ser Val Leu Thr Val Leu His Gln Asp Trp Leu Asn Gly Lys Glu
                    340                 345                 350

Tyr Lys Cys Lys Val Ser Asn Lys Ala Leu Pro Ala Pro Ile Glu Lys
                    355                 360                 365

Thr Ile Ser Lys Ala Lys Gly Gln Pro Arg Glu Pro Gln Val Tyr Thr
                    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                    405                 410                 415

Ser Asn Gly Gln Pro Glu Asn Asn Tyr Lys Thr Thr Pro Pro Val Leu
                    420                 425                 430

Asp Ser Asp Gly Ser Phe Phe Leu Tyr Ser Lys Leu Thr Val Asp Lys
                    435                 440                 445

Ser Arg Trp Gln Gln Gly Asn Val Phe Ser Cys Ser Val Met His Glu
450                 455                 460

Ala Leu His Asn His Tyr Thr Gln Lys Ser Leu Ser Leu Ser Pro Gly
465                 470                 475                 480

Lys

<210> SEQ ID NO 395
<211> LENGTH: 487
<212> TYPE: PRT
<213> ORGANISM: Artificial Sequence
<220> FEATURE:
<223> OTHER INFORMATION: Synthetic Construct

<400> SEQUENCE: 395

Asp Thr Ala Thr Cys Tyr Thr Thr Gly Trp Cys Glu Gly Met Val
1               5                   10                  15

Gly Gly Gly Ser Ser Gly Gly Ser Thr Ser Thr Ser Gly Arg Ser Ala
                    20                  25                  30
```

```
Asn Pro Arg Ser Gly Gly Gln Val Gln Leu Val Gln Ser Gly Ala Glu
        35                  40                  45

Val Lys Lys Pro Gly Ser Ser Val Lys Val Ser Cys Lys Ala Ser Gly
 50                  55                  60

Tyr Thr Phe Thr Asn Tyr Phe Met Asn Trp Val Arg Gln Ala Pro Gly
 65                  70                  75                  80

Gln Gly Leu Glu Trp Met Gly Arg Val Asp Pro Glu Gln Gly Arg Ala
                 85                  90                  95

Asp Tyr Ala Glu Lys Phe Lys Lys Arg Val Thr Ile Thr Ala Asp Lys
            100                 105                 110

Ser Thr Ser Thr Ala Tyr Met Glu Leu Ser Ser Leu Arg Ser Glu Asp
        115                 120                 125

Thr Ala Val Tyr Tyr Cys Ala Arg Arg Ala Met Asp Asn Tyr Gly Phe
130                 135                 140

Ala Tyr Trp Gly Gln Gly Thr Leu Val Thr Val Ser Ser Ala Ser Thr
145                 150                 155                 160

Lys Gly Pro Ser Val Phe Pro Leu Ala Pro Ser Ser Lys Ser Thr Ser
                165                 170                 175

Gly Gly Thr Ala Ala Leu Gly Cys Leu Val Lys Asp Tyr Phe Pro Glu
            180                 185                 190

Pro Val Thr Val Ser Trp Asn Ser Gly Ala Leu Thr Ser Gly Val His
        195                 200                 205

Thr Phe Pro Ala Val Leu Gln Ser Ser Gly Leu Tyr Ser Leu Ser Ser
210                 215                 220

Val Val Thr Val Pro Ser Ser Leu Gly Thr Gln Thr Tyr Ile Cys
225                 230                 235                 240

Asn Val Asn His Lys Pro Ser Asn Thr Lys Val Asp Lys Lys Val Glu
                245                 250                 255

Pro Lys Ser Cys Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
        355                 360                 365

Pro Ala Pro Ile Glu Lys Thr Ile Ser Lys Ala Lys Gly Gln Pro Arg
370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
        435                 440                 445
```

-continued

Lys Leu Thr Val Asp Lys Ser Arg Trp Gln Gln Gly Asn Val Phe Ser
            450                 455                 460

Cys Ser Val Met His Glu Ala Leu His Asn His Tyr Thr Gln Lys Ser
465                 470                 475                 480

Leu Ser Leu Ser Pro Gly Lys
                485

<210> SEQ ID NO 396
<211> LENGTH: 487
<212> TYPE: PRT
<213> ORGANISM: Artificial Sequence
<220> FEATURE:
<223> OTHER INFORMATION: Synthetic Construct

<400> SEQUENCE: 396

Asn Ser Asp Asn Cys Gly Pro Ala Lys Ser Thr Cys Met Tyr Asn Asp
1               5                   10                  15

Gly Gly Gly Ser Ser Gly Gly Ser Thr Ser Thr Ser Gly Arg Ser Ala
                20                  25                  30

Asn Pro Arg Ser Gly Gly Gln Val Gln Leu Val Gln Ser Gly Ala Glu
            35                  40                  45

Val Lys Lys Pro Gly Ser Ser Val Lys Val Ser Cys Lys Ala Ser Gly
50                  55                  60

Tyr Thr Phe Thr Asn Tyr Phe Met Asn Trp Val Arg Gln Ala Pro Gly
65                  70                  75                  80

Gln Gly Leu Glu Trp Met Gly Arg Val Asp Pro Glu Gln Gly Arg Ala
                85                  90                  95

Asp Tyr Ala Glu Lys Phe Lys Lys Arg Val Thr Ile Thr Ala Asp Lys
            100                 105                 110

Ser Thr Ser Thr Ala Tyr Met Glu Leu Ser Ser Leu Arg Ser Glu Asp
        115                 120                 125

Thr Ala Val Tyr Tyr Cys Ala Arg Arg Ala Met Asp Asn Tyr Gly Phe
130                 135                 140

Ala Tyr Trp Gly Gln Gly Thr Leu Val Thr Val Ser Ser Ala Ser Thr
145                 150                 155                 160

Lys Gly Pro Ser Val Phe Pro Leu Ala Pro Ser Ser Lys Ser Thr Ser
                165                 170                 175

Gly Gly Thr Ala Ala Leu Gly Cys Leu Val Lys Asp Tyr Phe Pro Glu
            180                 185                 190

Pro Val Thr Val Ser Trp Asn Ser Gly Ala Leu Thr Ser Gly Val His
        195                 200                 205

Thr Phe Pro Ala Val Leu Gln Ser Ser Gly Leu Tyr Ser Leu Ser Ser
210                 215                 220

Val Val Thr Val Pro Ser Ser Ser Leu Gly Thr Gln Thr Tyr Ile Cys
225                 230                 235                 240

Asn Val Asn His Lys Pro Ser Asn Thr Lys Val Asp Lys Lys Val Glu
                245                 250                 255

Pro Lys Ser Cys Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
        275                 280                 285

Asp Thr Leu Met Ile Ser Arg Thr Pro Glu Val Thr Cys Val Val Val
290                 295                 300

Asp Val Ser His Glu Asp Pro Glu Val Lys Phe Asn Trp Tyr Val Asp
305                 310                 315                 320

```
Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Ala Leu
        355                 360                 365

Pro Ala Pro Ile Glu Lys Thr Ile Ser Lys Ala Lys Gly Gln Pro Arg
370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
        435                 440                 445

Lys Leu Thr Val Asp Lys Ser Arg Trp Gln Gln Gly Asn Val Phe Ser
450                 455                 460

Cys Ser Val Met His Glu Ala Leu His Asn His Tyr Thr Gln Lys Ser
465                 470                 475                 480

Leu Ser Leu Ser Pro Gly Lys
                485

<210> SEQ ID NO 397
<211> LENGTH: 486
<212> TYPE: PRT
<213> ORGANISM: Artificial Sequence
<220> FEATURE:
<223> OTHER INFORMATION: Synthetic Construct

<400> SEQUENCE: 397

Pro Pro Gly Lys Cys Thr Gln Pro His Arg Cys Pro Leu Asn Gly
1               5                   10                  15

Gly Gly Ser Ser Gly Gly Ser Thr Ser Thr Ser Gly Arg Ser Ala Asn
                20                  25                  30

Pro Arg Ser Gly Gly Gln Val Gln Leu Val Gln Ser Gly Ala Glu Val
            35                  40                  45

Lys Lys Pro Gly Ser Ser Val Lys Val Ser Cys Lys Ala Ser Gly Tyr
50                  55                  60

Thr Phe Thr Asn Tyr Phe Met Asn Trp Val Arg Gln Ala Pro Gly Gln
65                  70                  75                  80

Gly Leu Glu Trp Met Gly Arg Val Asp Pro Glu Gln Gly Arg Ala Asp
                85                  90                  95

Tyr Ala Glu Lys Phe Lys Lys Arg Val Thr Ile Thr Ala Asp Lys Ser
            100                 105                 110

Thr Ser Thr Ala Tyr Met Glu Leu Ser Ser Leu Arg Ser Glu Asp Thr
        115                 120                 125

Ala Val Tyr Tyr Cys Ala Arg Arg Ala Met Asp Asn Tyr Gly Phe Ala
130                 135                 140

Tyr Trp Gly Gln Gly Thr Leu Val Thr Val Ser Ser Ala Ser Thr Lys
145                 150                 155                 160

Gly Pro Ser Val Phe Pro Leu Ala Pro Ser Ser Lys Ser Thr Ser Gly
                165                 170                 175

Gly Thr Ala Ala Leu Gly Cys Leu Val Lys Asp Tyr Phe Pro Glu Pro
            180                 185                 190
```

-continued

```
Val Thr Val Ser Trp Asn Ser Gly Ala Leu Thr Ser Gly Val His Thr
            195                 200                 205
Phe Pro Ala Val Leu Gln Ser Ser Gly Leu Tyr Ser Leu Ser Ser Val
    210                 215                 220
Val Thr Val Pro Ser Ser Ser Leu Gly Thr Gln Thr Tyr Ile Cys Asn
225                 230                 235                 240
Val Asn His Lys Pro Ser Asn Thr Lys Val Asp Lys Val Glu Pro
                245                 250                 255
Lys Ser Cys Asp Lys Thr His Thr Cys Pro Pro Cys Pro Ala Pro Glu
            260                 265                 270
Leu Leu Gly Gly Pro Ser Val Phe Leu Phe Pro Pro Lys Pro Lys Asp
            275                 280                 285
Thr Leu Met Ile Ser Arg Thr Pro Glu Val Thr Cys Val Val Val Asp
    290                 295                 300
Val Ser His Glu Asp Pro Glu Val Lys Phe Asn Trp Tyr Val Asp Gly
305                 310                 315                 320
Val Glu Val His Asn Ala Lys Thr Lys Pro Arg Glu Glu Gln Tyr Asn
                325                 330                 335
Ser Thr Tyr Arg Val Val Ser Val Leu Thr Val Leu His Gln Asp Trp
            340                 345                 350
Leu Asn Gly Lys Glu Tyr Lys Cys Lys Val Ser Asn Lys Ala Leu Pro
    355                 360                 365
Ala Pro Ile Glu Lys Thr Ile Ser Lys Ala Lys Gly Gln Pro Arg Glu
            370                 375                 380
Pro Gln Val Tyr Thr Leu Pro Pro Ser Arg Asp Glu Leu Thr Lys Asn
385                 390                 395                 400
Gln Val Ser Leu Thr Cys Leu Val Lys Gly Phe Tyr Pro Ser Asp Ile
                405                 410                 415
Ala Val Glu Trp Glu Ser Asn Gly Gln Pro Glu Asn Asn Tyr Lys Thr
            420                 425                 430
Thr Pro Pro Val Leu Asp Ser Asp Gly Ser Phe Phe Leu Tyr Ser Lys
    435                 440                 445
Leu Thr Val Asp Lys Ser Arg Trp Gln Gln Gly Asn Val Phe Ser Cys
450                 455                 460
Ser Val Met His Glu Ala Leu His Asn His Tyr Thr Gln Lys Ser Leu
465                 470                 475                 480
Ser Leu Ser Pro Gly Lys
                485
```

<210> SEQ ID NO 398
<211> LENGTH: 9
<212> TYPE: PRT
<213> ORGANISM: Artificial Sequence
<220> FEATURE:
<223> OTHER INFORMATION: Synthetic Construct

<400> SEQUENCE: 398

```
Tyr Pro Tyr Asp Val Pro Asp Tyr Ala
1               5
```

<210> SEQ ID NO 399
<211> LENGTH: 8
<212> TYPE: PRT
<213> ORGANISM: Artificial Sequence
<220> FEATURE:
<223> OTHER INFORMATION: Synthetic Construct

<400> SEQUENCE: 399

```
Asp Tyr Lys Asp Asp Asp Lys
1               5

<210> SEQ ID NO 400
<211> LENGTH: 10
<212> TYPE: PRT
<213> ORGANISM: Artificial Sequence
<220> FEATURE:
<223> OTHER INFORMATION: Synthetic Construct

<400> SEQUENCE: 400

Glu Gln Lys Leu Ile Ser Glu Glu Asp Leu
1               5                   10

<210> SEQ ID NO 401
<211> LENGTH: 15
<212> TYPE: PRT
<213> ORGANISM: Artificial Sequence
<220> FEATURE:
<223> OTHER INFORMATION: Synthetic Construct

<400> SEQUENCE: 401

Gly Leu Asn Asp Ile Phe Glu Ala Gln Lys Ile Glu Trp His Glu
1               5                   10                  15

<210> SEQ ID NO 402
<211> LENGTH: 11
<212> TYPE: PRT
<213> ORGANISM: Artificial Sequence
<220> FEATURE:
<223> OTHER INFORMATION: Synthetic Construct

<400> SEQUENCE: 402

Gln Ser Leu Leu Asn Ser Asp Gly Asn Thr Tyr
1               5                   10

<210> SEQ ID NO 403
<211> LENGTH: 3
<212> TYPE: PRT
<213> ORGANISM: Artificial Sequence
<220> FEATURE:
<223> OTHER INFORMATION: Synthetic Construct

<400> SEQUENCE: 403

Leu Val Ser
1

<210> SEQ ID NO 404
<211> LENGTH: 7
<212> TYPE: PRT
<213> ORGANISM: Artificial Sequence
<220> FEATURE:
<223> OTHER INFORMATION: Synthetic Construct

<400> SEQUENCE: 404

Val Gln Gly Thr His Asp Pro
1               5

<210> SEQ ID NO 405
<211> LENGTH: 8
<212> TYPE: PRT
<213> ORGANISM: Artificial Sequence
<220> FEATURE:
<223> OTHER INFORMATION: Synthetic Construct

<400> SEQUENCE: 405
```

Tyr His Thr Ile Thr Ser Gly Tyr
1               5

<210> SEQ ID NO 406
<211> LENGTH: 7
<212> TYPE: PRT
<213> ORGANISM: Artificial Sequence
<220> FEATURE:
<223> OTHER INFORMATION: Synthetic Construct

<400> SEQUENCE: 406

Ile Ser Tyr Ser Gly Asn Thr
1               5

<210> SEQ ID NO 407
<211> LENGTH: 13
<212> TYPE: PRT
<213> ORGANISM: Artificial Sequence
<220> FEATURE:
<223> OTHER INFORMATION: Synthetic Construct

<400> SEQUENCE: 407

Ala Ser Met Met Val Pro His Tyr Tyr Val Met Asp Ala
1               5                   10

<210> SEQ ID NO 408
<211> LENGTH: 6
<212> TYPE: PRT
<213> ORGANISM: Artificial Sequence
<220> FEATURE:
<223> OTHER INFORMATION: Synthetic Construct

<400> SEQUENCE: 408

Ser Ala Leu Ser Tyr Met
1               5

<210> SEQ ID NO 409
<211> LENGTH: 3
<212> TYPE: PRT
<213> ORGANISM: Artificial Sequence
<220> FEATURE:
<223> OTHER INFORMATION: Synthetic Construct

<400> SEQUENCE: 409

Gly Thr Ser
1

<210> SEQ ID NO 410
<211> LENGTH: 7
<212> TYPE: PRT
<213> ORGANISM: Artificial Sequence
<220> FEATURE:
<223> OTHER INFORMATION: Synthetic Construct

<400> SEQUENCE: 410

His His Trp Ser Asn Thr Gln
1               5

<210> SEQ ID NO 411
<211> LENGTH: 8
<212> TYPE: PRT
<213> ORGANISM: Artificial Sequence
<220> FEATURE:
<223> OTHER INFORMATION: Synthetic Construct

<400> SEQUENCE: 411

Gly Tyr Thr Phe Thr Asn Tyr Phe

<210> SEQ ID NO 412
<211> LENGTH: 9
<212> TYPE: PRT
<213> ORGANISM: Artificial Sequence
<220> FEATURE:
<223> OTHER INFORMATION: Synthetic Construct

<400> SEQUENCE: 412

Val Asp Pro Glu Gln Gly Arg Ala Asp
1               5

<210> SEQ ID NO 413
<211> LENGTH: 11
<212> TYPE: PRT
<213> ORGANISM: Artificial Sequence
<220> FEATURE:
<223> OTHER INFORMATION: Synthetic Construct

<400> SEQUENCE: 413

Arg Arg Ala Met Asp Asn Tyr Gly Phe Ala Tyr
1               5                   10

<210> SEQ ID NO 414
<211> LENGTH: 6
<212> TYPE: PRT
<213> ORGANISM: Artificial Sequence
<220> FEATURE:
<223> OTHER INFORMATION: Synthetic Construct

<400> SEQUENCE: 414

Gly Ser Gly Gly Ser Gly
1               5

<210> SEQ ID NO 415
<211> LENGTH: 6
<212> TYPE: PRT
<213> ORGANISM: Artificial Sequence
<220> FEATURE:
<223> OTHER INFORMATION: Synthetic Construct

<400> SEQUENCE: 415

Gly Gly Ser Gly Gly Ser
1               5

<210> SEQ ID NO 416
<211> LENGTH: 7
<212> TYPE: PRT
<213> ORGANISM: Artificial Sequence
<220> FEATURE:
<223> OTHER INFORMATION: Synthetic Construct

<400> SEQUENCE: 416

Gly Gly Pro Gly Ser Ser Pro
1               5

<210> SEQ ID NO 417
<211> LENGTH: 6
<212> TYPE: PRT
<213> ORGANISM: Artificial Sequence
<220> FEATURE:
<223> OTHER INFORMATION: Synthetic Construct

<400> SEQUENCE: 417

Gly Gly Ser Ser Pro Pro
1               5

<210> SEQ ID NO 418
<211> LENGTH: 8
<212> TYPE: PRT
<213> ORGANISM: Artificial Sequence
<220> FEATURE:
<223> OTHER INFORMATION: Synthetic Construct

<400> SEQUENCE: 418

Ser Ser Pro Ser Pro Ser Gly Gly
1               5

<210> SEQ ID NO 419
<211> LENGTH: 6
<212> TYPE: PRT
<213> ORGANISM: Artificial Sequence
<220> FEATURE:
<223> OTHER INFORMATION: Synthetic Construct

<400> SEQUENCE: 419

Gly Ser Pro Gly Ser Pro
1               5

<210> SEQ ID NO 420
<211> LENGTH: 7
<212> TYPE: PRT
<213> ORGANISM: Artificial Sequence
<220> FEATURE:
<223> OTHER INFORMATION: Synthetic Construct

<400> SEQUENCE: 420

Ser Ser Gly Gly Ser Gly Pro
1               5

<210> SEQ ID NO 421
<211> LENGTH: 449
<212> TYPE: PRT
<213> ORGANISM: Artificial Sequence
<220> FEATURE:
<223> OTHER INFORMATION: Synthetic Construct

<400> SEQUENCE: 421

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Phe Met Asn Trp Val Arg Gln Ala Pro Gly Gln Gly Leu Glu Trp Met
        35                  40                  45

Gly Arg Val Asp Pro Glu Gln Gly Arg Ala Asp Tyr Ala Glu Lys Phe
    50                  55                  60

Lys Lys Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ala Met Asp Asn Tyr Gly Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Asp Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 422
<211> LENGTH: 241
<212> TYPE: PRT
<213> ORGANISM: Artificial Sequence
<220> FEATURE:
<223> OTHER INFORMATION: Synthetic Construct

<400> SEQUENCE: 422

Ala Cys Pro Phe Pro Ala Leu Glu Leu Cys Ser Ser Gly Gly Ser Gly
1               5                   10                  15

Pro Asp Ser Gly Gly Phe Met Leu Thr Ser Gly Gly Glu Ile Val Leu
            20                  25                  30

Thr Gln Ser Pro Asp Phe Gln Ser Val Thr Pro Lys Glu Lys Val Thr
        35                  40                  45

Ile Thr Cys Ser Ala Asn Ser Ala Leu Ser Tyr Met Tyr Trp Tyr Gln
    50                  55                  60
```

```
Gln Lys Pro Asp Gln Ser Pro Lys Leu Trp Val His Gly Thr Ser Asn
 65                  70                  75                  80

Leu Ala Ser Gly Val Pro Ser Arg Phe Ser Gly Ser Gly Ser Gly Thr
                 85                  90                  95

Asp Phe Thr Leu Thr Ile Asn Ser Leu Glu Ala Glu Asp Ala Ala Thr
            100                 105                 110

Tyr Tyr Cys His His Trp Ser Asn Thr Gln Trp Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 423
<211> LENGTH: 241
<212> TYPE: PRT
<213> ORGANISM: Artificial Sequence
<220> FEATURE:
<223> OTHER INFORMATION: Synthetic Construct

<400> SEQUENCE: 423

Ala Cys Pro Gly Lys Gly Leu Pro Ser Cys Gly Gly Gly Ser Ser Gly
  1               5                  10                  15

Gly Ser Gly Gly Ser Gly Gly Ser Gly Gly Glu Ile Val Leu
                 20                  25                  30

Thr Gln Ser Pro Asp Phe Gln Ser Val Thr Pro Lys Glu Lys Val Thr
             35                  40                  45

Ile Thr Cys Ser Ala Asn Ser Ala Leu Ser Tyr Met Tyr Trp Tyr Gln
 50                  55                  60

Gln Lys Pro Asp Gln Ser Pro Lys Leu Trp Val His Gly Thr Ser Asn
 65                  70                  75                  80

Leu Ala Ser Gly Val Pro Ser Arg Phe Ser Gly Ser Gly Ser Gly Thr
                 85                  90                  95

Asp Phe Thr Leu Thr Ile Asn Ser Leu Glu Ala Glu Asp Ala Ala Thr
            100                 105                 110

Tyr Tyr Cys His His Trp Ser Asn Thr Gln Trp Thr Phe Gly Gly Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
```

```
                    180                 185                 190
Gln Asp Ser Lys Asp Ser Thr Tyr Ser Leu Ser Ser Thr Leu Thr Leu
                195                 200                 205

Ser Lys Ala Asp Tyr Glu Lys His Lys Val Tyr Ala Cys Glu Val Thr
        210                 215                 220

His Gln Gly Leu Ser Ser Pro Val Thr Lys Ser Phe Asn Arg Gly Glu
225                 230                 235                 240

Cys

<210> SEQ ID NO 424
<211> LENGTH: 238
<212> TYPE: PRT
<213> ORGANISM: Artificial Sequence
<220> FEATURE:
<223> OTHER INFORMATION: Synthetic Construct

<400> SEQUENCE: 424

Ala Cys Pro Phe Pro Ala Leu Glu Leu Cys Gly Gly Ser Gly Gly Ser
1               5                   10                  15

Val Pro Leu Ser Leu Tyr Ser Gly Gly Glu Ile Val Leu Thr Gln Ser
            20                  25                  30

Pro Asp Phe Gln Ser Val Thr Pro Lys Glu Lys Val Thr Ile Thr Cys
        35                  40                  45

Ser Ala Asn Ser Ala Leu Ser Tyr Met Tyr Trp Tyr Gln Gln Lys Pro
    50                  55                  60

Asp Gln Ser Pro Lys Leu Trp Val His Gly Thr Ser Asn Leu Ala Ser
65                  70                  75                  80

Gly Val Pro Ser Arg Phe Ser Gly Ser Gly Ser Gly Thr Asp Phe Thr
                85                  90                  95

Leu Thr Ile Asn Ser Leu Glu Ala Glu Asp Ala Ala Thr Tyr Tyr Cys
            100                 105                 110

His His Trp Ser Asn Thr Gln Trp Thr Phe Gly Gly Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 425
<211> LENGTH: 241
<212> TYPE: PRT
<213> ORGANISM: Artificial Sequence
<220> FEATURE:
<223> OTHER INFORMATION: Synthetic Construct

<400> SEQUENCE: 425

Ala Cys Pro Phe Pro Ala Leu Glu Leu Cys Gly Gly Pro Gly Ser Ser
```

```
            1               5                  10                 15
        Pro Met Pro Tyr Asp Leu Tyr His Pro Ser Gly Gly Glu Ile Val Leu
                        20                 25                 30
        Thr Gln Ser Pro Asp Phe Gln Ser Val Thr Pro Lys Glu Lys Val Thr
                        35                 40                 45
        Ile Thr Cys Ser Ala Asn Ser Ala Leu Ser Tyr Met Tyr Trp Tyr Gln
            50                 55                 60
        Gln Lys Pro Asp Gln Ser Pro Lys Leu Trp Val His Gly Thr Ser Asn
        65                 70                 75                 80
        Leu Ala Ser Gly Val Pro Ser Arg Phe Ser Gly Ser Gly Ser Gly Thr
                        85                 90                 95
        Asp Phe Thr Leu Thr Ile Asn Ser Leu Glu Ala Glu Asp Ala Ala Thr
                        100                105                110
        Tyr Tyr Cys His His Trp Ser Asn Thr Gln Trp Thr Phe Gly Gly Gly
                        115                120                125
        Thr Lys Val Glu Ile Lys Arg Thr Val Ala Ala Pro Ser Val Phe Ile
                        130                135                140
        Phe Pro Pro Ser Asp Glu Gln Leu Lys Ser Gly Thr Ala Ser Val Val
        145                150                155                160
        Cys Leu Leu Asn Asn Phe Tyr Pro Arg Glu Ala Lys Val Gln Trp Lys
                        165                170                175
        Val Asp Asn Ala Leu Gln Ser Gly Asn Ser Gln Glu Ser Val Thr Glu
                        180                185                190
        Gln Asp Ser Lys Asp Ser Thr Tyr Ser Leu Ser Ser Thr Leu Thr Leu
                        195                200                205
        Ser Lys Ala Asp Tyr Glu Lys His Lys Val Tyr Ala Cys Glu Val Thr
                        210                215                220
        His Gln Gly Leu Ser Ser Pro Val Thr Lys Ser Phe Asn Arg Gly Glu
        225                230                235                240
        Cys

<210> SEQ ID NO 426
<211> LENGTH: 238
<212> TYPE: PRT
<213> ORGANISM: Artificial Sequence
<220> FEATURE:
<223> OTHER INFORMATION: Synthetic Construct

<400> SEQUENCE: 426

Ala Cys Pro Phe Pro Ala Leu Glu Leu Cys Gly Gly Ser Ser Pro Pro
        1               5                  10                 15
        His Glu Gln Leu Thr Val Ser Gly Gly Glu Ile Val Leu Thr Gln Ser
                        20                 25                 30
        Pro Asp Phe Gln Ser Val Thr Pro Lys Glu Lys Val Thr Ile Thr Cys
                        35                 40                 45
        Ser Ala Asn Ser Ala Leu Ser Tyr Met Tyr Trp Tyr Gln Gln Lys Pro
            50                 55                 60
        Asp Gln Ser Pro Lys Leu Trp Val His Gly Thr Ser Asn Leu Ala Ser
        65                 70                 75                 80
        Gly Val Pro Ser Arg Phe Ser Gly Ser Gly Ser Gly Thr Asp Phe Thr
                        85                 90                 95
        Leu Thr Ile Asn Ser Leu Glu Ala Glu Asp Ala Ala Thr Tyr Tyr Cys
                        100                105                110
        His His Trp Ser Asn Thr Gln Trp Thr Phe Gly Gly Gly Thr Lys Val
                        115                120                125
```

```
Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
            210                 215                 220

Leu Ser Ser Pro Val Thr Lys Ser Phe Asn Arg Gly Glu Cys
225                 230                 235
```

<210> SEQ ID NO 427
<211> LENGTH: 241
<212> TYPE: PRT
<213> ORGANISM: Artificial Sequence
<220> FEATURE:
<223> OTHER INFORMATION: Synthetic Construct

<400> SEQUENCE: 427

```
Ala Cys Pro Phe Pro Ala Leu Glu Leu Cys Gly Gly Gly Ser Ser Gly
1               5                   10                  15

Gly Ser Gly Gly Ser Gly Gly Ser Gly Gly Glu Ile Val Leu
            20                  25                  30

Thr Gln Ser Pro Asp Phe Gln Ser Val Thr Pro Lys Glu Lys Val Thr
            35                  40                  45

Ile Thr Cys Ser Ala Asn Ser Ala Leu Ser Tyr Met Tyr Trp Tyr Gln
        50                  55                  60

Gln Lys Pro Asp Gln Ser Pro Lys Leu Trp Val His Gly Thr Ser Asn
65                  70                  75                  80

Leu Ala Ser Gly Val Pro Ser Arg Phe Ser Gly Ser Gly Ser Gly Thr
                85                  90                  95

Asp Phe Thr Leu Thr Ile Asn Ser Leu Glu Ala Glu Asp Ala Ala Thr
            100                 105                 110

Tyr Tyr Cys His His Trp Ser Asn Thr Gln Trp Thr Phe Gly Gly Gly
            115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
            195                 200                 205

Ser Lys Ala Asp Tyr Glu Lys His Lys Val Tyr Ala Cys Glu Val Thr
        210                 215                 220

His Gln Gly Leu Ser Ser Pro Val Thr Lys Ser Phe Asn Arg Gly Glu
225                 230                 235                 240

Cys
```

```
<210> SEQ ID NO 428
<211> LENGTH: 242
<212> TYPE: PRT
<213> ORGANISM: Artificial Sequence
<220> FEATURE:
<223> OTHER INFORMATION: Synthetic Construct

<400> SEQUENCE: 428

Ala Cys Pro Phe Pro Ala Leu Glu Leu Cys Ser Ser Pro Pro Ser
1               5                   10                  15

Gly Gly Gly Gly Ile Gly Gln Leu Thr Ala Ser Gly Gly Glu Ile Val
            20                  25                  30

Leu Thr Gln Ser Pro Asp Phe Gln Ser Val Thr Pro Lys Glu Lys Val
        35                  40                  45

Thr Ile Thr Cys Ser Ala Asn Ser Ala Leu Ser Tyr Met Tyr Trp Tyr
    50                  55                  60

Gln Gln Lys Pro Asp Gln Ser Pro Lys Leu Trp Val His Gly Thr Ser
65                  70                  75                  80

Asn Leu Ala Ser Gly Val Pro Ser Arg Phe Ser Gly Ser Gly Ser Gly
                85                  90                  95

Thr Asp Phe Thr Leu Thr Ile Asn Ser Leu Glu Ala Glu Asp Ala Ala
            100                 105                 110

Thr Tyr Tyr Cys His His Trp Ser Asn Thr Gln Trp Thr Phe Gly Gly
        115                 120                 125

Gly Thr Lys Val Glu Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys

<210> SEQ ID NO 429
<211> LENGTH: 240
<212> TYPE: PRT
<213> ORGANISM: Artificial Sequence
<220> FEATURE:
<223> OTHER INFORMATION: Synthetic Construct

<400> SEQUENCE: 429

Ala Cys Pro Phe Pro Ala Leu Glu Leu Cys Gly Gly Ser Ser Pro Pro
1               5                   10                  15

Arg Ala Ala Val Lys Ser Pro Ser Gly Gly Glu Ile Val Leu Thr
            20                  25                  30

Gln Ser Pro Asp Phe Gln Ser Val Thr Pro Lys Glu Lys Val Thr Ile
        35                  40                  45

Thr Cys Ser Ala Asn Ser Ala Leu Ser Tyr Met Tyr Trp Tyr Gln Gln
    50                  55                  60
```

Lys Pro Asp Gln Ser Pro Lys Leu Trp Val His Gly Thr Ser Asn Leu
65                  70                  75                  80

Ala Ser Gly Val Pro Ser Arg Phe Ser Gly Ser Gly Ser Gly Thr Asp
                85                  90                  95

Phe Thr Leu Thr Ile Asn Ser Leu Glu Ala Glu Asp Ala Ala Thr Tyr
            100                 105                 110

Tyr Cys His His Trp Ser Asn Thr Gln Trp Thr Phe Gly Gly Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 430
<211> LENGTH: 240
<212> TYPE: PRT
<213> ORGANISM: Artificial Sequence
<220> FEATURE:
<223> OTHER INFORMATION: Synthetic Construct

<400> SEQUENCE: 430

Ala Cys Pro Phe Pro Ala Leu Glu Leu Cys Gly Gly Ser Ser Pro Pro
1               5                   10                  15

Thr Ser Val Leu Met Ala Ala Pro Ser Gly Gly Glu Ile Val Leu Thr
            20                  25                  30

Gln Ser Pro Asp Phe Gln Ser Val Thr Pro Lys Glu Lys Val Thr Ile
        35                  40                  45

Thr Cys Ser Ala Asn Ser Ala Leu Ser Tyr Met Tyr Trp Tyr Gln Gln
    50                  55                  60

Lys Pro Asp Gln Ser Pro Lys Leu Trp Val His Gly Thr Ser Asn Leu
65                  70                  75                  80

Ala Ser Gly Val Pro Ser Arg Phe Ser Gly Ser Gly Ser Gly Thr Asp
                85                  90                  95

Phe Thr Leu Thr Ile Asn Ser Leu Glu Ala Glu Asp Ala Ala Thr Tyr
            100                 105                 110

Tyr Cys His His Trp Ser Asn Thr Gln Trp Thr Phe Gly Gly Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

```
Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240

<210> SEQ ID NO 431
<211> LENGTH: 240
<212> TYPE: PRT
<213> ORGANISM: Artificial Sequence
<220> FEATURE:
<223> OTHER INFORMATION: Synthetic Construct

<400> SEQUENCE: 431

Ala Cys Pro Phe Pro Ala Leu Glu Leu Cys Gly Ser Pro Gly Ser Pro
1               5                   10                  15

Lys Pro Ile Leu Phe Phe Arg Leu Ser Gly Gly Glu Ile Val Leu Thr
            20                  25                  30

Gln Ser Pro Asp Phe Gln Ser Val Thr Pro Lys Glu Lys Val Thr Ile
        35                  40                  45

Thr Cys Ser Ala Asn Ser Ala Leu Ser Tyr Met Tyr Trp Tyr Gln Gln
    50                  55                  60

Lys Pro Asp Gln Ser Pro Lys Leu Trp Val His Gly Thr Ser Asn Leu
65                  70                  75                  80

Ala Ser Gly Val Pro Ser Arg Phe Ser Gly Ser Gly Ser Gly Thr Asp
                85                  90                  95

Phe Thr Leu Thr Ile Asn Ser Leu Glu Ala Glu Asp Ala Ala Thr Tyr
            100                 105                 110

Tyr Cys His His Trp Ser Asn Thr Gln Trp Thr Phe Gly Gly Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
            195                 200                 205

Lys Ala Asp Tyr Glu Lys His Lys Val Tyr Ala Cys Glu Val Thr His
        210                 215                 220

Gln Gly Leu Ser Ser Pro Val Thr Lys Ser Phe Asn Arg Gly Glu Cys
225                 230                 235                 240

<210> SEQ ID NO 432
<211> LENGTH: 16
<212> TYPE: PRT
<213> ORGANISM: Artificial Sequence
<220> FEATURE:
<223> OTHER INFORMATION: Synthetic Construct

<400> SEQUENCE: 432

Arg Ser Ser Gln Ser Leu Leu Asn Ser Asp Gly Asn Thr Tyr Leu Tyr
1               5                   10                  15

<210> SEQ ID NO 433
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 433

Leu Val Ser Lys Leu Gly Ser
1               5

<210> SEQ ID NO 434
<211> LENGTH: 9
<212> TYPE: PRT
<213> ORGANISM: Artificial Sequence
<220> FEATURE:
<223> OTHER INFORMATION: Synthetic Construct

<400> SEQUENCE: 434

Val Gln Gly Thr His Asp Pro Trp Thr
1               5

<210> SEQ ID NO 435
<211> LENGTH: 6
<212> TYPE: PRT
<213> ORGANISM: Artificial Sequence
<220> FEATURE:
<223> OTHER INFORMATION: Synthetic Construct

<400> SEQUENCE: 435

Ser Gly Tyr Asp Trp Thr
1               5

<210> SEQ ID NO 436
<211> LENGTH: 16
<212> TYPE: PRT
<213> ORGANISM: Artificial Sequence
<220> FEATURE:
<223> OTHER INFORMATION: Synthetic Construct

<400> SEQUENCE: 436

Tyr Ile Ser Tyr Ser Gly Asn Thr Asn Tyr Asn Pro Ser Leu Lys Ser
1               5                   10                  15

<210> SEQ ID NO 437
<211> LENGTH: 11
<212> TYPE: PRT
<213> ORGANISM: Artificial Sequence
<220> FEATURE:
<223> OTHER INFORMATION: Synthetic Construct

<400> SEQUENCE: 437

Met Met Val Pro His Tyr Tyr Val Met Asp Ala
1               5                   10

<210> SEQ ID NO 438
<211> LENGTH: 10
<212> TYPE: PRT
<213> ORGANISM: Artificial Sequence
<220> FEATURE:
<223> OTHER INFORMATION: Synthetic Construct

<400> SEQUENCE: 438

Ser Ala Asn Ser Ala Leu Ser Tyr Met Tyr
1               5                   10

<210> SEQ ID NO 439
<211> LENGTH: 7
```

```
<212> TYPE: PRT
<213> ORGANISM: Artificial Sequence
<220> FEATURE:
<223> OTHER INFORMATION: Synthetic Construct

<400> SEQUENCE: 439

Gly Thr Ser Asn Leu Ala Ser
1               5

<210> SEQ ID NO 440
<211> LENGTH: 9
<212> TYPE: PRT
<213> ORGANISM: Artificial Sequence
<220> FEATURE:
<223> OTHER INFORMATION: Synthetic Construct

<400> SEQUENCE: 440

His His Trp Ser Asn Thr Gln Trp Thr
1               5

<210> SEQ ID NO 441
<211> LENGTH: 5
<212> TYPE: PRT
<213> ORGANISM: Artificial Sequence
<220> FEATURE:
<223> OTHER INFORMATION: Synthetic Construct

<400> SEQUENCE: 441

Asn Tyr Phe Met Asn
1               5

<210> SEQ ID NO 442
<211> LENGTH: 17
<212> TYPE: PRT
<213> ORGANISM: Artificial Sequence
<220> FEATURE:
<223> OTHER INFORMATION: Synthetic Construct

<400> SEQUENCE: 442

Arg Val Asp Pro Glu Gln Gly Arg Ala Asp Tyr Ala Glu Lys Phe Lys
1               5                   10                  15

Lys

<210> SEQ ID NO 443
<211> LENGTH: 10
<212> TYPE: PRT
<213> ORGANISM: Artificial Sequence
<220> FEATURE:
<223> OTHER INFORMATION: Synthetic Construct

<400> SEQUENCE: 443

Arg Ala Met Asp Asn Tyr Gly Phe Ala Tyr
1               5                   10

<210> SEQ ID NO 444
<211> LENGTH: 28
<212> TYPE: PRT
<213> ORGANISM: Artificial Sequence
<220> FEATURE:
<223> OTHER INFORMATION: Synthetic Construct

<400> SEQUENCE: 444

Ala Cys Pro Phe Pro Ala Leu Glu Leu Cys Ser Ser Gly Gly Ser Gly
1               5                   10                  15

Pro Asp Ser Gly Gly Phe Met Leu Thr Ser Gly Gly
            20                  25
```

<210> SEQ ID NO 445
<211> LENGTH: 28
<212> TYPE: PRT
<213> ORGANISM: Artificial Sequence
<220> FEATURE:
<223> OTHER INFORMATION: Synthetic Construct

<400> SEQUENCE: 445

Ala Cys Pro Gly Lys Gly Leu Pro Ser Cys Gly Gly Gly Ser Ser Gly
1               5                   10                  15

Gly Ser Gly Gly Ser Gly Gly Ser Gly Ser Gly Gly
            20                  25

<210> SEQ ID NO 446
<211> LENGTH: 25
<212> TYPE: PRT
<213> ORGANISM: Artificial Sequence
<220> FEATURE:
<223> OTHER INFORMATION: Synthetic Construct

<400> SEQUENCE: 446

Ala Cys Pro Phe Pro Ala Leu Glu Leu Cys Gly Gly Ser Gly Gly Ser
1               5                   10                  15

Val Pro Leu Ser Leu Tyr Ser Gly Gly
            20                  25

<210> SEQ ID NO 447
<211> LENGTH: 28
<212> TYPE: PRT
<213> ORGANISM: Artificial Sequence
<220> FEATURE:
<223> OTHER INFORMATION: Synthetic Construct

<400> SEQUENCE: 447

Ala Cys Pro Phe Pro Ala Leu Glu Leu Cys Gly Gly Pro Gly Ser Ser
1               5                   10                  15

Pro Met Pro Tyr Asp Leu Tyr His Pro Ser Gly Gly
            20                  25

<210> SEQ ID NO 448
<211> LENGTH: 25
<212> TYPE: PRT
<213> ORGANISM: Artificial Sequence
<220> FEATURE:
<223> OTHER INFORMATION: Synthetic Construct

<400> SEQUENCE: 448

Ala Cys Pro Phe Pro Ala Leu Glu Leu Cys Gly Gly Ser Ser Pro Pro
1               5                   10                  15

His Glu Gln Leu Thr Val Ser Gly Gly
            20                  25

<210> SEQ ID NO 449
<211> LENGTH: 28
<212> TYPE: PRT
<213> ORGANISM: Artificial Sequence
<220> FEATURE:
<223> OTHER INFORMATION: Synthetic Construct

<400> SEQUENCE: 449

Ala Cys Pro Phe Pro Ala Leu Glu Leu Cys Gly Gly Gly Ser Ser Gly
1               5                   10                  15

Gly Ser Gly Gly Ser Gly Gly Ser Gly Ser Gly Gly

```
                20                  25

<210> SEQ ID NO 450
<211> LENGTH: 29
<212> TYPE: PRT
<213> ORGANISM: Artificial Sequence
<220> FEATURE:
<223> OTHER INFORMATION: Synthetic Construct

<400> SEQUENCE: 450

Ala Cys Pro Phe Pro Ala Leu Glu Leu Cys Ser Ser Pro Ser Pro Ser
1               5                   10                  15

Gly Gly Gly Gly Ile Gly Gln Leu Thr Ala Ser Gly Gly
            20                  25

<210> SEQ ID NO 451
<211> LENGTH: 27
<212> TYPE: PRT
<213> ORGANISM: Artificial Sequence
<220> FEATURE:
<223> OTHER INFORMATION: Synthetic Construct

<400> SEQUENCE: 451

Ala Cys Pro Phe Pro Ala Leu Glu Leu Cys Gly Gly Ser Ser Pro Pro
1               5                   10                  15

Arg Ala Ala Ala Val Lys Ser Pro Ser Gly Gly
            20                  25

<210> SEQ ID NO 452
<211> LENGTH: 27
<212> TYPE: PRT
<213> ORGANISM: Artificial Sequence
<220> FEATURE:
<223> OTHER INFORMATION: Synthetic Construct

<400> SEQUENCE: 452

Ala Cys Pro Phe Pro Ala Leu Glu Leu Cys Gly Gly Ser Ser Pro Pro
1               5                   10                  15

Thr Ser Val Leu Met Ala Ala Pro Ser Gly Gly
            20                  25

<210> SEQ ID NO 453
<211> LENGTH: 27
<212> TYPE: PRT
<213> ORGANISM: Artificial Sequence
<220> FEATURE:
<223> OTHER INFORMATION: Synthetic Construct

<400> SEQUENCE: 453

Ala Cys Pro Phe Pro Ala Leu Glu Leu Cys Gly Ser Pro Gly Ser Pro
1               5                   10                  15

Lys Pro Ile Leu Phe Phe Arg Leu Ser Gly Gly
            20                  25

<210> SEQ ID NO 454
<211> LENGTH: 18
<212> TYPE: PRT
<213> ORGANISM: Artificial Sequence
<220> FEATURE:
<223> OTHER INFORMATION: Synthetic Construct

<400> SEQUENCE: 454

Gly Gly Gly Ser Ser Gly Gly Ser Gly Val Pro Leu Ser Leu Tyr Ser
1               5                   10                  15
```

Gly Gly

<210> SEQ ID NO 455
<211> LENGTH: 18
<212> TYPE: PRT
<213> ORGANISM: Artificial Sequence
<220> FEATURE:
<223> OTHER INFORMATION: Synthetic Construct

<400> SEQUENCE: 455

Ser Ser Gly Gly Ser Gly Pro Asp Ser Gly Gly Phe Met Leu Thr Ser
1               5                   10                  15

Gly Gly

<210> SEQ ID NO 456
<211> LENGTH: 15
<212> TYPE: PRT
<213> ORGANISM: Artificial Sequence
<220> FEATURE:
<223> OTHER INFORMATION: Synthetic Construct

<400> SEQUENCE: 456

Gly Gly Ser Gly Gly Ser Val Pro Leu Ser Leu Tyr Ser Gly Gly
1               5                   10                  15

<210> SEQ ID NO 457
<211> LENGTH: 18
<212> TYPE: PRT
<213> ORGANISM: Artificial Sequence
<220> FEATURE:
<223> OTHER INFORMATION: Synthetic Construct

<400> SEQUENCE: 457

Gly Gly Pro Gly Ser Ser Pro Met Pro Tyr Asp Leu Tyr His Pro Ser
1               5                   10                  15

Gly Gly

<210> SEQ ID NO 458
<211> LENGTH: 15
<212> TYPE: PRT
<213> ORGANISM: Artificial Sequence
<220> FEATURE:
<223> OTHER INFORMATION: Synthetic Construct

<400> SEQUENCE: 458

Gly Gly Ser Ser Pro Pro His Glu Gln Leu Thr Val Ser Gly Gly
1               5                   10                  15

<210> SEQ ID NO 459
<211> LENGTH: 19
<212> TYPE: PRT
<213> ORGANISM: Artificial Sequence
<220> FEATURE:
<223> OTHER INFORMATION: Synthetic Construct

<400> SEQUENCE: 459

Ser Ser Pro Ser Pro Ser Gly Gly Gly Gly Ile Gly Gln Leu Thr Ala
1               5                   10                  15

Ser Gly Gly

<210> SEQ ID NO 460
<211> LENGTH: 17
<212> TYPE: PRT
<213> ORGANISM: Artificial Sequence
<220> FEATURE:

<223> OTHER INFORMATION: Synthetic Construct

<400> SEQUENCE: 460

Gly Gly Ser Ser Pro Pro Arg Ala Ala Ala Val Lys Ser Pro Ser Gly
1               5                   10                  15

Gly

<210> SEQ ID NO 461
<211> LENGTH: 17
<212> TYPE: PRT
<213> ORGANISM: Artificial Sequence
<220> FEATURE:
<223> OTHER INFORMATION: Synthetic Construct

<400> SEQUENCE: 461

Gly Gly Ser Ser Pro Pro Thr Ser Val Leu Met Ala Ala Pro Ser Gly
1               5                   10                  15

Gly

<210> SEQ ID NO 462
<211> LENGTH: 17
<212> TYPE: PRT
<213> ORGANISM: Artificial Sequence
<220> FEATURE:
<223> OTHER INFORMATION: Synthetic Construct

<400> SEQUENCE: 462

Gly Ser Pro Gly Ser Pro Lys Pro Ile Leu Phe Phe Arg Leu Ser Gly
1               5                   10                  15

Gly

<210> SEQ ID NO 463
<211> LENGTH: 329
<212> TYPE: PRT
<213> ORGANISM: Artificial Sequence
<220> FEATURE:
<223> OTHER INFORMATION: Synthetic Construct

<400> SEQUENCE: 463

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110

Ala Pro Glu Leu Leu Gly Gly Pro Asp Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

```
Val Asp Gly Val Glu Val His Asn Ala Lys Thr Lys Pro Arg Glu Glu
            165                 170                 175

Gln Tyr Asn Ser Thr Tyr Arg Val Val Ser Val Leu Thr Val Leu His
        180                 185                 190

Gln Asp Trp Leu Asn Gly Lys Glu Tyr Lys Cys Lys Val Ser Asn Lys
        195                 200                 205

Ala Leu Pro Ala Pro Glu Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 464
<211> LENGTH: 13
<212> TYPE: PRT
<213> ORGANISM: Artificial Sequence
<220> FEATURE:
<223> OTHER INFORMATION: Synthetic Construct

<400> SEQUENCE: 464

Ile Ser Ser Gly Leu Leu Ser Gly Arg Ser Asp Asn His
1               5                   10

<210> SEQ ID NO 465
<211> LENGTH: 18
<212> TYPE: PRT
<213> ORGANISM: Artificial Sequence
<220> FEATURE:
<223> OTHER INFORMATION: Synthetic Construct

<400> SEQUENCE: 465

Ala Val Gly Leu Leu Ala Pro Pro Gly Gly Leu Ser Gly Arg Ser Asp
1               5                   10                  15

Asn His

<210> SEQ ID NO 466
<211> LENGTH: 8
<212> TYPE: PRT
<213> ORGANISM: Artificial Sequence
<220> FEATURE:
<223> OTHER INFORMATION: Synthetic Construct

<400> SEQUENCE: 466

Val Pro Leu Ser Leu Tyr Ser Gly
1               5

<210> SEQ ID NO 467
<211> LENGTH: 7
<212> TYPE: PRT
<213> ORGANISM: Artificial Sequence
```

-continued

<220> FEATURE:
<223> OTHER INFORMATION: Synthetic Construct

<400> SEQUENCE: 467

Arg Gln Ala Arg Val Val Gly
1               5

<210> SEQ ID NO 468
<211> LENGTH: 15
<212> TYPE: PRT
<213> ORGANISM: Artificial Sequence
<220> FEATURE:
<223> OTHER INFORMATION: Synthetic Construct

<400> SEQUENCE: 468

Leu Ser Gly Arg Ser Asn Ala Met Pro Tyr Asp Leu Tyr His Pro
1               5                   10                  15

<210> SEQ ID NO 469
<211> LENGTH: 15
<212> TYPE: PRT
<213> ORGANISM: Artificial Sequence
<220> FEATURE:
<223> OTHER INFORMATION: Synthetic Construct

<400> SEQUENCE: 469

Met Pro Tyr Asp Leu Tyr His Pro Arg Gln Ala Arg Val Val Gly
1               5                   10                  15

<210> SEQ ID NO 470
<211> LENGTH: 14
<212> TYPE: PRT
<213> ORGANISM: Artificial Sequence
<220> FEATURE:
<223> OTHER INFORMATION: Synthetic Construct

<400> SEQUENCE: 470

Lys Ile Ser Ser Gly Leu Leu Ser Gly Arg Ser Asp Asn His
1               5                   10

<210> SEQ ID NO 471
<211> LENGTH: 19
<212> TYPE: PRT
<213> ORGANISM: Artificial Sequence
<220> FEATURE:
<223> OTHER INFORMATION: Synthetic Construct

<400> SEQUENCE: 471

Arg Ala Val Gly Leu Leu Ala Pro Pro Gly Gly Leu Ser Gly Arg Ser
1               5                   10                  15

Asp Asn His

<210> SEQ ID NO 472
<211> LENGTH: 14
<212> TYPE: PRT
<213> ORGANISM: Artificial Sequence
<220> FEATURE:
<223> OTHER INFORMATION: Synthetic Construct

<400> SEQUENCE: 472

Arg Gly Gly Val Pro Leu Ser Leu Tyr Ser Gly Gly Gly Lys
1               5                   10

<210> SEQ ID NO 473
<211> LENGTH: 14
<212> TYPE: PRT

```
<213> ORGANISM: Artificial Sequence
<220> FEATURE:
<223> OTHER INFORMATION: Synthetic Construct

<400> SEQUENCE: 473

Arg Gly Gly Met Pro Tyr Asp Leu Tyr His Pro Gly Gly Lys
1               5                   10

<210> SEQ ID NO 474
<211> LENGTH: 14
<212> TYPE: PRT
<213> ORGANISM: Artificial Sequence
<220> FEATURE:
<223> OTHER INFORMATION: Synthetic Construct

<400> SEQUENCE: 474

Arg Gly Gly Asp Ser Gly Gly Phe Met Leu Thr Gly Gly Lys
1               5                   10

<210> SEQ ID NO 475
<211> LENGTH: 14
<212> TYPE: PRT
<213> ORGANISM: Artificial Sequence
<220> FEATURE:
<223> OTHER INFORMATION: Synthetic Construct

<400> SEQUENCE: 475

Arg Gly Ser Gly His Glu Gln Leu Thr Val Gly Gly Ser Lys
1               5                   10

<210> SEQ ID NO 476
<211> LENGTH: 14
<212> TYPE: PRT
<213> ORGANISM: Artificial Sequence
<220> FEATURE:
<223> OTHER INFORMATION: Synthetic Construct

<400> SEQUENCE: 476

Gly Ser Gly Arg Ala Ala Ala Val Lys Ser Pro Gly Ser Lys
1               5                   10

<210> SEQ ID NO 477
<211> LENGTH: 14
<212> TYPE: PRT
<213> ORGANISM: Artificial Sequence
<220> FEATURE:
<223> OTHER INFORMATION: Synthetic Construct

<400> SEQUENCE: 477

Gly Ser Gly Arg Gln Ala Arg Val Val Gly Gly Gly Ser Lys
1               5                   10

<210> SEQ ID NO 478
<211> LENGTH: 450
<212> TYPE: PRT
<213> ORGANISM: Artificial Sequence
<220> FEATURE:
<223> OTHER INFORMATION: Synthetic Construct

<400> SEQUENCE: 478

Gln Val Gln Leu Gln Glu Ser Gly Pro Gly Leu Val Lys Pro Ser Glu
1               5                   10                  15

Thr Leu Ser Leu Thr Cys Ser Val Thr Tyr His Thr Ile Thr Ser Gly
            20                  25                  30

Tyr Asp Trp Thr Trp Ile Arg Lys Pro Pro Gly Lys Gly Met Glu Trp
        35                  40                  45
```

-continued

```
Ile Gly Tyr Ile Ser Tyr Ser Gly Asn Thr Asn Tyr Asn Pro Ser Leu
     50                  55                  60

Lys Ser Arg Val Thr Ile Ser Arg Asp Thr Ser Lys Asn Gln Phe Phe
 65                  70                  75                  80

Leu Lys Leu Ser Ser Val Thr Ala Ala Asp Thr Ala Val Tyr Tyr Cys
                 85                  90                  95

Ala Ser Met Met Val Pro His Tyr Tyr Val Met Asp Ala Trp Gly Gln
             100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
         195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Asp Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Glu Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Asp Glu Leu Thr Lys Asn Gln Val Ser Leu
         355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
         435                 440                 445

Gly Lys
    450
```

<210> SEQ ID NO 479
<211> LENGTH: 8
<212> TYPE: PRT
<213> ORGANISM: Artificial Sequence
<220> FEATURE:
<223> OTHER INFORMATION: Synthetic Construct

<400> SEQUENCE: 479

Ile Pro Glu Ser Leu Arg Ala Gly
1               5

<210> SEQ ID NO 480
<211> LENGTH: 8
<212> TYPE: PRT
<213> ORGANISM: Artificial Sequence
<220> FEATURE:
<223> OTHER INFORMATION: Synthetic Construct

<400> SEQUENCE: 480

Ile Pro Val Ser Leu Arg Ser Gly
1               5

<210> SEQ ID NO 481
<211> LENGTH: 6
<212> TYPE: PRT
<213> ORGANISM: Artificial Sequence
<220> FEATURE:
<223> OTHER INFORMATION: Synthetic Construct

<400> SEQUENCE: 481

Ile Tyr Asp Gln Lys Thr
1               5

<210> SEQ ID NO 482
<211> LENGTH: 6
<212> TYPE: PRT
<213> ORGANISM: Artificial Sequence
<220> FEATURE:
<223> OTHER INFORMATION: Synthetic Construct

<400> SEQUENCE: 482

Ala His Asn Tyr Lys Thr
1               5

<210> SEQ ID NO 483
<211> LENGTH: 6
<212> TYPE: PRT
<213> ORGANISM: Artificial Sequence
<220> FEATURE:
<223> OTHER INFORMATION: Synthetic Construct

<400> SEQUENCE: 483

Met Met Asp Gln Ala Asn
1               5

<210> SEQ ID NO 484
<211> LENGTH: 8
<212> TYPE: PRT
<213> ORGANISM: Artificial Sequence
<220> FEATURE:
<223> OTHER INFORMATION: Synthetic Construct

<400> SEQUENCE: 484

Met Leu Gly Glu Phe Val Ser Glu
1               5

```
<210> SEQ ID NO 485
<211> LENGTH: 8
<212> TYPE: PRT
<213> ORGANISM: Artificial Sequence
<220> FEATURE:
<223> OTHER INFORMATION: Synthetic Construct

<400> SEQUENCE: 485

Gly Leu Val Ala Leu Arg Gly Ala
1               5

<210> SEQ ID NO 486
<211> LENGTH: 8
<212> TYPE: PRT
<213> ORGANISM: Artificial Sequence
<220> FEATURE:
<223> OTHER INFORMATION: Synthetic Construct

<400> SEQUENCE: 486

Lys Glu His Lys Tyr Lys Ala Glu
1               5

<210> SEQ ID NO 487
<211> LENGTH: 8
<212> TYPE: PRT
<213> ORGANISM: Artificial Sequence
<220> FEATURE:
<223> OTHER INFORMATION: Synthetic Construct

<400> SEQUENCE: 487

Leu Ala Gln Ala Val Arg Ser Ser
1               5

<210> SEQ ID NO 488
<211> LENGTH: 14
<212> TYPE: PRT
<213> ORGANISM: Artificial Sequence
<220> FEATURE:
<223> OTHER INFORMATION: Synthetic Construct

<400> SEQUENCE: 488

Leu Gly Gly Ser Gly Arg Ser Asn Ala Gln Val Arg Leu Glu
1               5                   10

<210> SEQ ID NO 489
<211> LENGTH: 13
<212> TYPE: PRT
<213> ORGANISM: Artificial Sequence
<220> FEATURE:
<223> OTHER INFORMATION: Synthetic Construct

<400> SEQUENCE: 489

Leu Gly Gly Ser Gly Arg Lys Ala Ser Leu Ser Leu Glu
1               5                   10

<210> SEQ ID NO 490
<211> LENGTH: 10
<212> TYPE: PRT
<213> ORGANISM: Artificial Sequence
<220> FEATURE:
<223> OTHER INFORMATION: Synthetic Construct

<400> SEQUENCE: 490

Ser Gly Arg Ile Gly Phe Leu Arg Thr Ala
1               5                   10

<210> SEQ ID NO 491
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 491

Ser Gly Ala Ile Gly Phe Leu Arg Thr Ala
1               5                   10

<210> SEQ ID NO 492
<211> LENGTH: 14
<212> TYPE: PRT
<213> ORGANISM: Artificial Sequence
<220> FEATURE:
<223> OTHER INFORMATION: Synthetic Construct

<400> SEQUENCE: 492

Arg Pro Ala Arg Ser Gly Arg Ser Ala Gly Gly Ser Val Ala
1               5                   10

<210> SEQ ID NO 493
<211> LENGTH: 11
<212> TYPE: PRT
<213> ORGANISM: Artificial Sequence
<220> FEATURE:
<223> OTHER INFORMATION: Synthetic Construct

<400> SEQUENCE: 493

Val Thr Gly Arg Gly Asp Ser Pro Ala Ser Ser
1               5                   10

<210> SEQ ID NO 494
<211> LENGTH: 8
<212> TYPE: PRT
<213> ORGANISM: Artificial Sequence
<220> FEATURE:
<223> OTHER INFORMATION: Synthetic Construct

<400> SEQUENCE: 494

Pro Arg Phe Lys Ile Ile Gly Gly
1               5

<210> SEQ ID NO 495
<211> LENGTH: 11
<212> TYPE: PRT
<213> ORGANISM: Artificial Sequence
<220> FEATURE:
<223> OTHER INFORMATION: Synthetic Construct

<400> SEQUENCE: 495

Leu Ser Gly Arg Ile Gly Phe Leu Arg Thr Ala
1               5                   10

<210> SEQ ID NO 496
<211> LENGTH: 15
<212> TYPE: PRT
<213> ORGANISM: Artificial Sequence
<220> FEATURE:
<223> OTHER INFORMATION: Synthetic Construct

<400> SEQUENCE: 496

Leu Ser Gly Arg Ser Asn Ala Gly Gly Ile Gly Gln Leu Thr Ala
1               5                   10                  15

<210> SEQ ID NO 497
<211> LENGTH: 13
```

```
<212> TYPE: PRT
<213> ORGANISM: Artificial Sequence
<220> FEATURE:
<223> OTHER INFORMATION: Synthetic Construct

<400> SEQUENCE: 497

Leu Ser Gly Arg Ser Asn Ala Val Pro Leu Ser Leu Tyr
1               5                   10

<210> SEQ ID NO 498
<211> LENGTH: 15
<212> TYPE: PRT
<213> ORGANISM: Artificial Sequence
<220> FEATURE:
<223> OTHER INFORMATION: Synthetic Construct

<400> SEQUENCE: 498

Leu Ser Gly Arg Ser Asn Ala Asp Ser Gly Gly Phe Met Leu Thr
1               5                   10                  15

<210> SEQ ID NO 499
<211> LENGTH: 13
<212> TYPE: PRT
<213> ORGANISM: Artificial Sequence
<220> FEATURE:
<223> OTHER INFORMATION: Synthetic Construct

<400> SEQUENCE: 499

Leu Ser Gly Arg Ser Asn Ala His Glu Gln Leu Thr Ala
1               5                   10

<210> SEQ ID NO 500
<211> LENGTH: 15
<212> TYPE: PRT
<213> ORGANISM: Artificial Sequence
<220> FEATURE:
<223> OTHER INFORMATION: Synthetic Construct

<400> SEQUENCE: 500

Leu Ser Gly Arg Ser Asn Ala Arg Ala Ala Ala Val Lys Ser Pro
1               5                   10                  15

<210> SEQ ID NO 501
<211> LENGTH: 15
<212> TYPE: PRT
<213> ORGANISM: Artificial Sequence
<220> FEATURE:
<223> OTHER INFORMATION: Synthetic Construct

<400> SEQUENCE: 501

Leu Ser Gly Arg Ser Asn Ala Thr Ser Val Leu Met Ala Ala Pro
1               5                   10                  15

<210> SEQ ID NO 502
<211> LENGTH: 13
<212> TYPE: PRT
<213> ORGANISM: Artificial Sequence
<220> FEATURE:
<223> OTHER INFORMATION: Synthetic Construct

<400> SEQUENCE: 502

Val Pro Leu Ser Leu Tyr Leu Ser Gly Arg Ser Asn Ala
1               5                   10

<210> SEQ ID NO 503
<211> LENGTH: 15
<212> TYPE: PRT
```

```
<213> ORGANISM: Artificial Sequence
<220> FEATURE:
<223> OTHER INFORMATION: Synthetic Construct

<400> SEQUENCE: 503

Asp Ser Gly Gly Phe Met Leu Thr Leu Ser Gly Arg Ser Asn Ala
1               5                   10                  15

<210> SEQ ID NO 504
<211> LENGTH: 15
<212> TYPE: PRT
<213> ORGANISM: Artificial Sequence
<220> FEATURE:
<223> OTHER INFORMATION: Synthetic Construct

<400> SEQUENCE: 504

Gly Gly Ile Gly Gln Leu Thr Ala Leu Ser Gly Arg Ser Asn Ala
1               5                   10                  15

<210> SEQ ID NO 505
<211> LENGTH: 15
<212> TYPE: PRT
<213> ORGANISM: Artificial Sequence
<220> FEATURE:
<223> OTHER INFORMATION: Synthetic Construct

<400> SEQUENCE: 505

Met Pro Tyr Asp Leu Tyr His Pro Leu Ser Gly Arg Ser Asn Ala
1               5                   10                  15

<210> SEQ ID NO 506
<211> LENGTH: 13
<212> TYPE: PRT
<213> ORGANISM: Artificial Sequence
<220> FEATURE:
<223> OTHER INFORMATION: Synthetic Construct

<400> SEQUENCE: 506

His Glu Gln Leu Thr Val Leu Ser Gly Arg Ser Asn Ala
1               5                   10

<210> SEQ ID NO 507
<211> LENGTH: 15
<212> TYPE: PRT
<213> ORGANISM: Artificial Sequence
<220> FEATURE:
<223> OTHER INFORMATION: Synthetic Construct

<400> SEQUENCE: 507

Arg Ala Ala Ala Val Lys Ser Pro Leu Ser Gly Arg Ser Asn Ala
1               5                   10                  15

<210> SEQ ID NO 508
<211> LENGTH: 15
<212> TYPE: PRT
<213> ORGANISM: Artificial Sequence
<220> FEATURE:
<223> OTHER INFORMATION: Synthetic Construct

<400> SEQUENCE: 508

Thr Ser Val Leu Met Ala Ala Pro Leu Ser Gly Arg Ser Asn Ala
1               5                   10                  15
```